US008618128B1

(12) United States Patent
Hood et al.

(10) Patent No.: US 8,618,128 B1
(45) Date of Patent: Dec. 31, 2013

(54) **1H-PYRAZOLO[3,4-*B*]PYRIDINES AND THERAPEUTIC USES THEREOF**

(71) Applicant: Samumed, LLC, San Diego, CA (US)

(72) Inventors: John Hood, San Diego, CA (US); Sunil Kumar KC, San Diego, CA (US); David Mark Wallace, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 14/019,147

(22) Filed: Sep. 5, 2013

Related U.S. Application Data

(63) Continuation of application No. 13/887,177, filed on May 3, 2013.

(60) Provisional application No. 61/642,915, filed on May 4, 2012.

(51) Int. Cl.

| | |
|---|---|
| ***A01N 43/42*** | (2006.01) |
| ***C07D 471/02*** | (2006.01) |
| ***C07D 491/02*** | (2006.01) |
| ***C07D 498/02*** | (2006.01) |

(52) U.S. Cl.
USPC .......... 514/300; 546/119

(58) Field of Classification Search
USPC .......... 546/119; 514/300
See application file for complete search history.

(56) References Cited

U.S. PATENT DOCUMENTS

| | | | |
|---|---|---|---|
| 4,164,559 | A | 8/1979 | Miyata et al. |
| 4,474,752 | A | 10/1984 | Haslam et al. |
| 5,922,733 | A | 7/1999 | Forbes et al. |
| 6,120,484 | A | 9/2000 | Silverstein |
| 6,358,978 | B1 | 3/2002 | Ritzeler et al. |
| 6,377,849 | B1 | 4/2002 | Lenarz et al. |
| 6,440,102 | B1 | 8/2002 | Arenberg et al. |
| 6,555,539 | B2 | 4/2003 | Reich et al. |
| 6,648,873 | B2 | 11/2003 | Arenberg et al. |
| 6,831,175 | B2 | 12/2004 | Li et al. |
| 6,884,890 | B2 | 4/2005 | Kania et al. |
| 6,897,208 | B2 | 5/2005 | Edwards et al. |
| 6,911,211 | B2 | 6/2005 | Eini et al. |
| 6,919,461 | B2 | 7/2005 | Reich et al. |
| 7,008,953 | B2 | 3/2006 | Kephart et al. |
| 7,064,215 | B2 | 6/2006 | Renhowe et al. |
| 7,232,912 | B2 | 6/2007 | Reich et al. |
| 7,285,565 | B2 | 10/2007 | Zhu et al. |
| 7,429,609 | B2 | 9/2008 | Ohi et al. |
| 7,452,993 | B2 | 11/2008 | Arnold et al. |
| 7,468,376 | B2 | 12/2008 | Rosales et al. |
| 7,482,342 | B2 | 1/2009 | D'Orchymont et al. |
| 7,491,710 | B2 | 2/2009 | Cherrier et al. |
| 7,541,367 | B2 | 6/2009 | Chiu et al. |
| 7,626,021 | B2 | 12/2009 | Arnold et al. |
| 7,642,278 | B2 | 1/2010 | Jansen et al. |
| 7,666,867 | B2 | 2/2010 | Makriyannis et al. |
| 7,812,043 | B2 | 10/2010 | Lau et al. |
| 7,829,558 | B2 | 11/2010 | Arnold et al. |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

"Application of Hamish Christopher Swan Wood, Norman Whittaker, Irene Stirling and Kyuji Ohta.," 582 F.2d 638 (Fed. Cir. 1978), 2 pages.
Adaimy et al., "Mutation in WNT10A Is Associated with an Autosomal Recessive Ectodermal Dysplasia: The Odonto-onycho-dermal Dysplasia," *Am. J. Hum. Genet.*, (Oct. 2007), 81(4), 821-828.
Anastas and Moon, "WNT signalling pathways as therapeutic targets in cancer," *Nat Rev Cancer*, 13(1):11-26, Jan. 2013.
Andres, "Molecular genetics and animal models in autistic disorder," *Brain Research Bulletin*, (2002), 57(1), 109-119.
Barker and Clevers, "Mining the Wnt pathway for cancer therapeutics," *Nat Rev Drug Discov.*, 5(12):997-1014, Dec. 2006.
Beyer et al., "Extended report: β-catenin is a central mediator of pro-fibrotic Wnt signaling in systemic sclerosis," *Ann Rheum Dis*, 71:761-767, online Feb. 2012.

(Continued)

*Primary Examiner* — Niloofar Rahmani
(74) *Attorney, Agent, or Firm* — Fish & Richardson P.C.

(57) ABSTRACT

Provided herein are compounds according to Formulas (I) or (II) and pharmaceutically acceptable salts thereof, and compositions comprising the same, for use in various methods, including treating cancer, abnormal cellular proliferation, angiogenesis, Alzheimer's disease, lung disease, osteoarthritis, idiopathic pulmonary fibrosis and neurological conditions/disorders/diseases.

I

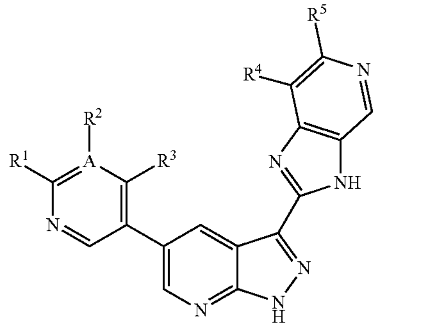

II

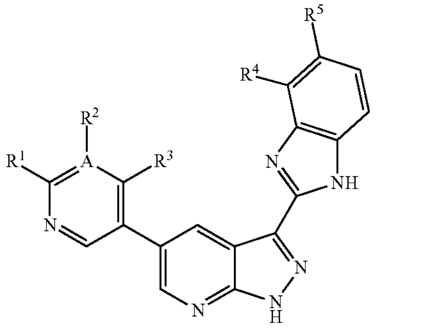

30 Claims, No Drawings

(56) References Cited

U.S. PATENT DOCUMENTS

| | | | | |
|---|---|---|---|---|
| 7,842,711 | B2 | 11/2010 | D'Orchymont et al. | |
| 8,008,481 | B2 | 8/2011 | Ericsson et al. | |
| 8,088,772 | B2 | 1/2012 | Garcia et al. | |
| 8,129,519 | B2 | 3/2012 | Cholody et al. | |
| 8,158,647 | B2 | 4/2012 | Blaney et al. | |
| 8,252,812 | B2 | 8/2012 | Hood et al. | |
| 8,288,425 | B2 | 10/2012 | Edwards et al. | |
| 8,304,408 | B2 | 11/2012 | Wrasidlo et al. | |
| 8,450,340 | B2 * | 5/2013 | Hood et al. | 514/300 |
| 2002/0103229 | A1 | 8/2002 | Bhagwat et al. | |
| 2002/0161022 | A1 | 10/2002 | Reich et al. | |
| 2003/0199516 | A1 | 10/2003 | Moser et al. | |
| 2004/0077681 | A1 | 4/2004 | Rawlings et al. | |
| 2004/0236101 | A1 | 11/2004 | Makriyannis et al. | |
| 2005/0026960 | A1 | 2/2005 | Kephart et al. | |
| 2005/0090529 | A1 | 4/2005 | McAlpine et al. | |
| 2005/0192262 | A1 | 9/2005 | Hagstrom et al. | |
| 2005/0208582 | A1 | 9/2005 | Ohi et al. | |
| 2005/0261339 | A1 | 11/2005 | Ohi et al. | |
| 2006/0004000 | A1 | 1/2006 | D'Orchymont et al. | |
| 2006/0014756 | A1 | 1/2006 | Edwards et al. | |
| 2006/0079564 | A1 | 4/2006 | Jansen et al. | |
| 2006/0094706 | A1 | 5/2006 | Paruch et al. | |
| 2006/0111322 | A1 | 5/2006 | Reich et al. | |
| 2006/0116519 | A1 | 6/2006 | Ma et al. | |
| 2006/0135589 | A1 | 6/2006 | Berdino et al. | |
| 2006/0142345 | A1 | 6/2006 | Kephart et al. | |
| 2006/0167056 | A1 | 7/2006 | Rynberg et al. | |
| 2006/0264897 | A1 | 11/2006 | Lobl | |
| 2007/0027140 | A1 | 2/2007 | Lau et al. | |
| 2007/0060616 | A1 | 3/2007 | Bennett et al. | |
| 2007/0185187 | A1 | 8/2007 | D'Orchymont et al. | |
| 2007/0219257 | A1 | 9/2007 | Beachy et al. | |
| 2007/0282101 | A1 | 12/2007 | Ericsson et al. | |
| 2008/0004270 | A1 | 1/2008 | Gill et al. | |
| 2008/0255085 | A1 | 10/2008 | Arvidsson et al. | |
| 2008/0262205 | A1 | 10/2008 | Haar et al. | |
| 2009/0005356 | A1 | 1/2009 | Blaney et al. | |
| 2009/0005377 | A1 | 1/2009 | Almansa Rosales et al. | |
| 2009/0054397 | A1 | 2/2009 | Ohi et al. | |
| 2009/0099062 | A1 | 4/2009 | Lee et al. | |
| 2009/0203690 | A1 | 8/2009 | Akritopoulou-Zanze et al. | |
| 2009/0286983 | A1 | 11/2009 | Almansa Rosales et al. | |
| 2011/0009353 | A1 | 1/2011 | Chen-Kiang et al. | |
| 2011/0021467 | A1 | 1/2011 | D'Orchymont et al. | |
| 2011/0034441 | A1 | 2/2011 | Hood et al. | |
| 2011/0034497 | A1 | 2/2011 | Hood et al. | |
| 2011/0082144 | A1 | 4/2011 | Lau et al. | |
| 2011/0190290 | A1 | 8/2011 | Hood et al. | |
| 2012/0129837 | A1 | 5/2012 | Cholody et al. | |
| 2012/0277229 | A1 | 11/2012 | Bearss et al. | |
| 2013/0040976 | A1 | 2/2013 | Hood et al. | |
| 2013/0079329 | A1 | 3/2013 | Hood et al. | |
| 2013/0225576 | A1 | 8/2013 | Hood et al. | |

FOREIGN PATENT DOCUMENTS

| | | |
|---|---|---|
| CN | 1829713 | 9/2006 |
| CN | 101440092 | 5/2009 |
| WO | WO8705297 | 9/1987 |
| WO | WO9602537 | 2/1996 |
| WO | WO0102369 | 1/2001 |
| WO | WO0153268 | 7/2001 |
| WO | WO03004488 | 1/2003 |
| WO | WO03035005 | 5/2003 |
| WO | WO03035065 | 5/2003 |
| WO | WO03035644 | 5/2003 |
| WO | WO03051366 | 6/2003 |
| WO | WO03070236 | 8/2003 |
| WO | WO03070706 | 8/2003 |
| WO | WO03097610 | 11/2003 |
| WO | WO03101968 | 12/2003 |
| WO | WO03101993 | 12/2003 |
| WO | WO2004014864 | 2/2004 |
| WO | WO2004031158 | 4/2004 |
| WO | WO2004076450 | 9/2004 |
| WO | WO2005009997 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006015124 | 2/2006 |
| WO | WO2006024945 | 3/2006 |
| WO | WO2006054143 | 5/2006 |
| WO | WO2006054151 | 5/2006 |
| WO | WO2006063302 | 6/2006 |
| WO | WO2006063841 | 6/2006 |
| WO | WO2006130673 | 12/2006 |
| WO | WO2007061360 | 5/2007 |
| WO | WO2007107346 | 9/2007 |
| WO | WO2007117465 | 10/2007 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |
| WO | WO2009011850 | 1/2009 |
| WO | WO2009016072 | 2/2009 |
| WO | WO2009061345 | 5/2009 |
| WO | WO2010107765 | 9/2010 |
| WO | WO2010111060 | 9/2010 |
| WO | WO2011011722 | 1/2011 |
| WO | WO2011019648 | 2/2011 |
| WO | WO2011019651 | 2/2011 |
| WO | WO2011050245 | 4/2011 |
| WO | WO2011084486 | 7/2011 |
| WO | WO2011123890 | 10/2011 |
| WO | WO2012068589 | 5/2012 |
| WO | WO2012129562 | 9/2012 |
| WO | WO2013024011 | 2/2013 |

OTHER PUBLICATIONS

Biason-Lauber et al., "A WNT4 Mutation Associated with Müllerian-Duct Regression and Virilization in a 46,XX Woman," *N. Engl. J. Med.*, (Aug. 2004), 351(8), 792-798.

Blaydon et al., "The gene encoding R-spondin 4 (RSPO4), a secreted protein implicated in Wnt signaling, is mutated in inherited anonychia," *Nat. Genet.*, (Nov. 2006), 38(11), 1245-1247.

Blom et al., "Involvement of the Wnt signaling pathway in experimental and human osteoarthritis: prominent role of Wnt-induced signaling protein 1," *Arthritis Rheum.*, 60(2):501-512, Feb. 2009.

Boyden et al., "High Bone Density Due to a Mutation in LDL-Receptor-Related Protein 5," *N. Engl. J. Med.*, (May 2002), 346(20):1513-1521.

Brack et al., "Increased Wnt signaling during aging alters muscle stem cell fate and increases fibrosis," *Science.*, 317(5839):807-810, Aug. 2007.

Brown et al., "Toxicity and toxicokinetics of the cyclin-dependent kinase inhibitor AG-024322 in cynomolgus monkeys following intravenous infusion," *Cancer Chemother Pharmacol.*, 62(6):1091-1101, Epub May 2008.

Chilosi et al., "The pathogenesis of COPD and IPF: Distinct horns of the same devil?," *Respiratory Research*, 13:3, 2012.

Chou and Talalay, "Quantitative analysis of dose-effect relationships: the combined effects of multiple drugs or enzyme inhibitors," *Advances in Enzyme Regulation* (1984), 22, 27-55.

Chou, "Drug combination studies and their synergy quantification using the Chou-Talalay method," *Cancer Res.*, 70(2):440-446, Jan. 2010.

Chou, "Graphic rule for drug metabolism systems," *Current Drug Metabolism*, (May 2010) 11(4): 369-378.

Christodoulides et al., "WNT10B mutations in human obesity," *Diabetologia*, (2006) 49(4):678-684.

(56) References Cited

OTHER PUBLICATIONS

Clevers and Nusse, "Wnt/β-catenin 1205 signaling and disease," *Cell*, (Jun. 2012), 149(6):1192-1205.
Clevers, "Wnt/beta-catenin signaling in development and disease," *Cell*, (Nov. 2006), 127(3), 469-480.
D'Alessio et al., "Benzodipyrazoles: a new class of potent CDK2 inhibitors," *Bioorganic & Medicinal Chemistry Letters* (2005), 15(5), 1315-1319.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," *Br J Pharmacol.*, 163(1):141-172, May 2011.
De Ferrari and Inestrosa, "Wnt signaling function in Alzheimer's disease," *Brain Research Reviews*, (2000), 33(1):1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.
Dessalew et al., "3D-QSAR CoMFA and CoMSIA study on benzodipyrazoles as cyclin dependent kinase 2 inhibitors," *Medicinal Chemistry*, (2008), 4(4), 313-321.
Dong et al., "QSAR study of Akt/protein kinase B (PKB) inhibitors using support vector machine," *European Journal of Medicinal Chemistry*, (Oct. 2009), pp. 44(10): 4090-4097.
du Bois, "Strategies for treating idiopathic pulmonary fibrosis," *Nature Reviews Drug Discovery*, 9(2): 129-140 (Feb. 2010).
Egloff et al., "Gastrin-releasing peptide receptor expression in non-cancerous bronchial epithelia is associated with lung cancer: a case-control study," *Respiratory Research*, 13:9, Feb. 2012.
Espada et al., "Wnt signalling and cancer stem cells," *Clin. Transl. Oncol.*, (2009), 11(7), 411-27.
Ewan et al., "A useful approach to identify novel small-molecule inhibitors of Wnt-dependent transcription," *Cancer Res.* (2010), 70(14), 5963-5973.
Florez et al., "TCF7L2 Polymorphisms and Progression to Diabetes in the Diabetes Prevention Program," *N. Engl. J. Med.*, (Jul. 2006), 355(3):241-250.
Freese et al., "Wnt signaling in development and disease," *Neurobiology of Disease*, (2010) 38(2):148-153.
Fujii et al., "An antagonist of dishevelled protein-protein interaction suppresses beta-catenin-dependent tumor cell growth," *Cancer Res.*, 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," *Pediatric and Developmental Pathology* (2003), 6(4): 299-306.
Giles et al., "Caught up in a Wnt storm: Wnt signaling in cancer," *Biochim Biophys Acta.*, 1653(1):1-24, Jun. 2003.
Handeli and Simon, "A small-molecule inhibitor of Tcf/beta-catenin signaling down-regulates PPARgamma and PPARdelta activities," *Mol Cancer Ther.*, 7(3):521-529, Mar. 2008.
Henderson Jr. et al., "Inhibition of Wnt/beta-catenin/CREB binding protein (CBP) signaling reverses pulmonary fibrosis," *Proc Natl Acad Sci U S A.*, 107(32):14309-14314, Epub Jul. 2010.
Hu et al., "Discovery of indazoles as inhibitors of Tpl2 kinase," *Bioorganic & Medicinal Chemistry Letters*, (Aug. 2011) 21(16): 4758-4761.
Huang et al., "Tankyrase inhibition stabilizes axin and antagonizes Wnt signaling," *Nature*, (Oct. 2009), 461(7264): 614-620.
Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," *Bioorganic & Medicinal Chemistry Letters*, (2007) 17(5): 1243-1245.
Hübner et al., "Standardized quantification of pulmonary fibrosis in histological samples," *Biotechniques*, 44(4):507-511, 514-517, Apr. 2008.
Im et al., "Wnt inhibitors enhance chondrogenesis of human mesenchymal stem cells in a long-term pellet culture," *Biotechnol Lett.*, 33(5):1061-1068, Epub Jan. 2011.
Inestrosa and Toledo, "The role of Wnt signaling in neuronal dysfunction in Alzheimer's Disease," *Mol Neurodegener*, 3:9, doi:10.1186/1750-1326-3-9, 13 pages, Jul. 2008.
Janssens et al., "The Wnt-dependent signaling pathways as target in oncology drug discovery," *Invest New Drugs.*, 24(4):263-280, Jul. 2006.
Jenkins et al., "Germline mutations in WTX cause a sclerosing skeletal dysplasia but do not predispose to tumorigenesis," *Nat. Genet.* (Jan. 2009), 41(1), 95-100.
Jessen et al., "Peripheral white blood cell toxicity induced by broad spectrum cyclin-dependent kinase inhibitors," *Journal of Applied Toxicology* (Jan. 2007), 27(2), 133-142.
Kanazawa et al., "Association of the Gene Encoding Wingless-Type Mammary Tumor Virus Integration-Site Family Member 5B (WNT5B) with Type 2 Diabetes," *Am. J. Hum. Genet.* (2004), 75(5), 832-843.
Karlberg et al., "Structural basis for the interaction between tankyrase-2 and a potent Wnt-signaling inhibitor," *J. Med. Chem.* (2010), 53(14), 5352-5.
Kibar et al., "Mutations in VANGL1 Associated with Neural-Tube Defects," *N. Engl. J. Med.*, (Apr. 2007), 356(14):1432-1437.
King et al., "BUILD-3: a randomized, controlled trial of bosentan in idiopathic pulmonary fibrosis," *Am J Respir Crit Care Med.*, 184(1):92-99, Epub Apr. 2011.
Kuwajima et al., "Necdin Promotes GABAergic Neuron Differentiation in Cooperation with Dlx Homeodomain Proteins," *Journal of Neuroscience* (May 2006), 26(20), 5383-5392.
Lammi et al., "Mutations in AXIN2 Cause Familial Tooth Agenesis and Predispose to Colorectal Cancer," *Am. J. Hum. Genet.* (2004), 74(5), 1043-1050.
Leyns et al., "Frzb-1 Is a Secreted Antagonist of Wnt Signaling Expressed in the Spemann Organizer," *Cell* (Mar. 1997), 88(6), 747-756.
Li et al., "Artesunate attenuates the growth of human colorectal carcinoma and inhibits hyperactive Wnt/beta-catenin pathway," *Int J Cancer.*, 121(6):1360-1365, Sep. 2007.
Lin et al., "Synthesis and evaluation of pyrazolo[3,4-b]pyridine CDK1 inhibitors as anti-tumor agents," *Bioorganic & Medicinal Chemistry Letters*, (Aug. 2007), 17(15): 4297-4302.
Lories et al., "To Wnt or not to Wnt: the bone and joint health dilemma," *Nat Rev Rheumatol.*, 9(6):328-339, Epub Mar. 2013.
Low et al., "Phenotypic fingerprinting of small molecule cell cycle kinase inhibitors for drug discovery," *Curr Chem Genomics.*, 3:13-21, Mar. 2009.
Lu et al., "Structure—activity relationship studies of small-molecule inhibitors of Wnt response," *Bioorganic & Medicinal Chemistry Letters*, ( Jul. 2009), 19(14):3825-3827.
Luo et al., "Fragile X Mental Retardation Protein Regulates Proliferation and Differentiation of Adult Neural Stem/Progenitor Cells," *PLoS Genetics*, (Apr. 2010), 6(4):e1000898, 15 pages.
Luu et al., "Wnt/beta-catenin signaling pathway as a novel cancer drug target," *Curr Cancer Drug Targets.*, 4(8):653-671, Dec. 2004.
MacDonald et al., "Wnt/beta-catenin signaling: components, mechanisms, and diseases," *Dev. Cell* (Jul. 2009), 17(1), 9-26.
Mandel et al., "SERKAL Syndrome: An Autosomal-Recessive Disorder Caused by a Loss-of-Function Mutation in WNT4," *Am. J. Hum. Genet.*, (Jan. 2008), 82(1), 39-47.
Mani, et al., "LRP6 Mutation in a Family with Early Coronary Disease and Metabolic Risk Factors," *Science*, (Mar. 2007), 315(5816), 1278-1282.
McBride, et al. "Design and structure-activity relationship of 3-benzimidazol-2-yl-1H-indazoles as inhibitors of receptor tyrosine kinases," *Bioorganic & Medicinal Chemistry Letters* (2006), 16(13), 3595-3599.
Misra et al., "1H-Pyrazolo[3,4-b]pyridine inhibitors of cyclin-dependent kinases: highly potent 2,6-Difluorophenacyl analogues," *Bioorganic & Medicinal Chemistry Letters* (2003), 13:2405-2408.
Muddassar et al., "Elucidation of binding mode and three dimensional quantitative structure—activity relationship studies of a novel

(56) References Cited

OTHER PUBLICATIONS series of protein kinase B/Akt inhibitors ," *Journal of Molecular Modeling*, (2009), 15(2): 183-192.
Niemann et al., "Homozygous WNT3 Mutation Causes Tetra-Amelia in a Large Consanguineous Family," *Am. J. Hum. Genet.* (2004), 74(3), 558-563.
Nishisho et al., "Mutations of chromosome 5q21 genes in FAP and colorectal cancer patients," *Science*, (Aug. 1991), 253(5020):665-669.
Nusse, "Wnt signaling in disease and in development," *Cell Res.*, 15(1):28-32, Jan. 2005.
Oates et al., "Increased DNA Methylation at the AXIN1 Gene in a Monozygotic Twin from a Pair Discordant for a Caudal Duplication Anomaly," *Am. J. Hum. Genet.* (2006 ), 79(1), 155-162.
Oduor et al., "Trypanosoma brucei glycogen synthase kinase-3, a target for anti-trypanosomal drug development: a public-private partnership to identify novel leads," *PLoS Negl Trop Dis.*, 5(4):e1017, Apr. 2011.
Okerlund and Cheyette, "Synaptic Wnt signaling—a contributor to major psychiatric disorders?" *J Neurodev Disord.*, (2011) 3(2):162-174.
Polakis, "Wnt signaling and cancer," *Genes Dev.*, 14: 1837-1851, 2000.
Qin et al. "Complexity of the genotype-phenotype correlation in familial exudative vitreoretinopathy with mutations in the LRP5 and/or FZD4 genes," *Hum. Mutat.* (2005), 26(2), 104-112.
Reya and Clevers, "Wnt signalling in stem cells and cancer," *Nature* 434: 843-850, Apr. 2005.
Richards et al., "Peripheral blood proteins predict mortality in idiopathic pulmonary fibrosis," *Am J Respir Crit Care Med.*, 185(1):67-76, Jan. 2012.
Rivera et al., "An X Chromosome Gene, WTX, Is Commonly Inactivated in Wilms Tumor," *Science*, (Feb. 2007), 315(5812):642-645, published online Jan. 4, 2007.
Robitaille et al., "Mutant frizzled-4 disrupts retinal angiogenesis in familial exudative vitreoretinopathy," *Nat. Genet.*, (Sep. 2002), 32(2):326-330.
Ryu et al., "Natural derivatives of curcumin attenuate the Wnt/beta-catenin pathway through down-regulation of the transcriptional coactivator p300," *Biochem Biophys Res Commun.*, 377(4):1304-1308, print Dec. 2008, Epub Nov. 2008.
Salinas, "Wnt signaling in the vertebrate central nervous system: from axon guidance to synaptic function," *Cold Spring Harb Perspect Biol.*, (2012) 4(2). pii: a008003, 15 pages.
Seah et al., "Neuronal Death Resulting from Targeted Disruption of the Snf2 Protein ATRX Is Mediated by p53," *Journal of Neuroscience* (Nov. 2008), 28(47), 12570-12580.
Shih et al., "Pharmacophore modeling and virtual screening to identify potential RET kinase inhibitors," *Bioorg Med Chem Lett.*, 21(15):4490-4497, Epub Jun. 2011.
Shruster et al., "Wnt signaling enhances neurogenesis and improves neurological function after focal ischemic injury," *PLoS One*, (Jul. 2012), 7(7):e40843, 11 pages.
Silva et al, "Advances in Prodrug Design," *Mini-Revs. In Med. Chem.* (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," *Biochemistry*, (2009), 48(29), 7019-7031.
Staines et al., "Cartilage development and degeneration: a Wnt Wnt situation," *Cell Biochem Funct.*, 30(8):633-642, Epub Jun. 2012.
Sutherland et al., "A robust high-content imaging approach for probing the mechanism of action and phenotypic outcomes of cell-cycle modulators," *Molecular Cancer Therapeutics*, (Feb. 2011), 10(2): 242-254.
Swaney et al., "A novel, orally active LPA(1) receptor antagonist inhibits lung fibrosis in the mouse bleomycin model," *Br J Pharmacol.*, 160(7):1699-1713, Aug. 2010.
Takahashi-Yanaga et al., "Celecoxib-induced degradation of T-cell fatcors-1 and -4 in human colon cancer cells," *Biochem Biophys Res Commun.*, 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," *J Biol Chem.*, 280(19):19185-95. Epub Mar. 2005.
Ugur et al., "Homozygous WNT10b mutation and complex inheritance in Split-Hand/Foot Malformation," *Hum. Mol. Genet.* (2008), 17(17), 2644-2653.
Vulpetti et al., "Structure-Based Approaches to Improve Selectivity: CDK2-GSK3β Binding Site Analysis," *Journal of Chemical Information and Modeling* (2005), 45(5), 1282-1290.
Walters and Kleeberger, "Mouse models of bleomycin-induced pulmonary fibrosis," *Current Protocols in Pharmacology*, (2008) Chapter 5: Unit 5.46, 1-17.
Wang, et al., "Mutations in X-linked PORCN, a putative regulator of Wnt signaling, cause focal dermal hypoplasia," *Nat. Genet.* (Jul. 2007), 39(7), 836-838.
Wantanabe and Dai, "Winning WNT: race to Wnt signaling inhibitors," *Proc Natl Acad Sci USA.* 108(15):5929-5930, Epub Mar. 2011.
Weng et al., "Control of Dkk-1 ameliorates chondrocyte apoptosis, cartilage destruction, and subchondral bone deterioration in osteoarthritic knees," *Arthritis Rheum.*, 62(5):1393-1402, May 2010.
Witherington et al., "5-Aryl-pyrazolo[3,4-b]pyridazines: potent inhibitors of glycogen synthase kinase-3 (GSK-3)," *Bioorganic & Medicinal Chemistry Letters*, (May 2003), 13(9):1581-1584.
Woods, S. et al., "Mutations in WNT7A Cause a Range of Limb Malformations, including Fuhrmann Syndrome and Al-Awadi/Raas-Rothschild/Schinzel Phocomelia Syndrome," *Am. J. Hum. Genet.* (Aug. 2006), 79(2), 402-408.
Zhang et al., "Small-molecule synergist of the Wnt/beta-catenin signaling pathway," *Proc Natl Acad Sci U S A.*, 104(18):7444-7448, Epub Apr. 2007 and correction 104(30):12581, Jul. 2007.
Zhong et al., "Characterization of in vitro and in vivo metabolism of AG-024322, a novel cyclin-dependent kinase (CDK) inhibitor," *Health* (2009), 1(4): 249-262.
Chinese Search Report for application No. 201080044979.2, dated Mar. 14, 2013, 4 pages.
Chinese Search Report for application No. 201080061866.3, dated Aug. 28, 2013, 4 pages.
European Search Report in Application No. 10808586.1, dated Jan. 8, 2013, 8 pages.
European Search Report in Application No. 10808589.5, dated Jan. 8, 2013, 4 pages.
European Search Report in Application No. 10842538, mailed Apr. 25, 2013, 5 pages.
International Preliminary Report on Patentability for PCT/US2010/060514 issued Jun. 26, 2012, 9 pages.
International Preliminary Report on Patentability PCT/US2010/044865 mailed Feb. 14, 2012, 6 pages.
International Preliminary Report on Patentability PCT/US2010/044872 mailed Feb. 14, 2012, 11 pages.
International Search Report and Written Opinion for PCT/US2010/060514, mailed Mar. 2, 2011, 11 pages.
International Search Report and Written Opinion for PCT/US2012/055172, mailed Nov. 13, 2012, 10 pages.
International Search Report and Written Opinion for PCT/US2013/031055, mailed May 21, 2013, 14 pages.
International Search Report and Written Opinion PCT/US2010/044865 mailed Sep. 29, 2010, 2 pages.
International Search Report and Written Opinion PCT/US2010/044872 mailed Oct. 5, 2010, 13 pages.
U.S. Appl. No. 13/800,963, filed Mar. 13, 2013, Hood.
U.S. Appl. No. 13/855,874, filed Apr. 3, 2013, Hood.
U.S. Appl. No. 13/887,177, filed May 3, 2013, Hood.
U.S. Appl. No. 13/938,691, filed Jul. 10, 2013, Hood.
U.S. Appl. No. 13/938,692, filed Jul. 10, 2013, Hood.
U.S. Appl. No. 14/019,103, filed Sep. 5, 2013, Hood.
U.S. Appl. No. 14/019,229, filed Sep. 5, 2013, Hood.

* cited by examiner

1H-PYRAZOLO[3,4-*B*]PYRIDINES AND THERAPEUTIC USES THEREOF

RELATED APPLICATIONS

Cross-Reference to Related Applications

This application is a continuation application of U.S. application Ser. No. 13/887,177, filed May 3, 2013, and claims the benefit of U.S. Provisional Application No. 61/642,915, filed May 4, 2012, each of which is incorporated herein by reference in its entirety.

BACKGROUND OF THE INVENTION

1. Field of the Invention

This invention relates to inhibitors of one or more proteins in the Wnt pathway, including inhibitors of one or more Wnt proteins, and compositions comprising the same. More particularly, it concerns the use of a 1H-pyrazolo[3,4-b]pyridine compound or salts or analogs thereof, in the treatment of disorders characterized by the activation of Wnt pathway signaling (e.g., cancer, abnormal cellular proliferation, angiogenesis, Alzheimer's disease, lung disease, osteoarthritis and idiopathic pulmonary fibrosis), the modulation of cellular events mediated by Wnt pathway signaling, as well as genetic diseases and neurological conditions/disorders/diseases. Also provided are methods for treating Wnt-related disease states.

2. Description of the Related Art

Pattern formation is the activity by which embryonic cells form ordered spatial arrangements of differentiated tissues. Speculation on the mechanisms underlying these patterning effects usually centers on the secretion of a signaling molecule that elicits an appropriate response from the tissues being patterned. More recent work aimed at the identification of such signaling molecules implicates secreted proteins encoded by individual members of a small number of gene families.

A longstanding idea in cancer biology is that cancers arise and grow due to the formation of cancer stem cells, which may constitute only a minority of the cells within a tumor but are nevertheless critical for its propagation. Stem cells are appealing as the cell of origin for cancer because of their pre-existing capacity for self-renewal and for unlimited replication. In addition, stem cells are relatively long-lived in comparison to other cells within tissues, providing a greater opportunity to accumulate the multiple additional mutations that may be required to increase the rate of cell proliferation and produce clinically significant cancers. Of particular recent interest in the origin of cancer is the observation that the Wnt signaling pathway, which has been implicated in stem cell self-renewal in normal tissues, upon continuous activation has also been associated with the initiation and growth of many types of cancer. This pathway thus provides a potential link between the normal self-renewal of stem cells and the aberrantly regulated proliferation of cancer stem cells.

The Wnt growth factor family includes more than 10 genes identified in the mouse and at least 19 genes identified in the human Members of the Wnt family of signaling molecules mediate many important short- and long-range patterning processes during invertebrate and vertebrate development. The Wnt signaling pathway is known for its important role in the inductive interactions that regulate growth and differentiation, and plays important roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. More recently, the Wnt pathway has been implicated in the maintenance of stem or progenitor cells in a growing list of adult tissues that now includes skin, blood, gut, prostate, muscle and the nervous system.

Pathological activation of the Wnt pathway is also believed to be the initial event leading to colorectal cancer in over 85% of all sporadic cases in the Western world. Activation of the Wnt pathway has also been extensively reported for hepatocellular carcinoma, breast cancer, ovarian cancer, pancreatic cancer, melanomas, mesotheliomas, lymphomas and leukemias. In addition to cancer, inhibitors of the Wnt pathway can be used for stem cell research or for the treatment of any diseases characterized by aberrant Wnt activation such as idiopathic pulmonary fibrosis (IPF), diabetic retinopathy, neovascular glaucoma, rheumatoid arthritis, psoriasis as well as mycotic and viral infections and bone and cartilage diseases. As such, it is a therapeutic target that is of great interest to the field.

Idiopathic pulmonary fibrosis (IPF) is a ravaging condition of progressive lung scarring and destruction. This is a chronic, progressive, usually fatal, lung disease characterized by excessive fibrosis which causes eventual deterioration of the lung's architecture [*Nature Reviews Drug Discovery* (2010), 9(2), 129-140]. Recently, the Wnt/β-catenin pathway has become implicated in the etiology of the disease [*Annals of the Rheumatic Diseases* (2012), 71(5), 761-767*; Respiratory Research* (2012), 13(3), pp. 9]. At the cellular level, it is has been shown that β-catenin is overexpressed in bronchial epithelial cells which contributes to an epithelial to mesenchymal cell transition (EMT). This results in increased presence of proliferating fibroblasts and myofibroblasts which leads to excess collagen deposition in the lungs [*Respiratory Research* (2012), 13(3), pp. 9]. The formation of these fibroblastic foci and increased extracellular matrix deposition are pathological hallmarks of IPF.

There are also many cases of genetic diseases due to mutations in Wnt signaling components. Examples of some of the many diseases are Alzheimer's disease [*Proc. Natl. Acad. Sci. USA* (2007), 104(22), 9434-9], osteoarthritis, polyposis coli [*Science* (1991), 253(5020), 665-669], bone density and vascular defects in the eye (osteoporosis-pseudoglioma syndrome, OPPG) [*N. Engl. J. Med.* (2002), 346(20), 1513-21], familial exudative vitreoretinopathy [*Hum. Mutat.* (2005), 26(2), 104-12], retinal angiogenesis [*Nat. Genet.* (2002), 32(2), 326-30], early coronary disease [*Science* (2007), 315 (5816), 1278-82], tetra-amelia syndrome [*Am. J. Hum. Genet.* (2004), 74(3), 558-63], Müllerian-duct regression and virilization [*Engl. J. Med.* (2004), 351(8), 792-8], SERKAL syndrome [*Am. J. Hum. Genet.* (2008), 82(1), 39-47], diabetes mellitus type 2 *[Am. J. Hum. Genet.* (2004), 75(5), 832-43*; N. Engl. J. Med.* (2006), 355(3), 241-50], Fuhrmann syndrome [*Am. J. Hum. Genet.* (2006), 79(2), 402-8], Al-Awadi/Raas-Rothschild/Schinzel phocomelia syndrome [*Am. J. Hum. Genet.* (2006), 79(2), 402-8], odonto-onycho-dermal dysplasia [*Am. J. Hum. Genet.* (2007), 81(4), 821-8], obesity [*Diabetologia* (2006), 49(4), 678-84], split-hand/foot malformation [*Hum. Mol. Genet.* (2008), 17(17), 2644-53], caudal duplication syndrome [*Am. J. Hum. Genet.* (2006), 79(1), 155-62], tooth agenesis [*Am. J. Hum. Genet.* (2004), 74(5), 1043-50], Wilms tumor [*Science* (2007), 315(5812), 642-5], skeletal dysplasia [*Nat. Genet.* (2009), 41(1), 95-100], focal dermal hypoplasia [*Nat. Genet.* (2007), 39(7), 836-8], autosomal recessive anonychia [*Nat. Genet.* (2006), 38(11), 1245-7], neural tube defects [*N. Engl. J. Med.* (2007), 356(14), 1432-7], alpha-thalassemia (ATRX) syndrome [*The Journal of Neuroscience* (2008), 28(47), 12570-12580], fragile X syndrome [*PLoS Genetics* (2010), 6(4), e1000898], ICF syndrome, Angelman syndrome [*Brain Research Bulletin* (2002), 57(1), 109-119], Prader-Willi syndrome [*Journal of Neuroscience* (2006), 26(20), 5383-5392], Beckwith-Wiedemann Syndrome [*Pediatric and Developmental Pathology* (2003), 6(4), 299-306] and Rett syndrome.

Regulation of cell signaling by the Wnt signaling pathway is critical for the formation of neuronal circuits. Wnt pathway modulates in neural tissue, among other things, axon pathfinding, dendritic development, and synaptic assembly. Through different receptors, Wnt pathway activates and/or regulates diverse signaling pathways and other processes that lead to local changes on the cytoskeleton or global cellular changes involving nuclear function. Recently, a link between neuronal activity, essential for the formation and refinement of neuronal connections, and Wnt signaling has been uncovered. Indeed, neuronal activity regulates the release of various Wnt proteins and the localization of their receptors. Wnt pathway mediates synaptic structural changes induced by neuronal activity or experience. Evidence suggests that dysfunction in Wnt signaling contributes to neurological disorders [*Brain Research Reviews* (2000), 33(1), 1-12; Oncogene (2006) 25(57), 7545-7553; *Molecular Neurodegeneration* (2008), 3, 9; *Neurobiology of Disease* (2010), 38(2), 148-153; *Journal of Neurodevelopmental Disorders* (2011), 3(2), 162-174 and *Cold Spring Harbor Perspectives in Biology* February (2012), 4(2)].

SUMMARY OF THE INVENTION

The present invention makes available methods and reagents, involving contacting a cell with an agent, such as a 1H-pyrazolo[3,4-b]pyridine compound, in a sufficient amount to antagonize Wnt activity, e.g., to reverse or control an aberrant growth state or correct a genetic disorder due to mutations in Wnt signaling components.

Some embodiments disclosed herein include Wnt inhibitors containing a 1H-pyrazolo[3,4-b]pyridine core. Other embodiments disclosed herein include pharmaceutical compositions and methods of treatment using these compounds.

One embodiment disclosed herein includes a compound having the structure of Formula I or a pharmaceutically acceptable salt thereof:

I

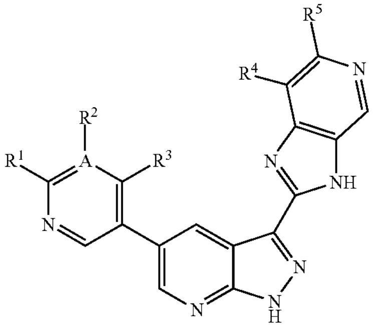

In some embodiments of Formula (I):

$R^1$ and $R^2$ are independently selected from the group consisting of H, lower alkyl, halide, —$(C_{1-9}$ alkyl$)_n$aryl$(R^6)_q$, —$(C_{1-9}$ alkyl$)_n$heteroaryl$(R^7)_q$, —$(C_{1-9}$ alkyl$)_n$heterocyclyl $(R^8)_q$, —$(C_{1-9}$ alkyl$)_n$N$(R^9)_2$, —$OR^{10}$ and —NHC(═O)$R^{11}$;

$R^3$ is selected from the group consisting of H, halide and lower alkyl;

with the proviso that at least two of $R^1$, $R^2$ and $R^3$ are H;

$R^4$ and $R^5$ are independently selected from the group consisting of H, —C(═O)N$(R^{12})_2$, -aryl$(R^{13})_q$, -heterocyclyl $(R^{14})_q$, and -heteroaryl$(R^{15})_q$;

with the proviso that at least one of $R^4$ and $R^5$ is H;

each $R^6$ is a substituent attached to the aryl ring and independently selected from the group consisting of H, —$C_{1-9}$ alkyl, halide, $CF_3$ and CN;

each $R^7$ is a substituent attached to the heteroaryl ring and independently selected from the group consisting of H, —$C_{1-9}$ alkyl, halide, $CF_3$ and CN;

each $R^8$ is a substituent attached to the heterocyclyl ring and independently selected from the group consisting of H, halide, —$(C_{1-3}$ alkyl$)_n$aryl$(R^6)_q$, and —$C_{1-4}$ alkyl;

each $R^9$ is independently selected from the group consisting of H, —$C_{1-9}$ alkyl, —$(C_{1-3}$ alkyl$)_n$aryl$(R^6)_q$, —$(C_{1-3}$ alkyl$)_n$carbocyclyl and —$(C_{1-9}$ alkyl$)$N$(R^{16})_2$;

alternatively, two adjacent $R^9$ or two adjacent $R^{12}$, may be taken together with the atoms to which they are attached to form a heterocyclyl$(R^{17})_q$;

$R^{10}$ is selected from the group consisting of H, —$CF_3$, —$(C_{1-3}$ alkyl$)_n$aryl$(R^6)_q$, and —$C_{1-9}$ alkyl;

$R^{11}$ is selected from the group consisting of —$(C_{1-3}$ alkyl$)_n$ aryl$(R^6)_q$, —$(C_{1-3}$ alkyl$)_n$carbocyclyl, —$C_{1-9}$ alkyl and —$CF_3$;

each $R^{12}$ is independently selected from the group consisting of H, —$(C_{1-9}$ alkyl$)_n$aryl$(R^6)_q$ and —$C_{1-9}$ alkyl;

each $R^{13}$ is a substituent attached to the aryl ring and independently selected from the group consisting of H, halide, —$CF_3$, CN, —$(C_{1-3}$ alkyl$)_n$heterocyclyl$(R^8)_q$, —$(C_{1-9}$ alkyl$)_n$N$(R^9)_2$ and —$(C_{1-9}$ alkyl$)_n$NHSO$_2R^{18}$;

each $R^{14}$ is a substituent attached to the heterocyclyl ring and independently selected from the group consisting of H, lower alkyl, halide, —$CF_3$ and CN;

each $R^{15}$ is a substituent attached to the heteroaryl ring and independently selected from the group consisting of H, lower alkyl, halide, —$CF_3$, CN, —C(═O)$(C_{1-3}$ alkyl), —$(C_{1-9}$ alkyl$)_n$N$(R^9)_2$ and —$(C_{1-9}$ alkyl$)_n$NHSO$_2R^{18}$;

each $R^{16}$ is independently selected from the group consisting of H and lower alkyl;

each $R^{17}$ is a substituent attached to the heterocyclyl ring and independently selected from the group consisting of H, —$(C_{1-9}$ alkyl$)_n$aryl$(R^6)_q$, and —$C_{1-9}$ alkyl;

each $R^{18}$ is a lower alkyl;

A is N or C;

with the proviso that if A is N then $R^2$ is nil;

each q is an integer of 1 to 5;

each n is an integer of 0 or 1; and with the proviso that Formula I is not a structure selected from the group consisting of:

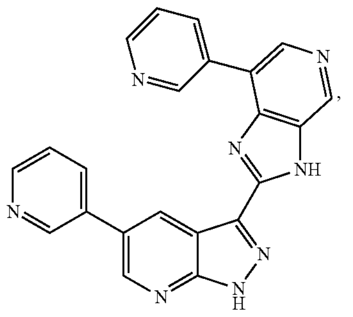
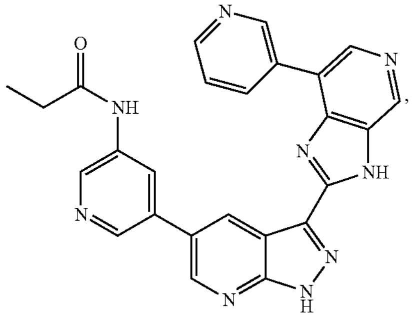
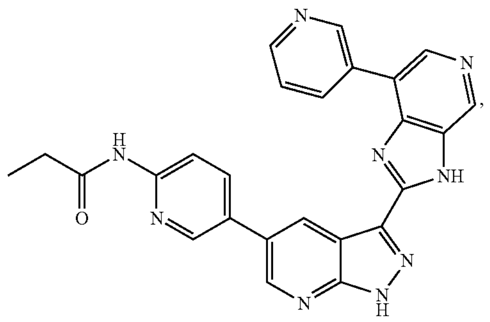
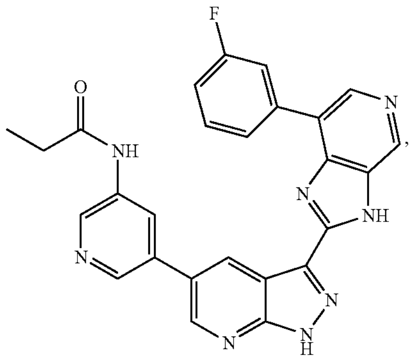
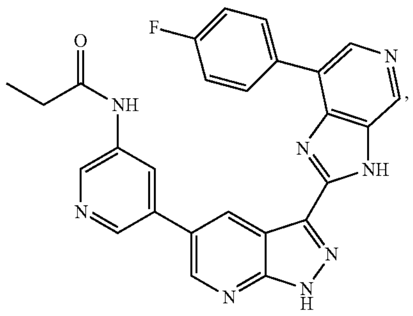
-continued
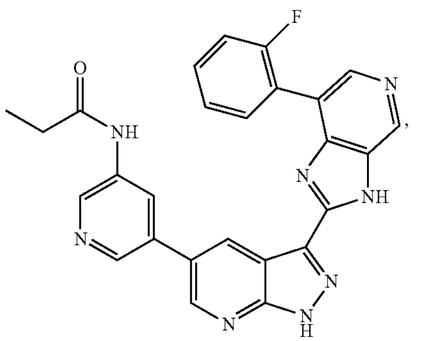
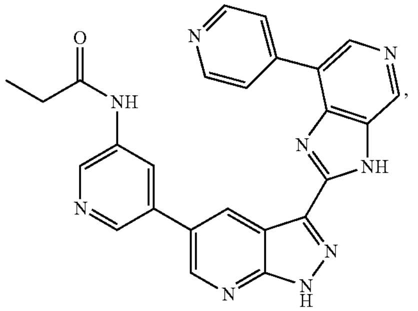
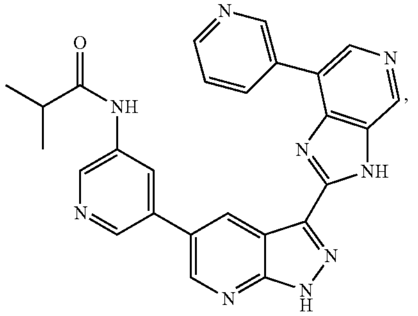
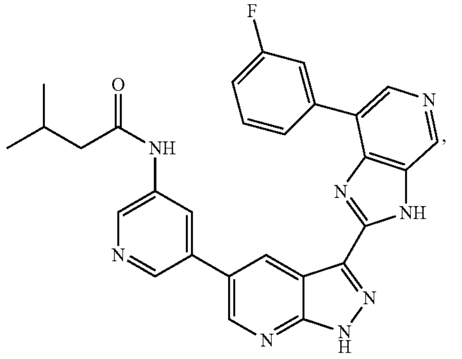
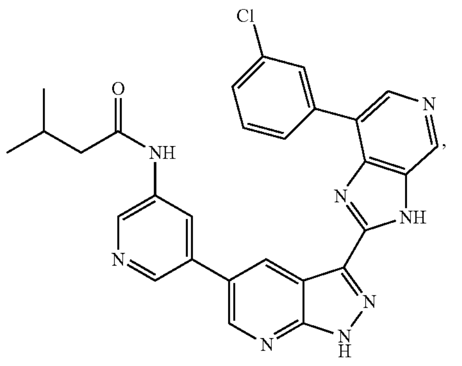

-continued
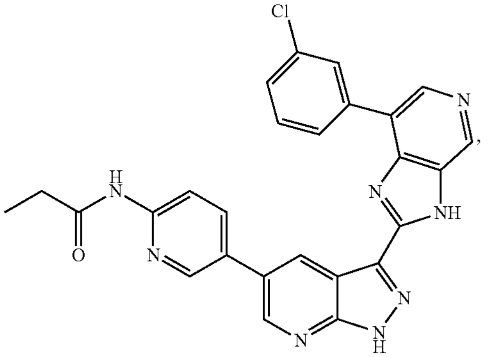
,
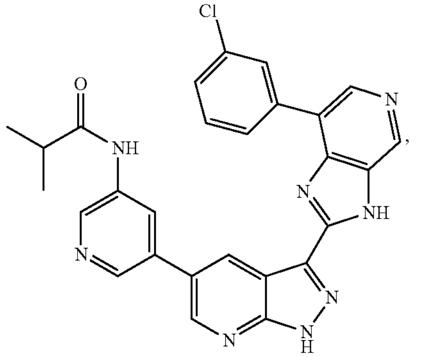
,
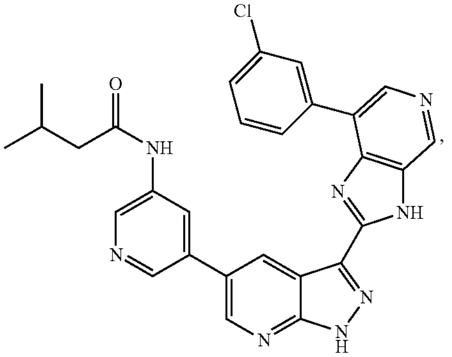
,
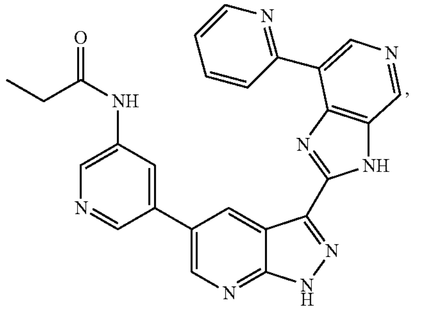
,
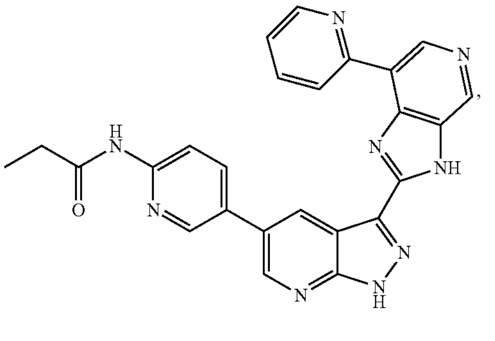
,
-continued
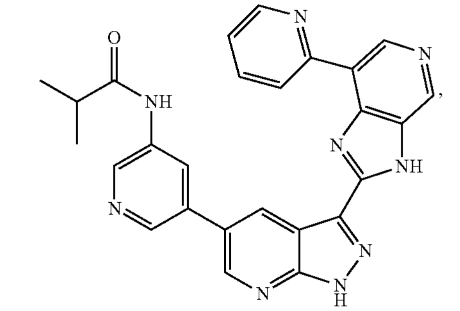
,
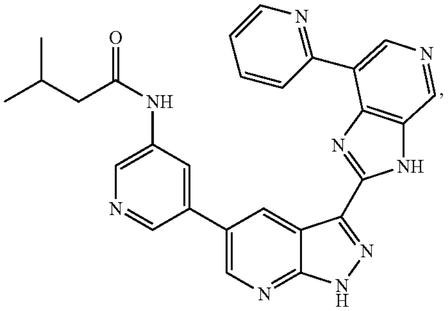
,
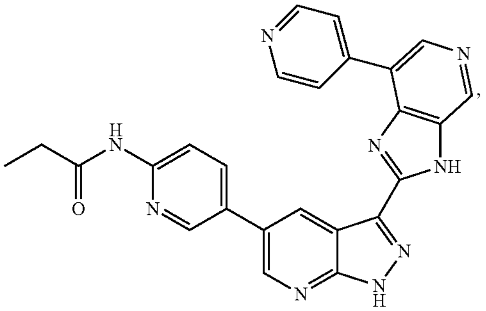
,
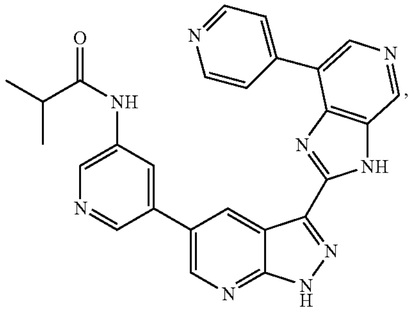
,
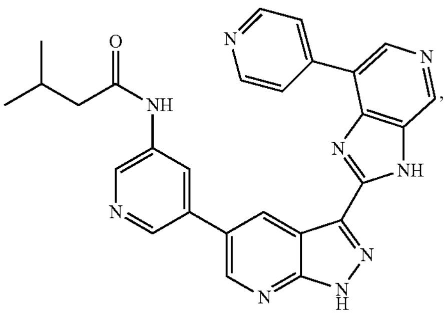
, -continued
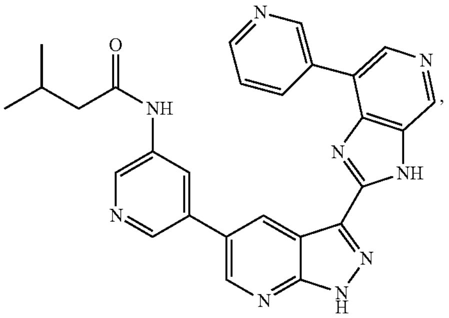
,
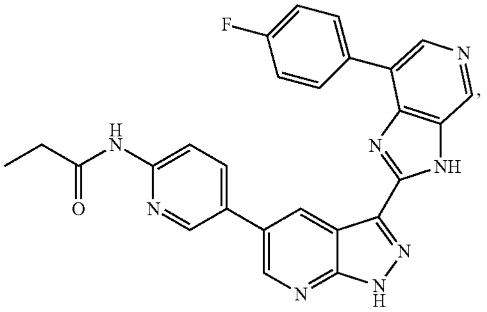
,
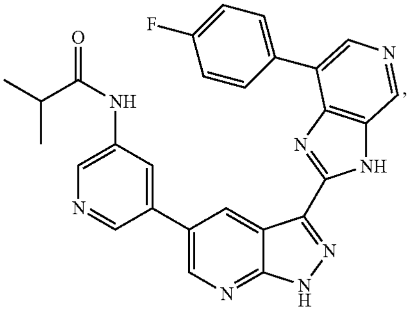
,
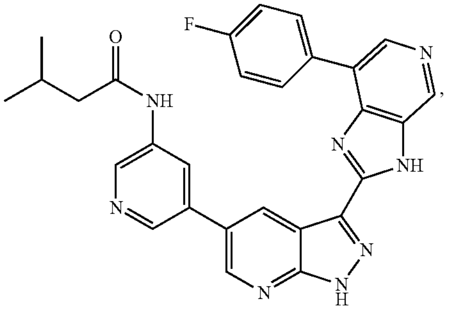
,
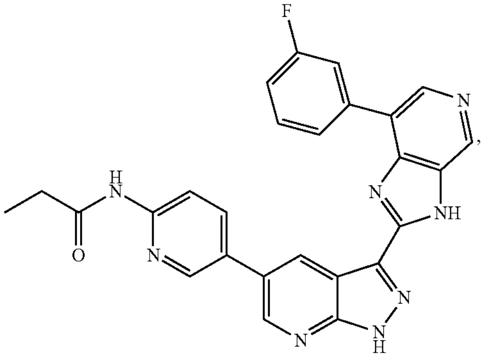
,
-continued
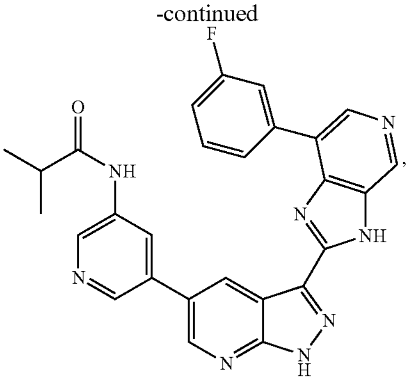
,
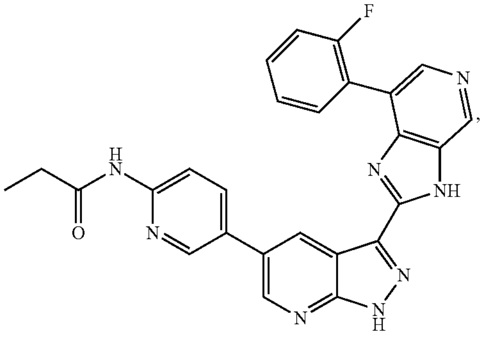
,
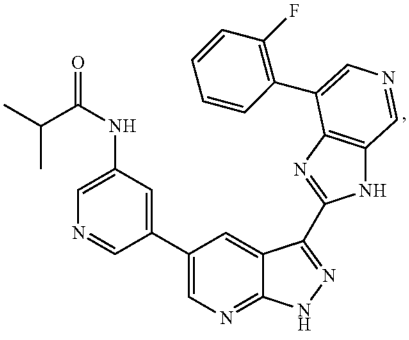
,
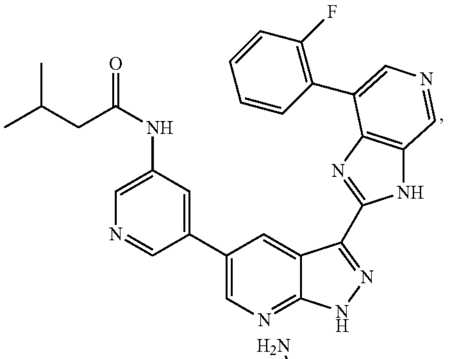
,
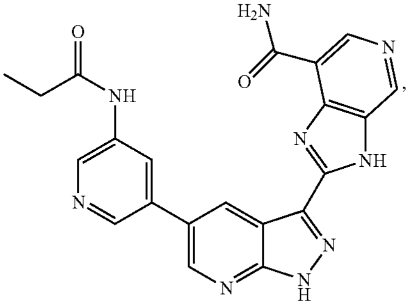
, -continued
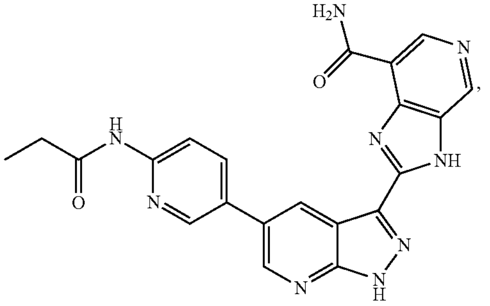
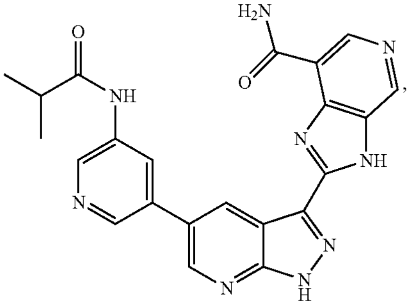
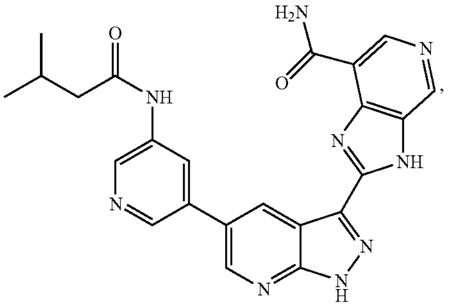
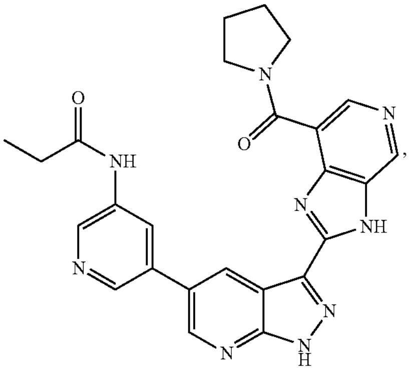
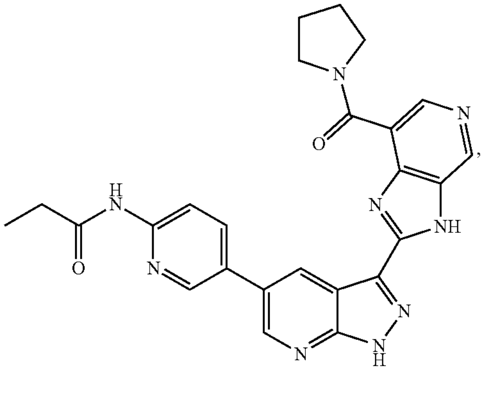
-continued
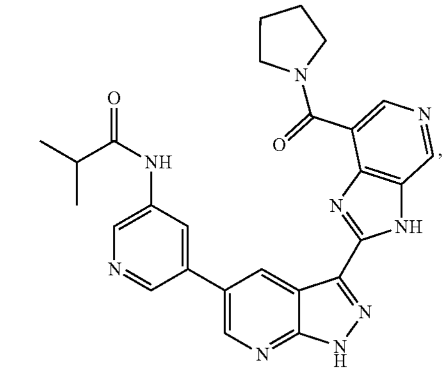
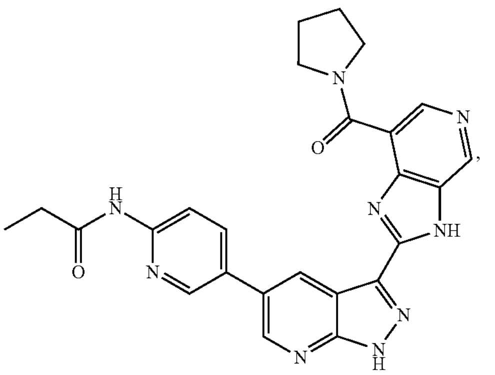
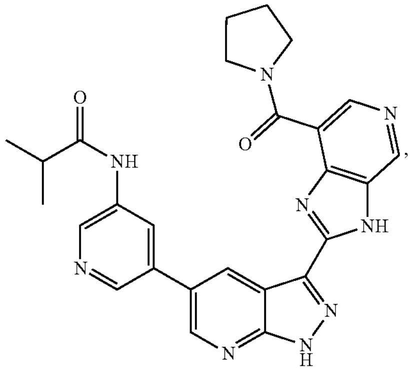
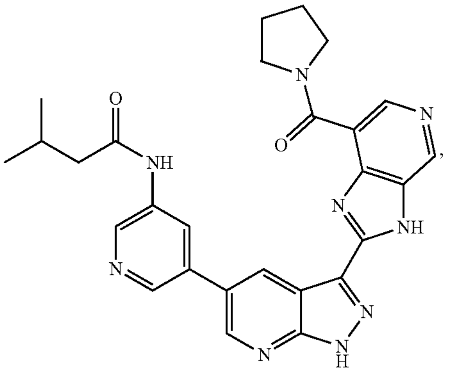

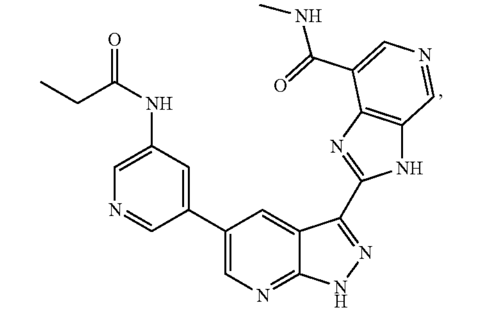
,
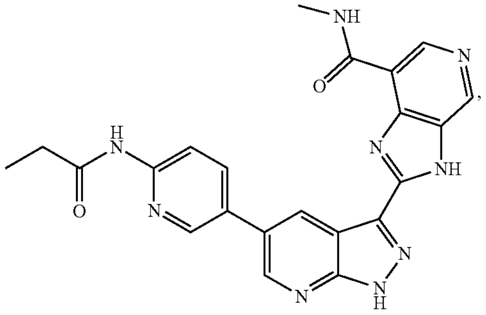
,
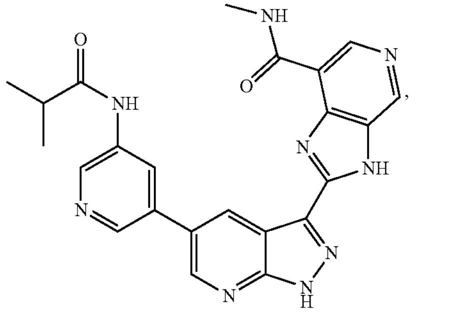
,
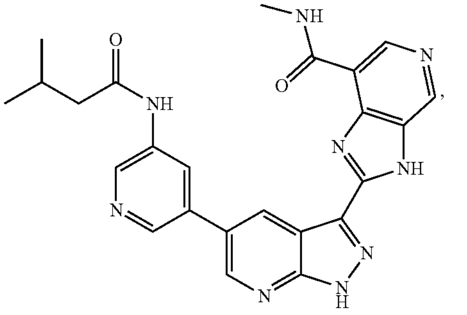
,
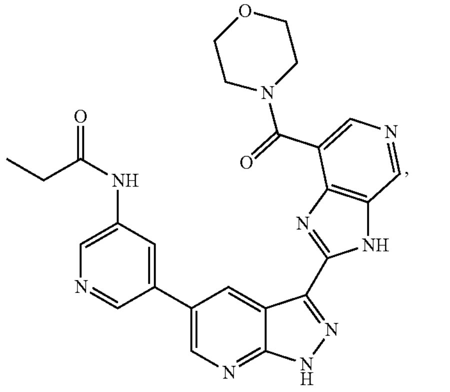
,
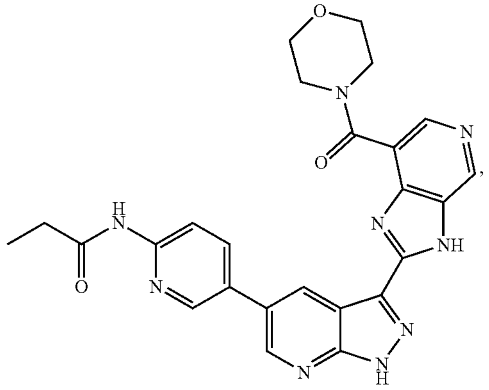
,
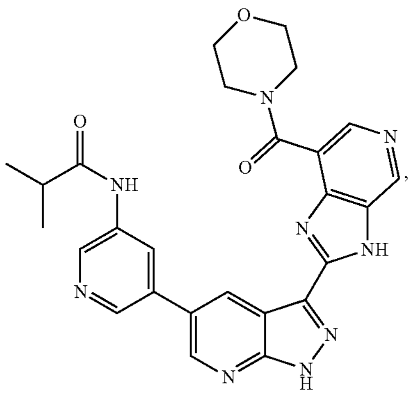
,
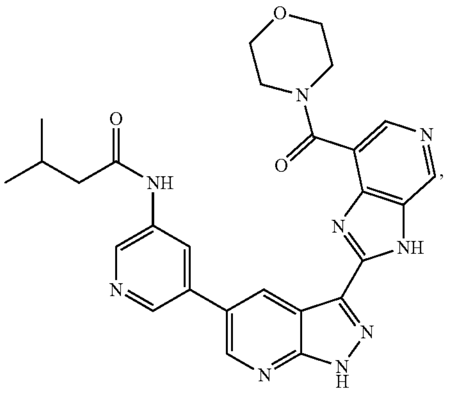
,
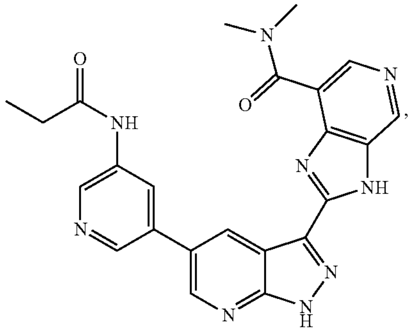
, -continued
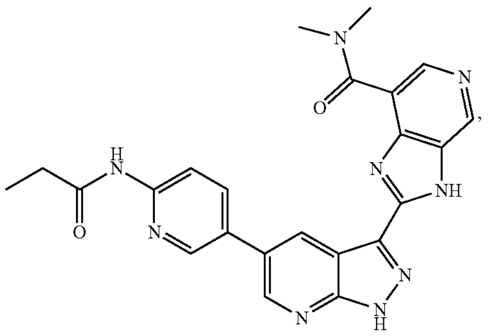
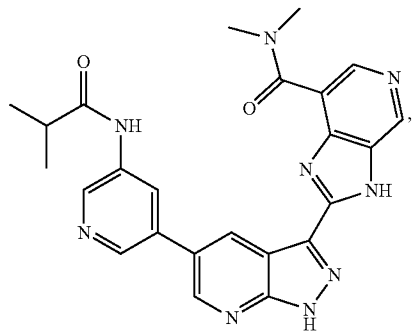
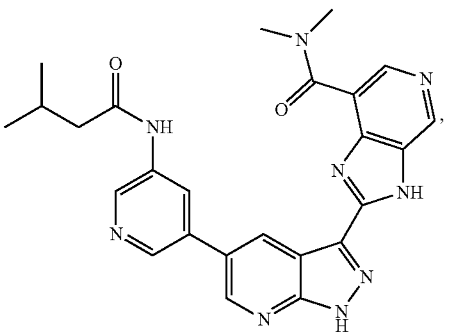
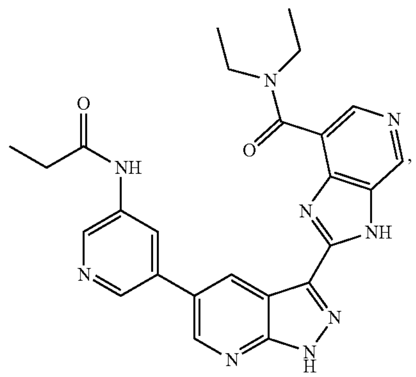
-continued
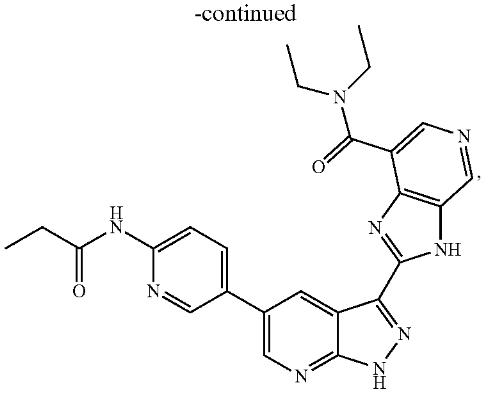
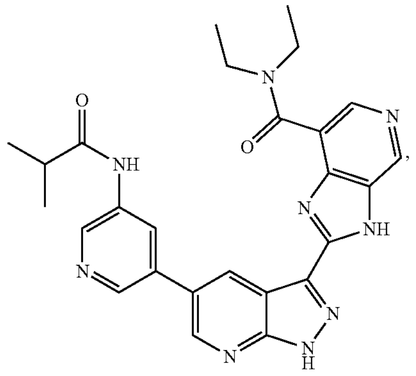
and
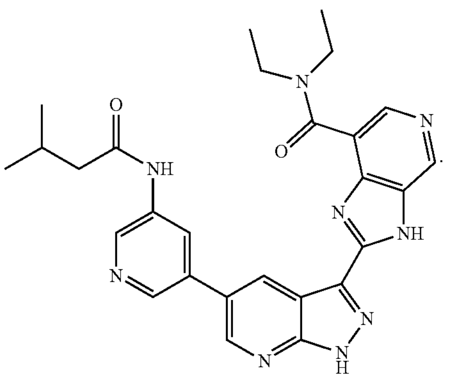
Another embodiment disclosed herein includes a compound having the structure of Formula II or a pharmaceutically acceptable salt thereof:
II
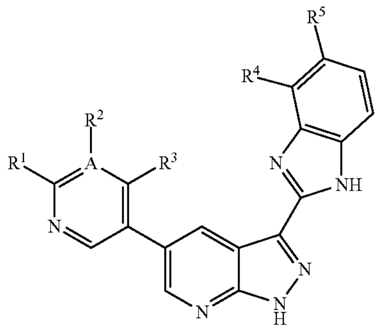

In some embodiments of Formula (II):

$R^1$ and $R^2$ are independently selected from the group consisting of H, lower alkyl, halide, —($C_{1-9}$ alkyl)$_n$aryl($R^6$)$_q$, —($C_{1-9}$ alkyl)$_n$heteroaryl($R^7$)$_q$, —($C_{1-9}$ alkyl)$_n$heterocyclyl ($R^8$)$_q$, —($C_{1-9}$ alkyl)$_n$N($R^9$)$_2$, —O$R^{10}$ and —NHC(═O)$R^{11}$;

$R^3$ is selected from the group consisting of H, halide and lower alkyl;

with the proviso that at least two of $R^1$, $R^2$ and $R^3$ are H;

$R^4$ and $R^5$ are independently selected from the group consisting of H, —C(═O)N($R^{12}$)$_2$, -aryl($R^{13}$)$_q$, -heterocyclyl ($R^{14}$)$_q$, and -heteroaryl($R^{15}$)$_q$;

with the proviso that at least one of $R^4$ and $R^5$ is H;

each $R^6$ is a substituent attached to the aryl ring and independently selected from the group consisting of H, —$C_{1-9}$ alkyl, halide, $CF_3$ and CN;

each $R^7$ is a substituent attached to the heteroaryl ring and independently selected from the group consisting of H, —$C_{1-9}$ alkyl, halide, $CF_3$ and CN;

each $R^8$ is a substituent attached to the heterocyclyl ring and independently selected from the group consisting of H, halide, —($C_{1-3}$ alkyl)$_n$aryl($R^6$)$_q$, and —$C_{1-4}$ alkyl;

each $R^9$ is independently selected from the group consisting of H, —$C_{1-9}$ alkyl, —($C_{1-3}$ alkyl)$_n$aryl($R^6$)$_q$, —($C_{1-3}$ alkyl)$_n$carbocyclyl and —($C_{1-9}$ alkyl)N($R^{16}$)$_2$;

alternatively, two adjacent $R^9$ or two adjacent $R^{12}$, may be taken together with the atoms to which they are attached to form a heterocyclyl($R^{17}$)$_q$;

$R^{10}$ is selected from the group consisting of H, —$CF_3$, —($C_{1-3}$ alkyl)$_n$aryl($R^6$)$_q$, and —$C_{1-9}$ alkyl;

is selected from the group consisting of —($C_{1-3}$ alkyl)$_n$aryl ($R^6$)$_q$, —($C_{1-3}$ alkyl)$_n$carbocyclyl, —$C_{1-9}$ alkyl and —$CF_3$;

each $R^{12}$ is independently selected from the group consisting of H, —($C_{1-9}$ alkyl)$_n$aryl($R^6$)$_q$ and —$C_{1-9}$ alkyl;

each $R^{13}$ is a substituent attached to the aryl ring and independently selected from the group consisting of H, halide, —$CF_3$, CN, —($C_{1-3}$ alkyl)$_n$heterocyclyl($R^8$)$_q$, —($C_{1-9}$ alkyl)$_n$N($R^9$)$_2$ and —($C_{1-9}$ alkyl)$_n$NHSO$_2R^{18}$;

each $R^{14}$ is a substituent attached to the heterocyclyl ring and independently selected from the group consisting of H, lower alkyl, halide, —$CF_3$ and CN;

each $R^{15}$ is a substituent attached to the heteroaryl ring and independently selected from the group consisting of H, lower alkyl, halide, —$CF_3$, CN, —C(═O)($C_{1-3}$ alkyl), —($C_{1-9}$ alkyl)$_n$N($R^9$)$_2$ and —($C_{1-9}$ alkyl)$_n$NHSO$_2R^{18}$;

each $R^{16}$ is independently selected from the group consisting of H and lower alkyl;

each $R^{17}$ is a substituent attached to the heterocyclyl ring and independently selected from the group consisting of H, —($C_{1-9}$ alkyl)$_n$aryl($R^6$)$_q$, and —$C_{1-9}$ alkyl;

each $R^{18}$ is a lower alkyl;

A is N or C;

with the proviso that if A is N then $R^2$ is nil;

each q is an integer of 1 to 5;

each n is an integer of 0 or 1; and with the proviso that Formula II is not a structure selected from the group consisting of:

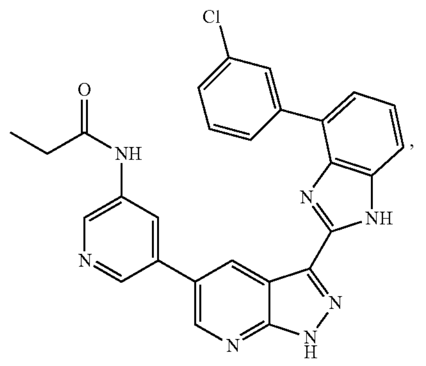

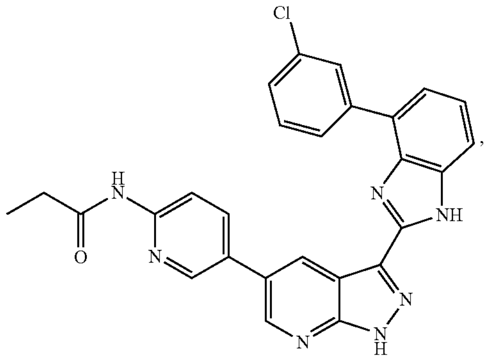

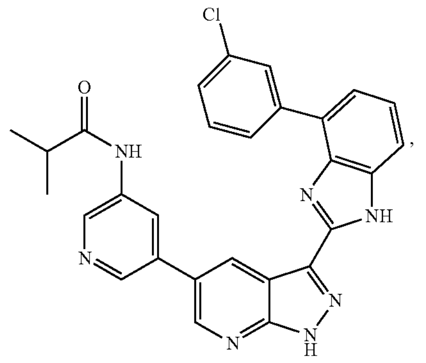

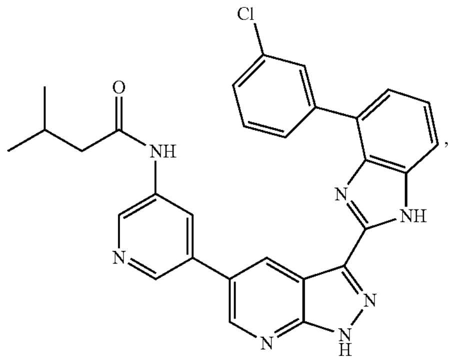

-continued
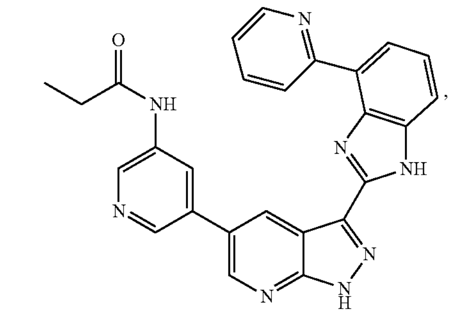
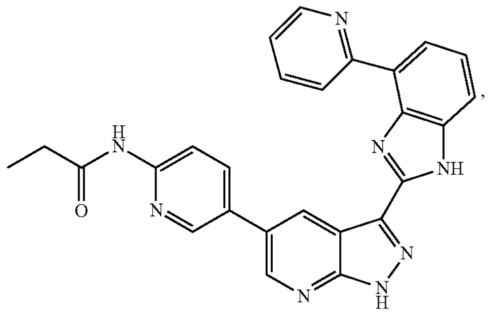
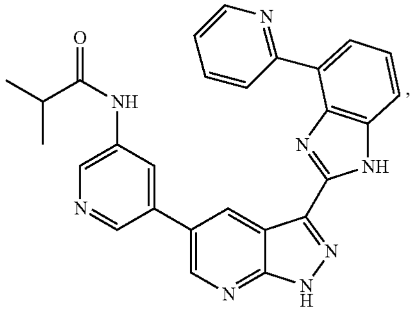
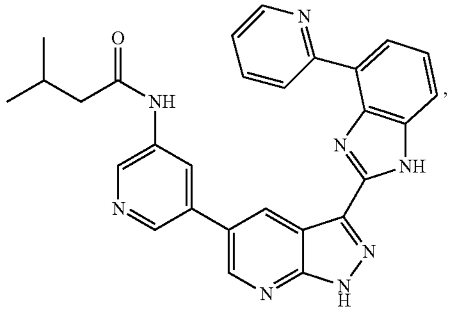
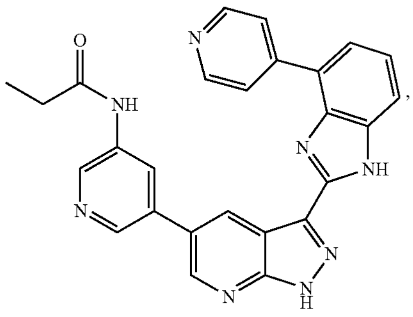
-continued
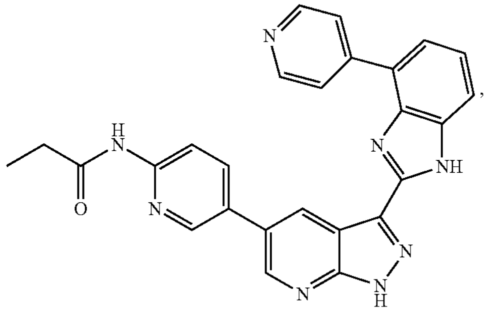
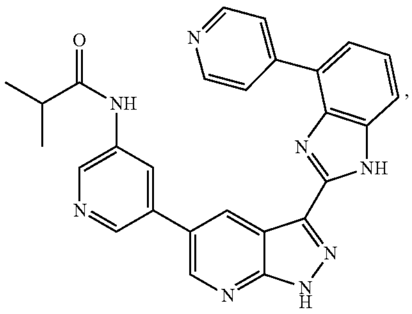
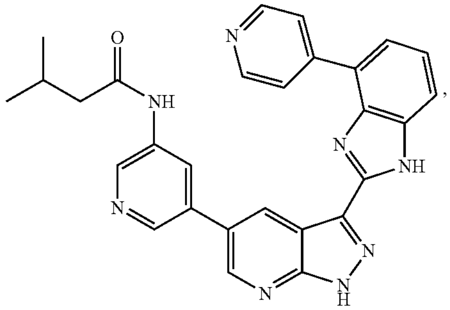
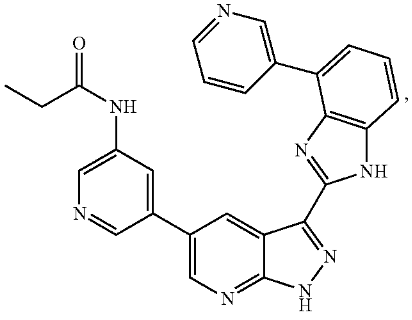
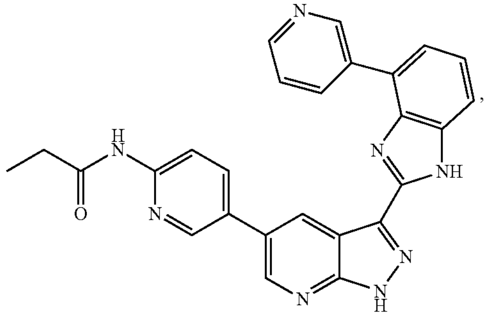

-continued
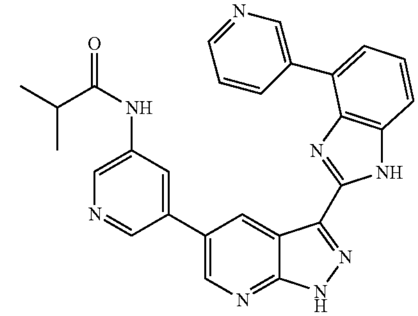
,
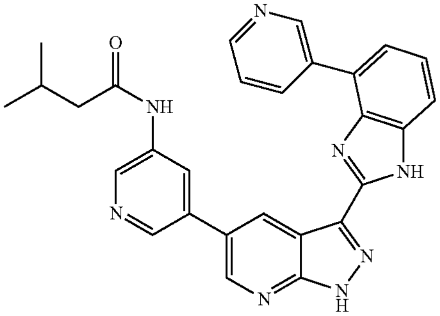
,
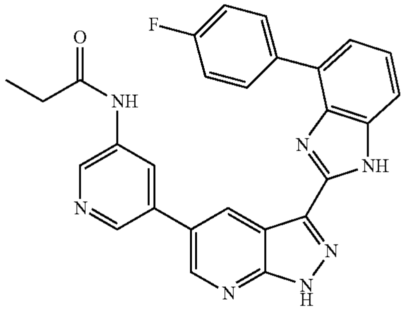
,
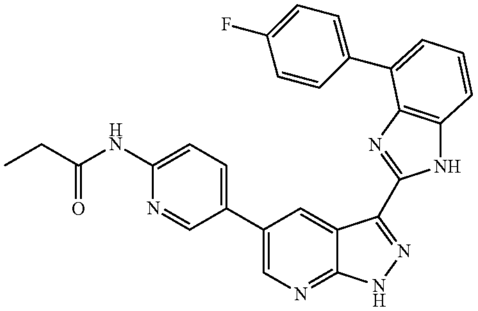
,
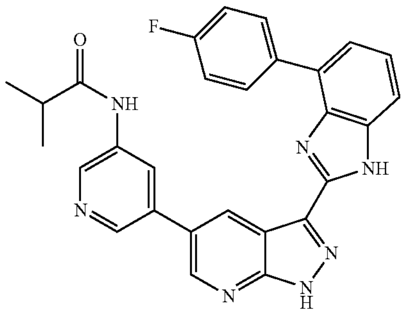
,
-continued
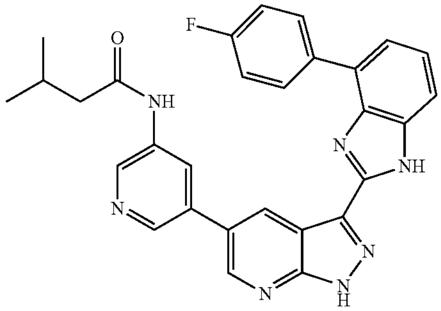
,
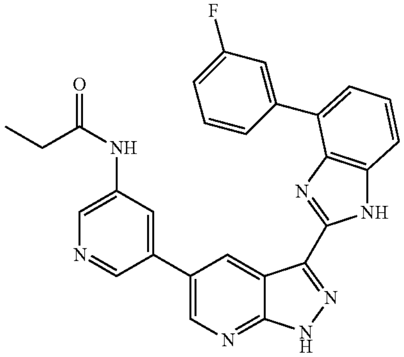
,
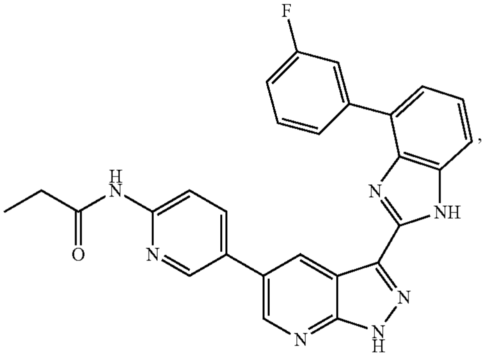
,
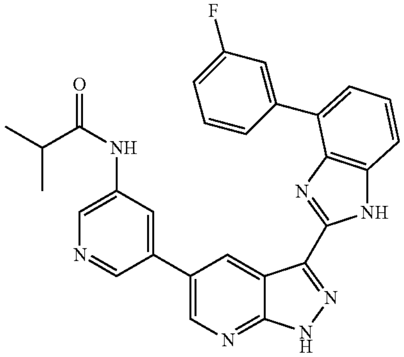
, -continued
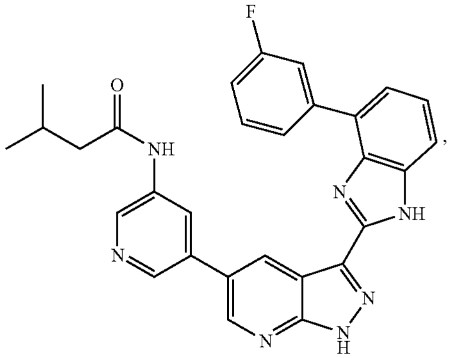
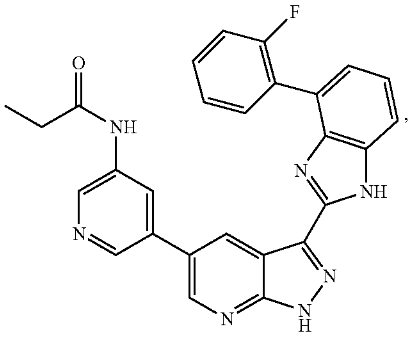
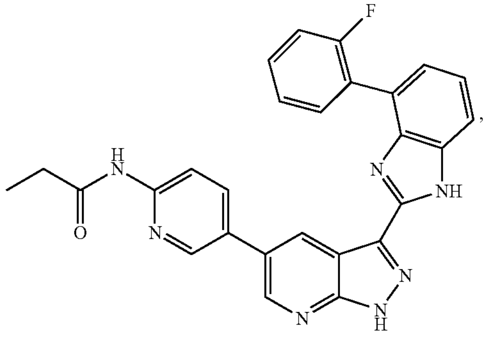
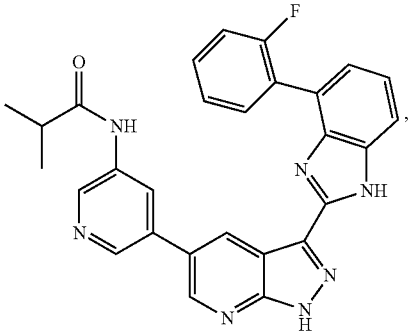
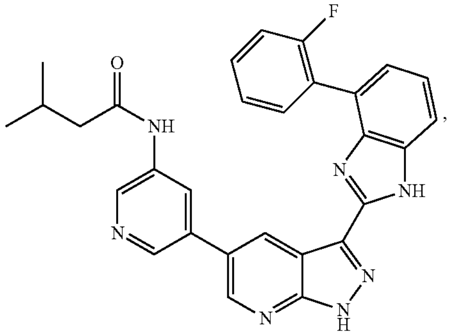
-continued
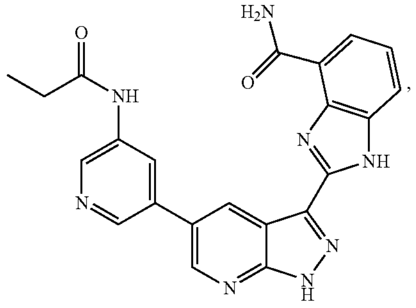
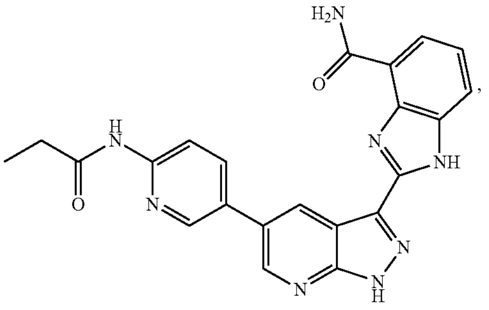
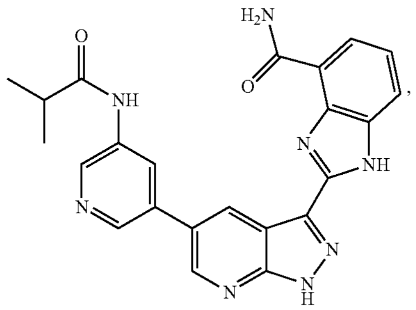
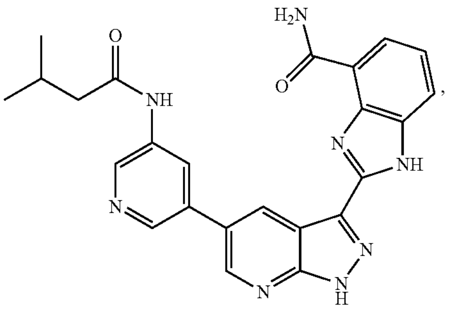
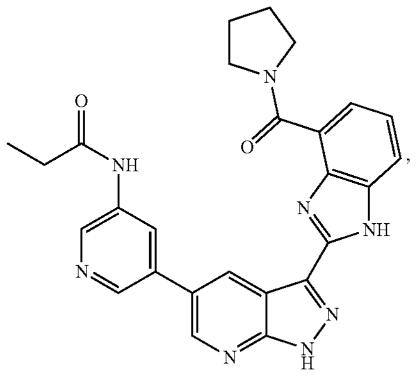

-continued
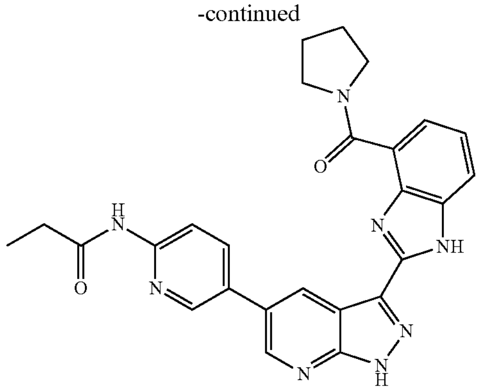
,
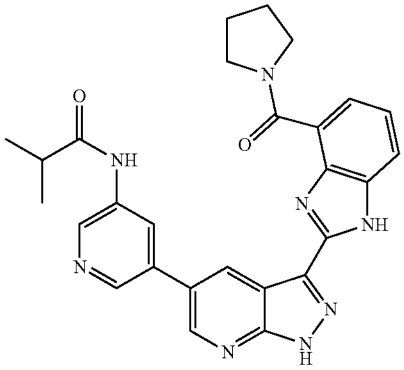
,
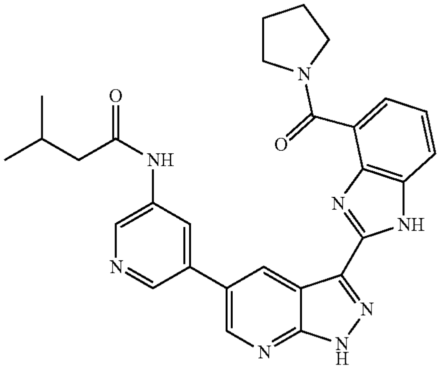
,
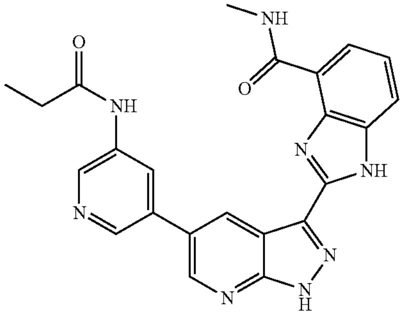
,
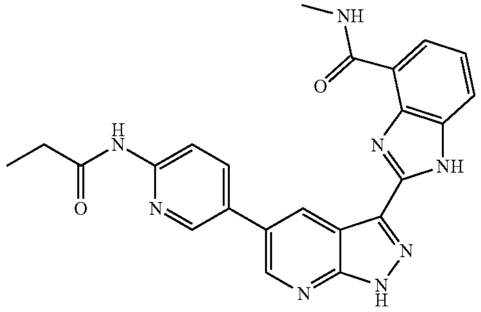
,
-continued
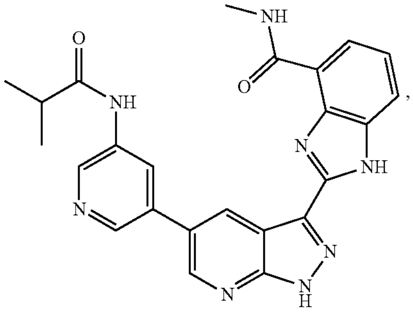
,
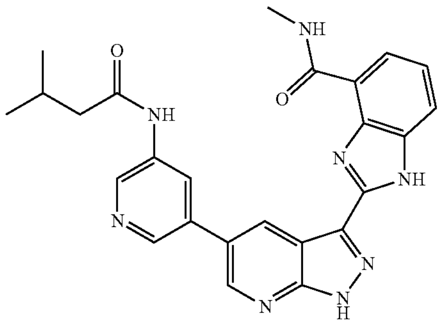
,
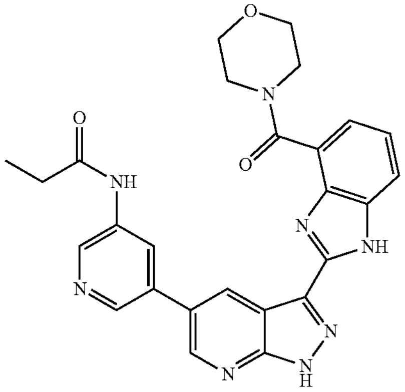
,
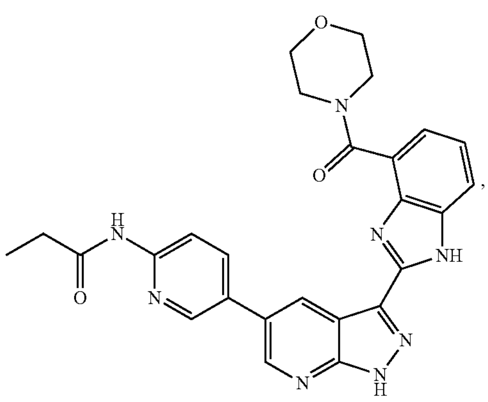
, -continued
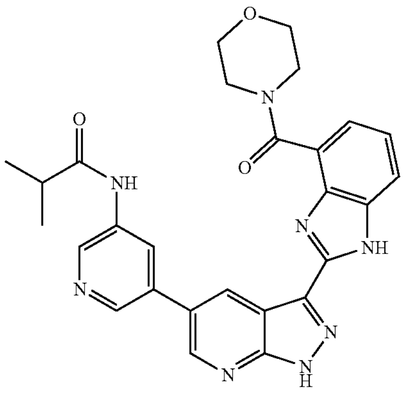
,
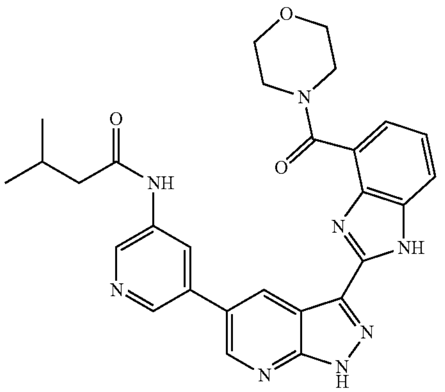
,
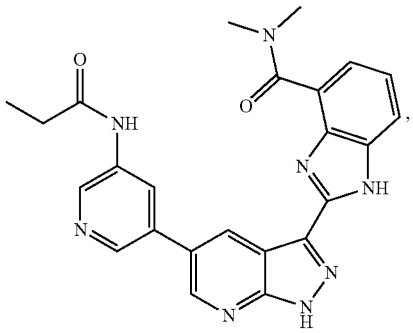
,
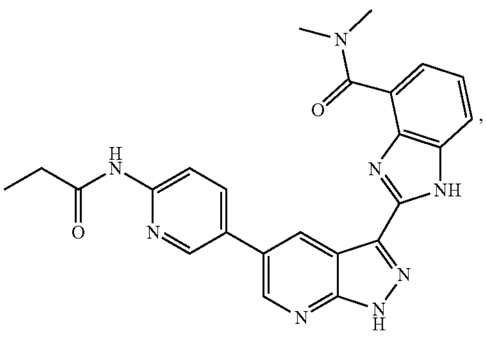
,
-continued
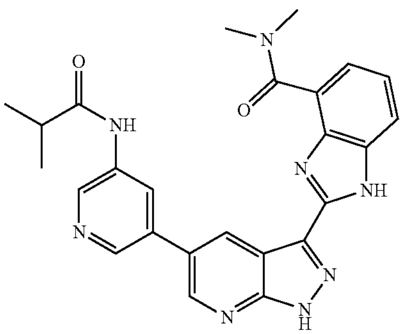
,
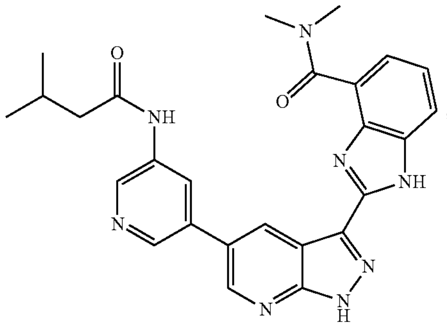
,
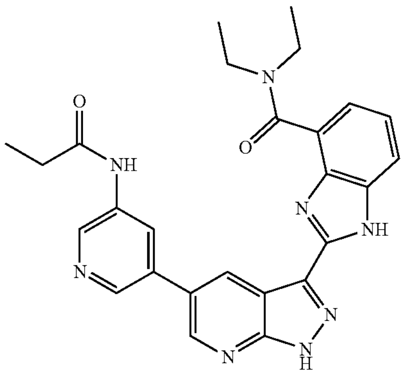
,
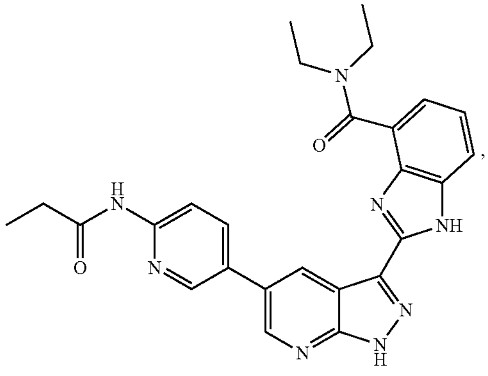
, -continued

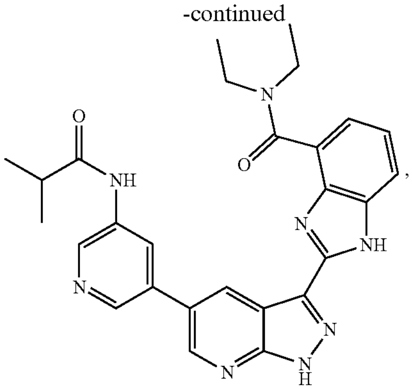

, and

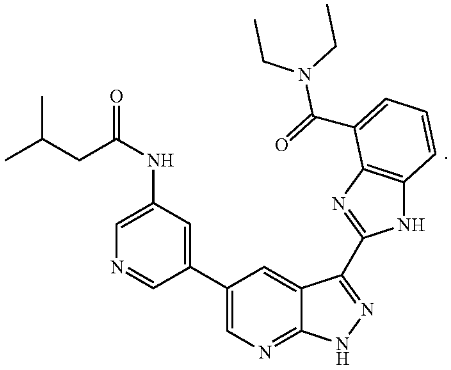

.

Some embodiments include stereoisomers and pharmaceutically acceptable salts of a compound of general Formulas (I) or (II).

Some embodiments include pro-drugs of a compound of general Formulas (I) or (II).

Some embodiments of the present invention include pharmaceutical compositions comprising a compound of general Formulas (I) or (II) and a pharmaceutically acceptable carrier, diluent, or excipient.

Other embodiments disclosed herein include methods of inhibiting one or more members of the Wnt pathway, including one or more Wnt proteins by administering to a subject affected by a disorder or disease in which aberrant Wnt signaling is implicated, such as cancer and other diseases associated with abnormal angiogenesis, cellular proliferation, cell cycling and mutations in Wnt signaling components, a compound according to Formulas (I) or (II). Accordingly, the compounds and compositions provided herein can be used to treat cancer, to reduce or inhibit angiogenesis, to reduce or inhibit cellular proliferation and correct a genetic disorder due to mutations in Wnt signaling components. Non-limiting examples of diseases which can be treated with the compounds and compositions provided herein include a variety of cancers, diabetic retinopathy, pulmonary fibrosis, idiopathic pulmonary fibrosis, rheumatoid arthritis, scleroderma, mycotic and viral infections, osteochondrodysplasia, Alzheimer's disease, lung disease, osteoarthritis, polyposis coli, osteoporosis-pseudoglioma syndrome, familial exudative vitreoretinopathy, retinal angiogenesis, early coronary disease, tetra-ameliasyndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

Another embodiment disclosed herein includes a pharmaceutical composition that has a compound according to any of the above formulas and a pharmaceutically acceptable carrier, diluent, or excipient.

Some embodiments of the present invention include methods to prepare a compound of general Formulas (I) or (II).

It is to be understood that both the foregoing general description and the following detailed description are exemplary and explanatory only and are not restrictive of the invention, as claimed.

DETAILED DESCRIPTION OF THE INVENTION

Compositions and methods for inhibiting one or more members of the Wnt pathway, including one or more Wnt proteins would be of tremendous benefit. Certain embodiments provide such compositions and methods. Certain related compounds and methods are disclosed in U.S. application Ser. No. 12/968,505, filed Dec. 15, 2010, which claims priority to U.S. Provisional Application Ser. No. 61/288,544, all of which are incorporated by reference in their entirety herein.

Some embodiments relate to a method for treating a disease including, but not limited to, cancers, diabetic retinopathy, idiopathic pulmonary fibrosis, pulmonary fibrosis, rheumatoid arthritis, scleroderma, mycotic and viral infections, bone and cartilage diseases, Alzheimer's disease, lung disease, osteoarthritis, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a Wnt pathway inhibitor as described herein.

DEFINITIONS

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

In this specification and in the claims, the following terms have the meanings as defined. As used herein, "alkyl" means a branched, or straight chain chemical group containing only carbon and hydrogen, such as methyl, ethyl, n-propyl isopropyl, n-butyl, isobutyl, sec-butyl, tert-butyl, n-pentyl, tentpentyl, neopentyl, isopentyl and sec-pentyl. Alkyl groups can either be unsubstituted or substituted with one or more substituents, e.g., halide, alkoxy, acyloxy, amino, amido, cyano, nitro, hydroxyl, thio, carboxy, carbonyl, benzyloxy, aryl, heteroaryl, heterocyclyl, carbocyclyl, or other functionality that may be suitably blocked, if necessary for purposes of the invention, with a protecting group. Alkyl groups can be saturated or unsaturated (e.g., containing —C═C— or —C≡C— subunits), at one or several positions. Typically, alkyl groups will comprise 1 to 9 carbon atoms, preferably 1 to 6, more preferably 1 to 4, and most preferably 1 to 2 carbon atoms.

As used herein, “carbocyclyl” means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., alkyl, halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 10 carbon atoms, preferably 3 to 6.

As used herein, “lower alkyl” means a subset of alkyl, and thus is a hydrocarbon substituent, which is linear or branched. Preferred lower alkyls are of 1 to about 3 carbons, and may be branched or linear. Examples of lower alkyl include n-propyl, isopropyl, ethyl, and methyl. Likewise, radicals using the terminology “lower” refer to radicals preferably with 1 to about 3 carbons in the alkyl portion of the radical.

As used herein, “amido” means a H—CON— or alkyl-CON—, carbocyclyl-CON—, aryl-CON—, heteroaryl-CON— or heterocyclyl-CON group wherein the alkyl, carbocyclyl, heteroaryl, aryl or heterocyclyl group is as herein described.

As used herein, “aryl” means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., alkyl, amino, cyano, hydroxyl, lower alkyl, haloalkyl, alkoxy, nitro, halo, mercapto, and other substituents. A preferred carbocyclic aryl is phenyl.

As used herein, the term “heteroaryl” means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, lower alkyl, haloalkyl, alkoxy, nitro, halo, mercapto, and other substituents. Examples of heteroaryls include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido [2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo [4,3-b]pyridinyl, tetrazolyl, and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl or heteroaryl ring. Though many substituents will be useful, preferred substituents include those commonly found in aryl or heteroaryl compounds, such as alkyl, cycloalkyl, hydroxy, alkoxy, cyano, halo, haloalkyl, mercapto and the like.

As used herein, “amide” includes both RNR'CO— and RCONR'—. R can be substituted or unsubstituted alkyl, substituted or unsubstituted heterocyclyl, substituted or unsubstituted heteroaryl, substituted or unsubstituted aryl, or substituted or unsubstituted carbocyclyl. R' can be H or substituted or unsubstituted alkyl.

As used herein, “halo”, “halide” or “halogen” is a chloro, bromo, fluoro or iodo atom radical. Chloro, bromo and fluoro are preferred halides. Most preferred halide is fluorine.

As used herein, “haloalkyl” means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 3 carbons in length, more preferred haloalkyls are 1 to about 2 carbons, and most preferred are 1 carbon in length. The skilled artisan will recognize then that as used herein, “haloalkylene” means a diradical variant of haloalkyl, such diradicals may act as spacers between radicals, other atoms, or between the parent ring and another functional group.

As used herein, “heterocyclyl” means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted with one or more substituents, e.g., alkyl, halide, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. More preferred heterocycles are of 5-7 members. In six membered monocyclic heterocycles, the heteroatom(s) are selected from one up to three of O, N or S, and wherein when the heterocycle is five membered, preferably it has one or two heteroatoms selected from O, N, or S. Examples of heterocyclyl include azirinyl, aziridinyl, azetidinyl, oxetanyl, thietanyl, 1,4,2-dithiazolyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, “substituted amino” means an amino radical which is substituted by one or two alkyl, carbocyclyl, aryl, heteroaryl or heterocyclyl groups, wherein the alkyl, carbocyclyl, aryl, heteroaryl or heterocyclyl are defined as above.

As used herein, “sulfonamido” means an alkyl-$S(O)_2N$—, aryl-$S(O)_2N$—, heteroaryl-$S(O)_2N$—, carbocyclyl-$S(O)_2N$— or heterocyclyl-$S(O)_2N$— group wherein the alkyl, carbocyclyl, aryl, heteroaryl or heterocyclyl group is as herein described.

As used herein, when two groups are indicated to be “linked” or “bonded” to form a “ring,” it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically; the artisan recognizes that such structures are only a very small portion of a sample of such compound(s). Such compounds are clearly contemplated within the scope of this invention, though such resonance forms or tautomers are not represented herein.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated when a disclosed compound is named or depicted by a structure without specifying the stereochemistry and has one or more chiral centers, it is understood to represent all possible stereoisomers of the compound.

The term "administration" or "administering" refers to a method of giving a dosage of a compound or pharmaceutical composition comprising the same to a vertebrate or invertebrate, including a mammal, a bird, a fish, or an amphibian, where the method is, e.g., orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. The preferred method of administration can vary depending on various factors, e.g., the components of the pharmaceutical composition, the site of the disease, the disease involved, and the severity of the disease.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, and cats, but also includes many other species.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297.

"Solvate" refers to the compound formed by the interaction of a solvent and a Wnt pathway inhibitor, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

By "therapeutically effective amount" or "pharmaceutically effective amount" of a compound as provided herein is one which is sufficient to achieve the desired effect and may vary according to the nature and severity of the disease condition, and the potency of the compound. "Therapeutically effective amount" is also intended to include one or more of the compounds of Formula (I) in combination with one or more other agents that are effective to inhibit Wnt related diseases and/or conditions. The combination of compounds is preferably a synergistic combination. Synergy, as described, for example, by Chou, *Cancer Research* (2010), 70(2), 440-446, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

"Drug-eluting" and or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present invention include compounds, salts, pharmaceutically acceptable salts or pro-drugs thereof of Formula (I):

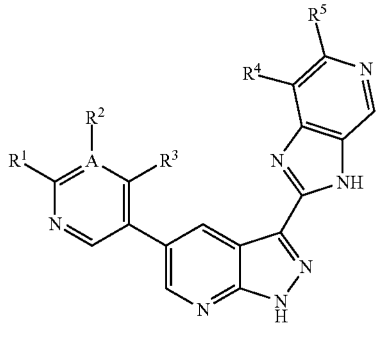

I

In some embodiments of Formula I, $R^1$ and $R^2$ are independently selected from the group consisting of H, lower alkyl, halide, —($C_{1-9}$ alkyl)$_n$aryl($R^6$)$_q$, —($C_{1-9}$ alkyl)$_n$heteroaryl($R^7$)$_q$, —($C_{1-9}$ alkyl)$_n$heterocyclyl($R^8$)$_q$, —($C_{1-9}$ alkyl)$_n$N($R^9$)$_2$, —$OR^{10}$ and —NHC(═O)$R^{11}$.

In some embodiments of Formula I, $R^3$ is selected from the group consisting of H, halide and lower alkyl.

In some embodiments of Formula I, there is the proviso that at least two of $R^1$, $R^2$ and $R^3$ are H.

In some embodiments of Formula I, $R^4$ and $R^5$ are independently selected from the group consisting of H, —C(═O)N($R^{12}$)$_2$, -aryl($R^{13}$)$_q$, -heterocyclyl($R^{14}$)$_q$, and -heteroaryl ($R^{15}$)$_q$ with the proviso that either $R^3$ or $R^4$ is H but not both.

In some embodiments of Formula I, each $R^6$ is a substituent attached to the aryl ring and independently selected from the group consisting of H, —$C_{1-9}$ alkyl, halide, $CF_3$ and CN.

In some embodiments of Formula I, each $R^7$ is a substituent attached to the heteroaryl ring and independently selected from the group consisting of H, —$C_{1-9}$ alkyl, halide, $CF_3$ and CN.

In some embodiments of Formula I, $R^8$ is a substituent attached to the heterocyclyl ring and independently selected from the group consisting of H, halide, —($C_{1-3}$ alkyl)$_n$aryl$R^6$, and —$C_{1-4}$ alkyl.

In some embodiments of Formula I, each $R^9$ is independently selected from the group consisting of H, —$C_{1-9}$ alkyl, —($C_{1-3}$ alkyl)$_n$aryl($R^6$)$_q$, —($C_{1-3}$ alkyl)$_n$carbocyclyl and —($C_{1-9}$ alkyl)N($R^{16}$)$_2$.

In some embodiments of Formula I, two adjacent $R^9$ or two adjacent $R^{12}$, may be taken together with the atoms to which they are attached to form a heterocyclyl($R^{17}$)$_q$.

In some embodiments, $R^{10}$ is selected from the group consisting of H, —$CF_3$, —($C_{1-3}$ alkyl)$_n$aryl($R^6$)$_q$, and —$C_{1-9}$ alkyl.

In some embodiments of Formula I, $R^{11}$ is selected from the group consisting of —($C_{1-3}$ alkyl)$_n$aryl($R^6$)$_q$, —($C_{1-3}$ alkyl)$_n$carbocyclyl, —$C_{1-9}$ alkyl and —$CF_3$.

In some embodiments of Formula I, each $R^{12}$ is independently selected from the group consisting of H, —($C_{1-9}$ alkyl)$_n$aryl($R^6$)$_q$ and —$C_{1-9}$ alkyl.

In some embodiments of Formula I, each $R^{13}$ is a substituent attached to the aryl ring and independently selected from the group consisting of H, halide, —$CF_3$, CN, —($C_{1-3}$ alkyl)$_n$ heterocyclyl($R^8$)$_q$, —($C_{1-9}$ alkyl)$_n$N($R^9$)$_2$ and —($C_{1-9}$ alkyl)$_n$ $NHSO_2R^{18}$.

In some embodiments of Formula I, each $R^{14}$ is a substituent attached to the heterocyclyl ring and independently selected from the group consisting of H, lower alkyl, halide, —$CF_3$ and CN.

In some embodiments of Formula I, each $R^{15}$ is a substituent attached to the heteroaryl ring and independently selected from the group consisting of H, lower alkyl, halide, —$CF_3$, CN, —C(═O)($C_{1-3}$ alkyl), —($C_{1-9}$ alkyl)$_n$N($R^9$)$_2$ and —($C_{1-9}$ alkyl)$_n$$NHSO_2R^{18}$.

In some embodiments of Formula I, each $R^{16}$ is independently selected from the group consisting of H and lower alkyl.

In some embodiments of Formula I, each $R^{17}$ is a substituent attached to the heterocyclyl ring and independently selected from the group consisting of H, —($C_{1-9}$ alkyl)$_n$aryl ($R^6$)$_q$, and —$C_{1-9}$ alkyl.

In some embodiments of Formula I, each $R^{18}$ is a lower alkyl.

In some embodiments of Formula I, A is N or C.

In some embodiments of Formula I, there is the proviso that if A is N then $R^2$ is nil;

In some embodiments of Formula I, each q is an integer of 1 to 5.

In some embodiments of Formula I, each n is an integer of 0 or 1.
In some embodiments, there is the proviso that Formula I is not a structure selected from the group consisting of:
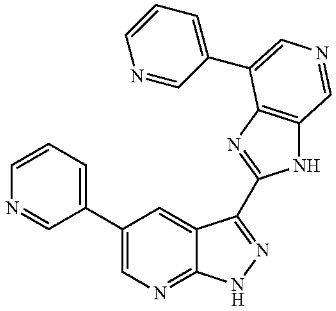
,
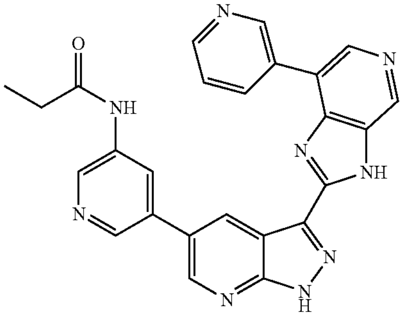
,
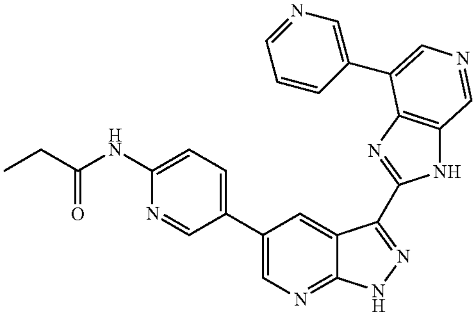
,
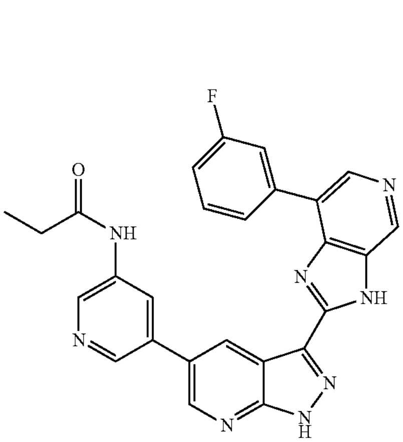
,
-continued
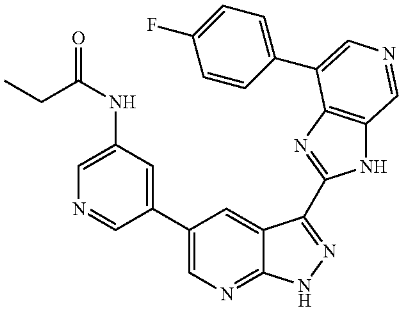
,
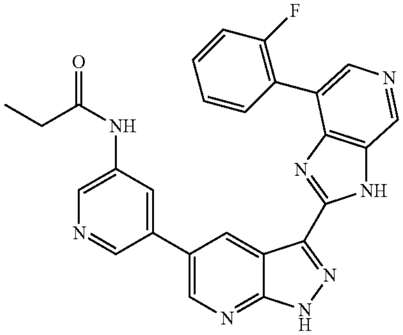
,
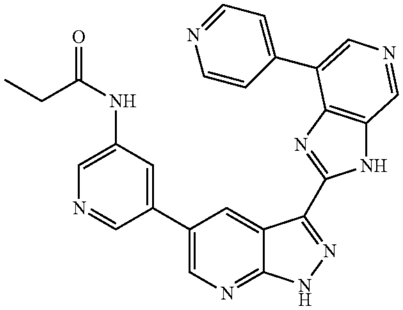
,
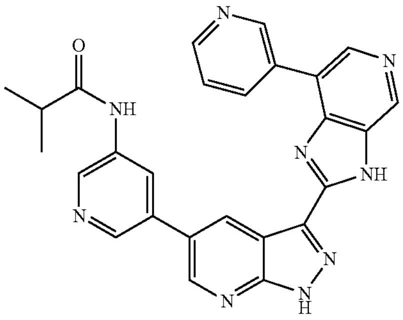
,
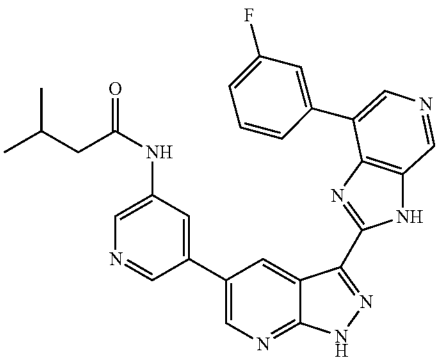
, -continued
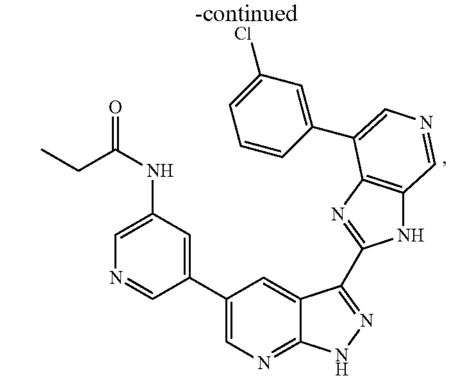
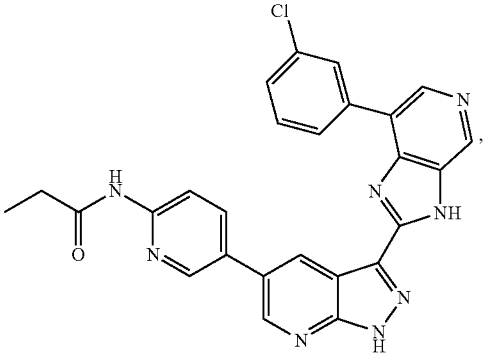
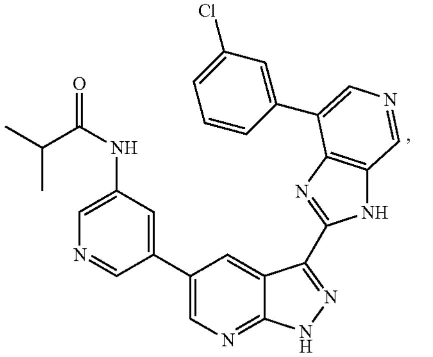
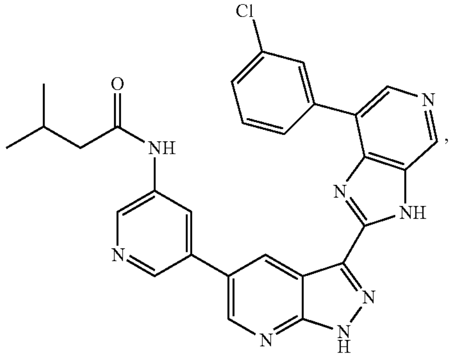
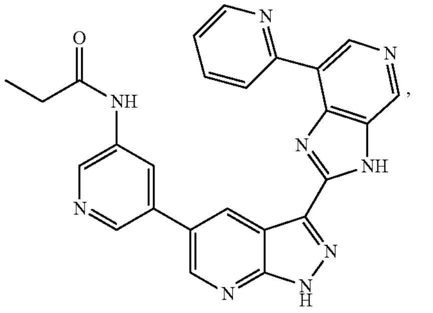
-continued
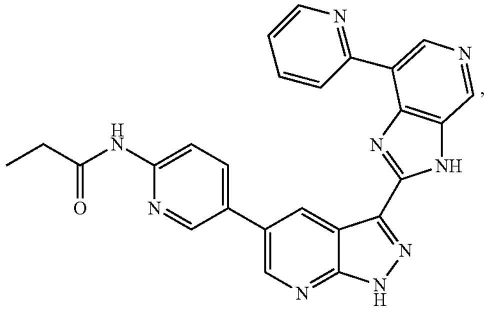
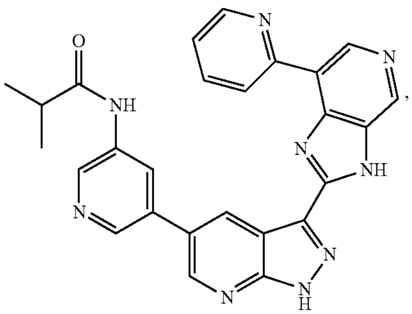
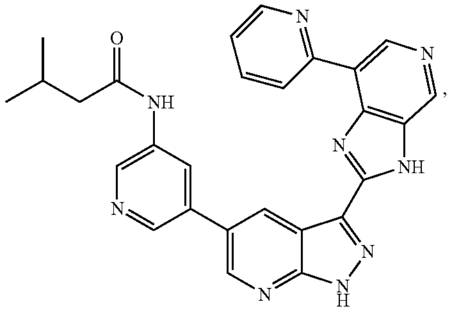
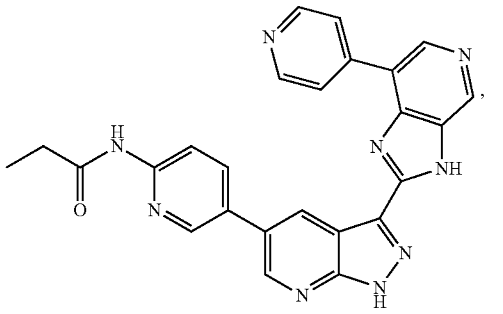
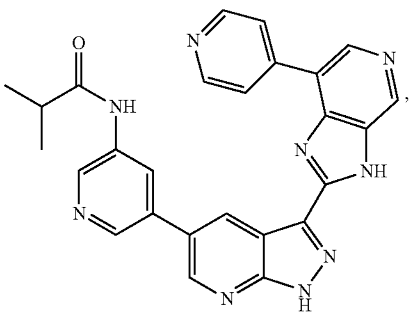

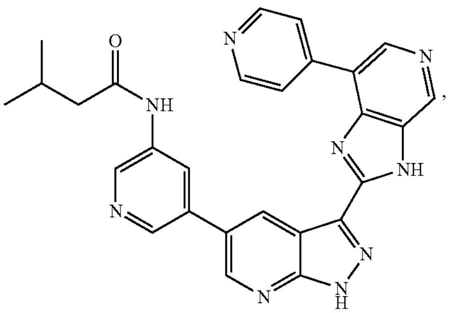
,
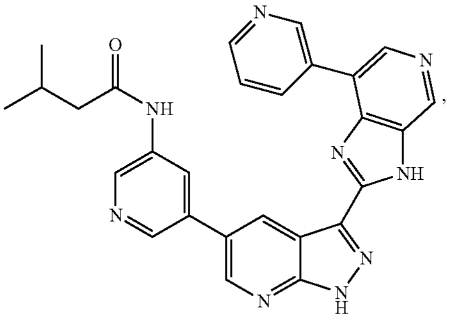
,
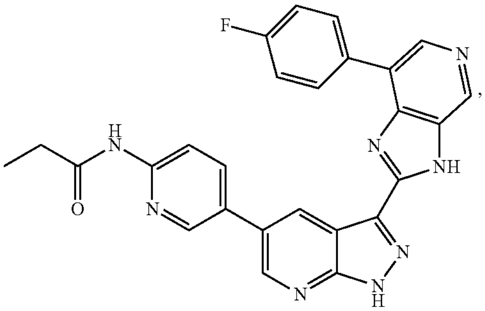
,
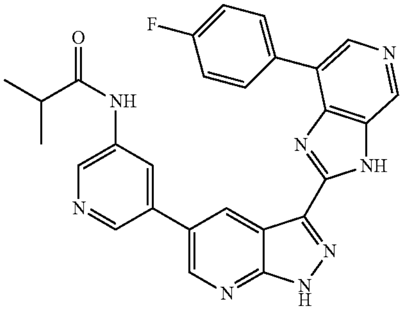
,
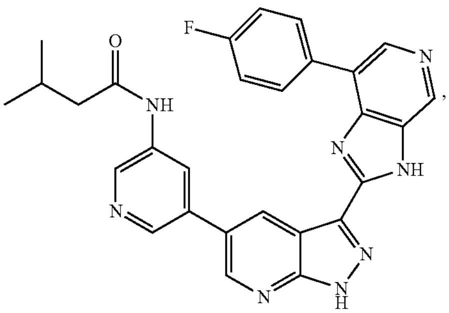
,
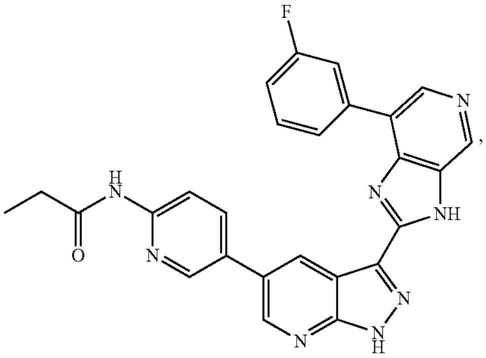
,
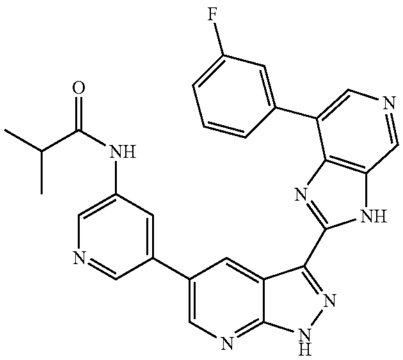
,
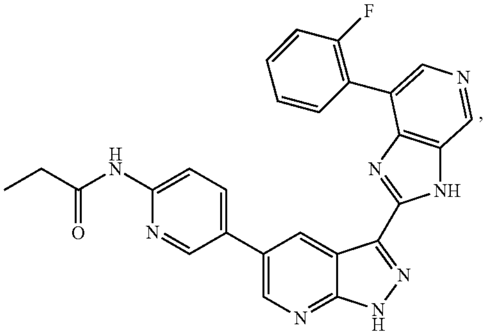
,
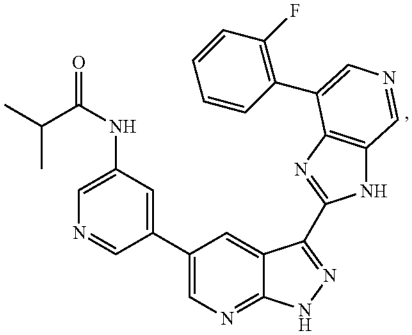
,
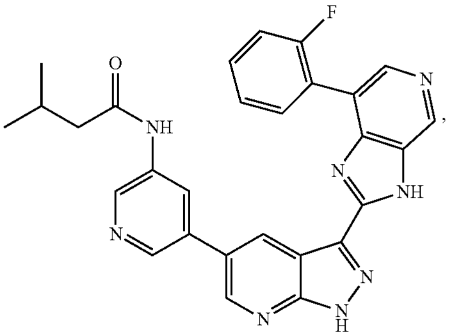
, -continued
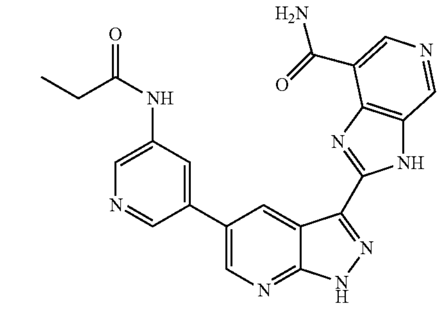
,
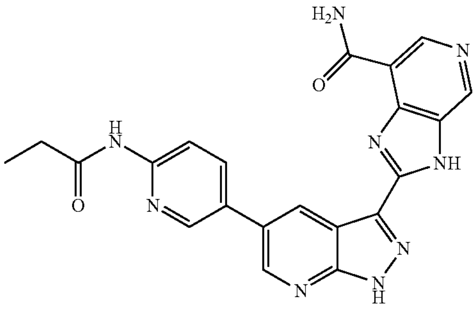
,
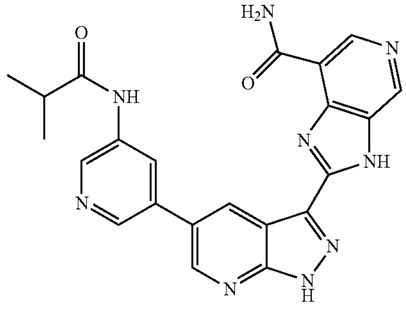
,
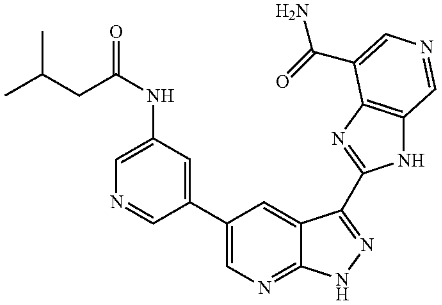
,
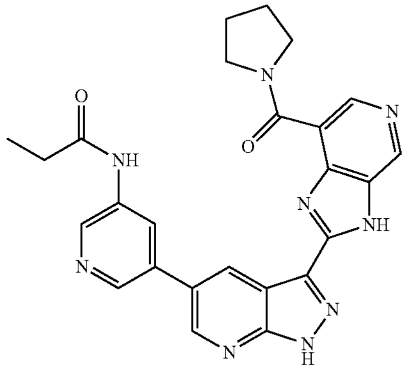
,
-continued
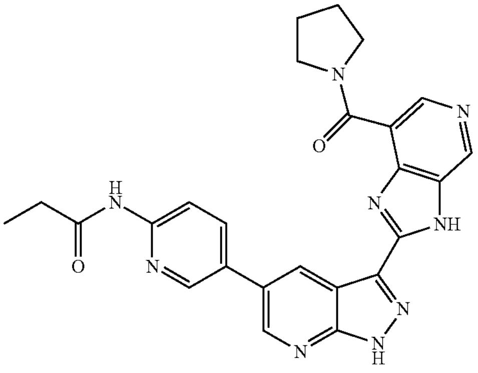
,
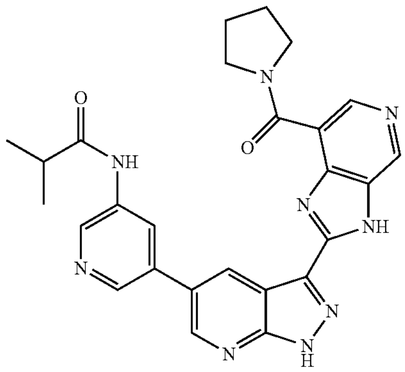
,
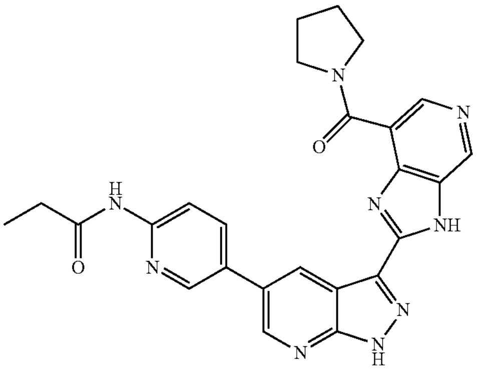
,
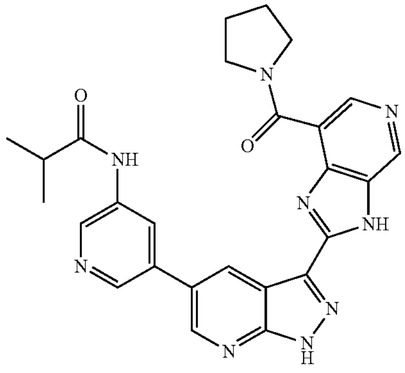
, -continued
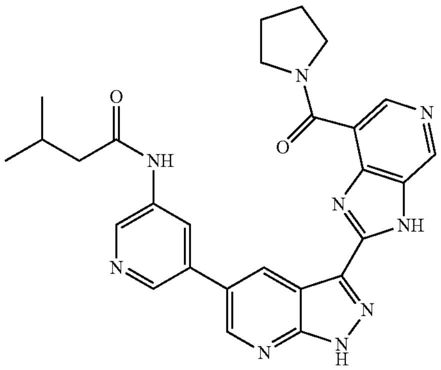
,
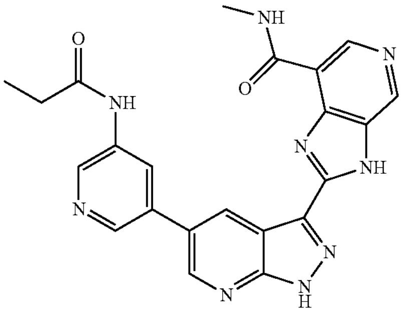
,
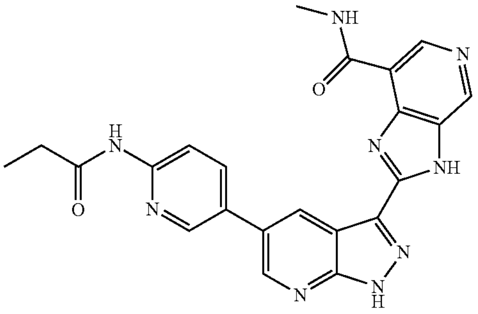
,
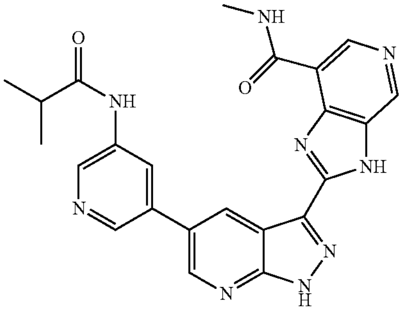
,
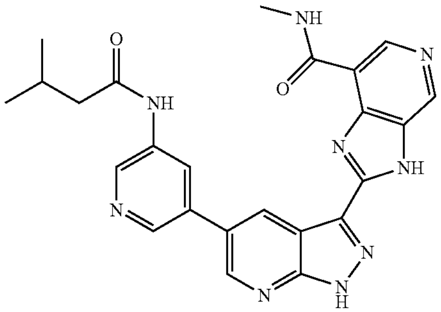
,
-continued
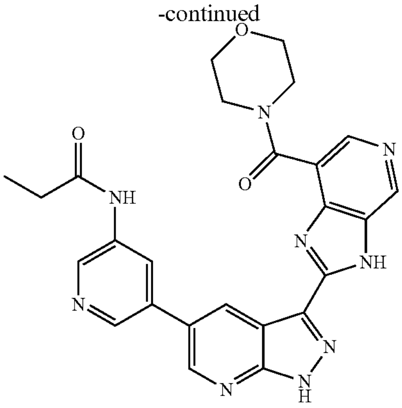
,
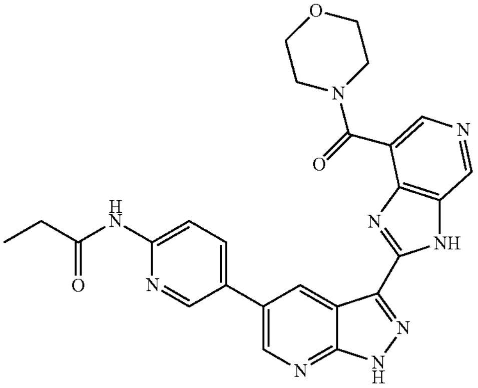
,
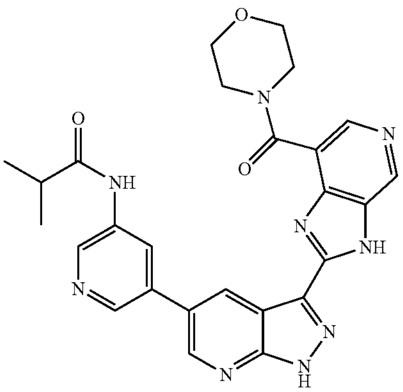
,
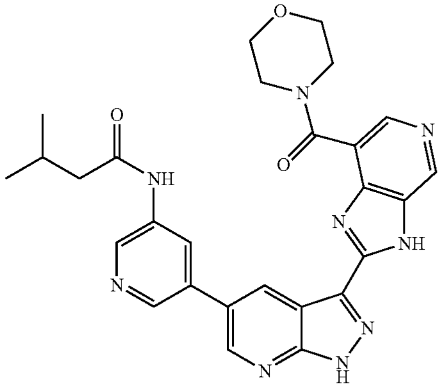
, -continued

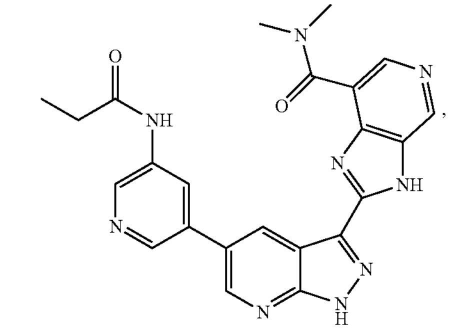

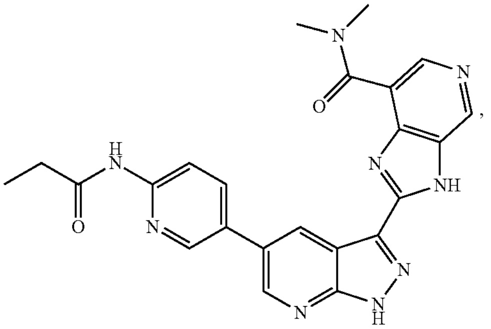

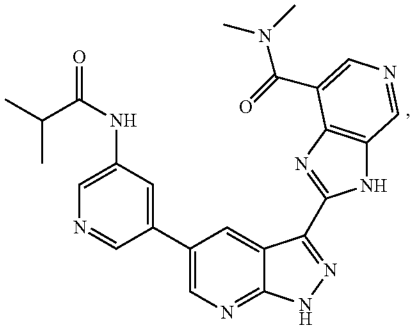

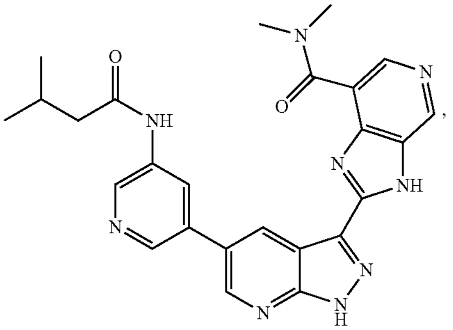

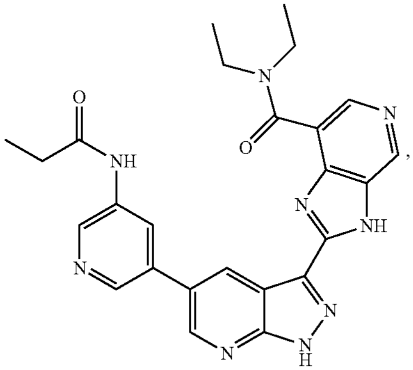

-continued

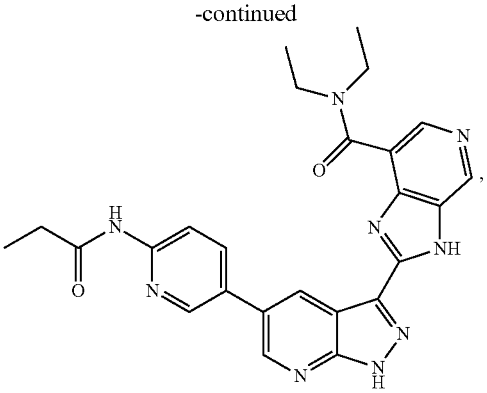

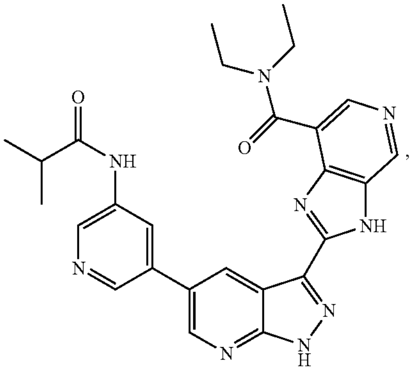

and

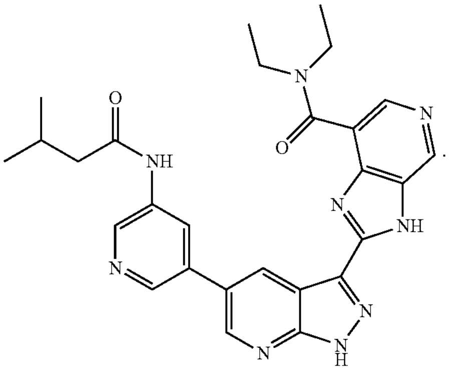

In some embodiments of either Formula I, A is C.

In some embodiments of Formula I, A is N and $R^2$ is nil.

In some embodiments of Formula I, A is N; and $R^1$ and $R^3$ are both H.

In some embodiments of Formula I, aryl is phenyl.

In some embodiments of Formula I, heteroaryl is pyridinyl.

In some embodiments of Formula I, heterocyclyl is selected from the group consisting of azetidinyl, pyrrolidinyl, morpholinyl, piperazinyl and piperidinyl.

In some embodiments of Formula I, $R^2$ is selected from the group consisting of H, $-(C_{1-9}$ alkyl$)_n$heterocyclyl$(R^8)_q$, $-NHC(=O)R^{11}$ and $-(C_{1-9}$ alkyl$)_nN(R^9)_2$ and $R^1$ and $R^3$ are both H.

In some embodiments of Formula I, $R^2$ is $-CH_2N(R^9)_2$ or $-N(R^9)_2$.

In some embodiments of Formula I, $R^9$ is independently selected from the group consisting of H, Me, Et, $-CH_2$phenyl and $-CH_2$carbocyclyl.

In some embodiments of Formula I, $R^2$ is $-NHC(=O)R^{11}$.

In some embodiments of Formula I, $R^{11}$ is selected from the group consisting of $-C_{1-5}$ alkyl, carbocyclyl, phenyl$(R^6)_q$, and $-CH_2$phenyl$(R^6)_q$.

In some embodiments of Formula I, $R^4$ is phenyl$(R^{13})_q$.

In some embodiments of Formula I, $R^4$ is -heterocyclyl $(R^{14})_q$.

In some embodiments of Formula I, $R^4$ is -heteroaryl $(R^{15})_q$.

In some embodiments of Formula I, $R^{13}$ is one substituent attached to the phenyl comprising a fluorine atom.

In some embodiments of Formula I, $R^{13}$ is two substituents each attached to the phenyl comprising a fluorine atom and either a $-(CH_2)_nN(R^5)_2$ or a $-(CH_2)_nNHSO_2R^{18}$.

In some embodiments of Formula I, the heterocyclyl is selected from the group consisting of piperazinyl and piperidinyl; and the $R^{14}$ is H or Me.

In some embodiments of Formula I, the heteroaryl is selected from the group consisting of pyridinyl, furyl, thiophenyl and imidazolyl; and $R^{15}$ is lower alkyl or halide.

Some embodiments of the present invention include compounds, salts, pharmaceutically acceptable salts or pro-drugs thereof of Formula (II):

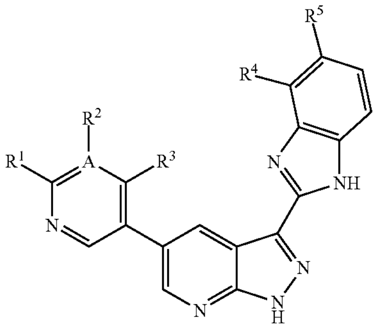

II

In some embodiments of Formula II, $R^1$ and $R^2$ are independently selected from the group consisting of H, lower alkyl, halide, $-(C_{1-9}$ alkyl$)_n$aryl$(R^6)_q$, $-(C_{1-9}$ alkyl$)_n$heteroaryl$(R^7)_q$, $-(C_{1-9}$ alkyl$)_n$heterocyclyl$(R^8)_q$, $-(C_{1-9}$ alkyl$)_nN(R^9)_2$, $-OR^{10}$ and $-NHC(=O)R^{11}$.

In some embodiments of Formula II, $R^3$ is selected from the group consisting of H, halide and lower alkyl.

In some embodiments of Formula II, there is the proviso that at least two of $R^1$, $R^2$ and $R^3$ are H.

In some embodiments of Formula II, there is the proviso that if A is N then $R^2$ is nil.

In some embodiments of Formula II, $R^4$ and $R^5$ are independently selected from the group consisting of H, $-C(=O)N(R^{12})_2$, -aryl$(R^{13})_q$, -heterocyclyl$(R^{14})_q$, and -heteroaryl $(R^{15})_q$ with the proviso that either $R^3$ or $R^4$ is H but not both.

In some embodiments of Formula II, each $R^6$ is a substituent attached to the aryl ring and independently selected from the group consisting of H, $-C_{1-9}$ alkyl, halide, $CF_3$ and CN.

In some embodiments of Formula II, each $R^7$ is a substituent attached to the heteroaryl ring and independently selected from the group consisting of H, $-C_{1-9}$ alkyl, halide, $CF_3$ and CN.

In some embodiments of Formula II, each $R^8$ is a substituent attached to the heterocyclyl ring and independently selected from the group consisting of H, halide, $-(C_{1-3}$ alkyl$)_n$ aryl$(R^6)_q$, and $-C_{1-4}$ alkyl.

In some embodiments of Formula II, each $R^9$ is independently selected from the group consisting of H, $-C_{1-9}$ alkyl, $-(C_{1-3}$ alkyl$)_n$aryl$(R^6)_q$, $-(C_{1-3}$ alkyl$)_n$carbocyclyl and $-(C_{1-9}$ alkyl$)N(R^{16})_2$.

In some embodiments of Formula II, two adjacent $R^9$ or two adjacent $R^{12}$, may be taken together with the atoms to which they are attached to form a heterocyclyl$(R^{17})_q$.

In some embodiments of Formula II, $R^{16}$ is selected from the group consisting of H, $-CF_3$, $-(C_{1-3}$ alkyl$)_n$aryl$(R^6)_q$, and $-C_{1-9}$ alkyl.

In some embodiments of Formula II, $R^{11}$ is selected from the group consisting of $-(C_{1-3}$ alkyl$)_n$aryl$(R^6)_q$, $-(C_{1-3}$ alkyl$)_n$carbocyclyl, $-C_{1-9}$ alkyl and $-CF_3$.

In some embodiments of Formula II, each $R^{12}$ is independently selected from the group consisting of H, $-(C_{1-9}$ alkyl$)_n$ aryl$(R^6)_q$ and $-C_{1-9}$ alkyl.

In some embodiments of Formula II, each $R^{13}$ is a substituent attached to the aryl ring and independently selected from the group consisting of H, halide, $-CF_3$, CN, $-(C_{1-3}$ alkyl$)_n$ heterocyclyl$(R^8)_q$, $-(C_{1-9}$ alkyl$)_nN(R^9)_2$ and $-(C_{1-9}$ alkyl$)_n$ $NHSO_2R^{18}$.

In some embodiments of Formula II, each $R^{14}$ is a substituent attached to the heterocyclyl ring and independently selected from the group consisting of H, lower alkyl, halide, $-CF_3$ and CN.

In some embodiments of Formula II, each $R^{15}$ is a substituent attached to the heteroaryl ring and independently selected from the group consisting of H, lower alkyl, halide, $-CF_3$, CN, $-C(=O)(C_{1-3}$ alkyl), $-(C_{1-9}$ alkyl$)_nN(R^9)_2$ and $-(C_{1-9}$ alkyl$)_nNHSO_2R^{18}$.

In some embodiments of Formula II, each $R^{16}$ is independently selected from the group consisting of H and lower alkyl.

In some embodiments of Formula II, each $R^{17}$ is a substituent attached to the heterocyclyl ring and independently selected from the group consisting of H, $-(C_{1-9}$ alkyl$)_n$aryl $(R^6)_q$, and $-C_{1-9}$ alkyl.

In some embodiments of Formula II, each $R^{18}$ is a lower alkyl.

In some embodiments of Formula II, A is N or C.

In some embodiments of Formula II, there is the proviso that if A is N then $R^2$ is nil;

In some embodiments of Formula II, each q is an integer of 1 to 5.

In some embodiments of Formula II, each n is an integer of 0 or 1.

In some embodiments, Formula II is not a structure selected from the group consisting of:

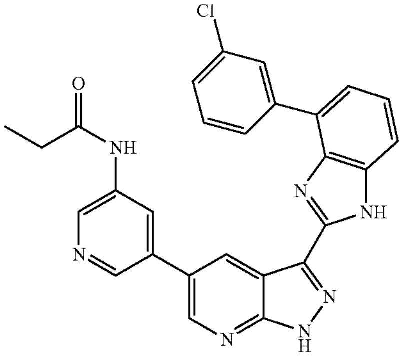

,

-continued
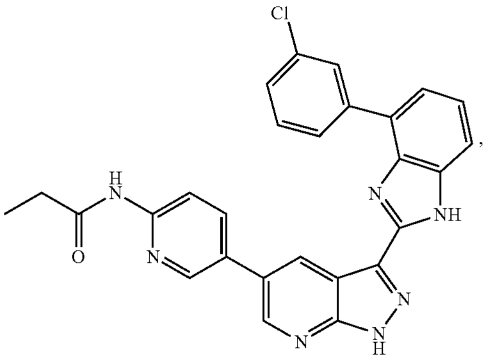
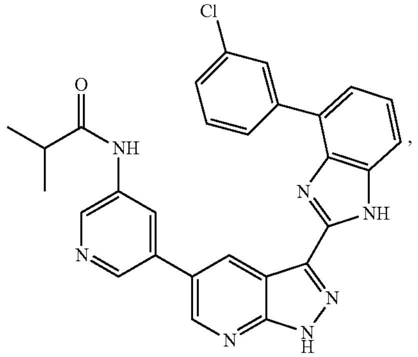
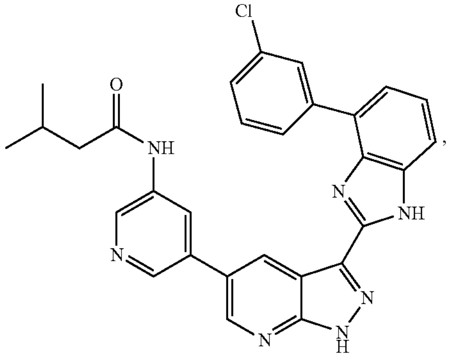
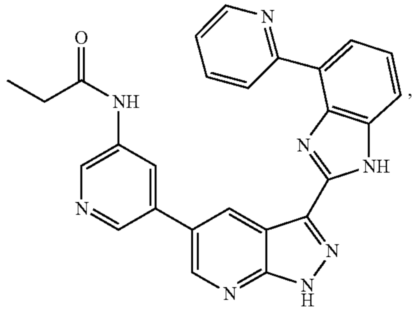
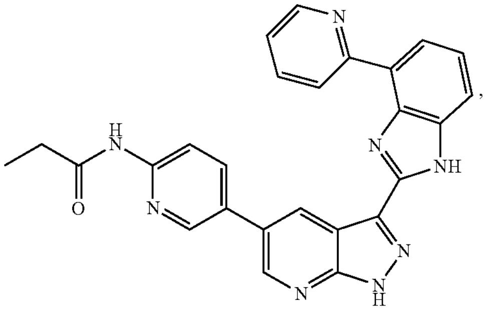
-continued
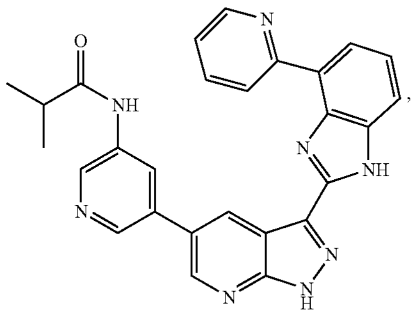
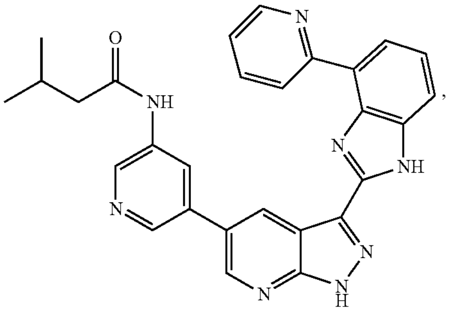
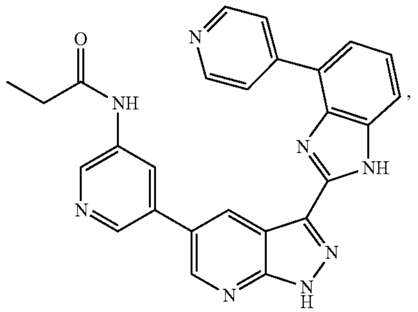
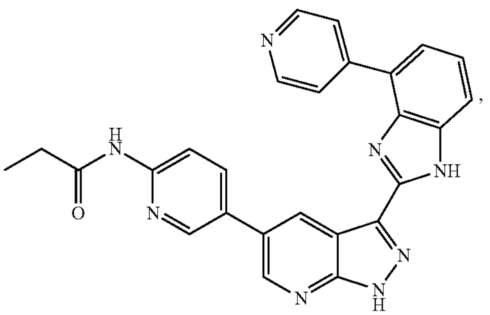
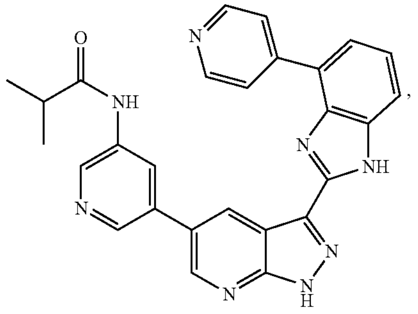

-continued
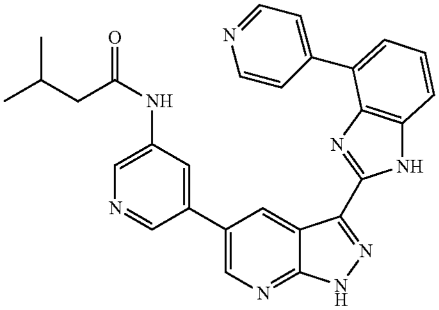,
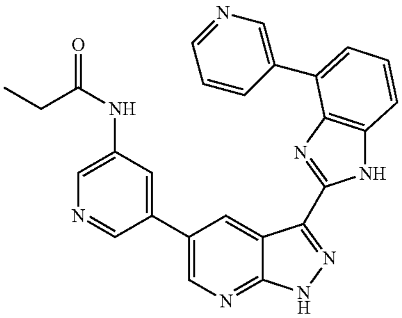,
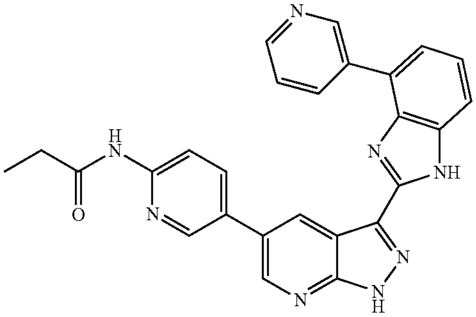,
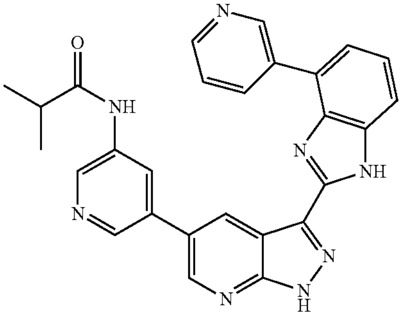,
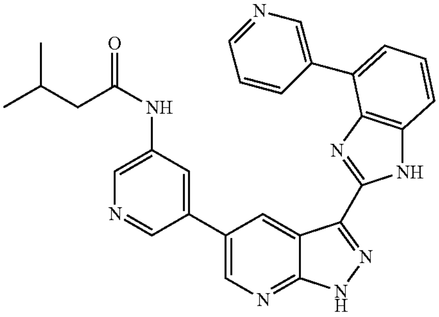,
-continued
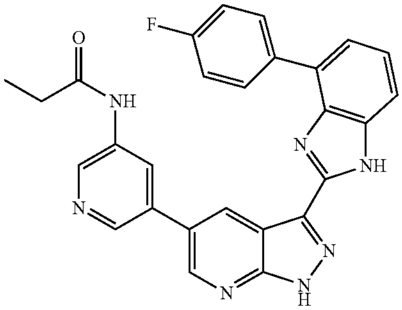,
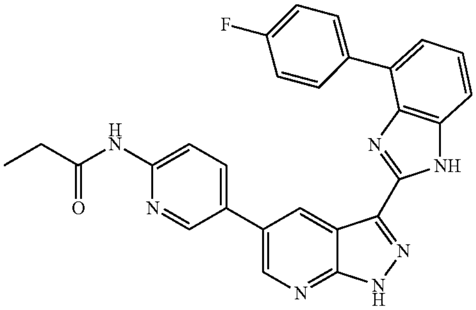,
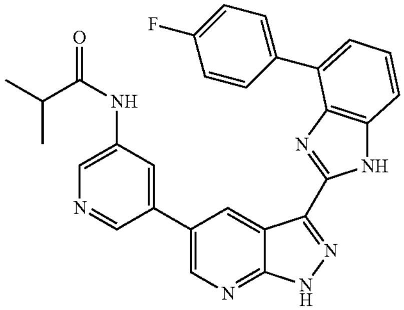,
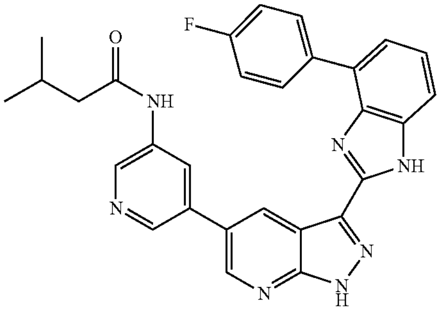,
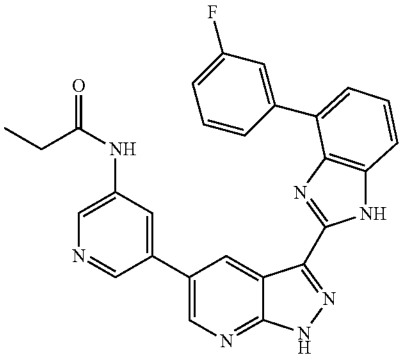, -continued
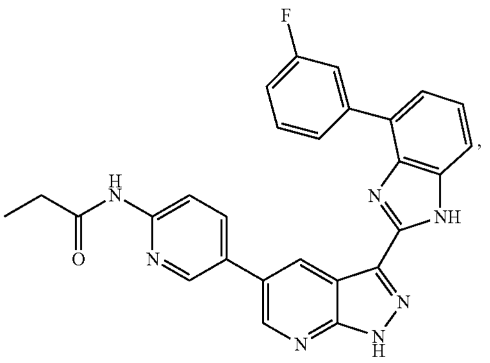
,
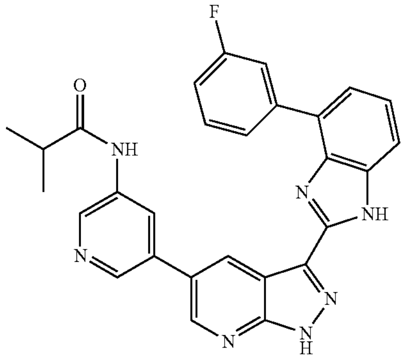
,
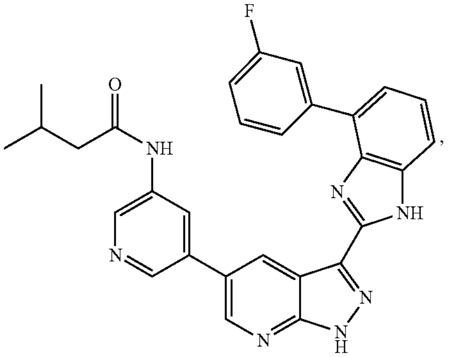
,
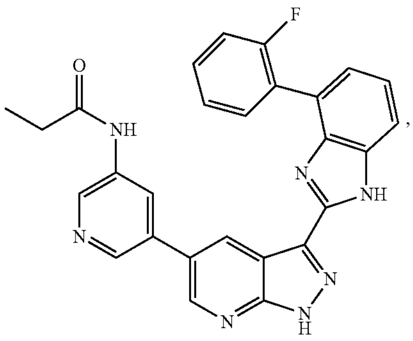
,
-continued
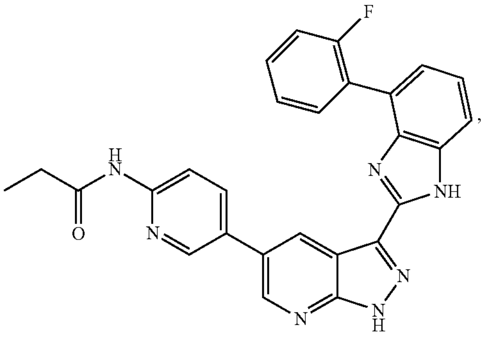
,
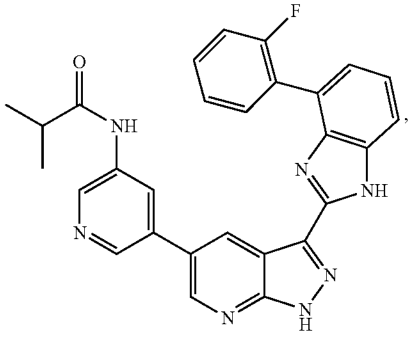
,
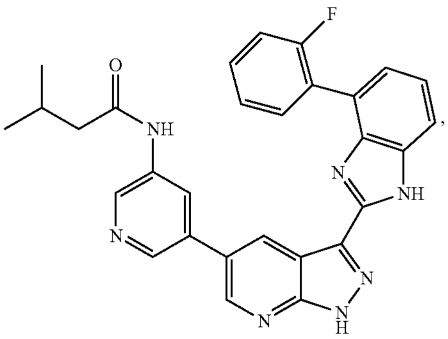
,
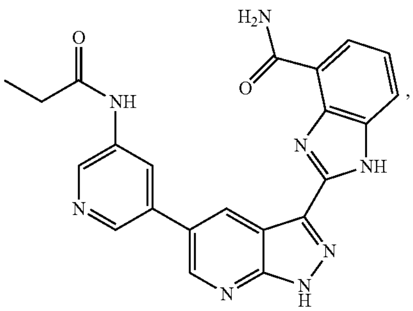
,
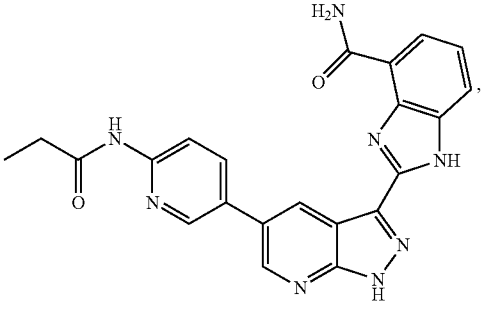
, -continued
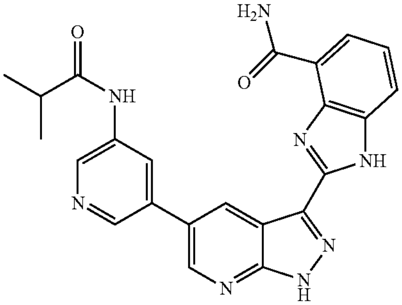
,
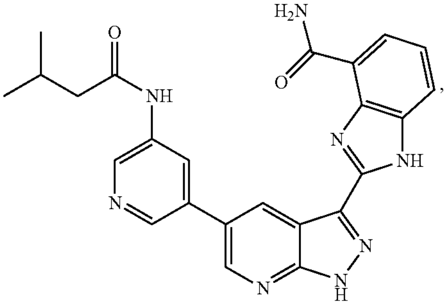
,
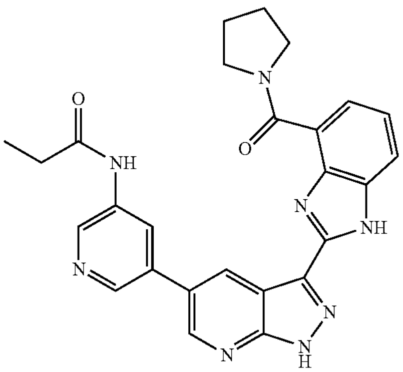
,
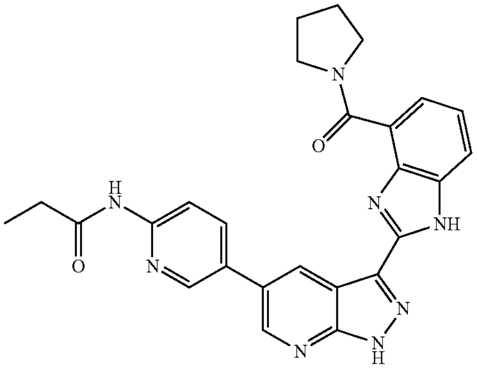
,
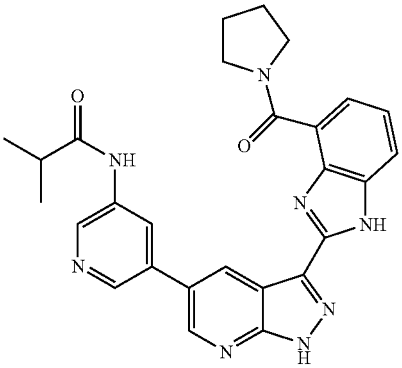
,
-continued
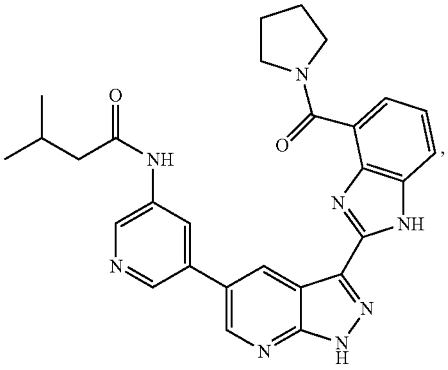
,
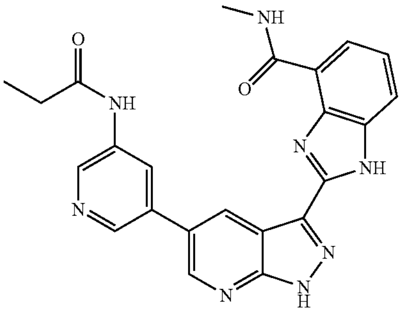
,
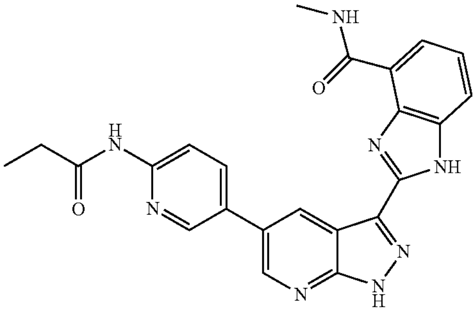
,
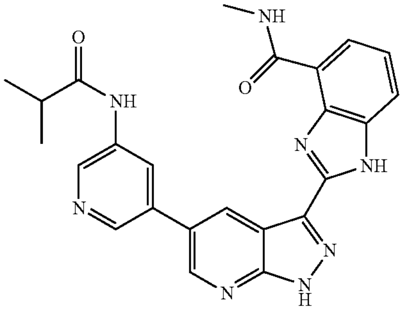
,
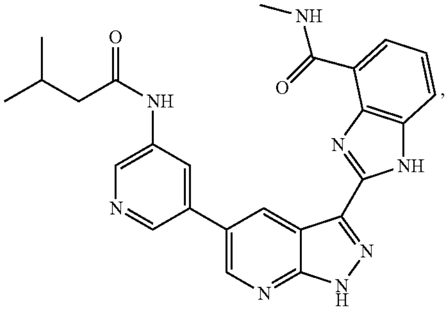
, -continued
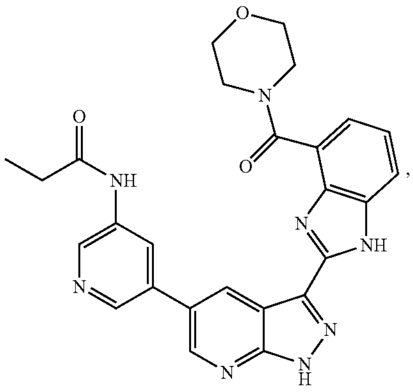
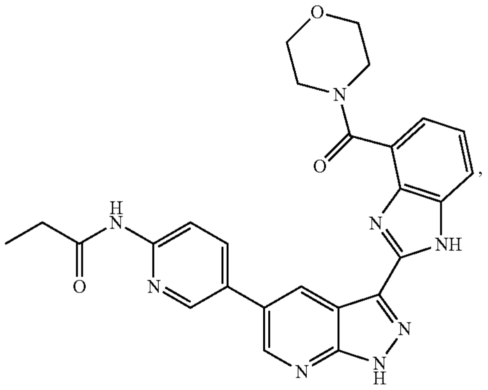
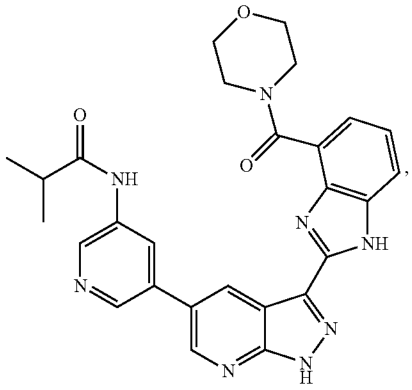
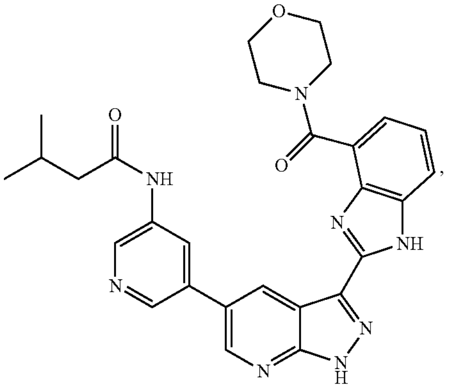
-continued
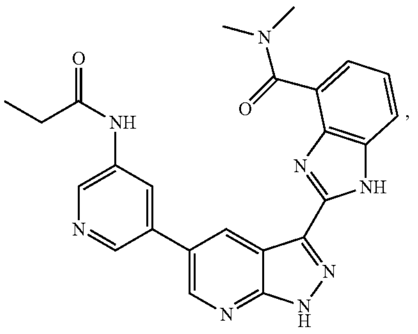
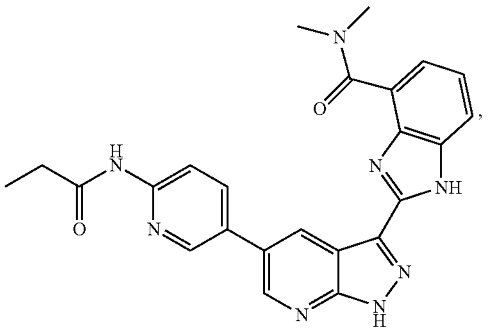
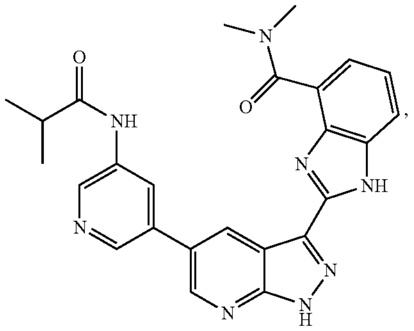
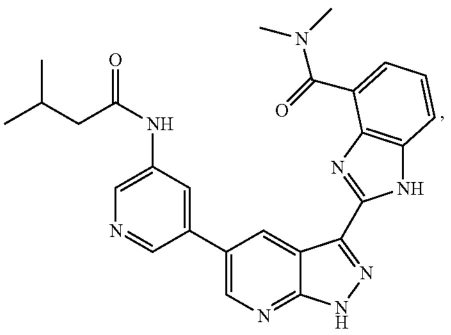
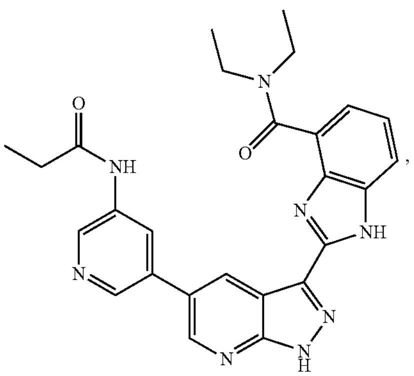

-continued

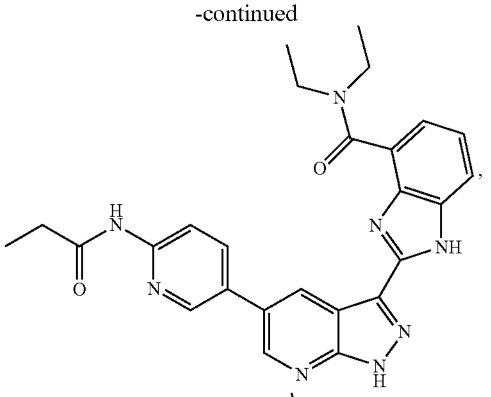

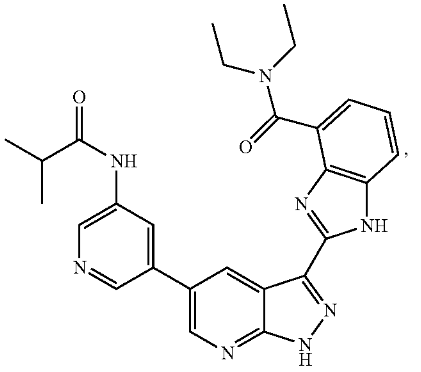

and

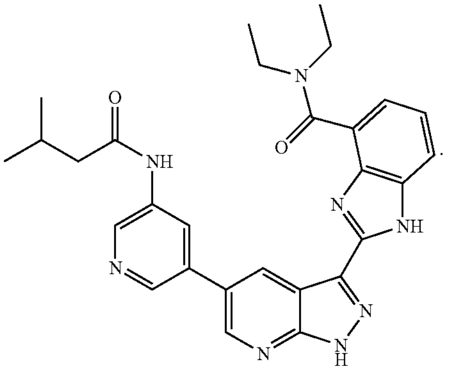

In some embodiments of Formula II, A is C.

In some embodiments of Formula II, A is N and $R^2$ is nil.

In some embodiments of Formula II, A is N; and $R^1$ and $R^3$ are both H.

In some embodiments of Formula II, aryl is phenyl.

In some embodiments of Formula II, heteroaryl is pyridinyl.

In some embodiments of Formula II, heterocyclyl is selected from the group consisting of azetidinyl, pyrrolidinyl, morpholinyl, piperazinyl and piperidinyl.

In some embodiments of Formula II, $R^2$ is selected from the group consisting of H, $-(C_{1-9}\ alkyl)_n heterocyclyl(R^8)_q$, $-NHC(=O)R^{11}$ and $-(C_{1-9}\ alkyl)_n N(R^9)_2$ and $R^1$ and $R^3$ are both H.

In some embodiments of Formula II, $R^2$ is $-CH_2N(R^9)_2$ or $-N(R^9)_2$.

In some embodiments of Formula II, $R^9$ is independently selected from the group consisting of H, Me, Et, $-CH_2$phenyl and $-CH_2$carbocyclyl.

In some embodiments of Formula II, $R^2$ is $-NHC(=O)R^{11}$.

In some embodiments of Formula II, $R^{11}$ is selected from the group consisting of $-C_{1-5}$ alkyl, carbocyclyl, phenyl $(R^6)_2$, and $-CH_2$phenyl$(R^6)_q$.

In some embodiments of Formula II, $R^4$ is phenyl$(R^{13})_q$.

In some embodiments of Formula II, $R^4$ is -heterocyclyl $(R^{14})_q$.

In some embodiments of Formula II, $R^4$ is -heteroaryl $(R^{15})_q$.

In some embodiments of Formula II, $R^{13}$ is one substituent attached to the phenyl comprising a fluorine atom.

In some embodiments of Formula II, $R^{13}$ is two substituents each attached to the phenyl comprising a fluorine atom and either a $-(CH_2)_n N(R^5)_2$ or a $-(CH_2)_n NHSO_2R^{18}$.

In some embodiments of Formula II, the heterocyclyl is selected from the group consisting of piperazinyl and piperidinyl; and the $R^{14}$ is H or Me.

In some embodiments of Formula II, the heteroaryl is selected from the group consisting of pyridinyl, furyl, thiophenyl and imidazolyl; and $R^{15}$ is lower alkyl or halide.

In some embodiments of either Formula I or II, $R^3$ is lower alkyl; and $R^1$ and $R^2$ are both H.

In some embodiments of either Formula I or II, $R^2$ is $-NHC(=O)(C_{1-2}\ alkyl)$.

In some embodiments of either Formula I or II, $R^2$ is $-NHC(=O)(C_{1-3}\ alkyl)$.

In some embodiments of either Formula I or II, $R^2$ is $-NHC(=O)(C_{1-4}\ alkyl)$.

In some embodiments of either Formula I or II, $R^2$ is $-NHC(=O)(C_{1-5}\ alkyl)$.

In some embodiments of either Formula I or II, $R^2$ is $-NHC(=O)$carbocyclyl.

In some embodiments of either Formula I or II, $R^2$ is

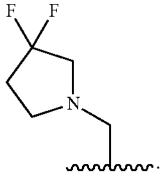 [SMILES: *CN1CCC(F)(F)C1]

In some embodiments of either Formula I or II, $R^2$ is $-NH(C_{1-3}\ alkyl)$.

In some embodiments of either Formula I or II, $R^2$ is $-N(C_{1-3}\ alkyl)_2$.

In some embodiments of either Formula I or II, $R^2$ is $-NH_2$.

In some embodiments of either Formula I or II, $R^4$ is pyridinyl.

In some embodiments of either Formula I or II, $R^4$ is furyl.

In some embodiments of either Formula I or II, $R^4$ is thiophenyl.

In some embodiments of either Formula I or II, $R^4$ is imidazolyl.

In some embodiments of either Formula I or II, $R^4$ is piperazinyl

In some embodiments of either Formula I or II, $R^4$ is piperidinyl.

In some embodiments of either Formula I or II, $R^4$ is 1-methylpiperazinyl.

In some embodiments of either Formula I or II, $R^4$ is selected from the group consisting of:

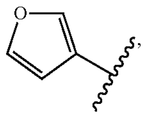, 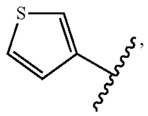, 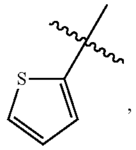,

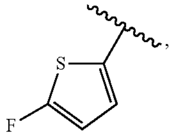, 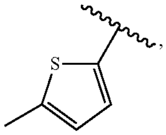,

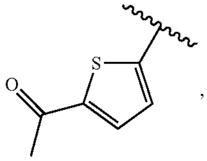, and 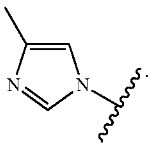.

In some embodiments of either Formula I or II, $R^{11}$ is cyclopropyl.

In some embodiments of either Formula I or II, $R^{11}$ is cyclobutyl.

In some embodiments of either Formula I or II, $R^{11}$ is cyclopentyl.

In some embodiments of either Formula I or II, $R^{11}$ is cyclohexyl.

In some embodiments of either Formula I or II, $R^{13}$ is 1-2 fluorine atoms.

In some embodiments of either Formula I or II, $R^{13}$ is —$(C_{1-6}$ alkyl)$NHSO_2R^{11}$.

In some embodiments of either Formula I or II, $R^{13}$ is —$(C_{1-4}$ alkyl)$NHSO_2R^{11}$.

In some embodiments of either Formula I or II, $R^{13}$ is —$(C_{1-2}$ alkyl)$NHSO_2R^{11}$.

In some embodiments of either Formula I or II, $R^{13}$ is —$CH_2NHSO_2R^{11}$.

In some embodiments of either Formula I or II, $R^{13}$ is —$CH_2NHSO_2CH_3$.

In some embodiments of either Formula I or II, $R^{13}$ is —$NR^{12}(C_{1-6}$ alkyl)$NR^{11}R^{12}$.

In some embodiments of either Formula I or II, $R^{13}$ is —$NR^{12}(C_{1-4}$ alkyl)$NR^{11}R^{12}$.

In some embodiments of either Formula I or II, $R^{13}$ is —$NR^{12}CH_2CH_2NR^{11}R^{12}$.

In some embodiments of either Formula I or II, $R^{13}$ is —$NHCH_2CH_2NR^{11}R^{12}$.

In some embodiments of either Formula I or II, $R^{13}$ is —$NHCH_2CH_2N(CH_3)_2$.

In some embodiments of either Formula I or II, $R^{13}$ is 2 substituents consisting of 1 fluorine atom and —$NR^{12}(C_{1-6}$ alkyl)$NR^{11}R^{12}$.

In some embodiments of either Formula I or II, $R^{13}$ is 2 substituents consisting of 1 fluorine atom and —$NHCH_2CH_2NR^{11}R^{12}$.

In some embodiments of either Formula I or II, $R^{13}$ is 2 substituents consisting of 1 fluorine atom and —$(C_{1-6}$ alkyl) $NHSO_2R^{11}$.

In some embodiments of either Formula I or II, $R^{13}$ is 2 substituents consisting of 1 fluorine atom and —$CH_2NHSO_2R^{11}$.

In some embodiments of either Formula I or II, $R^{15}$ is Me.

In some embodiments of either Formula I or II, $R^{15}$ is halide.

In some embodiments of either Formula I or II, $R^{15}$ is fluorine.

In some embodiments of either Formula I or II, $R^{13}$ is —C(═O)($C_{1-3}$ alkyl).

In some embodiments of either Formula I or II, q is an integer ranging from 1 to 5, preferably 1 or 3, more preferably 1-2.

In some embodiments of either Formula I or II, A is C; $R^1$, $R^2$ and $R^3$ are all H; $R^4$ is selected from the group consisting of pyridine and -heterocyclyl$(R^{14})_q$; q is 1 or 2 and $R^{14}$ is selected from the group consisting of H, F and —($C_{1-4}$ alkyl).

In some embodiments of either Formula I or II, A is C; $R^1$ and $R^3$ are H; $R^2$ is amino; $R^4$ is selected from the group consisting of -phenyl$(R^{13})_q$ and -heterocyclyl$(R^{14})_q$, -heteroaryl$(R^{15})_q$; q is 1 or 2; $R^{15}$ is H; $R^{14}$ is selected from the group consisting of H, F and —($C_{1-4}$ alkyl); $R^{13}$ is 1-2 fluorine atoms; and the heteroaryl is selected from the group consisting of pyridine, furan and thiophene.

In some embodiments of either Formula I or II, A is C; $R^1$ and $R^3$ are H; $R^2$ is —NHC(═O)$R^{11}$; $R^{11}$ is selected from the group consisting of ethyl, propyl, isopropyl, butyl, isobutyl, tert-butyl, neopentyl, cyclopropyl, cyclobutyl, cyclopentyl, cyclohexyl and phenyl; $R^4$ is selected from the group consisting of H, -heteroaryl$(R^{15})_q$, -phenyl$(R^{13})_q$ and -heterocyclyl$(R^{14})_q$; q is 1 or 2; $R^{15}$ is H or F; $R^{14}$ is selected from the group consisting of H, F and —($C_{1-4}$ alkyl); $R^{13}$ is selected from the group consisting of 1-2 fluorine atoms and —$CH_2NHSO_2R^{18}$; and the heteroaryl is selected from the group consisting of pyridine, furan and thiophene.

In some embodiments of either Formula I or II, A is C; $R^1$ and $R^3$ are H; $R^2$ is —$CH_2N(R^9)_2$; $R^4$ is selected from the group consisting of H, -heteroaryl$(R^{15})_q$, -phenyl$(R^{13})_q$ and -heterocyclyl$(R^{14})_q$; q is 1 or 2; $R^{15}$ is selected from the group consisting of H, F, Me and —C(═O)Me; $R^{14}$ is selected from the group consisting of H, F and —($C_{1-4}$ alkyl); $R^{13}$ is 1-2 fluorine atoms; the two $R^9$ are linked to form a five-membered heterocyclyl ring; the heterocyclyl ring is substituted with 1-2 fluorine atoms; and the heteroaryl is selected from the group consisting of pyridine, furan and thiophene.

Pharmaceutically acceptable salts of all of the above embodiments are also contemplated.

Illustrative compounds of Formulas (I) and (II) are shown in Table 1.

TABLE 1

| | |
|---|---|
| 1 | 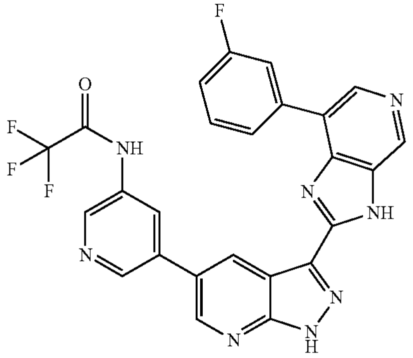 [SMILES: O=C(Nc1cncc(-c2cnc3[nH]nc(-c4nc5c(-c6cccc(F)c6)cncc5[nH]4)c3c2)c1)C(F)(F)F] |

TABLE 1-continued
2
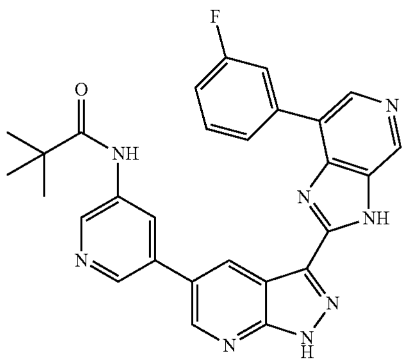 [SMILES: CC(C)(C)C(=O)Nc1cncc(-c2cnc3[nH]nc(-c4nc5c(-c6cccc(F)c6)cncc5[nH]4)c3c2)c1]
3
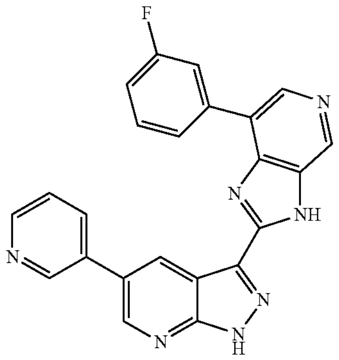
4
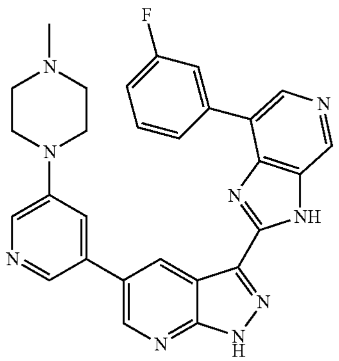 [SMILES: CN1CCN(c2cncc(-c3cnc4[nH]nc(-c5nc6c(-c7cccc(F)c7)cncc6[nH]5)c4c3)c2)CC1]
5
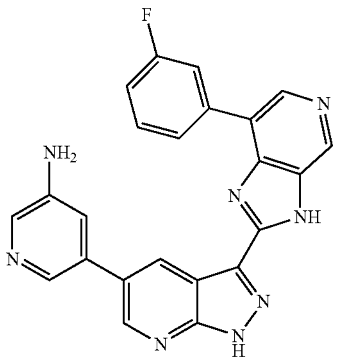 [SMILES: Nc1cncc(-c2cnc3[nH]nc(-c4nc5c(-c6cccc(F)c6)cncc5[nH]4)c3c2)c1]
TABLE 1-continued
6
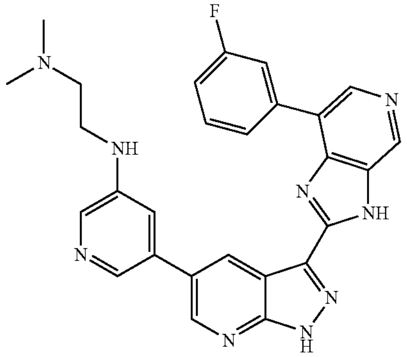 [SMILES: CN(C)CCNc1cncc(-c2cnc3[nH]nc(-c4nc5c(-c6cccc(F)c6)cncc5[nH]4)c3c2)c1]
7
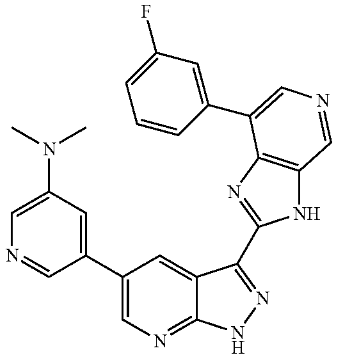 [SMILES: CN(C)c1cncc(-c2cnc3[nH]nc(-c4nc5c(-c6cccc(F)c6)cncc5[nH]4)c3c2)c1]
8
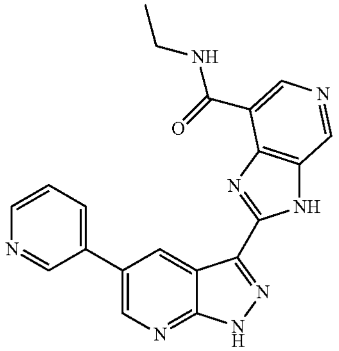 [SMILES: CCNC(=O)c1cncc2[nH]c(-c3n[nH]c4ncc(-c5cccnc5)cc34)nc12]
9
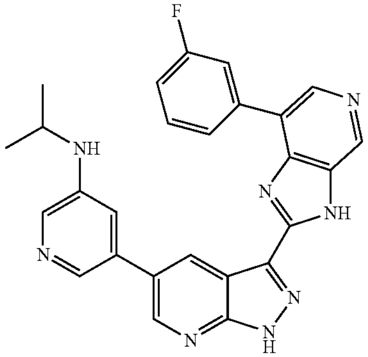 [SMILES: CC(C)Nc1cncc(-c2cnc3[nH]nc(-c4nc5c(-c6cccc(F)c6)cncc5[nH]4)c3c2)c1]

TABLE 1-continued
10
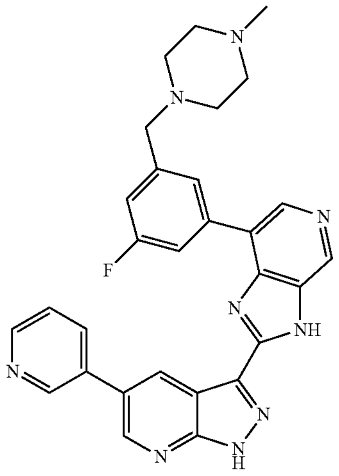
11
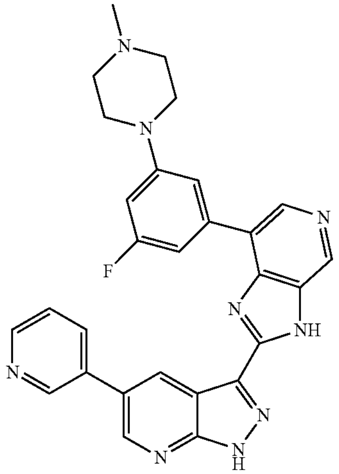
12
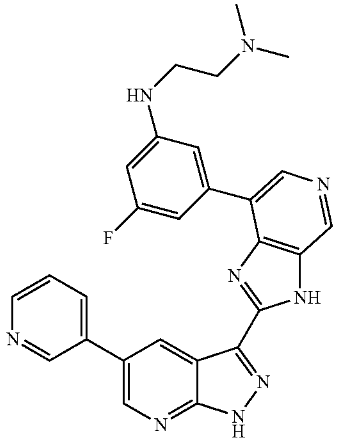 [SMILES: CN(C)CCNc1cc(F)cc(-c2cncc3[nH]c(-c4n[nH]c5ncc(-c6cccnc6)cc45)nc23)c1]
TABLE 1-continued
13
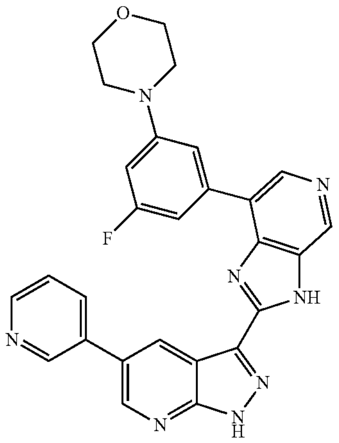 [SMILES: Fc1cc(-c2cncc3[nH]c(-c4n[nH]c5ncc(-c6cccnc6)cc45)nc23)cc(N2CCOCC2)c1]
14
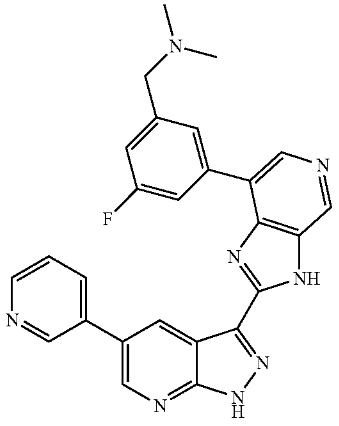 [SMILES: CN(C)Cc1cc(F)cc(-c2cncc3[nH]c(-c4n[nH]c5ncc(-c6cccnc6)cc45)nc23)c1]
15
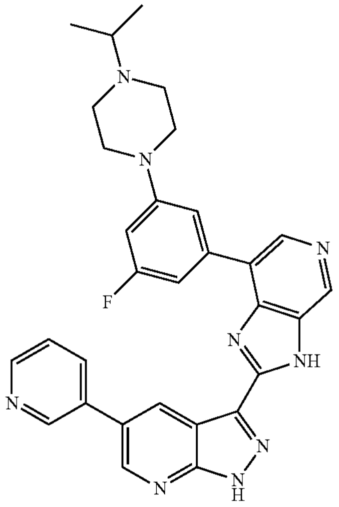 [SMILES: CC(C)N1CCN(c2cc(F)cc(-c3cncc4[nH]c(-c5n[nH]c6ncc(-c7cccnc7)cc56)nc34)c2)CC1]

TABLE 1-continued
16
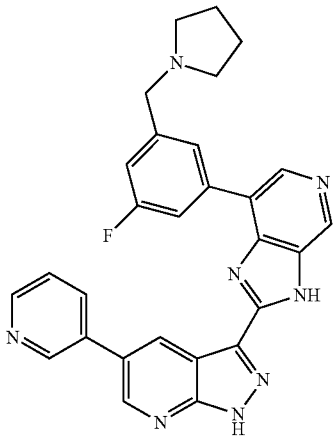
17
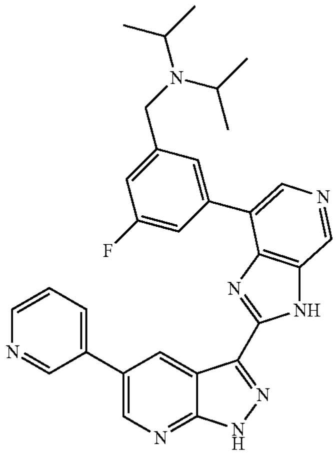 [SMILES: CC(C)N(Cc1cc(F)cc(-c2cncc3[nH]c(-c4n[nH]c5ncc(-c6cccnc6)cc45)nc23)c1)C(C)C]
18
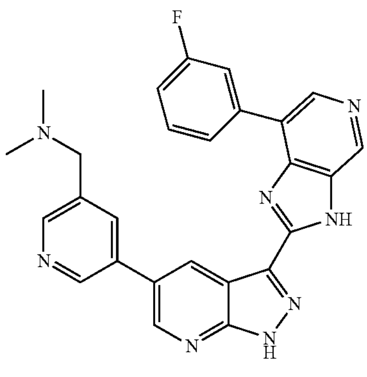 [SMILES: CN(C)Cc1cncc(-c2cnc3[nH]nc(-c4nc5c(-c6cccc(F)c6)cncc5[nH]4)c3c2)c1]
TABLE 1-continued
19
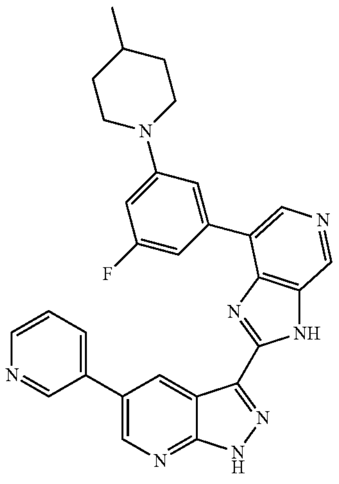
20
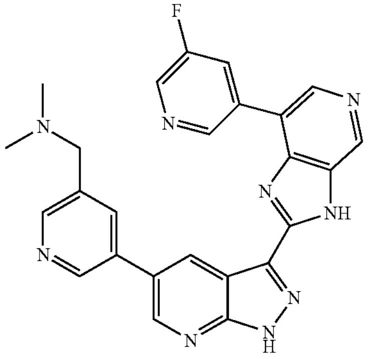 [SMILES: CN(C)Cc1cncc(-c2cnc3[nH]nc(-c4nc5c(-c6cncc(F)c6)cncc5[nH]4)c3c2)c1]
21
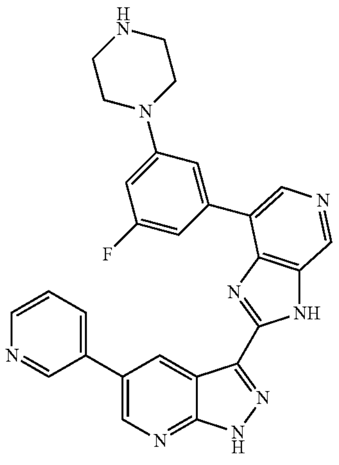 [SMILES: Fc1cc(-c2cncc3[nH]c(-c4n[nH]c5ncc(-c6cccnc6)cc45)nc23)cc(N2CCNCC2)c1]

TABLE 1-continued
22
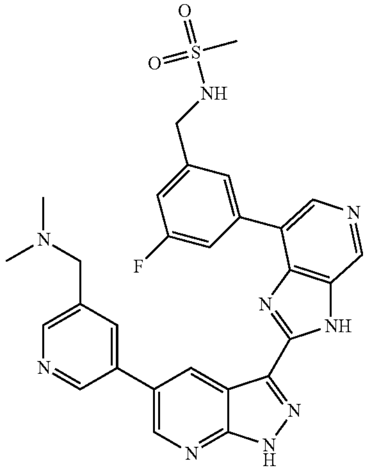 [SMILES: CN(C)Cc1cncc(-c2cnc3[nH]nc(-c4nc5c(-c6cc(F)cc(CNS(C)(=O)=O)c6)cncc5[nH]4)c3c2)c1]
23
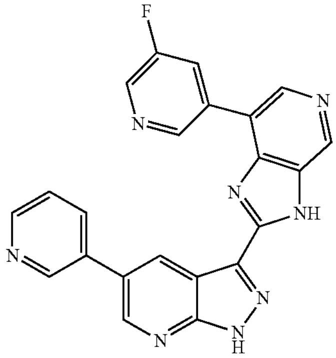 [SMILES: Fc1cncc(-c2cncc3[nH]c(-c4n[nH]c5ncc(-c6cccnc6)cc45)nc23)c1]
24
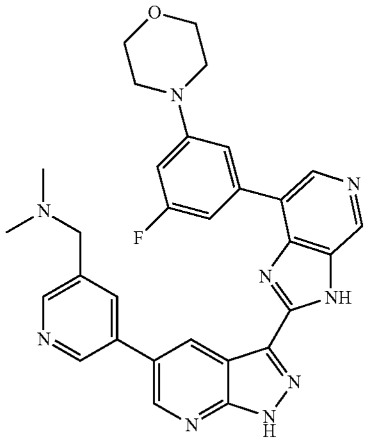 [SMILES: CN(C)Cc1cncc(-c2cnc3[nH]nc(-c4nc5c(-c6cc(F)cc(N7CCOCC7)c6)cncc5[nH]4)c3c2)c1]
25
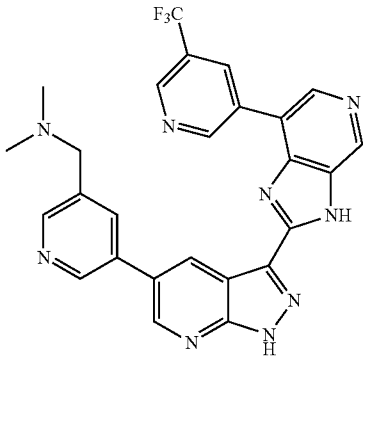
TABLE 1-continued
26
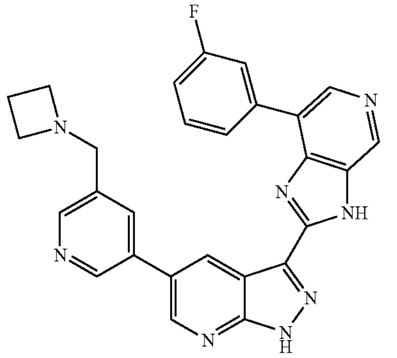 [SMILES: Fc1cccc(-c2cncc3[nH]c(-c4n[nH]c5ncc(-c6cncc(CN7CCC7)c6)cc45)nc23)c1]
27
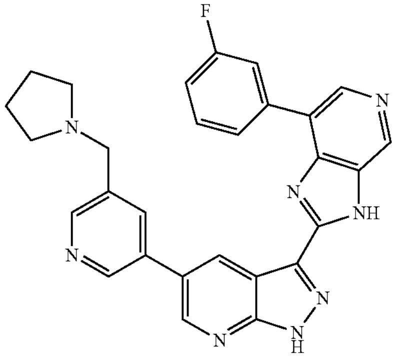 [SMILES: Fc1cccc(-c2cncc3[nH]c(-c4n[nH]c5ncc(-c6cncc(CN7CCCC7)c6)cc45)nc23)c1]
28
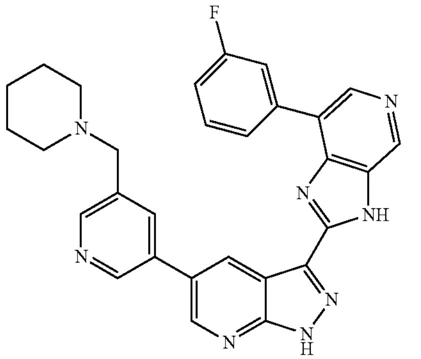 [SMILES: Fc1cccc(-c2cncc3[nH]c(-c4n[nH]c5ncc(-c6cncc(CN7CCCCC7)c6)cc45)nc23)c1]
29
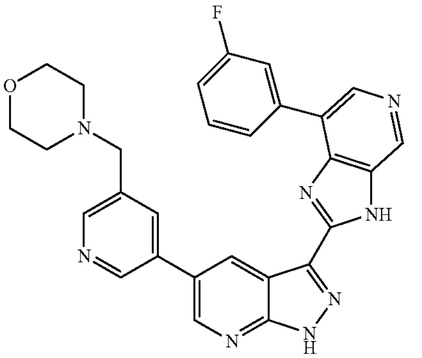 [SMILES: Fc1cccc(-c2cncc3[nH]c(-c4n[nH]c5ncc(-c6cncc(CN7CCOCC7)c6)cc45)nc23)c1]

TABLE 1-continued
30
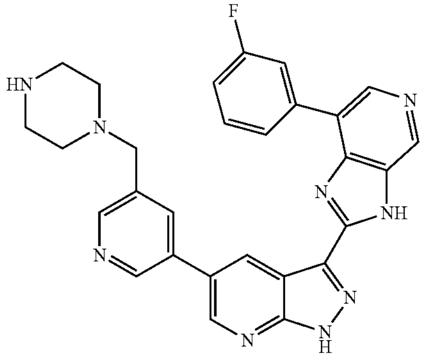 [SMILES: Fc1cccc(-c2cncc3[nH]c(-c4n[nH]c5ncc(-c6cncc(CN7CCNCC7)c6)cc45)nc23)c1]
31
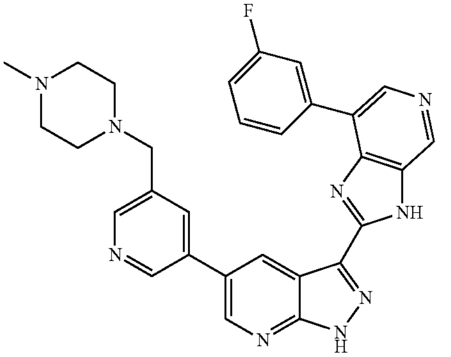 [SMILES: CN1CCN(Cc2cncc(-c3cnc4[nH]nc(-c5nc6c(-c7cccc(F)c7)cncc6[nH]5)c4c3)c2)CC1]
32
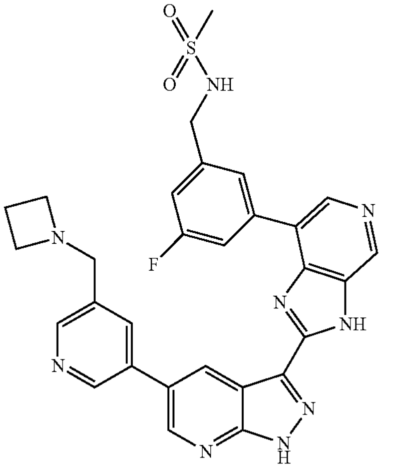 [SMILES: CS(=O)(=O)NCc1cc(F)cc(-c2cncc3[nH]c(-c4n[nH]c5ncc(-c6cncc(CN7CCC7)c6)cc45)nc23)c1]
33
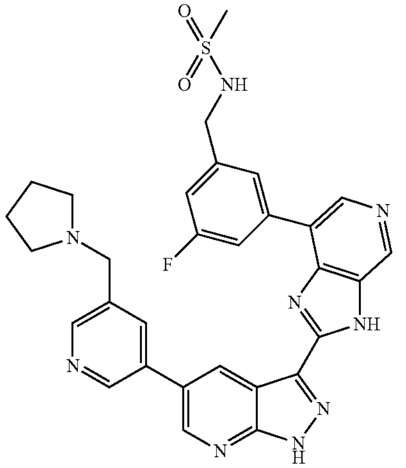 [SMILES: CS(=O)(=O)NCc1cc(F)cc(-c2cncc3[nH]c(-c4n[nH]c5ncc(-c6cncc(CN7CCCC7)c6)cc45)nc23)c1]
TABLE 1-continued
34
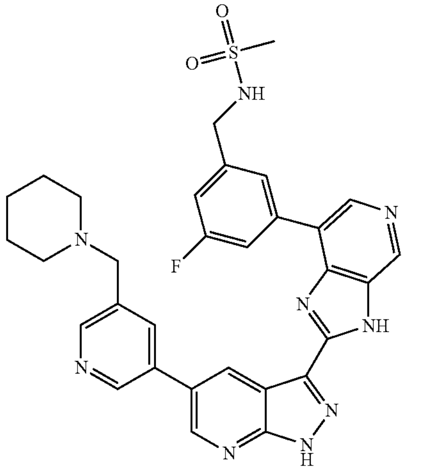 [SMILES: CS(=O)(=O)NCc1cc(F)cc(-c2cncc3[nH]c(-c4n[nH]c5ncc(-c6cncc(CN7CCCCC7)c6)cc45)nc23)c1]
35
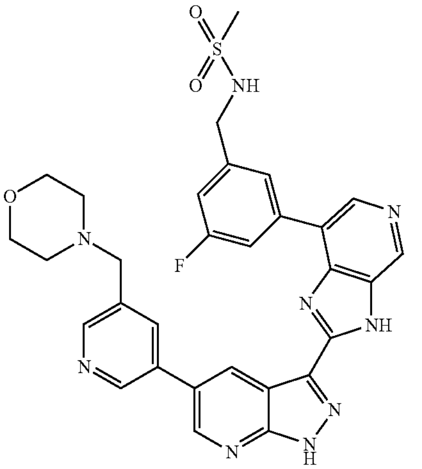 [SMILES: CS(=O)(=O)NCc1cc(F)cc(-c2cncc3[nH]c(-c4n[nH]c5ncc(-c6cncc(CN7CCOCC7)c6)cc45)nc23)c1]
36
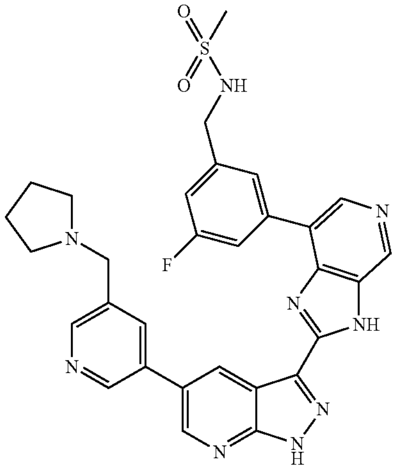 [SMILES: CS(=O)(=O)NCc1cc(F)cc(-c2cncc3[nH]c(-c4n[nH]c5ncc(-c6cncc(CN7CCCC7)c6)cc45)nc23)c1]

TABLE 1-continued
37
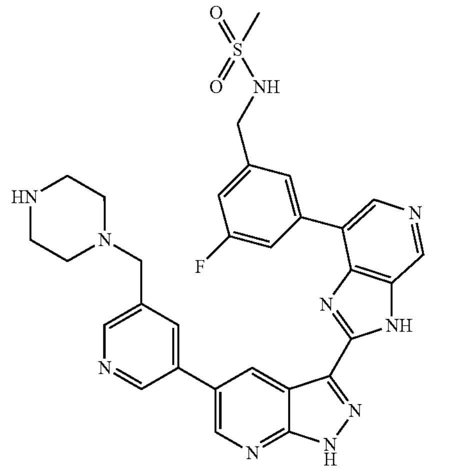 [SMILES: CS(=O)(=O)NCc1cc(F)cc(-c2cncc3[nH]c(-c4n[nH]c5ncc(-c6cncc(CN7CCNCC7)c6)cc45)nc23)c1]
38
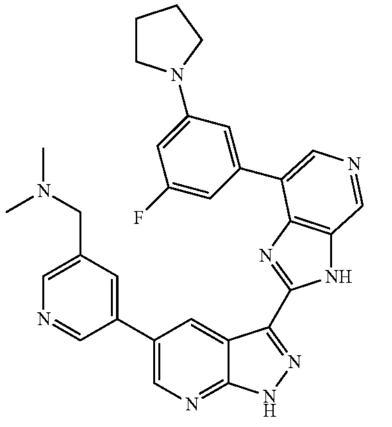 [SMILES: CN(C)Cc1cncc(-c2cnc3[nH]nc(-c4nc5c(-c6cc(F)cc(N7CCCC7)c6)cncc5[nH]4)c3c2)c1]
39
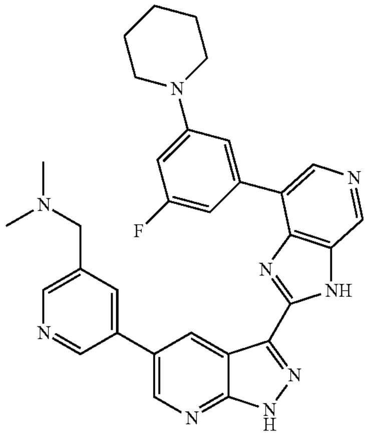 [SMILES: CN(C)Cc1cncc(-c2cnc3[nH]nc(-c4nc5c(-c6cc(F)cc(N7CCCCC7)c6)cncc5[nH]4)c3c2)c1]
TABLE 1-continued
40
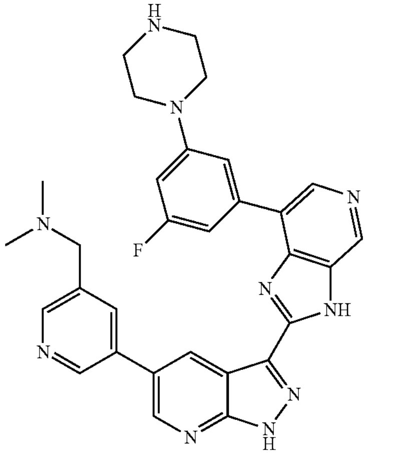 [SMILES: CN(C)Cc1cncc(-c2cnc3[nH]nc(-c4nc5c(-c6cc(F)cc(N7CCNCC7)c6)cncc5[nH]4)c3c2)c1]
41
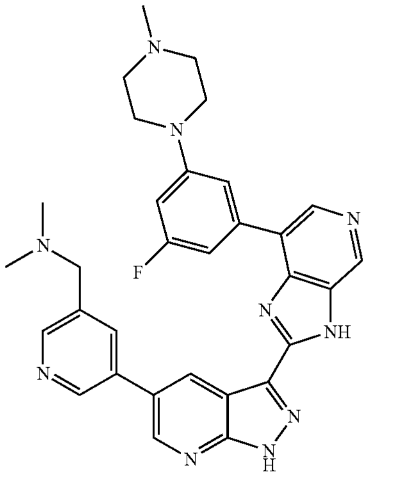 [SMILES: CN(C)Cc1cncc(-c2cnc3[nH]nc(-c4nc5c(-c6cc(F)cc(N7CCN(C)CC7)c6)cncc5[nH]4)c3c2)c1]
42
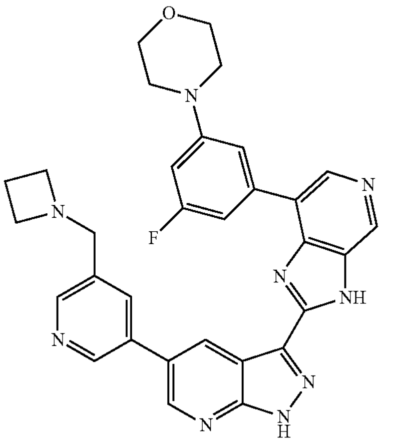 [SMILES: Fc1cc(-c2cncc3[nH]c(-c4n[nH]c5ncc(-c6cncc(CN7CCC7)c6)cc45)nc23)cc(N2CCOCC2)c1]

TABLE 1-continued
43
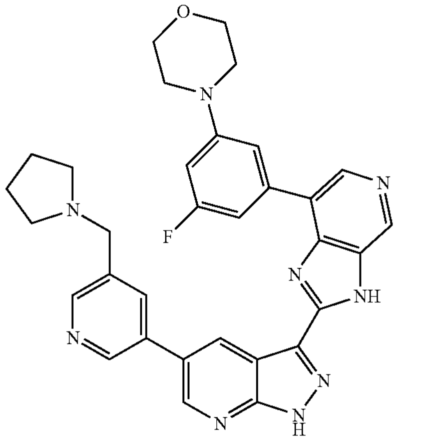 [SMILES: Fc1cc(-c2cncc3[nH]c(-c4n[nH]c5ncc(-c6cncc(CN7CCCC7)c6)cc45)nc23)cc(N2CCOCC2)c1]
44
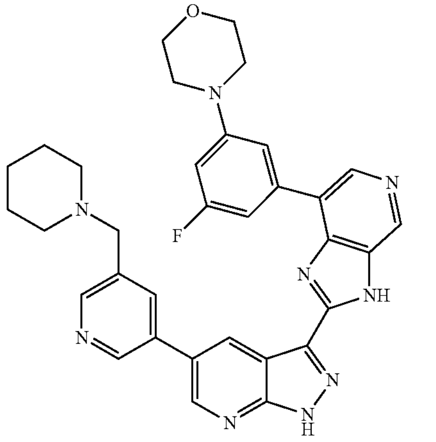 [SMILES: Fc1cc(-c2cncc3[nH]c(-c4n[nH]c5ncc(-c6cncc(CN7CCCCC7)c6)cc45)nc23)cc(N2CCOCC2)c1]
45
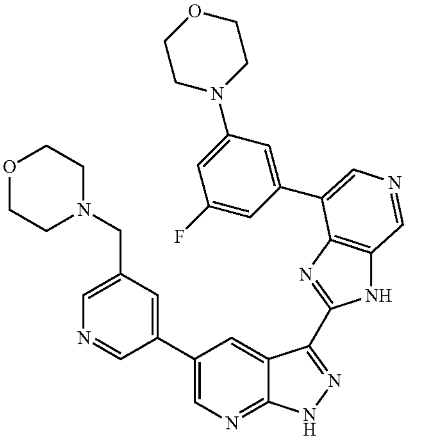 [SMILES: Fc1cc(-c2cncc3[nH]c(-c4n[nH]c5ncc(-c6cncc(CN7CCOCC7)c6)cc45)nc23)cc(N2CCOCC2)c1]
46
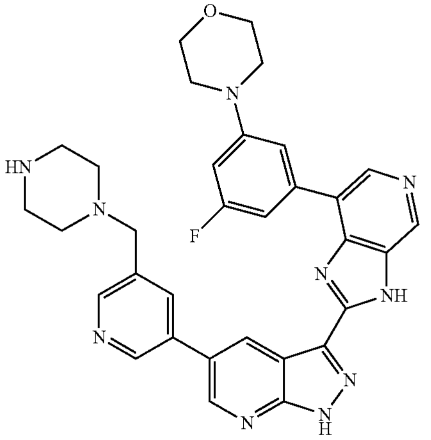 [SMILES: Fc1cc(-c2cncc3[nH]c(-c4n[nH]c5ncc(-c6cncc(CN7CCNCC7)c6)cc45)nc23)cc(N2CCOCC2)c1]
47
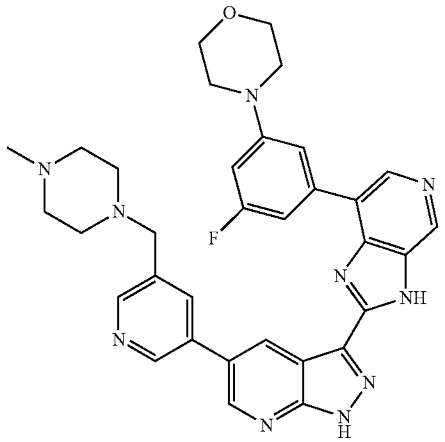 [SMILES: CN1CCN(Cc2cncc(-c3cnc4[nH]nc(-c5nc6c(-c7cc(F)cc(N8CCOCC8)c7)cncc6[nH]5)c4c3)c2)CC1]
48
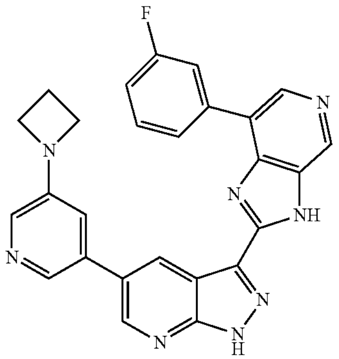 [SMILES: Fc1cccc(-c2cncc3[nH]c(-c4n[nH]c5ncc(-c6cncc(N7CCC7)c6)cc45)nc23)c1]
49
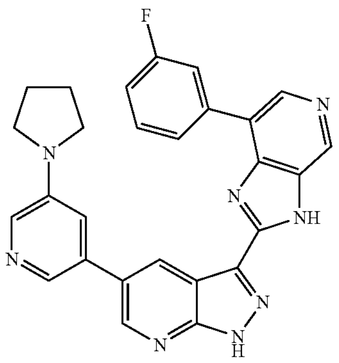 [SMILES: Fc1cccc(-c2cncc3[nH]c(-c4n[nH]c5ncc(-c6cncc(N7CCCC7)c6)cc45)nc23)c1]

TABLE 1-continued
50
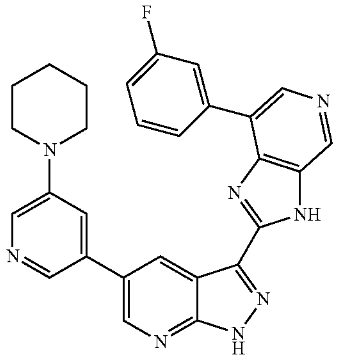
51
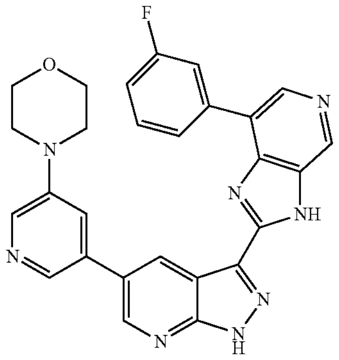 [SMILES: Fc1cccc(-c2cncc3[nH]c(-c4n[nH]c5ncc(-c6cncc(N7CCOCC7)c6)cc45)nc23)c1]
52
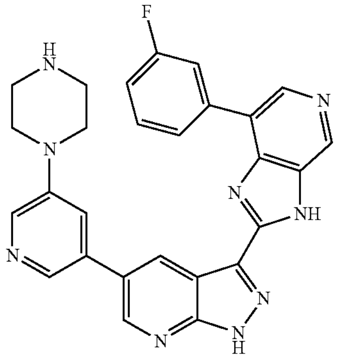 [SMILES: Fc1cccc(-c2cncc3[nH]c(-c4n[nH]c5ncc(-c6cncc(N7CCNCC7)c6)cc45)nc23)c1]
53
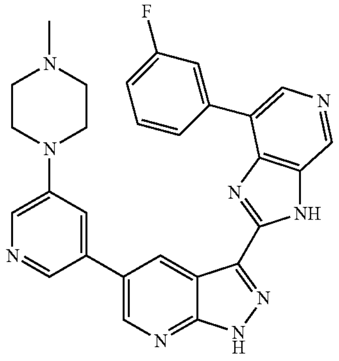 [SMILES: CN1CCN(c2cncc(-c3cnc4[nH]nc(-c5nc6c(-c7cccc(F)c7)cncc6[nH]5)c4c3)c2)CC1]
TABLE 1-continued
54
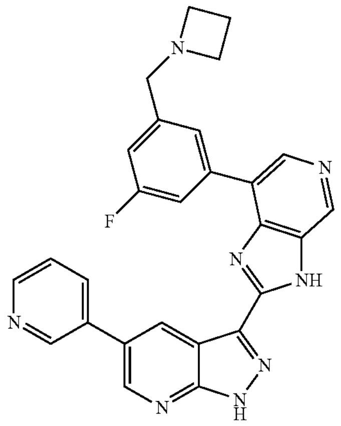 [SMILES: Fc1cc(CN2CCC2)cc(-c2cncc3[nH]c(-c4n[nH]c5ncc(-c6cccnc6)cc45)nc23)c1]
55
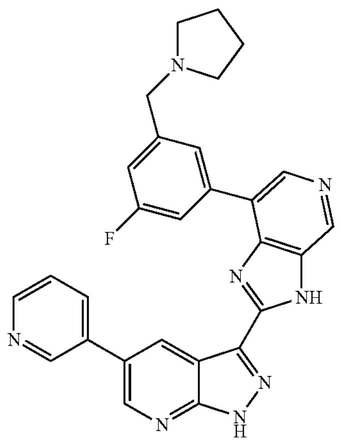
56
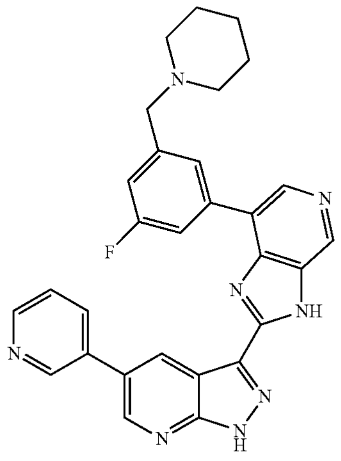

TABLE 1-continued
57
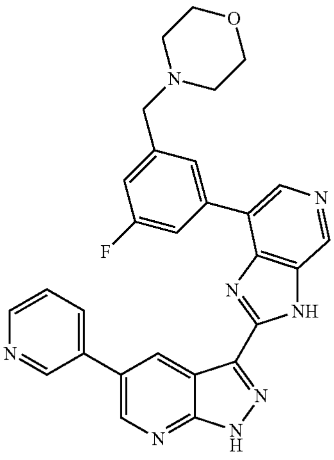 [SMILES: Fc1cc(CN2CCOCC2)cc(-c2cncc3[nH]c(-c4n[nH]c5ncc(-c6cccnc6)cc45)nc23)c1]
58
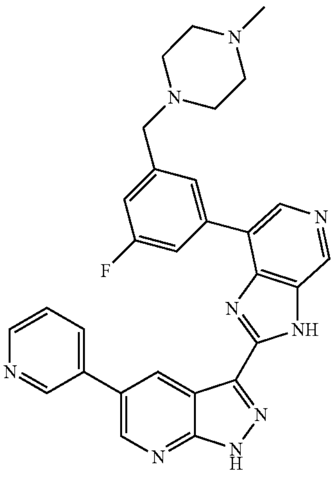
59
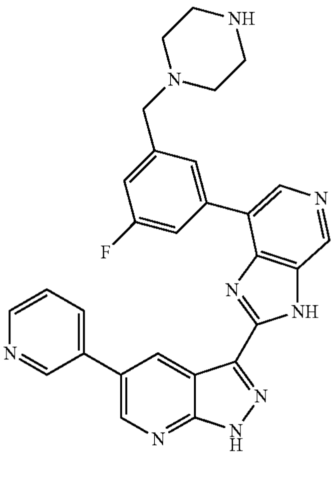 [SMILES: Fc1cc(CN2CCNCC2)cc(-c2cncc3[nH]c(-c4n[nH]c5ncc(-c6cccnc6)cc45)nc23)c1]
TABLE 1-continued
60
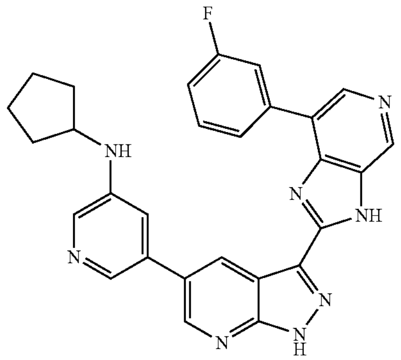 [SMILES: Fc1cccc(-c2cncc3[nH]c(-c4n[nH]c5ncc(-c6cncc(NC7CCCC7)c6)cc45)nc23)c1]
61
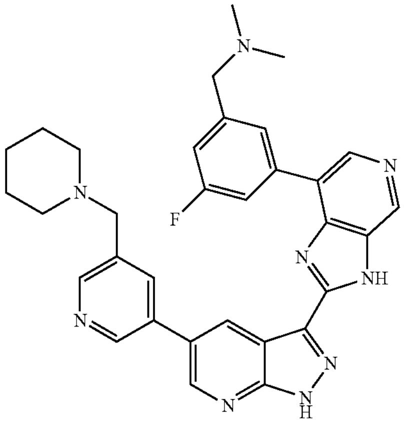
62
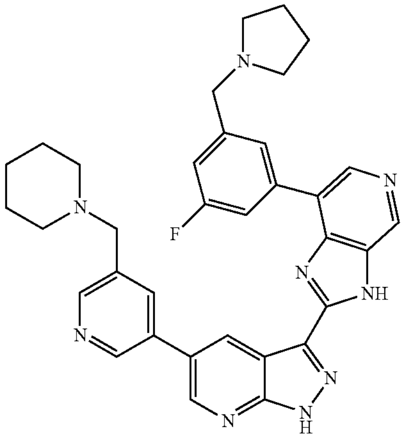 [SMILES: Fc1cc(CN2CCCC2)cc(-c2cncc3[nH]c(-c4n[nH]c5ncc(-c6cncc(CN7CCCCC7)c6)cc45)nc23)c1]
63
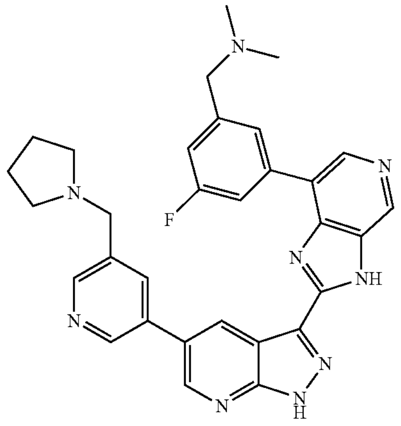

TABLE 1-continued
64
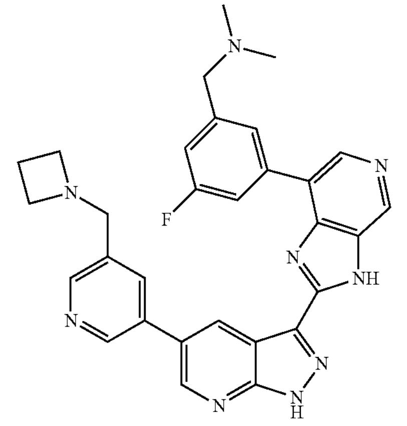 [SMILES: CN(C)Cc1cc(F)cc(-c2cncc3[nH]c(-c4n[nH]c5ncc(-c6cncc(CN7CCC7)c6)cc45)nc23)c1]
65
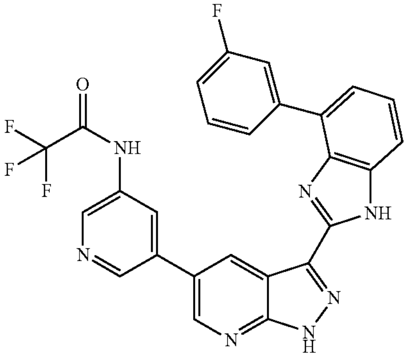
66
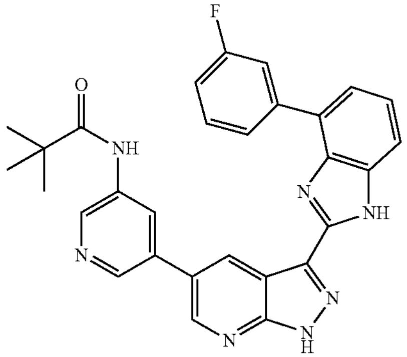 [SMILES: CC(C)(C)C(=O)Nc1cncc(-c2cnc3[nH]nc(-c4nc5c(-c6cccc(F)c6)cccc5[nH]4)c3c2)c1]
67
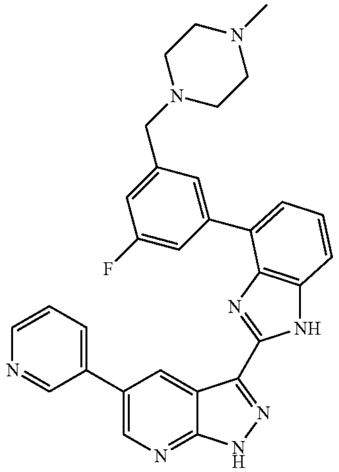 [SMILES: CN1CCN(Cc2cc(F)cc(-c3cccc4[nH]c(-c5n[nH]c6ncc(-c7cccnc7)cc56)nc34)c2)CC1]
TABLE 1-continued
68
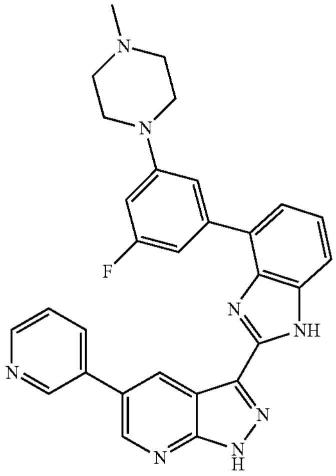 [SMILES: CN1CCN(c2cc(F)cc(-c3cccc4[nH]c(-c5n[nH]c6ncc(-c7cccnc7)cc56)nc34)c2)CC1]
69
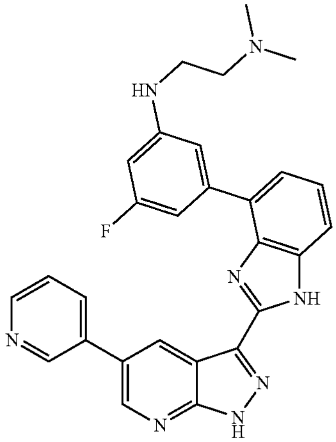 [SMILES: CN(C)CCNc1cc(F)cc(-c2cccc3[nH]c(-c4n[nH]c5ncc(-c6cccnc6)cc45)nc23)c1]
70
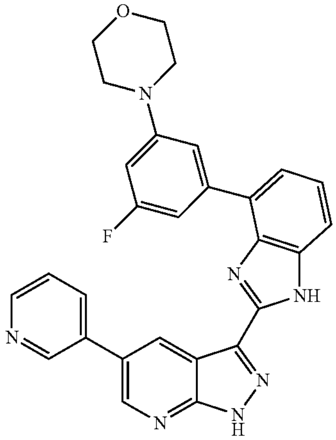 [SMILES: Fc1cc(-c2cccc3[nH]c(-c4n[nH]c5ncc(-c6cccnc6)cc45)nc23)cc(N2CCOCC2)c1]

TABLE 1-continued
71
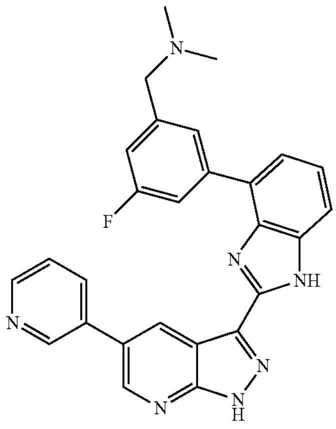 [SMILES: CN(C)Cc1cc(F)cc(-c2cccc3[nH]c(-c4n[nH]c5ncc(-c6cccnc6)cc45)nc23)c1]
72
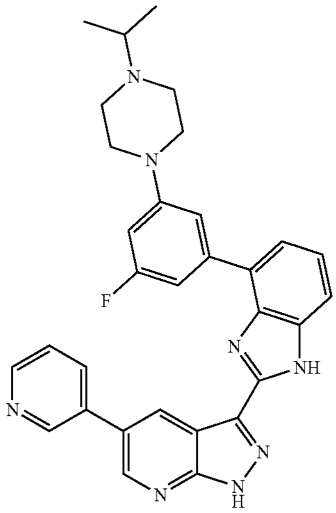 [SMILES: CC(C)N1CCN(c2cc(F)cc(-c3cccc4[nH]c(-c5n[nH]c6ncc(-c7cccnc7)cc56)nc34)c2)CC1]
73
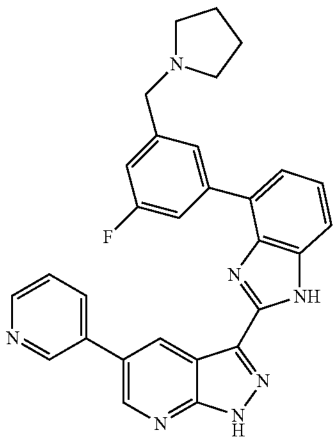 [SMILES: Fc1cc(CN2CCCC2)cc(-c2cccc3[nH]c(-c4n[nH]c5ncc(-c6cccnc6)cc45)nc23)c1]
TABLE 1-continued
74
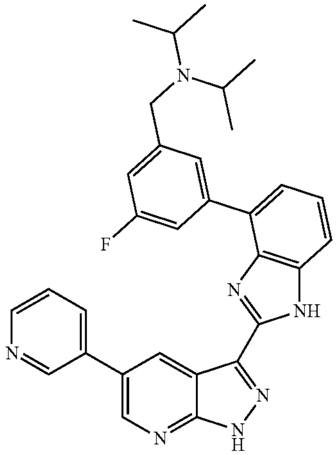 [SMILES: CC(C)N(Cc1cc(F)cc(-c2cccc3[nH]c(-c4n[nH]c5ncc(-c6cccnc6)cc45)nc23)c1)C(C)C]
75
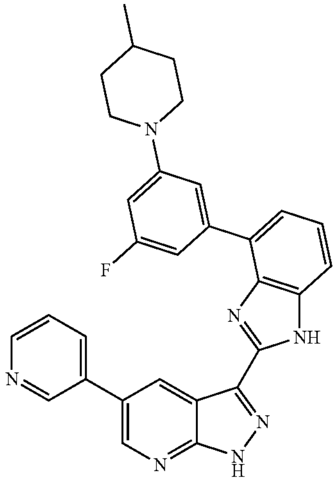 [SMILES: CC1CCN(c2cc(F)cc(-c3cccc4[nH]c(-c5n[nH]c6ncc(-c7cccnc7)cc56)nc34)c2)CC1]
76
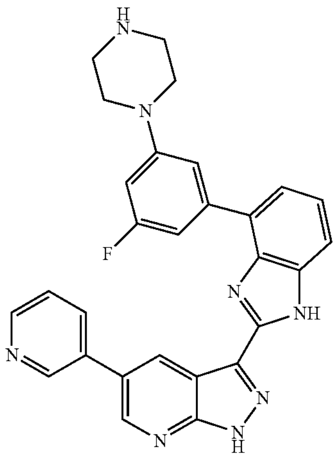 [SMILES: Fc1cc(-c2cccc3[nH]c(-c4n[nH]c5ncc(-c6cccnc6)cc45)nc23)cc(N2CCNCC2)c1]

TABLE 1-continued
77
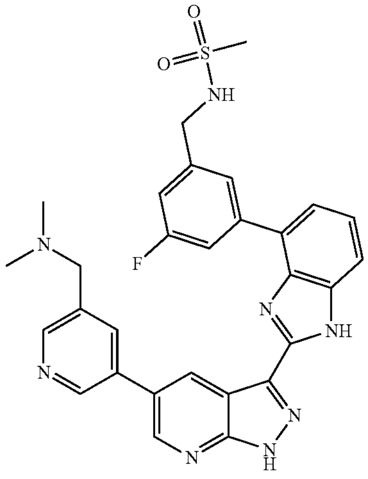 [SMILES: CN(C)Cc1cncc(-c2cnc3[nH]nc(-c4nc5c(-c6cc(F)cc(CNS(C)(=O)=O)c6)cccc5[nH]4)c3c2)c1]
78
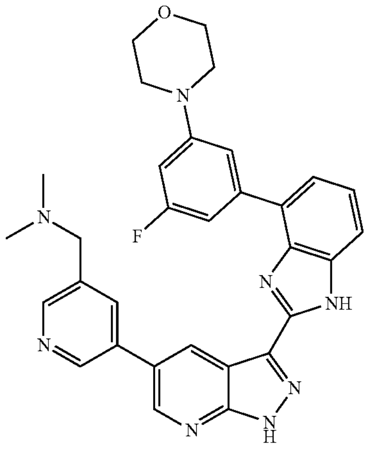 [SMILES: CN(C)Cc1cncc(-c2cnc3[nH]nc(-c4nc5c(-c6cc(F)cc(N7CCOCC7)c6)cccc5[nH]4)c3c2)c1]
79
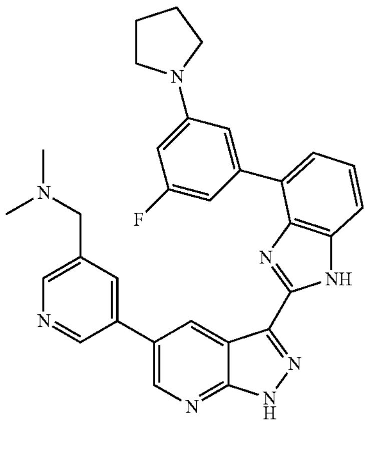 [SMILES: CN(C)Cc1cncc(-c2cnc3[nH]nc(-c4nc5c(-c6cc(F)cc(N7CCCC7)c6)cccc5[nH]4)c3c2)c1]
TABLE 1-continued
80
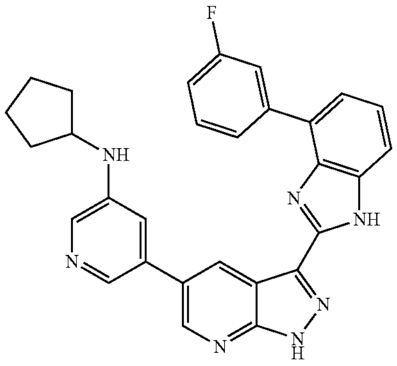 [SMILES: Fc1cccc(-c2cccc3[nH]c(-c4n[nH]c5ncc(-c6cncc(NC7CCCC7)c6)cc45)nc23)c1]
81
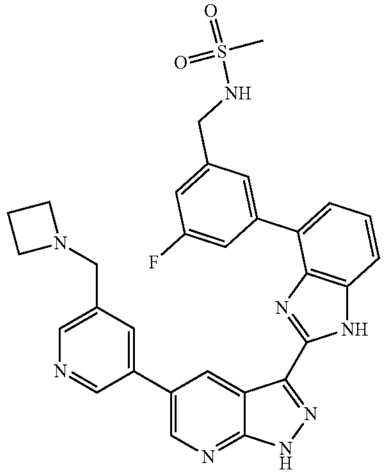 [SMILES: CS(=O)(=O)NCc1cc(F)cc(-c2cccc3[nH]c(-c4n[nH]c5ncc(-c6cncc(CN7CCC7)c6)cc45)nc23)c1]
82
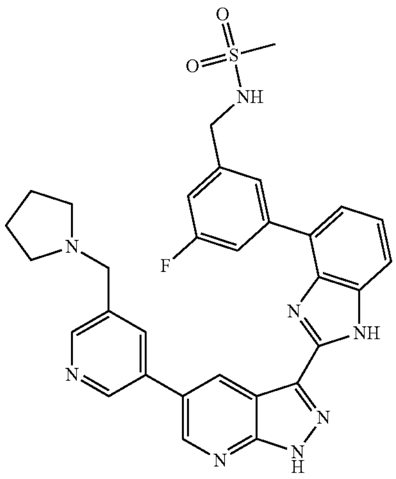 [SMILES: CS(=O)(=O)NCc1cc(F)cc(-c2cccc3[nH]c(-c4n[nH]c5ncc(-c6cncc(CN7CCCC7)c6)cc45)nc23)c1]

TABLE 1-continued
83
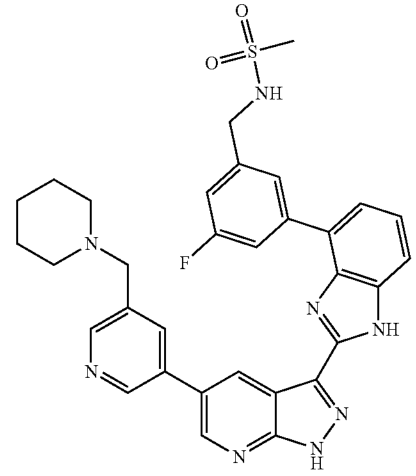 [SMILES: CS(=O)(=O)NCc1cc(F)cc(-c2cccc3[nH]c(-c4n[nH]c5ncc(-c6cncc(CN7CCCCC7)c6)cc45)nc23)c1]
84
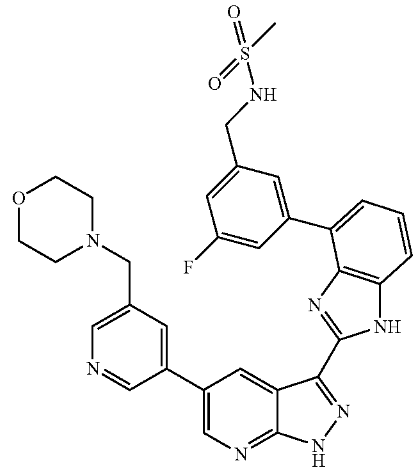 [SMILES: CS(=O)(=O)NCc1cc(F)cc(-c2cccc3[nH]c(-c4n[nH]c5ncc(-c6cncc(CN7CCOCC7)c6)cc45)nc23)c1]
85
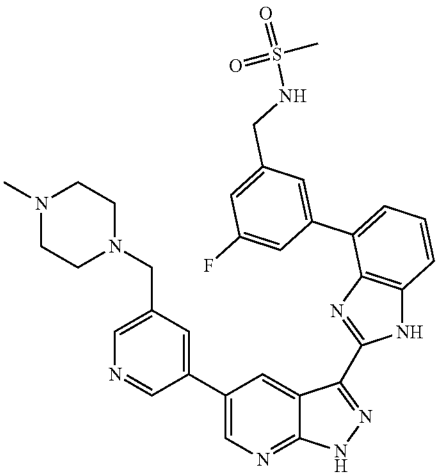 [SMILES: CN1CCN(Cc2cncc(-c3cnc4[nH]nc(-c5nc6c(-c7cc(F)cc(CNS(C)(=O)=O)c7)cccc6[nH]5)c4c3)c2)CC1]
TABLE 1-continued
86
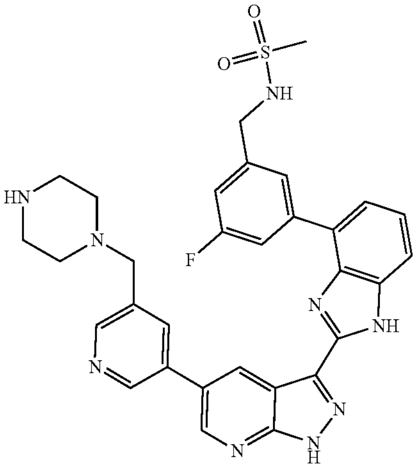 [SMILES: C[S@SP2](=O)(=O)NCc1cc(F)cc(-c2cccc3[nH]c(-c4n[nH]c5ncc(-c6cncc(CN7CCNCC7)c6)cc45)nc23)c1]
87
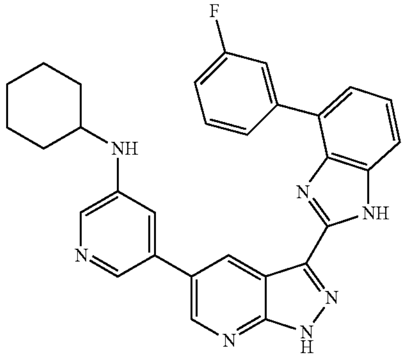 [SMILES: Fc1cccc(-c2cccc3[nH]c(-c4n[nH]c5ncc(-c6cncc(NC7CCCCC7)c6)cc45)nc23)c1]
88
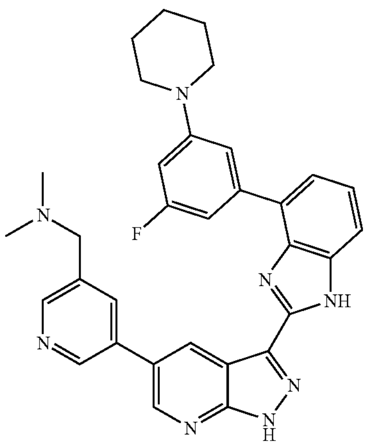 [SMILES: CN(C)Cc1cncc(-c2cnc3[nH]nc(-c4nc5c(-c6cc(F)cc(N7CCCCC7)c6)cccc5[nH]4)c3c2)c1]

TABLE 1-continued
89
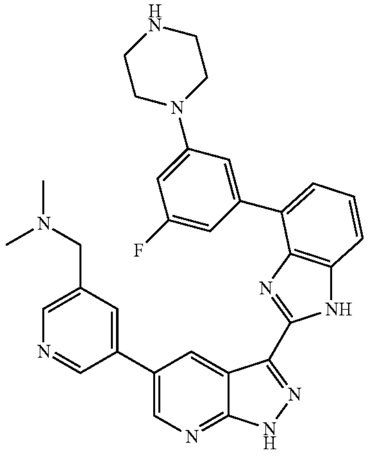
90
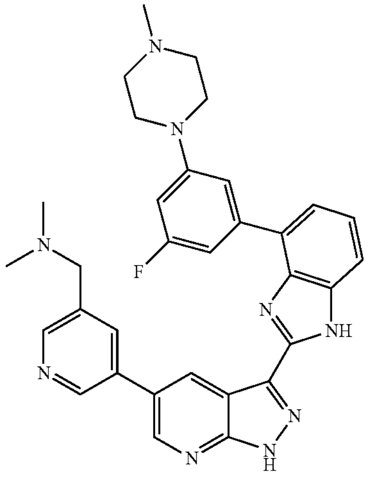
91
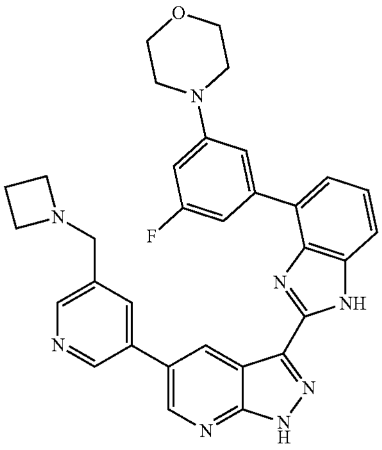 [SMILES: Fc1cc(-c2cccc3[nH]c(-c4n[nH]c5ncc(-c6cncc(CN7CCC7)c6)cc45)nc23)cc(N2CCOCC2)c1]
TABLE 1-continued
92
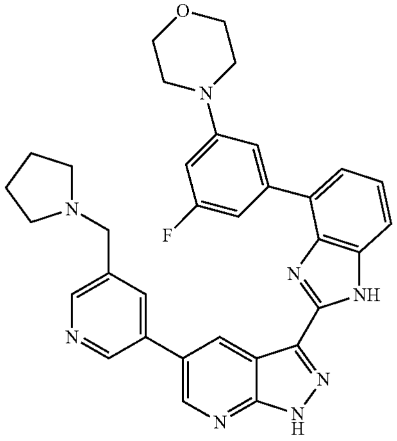 [SMILES: Fc1cc(-c2cccc3[nH]c(-c4n[nH]c5ncc(-c6cncc(CN7CCCC7)c6)cc45)nc23)cc(N2CCOCC2)c1]
93
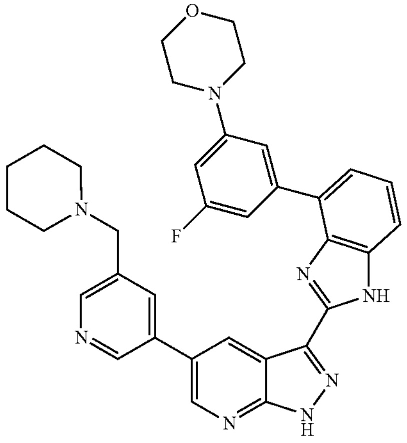 [SMILES: Fc1cc(-c2cccc3[nH]c(-c4n[nH]c5ncc(-c6cncc(CN7CCCCC7)c6)cc45)nc23)cc(N2CCOCC2)c1]
94
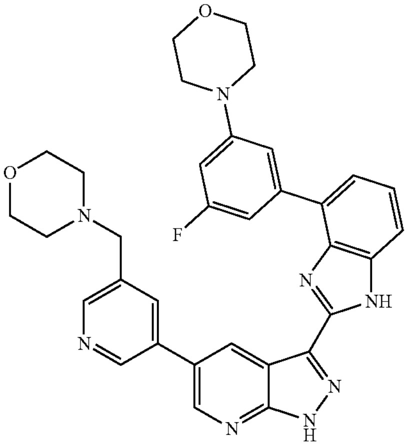 [SMILES: Fc1cc(-c2cccc3[nH]c(-c4n[nH]c5ncc(-c6cncc(CN7CCOCC7)c6)cc45)nc23)cc(N2CCOCC2)c1]

95
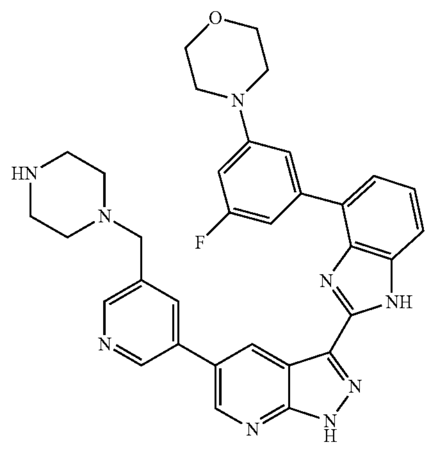 [SMILES: Fc1cc(-c2cccc3[nH]c(-c4n[nH]c5ncc(-c6cncc(CN7CCNCC7)c6)cc45)nc23)cc(N2CCOCC2)c1]
96
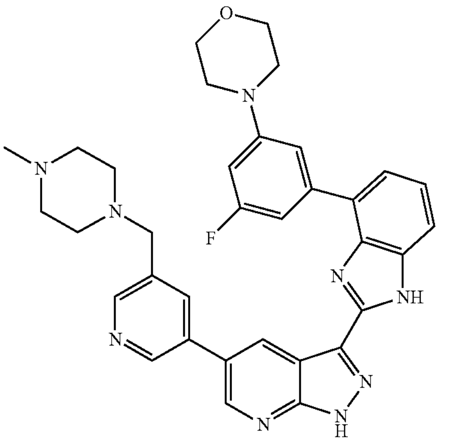 [SMILES: CN1CCN(Cc2cncc(-c3cnc4[nH]nc(-c5nc6c(-c7cc(F)cc(N8CCOCC8)c7)cccc6[nH]5)c4c3)c2)CC1]
97
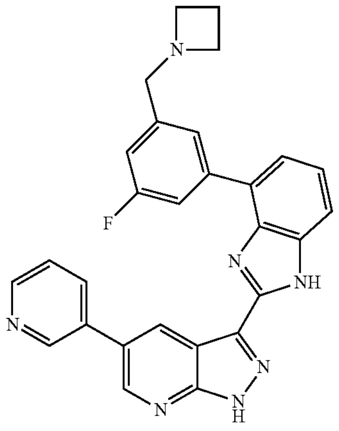 [SMILES: Fc1cc(CN2CCC2)cc(-c2cccc3[nH]c(-c4n[nH]c5ncc(-c6cccnc6)cc45)nc23)c1]
98
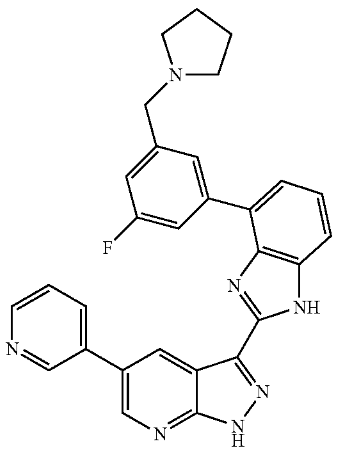 [SMILES: Fc1cc(CN2CCCC2)cc(-c2cccc3[nH]c(-c4n[nH]c5ncc(-c6cccnc6)cc45)nc23)c1]
99
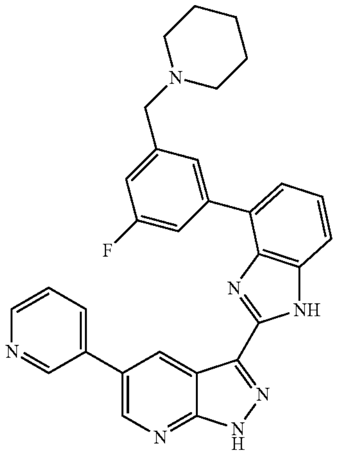
100
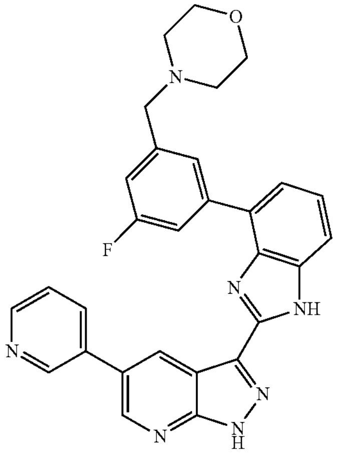

TABLE 1-continued
101
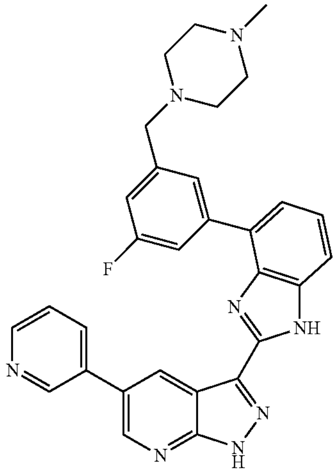 [SMILES: CN1CCN(Cc2cc(F)cc(-c3cccc4[nH]c(-c5n[nH]c6ncc(-c7cccnc7)cc56)nc34)c2)CC1]
102
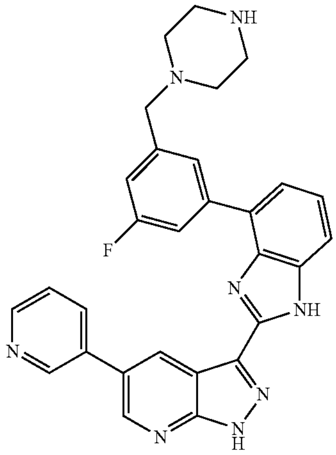
103
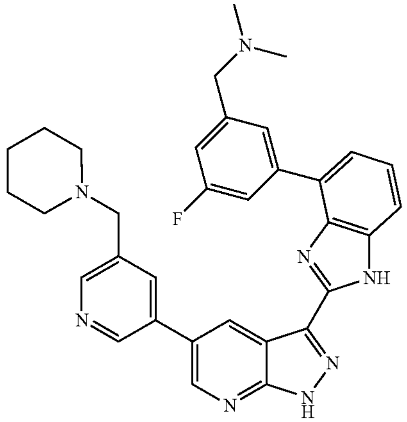 [SMILES: CN(C)Cc1cc(F)cc(-c2cccc3[nH]c(-c4n[nH]c5ncc(-c6cncc(CN7CCCCC7)c6)cc45)nc23)c1]
TABLE 1-continued
104
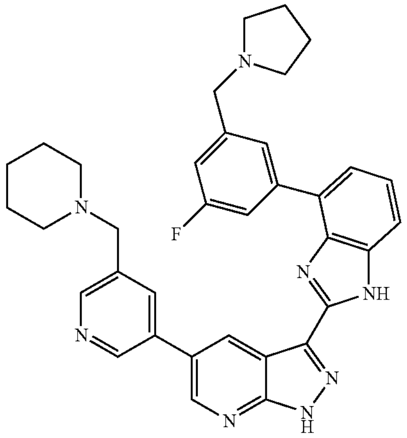
105
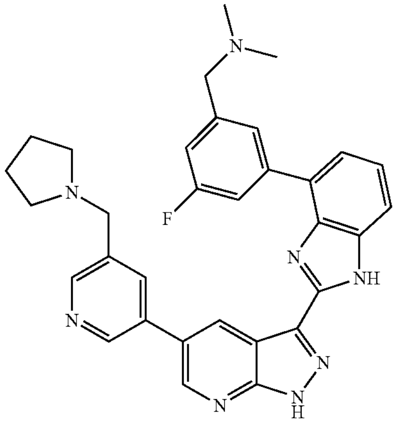 [SMILES: CN(C)Cc1cc(F)cc(-c2cccc3[nH]c(-c4n[nH]c5ncc(-c6cncc(CN7CCCC7)c6)cc45)nc23)c1]
106
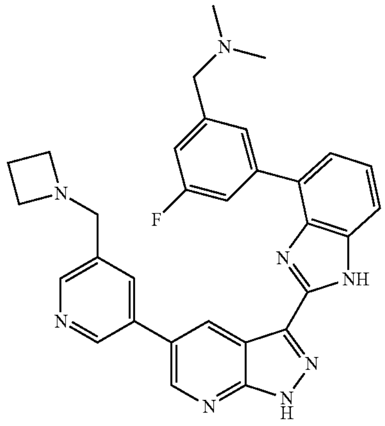 [SMILES: CN(C)Cc1cc(F)cc(-c2cccc3[nH]c(-c4n[nH]c5ncc(-c6cncc(CN7CCC7)c6)cc45)nc23)c1]
107
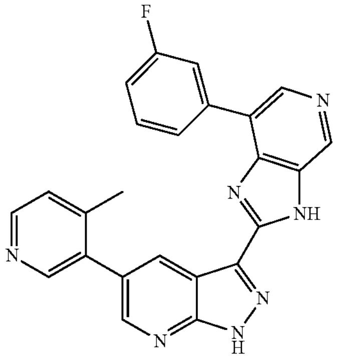 [SMILES: Cc1ccncc1-c1cnc2[nH]nc(-c3nc4c(-c5cccc(F)c5)cncc4[nH]3)c2c1]

TABLE 1-continued
108
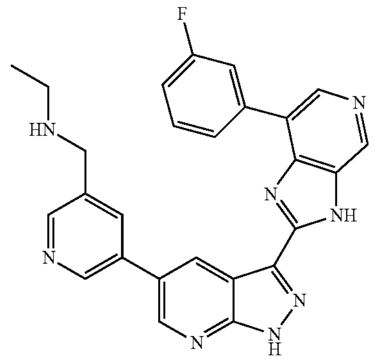 [SMILES: CCNCc1cncc(-c2cnc3[nH]nc(-c4nc5c(-c6cccc(F)c6)cncc5[nH]4)c3c2)c1]
109
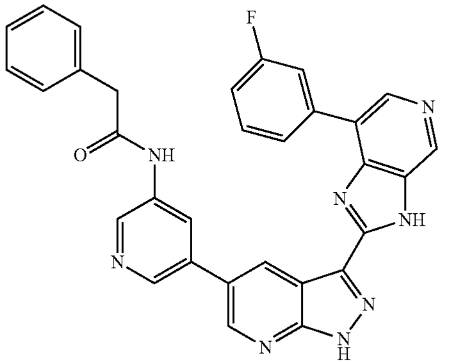 [SMILES: O=C(Cc1ccccc1)Nc1cncc(-c2cnc3[nH]nc(-c4nc5c(-c6cccc(F)c6)cncc5[nH]4)c3c2)c1]
110
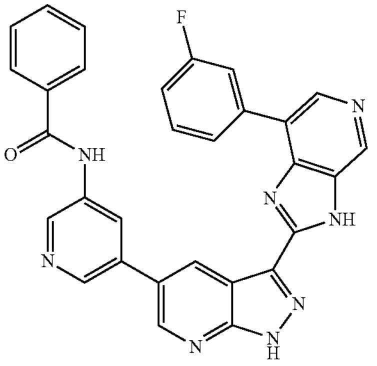 [SMILES: O=C(Nc1cncc(-c2cnc3[nH]nc(-c4nc5c(-c6cccc(F)c6)cncc5[nH]4)c3c2)c1)c1ccccc1]
111
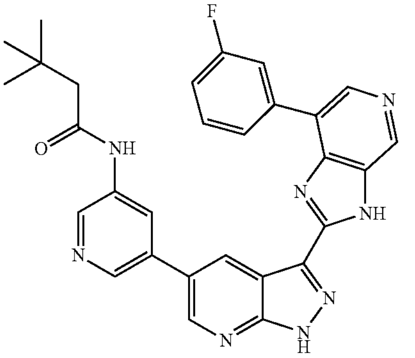 [SMILES: CC(C)(C)CC(=O)Nc1cncc(-c2cnc3[nH]nc(-c4nc5c(-c6cccc(F)c6)cncc5[nH]4)c3c2)c1]
TABLE 1-continued
112
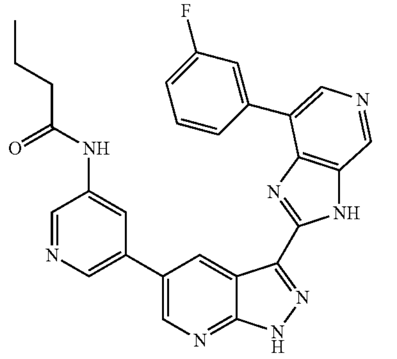 [SMILES: CCCC(=O)Nc1cncc(-c2cnc3[nH]nc(-c4nc5c(-c6cccc(F)c6)cncc5[nH]4)c3c2)c1]
113
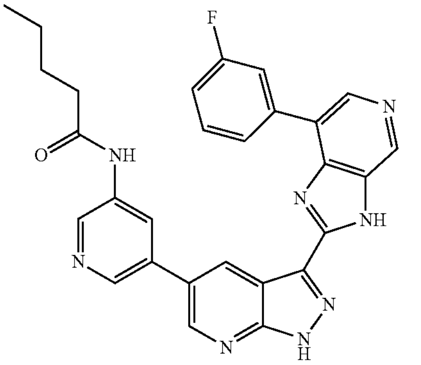 [SMILES: CCCCC(=O)Nc1cncc(-c2cnc3[nH]nc(-c4nc5c(-c6cccc(F)c6)cncc5[nH]4)c3c2)c1]
114
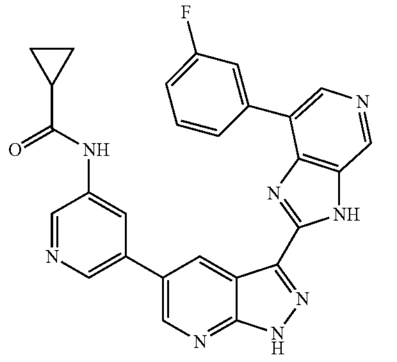 [SMILES: O=C(Nc1cncc(-c2cnc3[nH]nc(-c4nc5c(-c6cccc(F)c6)cncc5[nH]4)c3c2)c1)C1CC1]
115
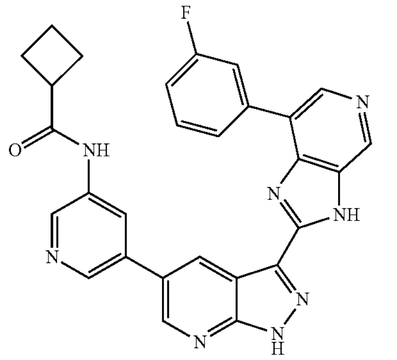 [SMILES: O=C(Nc1cncc(-c2cnc3[nH]nc(-c4nc5c(-c6cccc(F)c6)cncc5[nH]4)c3c2)c1)C1CCC1]

TABLE 1-continued
116
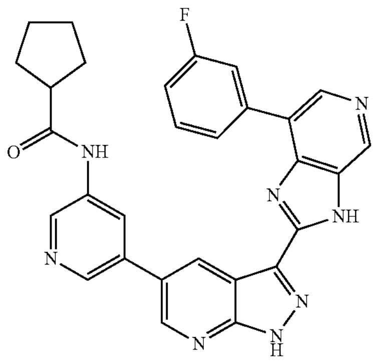 [SMILES: O=C(Nc1cncc(-c2cnc3[nH]nc(-c4nc5c(-c6cccc(F)c6)cncc5[nH]4)c3c2)c1)C1CCCC1]
117
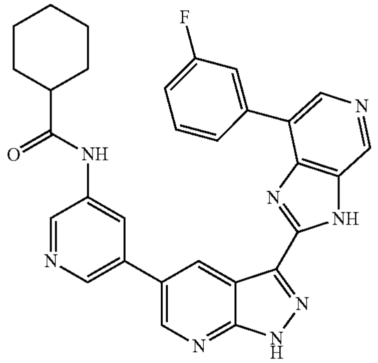 [SMILES: O=C(Nc1cncc(-c2cnc3[nH]nc(-c4nc5c(-c6cccc(F)c6)cncc5[nH]4)c3c2)c1)C1CCCCC1]
118
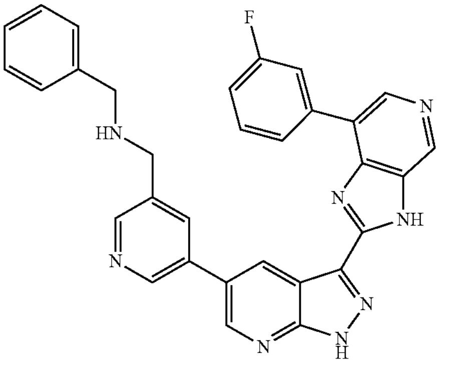 [SMILES: Fc1cccc(-c2cncc3[nH]c(-c4n[nH]c5ncc(-c6cncc(CNCc7ccccc7)c6)cc45)nc23)c1]
119
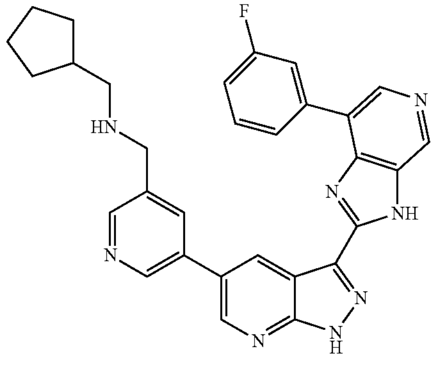 [SMILES: Fc1cccc(-c2cncc3[nH]c(-c4n[nH]c5ncc(-c6cncc(CNCC7CCCC7)c6)cc45)nc23)c1]
TABLE 1-continued
120
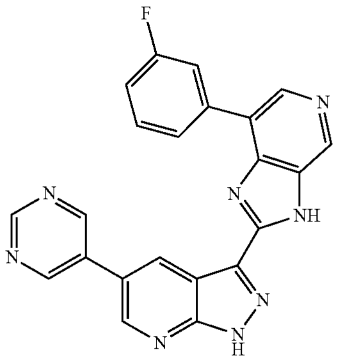 [SMILES: Fc1cccc(-c2cncc3[nH]c(-c4n[nH]c5ncc(-c6cncnc6)cc45)nc23)c1]
121
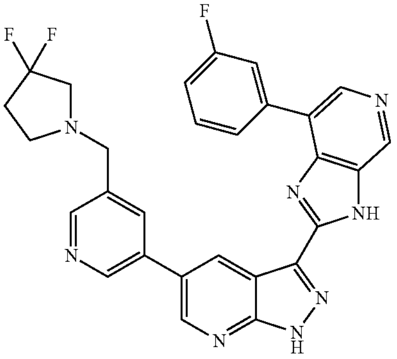 [SMILES: Fc1cccc(-c2cncc3[nH]c(-c4n[nH]c5ncc(-c6cncc(CN7CCC(F)(F)C7)c6)cc45)nc23)c1]
122
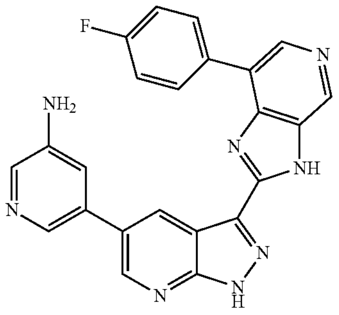
123
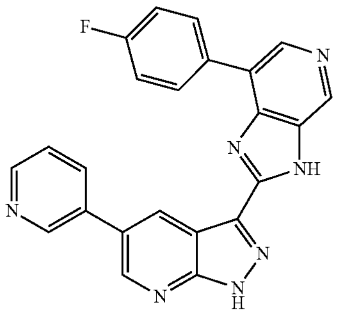 [SMILES: Fc1ccc(-c2cncc3[nH]c(-c4n[nH]c5ncc(-c6cccnc6)cc45)nc23)cc1]

TABLE 1-continued
124
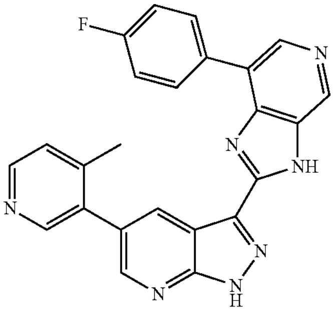 [SMILES: Cc1ccncc1-c1cnc2[nH]nc(-c3nc4c(-c5ccc(F)cc5)cncc4[nH]3)c2c1]
125
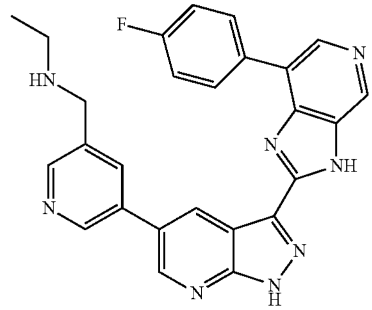 [SMILES: CCNCc1cncc(-c2cnc3[nH]nc(-c4nc5c(-c6ccc(F)cc6)cncc5[nH]4)c3c2)c1]
126
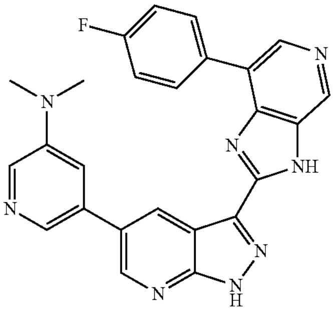 [SMILES: CN(C)c1cncc(-c2cnc3[nH]nc(-c4nc5c(-c6ccc(F)cc6)cncc5[nH]4)c3c2)c1]
127
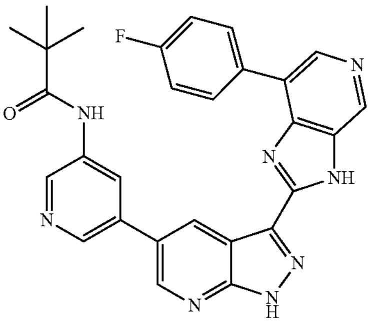 [SMILES: CC(C)(C)C(=O)Nc1cncc(-c2cnc3[nH]nc(-c4nc5c(-c6ccc(F)cc6)cncc5[nH]4)c3c2)c1]
128
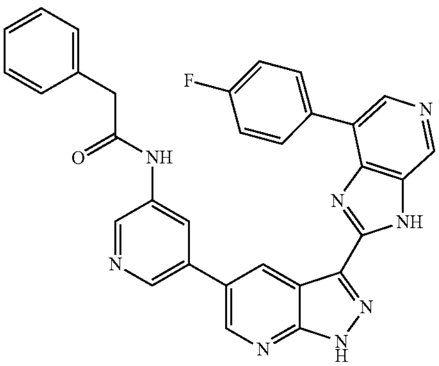 [SMILES: O=C(Cc1ccccc1)Nc1cncc(-c2cnc3[nH]nc(-c4nc5c(-c6ccc(F)cc6)cncc5[nH]4)c3c2)c1]
TABLE 1-continued
129
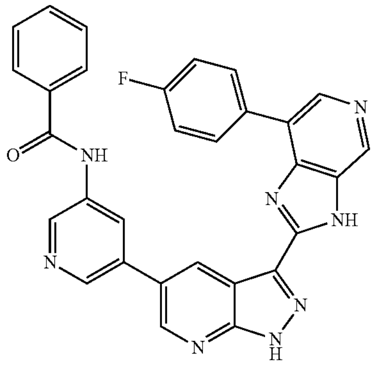 [SMILES: O=C(Nc1cncc(-c2cnc3[nH]nc(-c4nc5c(-c6ccc(F)cc6)cncc5[nH]4)c3c2)c1)c1ccccc1]
130
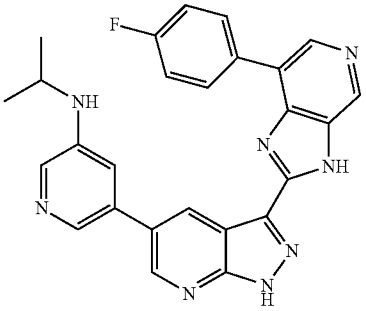 [SMILES: CC(C)Nc1cncc(-c2cnc3[nH]nc(-c4nc5c(-c6ccc(F)cc6)cncc5[nH]4)c3c2)c1]
131
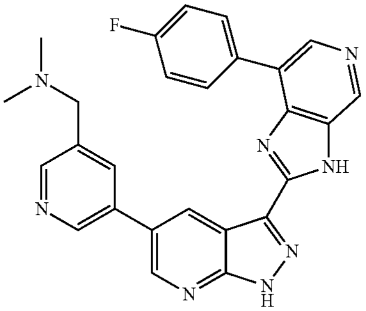 [SMILES: CN(C)Cc1cncc(-c2cnc3[nH]nc(-c4nc5c(-c6ccc(F)cc6)cncc5[nH]4)c3c2)c1]
132
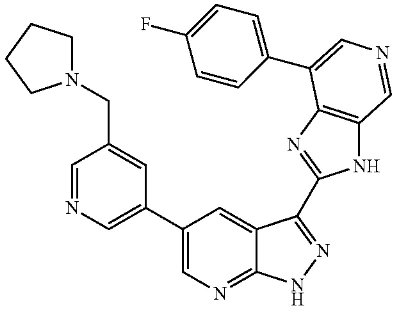 [SMILES: Fc1ccc(-c2cncc3[nH]c(-c4n[nH]c5ncc(-c6cncc(CN7CCCC7)c6)cc45)nc23)cc1]
133
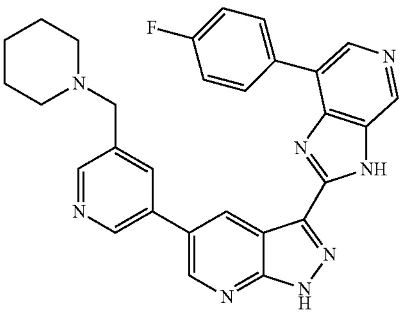 [SMILES: Fc1ccc(-c2cncc3[nH]c(-c4n[nH]c5ncc(-c6cncc(CN7CCCCC7)c6)cc45)nc23)cc1]

TABLE 1-continued
134
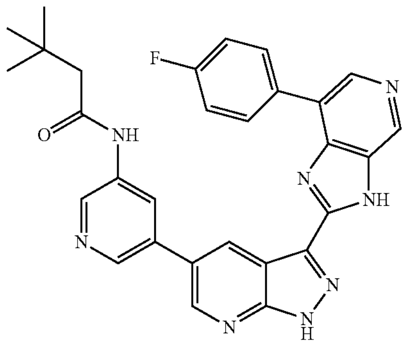 [SMILES: CC(C)(C)CC(=O)Nc1cncc(-c2cnc3[nH]nc(-c4nc5c(-c6ccc(F)cc6)cncc5[nH]4)c3c2)c1]
135
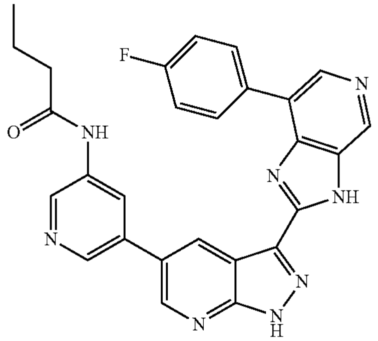 [SMILES: CCCC(=O)Nc1cncc(-c2cnc3[nH]nc(-c4nc5c(-c6ccc(F)cc6)cncc5[nH]4)c3c2)c1]
136
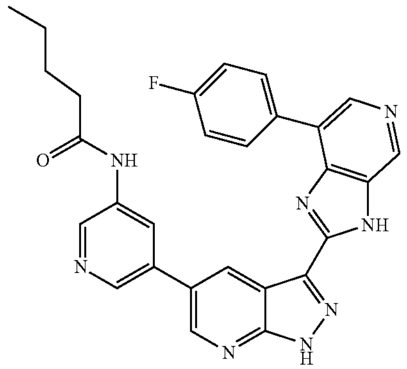 [SMILES: CCCCC(=O)Nc1cncc(-c2cnc3[nH]nc(-c4nc5c(-c6ccc(F)cc6)cncc5[nH]4)c3c2)c1]
137
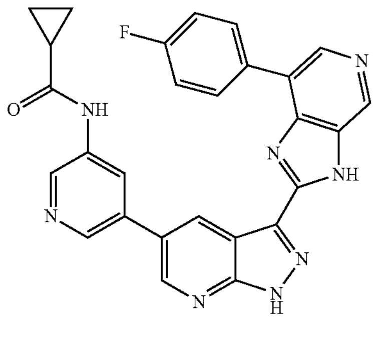 [SMILES: O=C(Nc1cncc(-c2cnc3[nH]nc(-c4nc5c(-c6ccc(F)cc6)cncc5[nH]4)c3c2)c1)C1CC1]
TABLE 1-continued
138
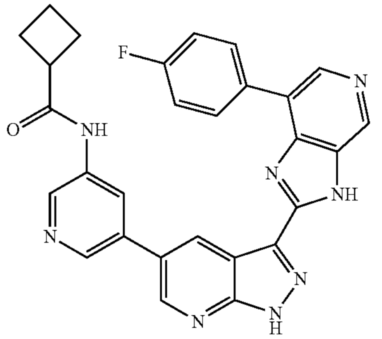 [SMILES: O=C(Nc1cncc(-c2cnc3[nH]nc(-c4nc5c(-c6ccc(F)cc6)cncc5[nH]4)c3c2)c1)C1CCC1]
139
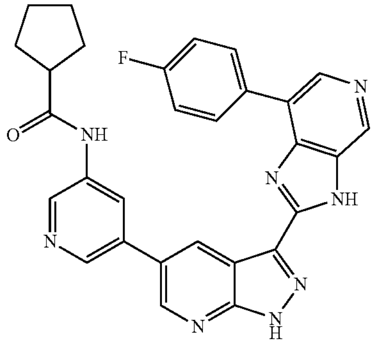 [SMILES: O=C(Nc1cncc(-c2cnc3[nH]nc(-c4nc5c(-c6ccc(F)cc6)cncc5[nH]4)c3c2)c1)C1CCCC1]
140
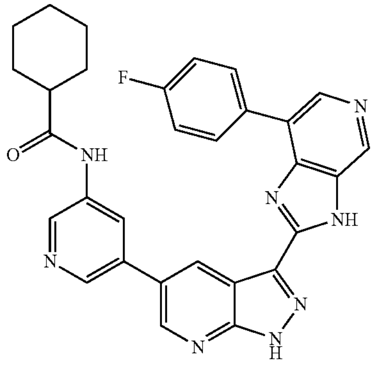 [SMILES: O=C(Nc1cncc(-c2cnc3[nH]nc(-c4nc5c(-c6ccc(F)cc6)cncc5[nH]4)c3c2)c1)C1CCCCC1]
141
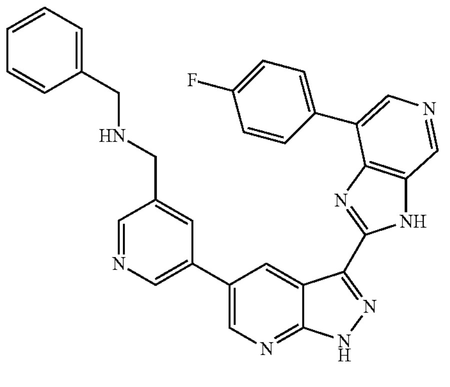 [SMILES: Fc1ccc(-c2cncc3[nH]c(-c4n[nH]c5ncc(-c6cncc(CNCc7ccccc7)c6)cc45)nc23)cc1]

TABLE 1-continued
142
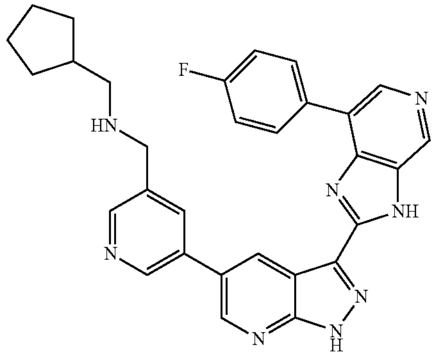 [SMILES: Fc1ccc(-c2cncc3[nH]c(-c4n[nH]c5ncc(-c6cncc(CNCC7CCCC7)c6)cc45)nc23)cc1]
143
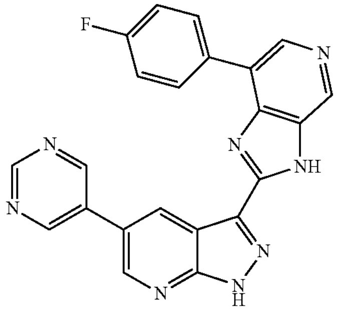 [SMILES: Fc1ccc(-c2cncc3[nH]c(-c4n[nH]c5ncc(-c6cncnc6)cc45)nc23)cc1]
144
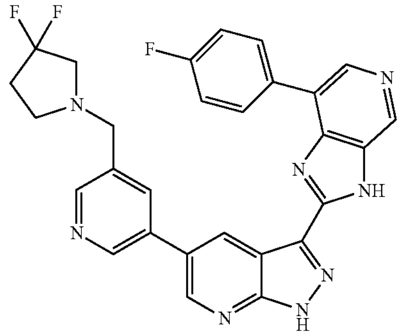 [SMILES: Fc1ccc(-c2cncc3[nH]c(-c4n[nH]c5ncc(-c6cncc(CN7CCC(F)(F)C7)c6)cc45)nc23)cc1]
145
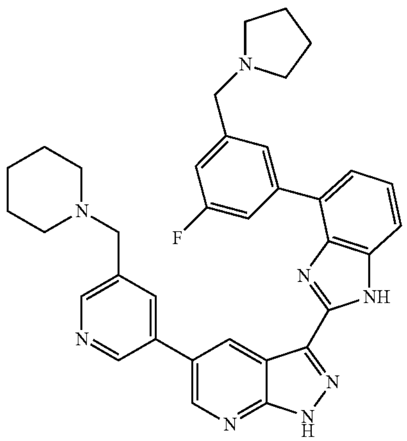
TABLE 1-continued
146
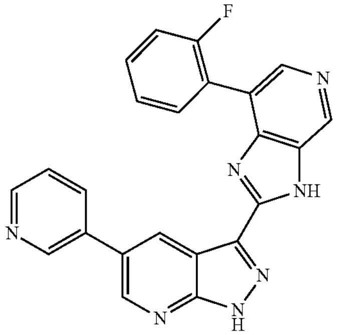
147
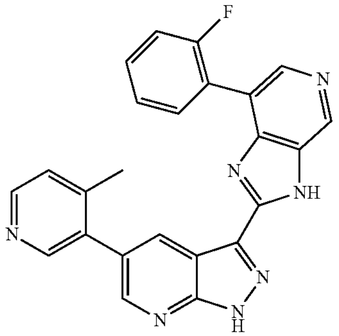
148
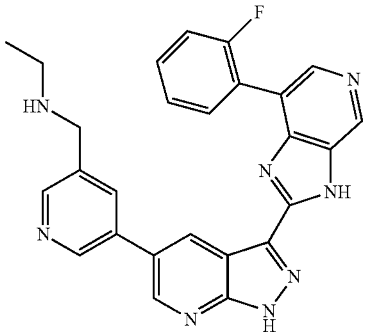
149
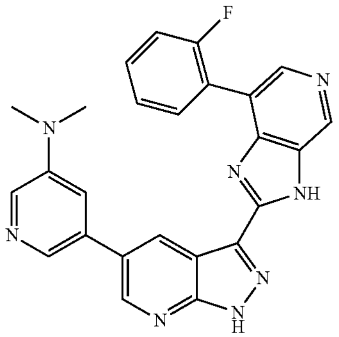 [SMILES: CN(C)c1cncc(-c2cnc3[nH]nc(-c4nc5c(-c6ccccc6F)cncc5[nH]4)c3c2)c1]

150
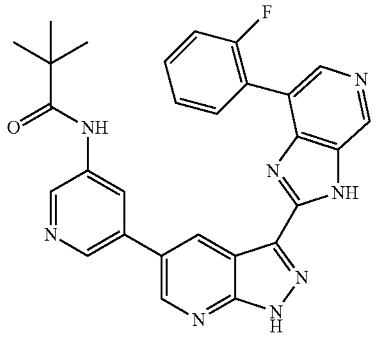 [SMILES: CC(C)(C)C(=O)Nc1cncc(-c2cnc3[nH]nc(-c4nc5c(-c6ccccc6F)cncc5[nH]4)c3c2)c1]
151
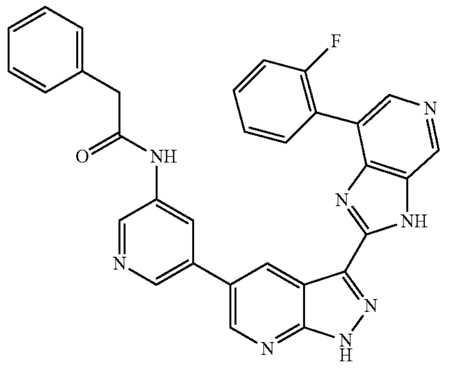
152
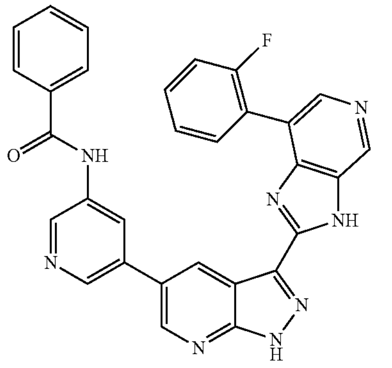 [SMILES: O=C(Nc1cncc(-c2cnc3[nH]nc(-c4nc5c(-c6ccccc6F)cncc5[nH]4)c3c2)c1)c1ccccc1]
153
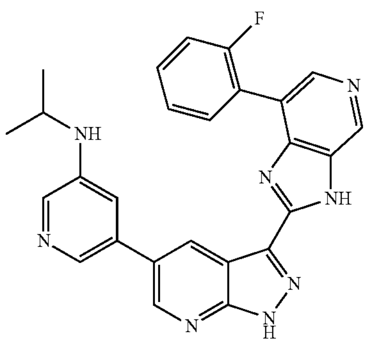
154
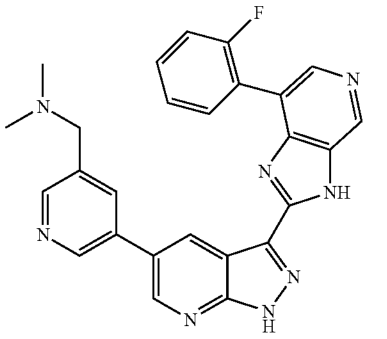
155
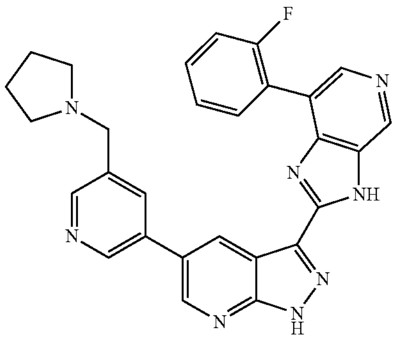 [SMILES: Fc1ccccc1-c1cncc2[nH]c(-c3n[nH]c4ncc(-c5cncc(CN6CCCC6)c5)cc34)nc12]
156
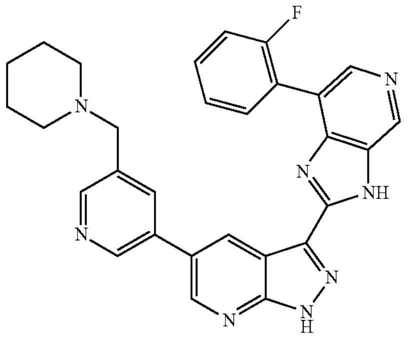 [SMILES: Fc1ccccc1-c1cncc2[nH]c(-c3n[nH]c4ncc(-c5cncc(CN6CCCCC6)c5)cc34)nc12]
157
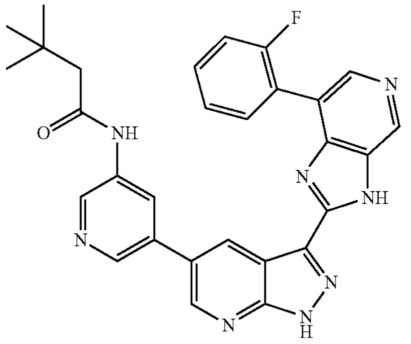 [SMILES: CC(C)(C)CC(=O)Nc1cncc(-c2cnc3[nH]nc(-c4nc5c(-c6ccccc6F)cncc5[nH]4)c3c2)c1]

TABLE 1-continued
158
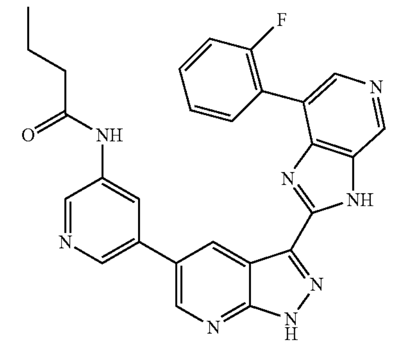 [SMILES: CCCC(=O)Nc1cncc(-c2cnc3[nH]nc(-c4nc5c(-c6ccccc6F)cncc5[nH]4)c3c2)c1]
159
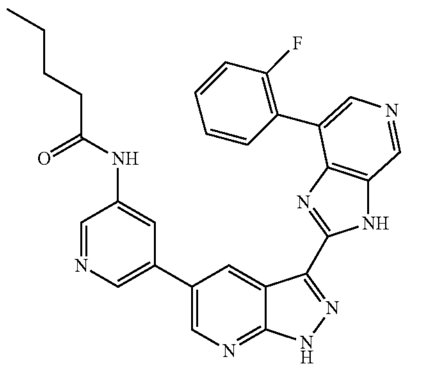 [SMILES: CCCCC(=O)Nc1cncc(-c2cnc3[nH]nc(-c4nc5c(-c6ccccc6F)cncc5[nH]4)c3c2)c1]
160
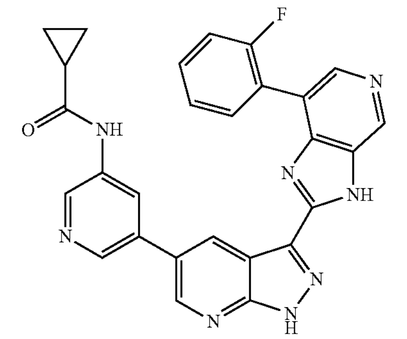 [SMILES: O=C(Nc1cncc(-c2cnc3[nH]nc(-c4nc5c(-c6ccccc6F)cncc5[nH]4)c3c2)c1)C1CC1]
161
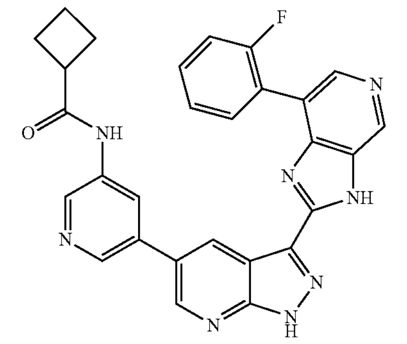 [SMILES: O=C(Nc1cncc(-c2cnc3[nH]nc(-c4nc5c(-c6ccccc6F)cncc5[nH]4)c3c2)c1)C1CCC1]
TABLE 1-continued
162
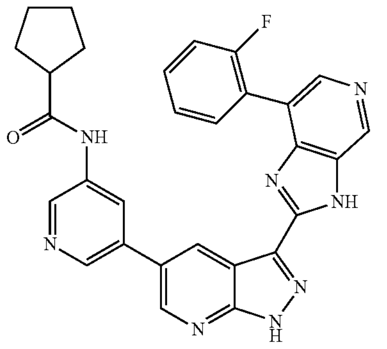 [SMILES: O=C(Nc1cncc(-c2cnc3[nH]nc(-c4nc5c(-c6ccccc6F)cncc5[nH]4)c3c2)c1)C1CCCC1]
163
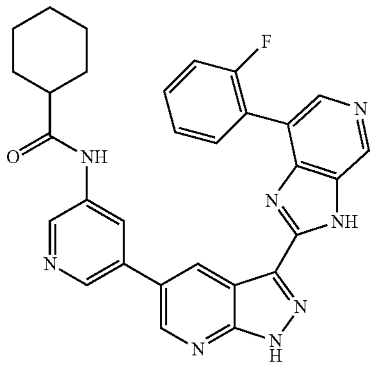 [SMILES: O=C(Nc1cncc(-c2cnc3[nH]nc(-c4nc5c(-c6ccccc6F)cncc5[nH]4)c3c2)c1)C1CCCCC1]
164
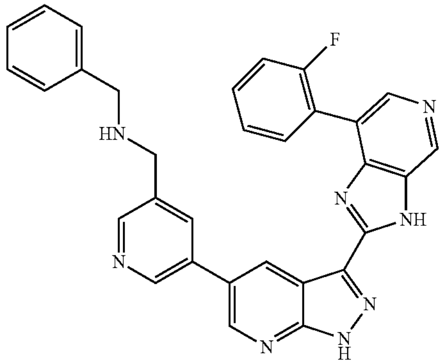 [SMILES: Fc1ccccc1-c1cncc2[nH]c(-c3n[nH]c4ncc(-c5cncc(CNCc6ccccc6)c5)cc34)nc12]
165
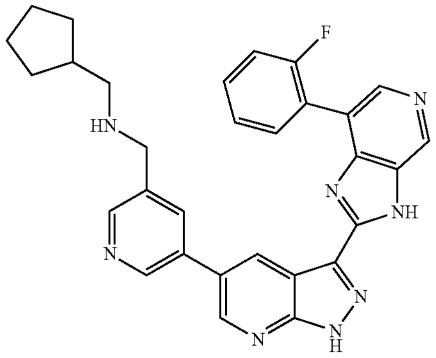 [SMILES: Fc1ccccc1-c1cncc2[nH]c(-c3n[nH]c4ncc(-c5cncc(CNCC6CCCC6)c5)cc34)nc12]

TABLE 1-continued
166
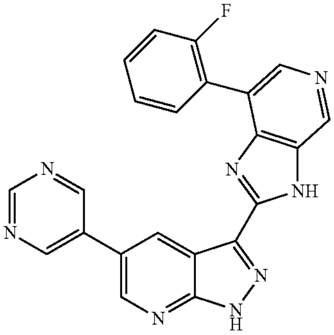
167
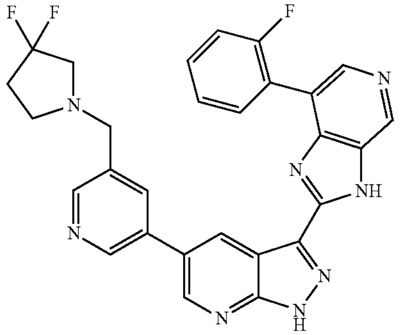
168
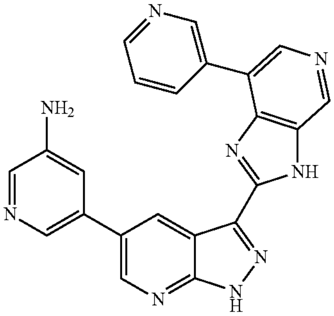 [SMILES: Nc1cncc(-c2cnc3[nH]nc(-c4nc5c(-c6cccnc6)cncc5[nH]4)c3c2)c1]
169
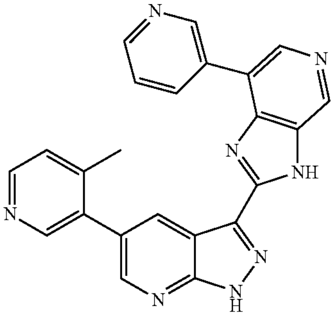 [SMILES: Cc1ccncc1-c1cnc2[nH]nc(-c3nc4c(-c5cccnc5)cncc4[nH]3)c2c1]
170
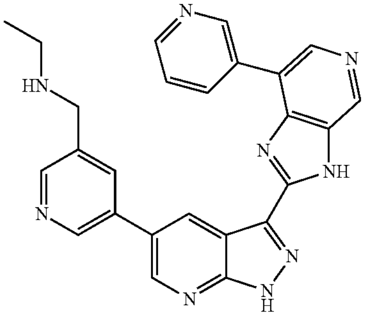 [SMILES: CCNCc1cncc(-c2cnc3[nH]nc(-c4nc5c(-c6cccnc6)cncc5[nH]4)c3c2)c1]
TABLE 1-continued
171
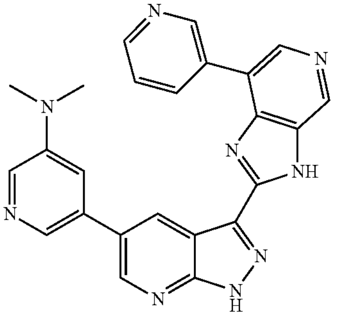 [SMILES: CN(C)c1cncc(-c2cnc3[nH]nc(-c4nc5c(-c6cccnc6)cncc5[nH]4)c3c2)c1]
172
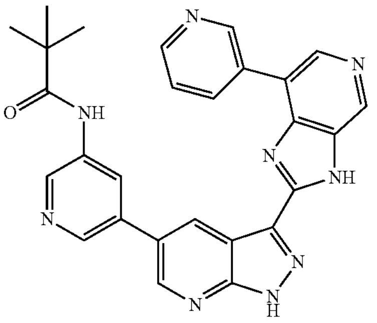 [SMILES: CC(C)(C)C(=O)Nc1cncc(-c2cnc3[nH]nc(-c4nc5c(-c6cccnc6)cncc5[nH]4)c3c2)c1]
173
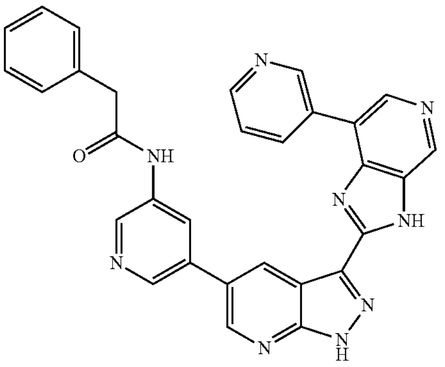
174
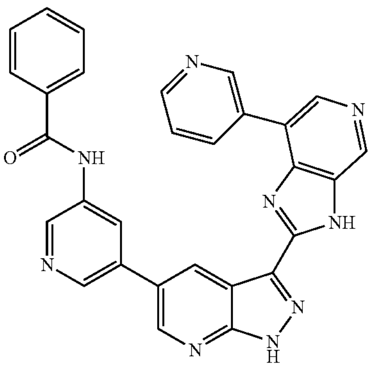 [SMILES: O=C(Nc1cncc(-c2cnc3[nH]nc(-c4nc5c(-c6cccnc6)cncc5[nH]4)c3c2)c1)c1ccccc1]

175
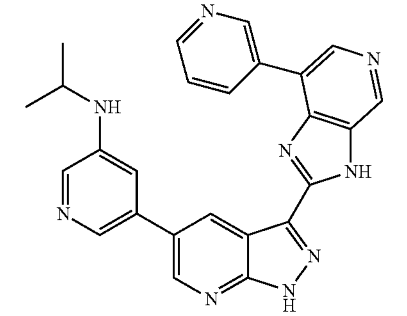 [SMILES: CC(C)Nc1cncc(-c2cnc3[nH]nc(-c4nc5c(-c6cccnc6)cncc5[nH]4)c3c2)c1]
176
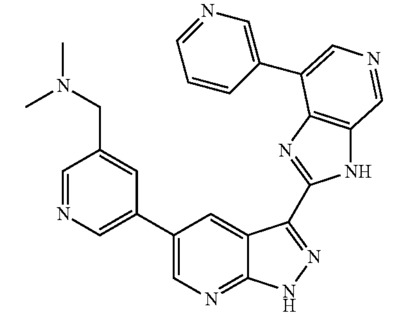 [SMILES: CN(C)Cc1cncc(-c2cnc3[nH]nc(-c4nc5c(-c6cccnc6)cncc5[nH]4)c3c2)c1]
177
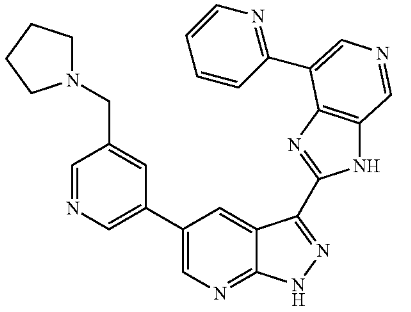 [SMILES: c1ccc(-c2cncc3[nH]c(-c4n[nH]c5ncc(-c6cncc(CN7CCCC7)c6)cc45)nc23)nc1]
178
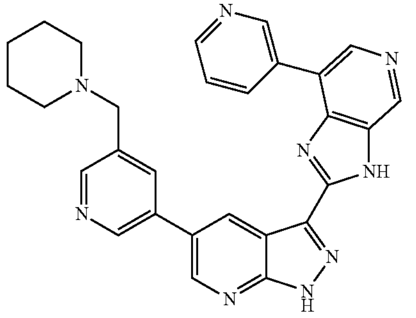
179
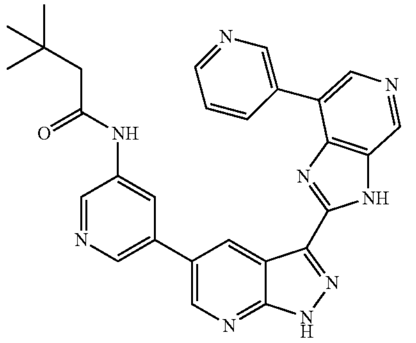
180
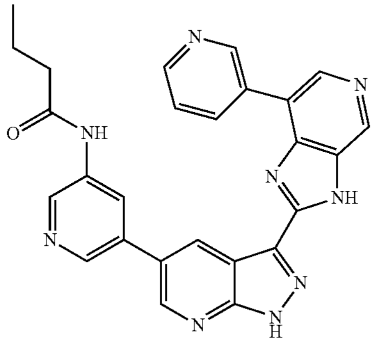 [SMILES: CCCC(=O)Nc1cncc(-c2cnc3[nH]nc(-c4nc5c(-c6cccnc6)cncc5[nH]4)c3c2)c1]
181
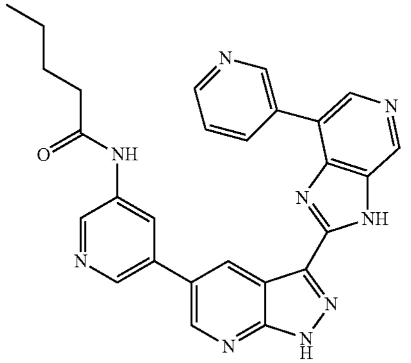 [SMILES: CCCCC(=O)Nc1cncc(-c2cnc3[nH]nc(-c4nc5c(-c6cccnc6)cncc5[nH]4)c3c2)c1]
182
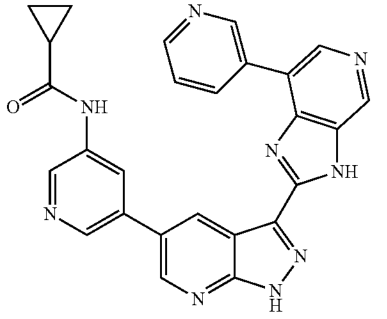
183
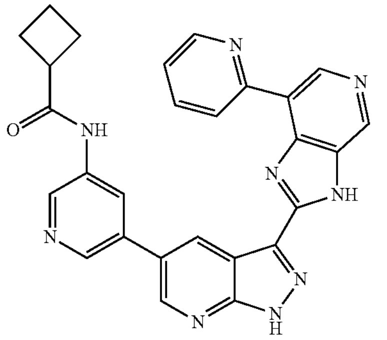 [SMILES: O=C(Nc1cncc(-c2cnc3[nH]nc(-c4nc5c(-c6ccccn6)cncc5[nH]4)c3c2)c1)C1CCC1]

TABLE 1-continued
184
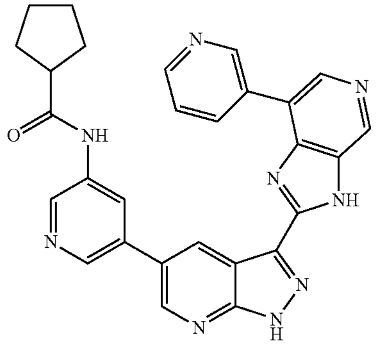 [SMILES: O=C(Nc1cncc(-c2cnc3[nH]nc(-c4nc5c(-c6cccnc6)cncc5[nH]4)c3c2)c1)C1CCCC1]
185
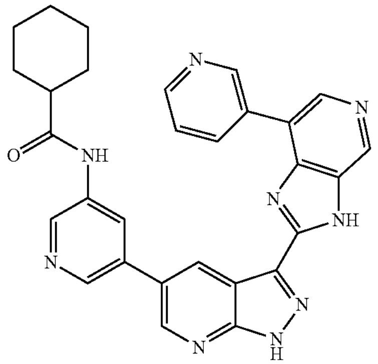 [SMILES: O=C(Nc1cncc(-c2cnc3[nH]nc(-c4nc5c(-c6cccnc6)cncc5[nH]4)c3c2)c1)C1CCCCC1]
186
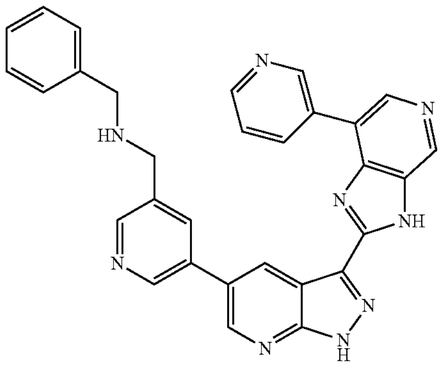
187
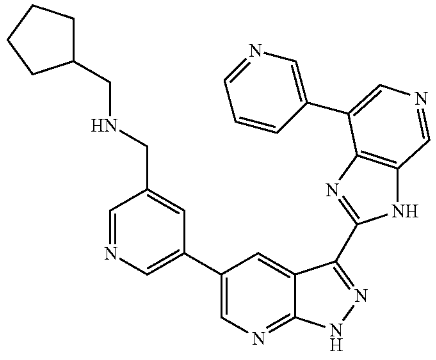
TABLE 1-continued
188
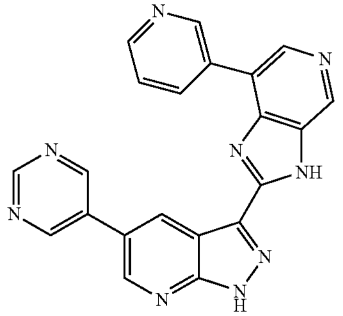 [SMILES: c1cncc(-c2cncc3[nH]c(-c4n[nH]c5ncc(-c6cncnc6)cc45)nc23)c1]
189
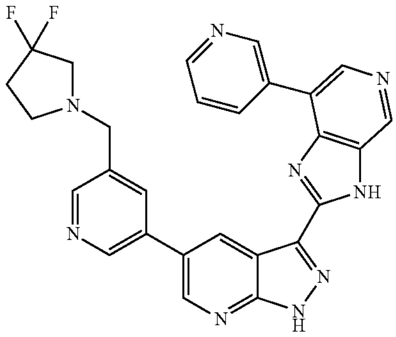
190
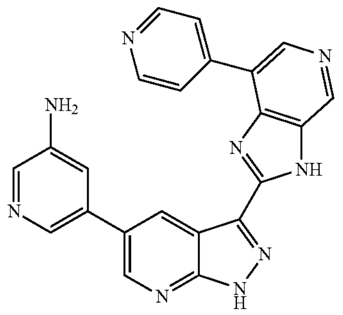 [SMILES: Nc1cncc(-c2cnc3[nH]nc(-c4nc5c(-c6ccncc6)cncc5[nH]4)c3c2)c1]
191
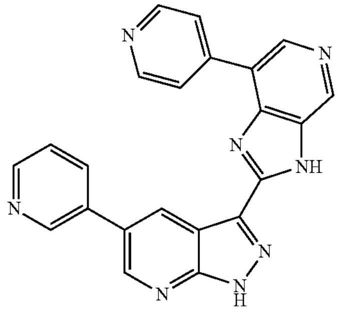
192
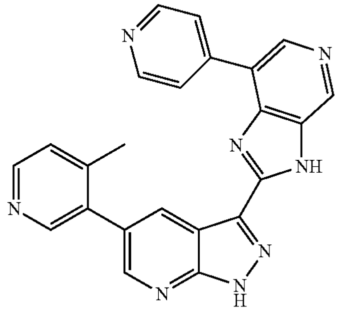 [SMILES: Cc1ccncc1-c1cnc2[nH]nc(-c3nc4c(-c5ccncc5)cncc4[nH]3)c2c1]

TABLE 1-continued
193
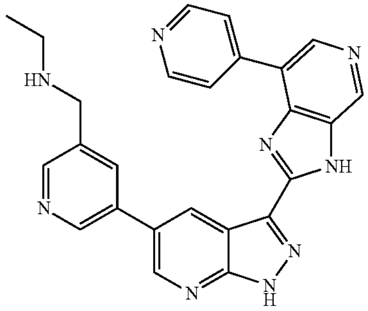 [SMILES: CCNCc1cncc(-c2cnc3[nH]nc(-c4nc5c(-c6ccncc6)cncc5[nH]4)c3c2)c1]
194
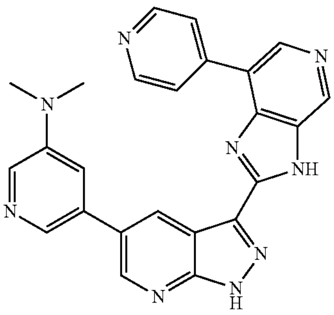 [SMILES: CN(C)c1cncc(-c2cnc3[nH]nc(-c4nc5c(-c6ccncc6)cncc5[nH]4)c3c2)c1]
195
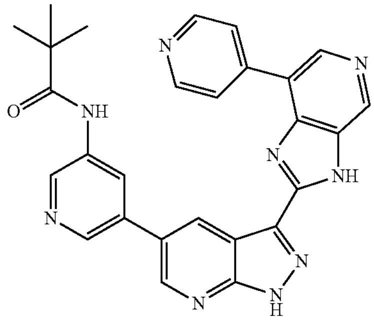 [SMILES: CC(C)(C)C(=O)Nc1cncc(-c2cnc3[nH]nc(-c4nc5c(-c6ccncc6)cncc5[nH]4)c3c2)c1]
196
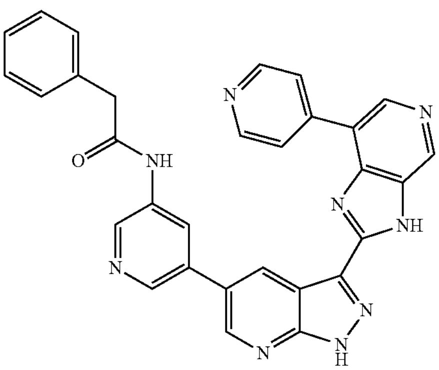
TABLE 1-continued
197
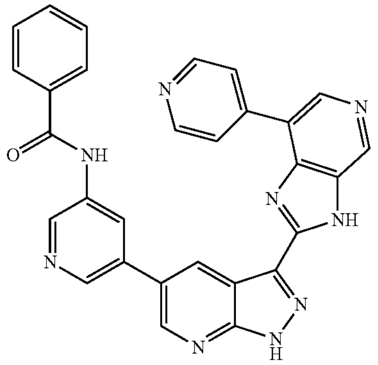 [SMILES: O=C(Nc1cncc(-c2cnc3[nH]nc(-c4nc5c(-c6ccncc6)cncc5[nH]4)c3c2)c1)c1ccccc1]
198
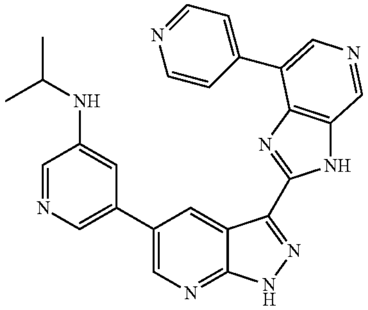
199
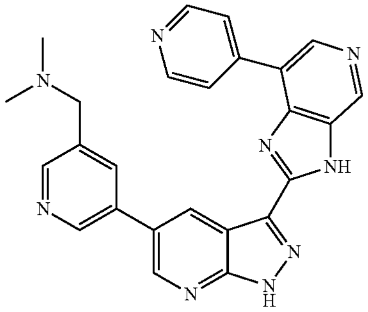
200
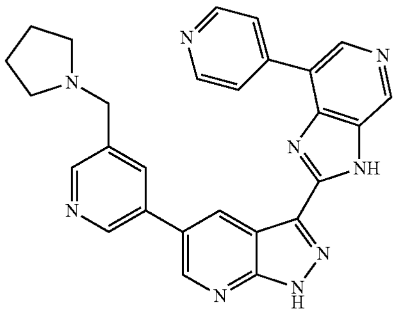 [SMILES: c1cc(-c2cncc3[nH]c(-c4n[nH]c5ncc(-c6cncc(CN7CCCC7)c6)cc45)nc23)ccn1]
201
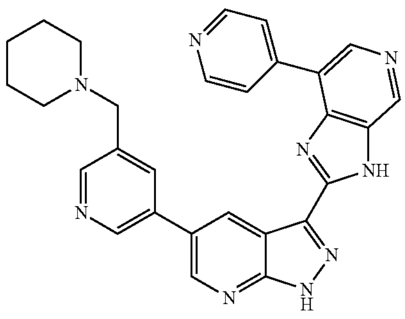 [SMILES: c1cc(-c2cncc3[nH]c(-c4n[nH]c5ncc(-c6cncc(CN7CCCCC7)c6)cc45)nc23)ccn1]

TABLE 1-continued
202
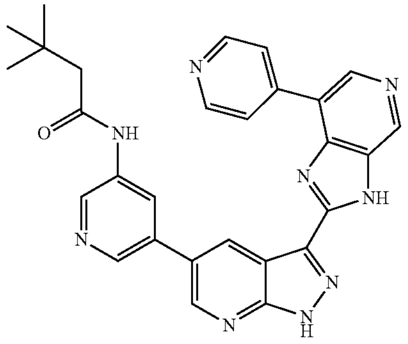 [SMILES: CC(C)(C)CC(=O)Nc1cncc(-c2cnc3[nH]nc(-c4nc5c(-c6ccncc6)cncc5[nH]4)c3c2)c1]
203
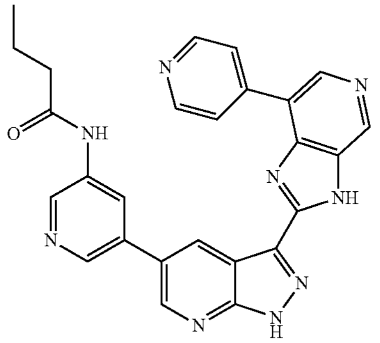 [SMILES: CCCC(=O)Nc1cncc(-c2cnc3[nH]nc(-c4nc5c(-c6ccncc6)cncc5[nH]4)c3c2)c1]
204
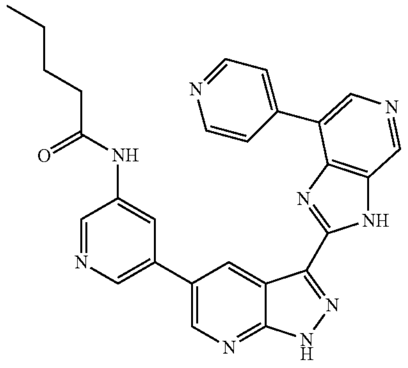 [SMILES: CCCCC(=O)Nc1cncc(-c2cnc3[nH]nc(-c4nc5c(-c6ccncc6)cncc5[nH]4)c3c2)c1]
205
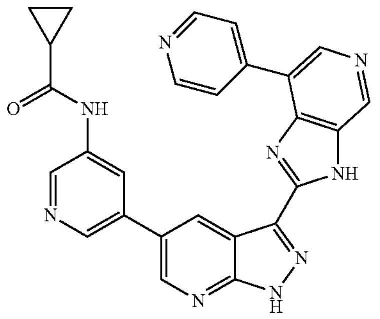
TABLE 1-continued
206
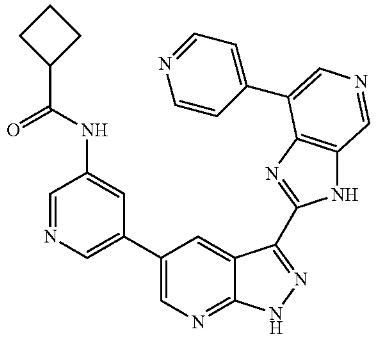 [SMILES: O=C(Nc1cncc(-c2cnc3[nH]nc(-c4nc5c(-c6ccncc6)cncc5[nH]4)c3c2)c1)C1CCC1]
207
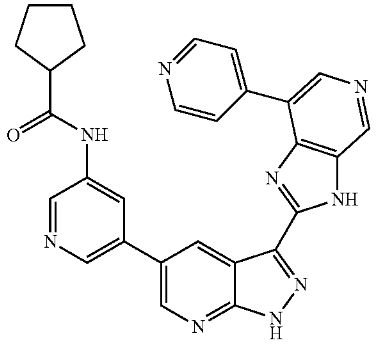 [SMILES: O=C(Nc1cncc(-c2cnc3[nH]nc(-c4nc5c(-c6ccncc6)cncc5[nH]4)c3c2)c1)C1CCCC1]
208
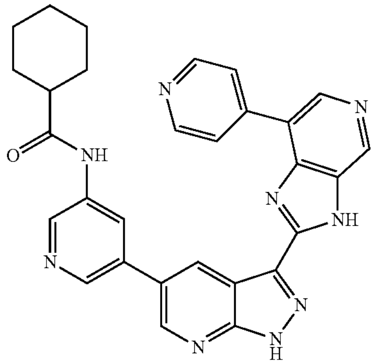 [SMILES: O=C(Nc1cncc(-c2cnc3[nH]nc(-c4nc5c(-c6ccncc6)cncc5[nH]4)c3c2)c1)C1CCCCC1]
209
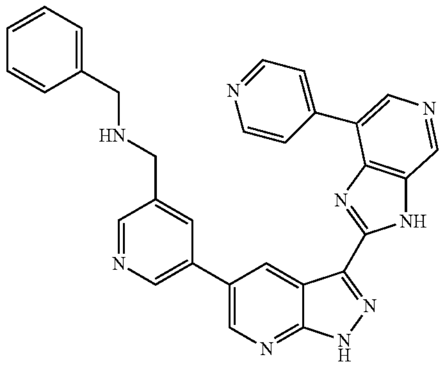 [SMILES: c1ccc(CNCc2cncc(-c3cnc4[nH]nc(-c5nc6c(-c7ccncc7)cncc6[nH]5)c4c3)c2)cc1]

TABLE 1-continued
210
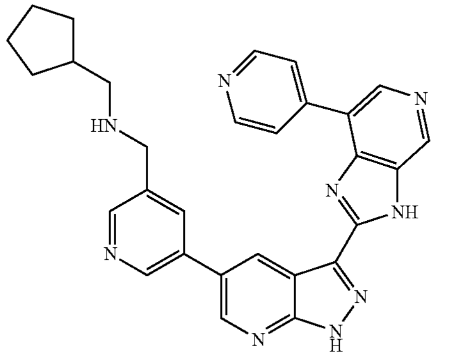 [SMILES: c1cc(-c2cncc3[nH]c(-c4n[nH]c5ncc(-c6cncc(CNCC7CCCC7)c6)cc45)nc23)ccn1]
211
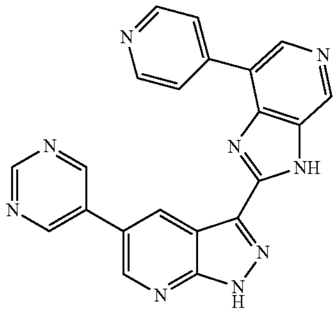 [SMILES: c1cc(-c2cncc3[nH]c(-c4n[nH]c5ncc(-c6cncnc6)cc45)nc23)ccn1]
212
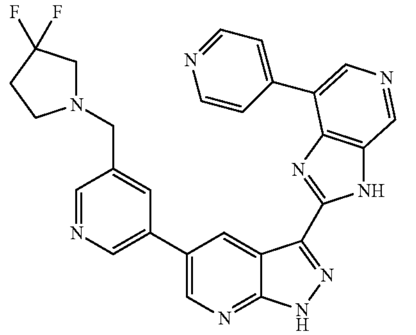 [SMILES: FC1(F)CCN(Cc2cncc(-c3cnc4[nH]nc(-c5nc6c(-c7ccncc7)cncc6[nH]5)c4c3)c2)C1]
213
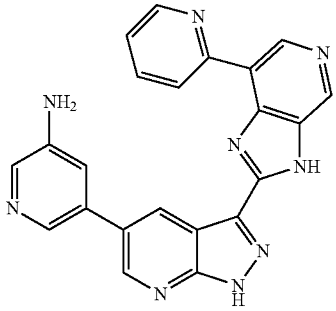 [SMILES: Nc1cncc(-c2cnc3[nH]nc(-c4nc5c(-c6ccccn6)cncc5[nH]4)c3c2)c1]
214
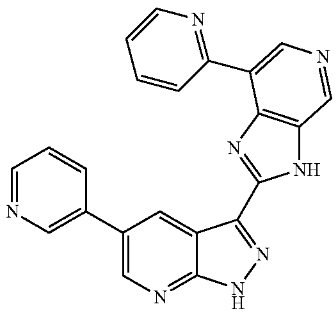 [SMILES: c1ccc(-c2cncc3[nH]c(-c4n[nH]c5ncc(-c6cccnc6)cc45)nc23)nc1]
TABLE 1-continued
215
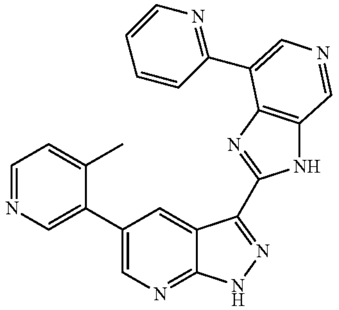
216
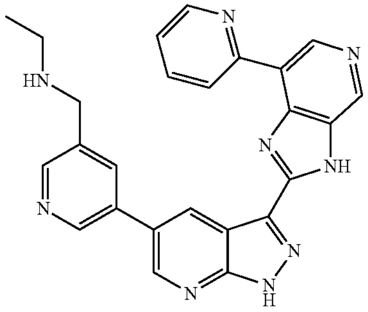 [SMILES: CCNCc1cncc(-c2cnc3[nH]nc(-c4nc5c(-c6ccccn6)cncc5[nH]4)c3c2)c1]
217
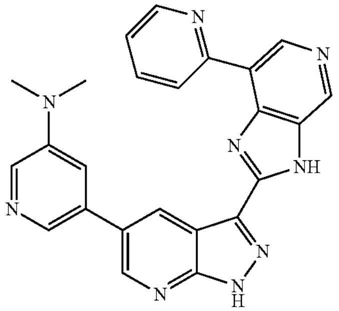 [SMILES: CN(C)c1cncc(-c2cnc3[nH]nc(-c4nc5c(-c6ccccn6)cncc5[nH]4)c3c2)c1]
218
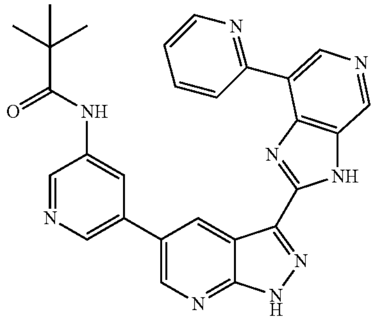 [SMILES: CC(C)(C)C(=O)Nc1cncc(-c2cnc3[nH]nc(-c4nc5c(-c6ccccn6)cncc5[nH]4)c3c2)c1]

TABLE 1-continued
219
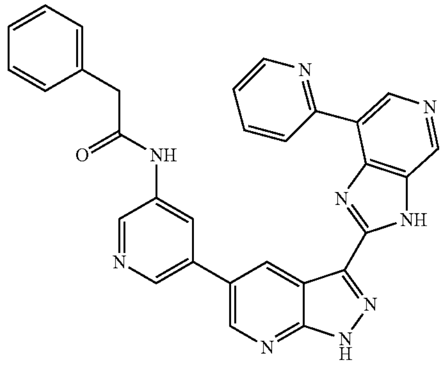 [SMILES: O=C(Cc1ccccc1)Nc1cncc(-c2cnc3[nH]nc(-c4nc5c(-c6ccccn6)cncc5[nH]4)c3c2)c1]
220
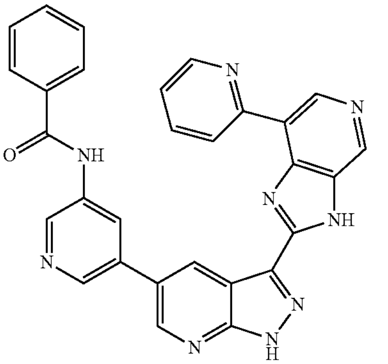 [SMILES: O=C(Nc1cncc(-c2cnc3[nH]nc(-c4nc5c(-c6ccccn6)cncc5[nH]4)c3c2)c1)c1ccccc1]
221
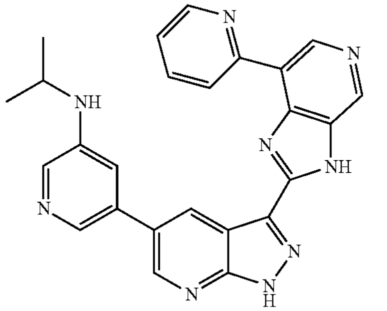
222
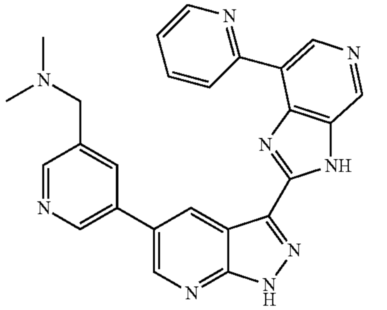
TABLE 1-continued
223
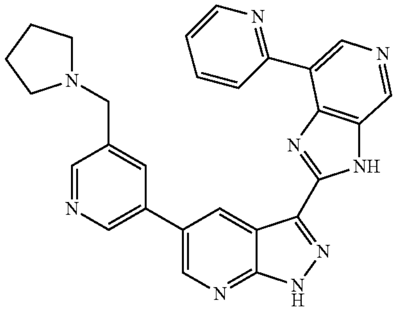 [SMILES: c1ccc(-c2cncc3[nH]c(-c4n[nH]c5ncc(-c6cncc(CN7CCCC7)c6)cc45)nc23)nc1]
224
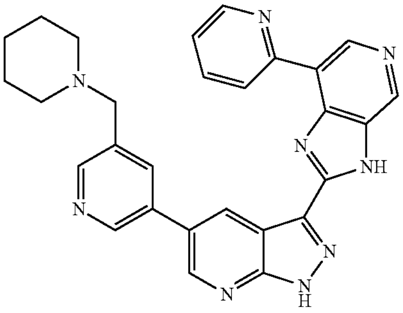 [SMILES: c1ccc(-c2cncc3[nH]c(-c4n[nH]c5ncc(-c6cncc(CN7CCCCC7)c6)cc45)nc23)nc1]
225
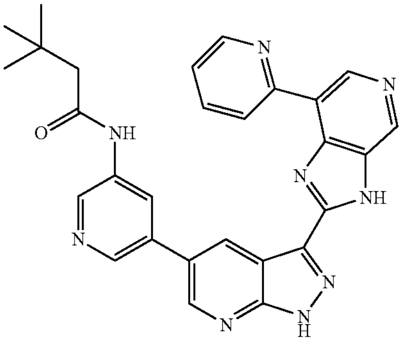 [SMILES: CC(C)(C)CC(=O)Nc1cncc(-c2cnc3[nH]nc(-c4nc5c(-c6ccccn6)cncc5[nH]4)c3c2)c1]
226
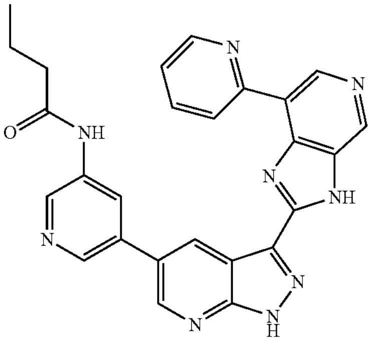 [SMILES: CCCC(=O)Nc1cncc(-c2cnc3[nH]nc(-c4nc5c(-c6ccccn6)cncc5[nH]4)c3c2)c1]

TABLE 1-continued
227
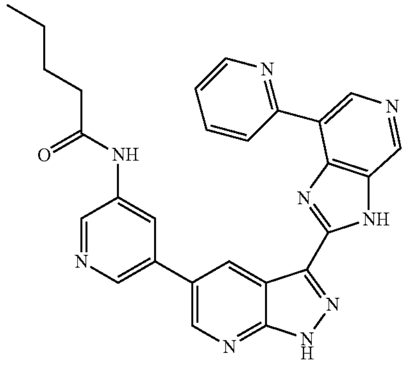 [SMILES: CCCCC(=O)Nc1cncc(-c2cnc3[nH]nc(-c4nc5c(-c6ccccn6)cncc5[nH]4)c3c2)c1]
228
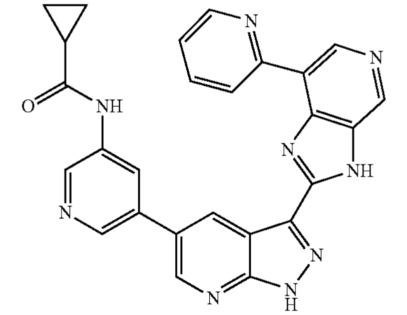 [SMILES: O=C(Nc1cncc(-c2cnc3[nH]nc(-c4nc5c(-c6ccccn6)cncc5[nH]4)c3c2)c1)C1CC1]
229
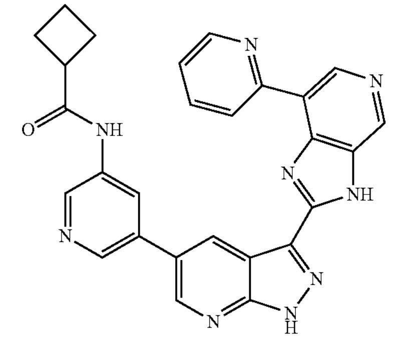 [SMILES: O=C(Nc1cncc(-c2cnc3[nH]nc(-c4nc5c(-c6ccccn6)cncc5[nH]4)c3c2)c1)C1CCC1]
230
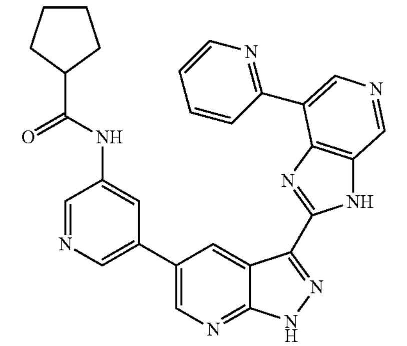 [SMILES: O=C(Nc1cncc(-c2cnc3[nH]nc(-c4nc5c(-c6ccccn6)cncc5[nH]4)c3c2)c1)C1CCCC1]
TABLE 1-continued
231
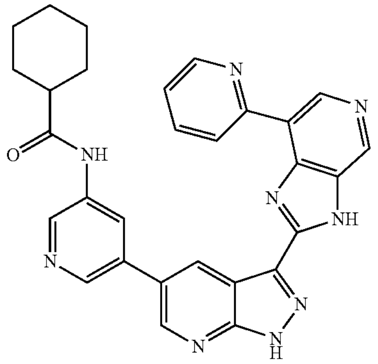 [SMILES: O=C(Nc1cncc(-c2cnc3[nH]nc(-c4nc5c(-c6ccccn6)cncc5[nH]4)c3c2)c1)C1CCCCC1]
232
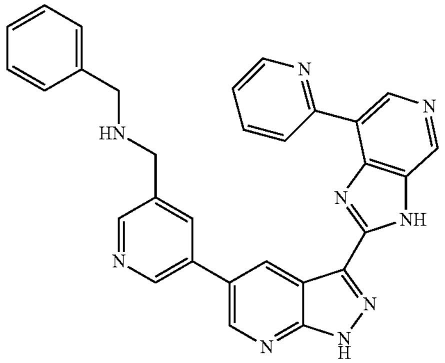
233
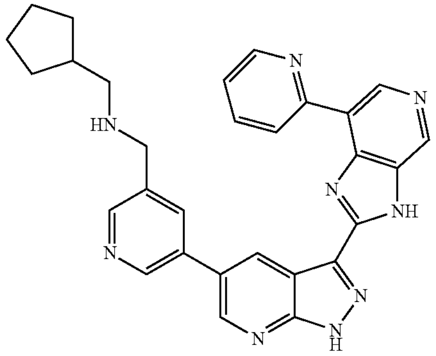
234
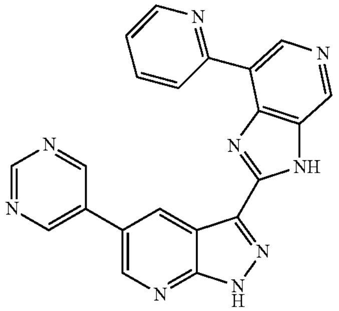

TABLE 1-continued
235
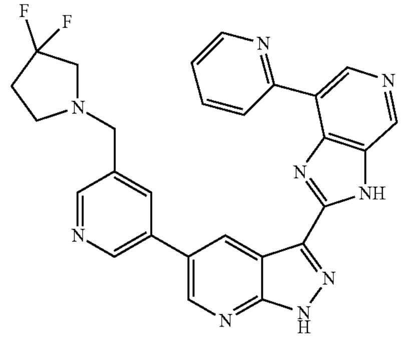 [SMILES: FC1(F)CCN(Cc2cncc(-c3cnc4[nH]nc(-c5nc6c(-c7ccccn7)cncc6[nH]5)c4c3)c2)C1]
236
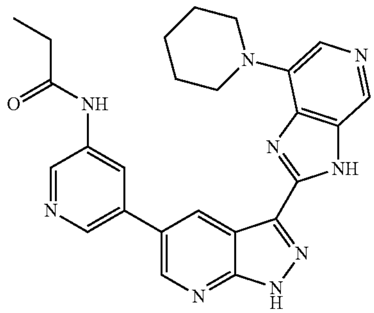 [SMILES: CCC(=O)Nc1cncc(-c2cnc3[nH]nc(-c4nc5c(N6CCCCC6)cncc5[nH]4)c3c2)c1]
237
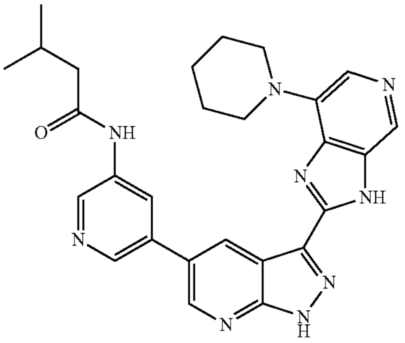 [SMILES: CC(C)CC(=O)Nc1cncc(-c2cnc3[nH]nc(-c4nc5c(N6CCCCC6)cncc5[nH]4)c3c2)c1]
238
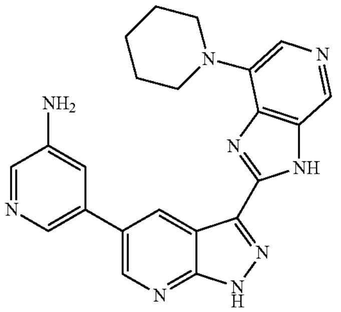 [SMILES: Nc1cncc(-c2cnc3[nH]nc(-c4nc5c(N6CCCCC6)cncc5[nH]4)c3c2)c1]
239
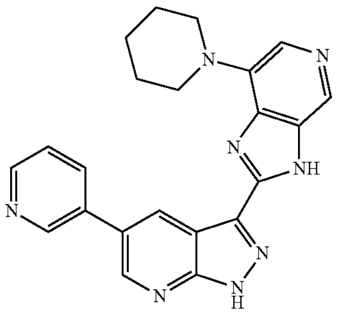 [SMILES: c1cncc(-c2cnc3[nH]nc(-c4nc5c(N6CCCCC6)cncc5[nH]4)c3c2)c1]
TABLE 1-continued
240
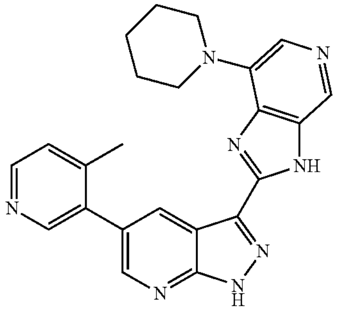 [SMILES: Cc1ccncc1-c1cnc2[nH]nc(-c3nc4c(N5CCCCC5)cncc4[nH]3)c2c1]
241
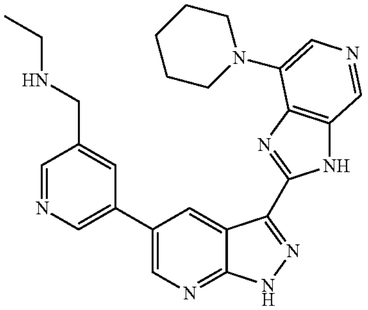
242
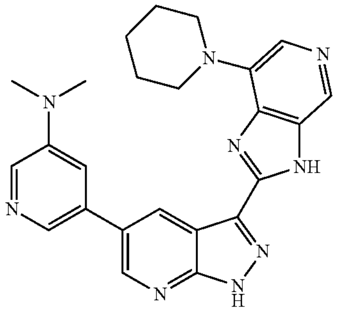
243
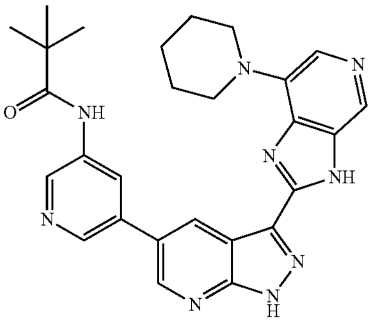 [SMILES: CC(C)(C)C(=O)Nc1cncc(-c2cnc3[nH]nc(-c4nc5c(N6CCCCC6)cncc5[nH]4)c3c2)c1]
244
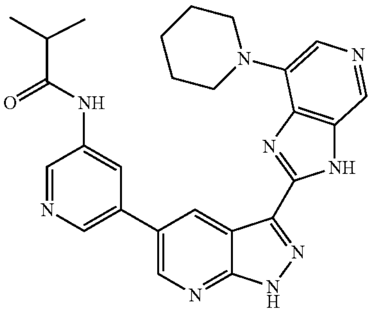 [SMILES: CC(C)C(=O)Nc1cncc(-c2cnc3[nH]nc(-c4nc5c(N6CCCCC6)cncc5[nH]4)c3c2)c1]

TABLE 1-continued
245
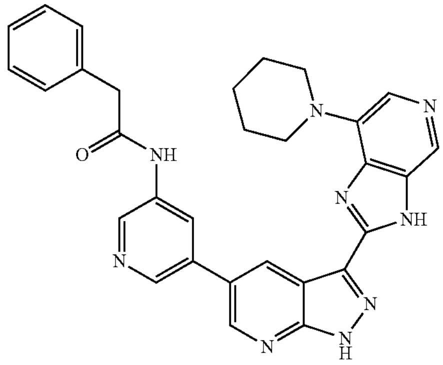 [SMILES: O=C(Cc1ccccc1)Nc1cncc(-c2cnc3[nH]nc(-c4nc5c(N6CCCCC6)cncc5[nH]4)c3c2)c1]
246
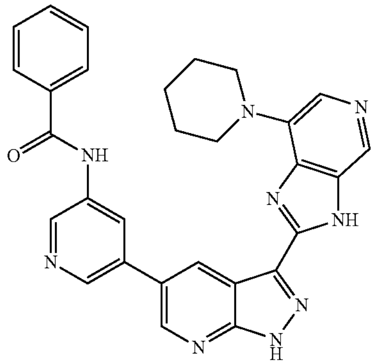
247
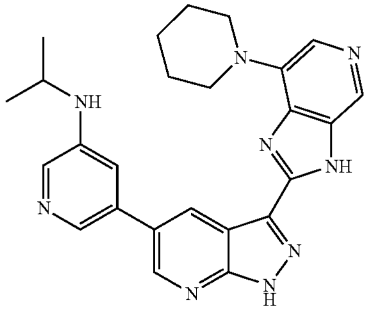 [SMILES: CC(C)Nc1cncc(-c2cnc3[nH]nc(-c4nc5c(N6CCCCC6)cncc5[nH]4)c3c2)c1]
248
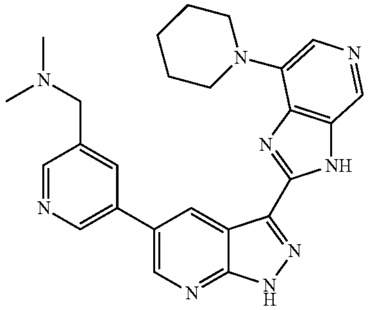 [SMILES: CN(C)Cc1cncc(-c2cnc3[nH]nc(-c4nc5c(N6CCCCC6)cncc5[nH]4)c3c2)c1]
TABLE 1-continued
249
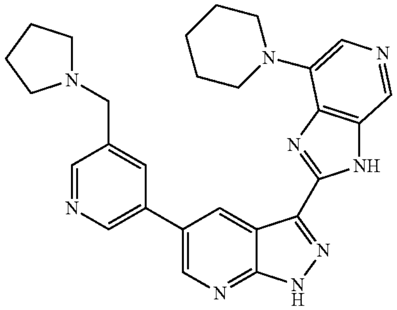 [SMILES: c1ncc(-c2cnc3[nH]nc(-c4nc5c(N6CCCCC6)cncc5[nH]4)c3c2)cc1CN1CCCC1]
250
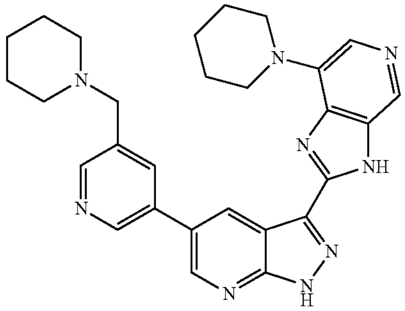 [SMILES: c1ncc(-c2cnc3[nH]nc(-c4nc5c(N6CCCCC6)cncc5[nH]4)c3c2)cc1CN1CCCCC1]
251
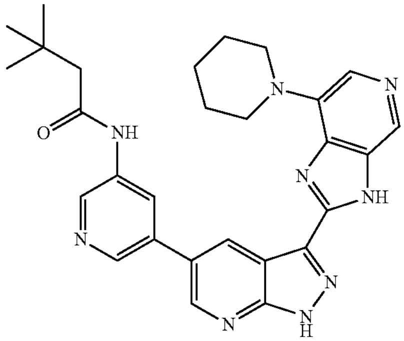
252
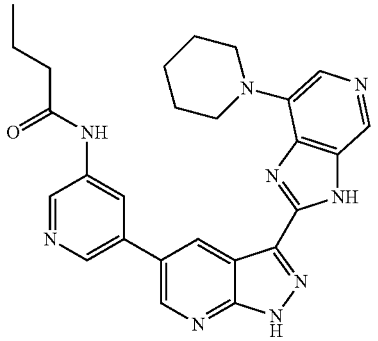 [SMILES: CCCC(=O)Nc1cncc(-c2cnc3[nH]nc(-c4nc5c(N6CCCCC6)cncc5[nH]4)c3c2)c1]

TABLE 1-continued
253
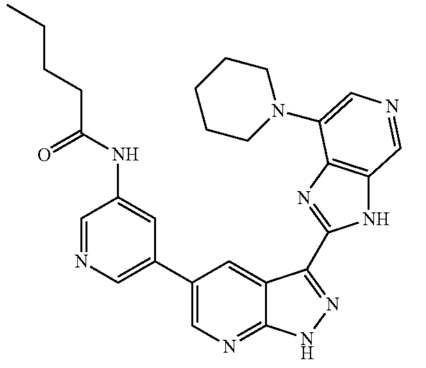
254
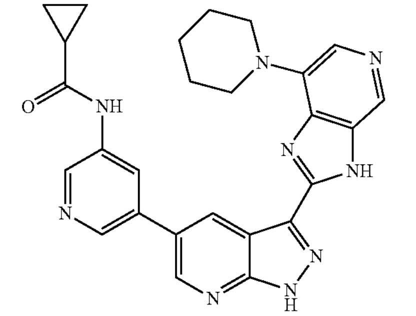 [SMILES: O=C(Nc1cncc(-c2cnc3[nH]nc(-c4nc5c(N6CCCCC6)cncc5[nH]4)c3c2)c1)C1CC1]
255
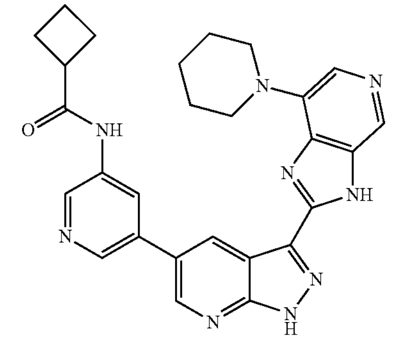 [SMILES: O=C(Nc1cncc(-c2cnc3[nH]nc(-c4nc5c(N6CCCCC6)cncc5[nH]4)c3c2)c1)C1CCC1]
256
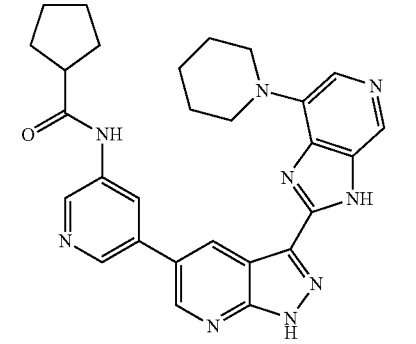
TABLE 1-continued
257
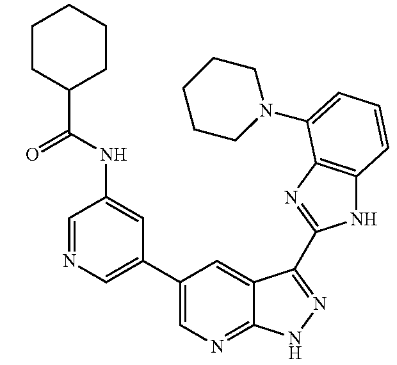 [SMILES: O=C(Nc1cncc(-c2cnc3[nH]nc(-c4nc5c(N6CCCCC6)cccc5[nH]4)c3c2)c1)C1CCCCC1]
258
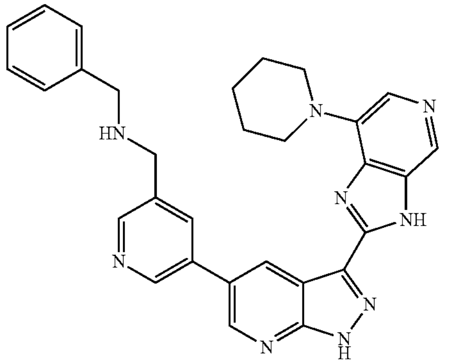 [SMILES: c1ccc(CNCc2cncc(-c3cnc4[nH]nc(-c5nc6c(N7CCCCC7)cncc6[nH]5)c4c3)c2)cc1]
259
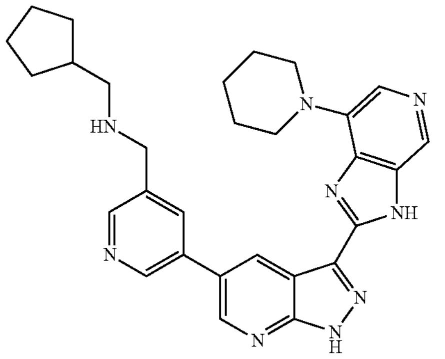 [SMILES: c1ncc(-c2cnc3[nH]nc(-c4nc5c(N6CCCCC6)cncc5[nH]4)c3c2)cc1CNCC1CCCC1]
260
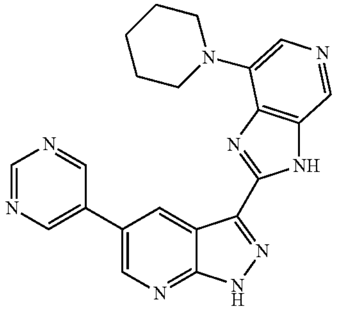

261
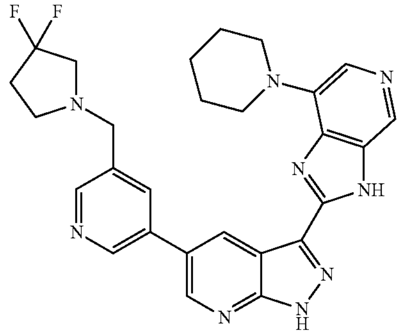 [SMILES: FC1(F)CCN(Cc2cncc(-c3cnc4[nH]nc(-c5nc6c(N7CCCCC7)cncc6[nH]5)c4c3)c2)C1]
262
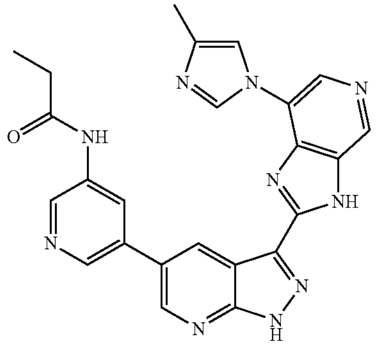
263
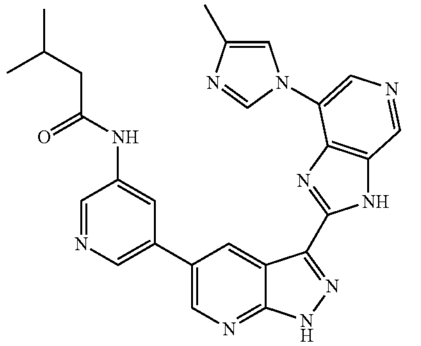 [SMILES: Cc1cn(-c2cncc3[nH]c(-c4n[nH]c5ncc(-c6cncc(NC(=O)CC(C)C)c6)cc45)nc23)cn1]
264
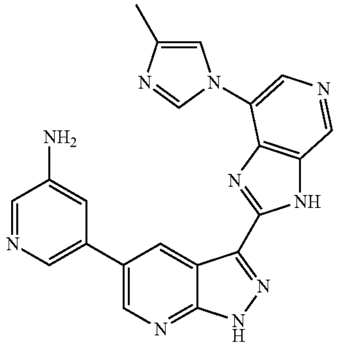 [SMILES: Cc1cn(-c2cncc3[nH]c(-c4n[nH]c5ncc(-c6cncc(N)c6)cc45)nc23)cn1]
265
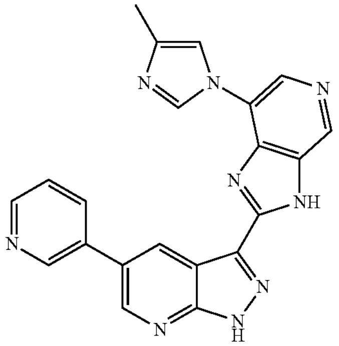
266
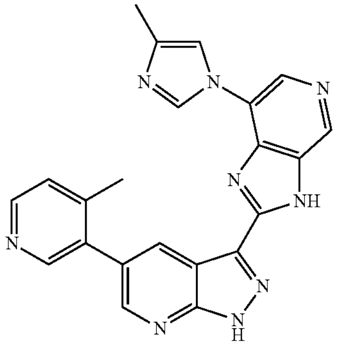 [SMILES: Cc1cn(-c2cncc3[nH]c(-c4n[nH]c5ncc(-c6cnccc6C)cc45)nc23)cn1]
267
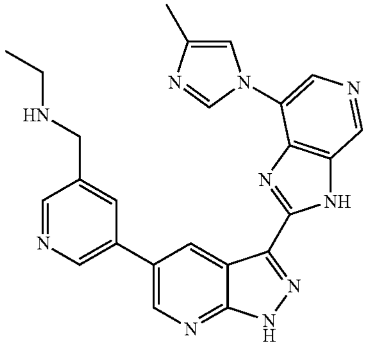
268
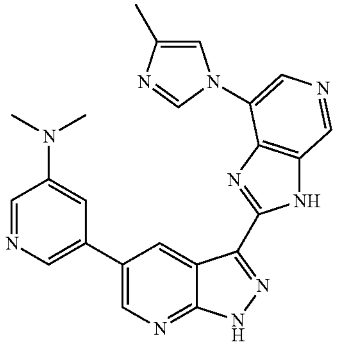 [SMILES: Cc1cn(-c2cncc3[nH]c(-c4n[nH]c5ncc(-c6cncc(N(C)C)c6)cc45)nc23)cn1]

TABLE 1-continued
269
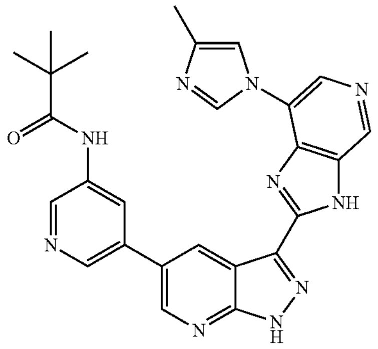 [SMILES: Cc1cn(-c2cncc3[nH]c(-c4n[nH]c5ncc(-c6cncc(NC(=O)C(C)(C)C)c6)cc45)nc23)cn1]
270
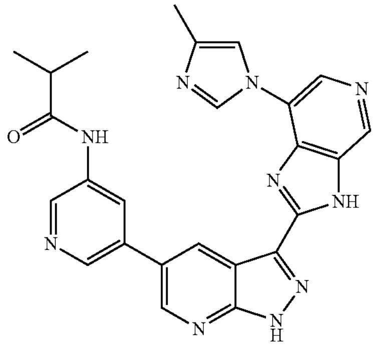 [SMILES: Cc1cn(-c2cncc3[nH]c(-c4n[nH]c5ncc(-c6cncc(NC(=O)C(C)C)c6)cc45)nc23)cn1]
271
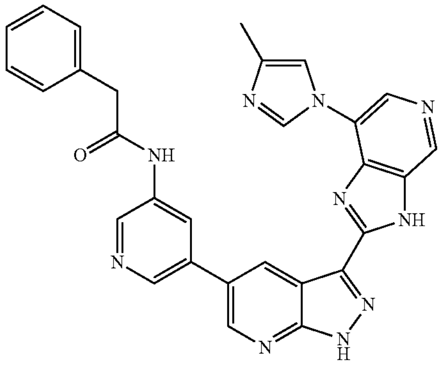 [SMILES: Cc1cn(-c2cncc3[nH]c(-c4n[nH]c5ncc(-c6cncc(NC(=O)Cc7ccccc7)c6)cc45)nc23)cn1]
272
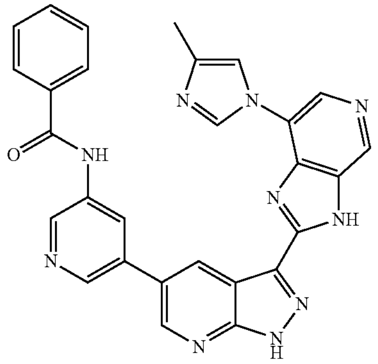
TABLE 1-continued
273
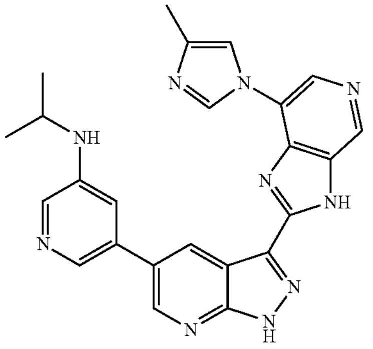 [SMILES: Cc1cn(-c2cncc3[nH]c(-c4n[nH]c5ncc(-c6cncc(NC(C)C)c6)cc45)nc23)cn1]
274
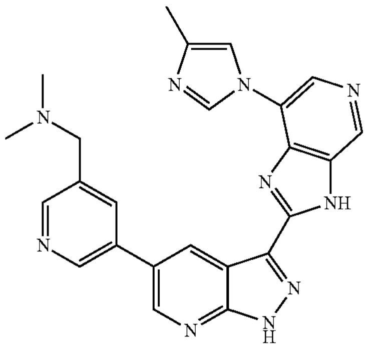 [SMILES: Cc1cn(-c2cncc3[nH]c(-c4n[nH]c5ncc(-c6cncc(CN(C)C)c6)cc45)nc23)cn1]
275
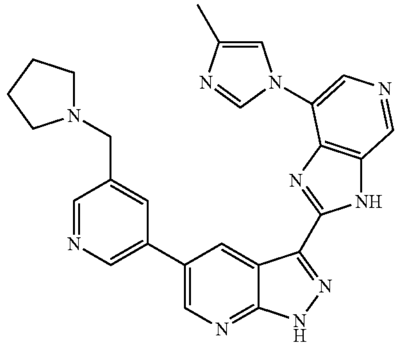 [SMILES: Cc1cn(-c2cncc3[nH]c(-c4n[nH]c5ncc(-c6cncc(CN7CCCC7)c6)cc45)nc23)cn1]
276
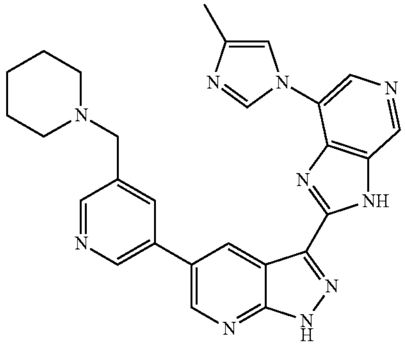 [SMILES: Cc1cn(-c2cncc3[nH]c(-c4n[nH]c5ncc(-c6cncc(CN7CCCCC7)c6)cc45)nc23)cn1]

TABLE 1-continued
277
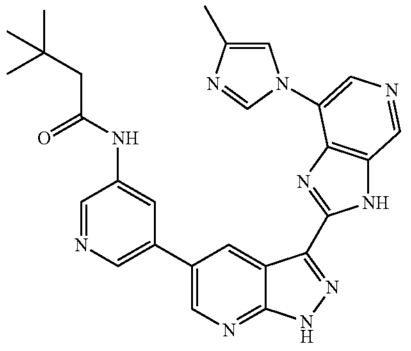
278
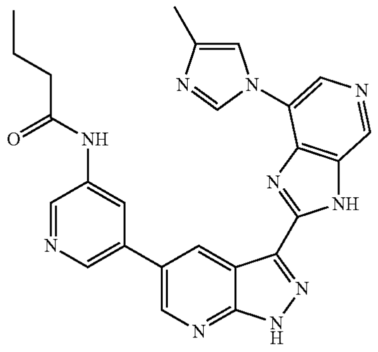 [SMILES: CCCC(=O)Nc1cncc(-c2cnc3[nH]nc(-c4nc5c(-n6cnc(C)c6)cncc5[nH]4)c3c2)c1]
279
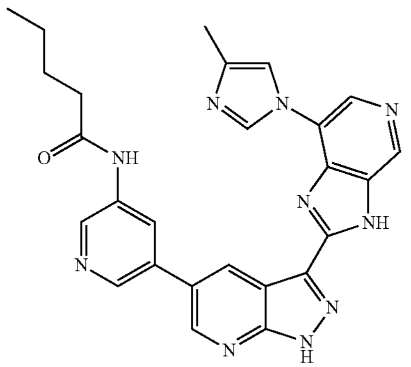 [SMILES: CCCCC(=O)Nc1cncc(-c2cnc3[nH]nc(-c4nc5c(-n6cnc(C)c6)cncc5[nH]4)c3c2)c1]
280
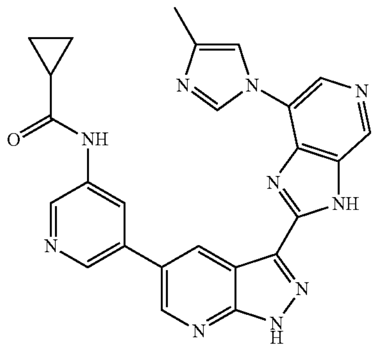 [SMILES: Cc1cn(-c2cncc3[nH]c(-c4n[nH]c5ncc(-c6cncc(NC(=O)C7CC7)c6)cc45)nc23)cn1]
TABLE 1-continued
281
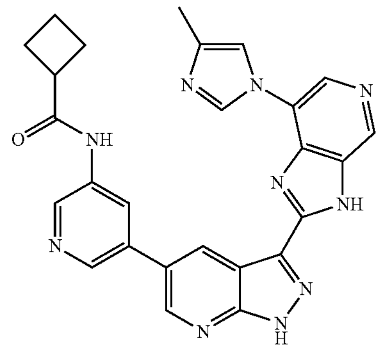 [SMILES: Cc1cn(-c2cncc3[nH]c(-c4n[nH]c5ncc(-c6cncc(NC(=O)C7CCC7)c6)cc45)nc23)cn1]
282
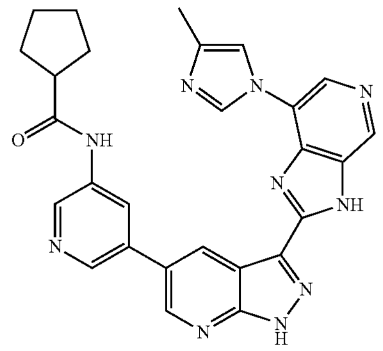 [SMILES: Cc1cn(-c2cncc3[nH]c(-c4n[nH]c5ncc(-c6cncc(NC(=O)C7CCCC7)c6)cc45)nc23)cn1]
283
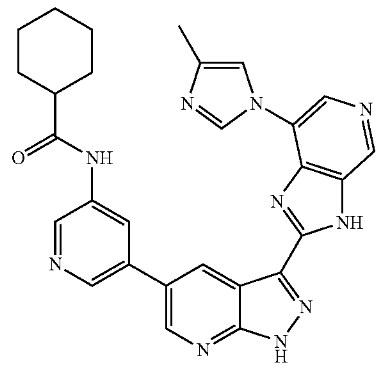
284
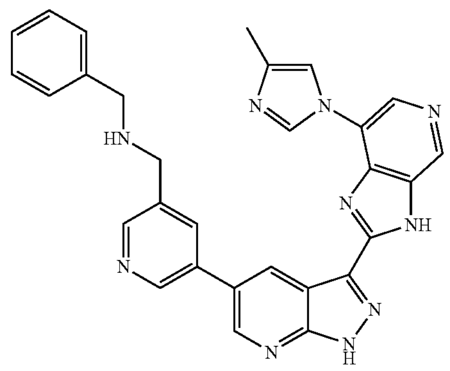 [SMILES: Cc1cn(-c2cncc3[nH]c(-c4n[nH]c5ncc(-c6cncc(CNCc7ccccc7)c6)cc45)nc23)cn1]

TABLE 1-continued
285
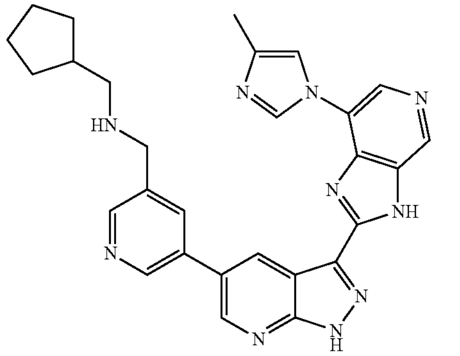 [SMILES: Cc1cn(-c2cncc3[nH]c(-c4n[nH]c5ncc(-c6cncc(CNCC7CCCC7)c6)cc45)nc23)cn1]
286
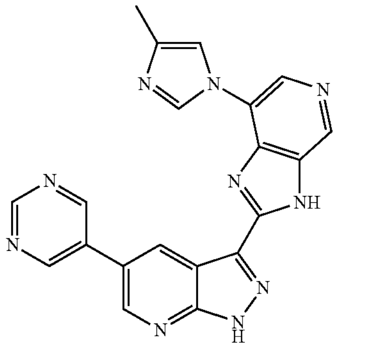 [SMILES: Cc1cn(-c2cncc3[nH]c(-c4n[nH]c5ncc(-c6cncnc6)cc45)nc23)cn1]
287
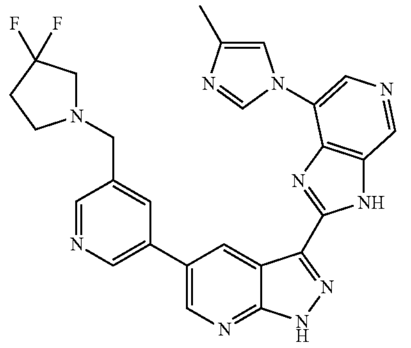
288
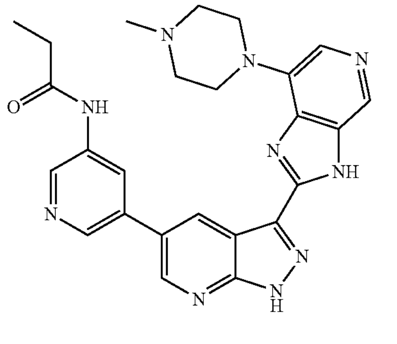 [SMILES: CCC(=O)Nc1cncc(-c2cnc3[nH]nc(-c4nc5c(N6CCN(C)CC6)cncc5[nH]4)c3c2)c1]
TABLE 1-continued
289
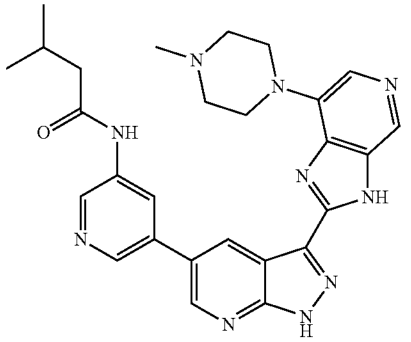 [SMILES: CC(C)CC(=O)Nc1cncc(-c2cnc3[nH]nc(-c4nc5c(N6CCN(C)CC6)cncc5[nH]4)c3c2)c1]
290
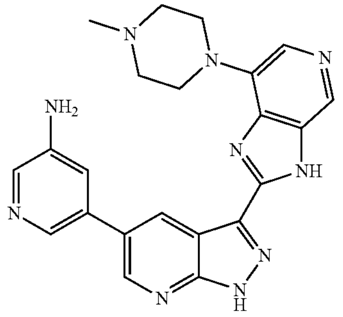 [SMILES: CN1CCN(c2cncc3[nH]c(-c4n[nH]c5ncc(-c6cncc(N)c6)cc45)nc23)CC1]
291
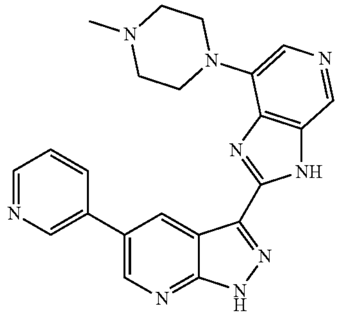 [SMILES: CN1CCN(c2cncc3[nH]c(-c4n[nH]c5ncc(-c6cccnc6)cc45)nc23)CC1]
292
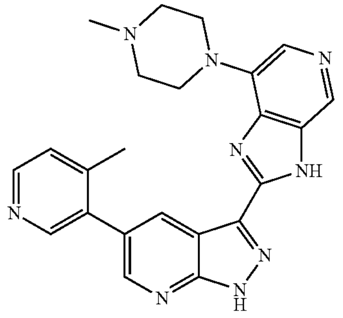 [SMILES: Cc1ccncc1-c1cnc2[nH]nc(-c3nc4c(N5CCN(C)CC5)cncc4[nH]3)c2c1]
293
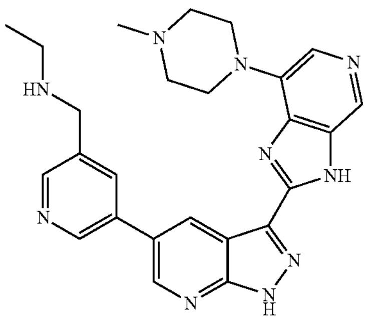 [SMILES: CCNCc1cncc(-c2cnc3[nH]nc(-c4nc5c(N6CCN(C)CC6)cncc5[nH]4)c3c2)c1]

TABLE 1-continued
294
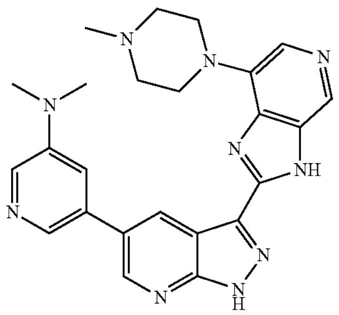 [SMILES: CN1CCN(c2cncc3[nH]c(-c4n[nH]c5ncc(-c6cncc(N(C)C)c6)cc45)nc23)CC1]
295
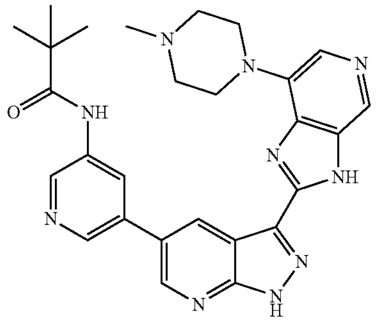 [SMILES: CN1CCN(c2cncc3[nH]c(-c4n[nH]c5ncc(-c6cncc(NC(=O)C(C)(C)C)c6)cc45)nc23)CC1]
296
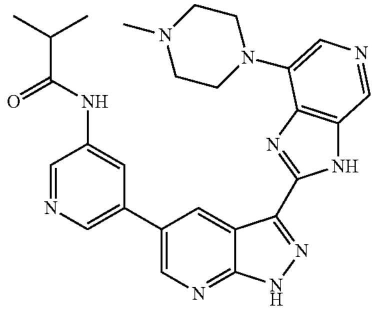 [SMILES: CC(C)C(=O)Nc1cncc(-c2cnc3[nH]nc(-c4nc5c(N6CCN(C)CC6)cncc5[nH]4)c3c2)c1]
297
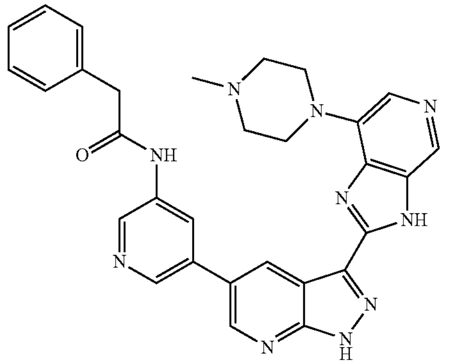 [SMILES: CN1CCN(c2cncc3[nH]c(-c4n[nH]c5ncc(-c6cncc(NC(=O)Cc7ccccc7)c6)cc45)nc23)CC1]
TABLE 1-continued
298
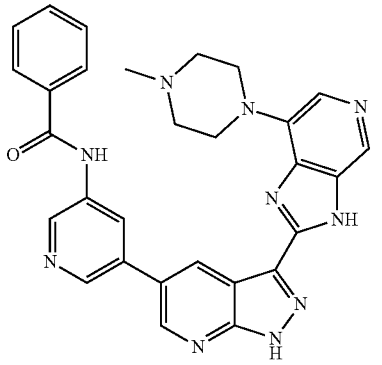 [SMILES: CN1CCN(c2cncc3[nH]c(-c4n[nH]c5ncc(-c6cncc(NC(=O)c7ccccc7)c6)cc45)nc23)CC1]
299
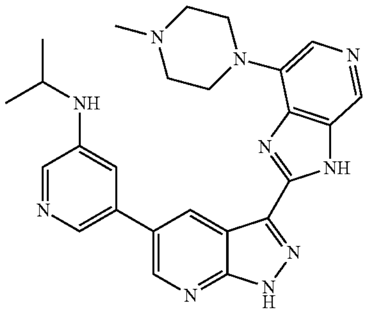 [SMILES: CC(C)Nc1cncc(-c2cnc3[nH]nc(-c4nc5c(N6CCN(C)CC6)cncc5[nH]4)c3c2)c1]
300
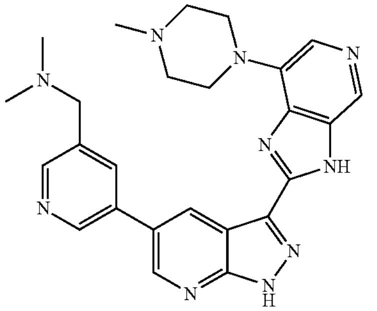
301
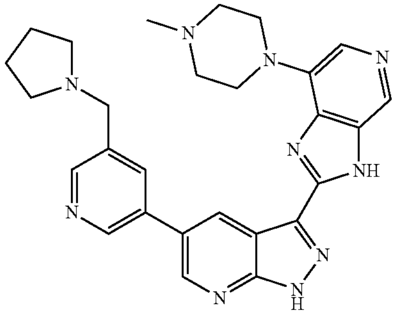 [SMILES: CN1CCN(c2cncc3[nH]c(-c4n[nH]c5ncc(-c6cncc(CN7CCCC7)c6)cc45)nc23)CC1]
302
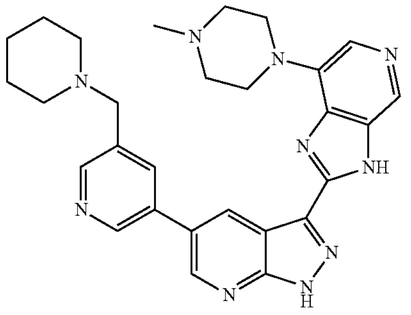 [SMILES: CN1CCN(c2cncc3[nH]c(-c4n[nH]c5ncc(-c6cncc(CN7CCCCC7)c6)cc45)nc23)CC1]

TABLE 1-continued
303
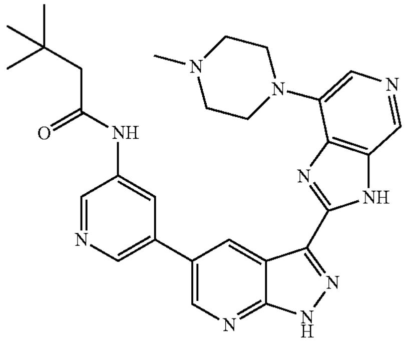 [SMILES: CN1CCN(c2cncc3[nH]c(-c4n[nH]c5ncc(-c6cncc(NC(=O)CC(C)(C)C)c6)cc45)nc23)CC1]
304
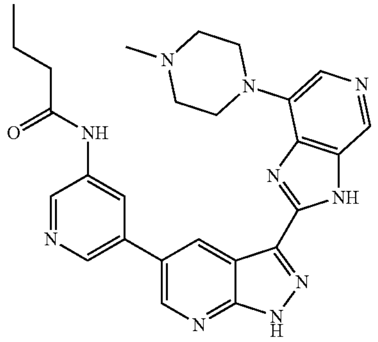 [SMILES: CCCC(=O)Nc1cncc(-c2cnc3[nH]nc(-c4nc5c(N6CCN(C)CC6)cncc5[nH]4)c3c2)c1]
305
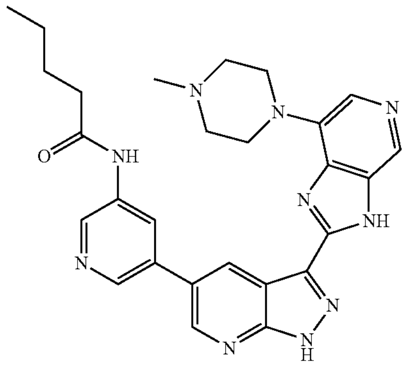 [SMILES: CCCCC(=O)Nc1cncc(-c2cnc3[nH]nc(-c4nc5c(N6CCN(C)CC6)cncc5[nH]4)c3c2)c1]
306
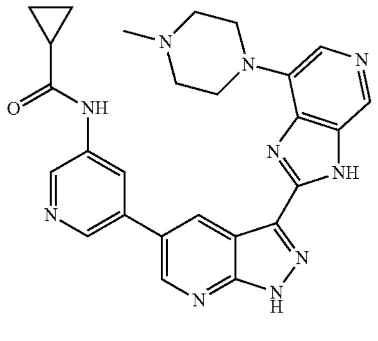 [SMILES: CN1CCN(c2cncc3[nH]c(-c4n[nH]c5ncc(-c6cncc(NC(=O)C7CC7)c6)cc45)nc23)CC1]
TABLE 1-continued
307
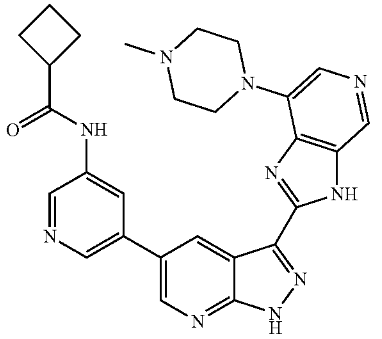 [SMILES: CN1CCN(c2cncc3[nH]c(-c4n[nH]c5ncc(-c6cncc(NC(=O)C7CCC7)c6)cc45)nc23)CC1]
308
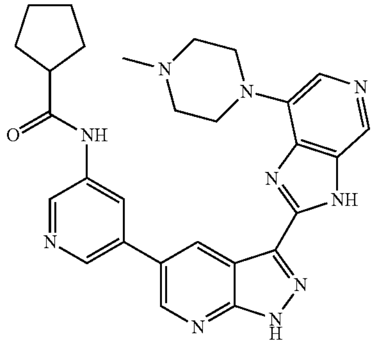 [SMILES: CN1CCN(c2cncc3[nH]c(-c4n[nH]c5ncc(-c6cncc(NC(=O)C7CCCC7)c6)cc45)nc23)CC1]
309
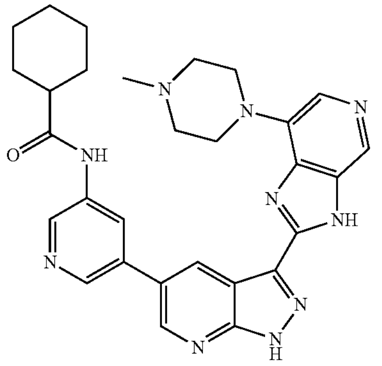 [SMILES: CN1CCN(c2cncc3[nH]c(-c4n[nH]c5ncc(-c6cncc(NC(=O)C7CCCCC7)c6)cc45)nc23)CC1]
310
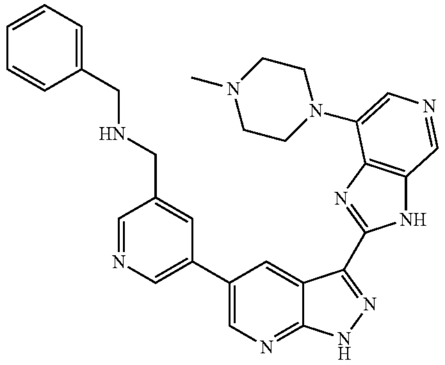 [SMILES: CN1CCN(c2cncc3[nH]c(-c4n[nH]c5ncc(-c6cncc(CNCc7ccccc7)c6)cc45)nc23)CC1]

311
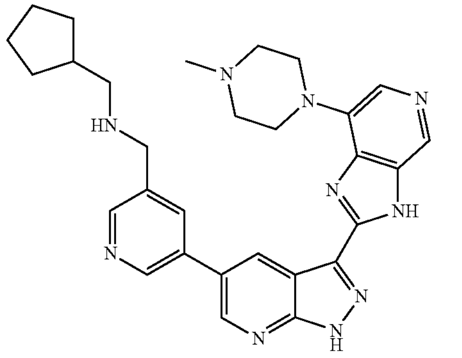 [SMILES: CN1CCN(c2cncc3[nH]c(-c4n[nH]c5ncc(-c6cncc(CNCC7CCCC7)c6)cc45)nc23)CC1]
312
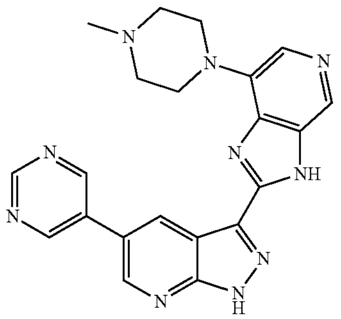 [SMILES: CN1CCN(c2cncc3[nH]c(-c4n[nH]c5ncc(-c6cncnc6)cc45)nc23)CC1]
313
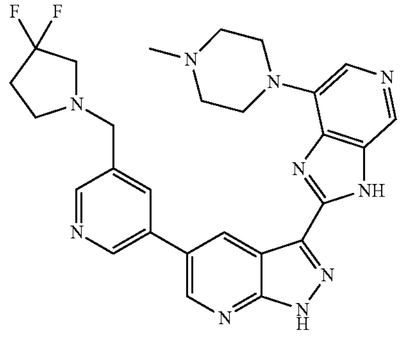 [SMILES: CN1CCN(c2cncc3[nH]c(-c4n[nH]c5ncc(-c6cncc(CN7CCC(F)(F)C7)c6)cc45)nc23)CC1]
314
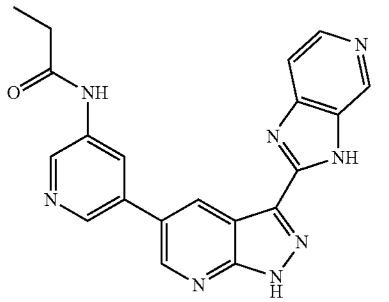
315
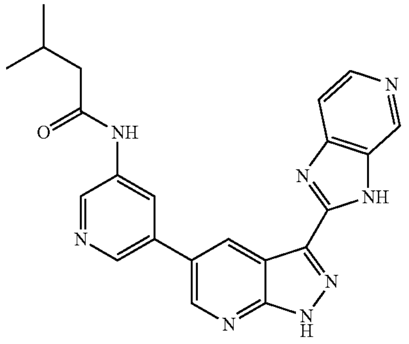
316
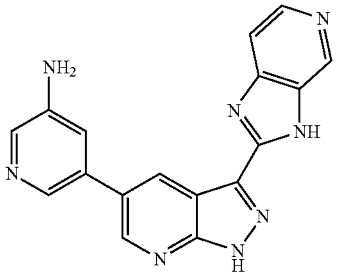 [SMILES: Nc1cncc(-c2cnc3[nH]nc(-c4nc5ccncc5[nH]4)c3c2)c1]
317
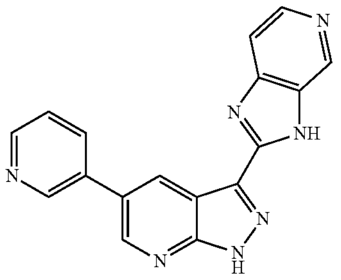 [SMILES: c1cncc(-c2cnc3[nH]nc(-c4nc5ccncc5[nH]4)c3c2)c1]
318
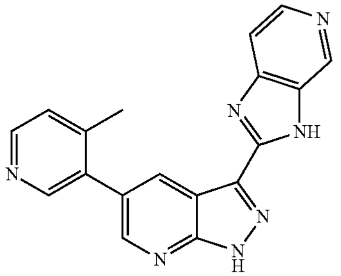 [SMILES: Cc1ccncc1-c1cnc2[nH]nc(-c3nc4ccncc4[nH]3)c2c1]
319
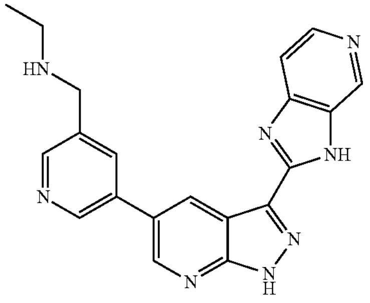

TABLE 1-continued
320
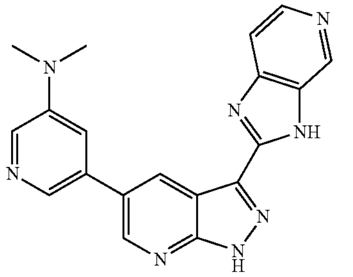 [SMILES: CN(C)c1cncc(-c2cnc3[nH]nc(-c4nc5ccncc5[nH]4)c3c2)c1]
321
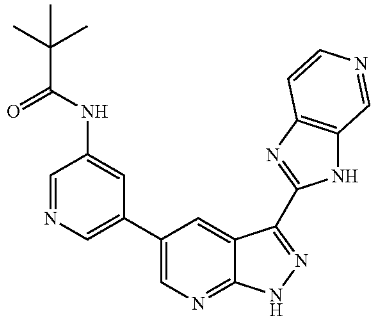 [SMILES: CC(C)(C)C(=O)Nc1cncc(-c2cnc3[nH]nc(-c4nc5ccncc5[nH]4)c3c2)c1]
322
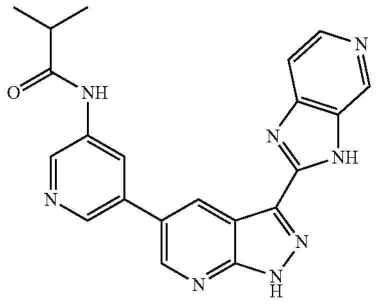
323
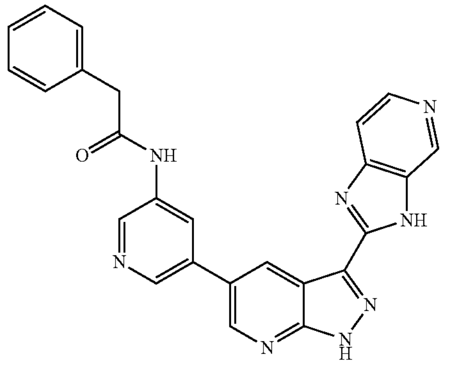 [SMILES: O=C(Cc1ccccc1)Nc1cncc(-c2cnc3[nH]nc(-c4nc5ccncc5[nH]4)c3c2)c1]
324
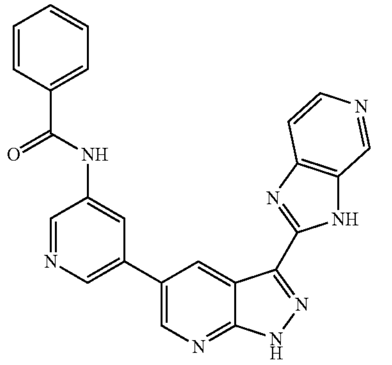 [SMILES: O=C(Nc1cncc(-c2cnc3[nH]nc(-c4nc5ccncc5[nH]4)c3c2)c1)c1ccccc1]
325
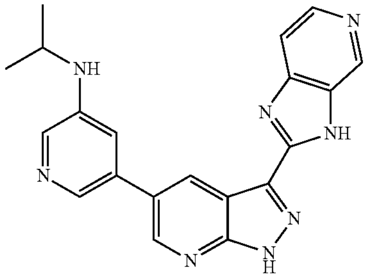 [SMILES: CC(C)Nc1cncc(-c2cnc3[nH]nc(-c4nc5ccncc5[nH]4)c3c2)c1]
326
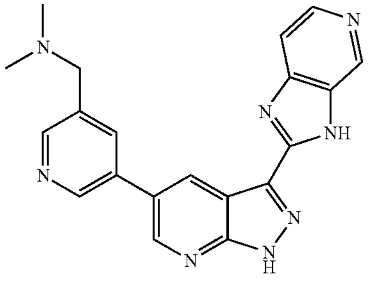 [SMILES: CN(C)Cc1cncc(-c2cnc3[nH]nc(-c4nc5ccncc5[nH]4)c3c2)c1]
327
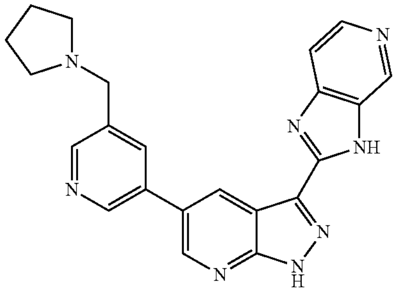 [SMILES: c1cc2nc(-c3n[nH]c4ncc(-c5cncc(CN6CCCC6)c5)cc34)[nH]c2cn1]
328
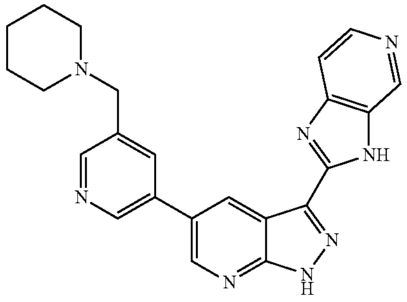 [SMILES: c1cc2nc(-c3n[nH]c4ncc(-c5cncc(CN6CCCCC6)c5)cc34)[nH]c2cn1]
329
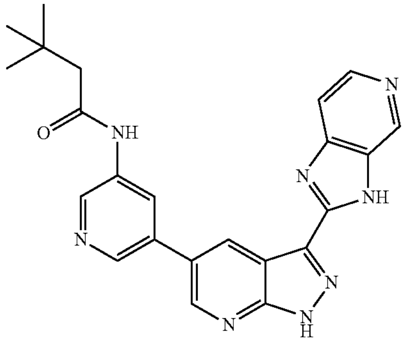

TABLE 1-continued
330
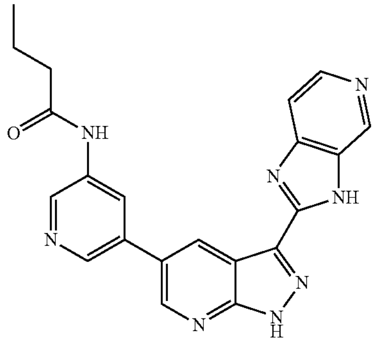 [SMILES: CCCC(=O)Nc1cncc(-c2cnc3[nH]nc(-c4nc5ccncc5[nH]4)c3c2)c1]
331
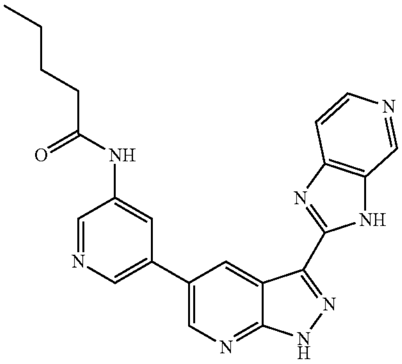 [SMILES: CCCCC(=O)Nc1cncc(-c2cnc3[nH]nc(-c4nc5ccncc5[nH]4)c3c2)c1]
332
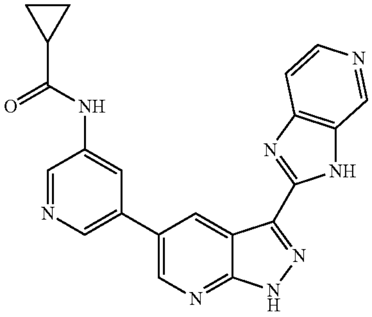 [SMILES: O=C(Nc1cncc(-c2cnc3[nH]nc(-c4nc5ccncc5[nH]4)c3c2)c1)C1CC1]
333
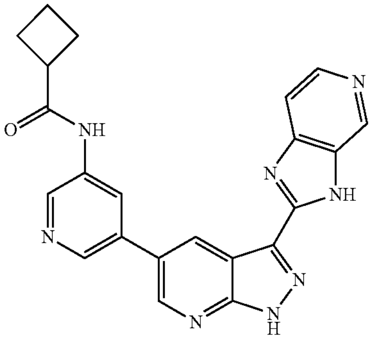 [SMILES: O=C(Nc1cncc(-c2cnc3[nH]nc(-c4nc5ccncc5[nH]4)c3c2)c1)C1CCC1]
TABLE 1-continued
334
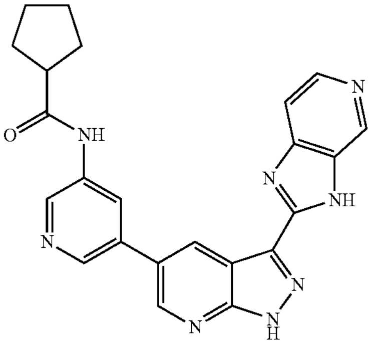 [SMILES: O=C(Nc1cncc(-c2cnc3[nH]nc(-c4nc5ccncc5[nH]4)c3c2)c1)C1CCCC1]
335
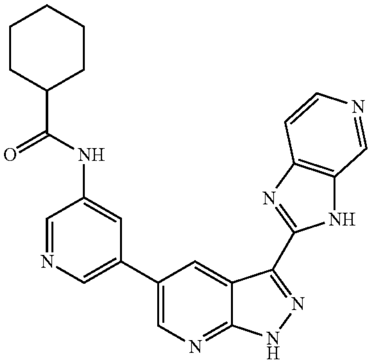 [SMILES: O=C(Nc1cncc(-c2cnc3[nH]nc(-c4nc5ccncc5[nH]4)c3c2)c1)C1CCCCC1]
336
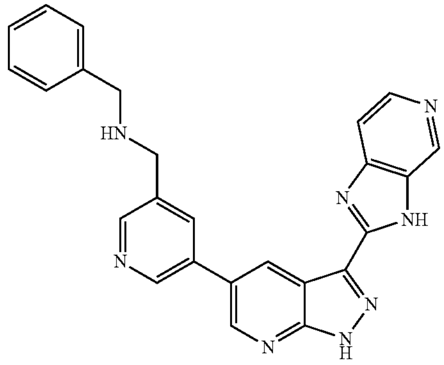 [SMILES: c1ccc(CNCc2cncc(-c3cnc4[nH]nc(-c5nc6ccncc6[nH]5)c4c3)c2)cc1]
337
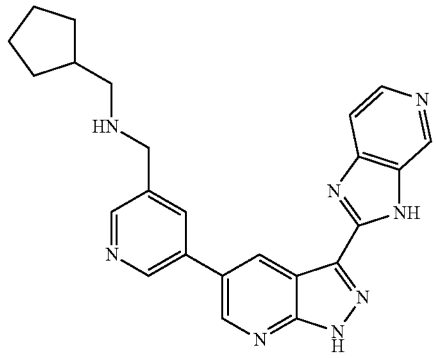

TABLE 1-continued
338
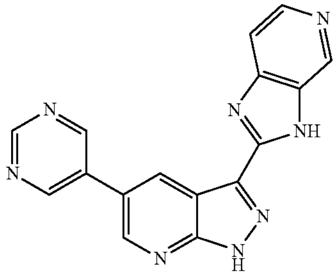 [SMILES: c1cc2nc(-c3n[nH]c4ncc(-c5cncnc5)cc34)[nH]c2cn1]
339
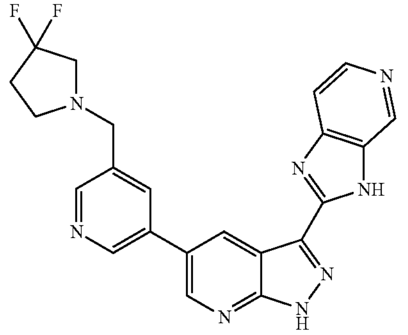 [SMILES: FC1(F)CCN(Cc2cncc(-c3cnc4[nH]nc(-c5nc6ccncc6[nH]5)c4c3)c2)C1]
340
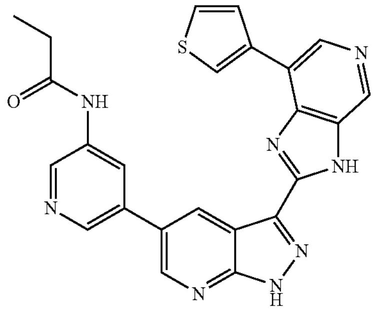 [SMILES: CCC(=O)Nc1cncc(-c2cnc3[nH]nc(-c4nc5c(-c6ccsc6)cncc5[nH]4)c3c2)c1]
341
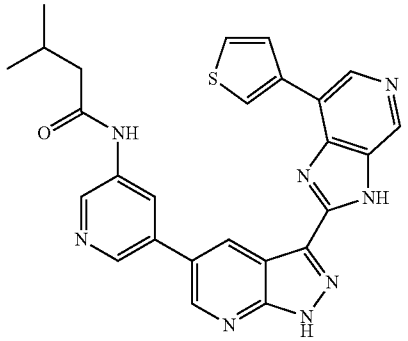 [SMILES: CC(C)CC(=O)Nc1cncc(-c2cnc3[nH]nc(-c4nc5c(-c6ccsc6)cncc5[nH]4)c3c2)c1]
342
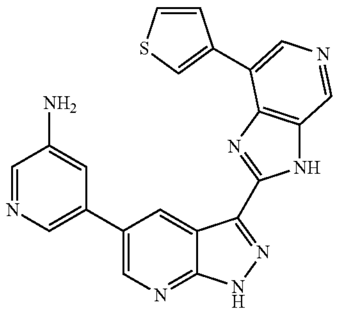
TABLE 1-continued
343
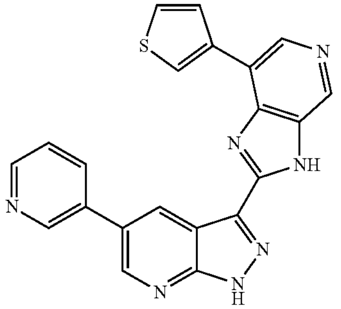
344
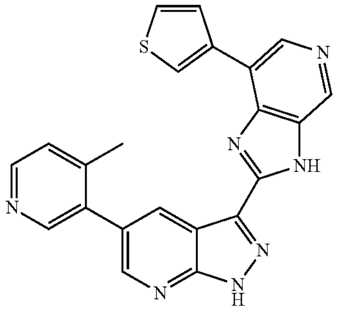 [SMILES: Cc1ccncc1-c1cnc2[nH]nc(-c3nc4c(-c5ccsc5)cncc4[nH]3)c2c1]
345
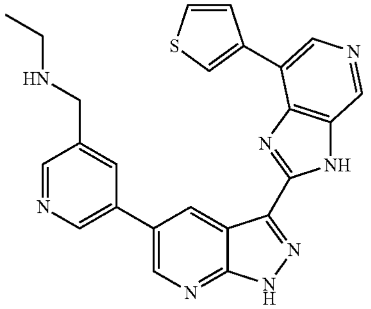 [SMILES: CCNCc1cncc(-c2cnc3[nH]nc(-c4nc5c(-c6ccsc6)cncc5[nH]4)c3c2)c1]
346
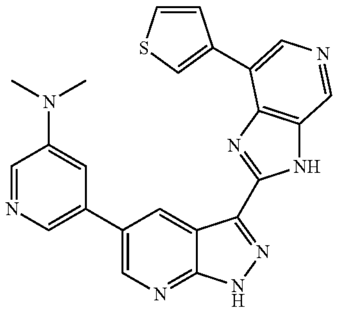
347
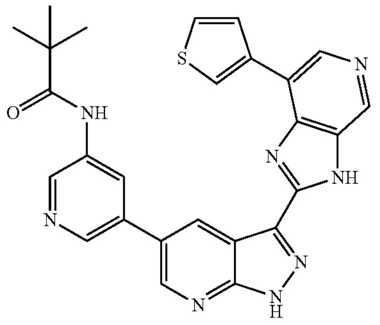 [SMILES: CC(C)(C)C(=O)Nc1cncc(-c2cnc3[nH]nc(-c4nc5c(-c6ccsc6)cncc5[nH]4)c3c2)c1]

TABLE 1-continued
348
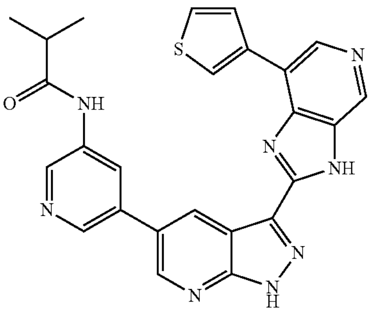 [SMILES: CC(C)C(=O)Nc1cncc(-c2cnc3[nH]nc(-c4nc5c(-c6ccsc6)cncc5[nH]4)c3c2)c1]
349
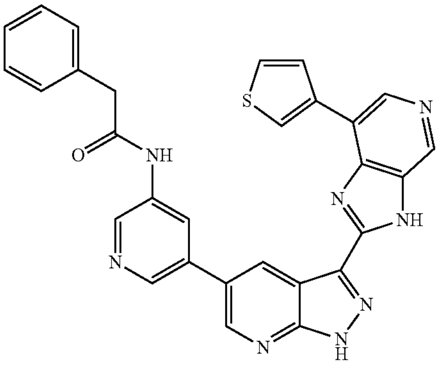 [SMILES: O=C(Cc1ccccc1)Nc1cncc(-c2cnc3[nH]nc(-c4nc5c(-c6ccsc6)cncc5[nH]4)c3c2)c1]
350
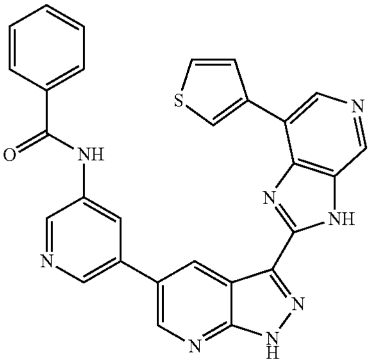
351
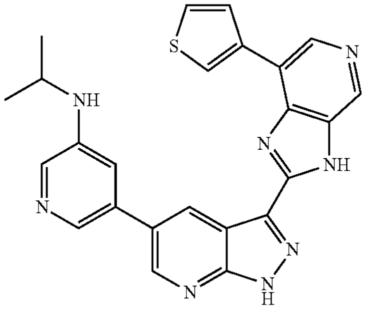 [SMILES: CC(C)Nc1cncc(-c2cnc3[nH]nc(-c4nc5c(-c6ccsc6)cncc5[nH]4)c3c2)c1]
TABLE 1-continued
352
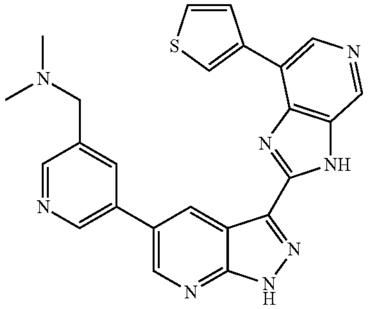
353
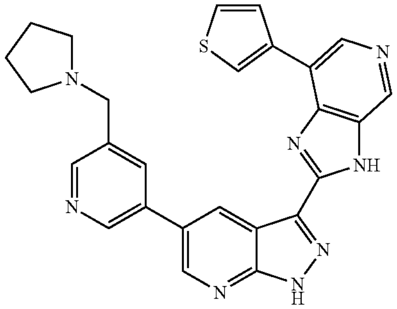 [SMILES: c1cc(-c2cncc3[nH]c(-c4n[nH]c5ncc(-c6cncc(CN7CCCC7)c6)cc45)nc23)cs1]
354
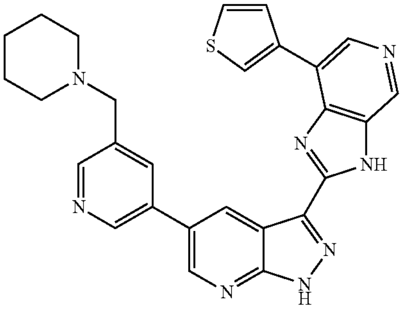 [SMILES: c1cc(-c2cncc3[nH]c(-c4n[nH]c5ncc(-c6cncc(CN7CCCCC7)c6)cc45)nc23)cs1]
355
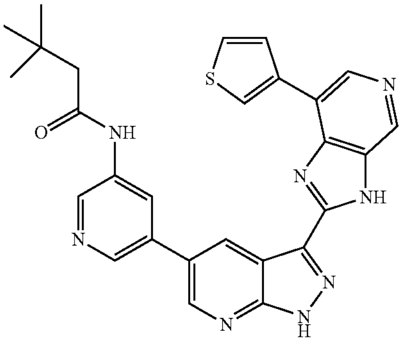 [SMILES: CC(C)(C)CC(=O)Nc1cncc(-c2cnc3[nH]nc(-c4nc5c(-c6ccsc6)cncc5[nH]4)c3c2)c1]
356
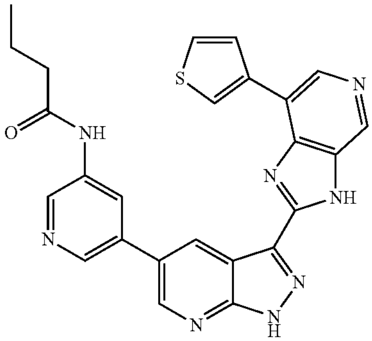 [SMILES: CCCC(=O)Nc1cncc(-c2cnc3[nH]nc(-c4nc5c(-c6ccsc6)cncc5[nH]4)c3c2)c1]

TABLE 1-continued
357
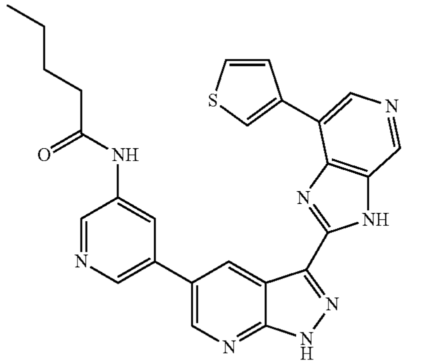
358
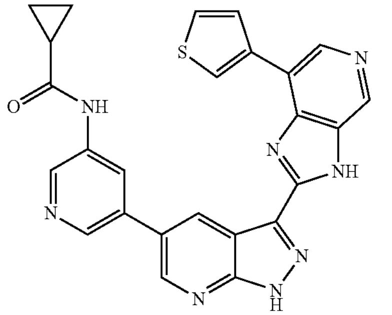
359
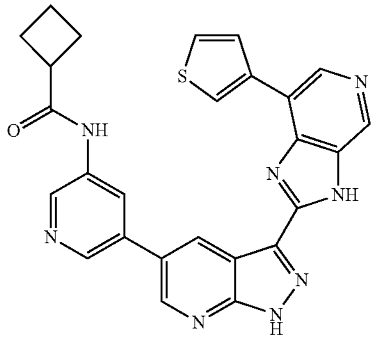
360
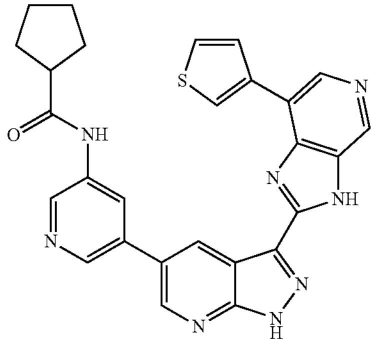 [SMILES: O=C(Nc1cncc(-c2cnc3[nH]nc(-c4nc5c(-c6ccsc6)cncc5[nH]4)c3c2)c1)C1CCCC1]
TABLE 1-continued
361
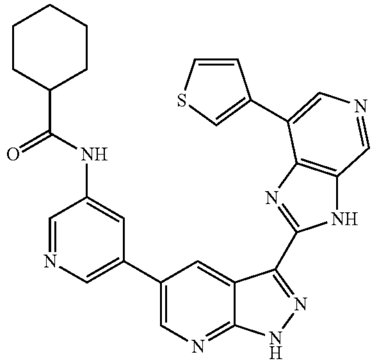 [SMILES: O=C(Nc1cncc(-c2cnc3[nH]nc(-c4nc5c(-c6ccsc6)cncc5[nH]4)c3c2)c1)C1CCCCC1]
362
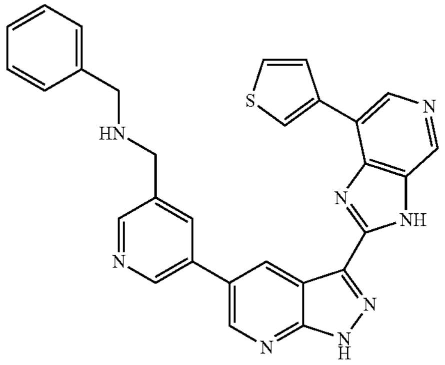
363
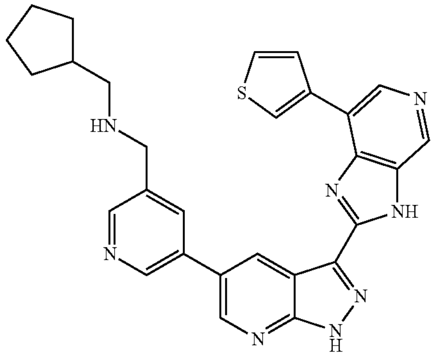
364
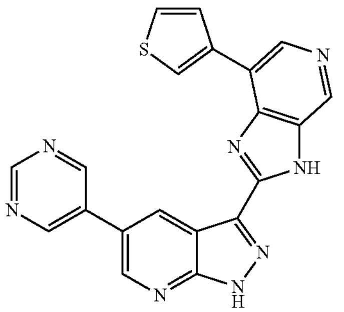

TABLE 1-continued
365
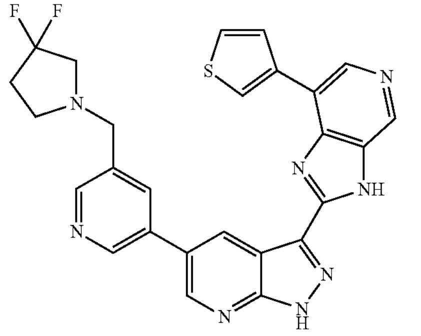 [SMILES: FC1(F)CCN(Cc2cncc(-c3cnc4[nH]nc(-c5nc6c(-c7ccsc7)cncc6[nH]5)c4c3)c2)C1]
366
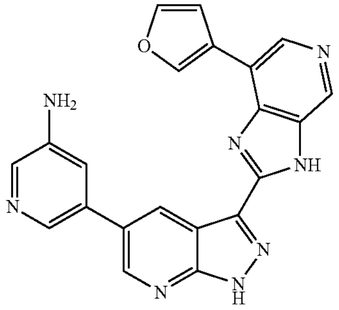
367
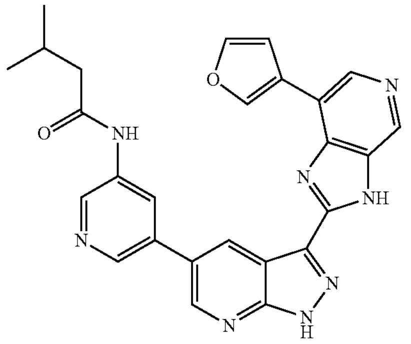 [SMILES: CC(C)CC(=O)Nc1cncc(-c2cnc3[nH]nc(-c4nc5c(-c6ccoc6)cncc5[nH]4)c3c2)c1]
368
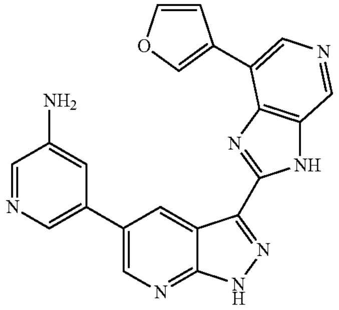
369
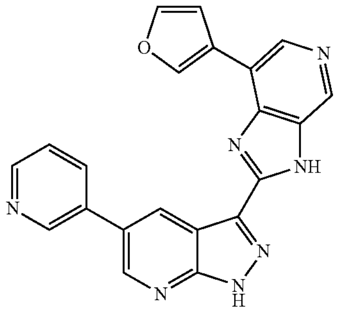
TABLE 1-continued
370
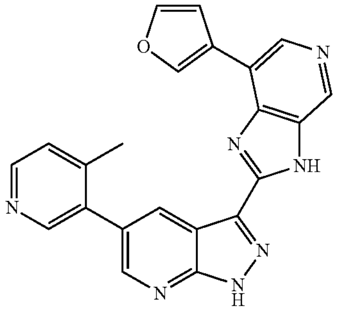
371
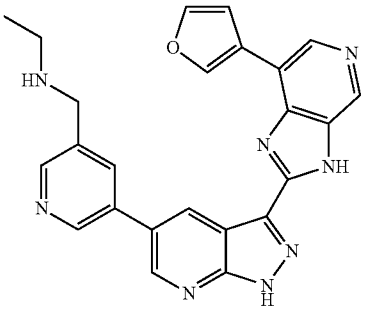
372
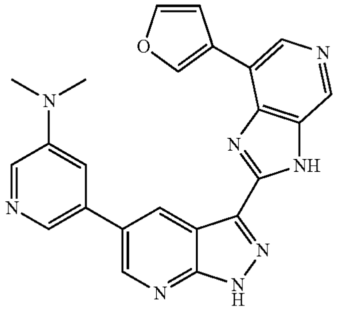 [SMILES: CN(C)c1cncc(-c2cnc3[nH]nc(-c4nc5c(-c6ccoc6)cncc5[nH]4)c3c2)c1]
373
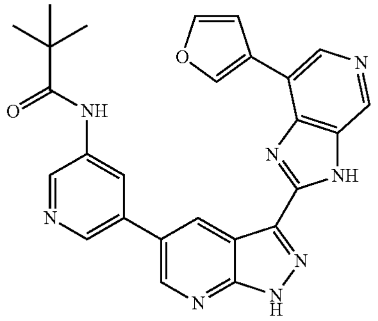 [SMILES: CC(C)(C)C(=O)Nc1cncc(-c2cnc3[nH]nc(-c4nc5c(-c6ccoc6)cncc5[nH]4)c3c2)c1]
374
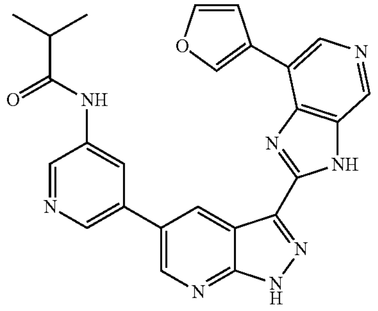

TABLE 1-continued
375
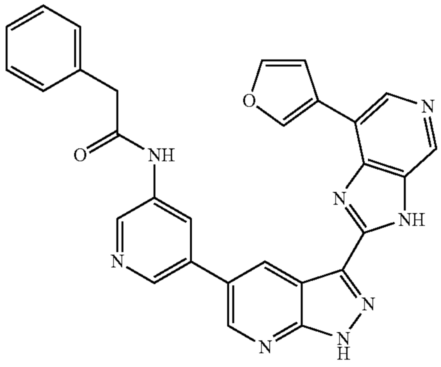 [SMILES: O=C(Cc1ccccc1)Nc1cncc(-c2cnc3[nH]nc(-c4nc5c(-c6ccoc6)cncc5[nH]4)c3c2)c1]
376
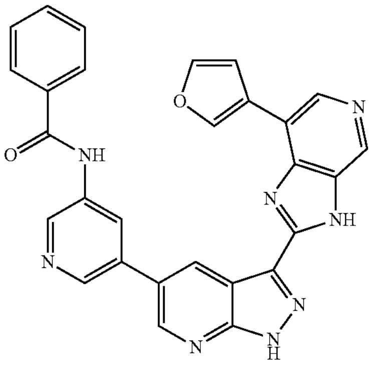 [SMILES: O=C(Nc1cncc(-c2cnc3[nH]nc(-c4nc5c(-c6ccoc6)cncc5[nH]4)c3c2)c1)c1ccccc1]
377
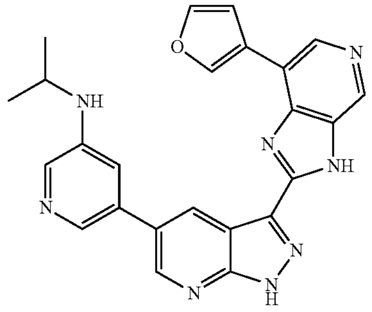
378
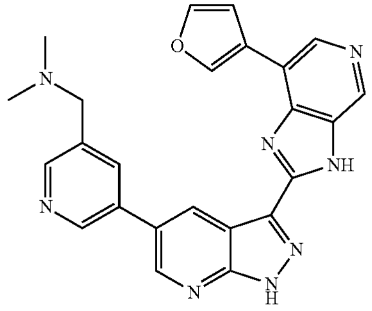
TABLE 1-continued
379
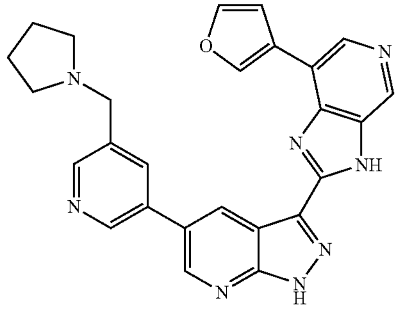
380
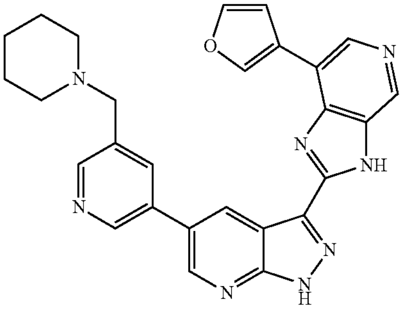
381
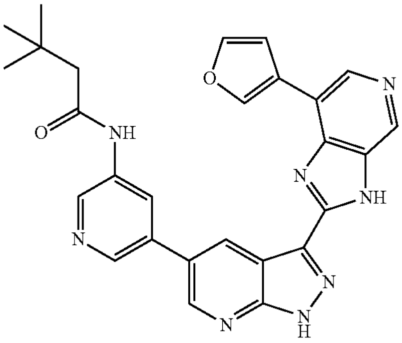
382
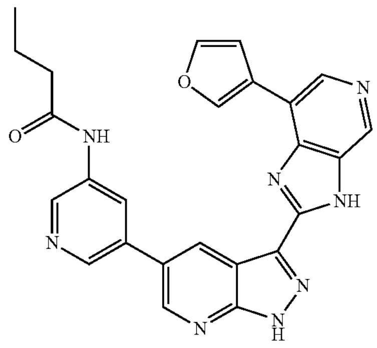

TABLE 1-continued
383
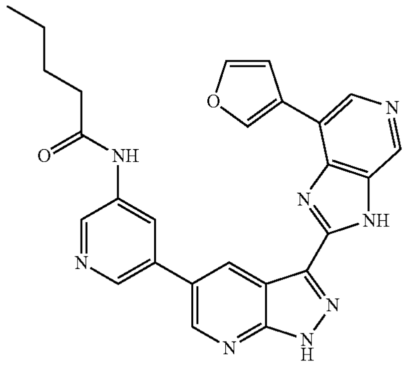 [SMILES: CCCCC(=O)Nc1cncc(-c2cnc3[nH]nc(-c4nc5c(-c6ccoc6)cncc5[nH]4)c3c2)c1]
384
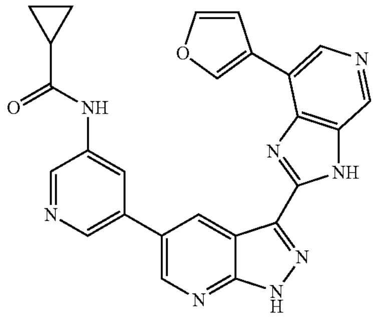 [SMILES: O=C(Nc1cncc(-c2cnc3[nH]nc(-c4nc5c(-c6ccoc6)cncc5[nH]4)c3c2)c1)C1CC1]
385
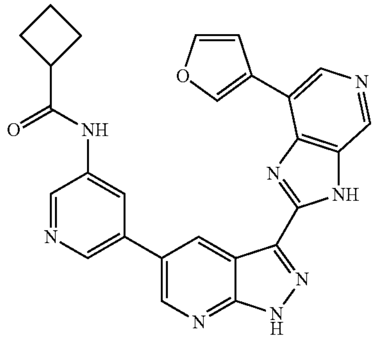 [SMILES: O=C(Nc1cncc(-c2cnc3[nH]nc(-c4nc5c(-c6ccoc6)cncc5[nH]4)c3c2)c1)C1CCC1]
386
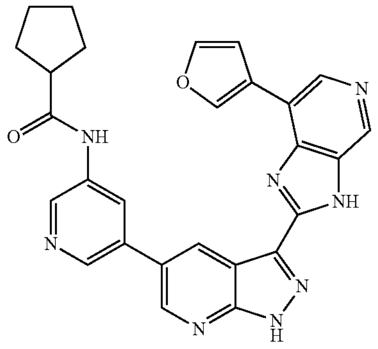
TABLE 1-continued
387
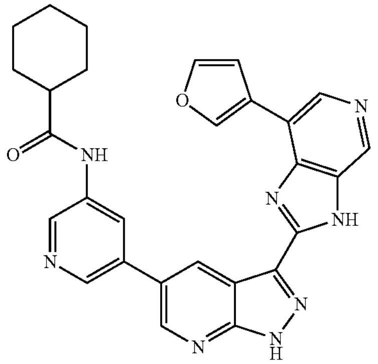 [SMILES: O=C(Nc1cncc(-c2cnc3[nH]nc(-c4nc5c(-c6ccoc6)cncc5[nH]4)c3c2)c1)C1CCCCC1]
388
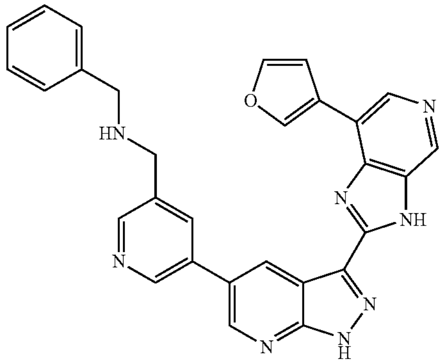 [SMILES: c1ccc(CNCc2cncc(-c3cnc4[nH]nc(-c5nc6c(-c7ccoc7)cncc6[nH]5)c4c3)c2)cc1]
389
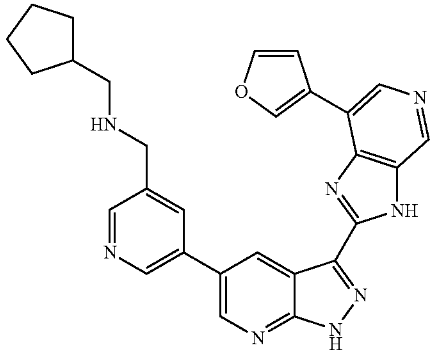 [SMILES: c1cc(-c2cncc3[nH]c(-c4n[nH]c5ncc(-c6cncc(CNCC7CCCC7)c6)cc45)nc23)co1]
390
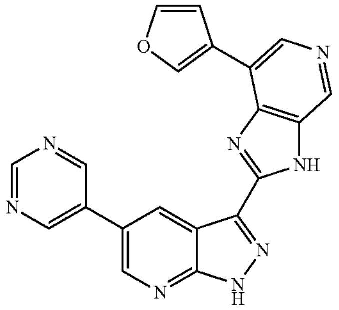 [SMILES: c1ncc(-c2cnc3[nH]nc(-c4nc5c(-c6ccoc6)cncc5[nH]4)c3c2)cn1]

TABLE 1-continued
391
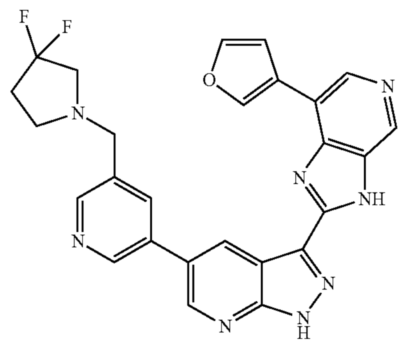
392
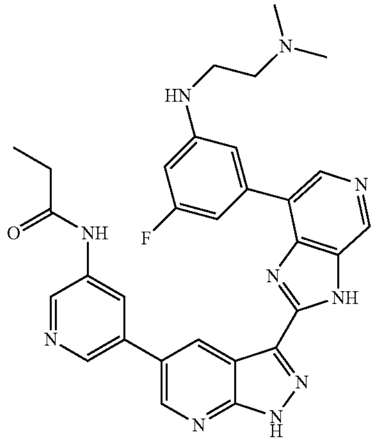 [SMILES: CCC(=O)Nc1cncc(-c2cnc3[nH]nc(-c4nc5c(-c6cc(F)cc(NCCN(C)C)c6)cncc5[nH]4)c3c2)c1]
393
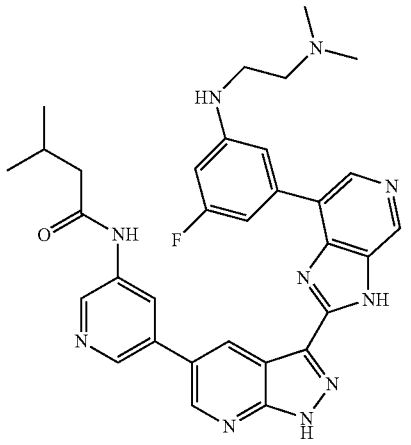 [SMILES: CC(C)CC(=O)Nc1cncc(-c2cnc3[nH]nc(-c4nc5c(-c6cc(F)cc(NCCN(C)C)c6)cncc5[nH]4)c3c2)c1]
TABLE 1-continued
394
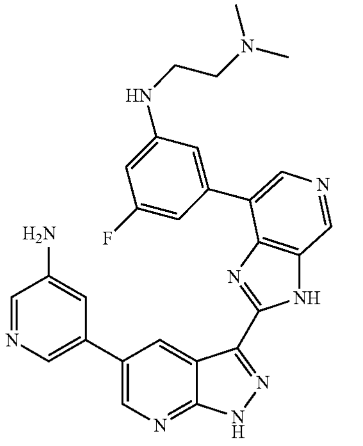 [SMILES: CN(C)CCNc1cc(F)cc(-c2cncc3[nH]c(-c4n[nH]c5ncc(-c6cncc(N)c6)cc45)nc23)c1]
395
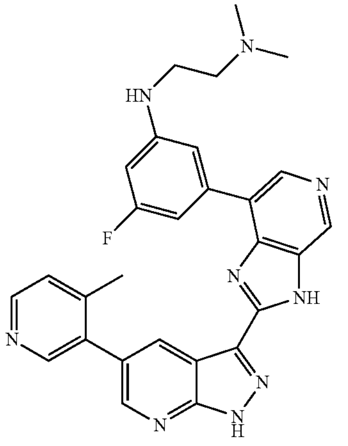
396
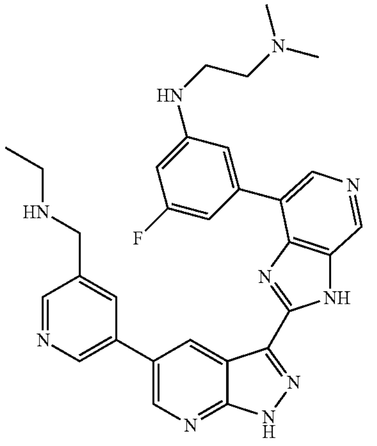 [SMILES: CCNCc1cncc(-c2cnc3[nH]nc(-c4nc5c(-c6cc(F)cc(NCCN(C)C)c6)cncc5[nH]4)c3c2)c1]

TABLE 1-continued
397
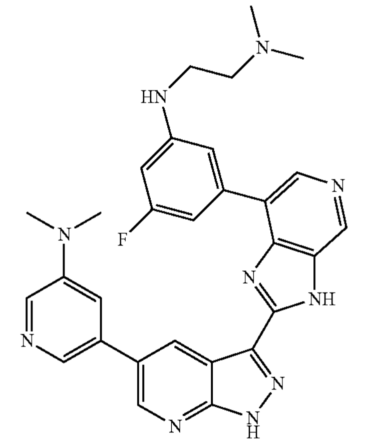
398
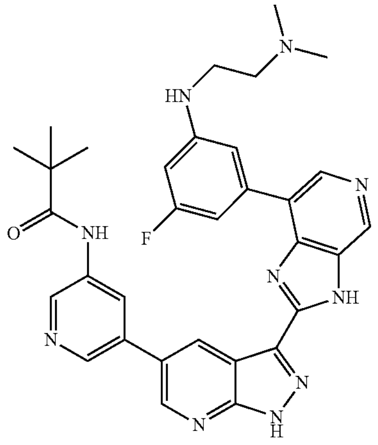 [SMILES: CN(C)CCNc1cc(F)cc(-c2cncc3[nH]c(-c4n[nH]c5ncc(-c6cncc(NC(=O)C(C)(C)C)c6)cc45)nc23)c1]
399
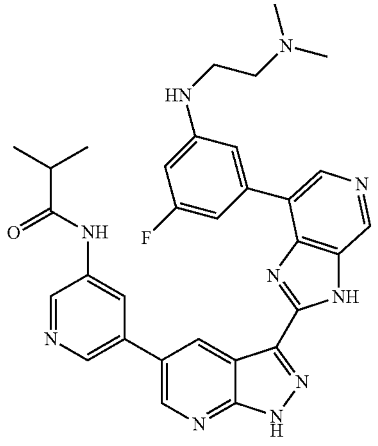 [SMILES: CC(C)C(=O)Nc1cncc(-c2cnc3[nH]nc(-c4nc5c(-c6cc(F)cc(NCCN(C)C)c6)cncc5[nH]4)c3c2)c1]
TABLE 1-continued
401
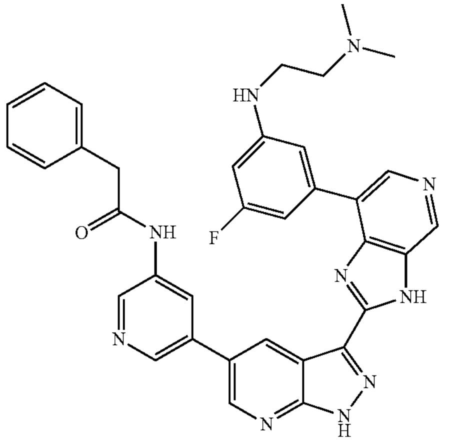
402
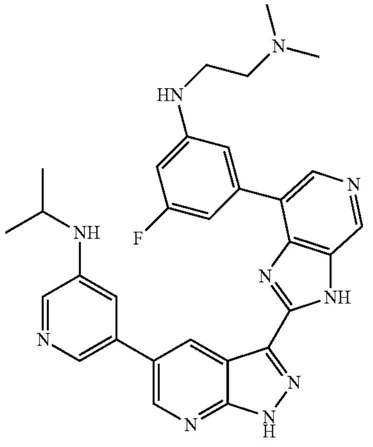 [SMILES: CC(C)Nc1cncc(-c2cnc3[nH]nc(-c4nc5c(-c6cc(F)cc(NCCN(C)C)c6)cncc5[nH]4)c3c2)c1]
403
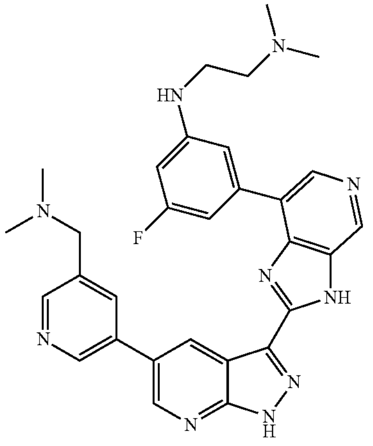

TABLE 1-continued
404
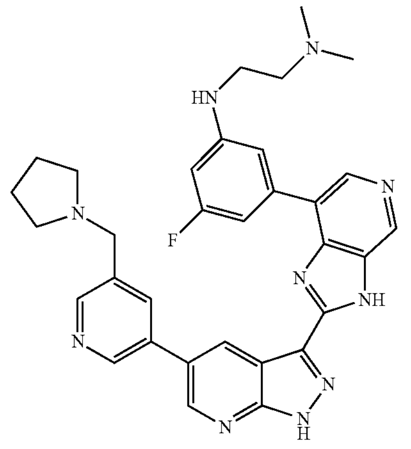 [SMILES: CN(C)CCNc1cc(F)cc(-c2cncc3[nH]c(-c4n[nH]c5ncc(-c6cncc(CN7CCCC7)c6)cc45)nc23)c1]
405
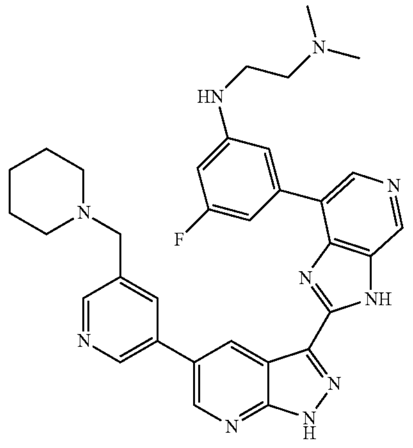
406
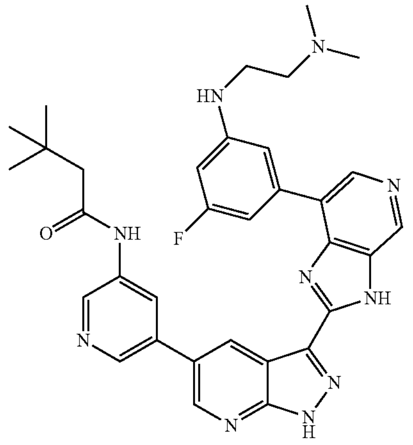 [SMILES: CN(C)CCNc1cc(F)cc(-c2cncc3[nH]c(-c4n[nH]c5ncc(-c6cncc(NC(=O)CC(C)(C)C)c6)cc45)nc23)c1]
TABLE 1-continued
407
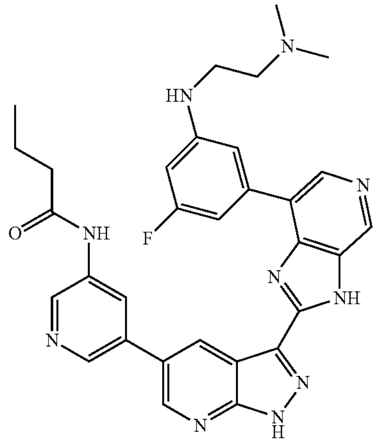 [SMILES: CCCC(=O)Nc1cncc(-c2cnc3[nH]nc(-c4nc5c(-c6cc(F)cc(NCCN(C)C)c6)cncc5[nH]4)c3c2)c1]
408
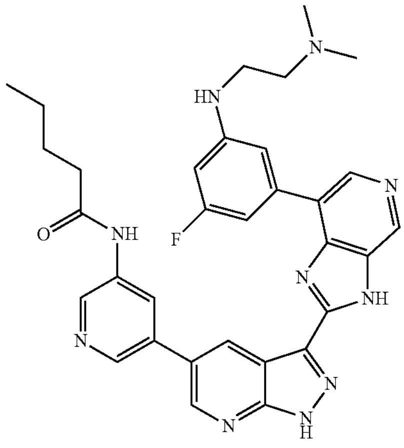 [SMILES: CCCCC(=O)Nc1cncc(-c2cnc3[nH]nc(-c4nc5c(-c6cc(F)cc(NCCN(C)C)c6)cncc5[nH]4)c3c2)c1]
409
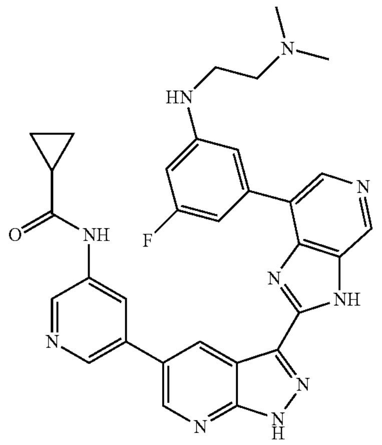 [SMILES: CN(C)CCNc1cc(F)cc(-c2cncc3[nH]c(-c4n[nH]c5ncc(-c6cncc(NC(=O)C7CC7)c6)cc45)nc23)c1]

410
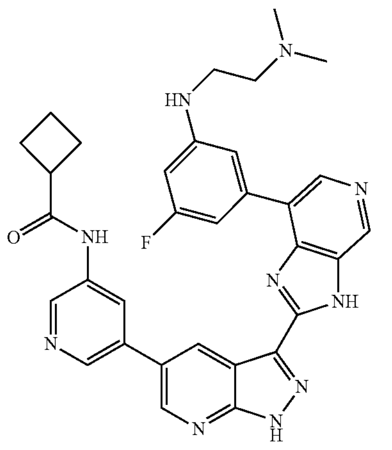 [SMILES: CN(C)CCNc1cc(F)cc(-c2cncc3[nH]c(-c4n[nH]c5ncc(-c6cncc(NC(=O)C7CCC7)c6)cc45)nc23)c1]
411
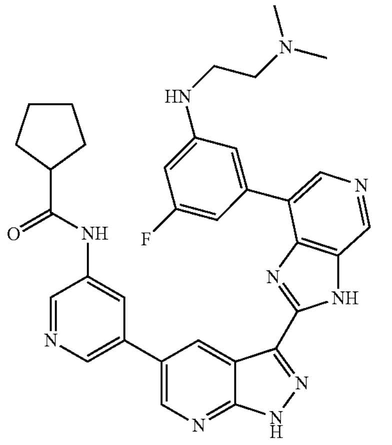 [SMILES: CN(C)CCNc1cc(F)cc(-c2cncc3[nH]c(-c4n[nH]c5ncc(-c6cncc(NC(=O)C7CCCC7)c6)cc45)nc23)c1]
412
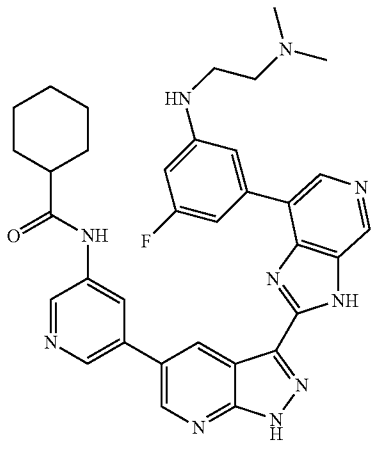 [SMILES: CN(C)CCNc1cc(F)cc(-c2cncc3[nH]c(-c4n[nH]c5ncc(-c6cncc(NC(=O)C7CCCCC7)c6)cc45)nc23)c1]
413
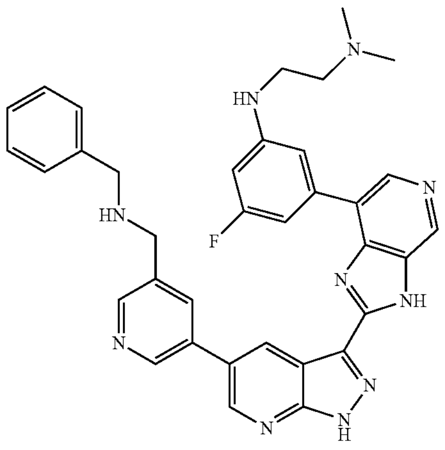
414
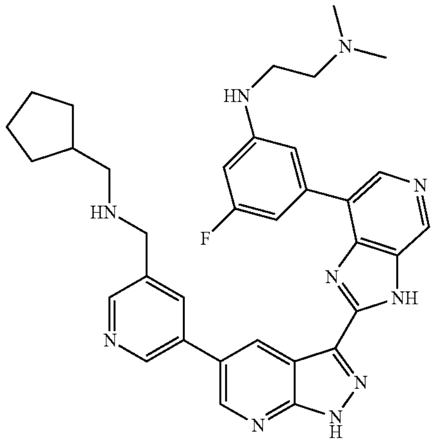 [SMILES: CN(C)CCNc1cc(F)cc(-c2cncc3[nH]c(-c4n[nH]c5ncc(-c6cncc(CNCC7CCCC7)c6)cc45)nc23)c1]
415
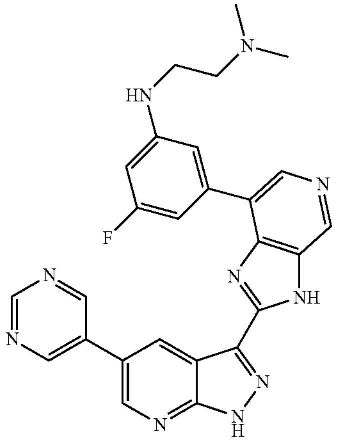

TABLE 1-continued
416
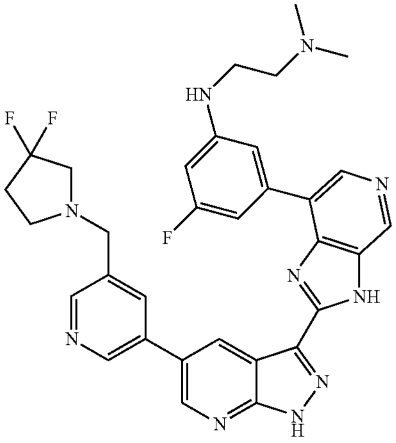
417
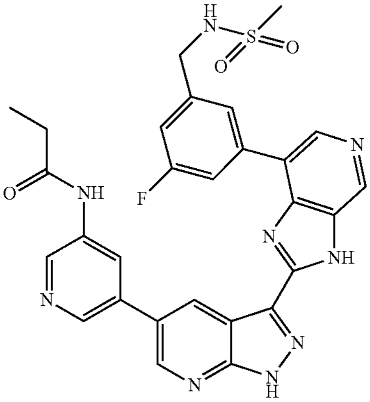 [SMILES: CCC(=O)Nc1cncc(-c2cnc3[nH]nc(-c4nc5c(-c6cc(F)cc(CNS(C)(=O)=O)c6)cncc5[nH]4)c3c2)c1]
418
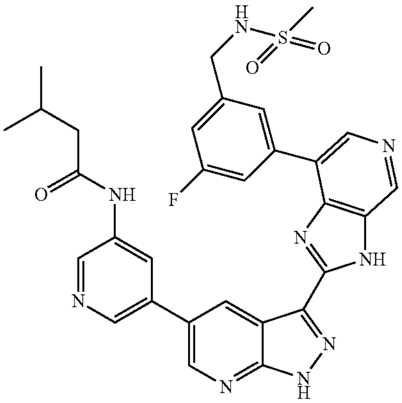 [SMILES: CC(C)CC(=O)Nc1cncc(-c2cnc3[nH]nc(-c4nc5c(-c6cc(F)cc(CNS(C)(=O)=O)c6)cncc5[nH]4)c3c2)c1]
419
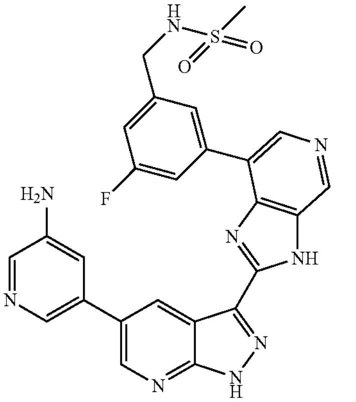 [SMILES: CS(=O)(=O)NCc1cc(F)cc(-c2cncc3[nH]c(-c4n[nH]c5ncc(-c6cncc(N)c6)cc45)nc23)c1]
TABLE 1-continued
420
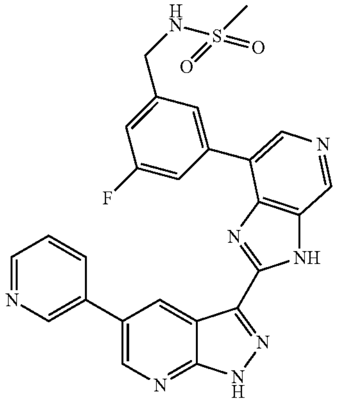
421
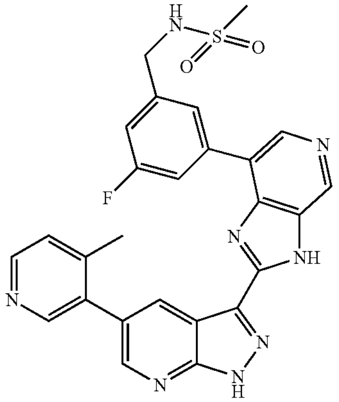 [SMILES: Cc1ccncc1-c1cnc2[nH]nc(-c3nc4c(-c5cc(F)cc(CNS(C)(=O)=O)c5)cncc4[nH]3)c2c1]
422
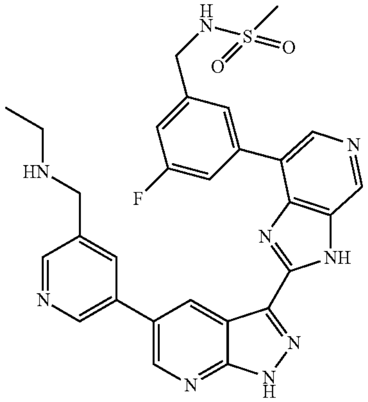 [SMILES: CCNCc1cncc(-c2cnc3[nH]nc(-c4nc5c(-c6cc(F)cc(CNS(C)(=O)=O)c6)cncc5[nH]4)c3c2)c1]
423
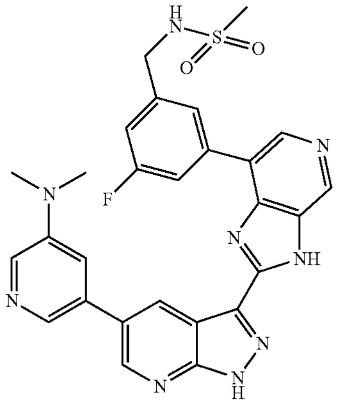 [SMILES: CN(C)c1cncc(-c2cnc3[nH]nc(-c4nc5c(-c6cc(F)cc(CNS(C)(=O)=O)c6)cncc5[nH]4)c3c2)c1]

TABLE 1-continued
424
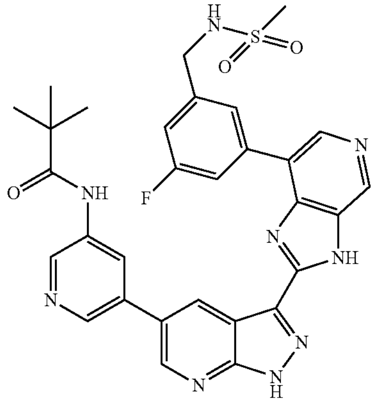 [SMILES: CC(C)(C)C(=O)Nc1cncc(-c2cnc3[nH]nc(-c4nc5c(-c6cc(F)cc(CNS(C)(=O)=O)c6)cncc5[nH]4)c3c2)c1]
425
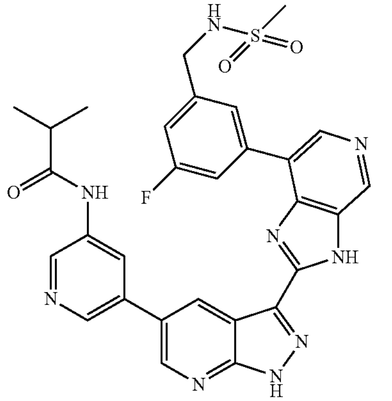 [SMILES: CC(C)C(=O)Nc1cncc(-c2cnc3[nH]nc(-c4nc5c(-c6cc(F)cc(CNS(C)(=O)=O)c6)cncc5[nH]4)c3c2)c1]
426
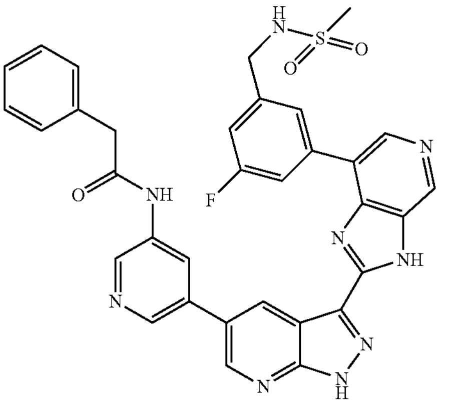 [SMILES: CS(=O)(=O)NCc1cc(F)cc(-c2cncc3[nH]c(-c4n[nH]c5ncc(-c6cncc(NC(=O)Cc7ccccc7)c6)cc45)nc23)c1]
427
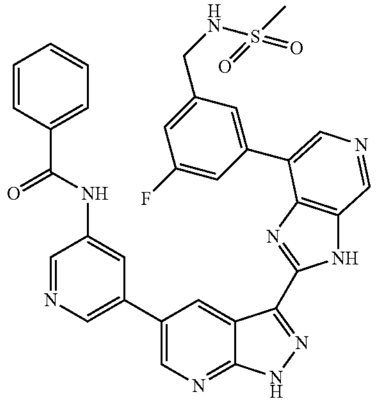
TABLE 1-continued
428
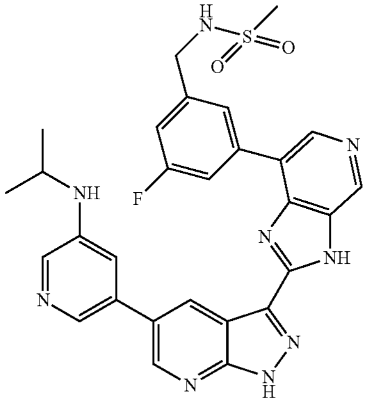
429
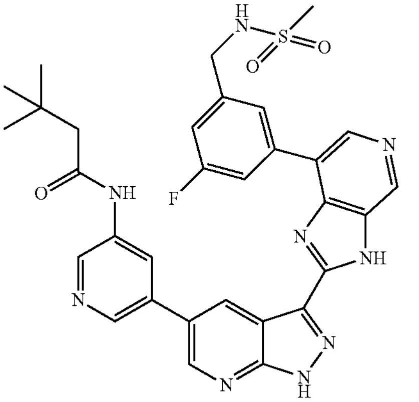 [SMILES: CC(C)(C)CC(=O)Nc1cncc(-c2cnc3[nH]nc(-c4nc5c(-c6cc(F)cc(CNS(C)(=O)=O)c6)cncc5[nH]4)c3c2)c1]
430
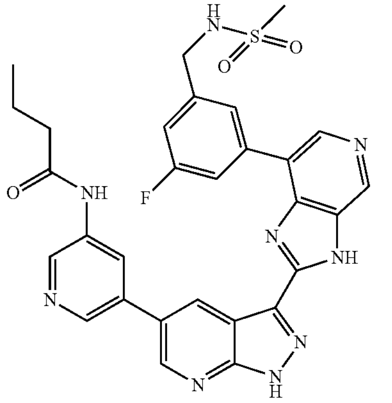 [SMILES: CCCC(=O)Nc1cncc(-c2cnc3[nH]nc(-c4nc5c(-c6cc(F)cc(CNS(C)(=O)=O)c6)cncc5[nH]4)c3c2)c1]
431
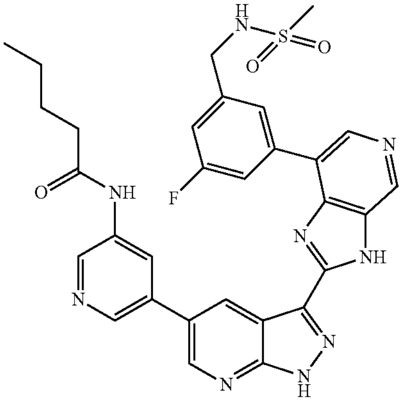 [SMILES: CCCCC(=O)Nc1cncc(-c2cnc3[nH]nc(-c4nc5c(-c6cc(F)cc(CNS(C)(=O)=O)c6)cncc5[nH]4)c3c2)c1]

TABLE 1-continued
432
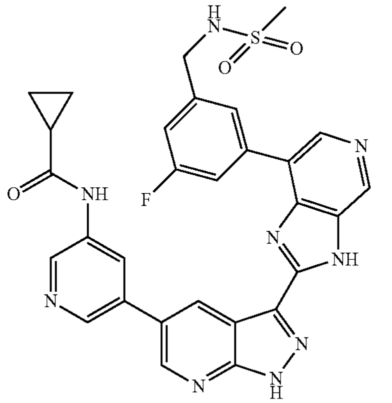 [SMILES: CS(=O)(=O)NCc1cc(F)cc(-c2cncc3[nH]c(-c4n[nH]c5ncc(-c6cncc(NC(=O)C7CC7)c6)cc45)nc23)c1]
433
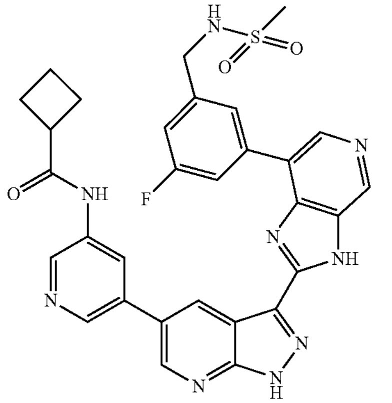 [SMILES: CS(=O)(=O)NCc1cc(F)cc(-c2cncc3[nH]c(-c4n[nH]c5ncc(-c6cncc(NC(=O)C7CCC7)c6)cc45)nc23)c1]
434
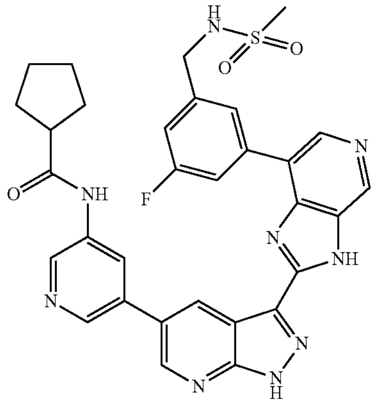 [SMILES: CS(=O)(=O)NCc1cc(F)cc(-c2cncc3[nH]c(-c4n[nH]c5ncc(-c6cncc(NC(=O)C7CCCC7)c6)cc45)nc23)c1]
435
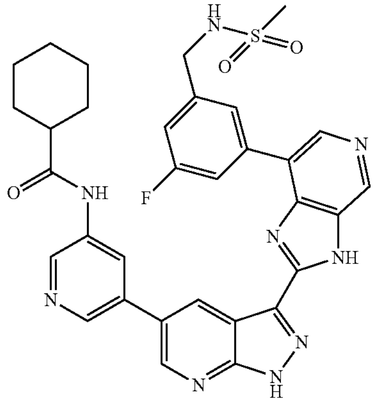 [SMILES: CS(=O)(=O)NCc1cc(F)cc(-c2cncc3[nH]c(-c4n[nH]c5ncc(-c6cncc(NC(=O)C7CCCCC7)c6)cc45)nc23)c1]
TABLE 1-continued
436
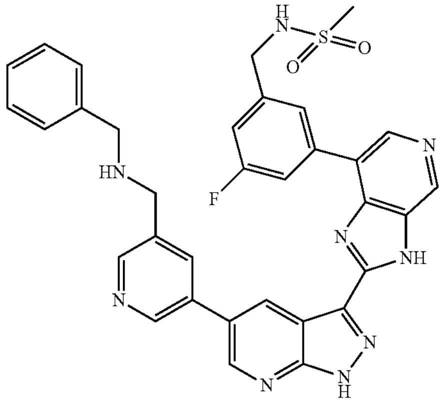 [SMILES: CS(=O)(=O)NCc1cc(F)cc(-c2cncc3[nH]c(-c4n[nH]c5ncc(-c6cncc(CNCc7ccccc7)c6)cc45)nc23)c1]
437
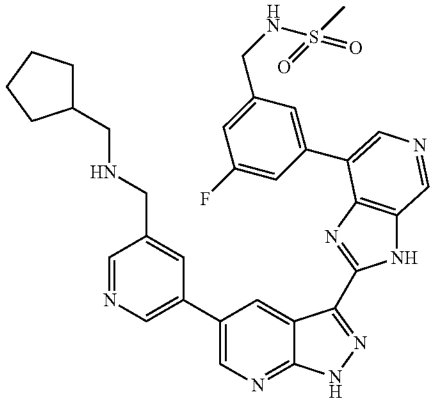 [SMILES: CS(=O)(=O)NCc1cc(F)cc(-c2cncc3[nH]c(-c4n[nH]c5ncc(-c6cncc(CNCC7CCCC7)c6)cc45)nc23)c1]
438
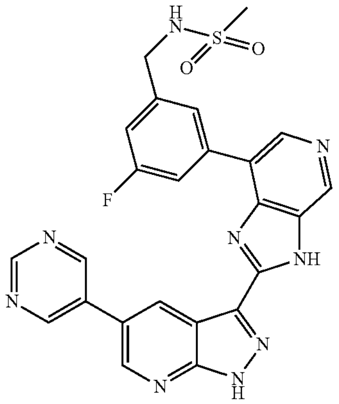
439
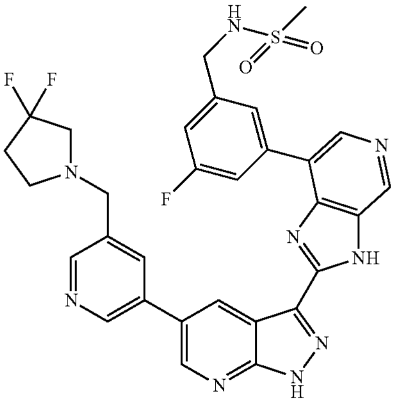 [SMILES: CS(=O)(=O)NCc1cc(F)cc(-c2cncc3[nH]c(-c4n[nH]c5ncc(-c6cncc(CN7CCC(F)(F)C7)c6)cc45)nc23)c1]

TABLE 1-continued
440
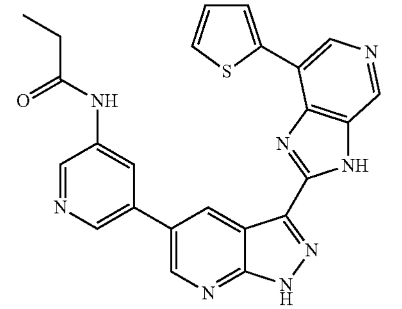 [SMILES: CCC(=O)Nc1cncc(-c2cnc3[nH]nc(-c4nc5c(-c6cccs6)cncc5[nH]4)c3c2)c1]
441
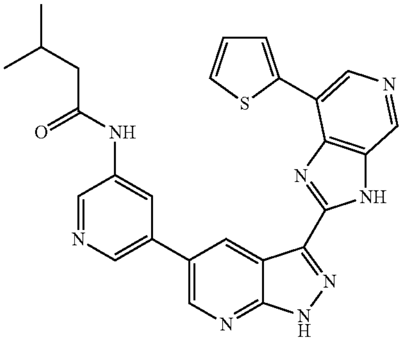
442
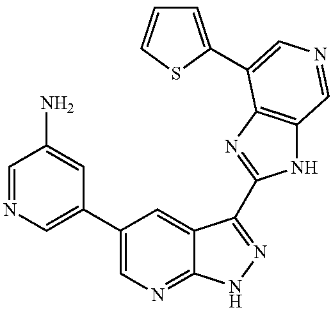 [SMILES: Nc1cncc(-c2cnc3[nH]nc(-c4nc5c(-c6cccs6)cncc5[nH]4)c3c2)c1]
443
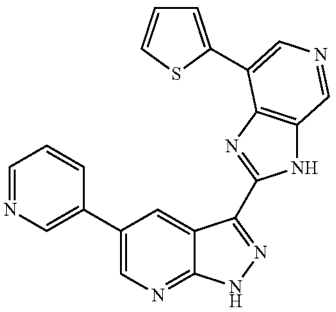
444
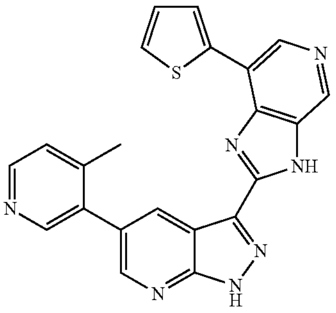
TABLE 1-continued
445
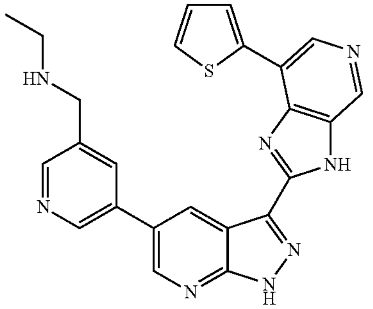
446
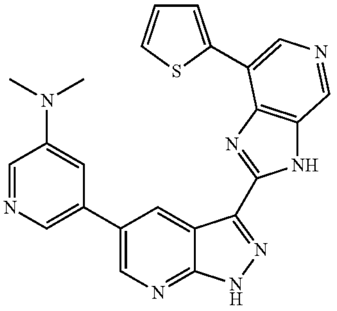 [SMILES: CN(C)c1cncc(-c2cnc3[nH]nc(-c4nc5c(-c6cccs6)cncc5[nH]4)c3c2)c1]
447
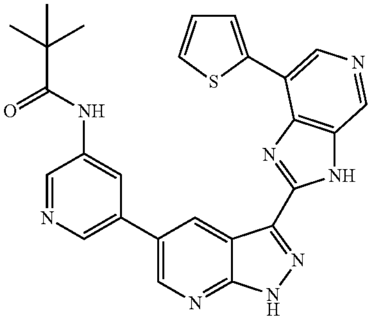
448
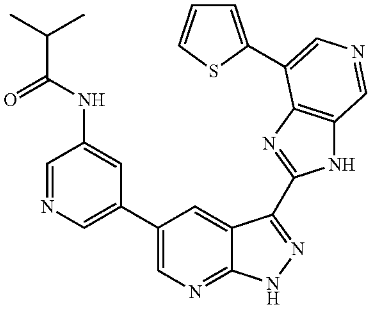
449
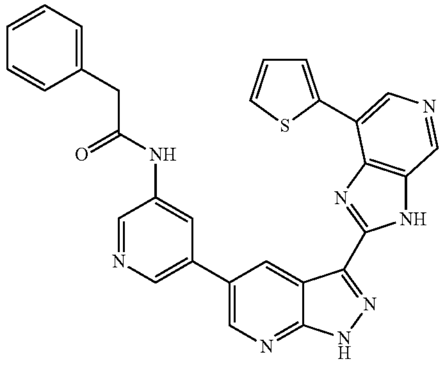 [SMILES: O=C(Cc1ccccc1)Nc1cncc(-c2cnc3[nH]nc(-c4nc5c(-c6cccs6)cncc5[nH]4)c3c2)c1]

TABLE 1-continued
450
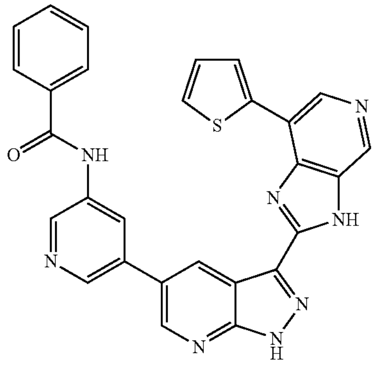
451
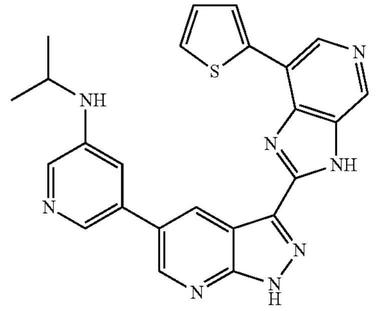
452
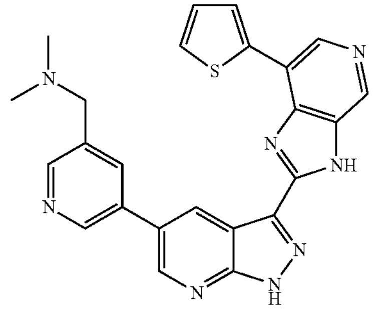 [SMILES: CN(C)Cc1cncc(-c2cnc3[nH]nc(-c4nc5c(-c6cccs6)cncc5[nH]4)c3c2)c1]
453
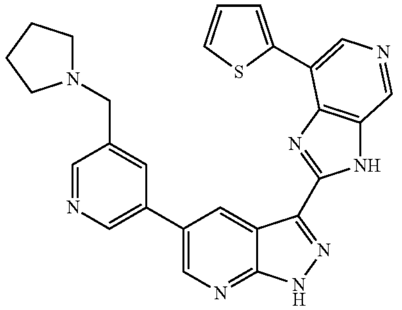
454
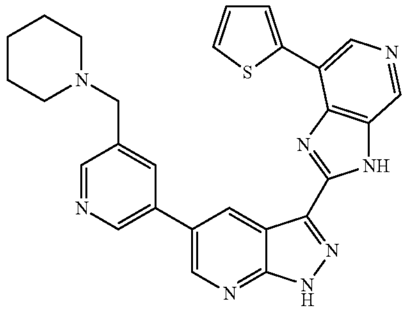
TABLE 1-continued
455
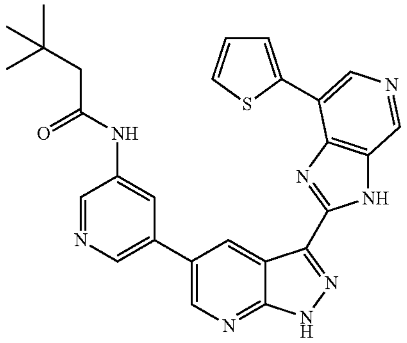
456
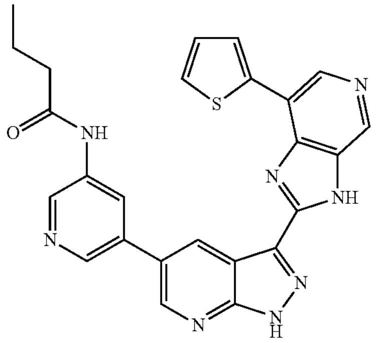
457
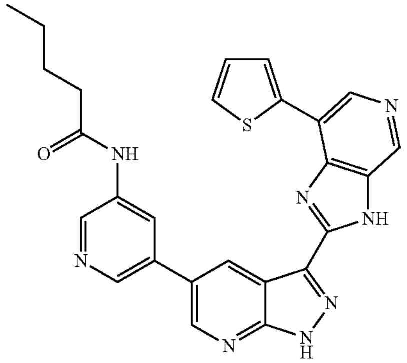
458
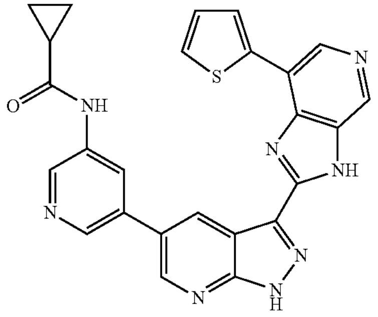

TABLE 1-continued
459
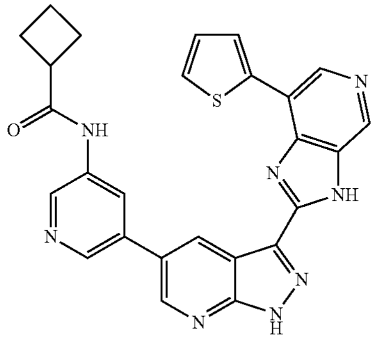
460
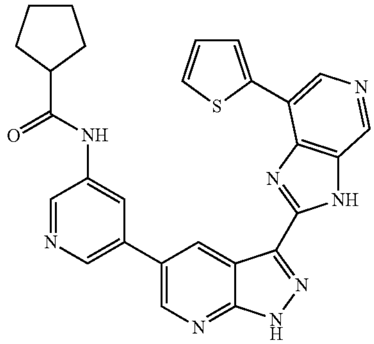
461
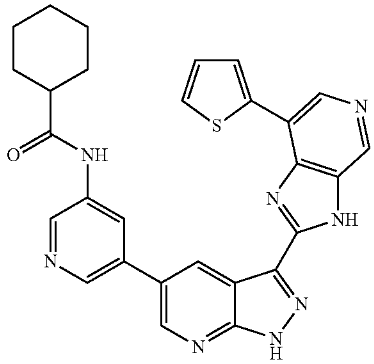
462
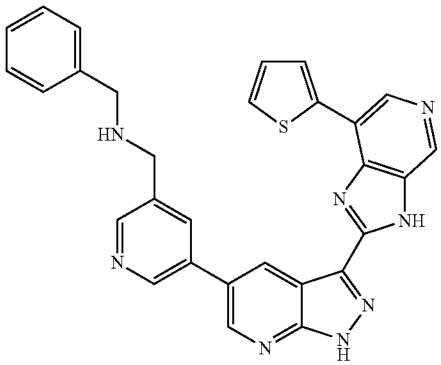
TABLE 1-continued
463
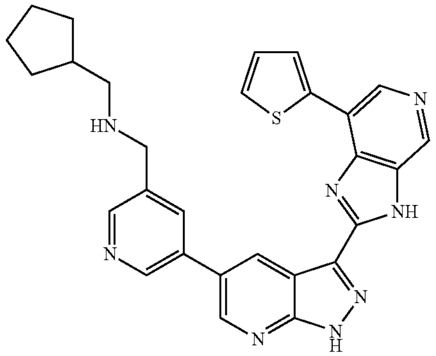
464
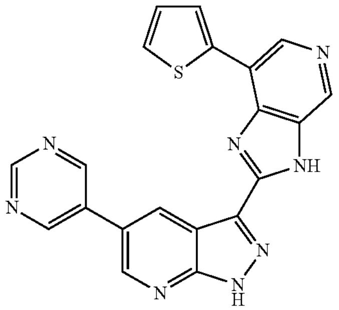
465
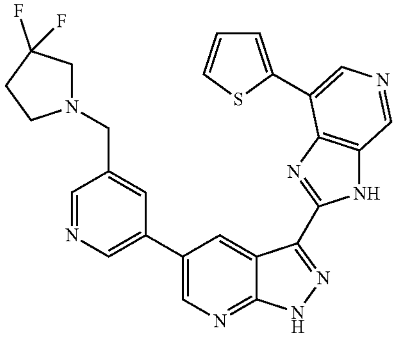
466
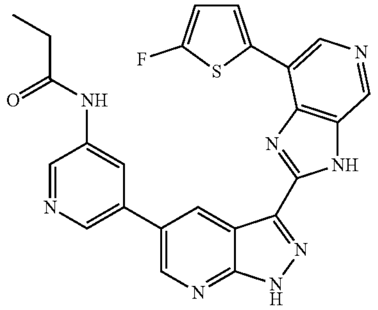

TABLE 1-continued
467
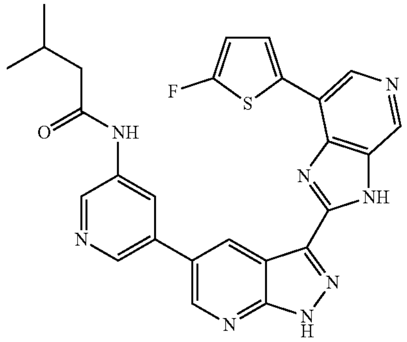
468
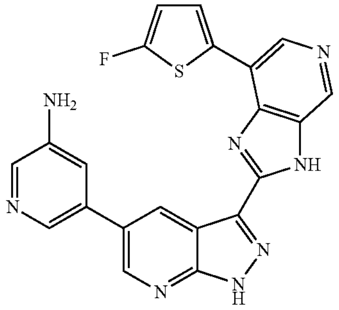
469
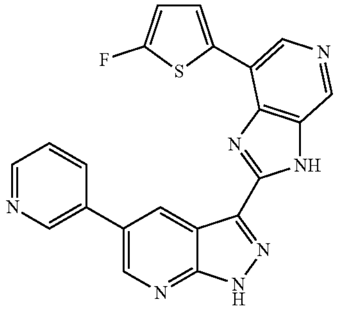
470
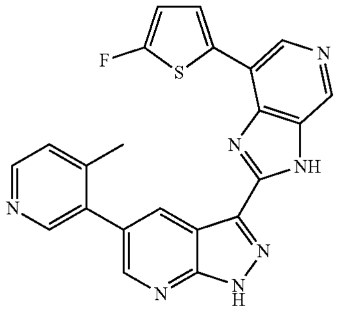
471
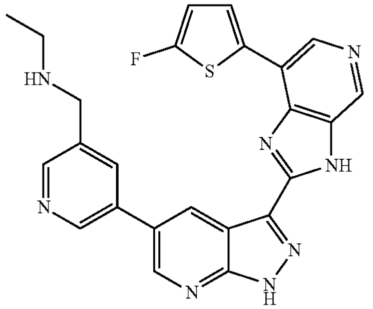
TABLE 1-continued
472
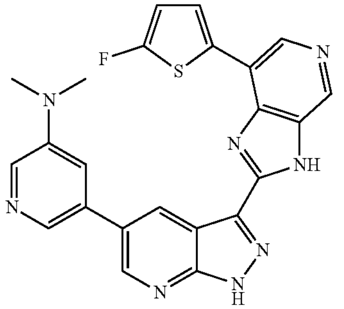
473
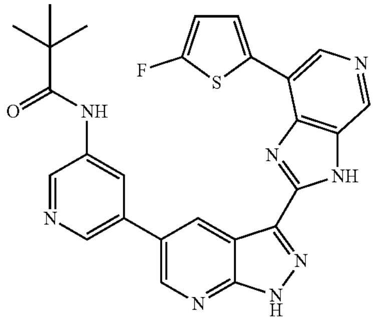
474
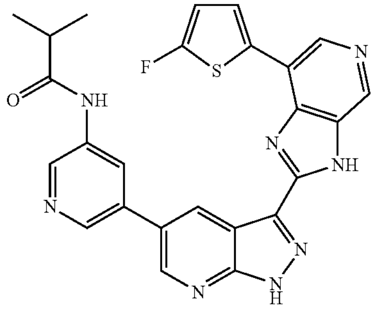 [SMILES: CC(C)C(=O)Nc1cncc(-c2cnc3[nH]nc(-c4nc5c(-c6ccc(F)s6)cncc5[nH]4)c3c2)c1]
475
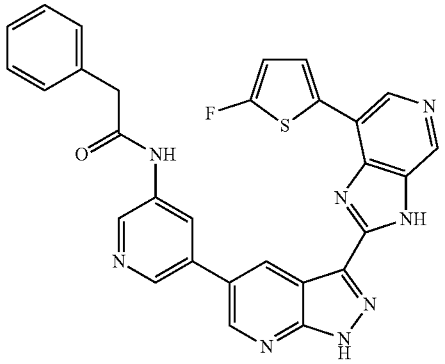

TABLE 1-continued
| | |
|---|---|
| 476 | 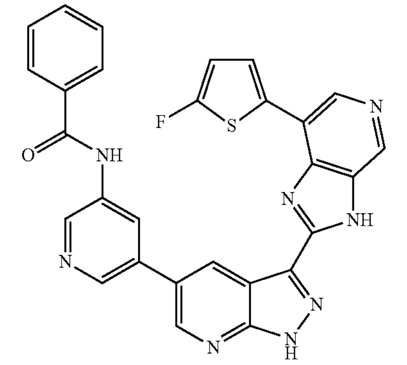 [SMILES: O=C(Nc1cncc(-c2cnc3[nH]nc(-c4nc5c(-c6ccc(F)s6)cncc5[nH]4)c3c2)c1)c1ccccc1] |
| 477 | 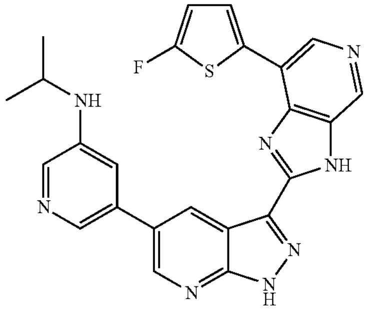 [SMILES: CC(C)Nc1cncc(-c2cnc3[nH]nc(-c4nc5c(-c6ccc(F)s6)cncc5[nH]4)c3c2)c1] |
| 478 | 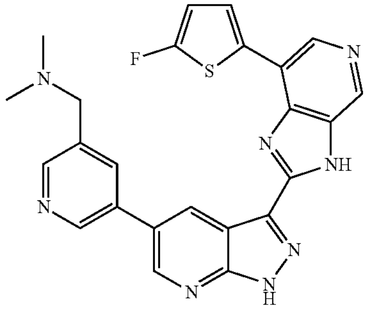 |
| 479 | 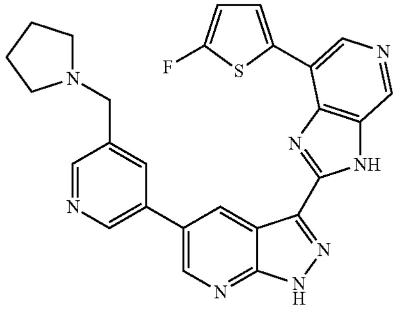 [SMILES: Fc1ccc(-c2cncc3[nH]c(-c4n[nH]c5ncc(-c6cncc(CN7CCCC7)c6)cc45)nc23)s1] |
| 480 | 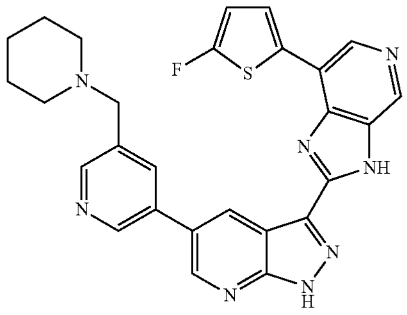 [SMILES: Fc1ccc(-c2cncc3[nH]c(-c4n[nH]c5ncc(-c6cncc(CN7CCCCC7)c6)cc45)nc23)s1] |
TABLE 1-continued
| | |
|---|---|
| 481 | 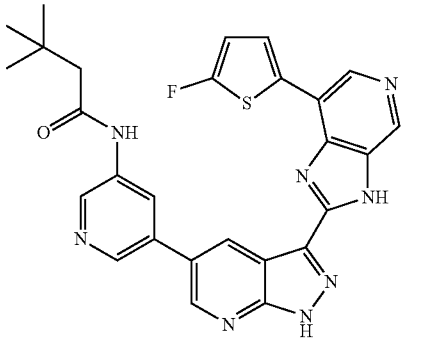 |
| 482 | 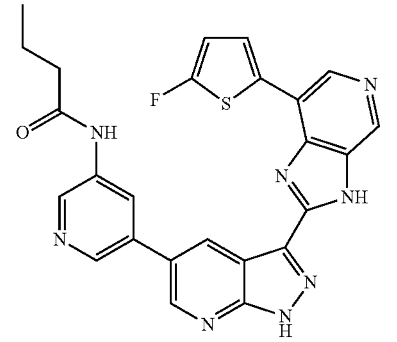 |
| 483 | 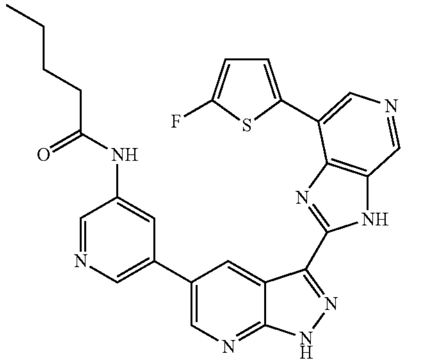 [SMILES: CCCCC(=O)Nc1cncc(-c2cnc3[nH]nc(-c4nc5c(-c6ccc(F)s6)cncc5[nH]4)c3c2)c1] |
| 484 | 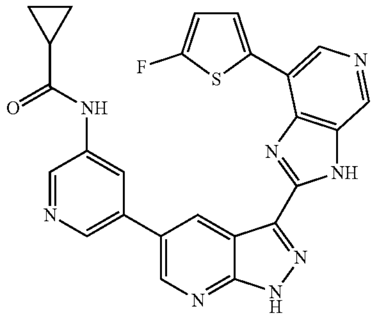 |

TABLE 1-continued
485
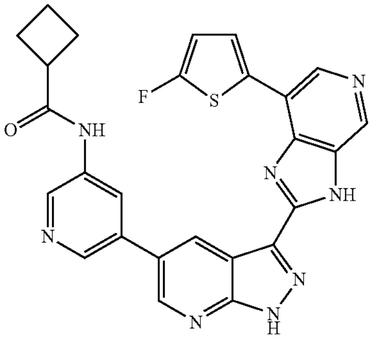
486
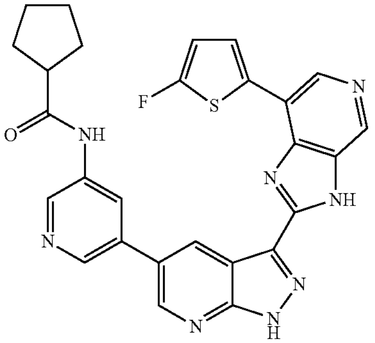 [SMILES: O=C(Nc1cncc(-c2cnc3[nH]nc(-c4nc5c(-c6ccc(F)s6)cncc5[nH]4)c3c2)c1)C1CCCC1]
487
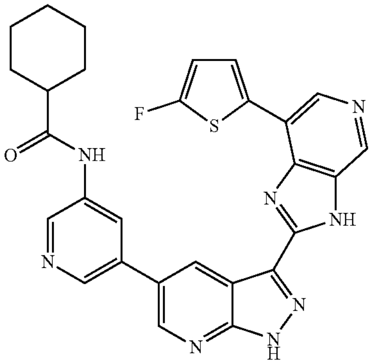
488
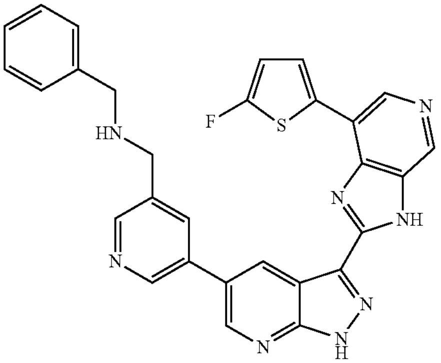
TABLE 1-continued
489
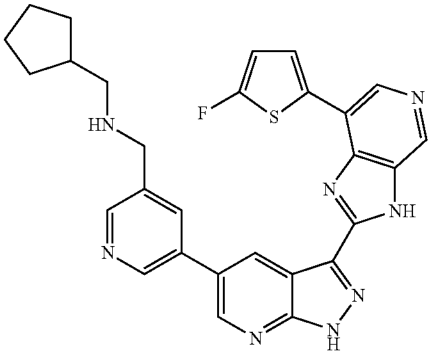 [SMILES: Fc1ccc(-c2cncc3[nH]c(-c4n[nH]c5ncc(-c6cncc(CNCC7CCCC7)c6)cc45)nc23)s1]
490
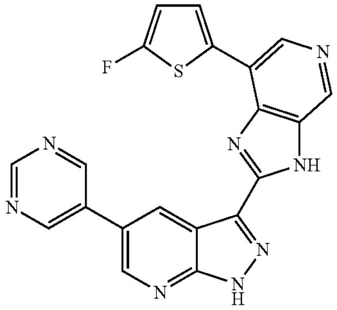 [SMILES: Fc1ccc(-c2cncc3[nH]c(-c4n[nH]c5ncc(-c6cncnc6)cc45)nc23)s1]
491
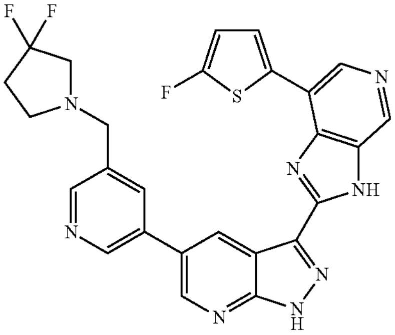 [SMILES: Fc1ccc(-c2cncc3[nH]c(-c4n[nH]c5ncc(-c6cncc(CN7CCC(F)(F)C7)c6)cc45)nc23)s1]
492
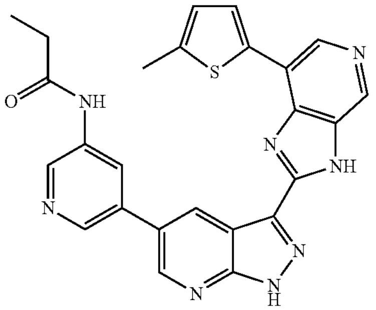 [SMILES: CCC(=O)Nc1cncc(-c2cnc3[nH]nc(-c4nc5c(-c6ccc(C)s6)cncc5[nH]4)c3c2)c1]

TABLE 1-continued
493
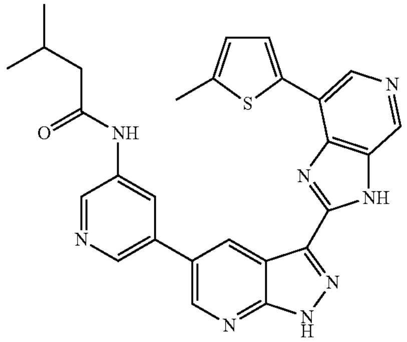 [SMILES: Cc1ccc(-c2cncc3[nH]c(-c4n[nH]c5ncc(-c6cncc(NC(=O)CC(C)C)c6)cc45)nc23)s1]
494
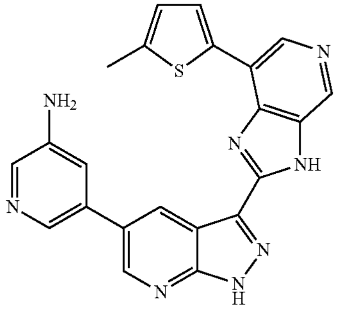 [SMILES: Cc1ccc(-c2cncc3[nH]c(-c4n[nH]c5ncc(-c6cncc(N)c6)cc45)nc23)s1]
495
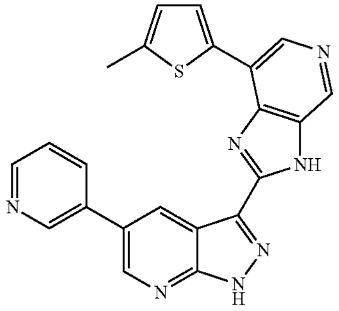 [SMILES: Cc1ccc(-c2cncc3[nH]c(-c4n[nH]c5ncc(-c6cccnc6)cc45)nc23)s1]
496
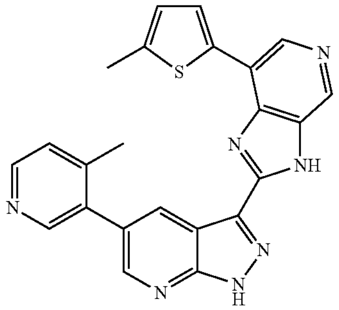 [SMILES: Cc1ccc(-c2cncc3[nH]c(-c4n[nH]c5ncc(-c6cnccc6C)cc45)nc23)s1]
497
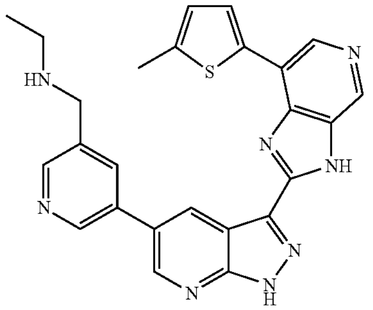 [SMILES: CCNCc1cncc(-c2cnc3[nH]nc(-c4nc5c(-c6ccc(C)s6)cncc5[nH]4)c3c2)c1]
TABLE 1-continued
498
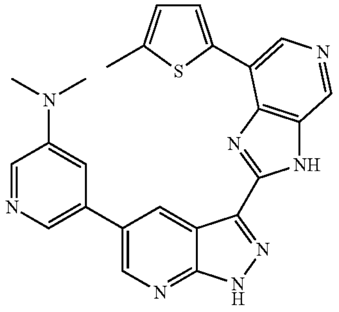 [SMILES: Cc1ccc(-c2cncc3[nH]c(-c4n[nH]c5ncc(-c6cncc(N(C)C)c6)cc45)nc23)s1]
499
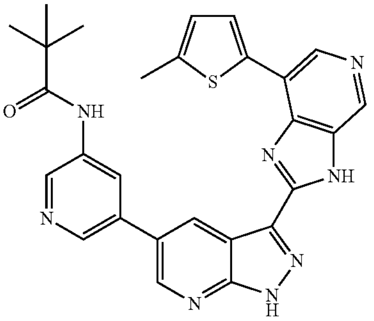 [SMILES: Cc1ccc(-c2cncc3[nH]c(-c4n[nH]c5ncc(-c6cncc(NC(=O)C(C)(C)C)c6)cc45)nc23)s1]
500
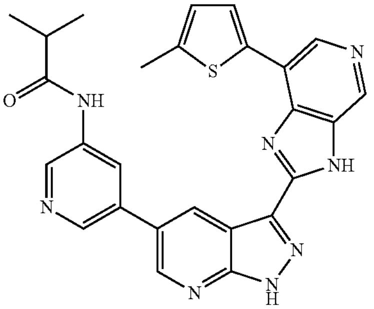 [SMILES: Cc1ccc(-c2cncc3[nH]c(-c4n[nH]c5ncc(-c6cncc(NC(=O)C(C)C)c6)cc45)nc23)s1]
501
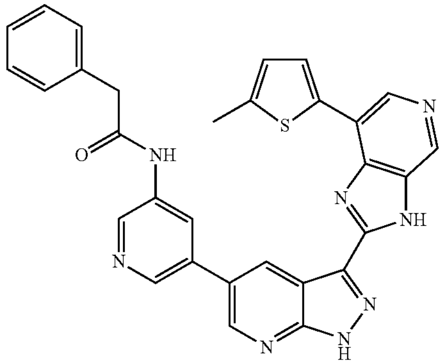 [SMILES: Cc1ccc(-c2cncc3[nH]c(-c4n[nH]c5ncc(-c6cncc(NC(=O)Cc7ccccc7)c6)cc45)nc23)s1]

TABLE 1-continued
502
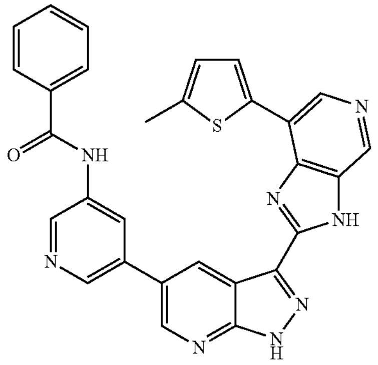 [SMILES: Cc1ccc(-c2cncc3[nH]c(-c4n[nH]c5ncc(-c6cncc(NC(=O)c7ccccc7)c6)cc45)nc23)s1]
503
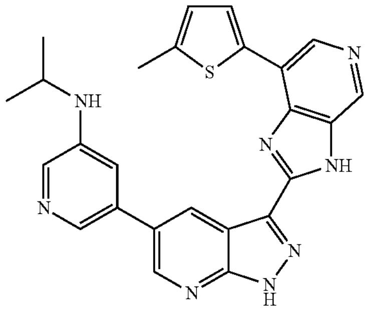 [SMILES: Cc1ccc(-c2cncc3[nH]c(-c4n[nH]c5ncc(-c6cncc(NC(C)C)c6)cc45)nc23)s1]
504
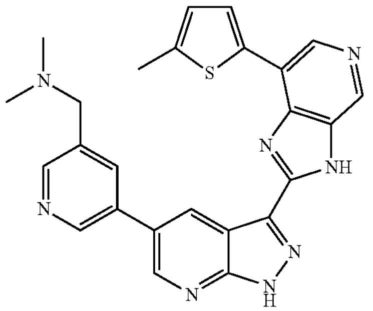 [SMILES: Cc1ccc(-c2cncc3[nH]c(-c4n[nH]c5ncc(-c6cncc(CN(C)C)c6)cc45)nc23)s1]
505
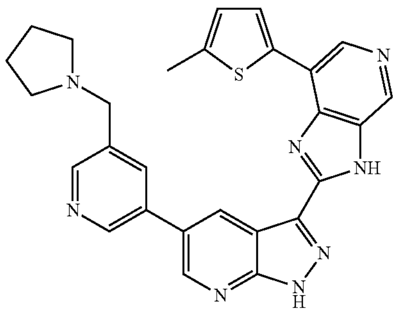 [SMILES: Cc1ccc(-c2cncc3[nH]c(-c4n[nH]c5ncc(-c6cncc(CN7CCCC7)c6)cc45)nc23)s1]
506
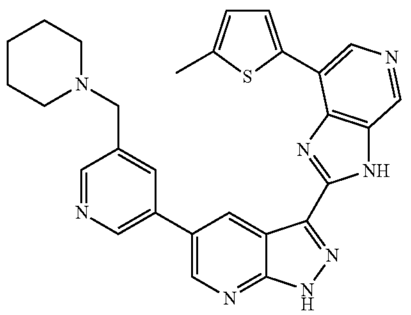 [SMILES: Cc1ccc(-c2cncc3[nH]c(-c4n[nH]c5ncc(-c6cncc(CN7CCCCC7)c6)cc45)nc23)s1]
TABLE 1-continued
507
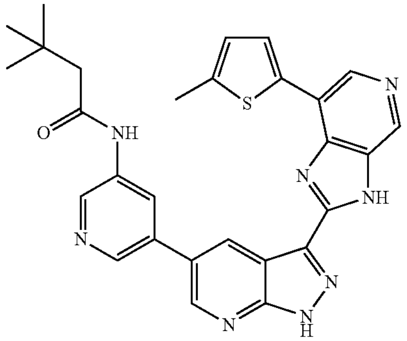 [SMILES: Cc1ccc(-c2cncc3[nH]c(-c4n[nH]c5ncc(-c6cncc(NC(=O)CC(C)(C)C)c6)cc45)nc23)s1]
508
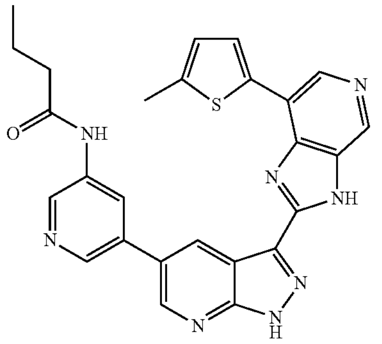 [SMILES: CCCC(=O)Nc1cncc(-c2cnc3[nH]nc(-c4nc5c(-c6ccc(C)s6)cncc5[nH]4)c3c2)c1]
509
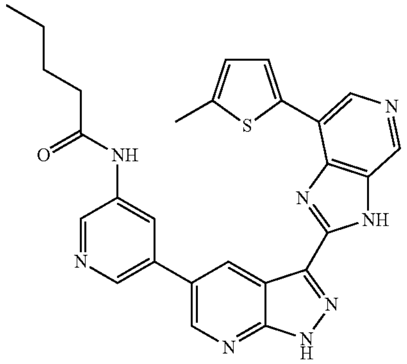
510
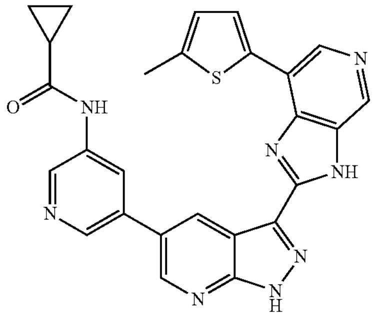 [SMILES: Cc1ccc(-c2cncc3[nH]c(-c4n[nH]c5ncc(-c6cncc(NC(=O)C7CC7)c6)cc45)nc23)s1]

TABLE 1-continued
511
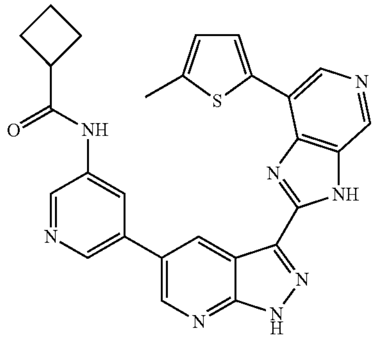 [SMILES: Cc1ccc(-c2cncc3[nH]c(-c4n[nH]c5ncc(-c6cncc(NC(=O)C7CCC7)c6)cc45)nc23)s1]
512
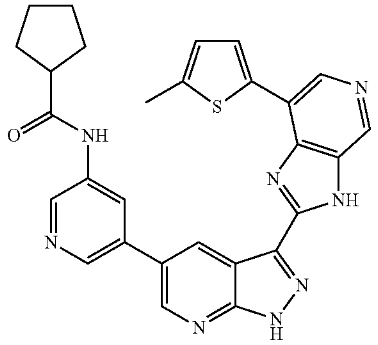 [SMILES: Cc1ccc(-c2cncc3[nH]c(-c4n[nH]c5ncc(-c6cncc(NC(=O)C7CCCC7)c6)cc45)nc23)s1]
513
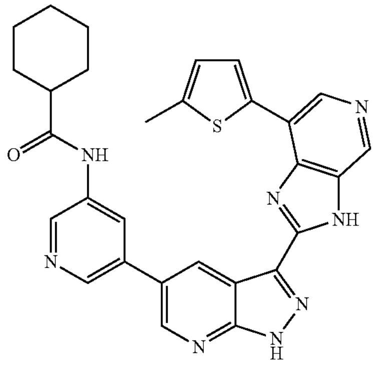 [SMILES: Cc1ccc(-c2cncc3[nH]c(-c4n[nH]c5ncc(-c6cncc(NC(=O)C7CCCCC7)c6)cc45)nc23)s1]
514
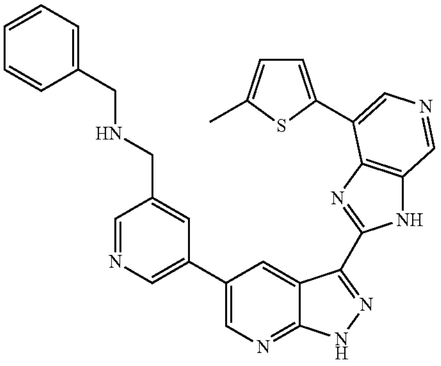 [SMILES: Cc1ccc(-c2cncc3[nH]c(-c4n[nH]c5ncc(-c6cncc(CNCc7ccccc7)c6)cc45)nc23)s1]
515
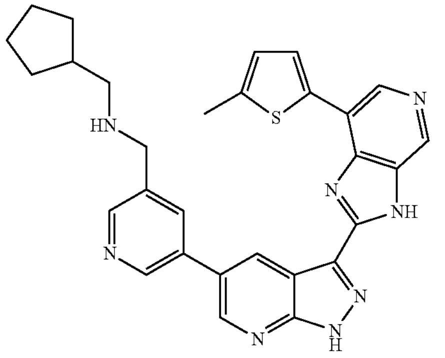 [SMILES: Cc1ccc(-c2cncc3[nH]c(-c4n[nH]c5ncc(-c6cncc(CNCC7CCCC7)c6)cc45)nc23)s1]
516
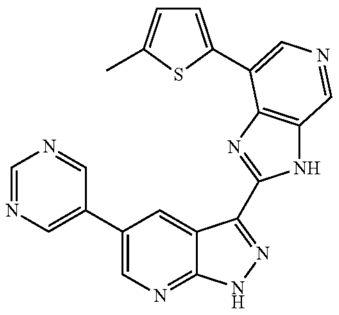
517
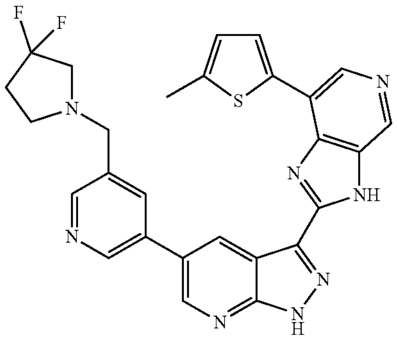 [SMILES: Cc1ccc(-c2cncc3[nH]c(-c4n[nH]c5ncc(-c6cncc(CN7CCC(F)(F)C7)c6)cc45)nc23)s1]
518
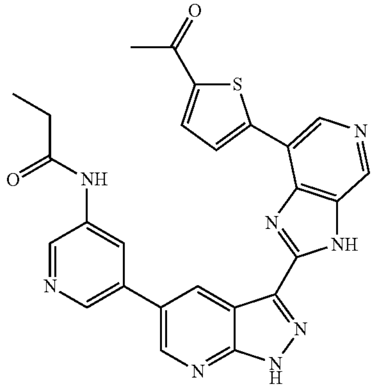 [SMILES: CCC(=O)Nc1cncc(-c2cnc3[nH]nc(-c4nc5c(-c6ccc(C(C)=O)s6)cncc5[nH]4)c3c2)c1]

TABLE 1-continued
519
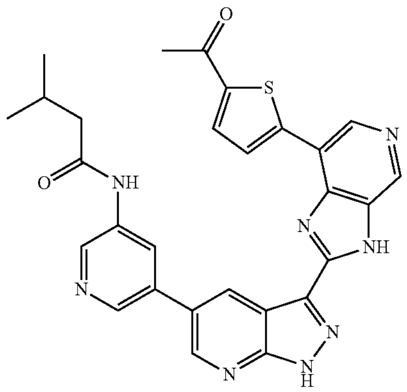 [SMILES: CC(=O)c1ccc(-c2cncc3[nH]c(-c4n[nH]c5ncc(-c6cncc(NC(=O)CC(C)C)c6)cc45)nc23)s1]
520
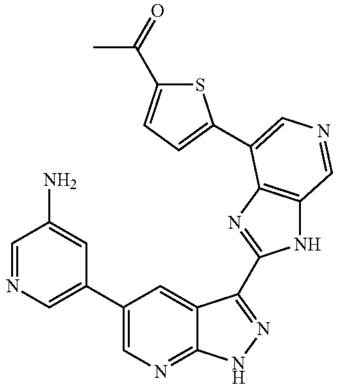
521
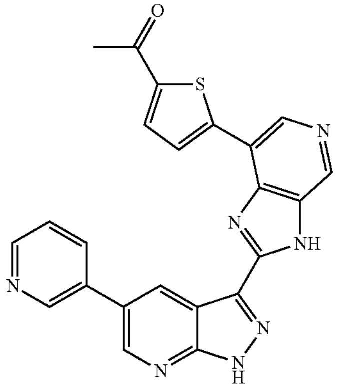
522
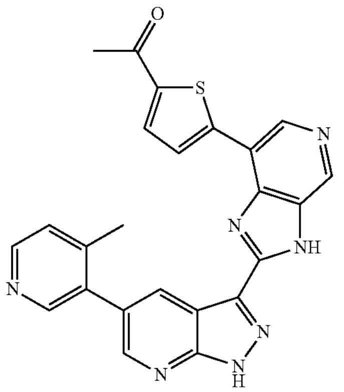
523
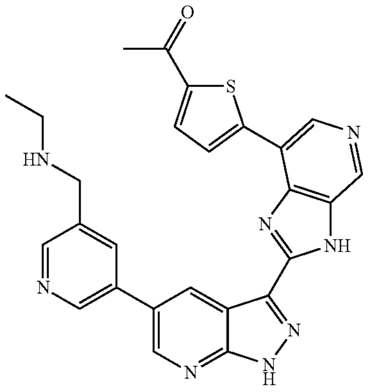 [SMILES: CCNCc1cncc(-c2cnc3[nH]nc(-c4nc5c(-c6ccc(C(C)=O)s6)cncc5[nH]4)c3c2)c1]
524
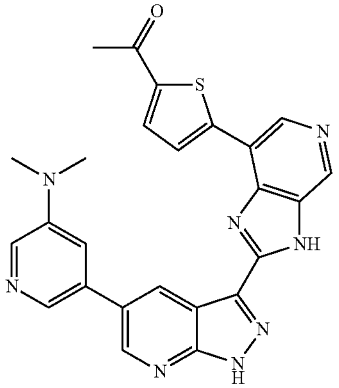
525
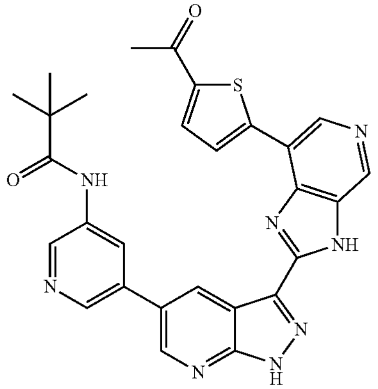
526
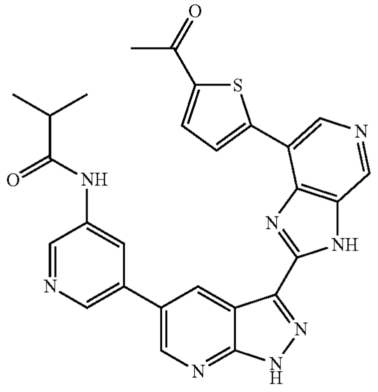

TABLE 1-continued
527
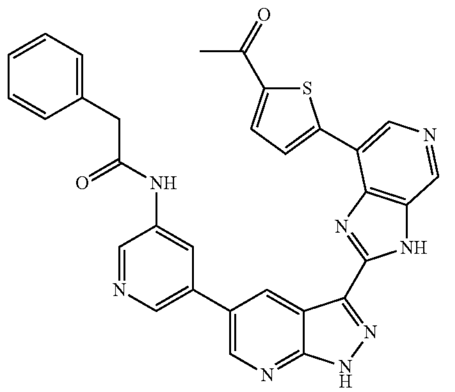
528
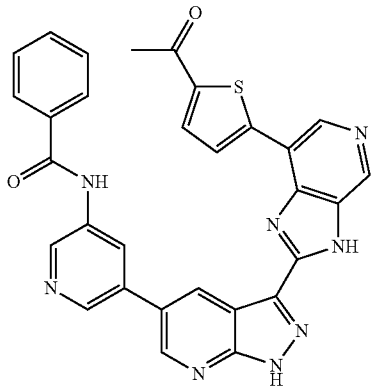
529
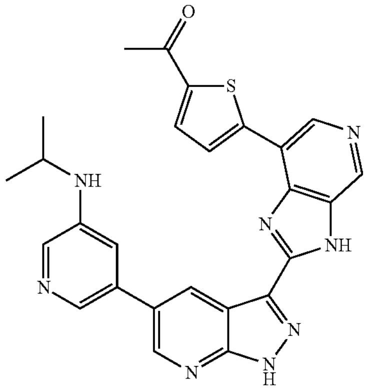
530
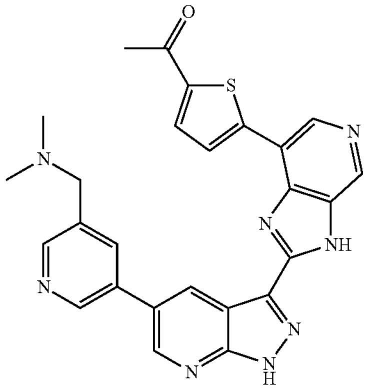
TABLE 1-continued
531
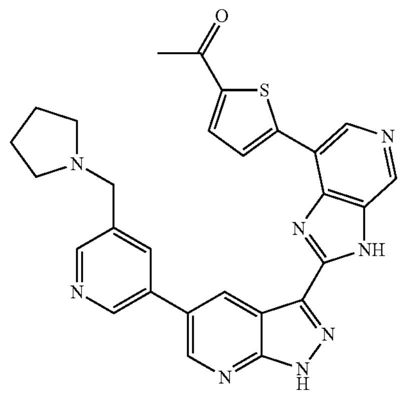
532
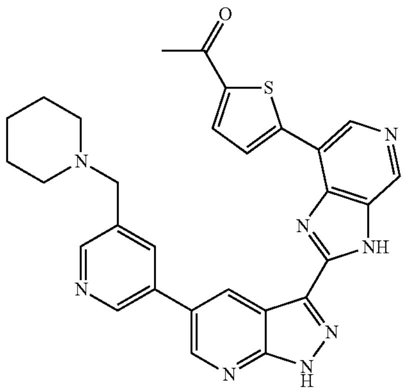
533
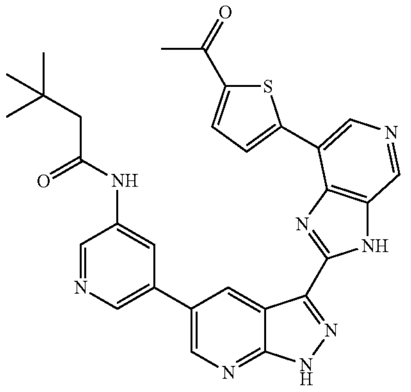
534
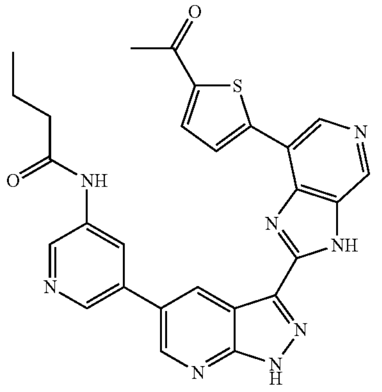

TABLE 1-continued
535
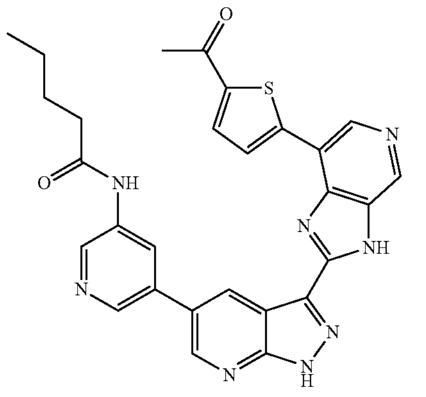
536
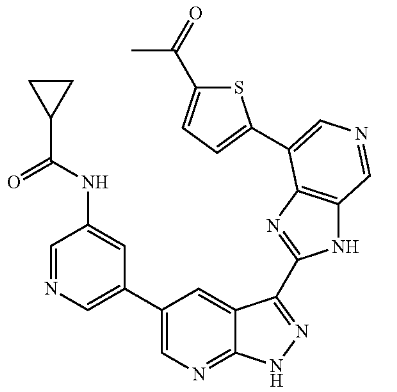
537
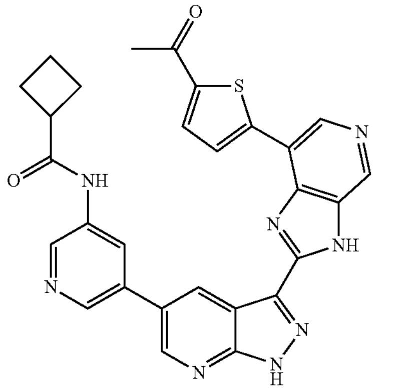
538
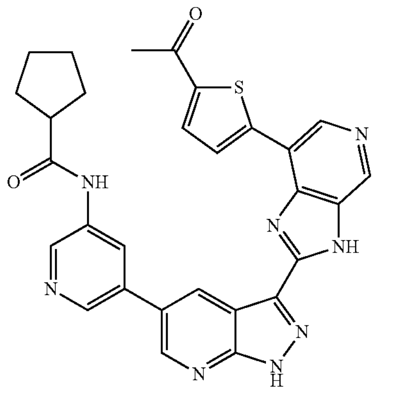
TABLE 1-continued
539
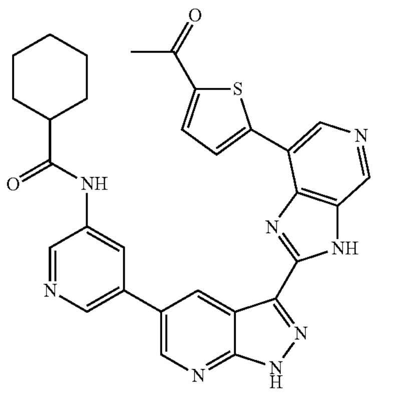 [SMILES: CC(=O)c1ccc(-c2cncc3[nH]c(-c4n[nH]c5ncc(-c6cncc(NC(=O)C7CCCCC7)c6)cc45)nc23)s1]
540
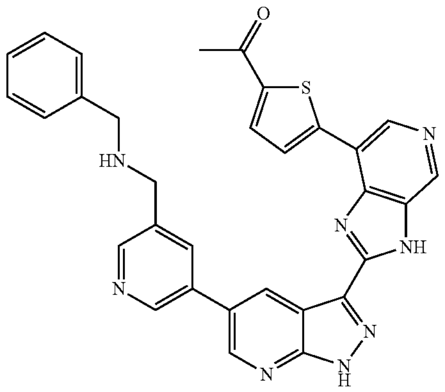
541
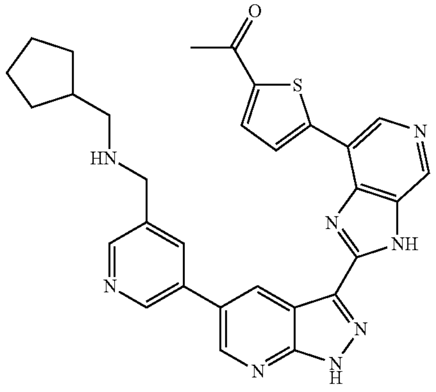
542
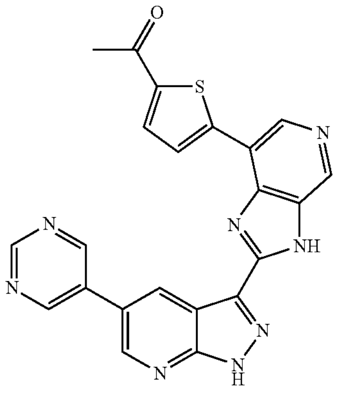

TABLE 1-continued
543
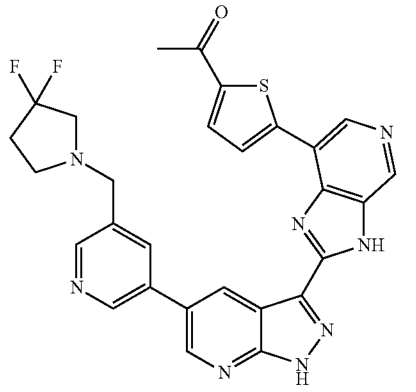
544
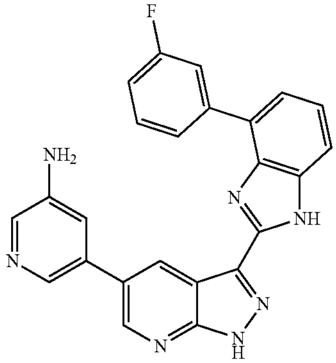 [SMILES: Nc1cncc(-c2cnc3[nH]nc(-c4nc5c(-c6cccc(F)c6)cccc5[nH]4)c3c2)c1]
545
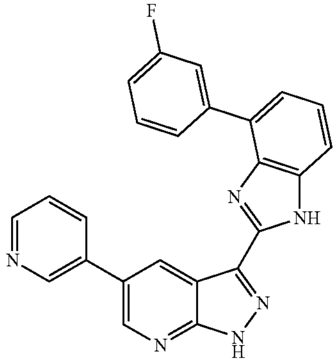 [SMILES: Fc1cccc(-c2cccc3[nH]c(-c4n[nH]c5ncc(-c6cccnc6)cc45)nc23)c1]
546
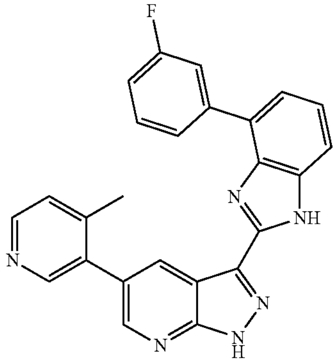 [SMILES: Cc1ccncc1-c1cnc2[nH]nc(-c3nc4c(-c5cccc(F)c5)cccc4[nH]3)c2c1]
TABLE 1-continued
547
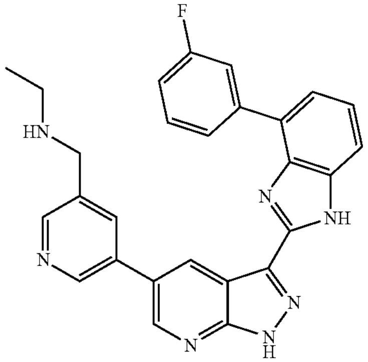 [SMILES: CCNCc1cncc(-c2cnc3[nH]nc(-c4nc5c(-c6cccc(F)c6)cccc5[nH]4)c3c2)c1]
548
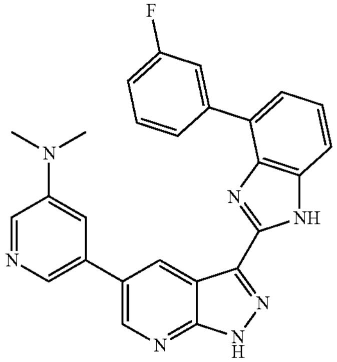 [SMILES: CN(C)c1cncc(-c2cnc3[nH]nc(-c4nc5c(-c6cccc(F)c6)cccc5[nH]4)c3c2)c1]
549
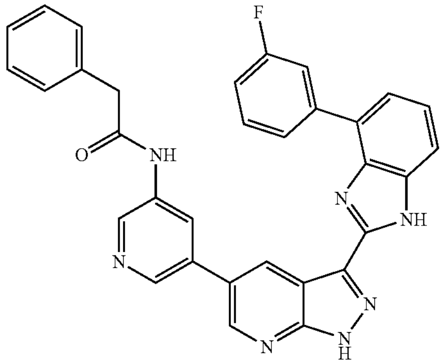 [SMILES: O=C(Cc1ccccc1)Nc1cncc(-c2cnc3[nH]nc(-c4nc5c(-c6cccc(F)c6)cccc5[nH]4)c3c2)c1]
550
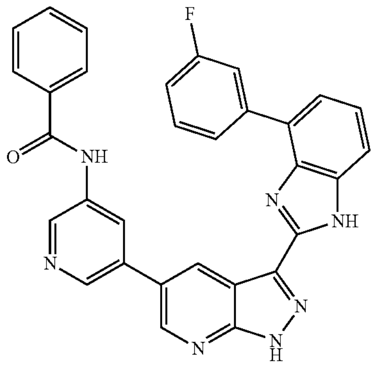 [SMILES: O=C(Nc1cncc(-c2cnc3[nH]nc(-c4nc5c(-c6cccc(F)c6)cccc5[nH]4)c3c2)c1)c1ccccc1]

TABLE 1-continued
551
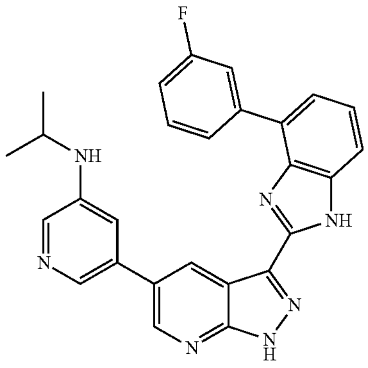 [SMILES: CC(C)Nc1cncc(-c2cnc3[nH]nc(-c4nc5c(-c6cccc(F)c6)cccc5[nH]4)c3c2)c1]
552
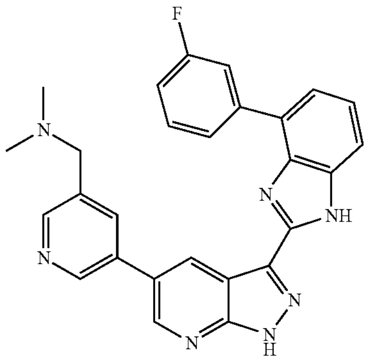 [SMILES: CN(C)Cc1cncc(-c2cnc3[nH]nc(-c4nc5c(-c6cccc(F)c6)cccc5[nH]4)c3c2)c1]
553
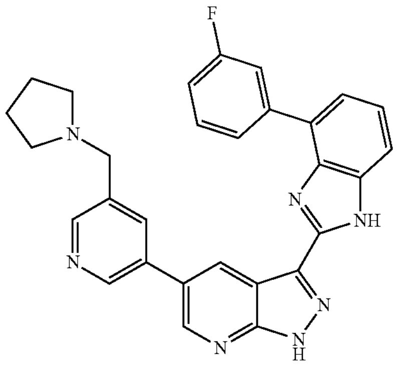 [SMILES: Fc1cccc(-c2cccc3[nH]c(-c4n[nH]c5ncc(-c6cncc(CN7CCCC7)c6)cc45)nc23)c1]
554
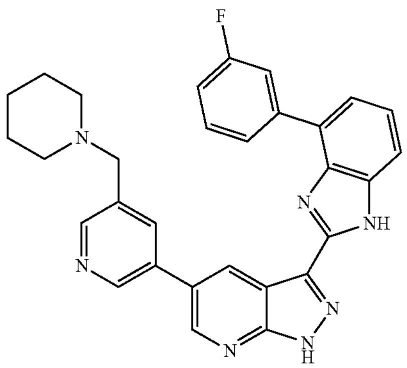 [SMILES: Fc1cccc(-c2cccc3[nH]c(-c4n[nH]c5ncc(-c6cncc(CN7CCCCC7)c6)cc45)nc23)c1]
TABLE 1-continued
555
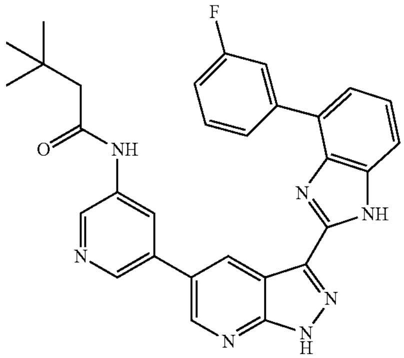 [SMILES: CC(C)(C)CC(=O)Nc1cncc(-c2cnc3[nH]nc(-c4nc5c(-c6cccc(F)c6)cccc5[nH]4)c3c2)c1]
556
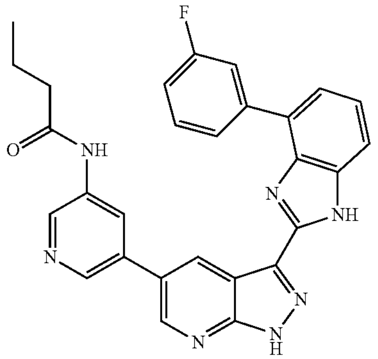 [SMILES: CCCC(=O)Nc1cncc(-c2cnc3[nH]nc(-c4nc5c(-c6cccc(F)c6)cccc5[nH]4)c3c2)c1]
557
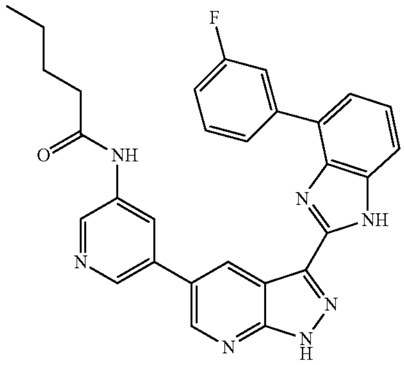 [SMILES: CCCCC(=O)Nc1cncc(-c2cnc3[nH]nc(-c4nc5c(-c6cccc(F)c6)cccc5[nH]4)c3c2)c1]
558
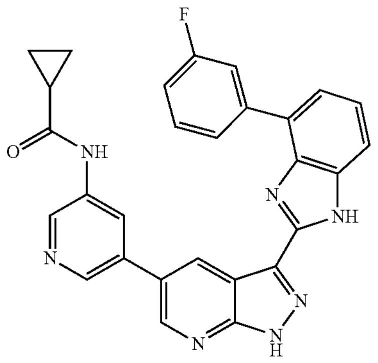 [SMILES: O=C(Nc1cncc(-c2cnc3[nH]nc(-c4nc5c(-c6cccc(F)c6)cccc5[nH]4)c3c2)c1)C1CC1]

TABLE 1-continued
559
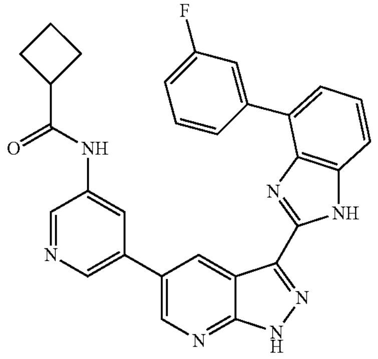 [SMILES: O=C(Nc1cncc(-c2cnc3[nH]nc(-c4nc5c(-c6cccc(F)c6)cccc5[nH]4)c3c2)c1)C1CCC1]
560
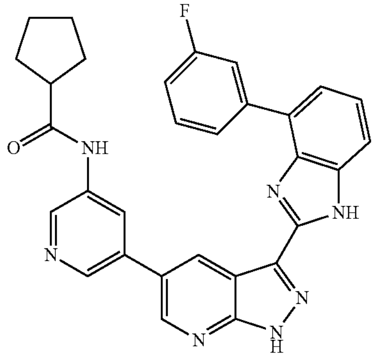 [SMILES: O=C(Nc1cncc(-c2cnc3[nH]nc(-c4nc5c(-c6cccc(F)c6)cccc5[nH]4)c3c2)c1)C1CCCC1]
561
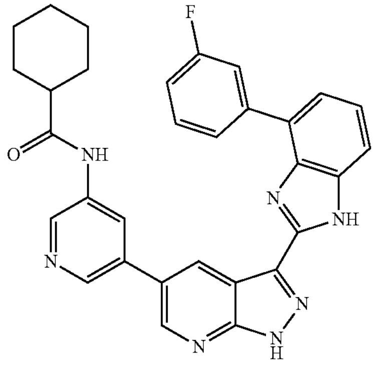 [SMILES: O=C(Nc1cncc(-c2cnc3[nH]nc(-c4nc5c(-c6cccc(F)c6)cccc5[nH]4)c3c2)c1)C1CCCCC1]
562
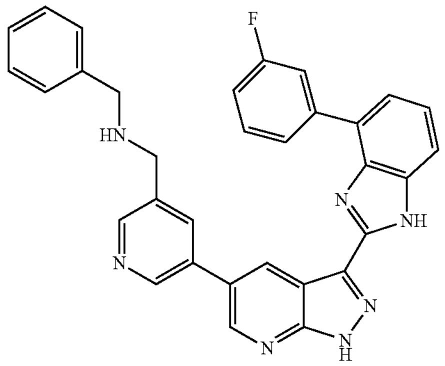 [SMILES: Fc1cccc(-c2cccc3[nH]c(-c4n[nH]c5ncc(-c6cncc(CNCc7ccccc7)c6)cc45)nc23)c1]
TABLE 1-continued
563
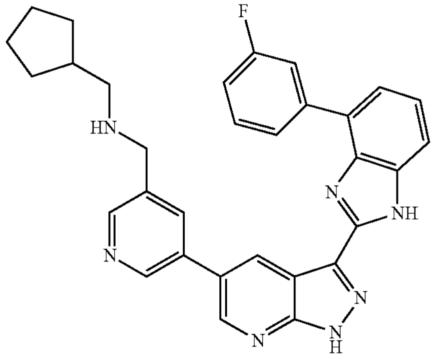
564
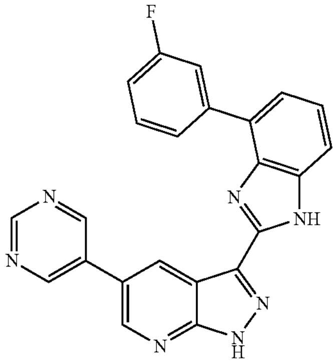 [SMILES: Fc1cccc(-c2cccc3[nH]c(-c4n[nH]c5ncc(-c6cncnc6)cc45)nc23)c1]
565
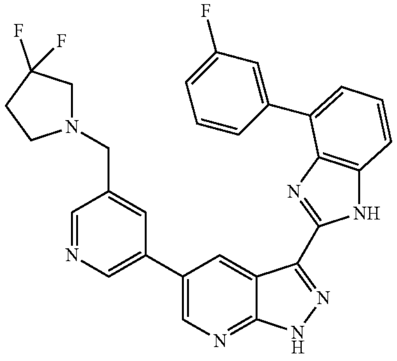 [SMILES: Fc1cccc(-c2cccc3[nH]c(-c4n[nH]c5ncc(-c6cncc(CN7CCC(F)(F)C7)c6)cc45)nc23)c1]
566
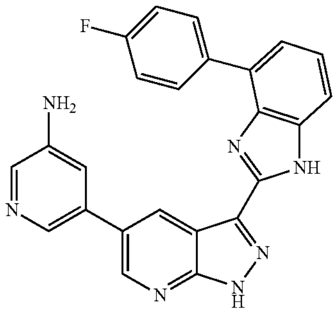 [SMILES: Nc1cncc(-c2cnc3[nH]nc(-c4nc5c(-c6ccc(F)cc6)cccc5[nH]4)c3c2)c1]

TABLE 1-continued
567
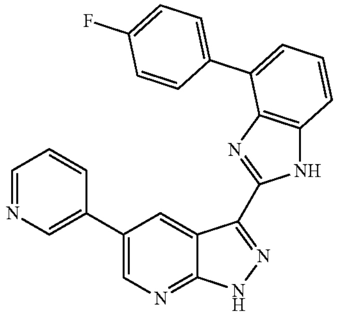 [SMILES: Fc1ccc(-c2cccc3[nH]c(-c4n[nH]c5ncc(-c6cccnc6)cc45)nc23)cc1]
568
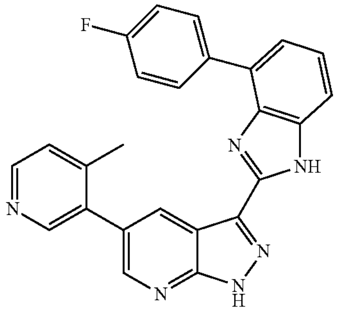
569
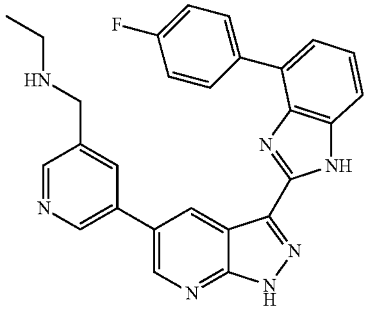 [SMILES: CCNCc1cncc(-c2cnc3[nH]nc(-c4nc5c(-c6ccc(F)cc6)cccc5[nH]4)c3c2)c1]
570
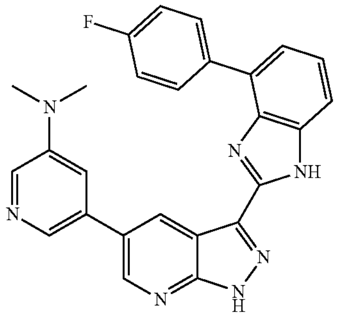 [SMILES: CN(C)c1cncc(-c2cnc3[nH]nc(-c4nc5c(-c6ccc(F)cc6)cccc5[nH]4)c3c2)c1]
571
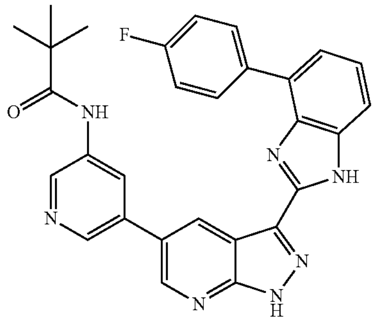 [SMILES: CC(C)(C)C(=O)Nc1cncc(-c2cnc3[nH]nc(-c4nc5c(-c6ccc(F)cc6)cccc5[nH]4)c3c2)c1]
TABLE 1-continued
572
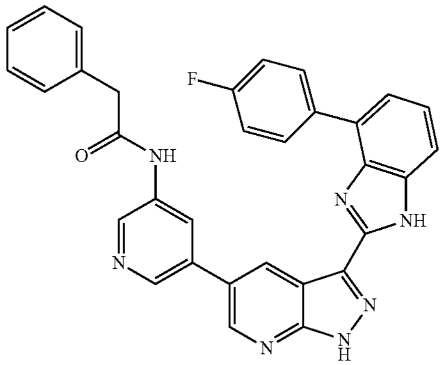 [SMILES: O=C(Cc1ccccc1)Nc1cncc(-c2cnc3[nH]nc(-c4nc5c(-c6ccc(F)cc6)cccc5[nH]4)c3c2)c1]
573
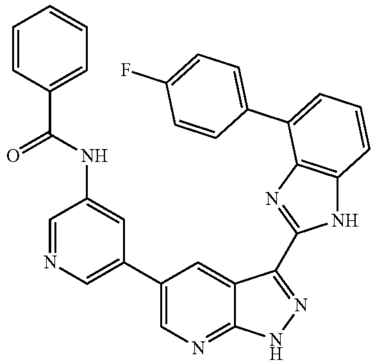 [SMILES: O=C(Nc1cncc(-c2cnc3[nH]nc(-c4nc5c(-c6ccc(F)cc6)cccc5[nH]4)c3c2)c1)c1ccccc1]
574
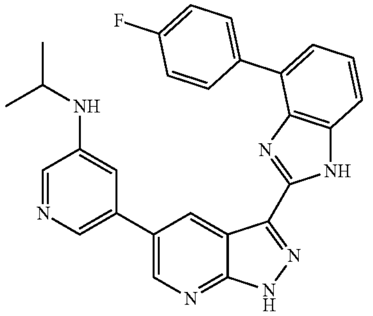 [SMILES: CC(C)Nc1cncc(-c2cnc3[nH]nc(-c4nc5c(-c6ccc(F)cc6)cccc5[nH]4)c3c2)c1]
575
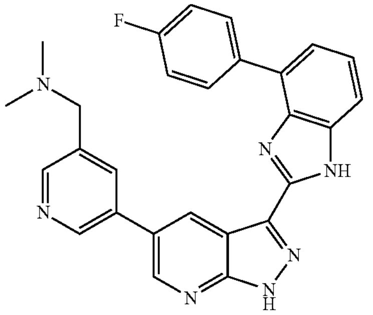 [SMILES: CN(C)Cc1cncc(-c2cnc3[nH]nc(-c4nc5c(-c6ccc(F)cc6)cccc5[nH]4)c3c2)c1]

TABLE 1-continued
576
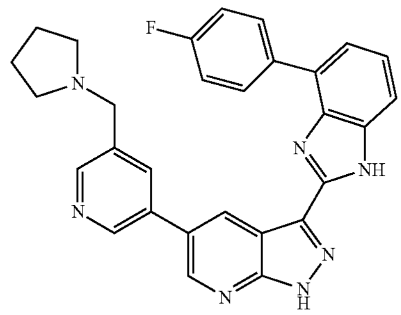 [SMILES: Fc1ccc(-c2cccc3[nH]c(-c4n[nH]c5ncc(-c6cncc(CN7CCCC7)c6)cc45)nc23)cc1]
577
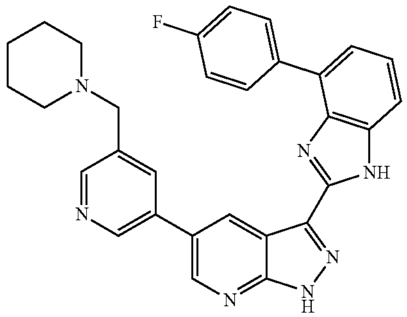 [SMILES: Fc1ccc(-c2cccc3[nH]c(-c4n[nH]c5ncc(-c6cncc(CN7CCCCC7)c6)cc45)nc23)cc1]
578
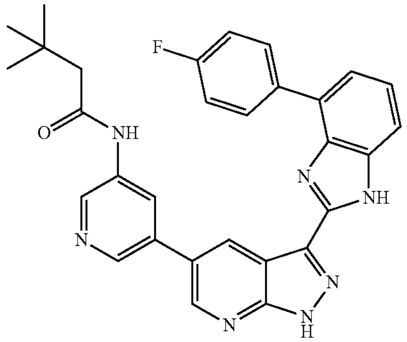 [SMILES: CC(C)(C)CC(=O)Nc1cncc(-c2cnc3[nH]nc(-c4nc5c(-c6ccc(F)cc6)cccc5[nH]4)c3c2)c1]
579
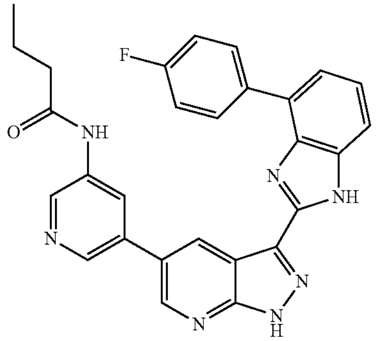 [SMILES: CCCC(=O)Nc1cncc(-c2cnc3[nH]nc(-c4nc5c(-c6ccc(F)cc6)cccc5[nH]4)c3c2)c1]
TABLE 1-continued
580
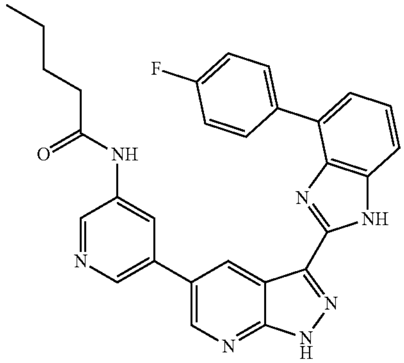 [SMILES: CCCCC(=O)Nc1cncc(-c2cnc3[nH]nc(-c4nc5c(-c6ccc(F)cc6)cccc5[nH]4)c3c2)c1]
581
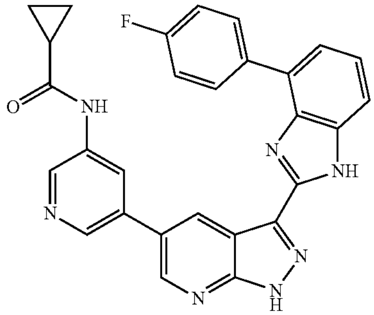 [SMILES: O=C(Nc1cncc(-c2cnc3[nH]nc(-c4nc5c(-c6ccc(F)cc6)cccc5[nH]4)c3c2)c1)C1CC1]
582
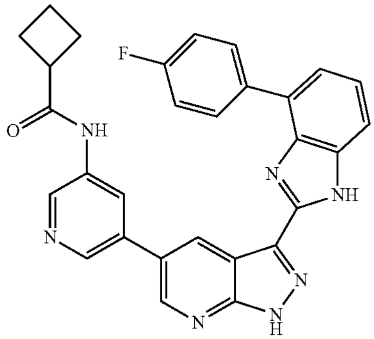 [SMILES: O=C(Nc1cncc(-c2cnc3[nH]nc(-c4nc5c(-c6ccc(F)cc6)cccc5[nH]4)c3c2)c1)C1CCC1]
583
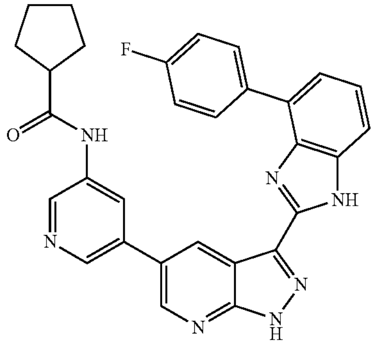 [SMILES: O=C(Nc1cncc(-c2cnc3[nH]nc(-c4nc5c(-c6ccc(F)cc6)cccc5[nH]4)c3c2)c1)C1CCCC1]

TABLE 1-continued
584
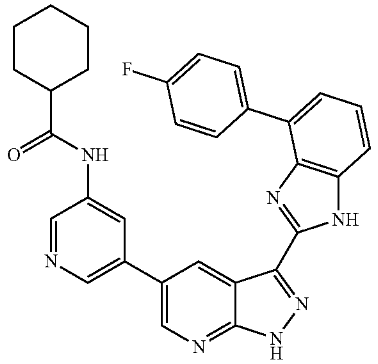 [SMILES: O=C(Nc1cncc(-c2cnc3[nH]nc(-c4nc5c(-c6ccc(F)cc6)cccc5[nH]4)c3c2)c1)C1CCCCC1]
585
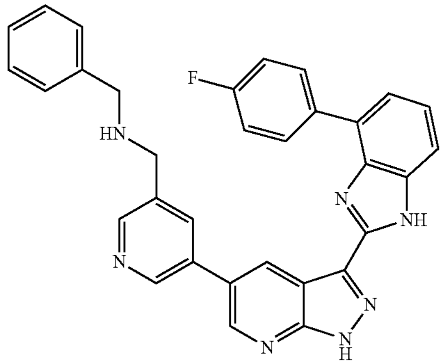 [SMILES: Fc1ccc(-c2cccc3[nH]c(-c4n[nH]c5ncc(-c6cncc(CNCc7ccccc7)c6)cc45)nc23)cc1]
586
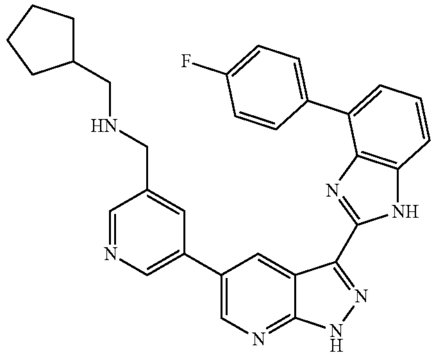 [SMILES: Fc1ccc(-c2cccc3[nH]c(-c4n[nH]c5ncc(-c6cncc(CNCC7CCCC7)c6)cc45)nc23)cc1]
587
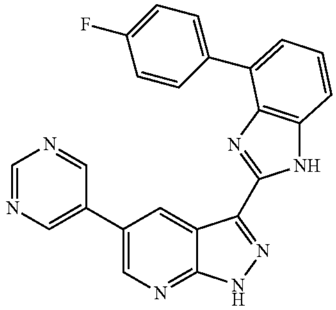 [SMILES: Fc1ccc(-c2cccc3[nH]c(-c4n[nH]c5ncc(-c6cncnc6)cc45)nc23)cc1]
TABLE 1-continued
588
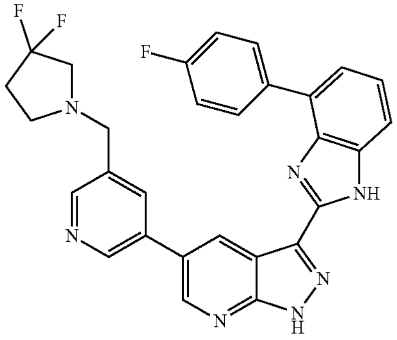 [SMILES: Fc1ccc(-c2cccc3[nH]c(-c4n[nH]c5ncc(-c6cncc(CN7CCC(F)(F)C7)c6)cc45)nc23)cc1]
589
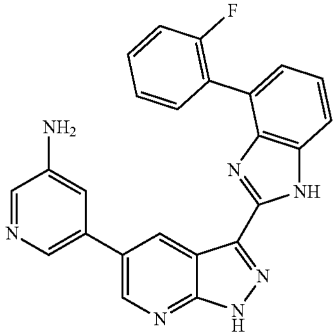 [SMILES: Nc1cncc(-c2cnc3[nH]nc(-c4nc5c(-c6ccccc6F)cccc5[nH]4)c3c2)c1]
590
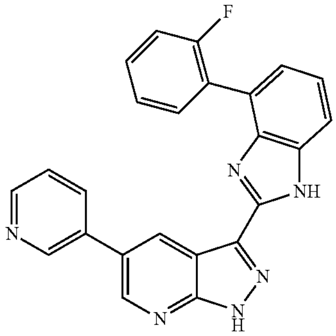 [SMILES: Fc1ccccc1-c1cccc2[nH]c(-c3n[nH]c4ncc(-c5cccnc5)cc34)nc12]
591
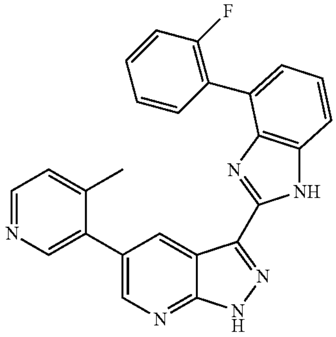 [SMILES: Cc1ccncc1-c1cnc2[nH]nc(-c3nc4c(-c5ccccc5F)cccc4[nH]3)c2c1]

TABLE 1-continued
592
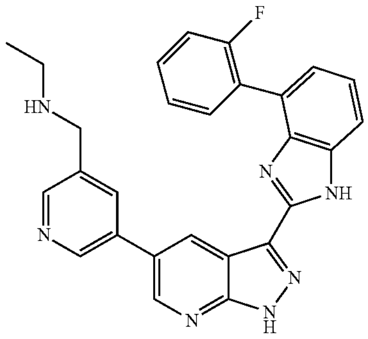 [SMILES: CCNCc1cncc(-c2cnc3[nH]nc(-c4nc5c(-c6ccccc6F)cccc5[nH]4)c3c2)c1]
593
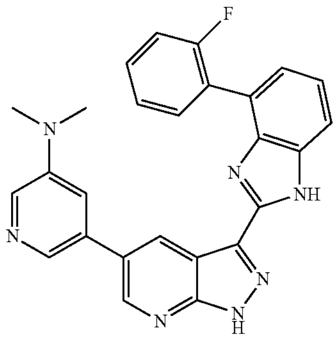
594
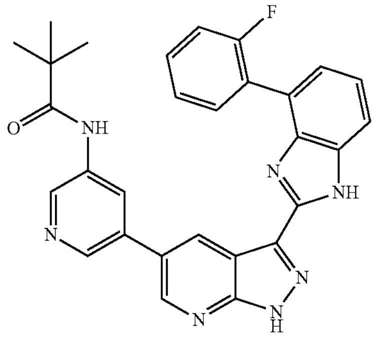 [SMILES: CC(C)(C)C(=O)Nc1cncc(-c2cnc3[nH]nc(-c4nc5c(-c6ccccc6F)cccc5[nH]4)c3c2)c1]
595
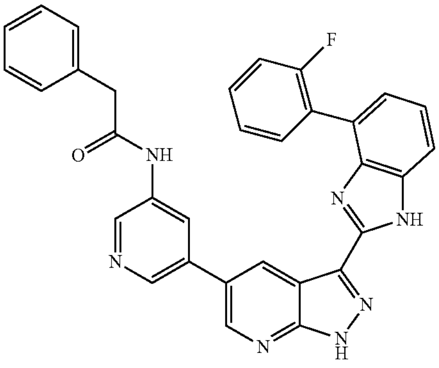 [SMILES: O=C(Cc1ccccc1)Nc1cncc(-c2cnc3[nH]nc(-c4nc5c(-c6ccccc6F)cccc5[nH]4)c3c2)c1]
TABLE 1-continued
596
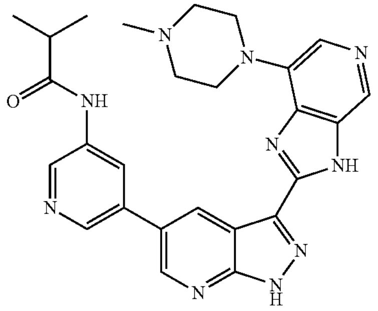 [SMILES: CC(C)C(=O)Nc1cncc(-c2cnc3[nH]nc(-c4nc5c(N6CCN(C)CC6)cncc5[nH]4)c3c2)c1]
597
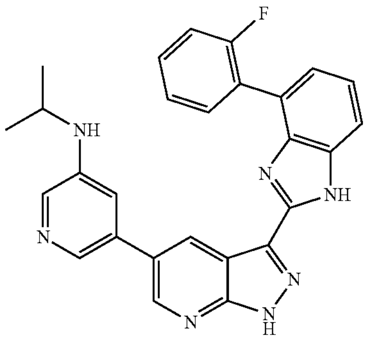 [SMILES: CC(C)Nc1cncc(-c2cnc3[nH]nc(-c4nc5c(-c6ccccc6F)cccc5[nH]4)c3c2)c1]
598
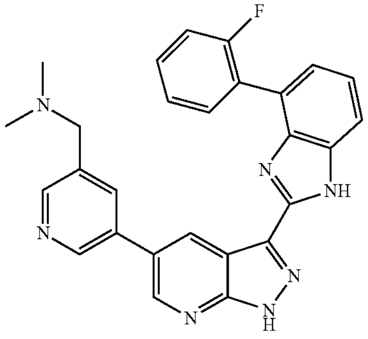 [SMILES: CN(C)Cc1cncc(-c2cnc3[nH]nc(-c4nc5c(-c6ccccc6F)cccc5[nH]4)c3c2)c1]
599
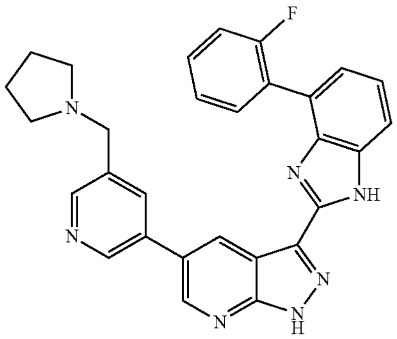 [SMILES: Fc1ccccc1-c1cccc2[nH]c(-c3n[nH]c4ncc(-c5cncc(CN6CCCC6)c5)cc34)nc12]

TABLE 1-continued
600
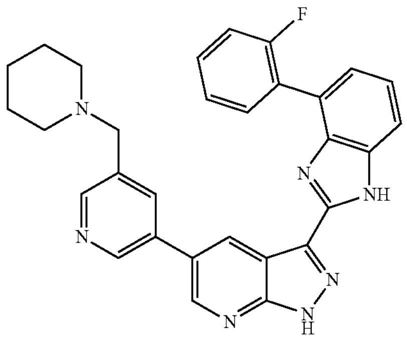 [SMILES: Fc1ccccc1-c1cccc2[nH]c(-c3n[nH]c4ncc(-c5cncc(CN6CCCCC6)c5)cc34)nc12]
601
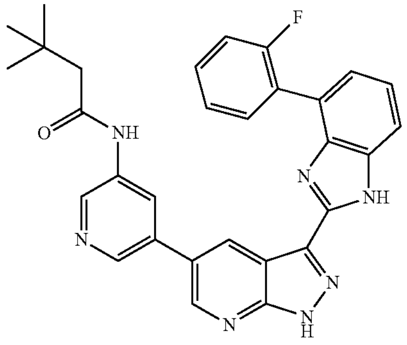 [SMILES: CC(C)(C)CC(=O)Nc1cncc(-c2cnc3[nH]nc(-c4nc5c(-c6ccccc6F)cccc5[nH]4)c3c2)c1]
602
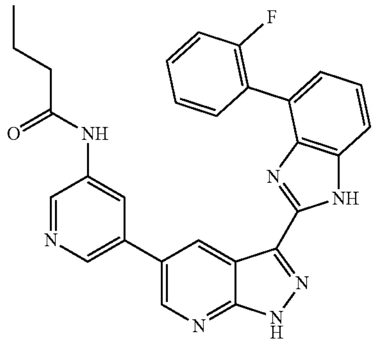 [SMILES: CCCC(=O)Nc1cncc(-c2cnc3[nH]nc(-c4nc5c(-c6ccccc6F)cccc5[nH]4)c3c2)c1]
603
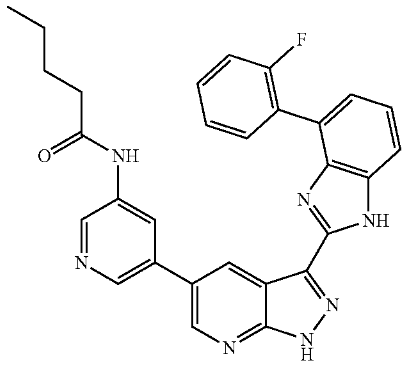 [SMILES: CCCCC(=O)Nc1cncc(-c2cnc3[nH]nc(-c4nc5c(-c6ccccc6F)cccc5[nH]4)c3c2)c1]
TABLE 1-continued
604
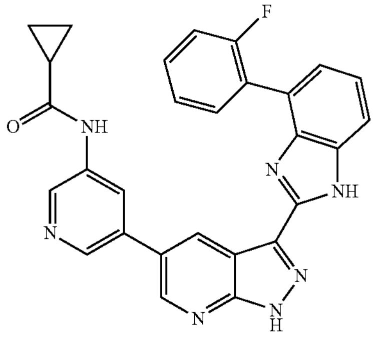 [SMILES: O=C(Nc1cncc(-c2cnc3[nH]nc(-c4nc5c(-c6ccccc6F)cccc5[nH]4)c3c2)c1)C1CC1]
605
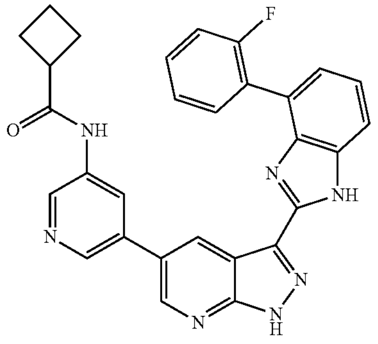 [SMILES: O=C(Nc1cncc(-c2cnc3[nH]nc(-c4nc5c(-c6ccccc6F)cccc5[nH]4)c3c2)c1)C1CCC1]
606
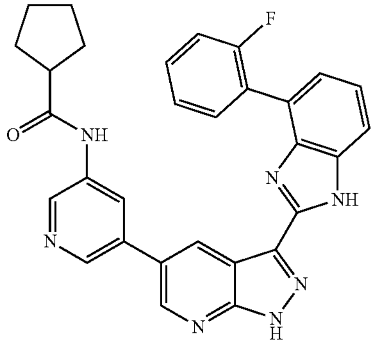 [SMILES: O=C(Nc1cncc(-c2cnc3[nH]nc(-c4nc5c(-c6ccccc6F)cccc5[nH]4)c3c2)c1)C1CCCC1]
607
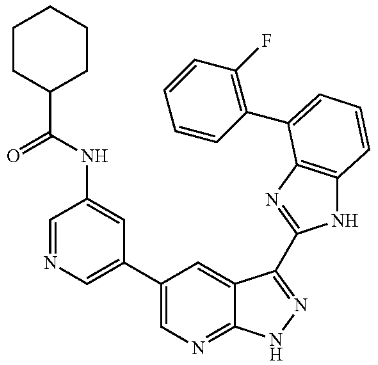 [SMILES: O=C(Nc1cncc(-c2cnc3[nH]nc(-c4nc5c(-c6ccccc6F)cccc5[nH]4)c3c2)c1)C1CCCCC1]

TABLE 1-continued
608
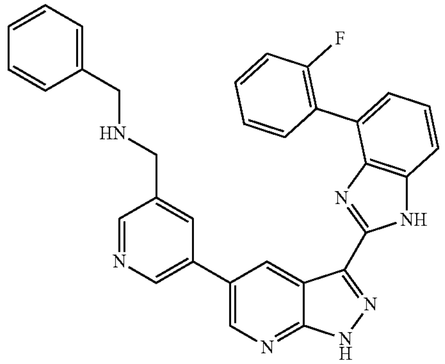 [SMILES: Fc1ccccc1-c1cccc2[nH]c(-c3n[nH]c4ncc(-c5cncc(CNCc6ccccc6)c5)cc34)nc12]
609
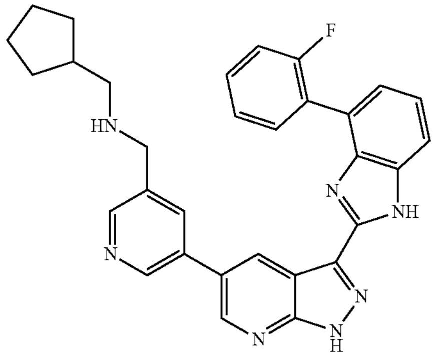 [SMILES: Fc1ccccc1-c1cccc2[nH]c(-c3n[nH]c4ncc(-c5cncc(CNCC6CCCC6)c5)cc34)nc12]
610
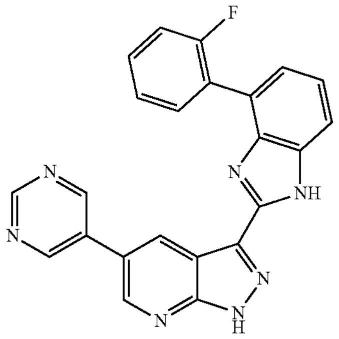 [SMILES: Fc1ccccc1-c1cccc2[nH]c(-c3n[nH]c4ncc(-c5cncnc5)cc34)nc12]
611
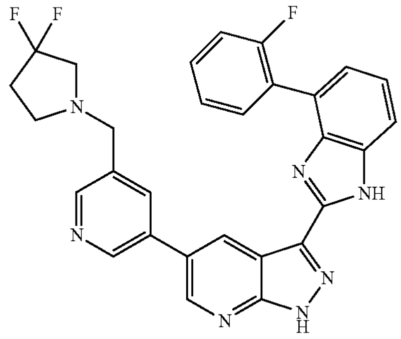 [SMILES: Fc1ccccc1-c1cccc2[nH]c(-c3n[nH]c4ncc(-c5cncc(CN6CCC(F)(F)C6)c5)cc34)nc12]
TABLE 1-continued
612
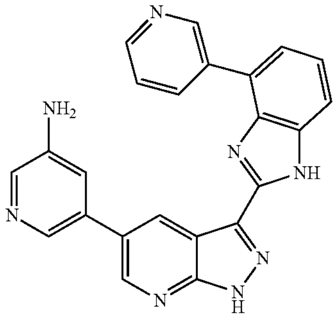 [SMILES: Nc1cncc(-c2cnc3[nH]nc(-c4nc5c(-c6cccnc6)cccc5[nH]4)c3c2)c1]
613
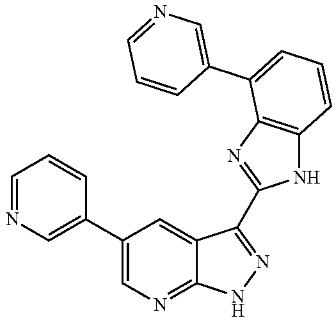 [SMILES: c1cncc(-c2cnc3[nH]nc(-c4nc5c(-c6cccnc6)cccc5[nH]4)c3c2)c1]
614
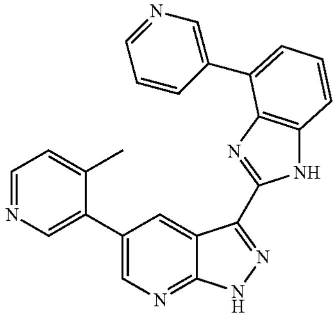
615
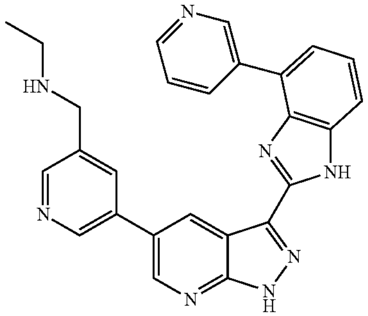 [SMILES: CCNCc1cncc(-c2cnc3[nH]nc(-c4nc5c(-c6cccnc6)cccc5[nH]4)c3c2)c1]
616
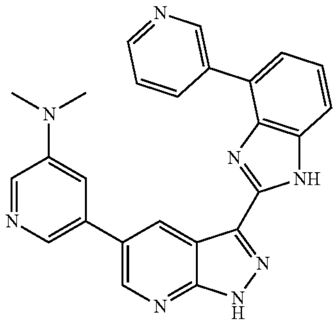 [SMILES: CN(C)c1cncc(-c2cnc3[nH]nc(-c4nc5c(-c6cccnc6)cccc5[nH]4)c3c2)c1]

617
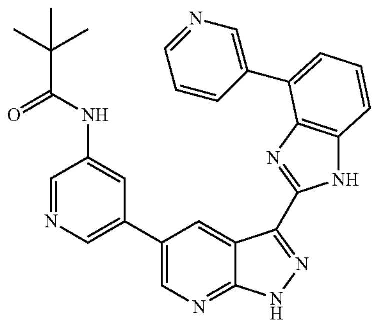 [SMILES: CC(C)(C)C(=O)Nc1cncc(-c2cnc3[nH]nc(-c4nc5c(-c6cccnc6)cccc5[nH]4)c3c2)c1]
618
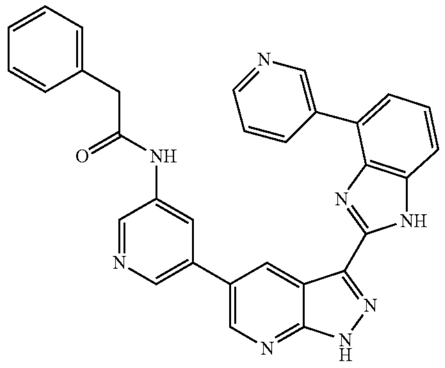 [SMILES: O=C(Cc1ccccc1)Nc1cncc(-c2cnc3[nH]nc(-c4nc5c(-c6cccnc6)cccc5[nH]4)c3c2)c1]
619
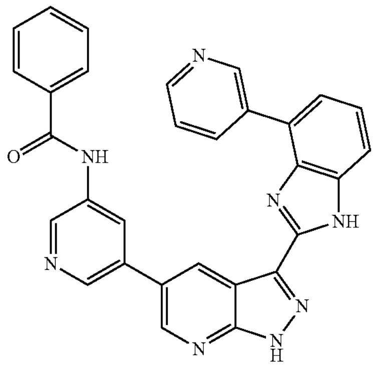 [SMILES: O=C(Nc1cncc(-c2cnc3[nH]nc(-c4nc5c(-c6cccnc6)cccc5[nH]4)c3c2)c1)c1ccccc1]
620
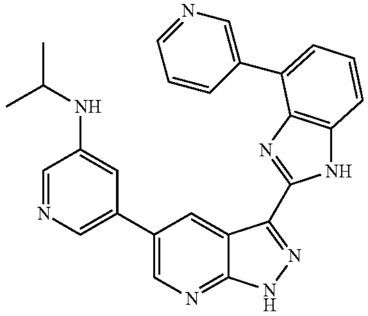 [SMILES: CC(C)Nc1cncc(-c2cnc3[nH]nc(-c4nc5c(-c6cccnc6)cccc5[nH]4)c3c2)c1]
621
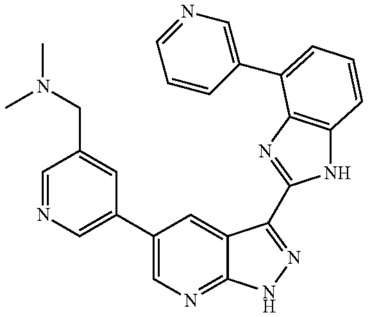 [SMILES: CN(C)Cc1cncc(-c2cnc3[nH]nc(-c4nc5c(-c6cccnc6)cccc5[nH]4)c3c2)c1]
622
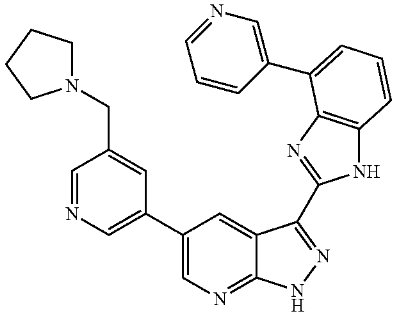 [SMILES: c1cncc(-c2cccc3[nH]c(-c4n[nH]c5ncc(-c6cncc(CN7CCCC7)c6)cc45)nc23)c1]
623
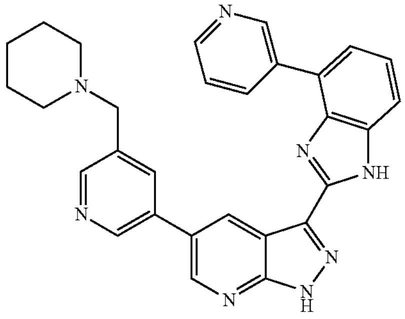 [SMILES: c1cncc(-c2cccc3[nH]c(-c4n[nH]c5ncc(-c6cncc(CN7CCCCC7)c6)cc45)nc23)c1]
624
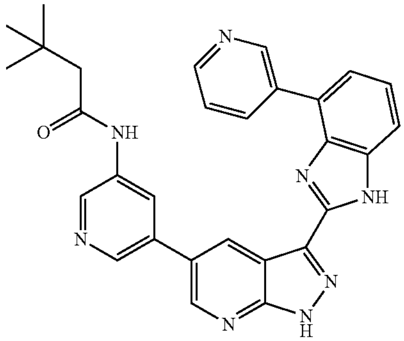 [SMILES: CC(C)(C)CC(=O)Nc1cncc(-c2cnc3[nH]nc(-c4nc5c(-c6cccnc6)cccc5[nH]4)c3c2)c1]
625
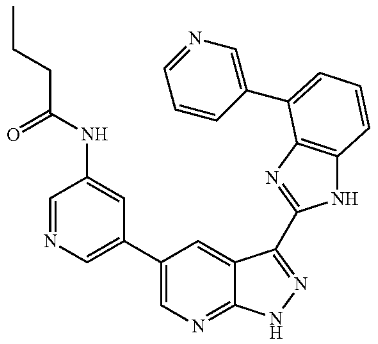 [SMILES: CCCC(=O)Nc1cncc(-c2cnc3[nH]nc(-c4nc5c(-c6cccnc6)cccc5[nH]4)c3c2)c1]

TABLE 1-continued
626
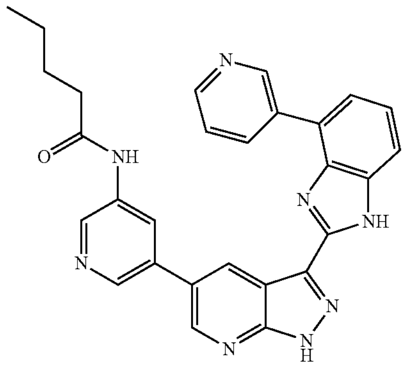 [SMILES: CCCCC(=O)Nc1cncc(-c2cnc3[nH]nc(-c4nc5c(-c6cccnc6)cccc5[nH]4)c3c2)c1]
627
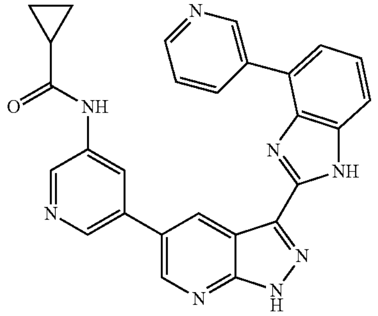 [SMILES: O=C(Nc1cncc(-c2cnc3[nH]nc(-c4nc5c(-c6cccnc6)cccc5[nH]4)c3c2)c1)C1CC1]
628
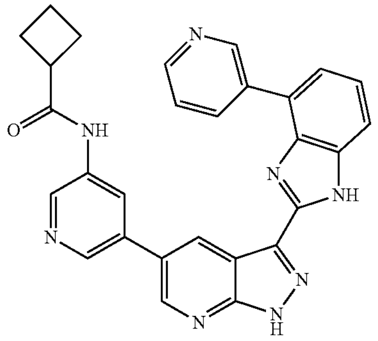 [SMILES: O=C(Nc1cncc(-c2cnc3[nH]nc(-c4nc5c(-c6cccnc6)cccc5[nH]4)c3c2)c1)C1CCC1]
629
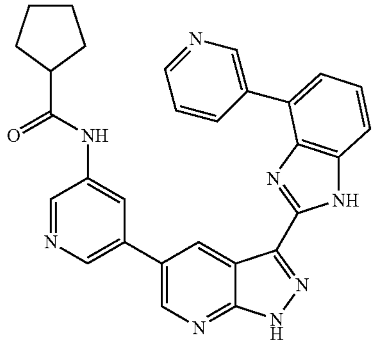
TABLE 1-continued
630
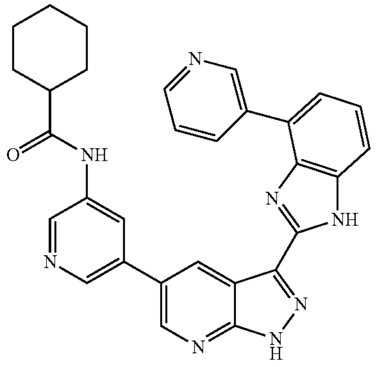 [SMILES: O=C(Nc1cncc(-c2cnc3[nH]nc(-c4nc5c(-c6cccnc6)cccc5[nH]4)c3c2)c1)C1CCCCC1]
631
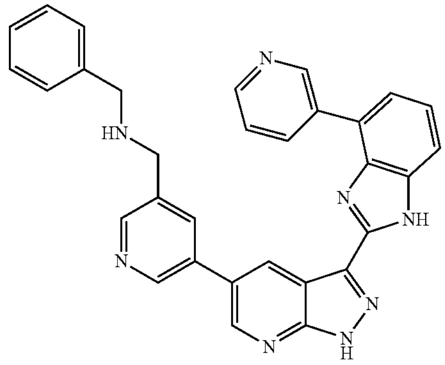 [SMILES: c1ccc(CNCc2cncc(-c3cnc4[nH]nc(-c5nc6c(-c7cccnc7)cccc6[nH]5)c4c3)c2)cc1]
632
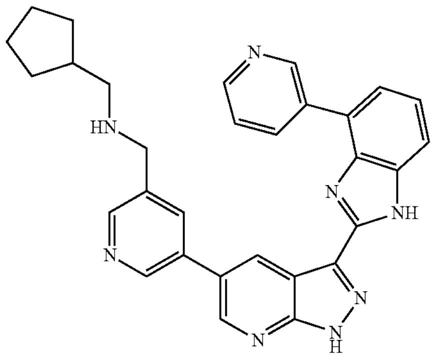 [SMILES: c1cncc(-c2cccc3[nH]c(-c4n[nH]c5ncc(-c6cncc(CNCC7CCCC7)c6)cc45)nc23)c1]
633
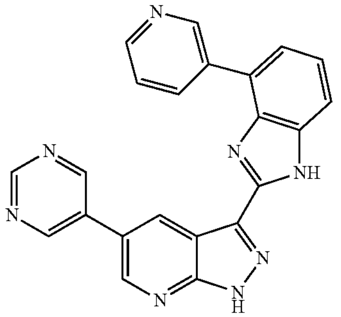

TABLE 1-continued
634 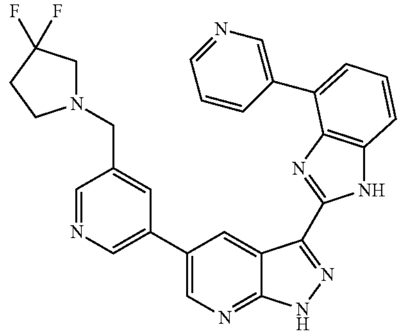 [SMILES: FC1(F)CCN(Cc2cncc(-c3cnc4[nH]nc(-c5nc6c(-c7cccnc7)cccc6[nH]5)c4c3)c2)C1]
635 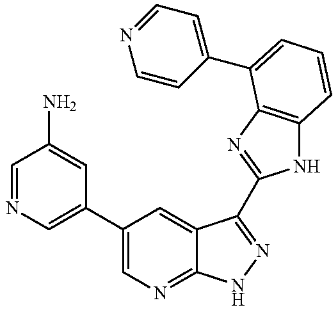 [SMILES: Nc1cncc(-c2cnc3[nH]nc(-c4nc5c(-c6ccncc6)cccc5[nH]4)c3c2)c1]
636 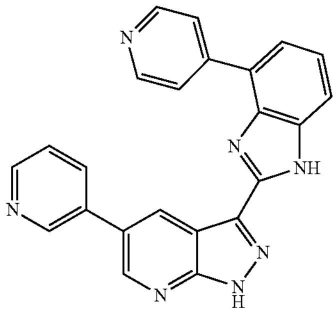 [SMILES: c1cncc(-c2cnc3[nH]nc(-c4nc5c(-c6ccncc6)cccc5[nH]4)c3c2)c1]
637 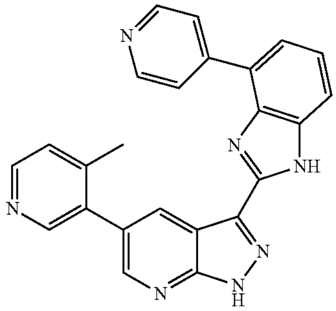 [SMILES: Cc1ccncc1-c1cnc2[nH]nc(-c3nc4c(-c5ccncc5)cccc4[nH]3)c2c1]
638 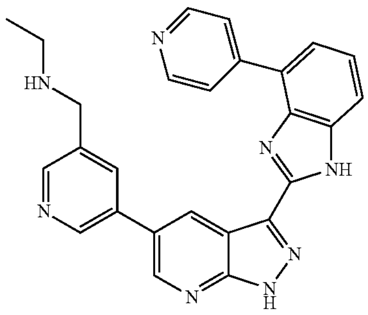 [SMILES: CCNCc1cncc(-c2cnc3[nH]nc(-c4nc5c(-c6ccncc6)cccc5[nH]4)c3c2)c1]
TABLE 1-continued
639 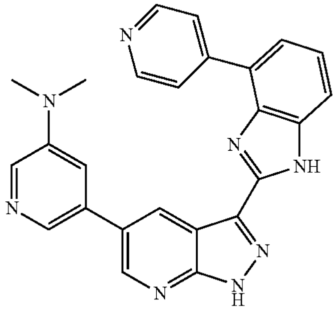
640 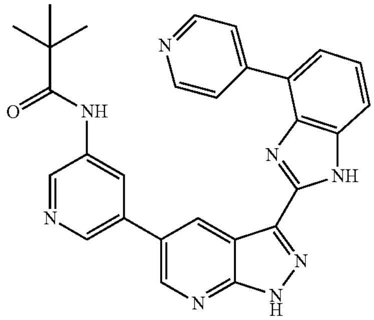 [SMILES: CC(C)(C)C(=O)Nc1cncc(-c2cnc3[nH]nc(-c4nc5c(-c6ccncc6)cccc5[nH]4)c3c2)c1]
641 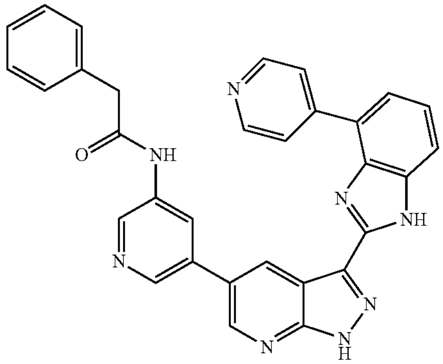 [SMILES: O=C(Cc1ccccc1)Nc1cncc(-c2cnc3[nH]nc(-c4nc5c(-c6ccncc6)cccc5[nH]4)c3c2)c1]
642 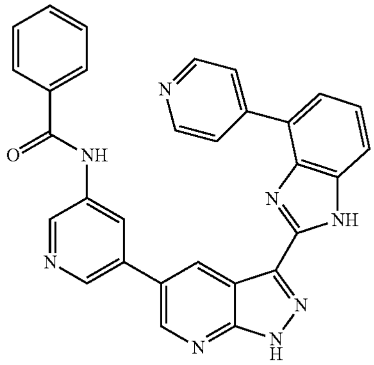 [SMILES: O=C(Nc1cncc(-c2cnc3[nH]nc(-c4nc5c(-c6ccncc6)cccc5[nH]4)c3c2)c1)c1ccccc1]

TABLE 1-continued
643
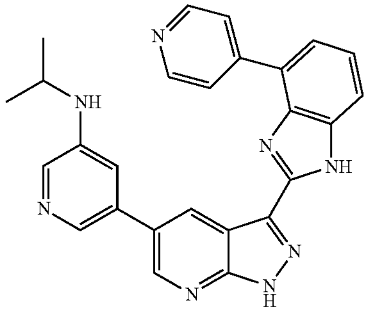 [SMILES: CC(C)Nc1cncc(-c2cnc3[nH]nc(-c4nc5c(-c6ccncc6)cccc5[nH]4)c3c2)c1]
644
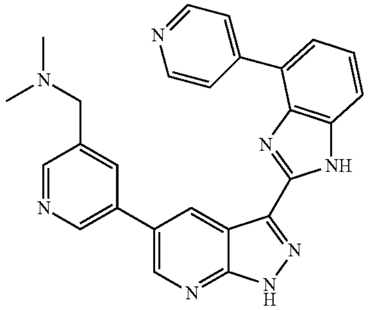 [SMILES: CN(C)Cc1cncc(-c2cnc3[nH]nc(-c4nc5c(-c6ccncc6)cccc5[nH]4)c3c2)c1]
645
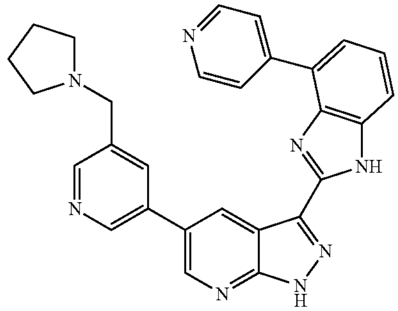 [SMILES: c1cc(-c2ccncc2)c2nc(-c3n[nH]c4ncc(-c5cncc(CN6CCCC6)c5)cc34)[nH]c2c1]
646
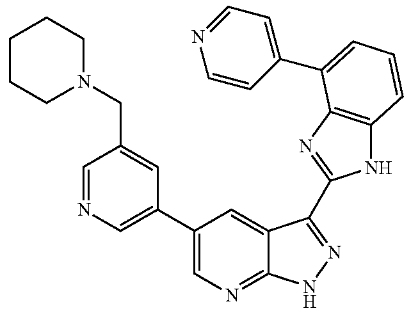 [SMILES: c1cc(-c2ccncc2)c2nc(-c3n[nH]c4ncc(-c5cncc(CN6CCCCC6)c5)cc34)[nH]c2c1]
647
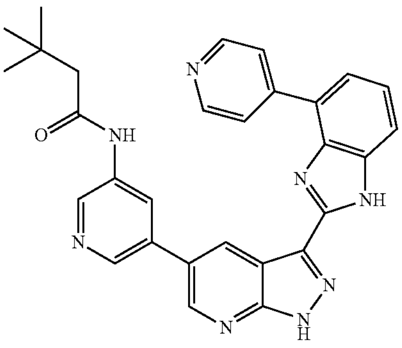 [SMILES: CC(C)(C)CC(=O)Nc1cncc(-c2cnc3[nH]nc(-c4nc5c(-c6ccncc6)cccc5[nH]4)c3c2)c1]
TABLE 1-continued
648
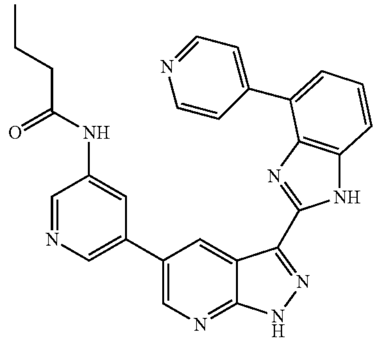 [SMILES: CCCC(=O)Nc1cncc(-c2cnc3[nH]nc(-c4nc5c(-c6ccncc6)cccc5[nH]4)c3c2)c1]
649
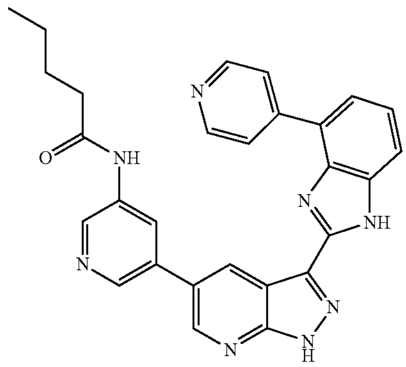 [SMILES: CCCCC(=O)Nc1cncc(-c2cnc3[nH]nc(-c4nc5c(-c6ccncc6)cccc5[nH]4)c3c2)c1]
650
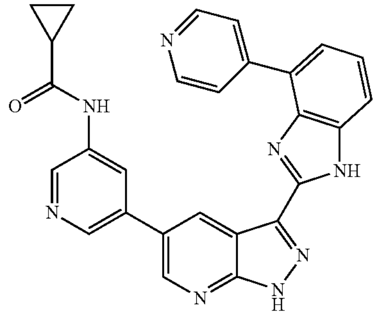 [SMILES: O=C(Nc1cncc(-c2cnc3[nH]nc(-c4nc5c(-c6ccncc6)cccc5[nH]4)c3c2)c1)C1CC1]
651
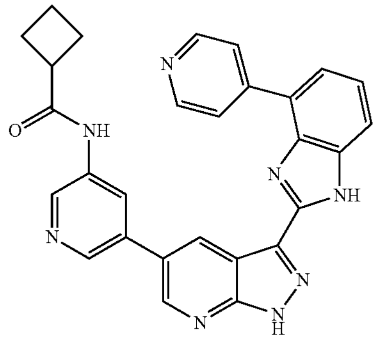 [SMILES: O=C(Nc1cncc(-c2cnc3[nH]nc(-c4nc5c(-c6ccncc6)cccc5[nH]4)c3c2)c1)C1CCC1]

TABLE 1-continued
652
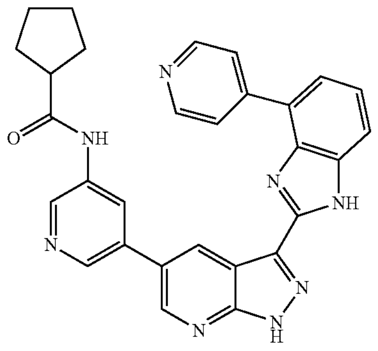 [SMILES: O=C(Nc1cncc(-c2cnc3[nH]nc(-c4nc5c(-c6ccncc6)cccc5[nH]4)c3c2)c1)C1CCCC1]
653
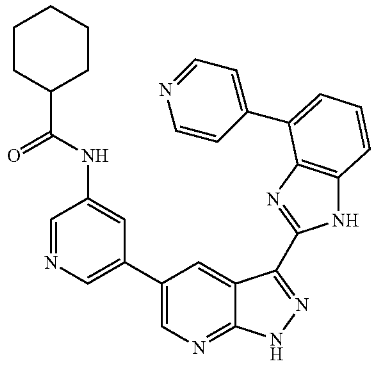 [SMILES: O=C(Nc1cncc(-c2cnc3[nH]nc(-c4nc5c(-c6ccncc6)cccc5[nH]4)c3c2)c1)C1CCCCC1]
654
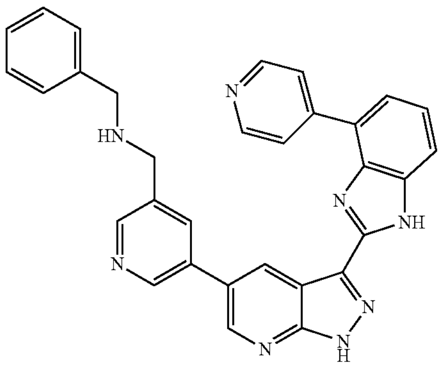 [SMILES: c1ccc(CNCc2cncc(-c3cnc4[nH]nc(-c5nc6c(-c7ccncc7)cccc6[nH]5)c4c3)c2)cc1]
655
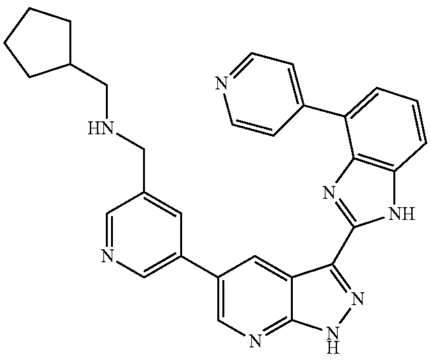 [SMILES: c1cc(-c2ccncc2)c2nc(-c3n[nH]c4ncc(-c5cncc(CNCC6CCCC6)c5)cc34)[nH]c2c1]
TABLE 1-continued
656
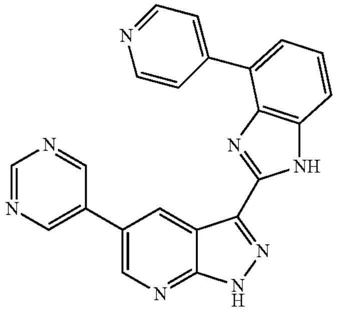
657
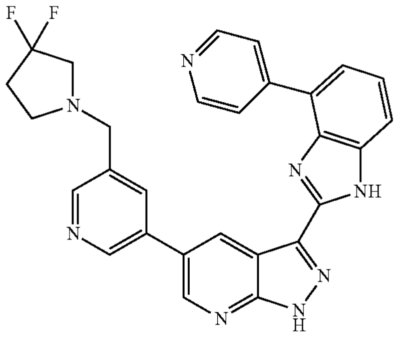
658
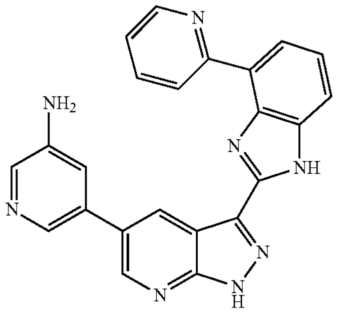 [SMILES: Nc1cncc(-c2cnc3[nH]nc(-c4nc5c(-c6ccccn6)cccc5[nH]4)c3c2)c1]
659
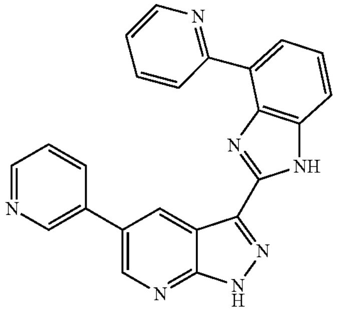
660
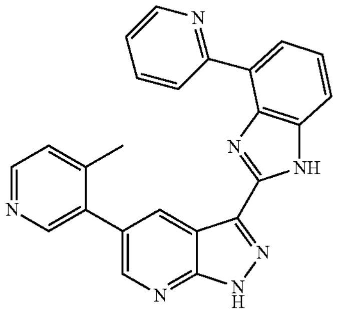 [SMILES: Cc1ccncc1-c1cnc2[nH]nc(-c3nc4c(-c5ccccn5)cccc4[nH]3)c2c1]

661
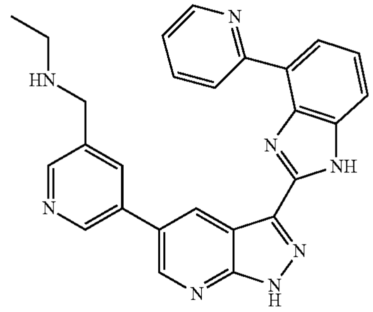
662
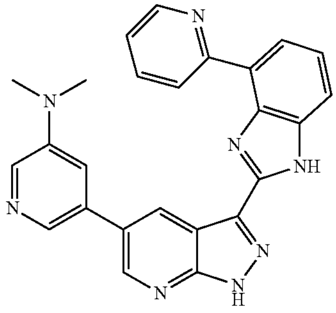
663
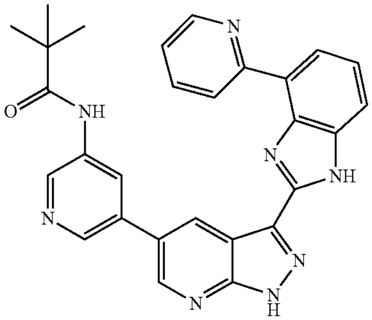 [SMILES: CC(C)(C)C(=O)Nc1cncc(-c2cnc3[nH]nc(-c4nc5c(-c6ccccn6)cccc5[nH]4)c3c2)c1]
664
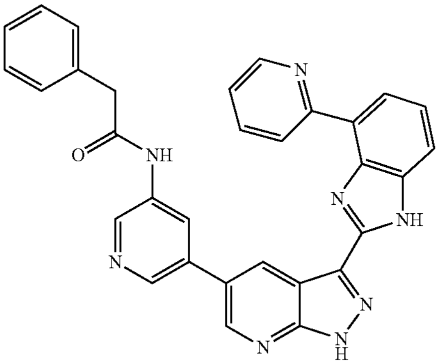 [SMILES: O=C(Cc1ccccc1)Nc1cncc(-c2cnc3[nH]nc(-c4nc5c(-c6ccccn6)cccc5[nH]4)c3c2)c1]
665
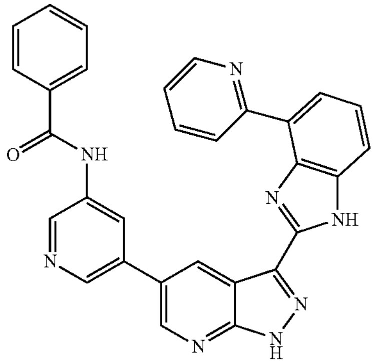 [SMILES: O=C(Nc1cncc(-c2cnc3[nH]nc(-c4nc5c(-c6ccccn6)cccc5[nH]4)c3c2)c1)c1ccccc1]
666
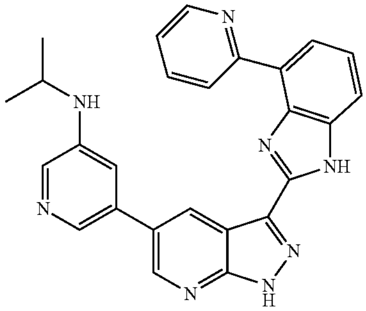 [SMILES: CC(C)Nc1cncc(-c2cnc3[nH]nc(-c4nc5c(-c6ccccn6)cccc5[nH]4)c3c2)c1]
667
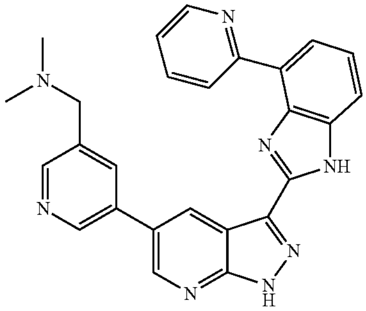 [SMILES: CN(C)Cc1cncc(-c2cnc3[nH]nc(-c4nc5c(-c6ccccn6)cccc5[nH]4)c3c2)c1]
668
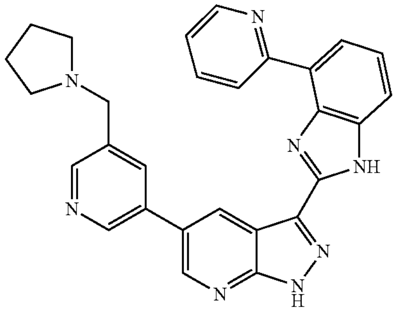 [SMILES: c1ccc(-c2cccc3[nH]c(-c4n[nH]c5ncc(-c6cncc(CN7CCCC7)c6)cc45)nc23)nc1]
669
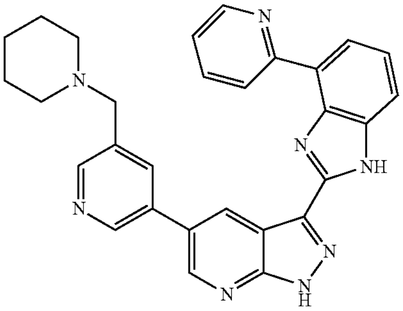 [SMILES: c1ccc(-c2cccc3[nH]c(-c4n[nH]c5ncc(-c6cncc(CN7CCCCC7)c6)cc45)nc23)nc1]

TABLE 1-continued
670
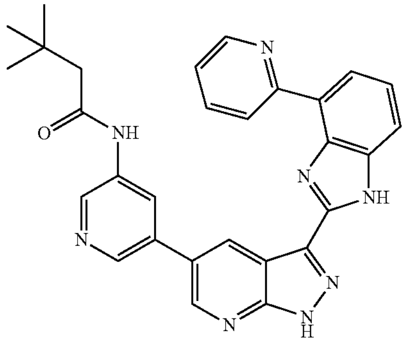 [SMILES: CC(C)(C)CC(=O)Nc1cncc(-c2cnc3[nH]nc(-c4nc5c(-c6ccccn6)cccc5[nH]4)c3c2)c1]
671
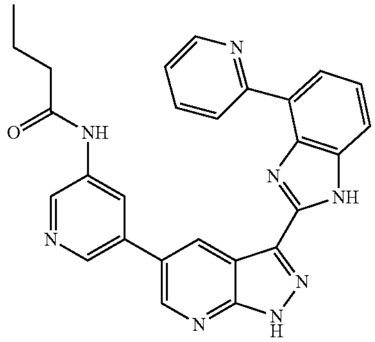 [SMILES: CCCC(=O)Nc1cncc(-c2cnc3[nH]nc(-c4nc5c(-c6ccccn6)cccc5[nH]4)c3c2)c1]
672
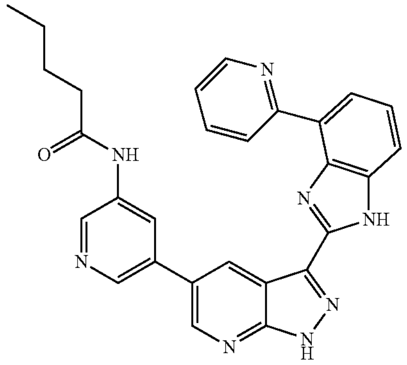 [SMILES: CCCCC(=O)Nc1cncc(-c2cnc3[nH]nc(-c4nc5c(-c6ccccn6)cccc5[nH]4)c3c2)c1]
673
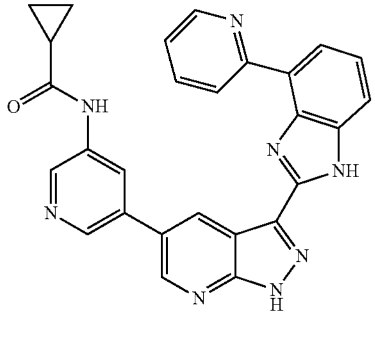 [SMILES: O=C(Nc1cncc(-c2cnc3[nH]nc(-c4nc5c(-c6ccccn6)cccc5[nH]4)c3c2)c1)C1CC1]
674
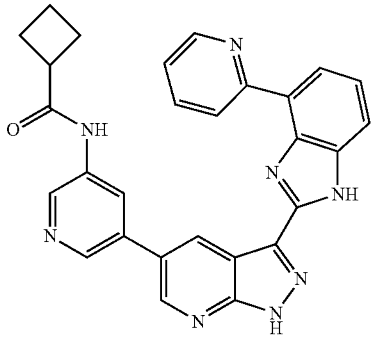 [SMILES: O=C(Nc1cncc(-c2cnc3[nH]nc(-c4nc5c(-c6ccccn6)cccc5[nH]4)c3c2)c1)C1CCC1]
675
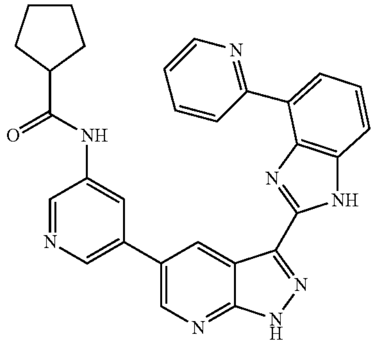 [SMILES: O=C(Nc1cncc(-c2cnc3[nH]nc(-c4nc5c(-c6ccccn6)cccc5[nH]4)c3c2)c1)C1CCCC1]
676
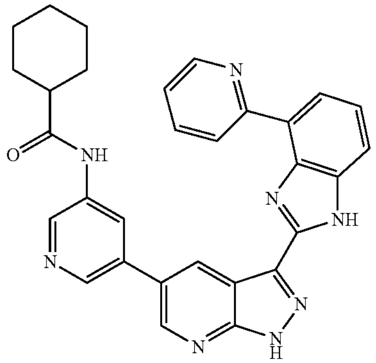 [SMILES: O=C(Nc1cncc(-c2cnc3[nH]nc(-c4nc5c(-c6ccccn6)cccc5[nH]4)c3c2)c1)C1CCCCC1]
677
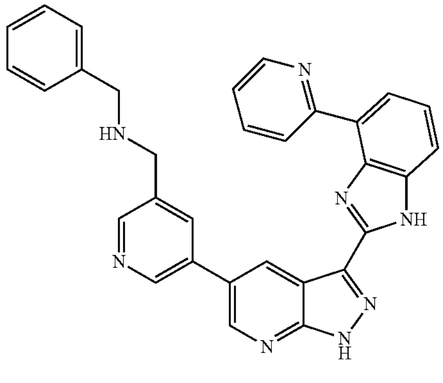 [SMILES: c1ccc(CNCc2cncc(-c3cnc4[nH]nc(-c5nc6c(-c7ccccn7)cccc6[nH]5)c4c3)c2)cc1]

TABLE 1-continued
678
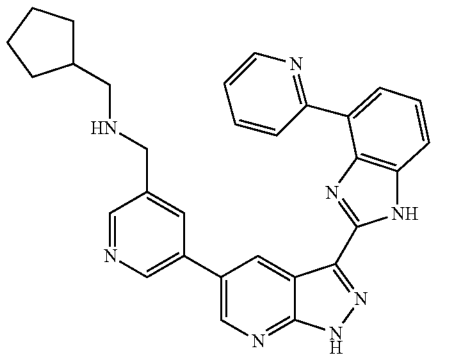 [SMILES: c1ccc(-c2cccc3[nH]c(-c4n[nH]c5ncc(-c6cncc(CNCC7CCCC7)c6)cc45)nc23)nc1]
679
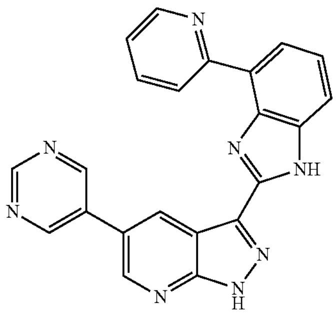
680
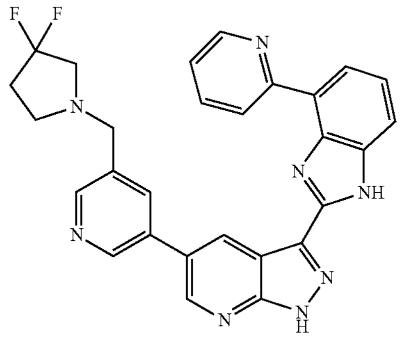 [SMILES: FC1(F)CCN(Cc2cncc(-c3cnc4[nH]nc(-c5nc6c(-c7ccccn7)cccc6[nH]5)c4c3)c2)C1]
681
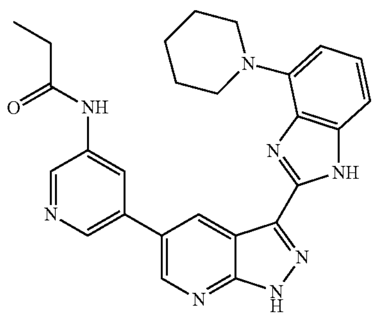 [SMILES: CCC(=O)Nc1cncc(-c2cnc3[nH]nc(-c4nc5c(N6CCCCC6)cccc5[nH]4)c3c2)c1]
TABLE 1-continued
682
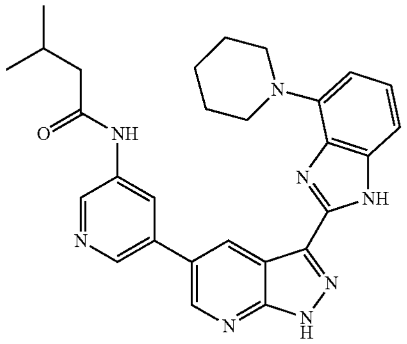
683
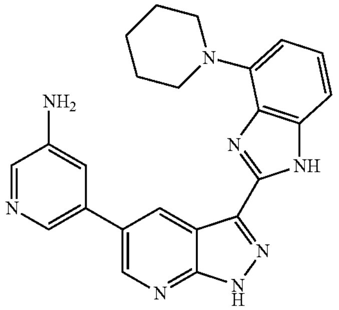 [SMILES: Nc1cncc(-c2cnc3[nH]nc(-c4nc5c(N6CCCCC6)cccc5[nH]4)c3c2)c1]
684
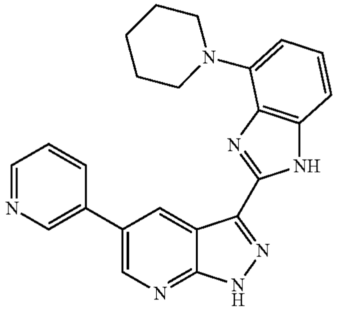
685
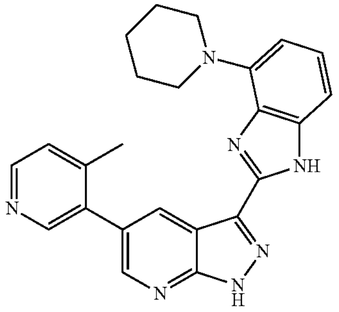 [SMILES: Cc1ccncc1-c1cnc2[nH]nc(-c3nc4c(N5CCCCC5)cccc4[nH]3)c2c1]
686
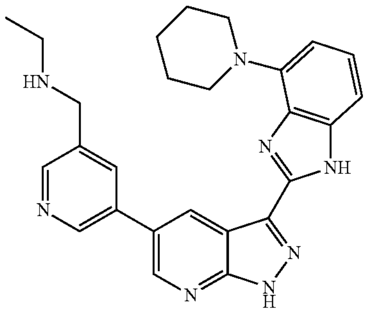

TABLE 1-continued
687
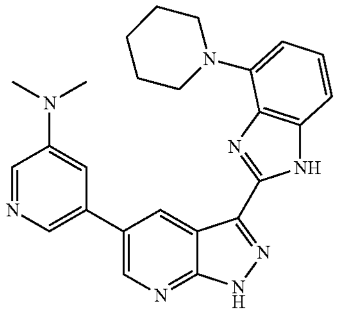 [SMILES: CN(C)c1cncc(-c2cnc3[nH]nc(-c4nc5c(N6CCCCC6)cccc5[nH]4)c3c2)c1]
688
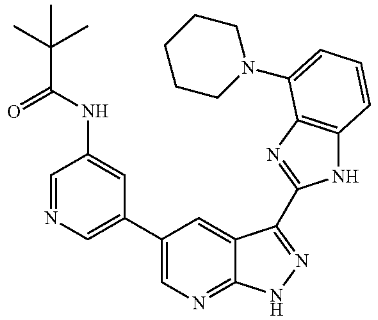 [SMILES: CC(C)(C)C(=O)Nc1cncc(-c2cnc3[nH]nc(-c4nc5c(N6CCCCC6)cccc5[nH]4)c3c2)c1]
689
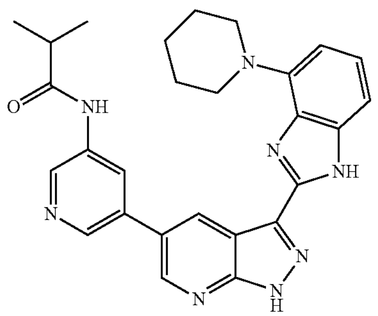 [SMILES: CC(C)C(=O)Nc1cncc(-c2cnc3[nH]nc(-c4nc5c(N6CCCCC6)cccc5[nH]4)c3c2)c1]
690
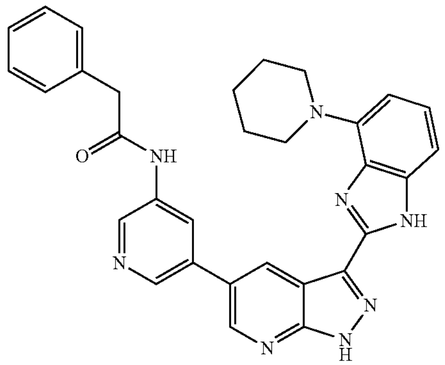
TABLE 1-continued
691
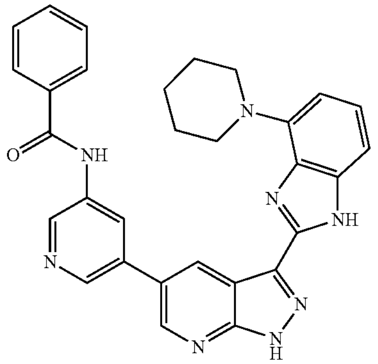 [SMILES: O=C(Nc1cncc(-c2cnc3[nH]nc(-c4nc5c(N6CCCCC6)cccc5[nH]4)c3c2)c1)c1ccccc1]
692
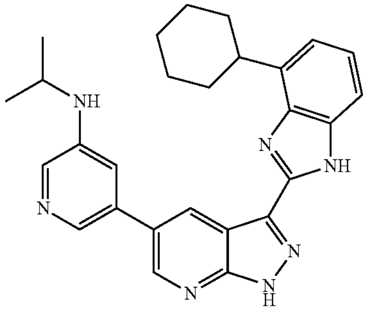
693
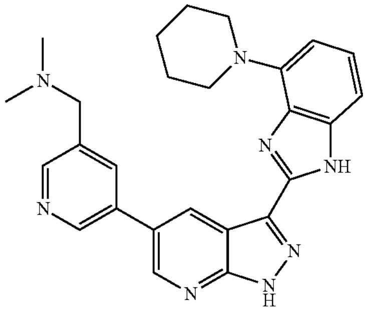 [SMILES: CN(C)Cc1cncc(-c2cnc3[nH]nc(-c4nc5c(N6CCCCC6)cccc5[nH]4)c3c2)c1]
694
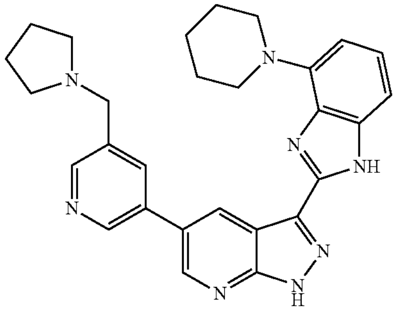 [SMILES: c1cc(N2CCCCC2)c2nc(-c3n[nH]c4ncc(-c5cncc(CN6CCCC6)c5)cc34)[nH]c2c1]
695
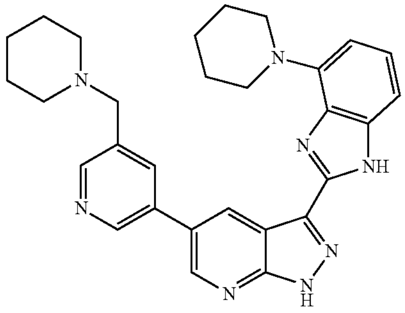 [SMILES: c1cc(N2CCCCC2)c2nc(-c3n[nH]c4ncc(-c5cncc(CN6CCCCC6)c5)cc34)[nH]c2c1]

TABLE 1-continued
696
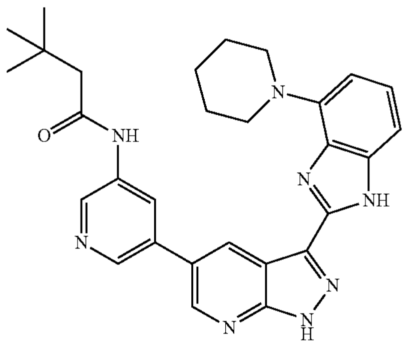 [SMILES: CC(C)(C)CC(=O)Nc1cncc(-c2cnc3[nH]nc(-c4nc5c(N6CCCCC6)cccc5[nH]4)c3c2)c1]
697
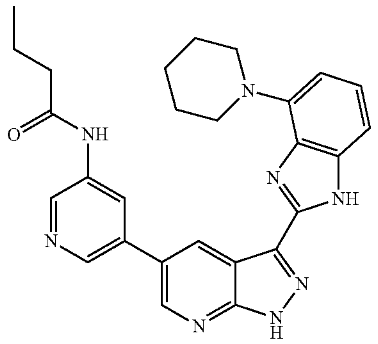 [SMILES: CCCC(=O)Nc1cncc(-c2cnc3[nH]nc(-c4nc5c(N6CCCCC6)cccc5[nH]4)c3c2)c1]
698
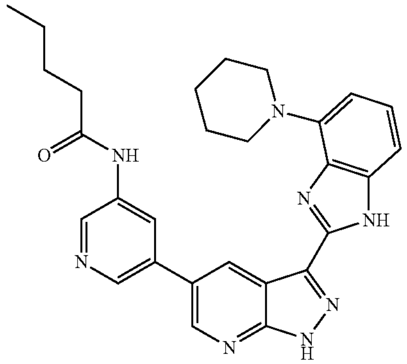 [SMILES: CCCCC(=O)Nc1cncc(-c2cnc3[nH]nc(-c4nc5c(N6CCCCC6)cccc5[nH]4)c3c2)c1]
699
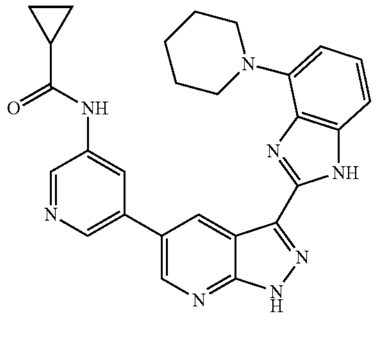 [SMILES: O=C(Nc1cncc(-c2cnc3[nH]nc(-c4nc5c(N6CCCCC6)cccc5[nH]4)c3c2)c1)C1CC1]
TABLE 1-continued
700
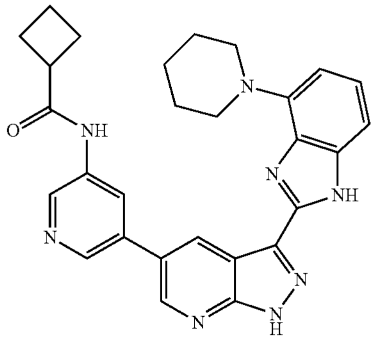 [SMILES: O=C(Nc1cncc(-c2cnc3[nH]nc(-c4nc5c(N6CCCCC6)cccc5[nH]4)c3c2)c1)C1CCC1]
701
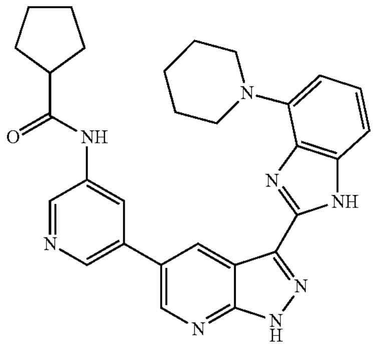 [SMILES: O=C(Nc1cncc(-c2cnc3[nH]nc(-c4nc5c(N6CCCCC6)cccc5[nH]4)c3c2)c1)C1CCCC1]
702
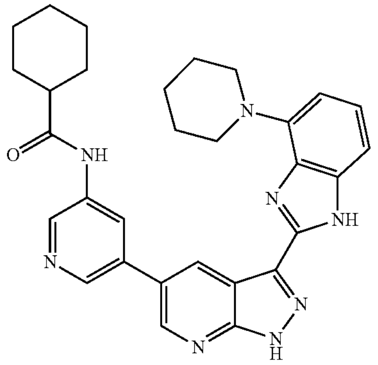 [SMILES: O=C(Nc1cncc(-c2cnc3[nH]nc(-c4nc5c(N6CCCCC6)cccc5[nH]4)c3c2)c1)C1CCCCC1]
703
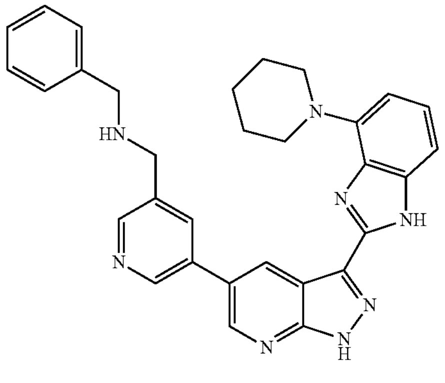 [SMILES: c1ccc(CNCc2cncc(-c3cnc4[nH]nc(-c5nc6c(N7CCCCC7)cccc6[nH]5)c4c3)c2)cc1]

TABLE 1-continued
704
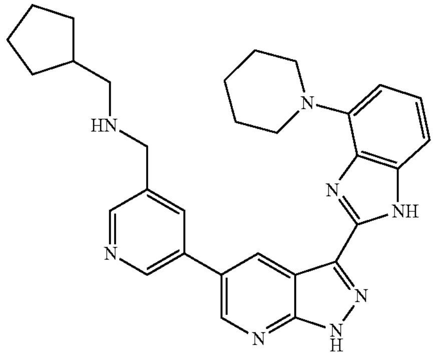 [SMILES: c1cc(N2CCCCC2)c2nc(-c3n[nH]c4ncc(-c5cncc(CNCC6CCCC6)c5)cc34)[nH]c2c1]
705
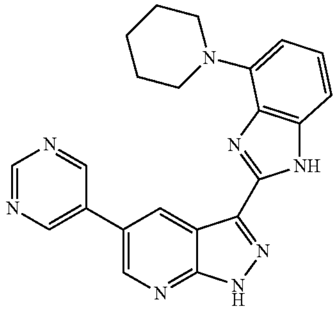 [SMILES: c1cc(N2CCCCC2)c2nc(-c3n[nH]c4ncc(-c5cncnc5)cc34)[nH]c2c1]
706
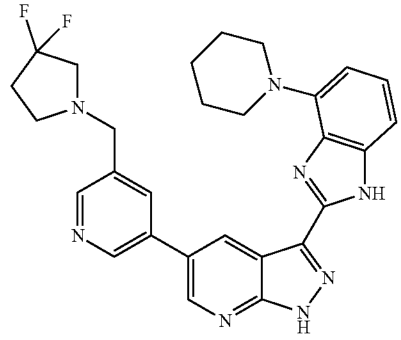 [SMILES: FC1(F)CCN(Cc2cncc(-c3cnc4[nH]nc(-c5nc6c(N7CCCCC7)cccc6[nH]5)c4c3)c2)C1]
707
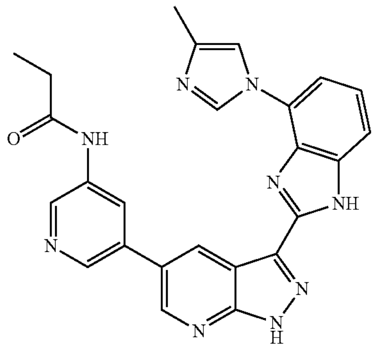 [SMILES: CCC(=O)Nc1cncc(-c2cnc3[nH]nc(-c4nc5c(-n6cnc(C)c6)cccc5[nH]4)c3c2)c1]
TABLE 1-continued
708
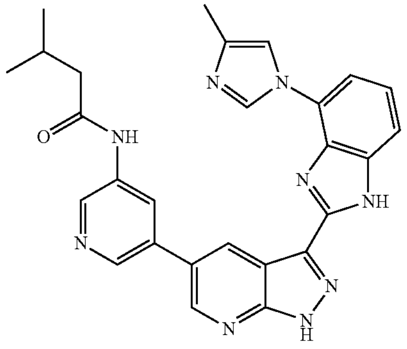 [SMILES: Cc1cn(-c2cccc3[nH]c(-c4n[nH]c5ncc(-c6cncc(NC(=O)CC(C)C)c6)cc45)nc23)cn1]
709
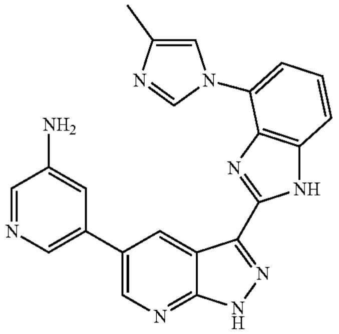 [SMILES: Cc1cn(-c2cccc3[nH]c(-c4n[nH]c5ncc(-c6cncc(N)c6)cc45)nc23)cn1]
710
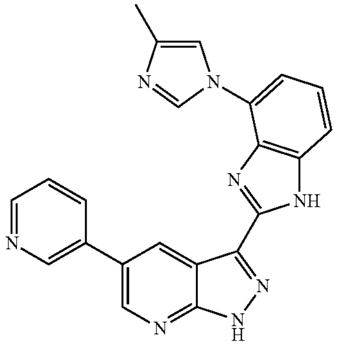 [SMILES: Cc1cn(-c2cccc3[nH]c(-c4n[nH]c5ncc(-c6cccnc6)cc45)nc23)cn1]
711
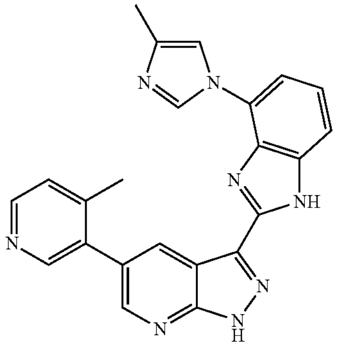 [SMILES: Cc1cn(-c2cccc3[nH]c(-c4n[nH]c5ncc(-c6cnccc6C)cc45)nc23)cn1]

TABLE 1-continued
712
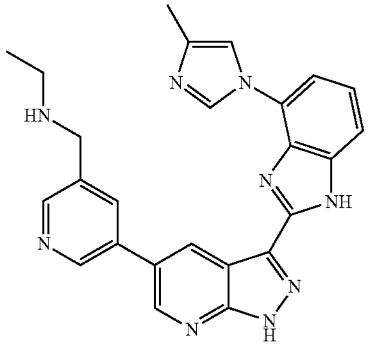
713
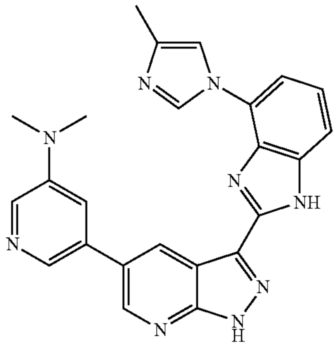 [SMILES: Cc1cn(-c2cccc3[nH]c(-c4n[nH]c5ncc(-c6cncc(N(C)C)c6)cc45)nc23)cn1]
714
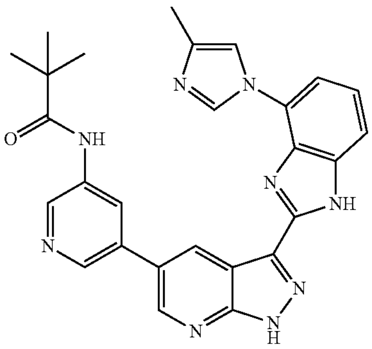 [SMILES: Cc1cn(-c2cccc3[nH]c(-c4n[nH]c5ncc(-c6cncc(NC(=O)C(C)(C)C)c6)cc45)nc23)cn1]
715
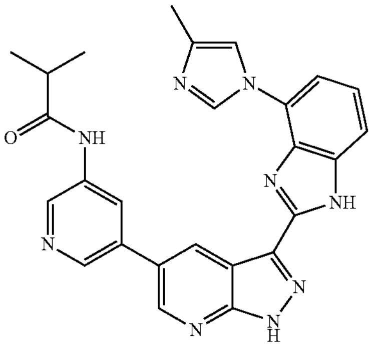 [SMILES: Cc1cn(-c2cccc3[nH]c(-c4n[nH]c5ncc(-c6cncc(NC(=O)C(C)C)c6)cc45)nc23)cn1]
TABLE 1-continued
716
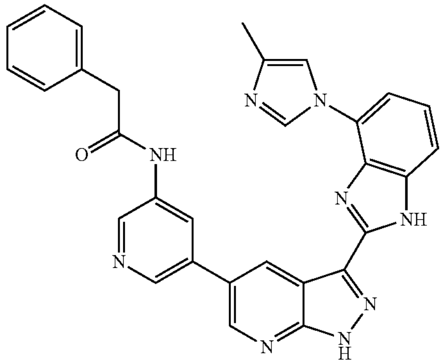 [SMILES: Cc1cn(-c2cccc3[nH]c(-c4n[nH]c5ncc(-c6cncc(NC(=O)Cc7ccccc7)c6)cc45)nc23)cn1]
717
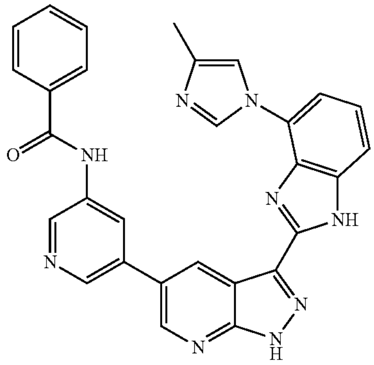 [SMILES: Cc1cn(-c2cccc3[nH]c(-c4n[nH]c5ncc(-c6cncc(NC(=O)c7ccccc7)c6)cc45)nc23)cn1]
718
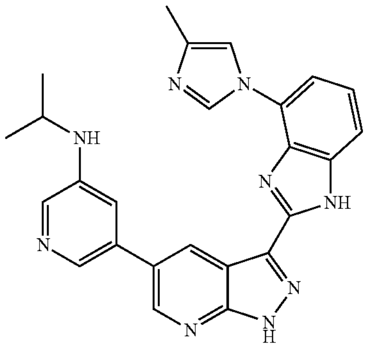
719
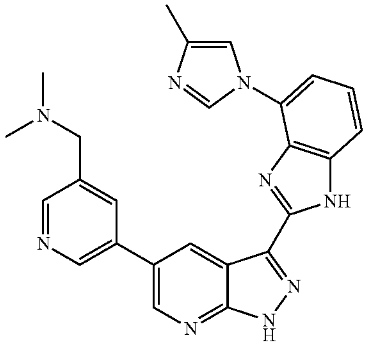

TABLE 1-continued
720
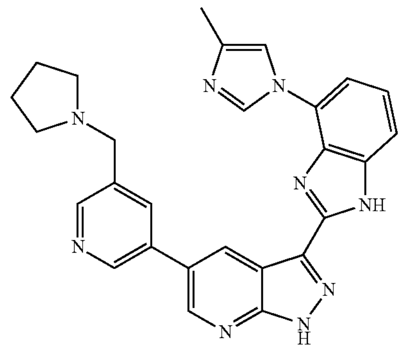 [SMILES: Cc1cn(-c2cccc3[nH]c(-c4n[nH]c5ncc(-c6cncc(CN7CCCC7)c6)cc45)nc23)cn1]
721
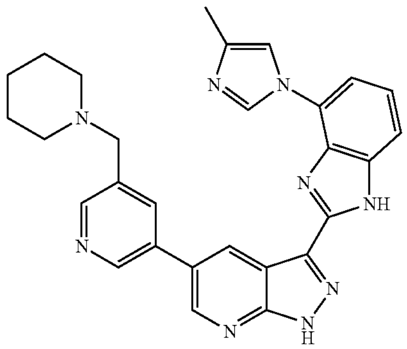
722
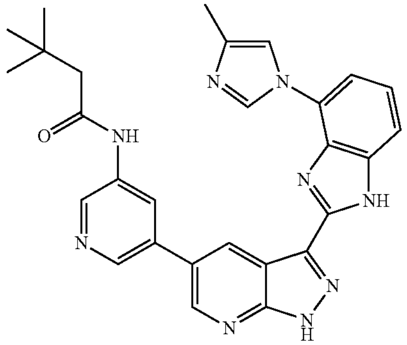 [SMILES: Cc1cn(-c2cccc3[nH]c(-c4n[nH]c5ncc(-c6cncc(NC(=O)CC(C)(C)C)c6)cc45)nc23)cn1]
723
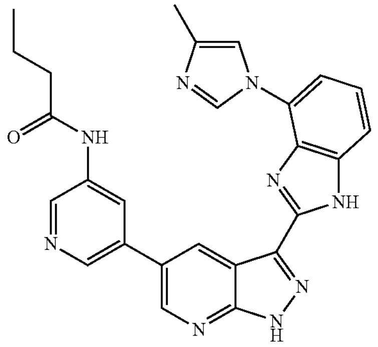 [SMILES: CCCC(=O)Nc1cncc(-c2cnc3[nH]nc(-c4nc5c(-n6cnc(C)c6)cccc5[nH]4)c3c2)c1]
TABLE 1-continued
724
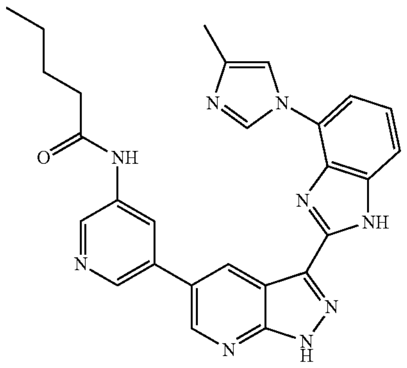 [SMILES: CCCCC(=O)Nc1cncc(-c2cnc3[nH]nc(-c4nc5c(-n6cnc(C)c6)cccc5[nH]4)c3c2)c1]
725
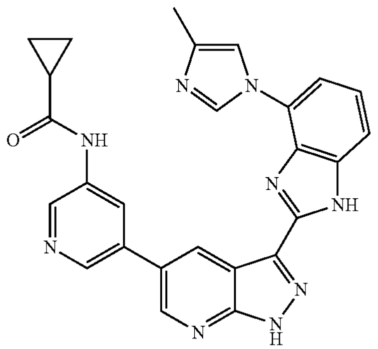 [SMILES: Cc1cn(-c2cccc3[nH]c(-c4n[nH]c5ncc(-c6cncc(NC(=O)C7CC7)c6)cc45)nc23)cn1]
726
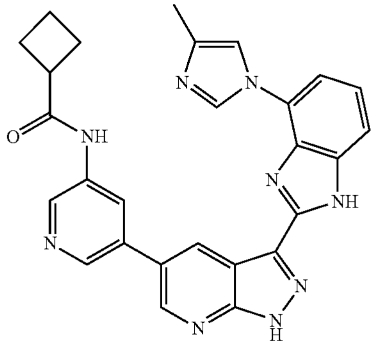 [SMILES: Cc1cn(-c2cccc3[nH]c(-c4n[nH]c5ncc(-c6cncc(NC(=O)C7CCC7)c6)cc45)nc23)cn1]
727
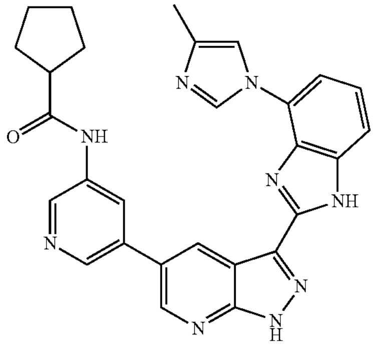 [SMILES: Cc1cn(-c2cccc3[nH]c(-c4n[nH]c5ncc(-c6cncc(NC(=O)C7CCCC7)c6)cc45)nc23)cn1]

728
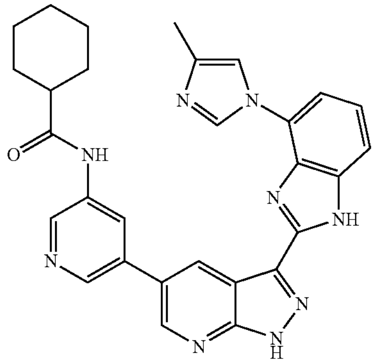 [SMILES: Cc1cn(-c2cccc3[nH]c(-c4n[nH]c5ncc(-c6cncc(NC(=O)C7CCCCC7)c6)cc45)nc23)cn1]
729
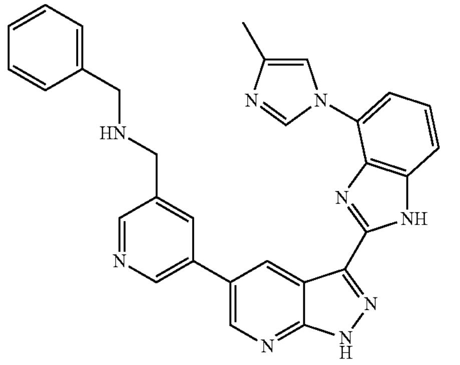 [SMILES: Cc1cn(-c2cccc3[nH]c(-c4n[nH]c5ncc(-c6cncc(CNCc7ccccc7)c6)cc45)nc23)cn1]
730
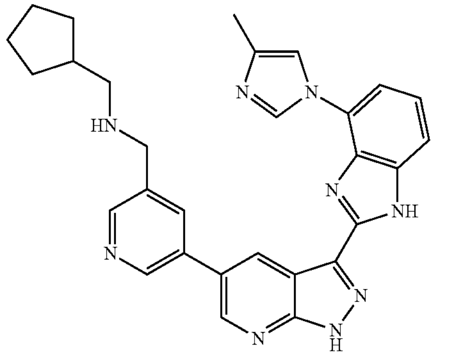
731
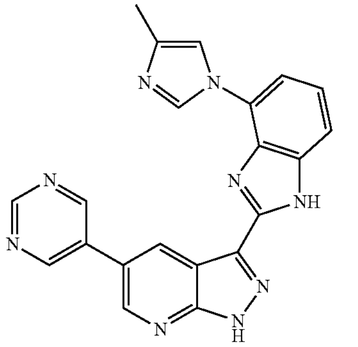
732
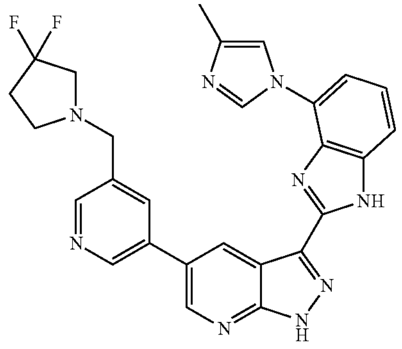 [SMILES: Cc1cn(-c2cccc3[nH]c(-c4n[nH]c5ncc(-c6cncc(CN7CCC(F)(F)C7)c6)cc45)nc23)cn1]
733
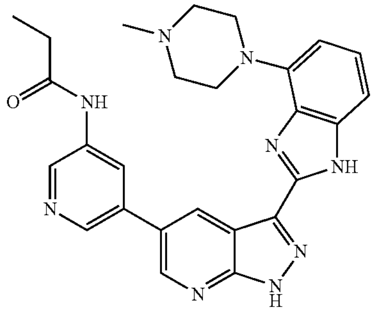 [SMILES: CCC(=O)Nc1cncc(-c2cnc3[nH]nc(-c4nc5c(N6CCN(C)CC6)cccc5[nH]4)c3c2)c1]
734
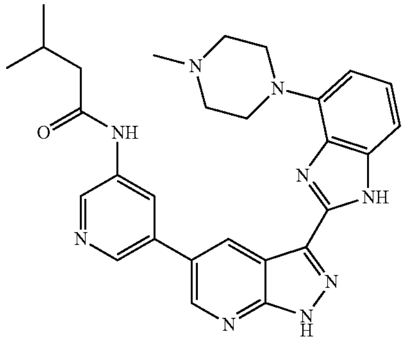 [SMILES: CC(C)CC(=O)Nc1cncc(-c2cnc3[nH]nc(-c4nc5c(N6CCN(C)CC6)cccc5[nH]4)c3c2)c1]
735
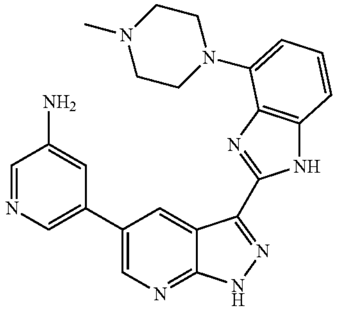 [SMILES: CN1CCN(c2cccc3[nH]c(-c4n[nH]c5ncc(-c6cncc(N)c6)cc45)nc23)CC1]
736
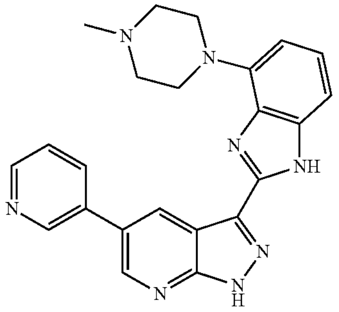

TABLE 1-continued
737
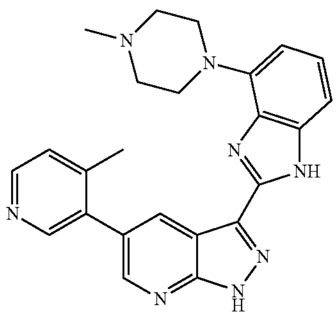 [SMILES: Cc1ccncc1-c1cnc2[nH]nc(-c3nc4c(N5CCN(C)CC5)cccc4[nH]3)c2c1]
738
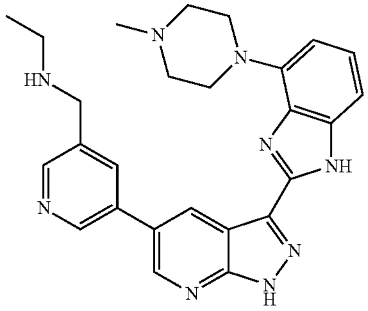 [SMILES: CCNCc1cncc(-c2cnc3[nH]nc(-c4nc5c(N6CCN(C)CC6)cccc5[nH]4)c3c2)c1]
739
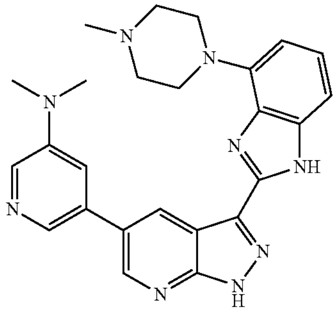
740
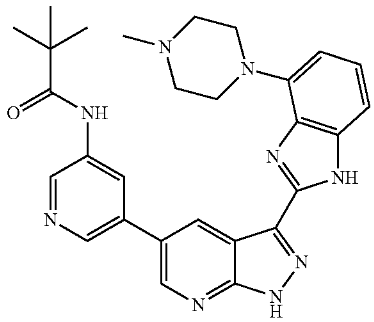 [SMILES: CN1CCN(c2cccc3[nH]c(-c4n[nH]c5ncc(-c6cncc(NC(=O)C(C)(C)C)c6)cc45)nc23)CC1]
741
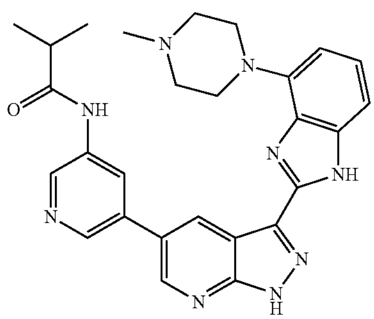 [SMILES: CC(C)C(=O)Nc1cncc(-c2cnc3[nH]nc(-c4nc5c(N6CCN(C)CC6)cccc5[nH]4)c3c2)c1]
TABLE 1-continued
742
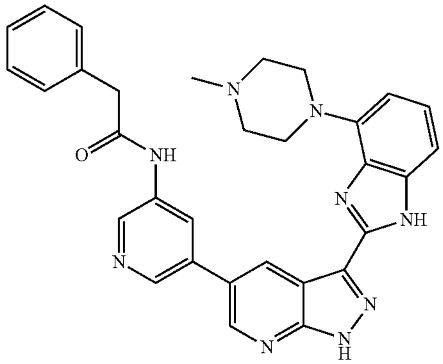 [SMILES: CN1CCN(c2cccc3[nH]c(-c4n[nH]c5ncc(-c6cncc(NC(=O)Cc7ccccc7)c6)cc45)nc23)CC1]
743
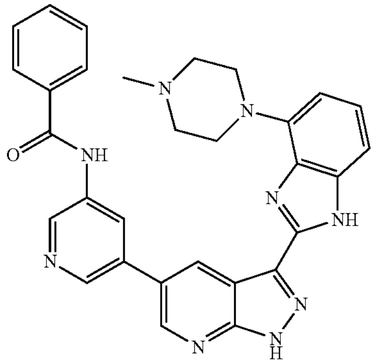 [SMILES: CN1CCN(c2cccc3[nH]c(-c4n[nH]c5ncc(-c6cncc(NC(=O)c7ccccc7)c6)cc45)nc23)CC1]
744
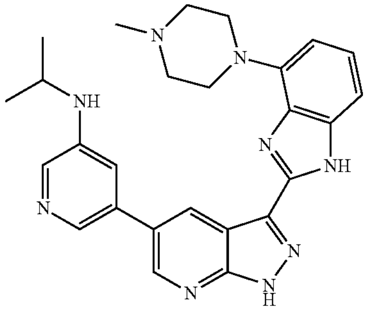 [SMILES: CC(C)Nc1cncc(-c2cnc3[nH]nc(-c4nc5c(N6CCN(C)CC6)cccc5[nH]4)c3c2)c1]
745
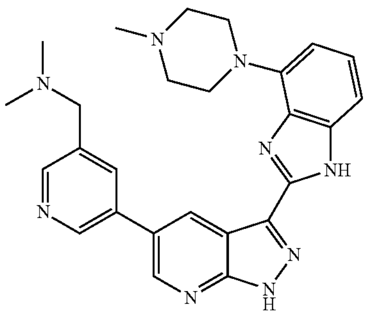 [SMILES: CN(C)Cc1cncc(-c2cnc3[nH]nc(-c4nc5c(N6CCN(C)CC6)cccc5[nH]4)c3c2)c1]

TABLE 1-continued
746 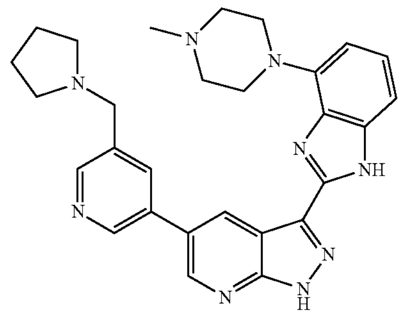 [SMILES: CN1CCN(c2cccc3[nH]c(-c4n[nH]c5ncc(-c6cncc(CN7CCCC7)c6)cc45)nc23)CC1]
747 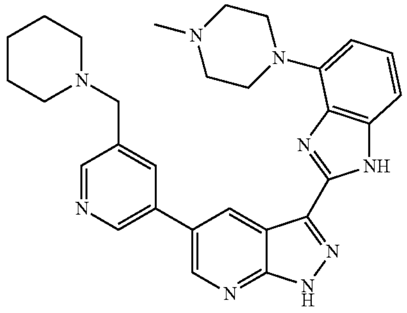 [SMILES: CN1CCN(c2cccc3[nH]c(-c4n[nH]c5ncc(-c6cncc(CN7CCCCC7)c6)cc45)nc23)CC1]
748 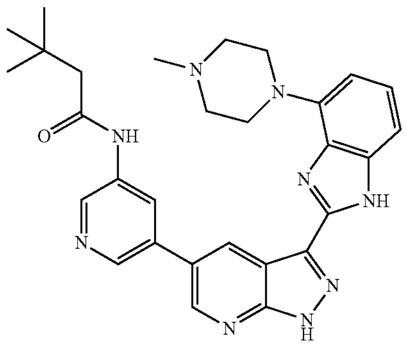 [SMILES: CN1CCN(c2cccc3[nH]c(-c4n[nH]c5ncc(-c6cncc(NC(=O)CC(C)(C)C)c6)cc45)nc23)CC1]
749 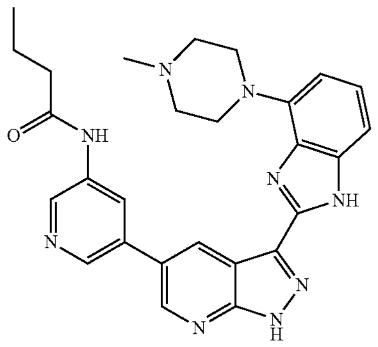 [SMILES: CCCC(=O)Nc1cncc(-c2cnc3[nH]nc(-c4nc5c(N6CCN(C)CC6)cccc5[nH]4)c3c2)c1]
TABLE 1-continued
750 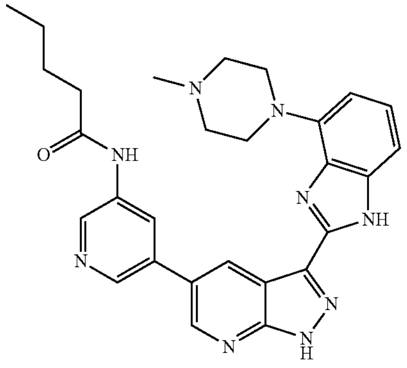 [SMILES: CCCCC(=O)Nc1cncc(-c2cnc3[nH]nc(-c4nc5c(N6CCN(C)CC6)cccc5[nH]4)c3c2)c1]
751 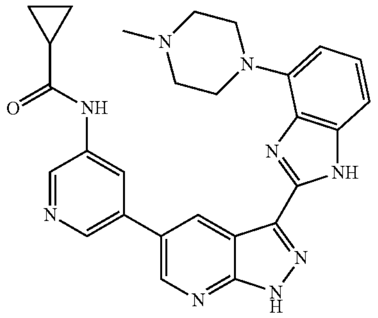 [SMILES: CN1CCN(c2cccc3[nH]c(-c4n[nH]c5ncc(-c6cncc(NC(=O)C7CC7)c6)cc45)nc23)CC1]
752 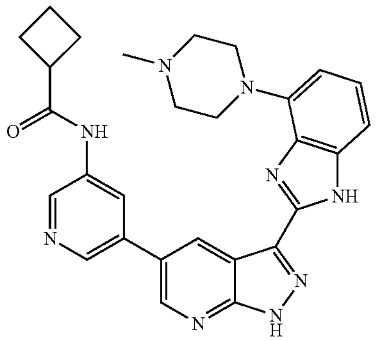 [SMILES: CN1CCN(c2cccc3[nH]c(-c4n[nH]c5ncc(-c6cncc(NC(=O)C7CCC7)c6)cc45)nc23)CC1]
753 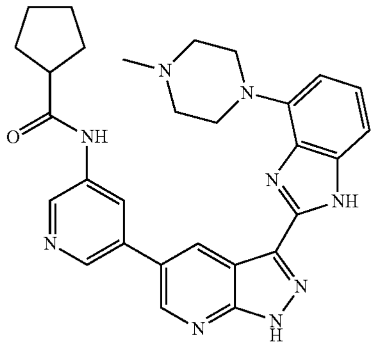

754
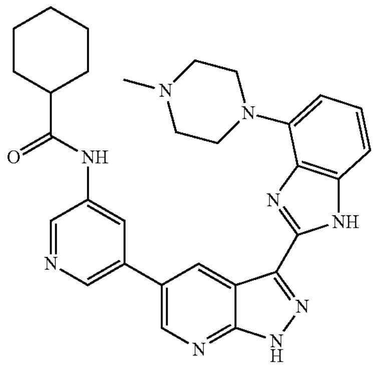 [SMILES: CN1CCN(c2cccc3[nH]c(-c4n[nH]c5ncc(-c6cncc(NC(=O)C7CCCCC7)c6)cc45)nc23)CC1]
755
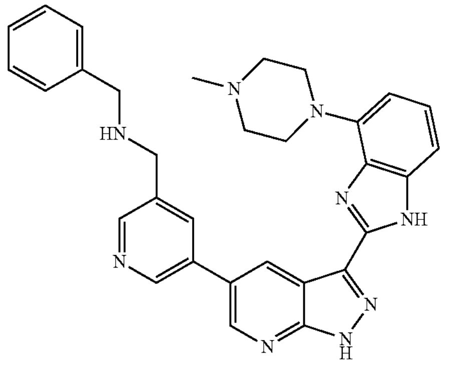 [SMILES: CN1CCN(c2cccc3[nH]c(-c4n[nH]c5ncc(-c6cncc(CNCc7ccccc7)c6)cc45)nc23)CC1]
756
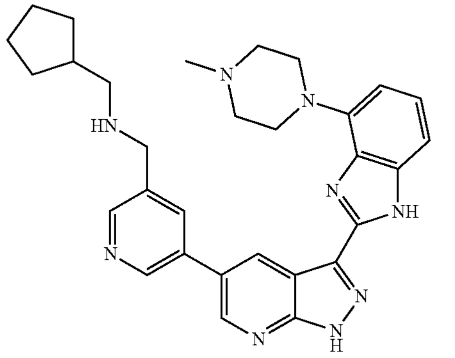
757
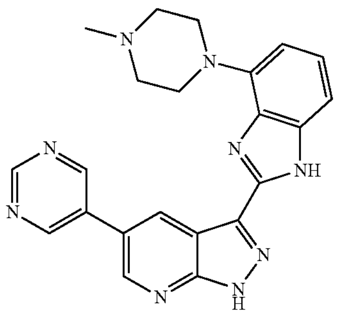 [SMILES: CN1CCN(c2cccc3[nH]c(-c4n[nH]c5ncc(-c6cncnc6)cc45)nc23)CC1]
758
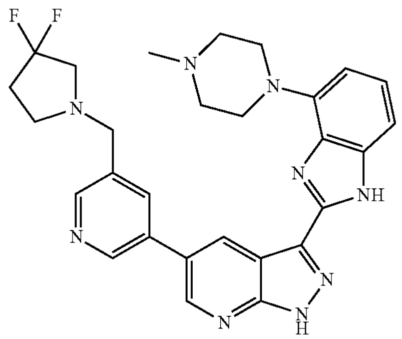 [SMILES: CN1CCN(c2cccc3[nH]c(-c4n[nH]c5ncc(-c6cncc(CN7CCC(F)(F)C7)c6)cc45)nc23)CC1]
759
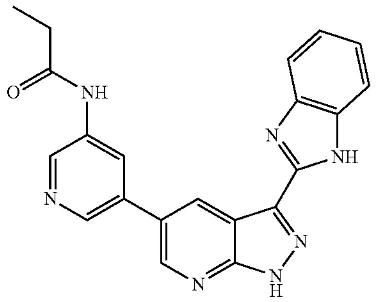 [SMILES: CCC(=O)Nc1cncc(-c2cnc3[nH]nc(-c4nc5ccccc5[nH]4)c3c2)c1]
760
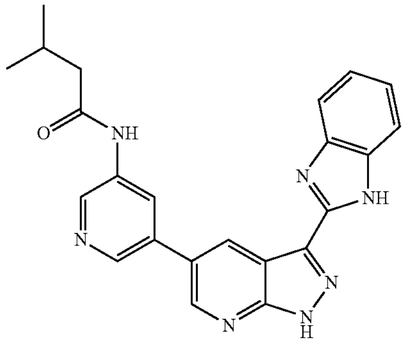 [SMILES: CC(C)CC(=O)Nc1cncc(-c2cnc3[nH]nc(-c4nc5ccccc5[nH]4)c3c2)c1]
761
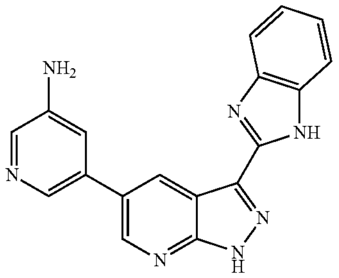
762
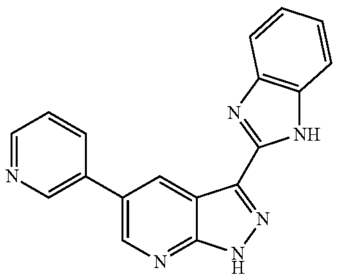

TABLE 1-continued
763
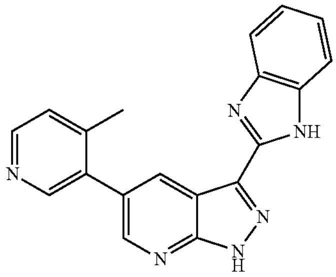 [SMILES: Cc1ccncc1-c1cnc2[nH]nc(-c3nc4ccccc4[nH]3)c2c1]
764
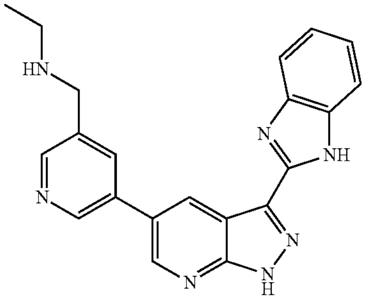 [SMILES: CCNCc1cncc(-c2cnc3[nH]nc(-c4nc5ccccc5[nH]4)c3c2)c1]
765
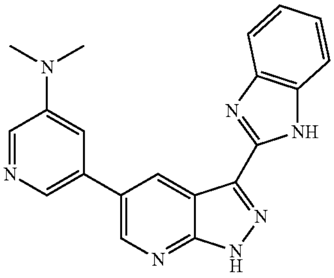 [SMILES: CN(C)c1cncc(-c2cnc3[nH]nc(-c4nc5ccccc5[nH]4)c3c2)c1]
766
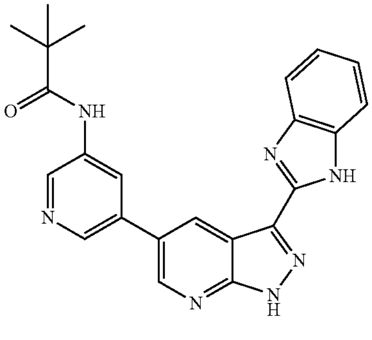 [SMILES: CC(C)(C)C(=O)Nc1cncc(-c2cnc3[nH]nc(-c4nc5ccccc5[nH]4)c3c2)c1]
767
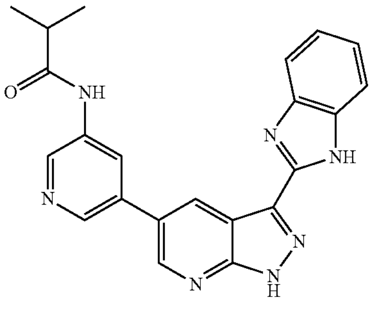 [SMILES: CC(C)C(=O)Nc1cncc(-c2cnc3[nH]nc(-c4nc5ccccc5[nH]4)c3c2)c1]
TABLE 1-continued
768
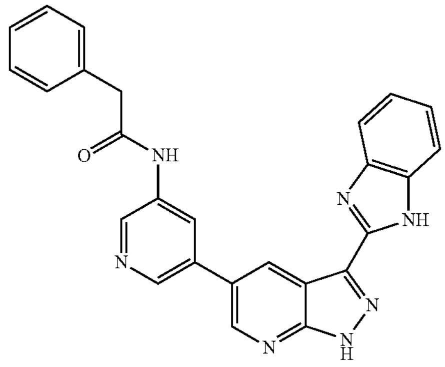
769
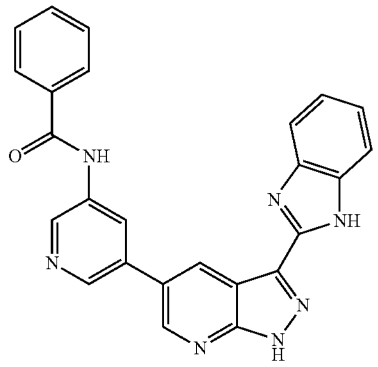 [SMILES: O=C(Nc1cncc(-c2cnc3[nH]nc(-c4nc5ccccc5[nH]4)c3c2)c1)c1ccccc1]
770
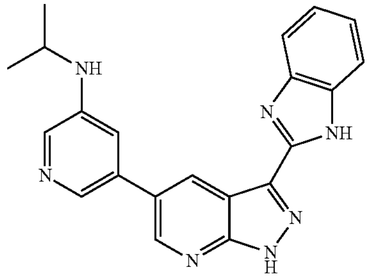 [SMILES: CC(C)Nc1cncc(-c2cnc3[nH]nc(-c4nc5ccccc5[nH]4)c3c2)c1]
771
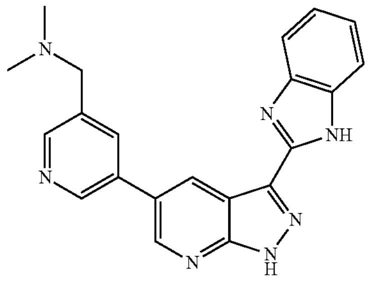 [SMILES: CN(C)Cc1cncc(-c2cnc3[nH]nc(-c4nc5ccccc5[nH]4)c3c2)c1]
772
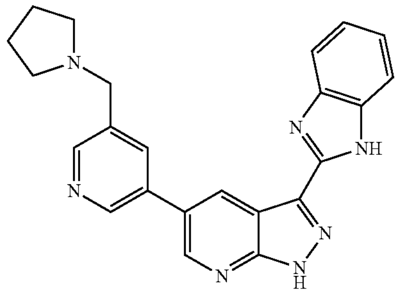 [SMILES: c1ccc2[nH]c(-c3n[nH]c4ncc(-c5cncc(CN6CCCC6)c5)cc34)nc2c1]

TABLE 1-continued
773
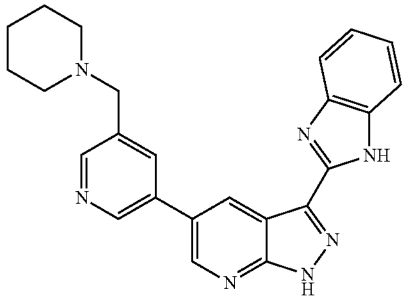 [SMILES: c1ccc2[nH]c(-c3n[nH]c4ncc(-c5cncc(CN6CCCCC6)c5)cc34)nc2c1]
774
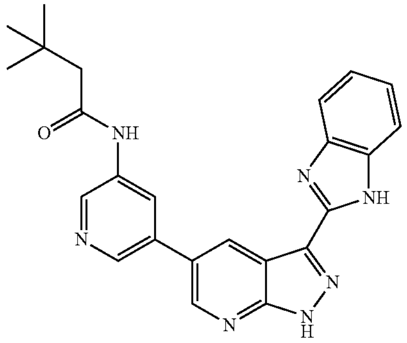 [SMILES: CC(C)(C)CC(=O)Nc1cncc(-c2cnc3[nH]nc(-c4nc5ccccc5[nH]4)c3c2)c1]
775
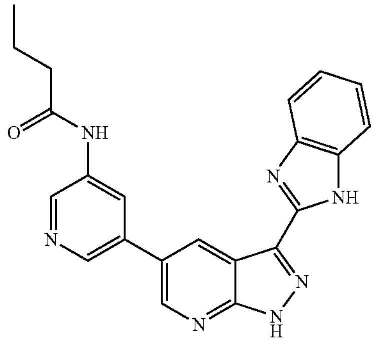 [SMILES: CCCC(=O)Nc1cncc(-c2cnc3[nH]nc(-c4nc5ccccc5[nH]4)c3c2)c1]
776
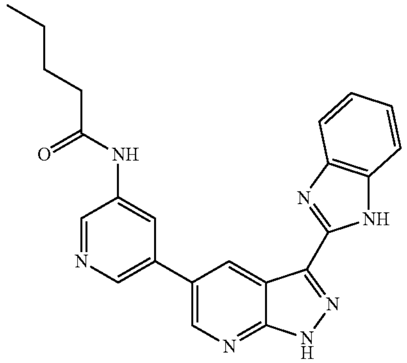 [SMILES: CCCCC(=O)Nc1cncc(-c2cnc3[nH]nc(-c4nc5ccccc5[nH]4)c3c2)c1]
TABLE 1-continued
777
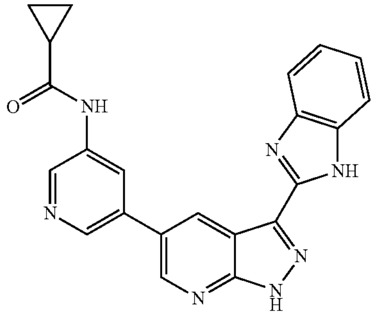 [SMILES: O=C(Nc1cncc(-c2cnc3[nH]nc(-c4nc5ccccc5[nH]4)c3c2)c1)C1CC1]
778
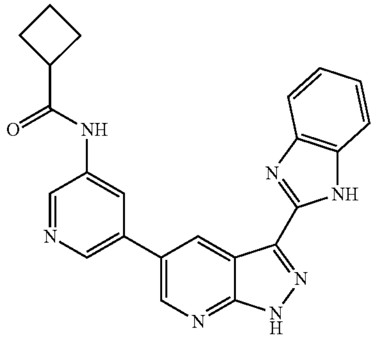 [SMILES: O=C(Nc1cncc(-c2cnc3[nH]nc(-c4nc5ccccc5[nH]4)c3c2)c1)C1CCC1]
779
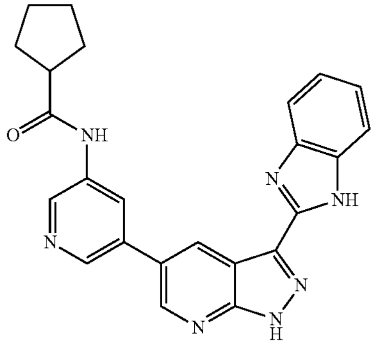 [SMILES: O=C(Nc1cncc(-c2cnc3[nH]nc(-c4nc5ccccc5[nH]4)c3c2)c1)C1CCCC1]
780
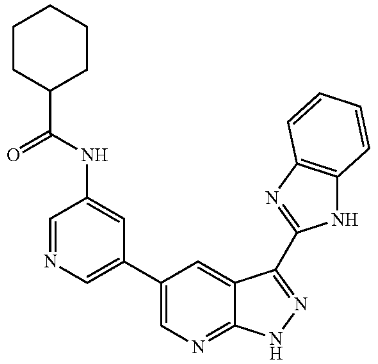 [SMILES: O=C(Nc1cncc(-c2cnc3[nH]nc(-c4nc5ccccc5[nH]4)c3c2)c1)C1CCCCC1]

TABLE 1-continued
781
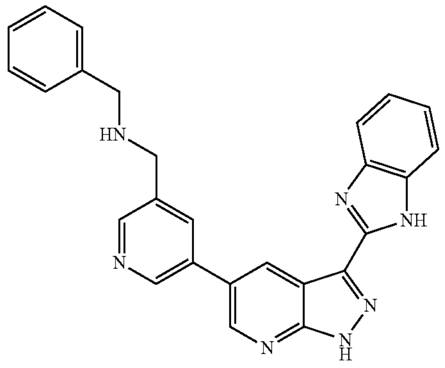 [SMILES: c1ccc(CNCc2cncc(-c3cnc4[nH]nc(-c5nc6ccccc6[nH]5)c4c3)c2)cc1]
782
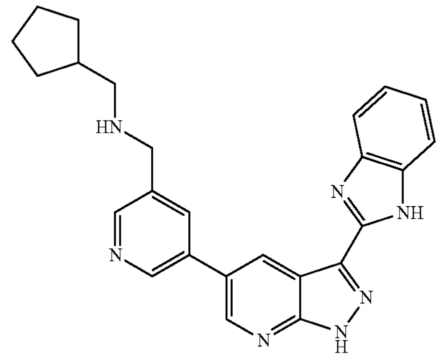 [SMILES: c1ccc2[nH]c(-c3n[nH]c4ncc(-c5cncc(CNCC6CCCC6)c5)cc34)nc2c1]
783
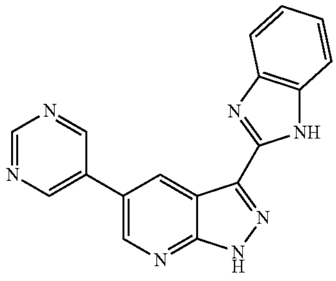 [SMILES: c1ccc2[nH]c(-c3n[nH]c4ncc(-c5cncnc5)cc34)nc2c1]
784
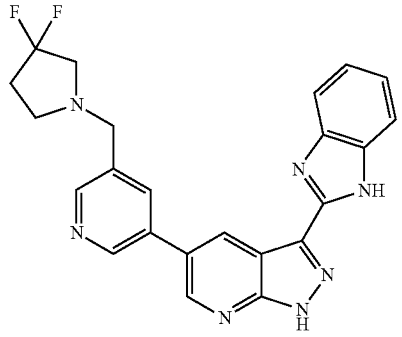 [SMILES: FC1(F)CCN(Cc2cncc(-c3cnc4[nH]nc(-c5nc6ccccc6[nH]5)c4c3)c2)C1]
TABLE 1-continued
785
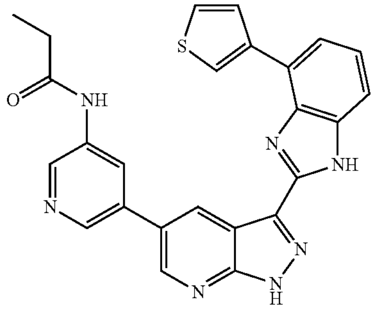 [SMILES: CCC(=O)Nc1cncc(-c2cnc3[nH]nc(-c4nc5c(-c6ccsc6)cccc5[nH]4)c3c2)c1]
786
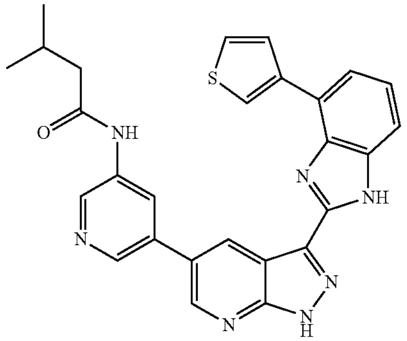 [SMILES: CC(C)CC(=O)Nc1cncc(-c2cnc3[nH]nc(-c4nc5c(-c6ccsc6)cccc5[nH]4)c3c2)c1]
787
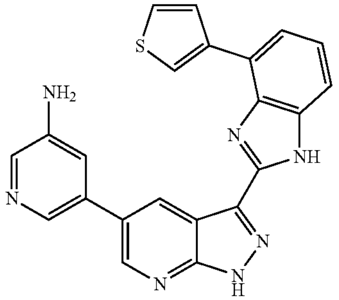 [SMILES: Nc1cncc(-c2cnc3[nH]nc(-c4nc5c(-c6ccsc6)cccc5[nH]4)c3c2)c1]
788
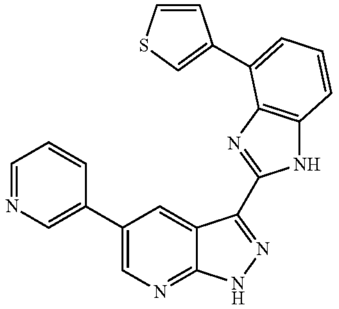
789
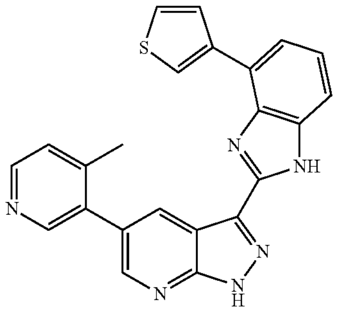 [SMILES: Cc1ccncc1-c1cnc2[nH]nc(-c3nc4c(-c5ccsc5)cccc4[nH]3)c2c1]

TABLE 1-continued
790
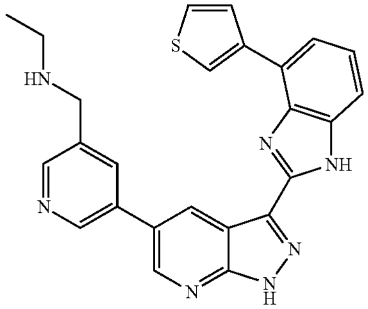
791
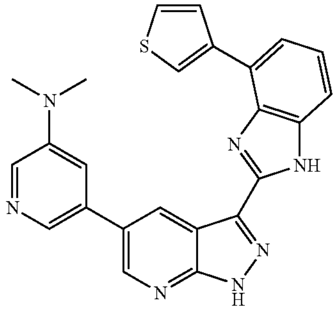 [SMILES: CN(C)c1cncc(-c2cnc3[nH]nc(-c4nc5c(-c6ccsc6)cccc5[nH]4)c3c2)c1]
792
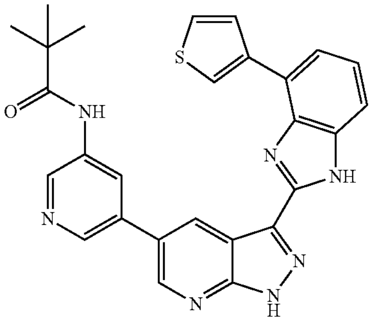
793
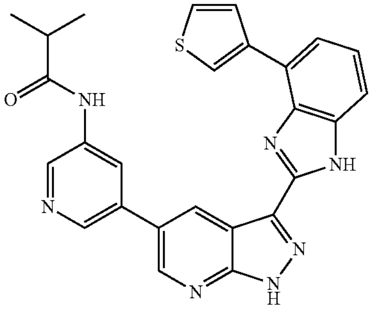 [SMILES: CC(C)C(=O)Nc1cncc(-c2cnc3[nH]nc(-c4nc5c(-c6ccsc6)cccc5[nH]4)c3c2)c1]
794
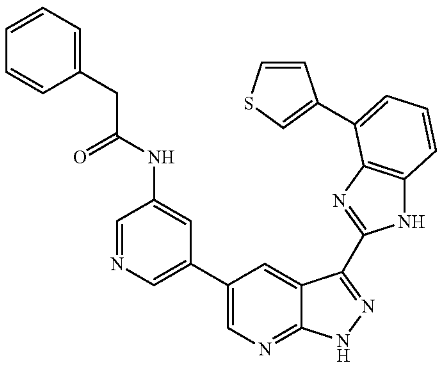 [SMILES: O=C(Cc1ccccc1)Nc1cncc(-c2cnc3[nH]nc(-c4nc5c(-c6ccsc6)cccc5[nH]4)c3c2)c1]
TABLE 1-continued
795
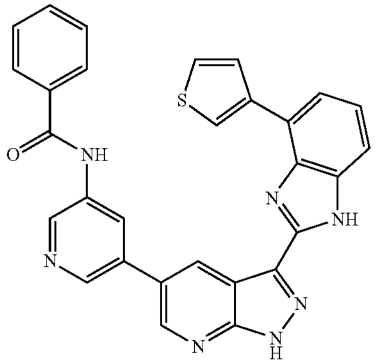 [SMILES: O=C(Nc1cncc(-c2cnc3[nH]nc(-c4nc5c(-c6ccsc6)cccc5[nH]4)c3c2)c1)c1ccccc1]
796
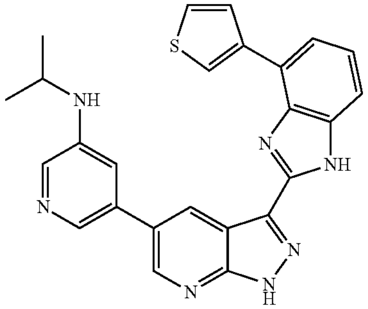
797
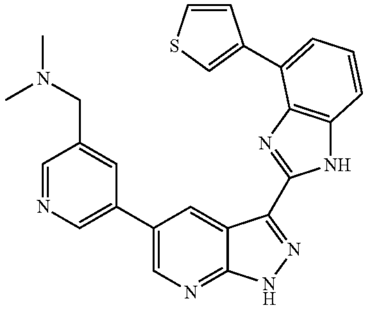 [SMILES: CN(C)Cc1cncc(-c2cnc3[nH]nc(-c4nc5c(-c6ccsc6)cccc5[nH]4)c3c2)c1]
798
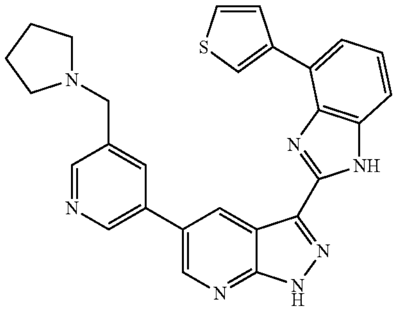
799
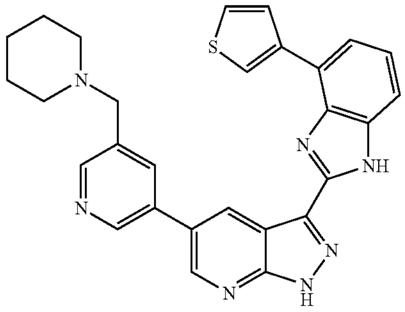

TABLE 1-continued
800
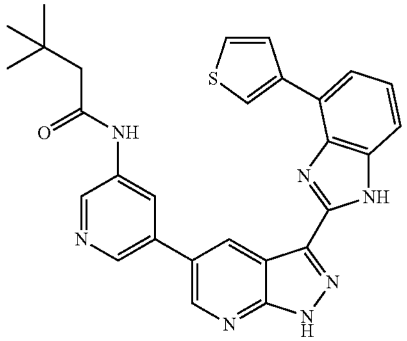 [SMILES: CC(C)(C)CC(=O)Nc1cncc(-c2cnc3[nH]nc(-c4nc5c(-c6ccsc6)cccc5[nH]4)c3c2)c1]
801
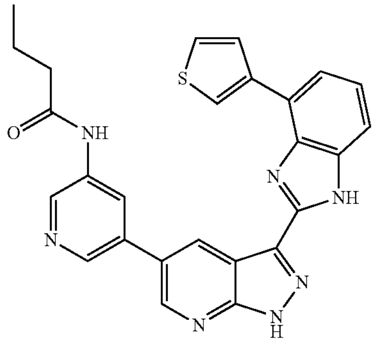
802
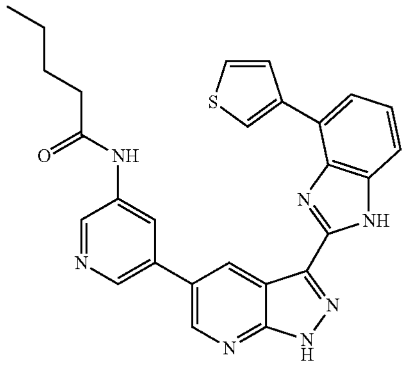 [SMILES: CCCCC(=O)Nc1cncc(-c2cnc3[nH]nc(-c4nc5c(-c6ccsc6)cccc5[nH]4)c3c2)c1]
803
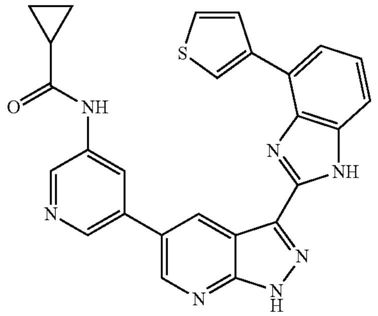 [SMILES: O=C(Nc1cncc(-c2cnc3[nH]nc(-c4nc5c(-c6ccsc6)cccc5[nH]4)c3c2)c1)C1CC1]
TABLE 1-continued
804
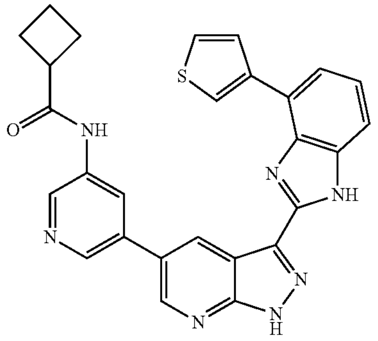
805
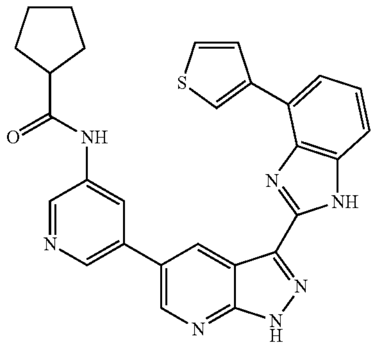
806
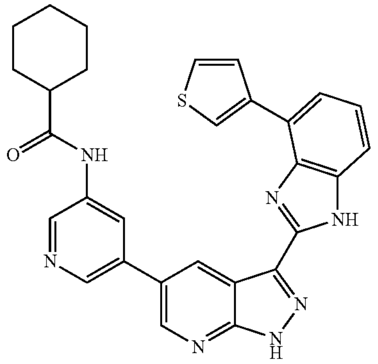 [SMILES: O=C(Nc1cncc(-c2cnc3[nH]nc(-c4nc5c(-c6ccsc6)cccc5[nH]4)c3c2)c1)C1CCCCC1]
807
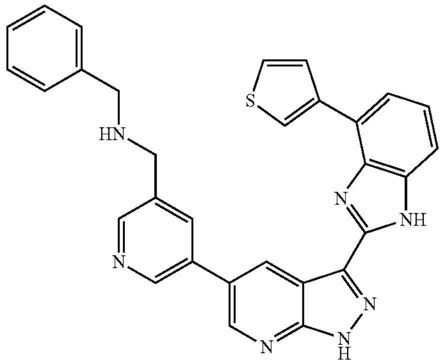 [SMILES: c1ccc(CNCc2cncc(-c3cnc4[nH]nc(-c5nc6c(-c7ccsc7)cccc6[nH]5)c4c3)c2)cc1]

TABLE 1-continued
808
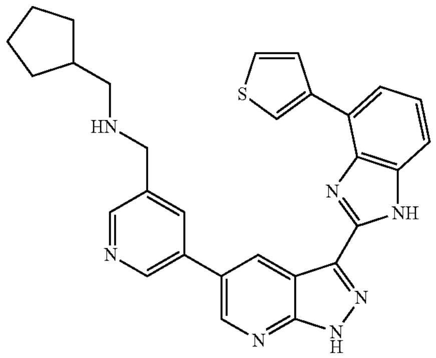
809
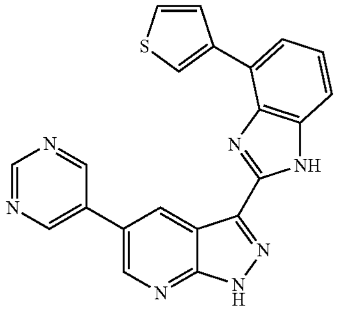
810
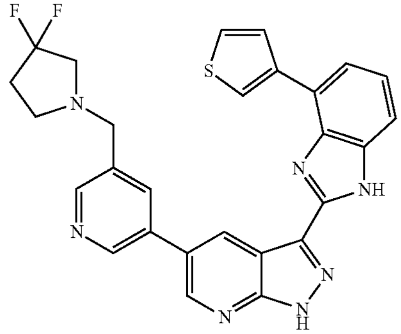 [SMILES: FC1(F)CCN(Cc2cncc(-c3cnc4[nH]nc(-c5nc6c(-c7ccsc7)cccc6[nH]5)c4c3)c2)C1]
811
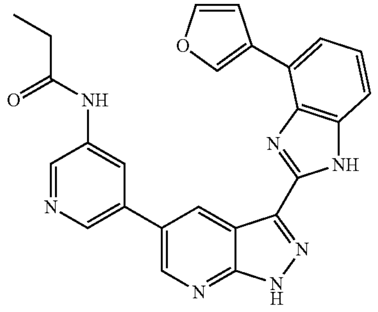
TABLE 1-continued
812
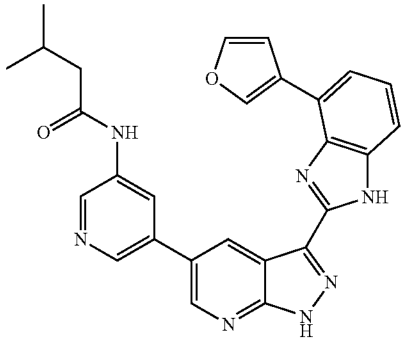 [SMILES: CC(C)CC(=O)Nc1cncc(-c2cnc3[nH]nc(-c4nc5c(-c6ccoc6)cccc5[nH]4)c3c2)c1]
813
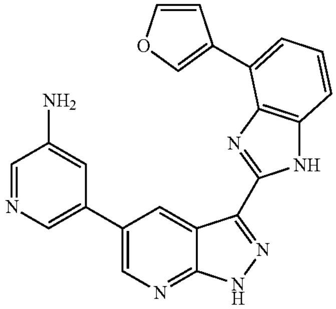 [SMILES: Nc1cncc(-c2cnc3[nH]nc(-c4nc5c(-c6ccoc6)cccc5[nH]4)c3c2)c1]
814
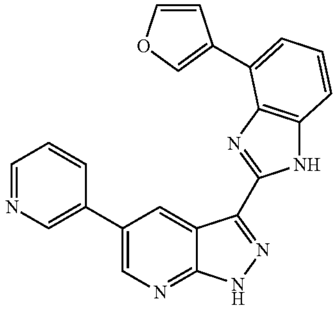
815
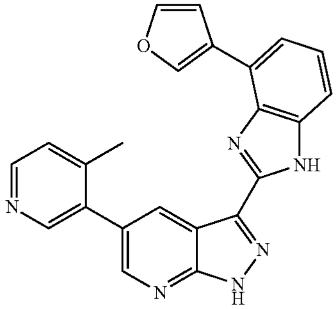
816
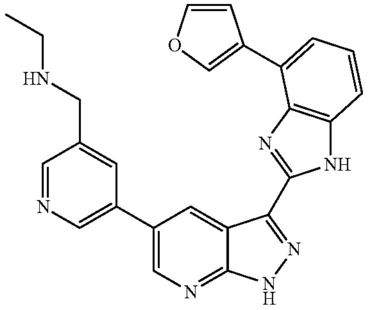 [SMILES: CCNCc1cncc(-c2cnc3[nH]nc(-c4nc5c(-c6ccoc6)cccc5[nH]4)c3c2)c1]

TABLE 1-continued
817
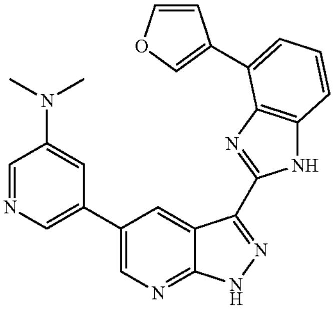
818
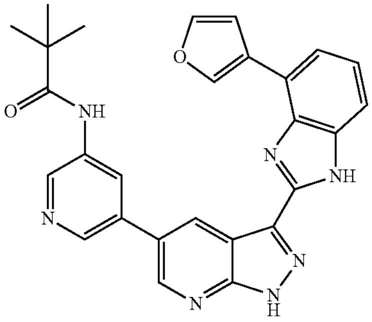 [SMILES: CC(C)(C)C(=O)Nc1cncc(-c2cnc3[nH]nc(-c4nc5c(-c6ccoc6)cccc5[nH]4)c3c2)c1]
819
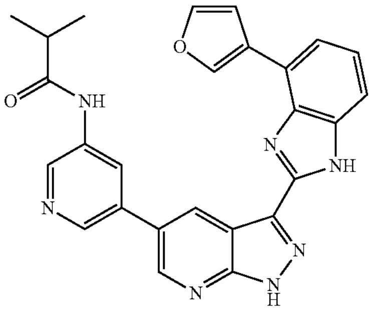
820
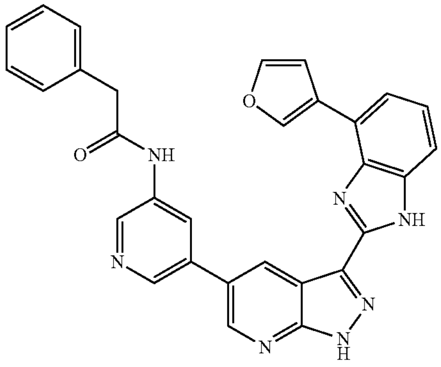 [SMILES: O=C(Cc1ccccc1)Nc1cncc(-c2cnc3[nH]nc(-c4nc5c(-c6ccoc6)cccc5[nH]4)c3c2)c1]
TABLE 1-continued
821
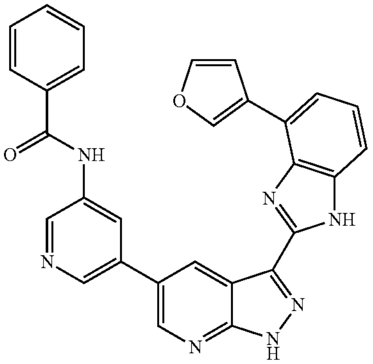
822
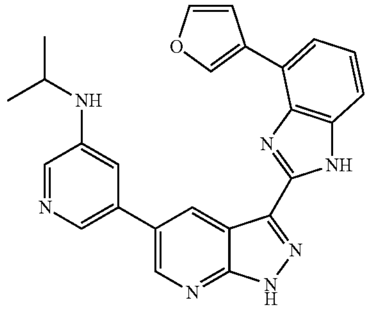 [SMILES: CC(C)Nc1cncc(-c2cnc3[nH]nc(-c4nc5c(-c6ccoc6)cccc5[nH]4)c3c2)c1]
823
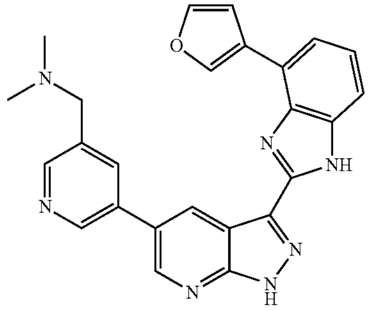
824
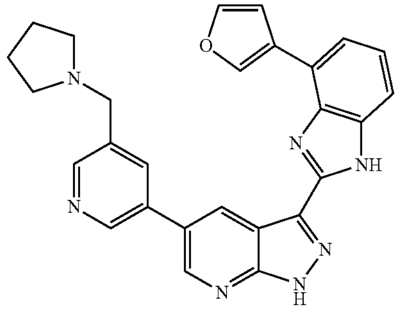 [SMILES: c1cc(-c2ccoc2)c2nc(-c3n[nH]c4ncc(-c5cncc(CN6CCCC6)c5)cc34)[nH]c2c1]
825
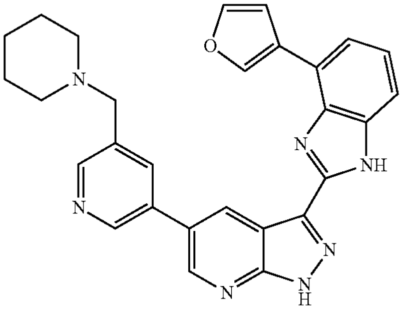 [SMILES: c1cc(-c2ccoc2)c2nc(-c3n[nH]c4ncc(-c5cncc(CN6CCCCC6)c5)cc34)[nH]c2c1]

TABLE 1-continued
826
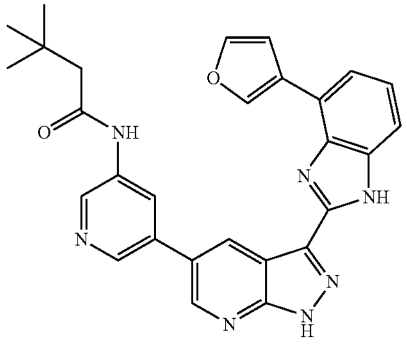 [SMILES: CC(C)(C)CC(=O)Nc1cncc(-c2cnc3[nH]nc(-c4nc5c(-c6ccoc6)cccc5[nH]4)c3c2)c1]
827
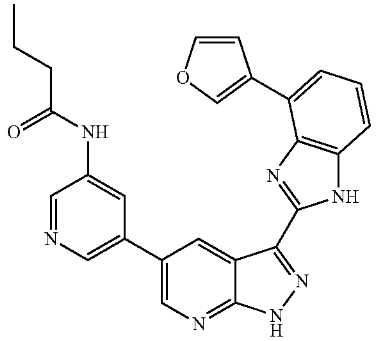 [SMILES: CCCC(=O)Nc1cncc(-c2cnc3[nH]nc(-c4nc5c(-c6ccoc6)cccc5[nH]4)c3c2)c1]
828
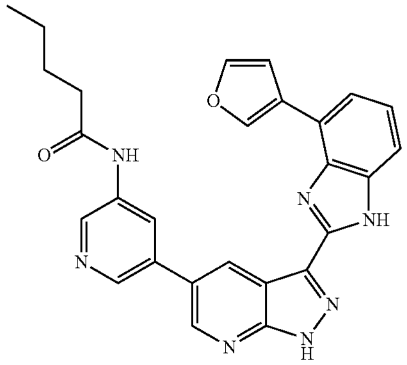 [SMILES: CCCCC(=O)Nc1cncc(-c2cnc3[nH]nc(-c4nc5c(-c6ccoc6)cccc5[nH]4)c3c2)c1]
829
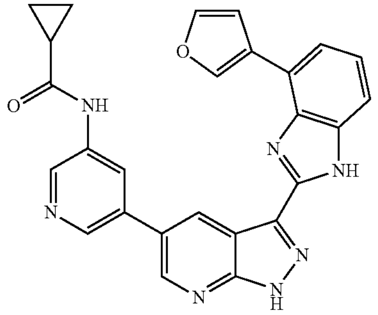 [SMILES: O=C(Nc1cncc(-c2cnc3[nH]nc(-c4nc5c(-c6ccoc6)cccc5[nH]4)c3c2)c1)C1CC1]
TABLE 1-continued
830
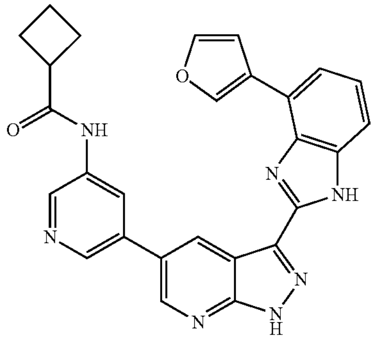 [SMILES: O=C(Nc1cncc(-c2cnc3[nH]nc(-c4nc5c(-c6ccoc6)cccc5[nH]4)c3c2)c1)C1CCC1]
831
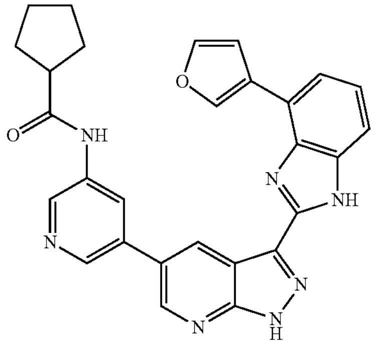 [SMILES: O=C(Nc1cncc(-c2cnc3[nH]nc(-c4nc5c(-c6ccoc6)cccc5[nH]4)c3c2)c1)C1CCCC1]
832
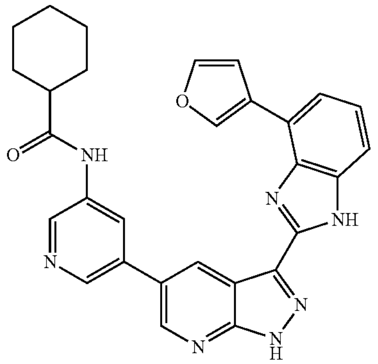 [SMILES: O=C(Nc1cncc(-c2cnc3[nH]nc(-c4nc5c(-c6ccoc6)cccc5[nH]4)c3c2)c1)C1CCCCC1]
833
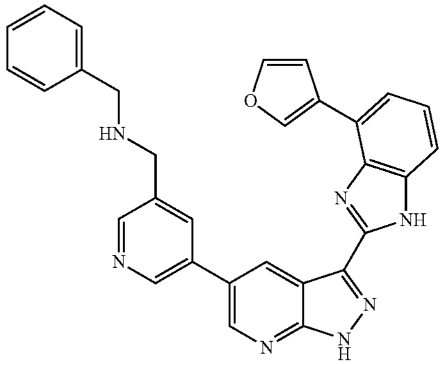 [SMILES: c1ccc(CNCc2cncc(-c3cnc4[nH]nc(-c5nc6c(-c7ccoc7)cccc6[nH]5)c4c3)c2)cc1]

TABLE 1-continued
834
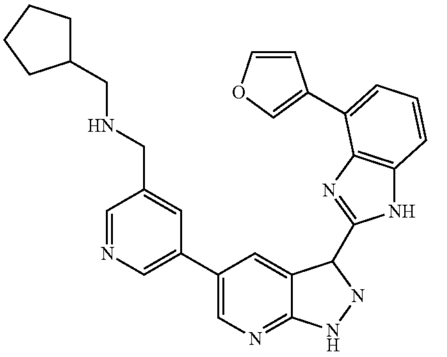 [SMILES: c1cc(-c2ccoc2)c2nc(C3NNc4ncc(-c5cncc(CNCC6CCCC6)c5)cc43)[nH]c2c1]
835
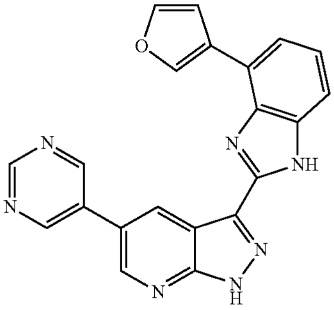 [SMILES: c1cc(-c2ccoc2)c2nc(-c3n[nH]c4ncc(-c5cncnc5)cc34)[nH]c2c1]
836
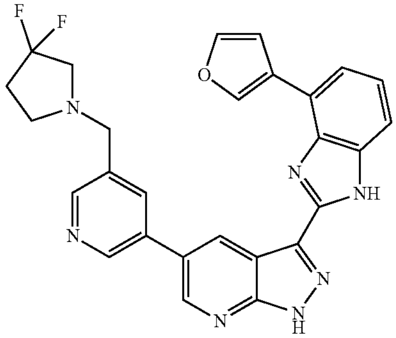 [SMILES: FC1(F)CCN(Cc2cncc(-c3cnc4[nH]nc(-c5nc6c(-c7ccoc7)cccc6[nH]5)c4c3)c2)C1]
837
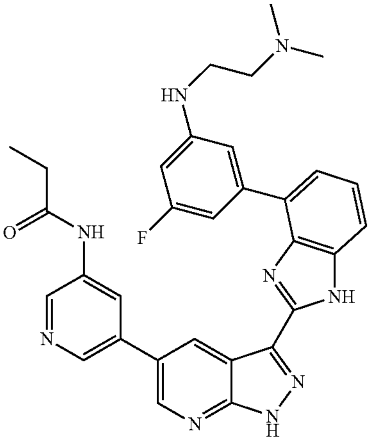 [SMILES: CCC(=O)Nc1cncc(-c2cnc3[nH]nc(-c4nc5c(-c6cc(F)cc(NCCN(C)C)c6)cccc5[nH]4)c3c2)c1]
TABLE 1-continued
838
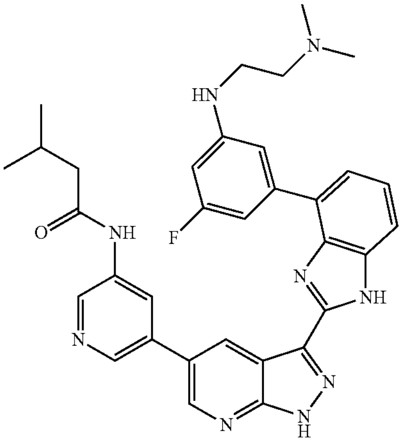 [SMILES: CC(C)CC(=O)Nc1cncc(-c2cnc3[nH]nc(-c4nc5c(-c6cc(F)cc(NCCN(C)C)c6)cccc5[nH]4)c3c2)c1]
839
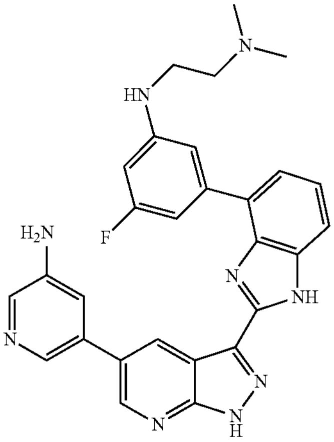
840
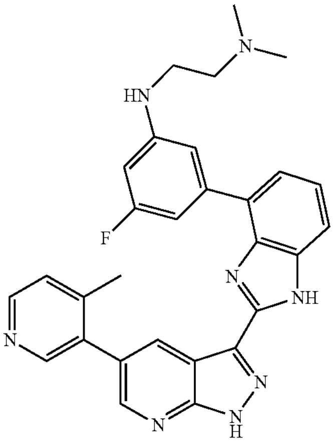 [SMILES: Cc1ccncc1-c1cnc2[nH]nc(-c3nc4c(-c5cc(F)cc(NCCN(C)C)c5)cccc4[nH]3)c2c1]

841
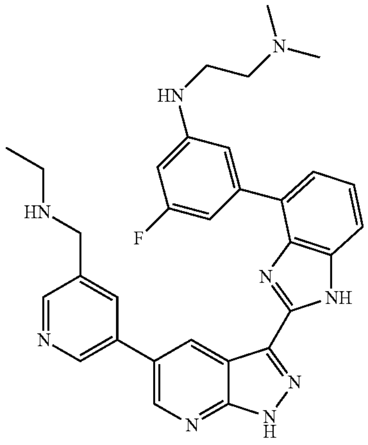 [SMILES: CCNCc1cncc(-c2cnc3[nH]nc(-c4nc5c(-c6cc(F)cc(NCCN(C)C)c6)cccc5[nH]4)c3c2)c1]
842
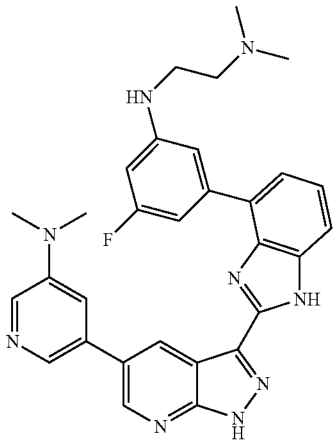 [SMILES: CN(C)CCNc1cc(F)cc(-c2cccc3[nH]c(-c4n[nH]c5ncc(-c6cncc(N(C)C)c6)cc45)nc23)c1]
843
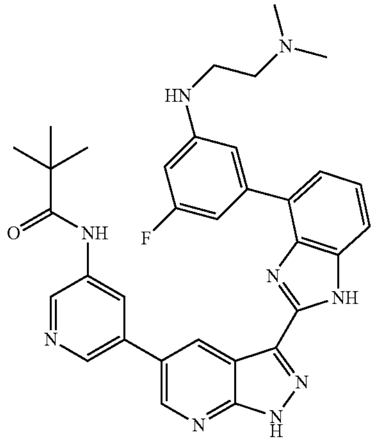 [SMILES: CN(C)CCNc1cc(F)cc(-c2cccc3[nH]c(-c4n[nH]c5ncc(-c6cncc(NC(=O)C(C)(C)C)c6)cc45)nc23)c1]
844
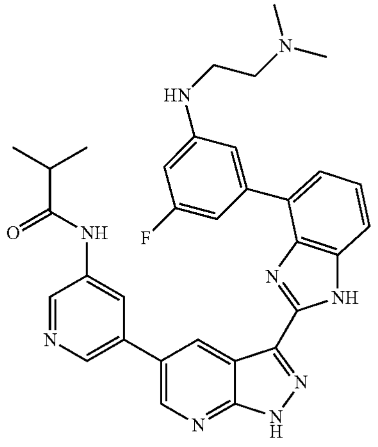 [SMILES: CC(C)C(=O)Nc1cncc(-c2cnc3[nH]nc(-c4nc5c(-c6cc(F)cc(NCCN(C)C)c6)cccc5[nH]4)c3c2)c1]
845
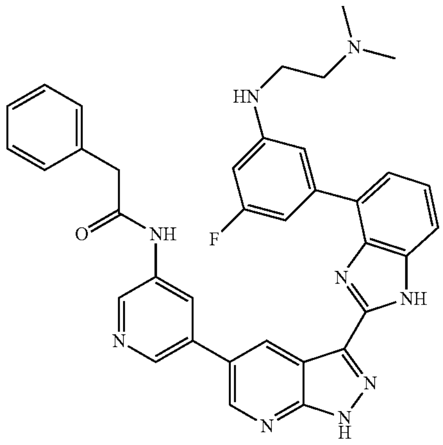 [SMILES: CN(C)CCNc1cc(F)cc(-c2cccc3[nH]c(-c4n[nH]c5ncc(-c6cncc(NC(=O)Cc7ccccc7)c6)cc45)nc23)c1]
846
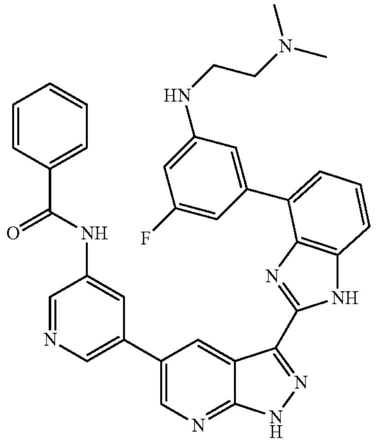 [SMILES: CN(C)CCNc1cc(F)cc(-c2cccc3[nH]c(-c4n[nH]c5ncc(-c6cncc(NC(=O)c7ccccc7)c6)cc45)nc23)c1]

TABLE 1-continued
847
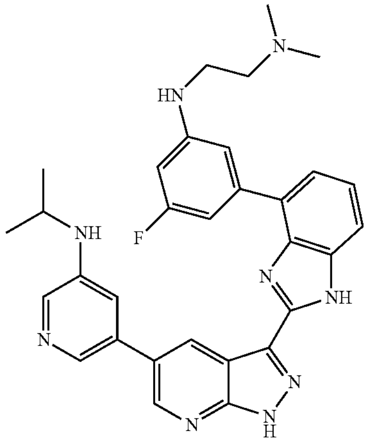 [SMILES: CC(C)Nc1cncc(-c2cnc3[nH]nc(-c4nc5c(-c6cc(F)cc(NCCN(C)C)c6)cccc5[nH]4)c3c2)c1]
848
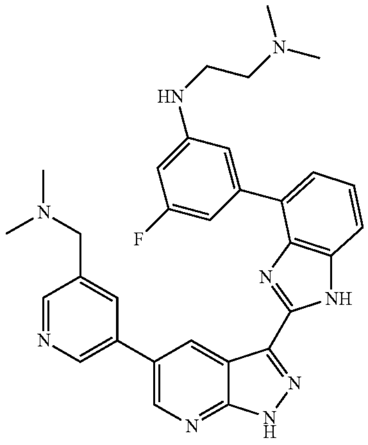 [SMILES: CN(C)CCNc1cc(F)cc(-c2cccc3[nH]c(-c4n[nH]c5ncc(-c6cncc(CN(C)C)c6)cc45)nc23)c1]
849
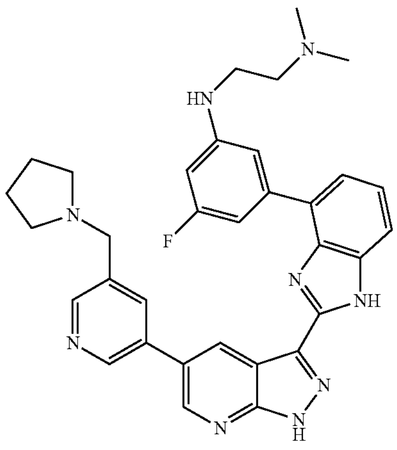 [SMILES: CN(C)CCNc1cc(F)cc(-c2cccc3[nH]c(-c4n[nH]c5ncc(-c6cncc(CN7CCCC7)c6)cc45)nc23)c1]
TABLE 1-continued
850
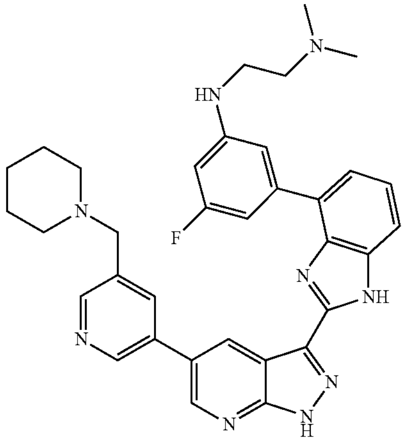 [SMILES: CN(C)CCNc1cc(F)cc(-c2cccc3[nH]c(-c4n[nH]c5ncc(-c6cncc(CN7CCCCC7)c6)cc45)nc23)c1]
851
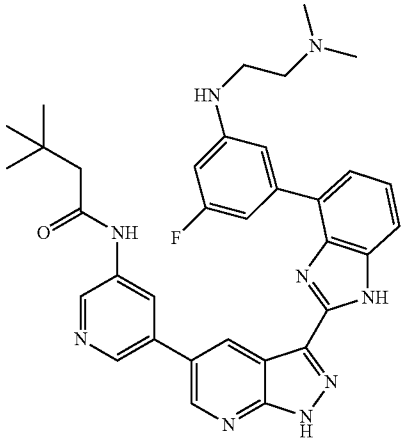
852
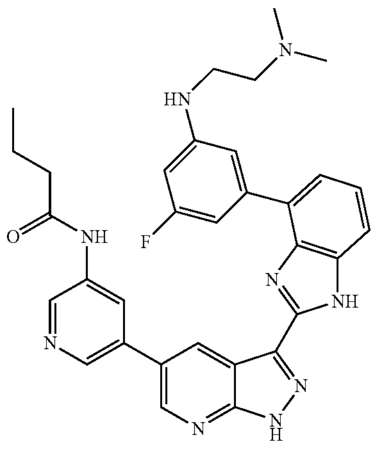 [SMILES: CCCC(=O)Nc1cncc(-c2cnc3[nH]nc(-c4nc5c(-c6cc(F)cc(NCCN(C)C)c6)cccc5[nH]4)c3c2)c1]

TABLE 1-continued
853
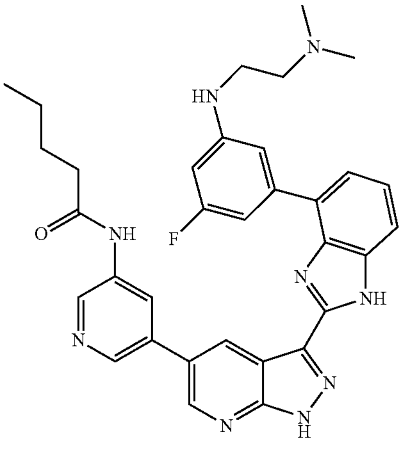 [SMILES: CCCCC(=O)Nc1cncc(-c2cnc3[nH]nc(-c4nc5c(-c6cc(F)cc(NCCN(C)C)c6)cccc5[nH]4)c3c2)c1]
854
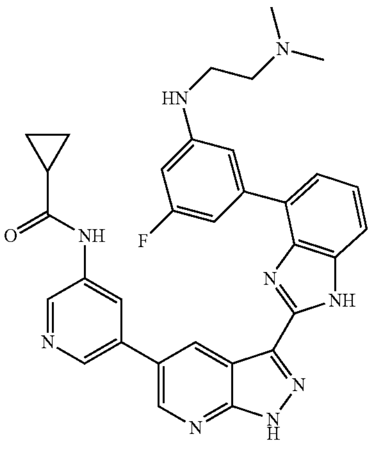 [SMILES: CN(C)CCNc1cc(F)cc(-c2cccc3[nH]c(-c4n[nH]c5ncc(-c6cncc(NC(=O)C7CC7)c6)cc45)nc23)c1]
855
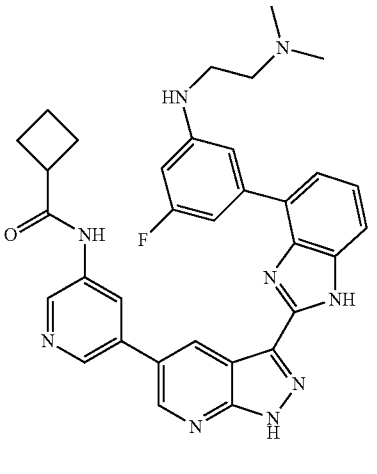 [SMILES: CN(C)CCNc1cc(F)cc(-c2cccc3[nH]c(-c4n[nH]c5ncc(-c6cncc(NC(=O)C7CCC7)c6)cc45)nc23)c1]
TABLE 1-continued
856
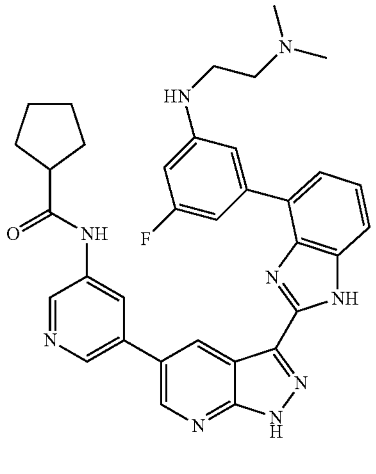
857
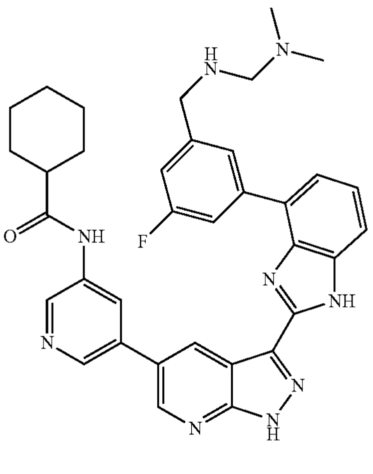 [SMILES: CN(C)CNCc1cc(F)cc(-c2cccc3[nH]c(-c4n[nH]c5ncc(-c6cncc(NC(=O)C7CCCCC7)c6)cc45)nc23)c1]
858
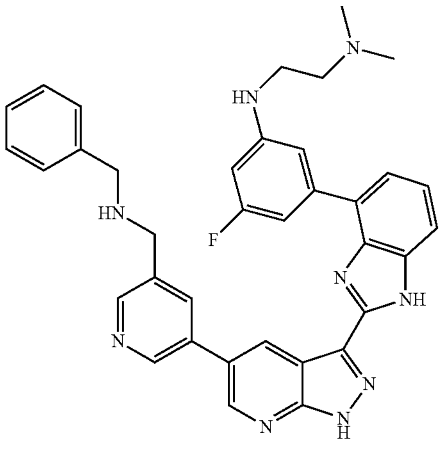 [SMILES: CN(C)CCNc1cc(F)cc(-c2cccc3[nH]c(-c4n[nH]c5ncc(-c6cncc(CNCc7ccccc7)c6)cc45)nc23)c1]

TABLE 1-continued
859
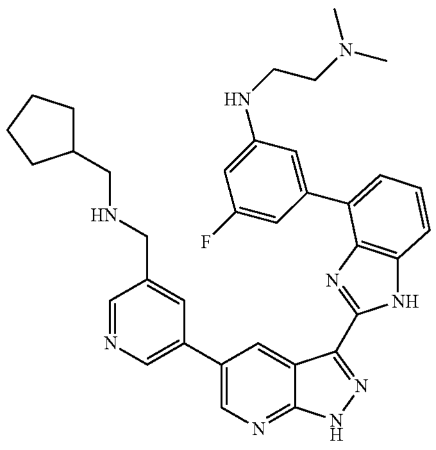 [SMILES: CN(C)CCNc1cc(F)cc(-c2cccc3[nH]c(-c4n[nH]c5ncc(-c6cncc(CNCC7CCCC7)c6)cc45)nc23)c1]
860
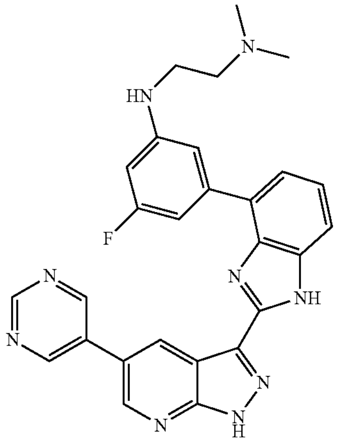 [SMILES: CN(C)CCNc1cc(F)cc(-c2cccc3[nH]c(-c4n[nH]c5ncc(-c6cncnc6)cc45)nc23)c1]
861
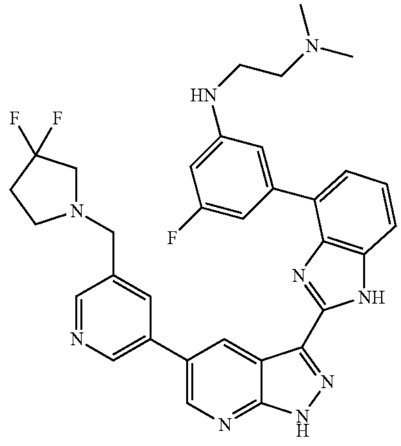 [SMILES: CN(C)CCNc1cc(F)cc(-c2cccc3[nH]c(-c4n[nH]c5ncc(-c6cncc(CN7CCC(F)(F)C7)c6)cc45)nc23)c1]
TABLE 1-continued
862
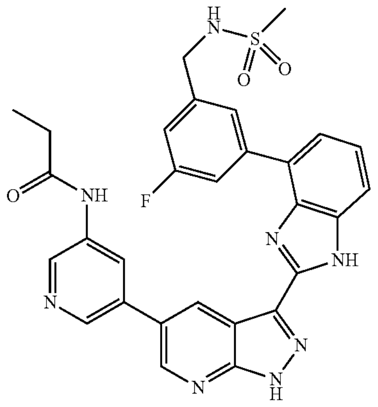 [SMILES: CCC(=O)Nc1cncc(-c2cnc3[nH]nc(-c4nc5c(-c6cc(F)cc(CNS(C)(=O)=O)c6)cccc5[nH]4)c3c2)c1]
863
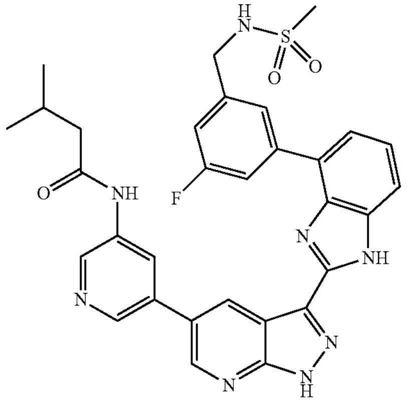 [SMILES: CC(C)CC(=O)Nc1cncc(-c2cnc3[nH]nc(-c4nc5c(-c6cc(F)cc(CNS(C)(=O)=O)c6)cccc5[nH]4)c3c2)c1]
864
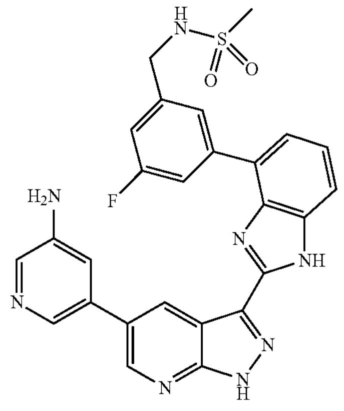 [SMILES: CS(=O)(=O)NCc1cc(F)cc(-c2cccc3[nH]c(-c4n[nH]c5ncc(-c6cncc(N)c6)cc45)nc23)c1]
865
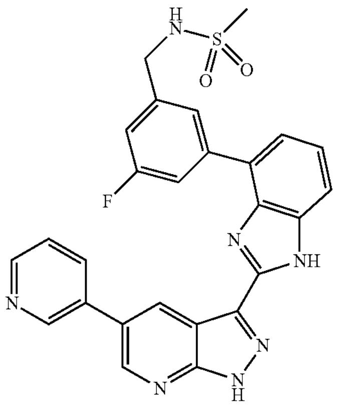 [SMILES: CS(=O)(=O)NCc1cc(F)cc(-c2cccc3[nH]c(-c4n[nH]c5ncc(-c6cccnc6)cc45)nc23)c1]

TABLE 1-continued
866
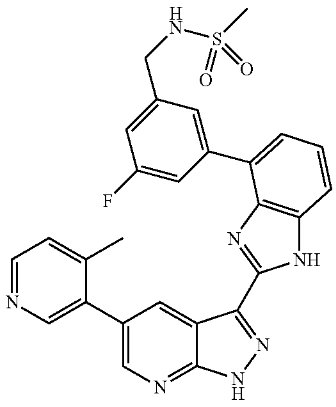 [SMILES: Cc1ccncc1-c1cnc2[nH]nc(-c3nc4c(-c5cc(F)cc(CNS(C)(=O)=O)c5)cccc4[nH]3)c2c1]
867
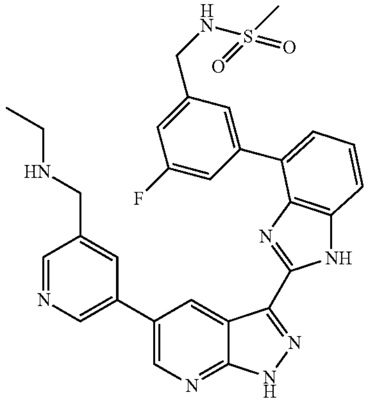 [SMILES: CCNCc1cncc(-c2cnc3[nH]nc(-c4nc5c(-c6cc(F)cc(CNS(C)(=O)=O)c6)cccc5[nH]4)c3c2)c1]
868
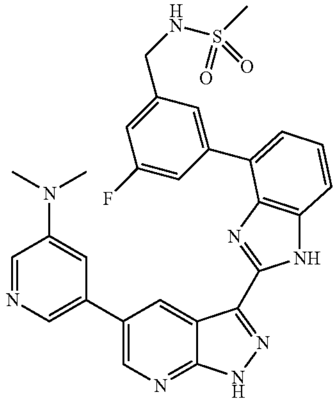 [SMILES: CN(C)c1cncc(-c2cnc3[nH]nc(-c4nc5c(-c6cc(F)cc(CNS(C)(=O)=O)c6)cccc5[nH]4)c3c2)c1]
869
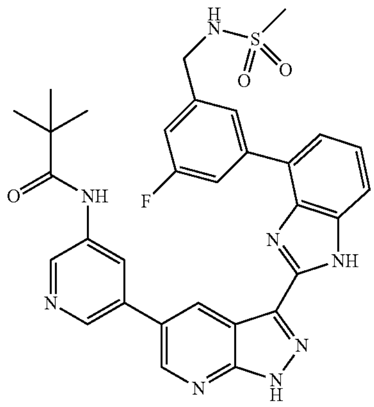 [SMILES: CC(C)(C)C(=O)Nc1cncc(-c2cnc3[nH]nc(-c4nc5c(-c6cc(F)cc(CNS(C)(=O)=O)c6)cccc5[nH]4)c3c2)c1]
TABLE 1-continued
870
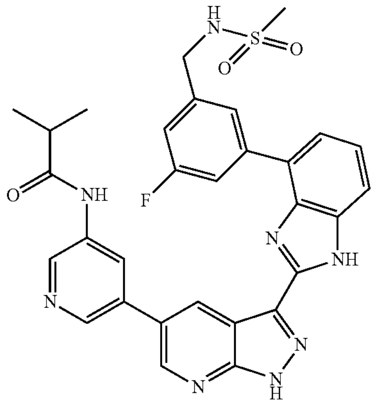 [SMILES: CC(C)C(=O)Nc1cncc(-c2cnc3[nH]nc(-c4nc5c(-c6cc(F)cc(CNS(C)(=O)=O)c6)cccc5[nH]4)c3c2)c1]
871
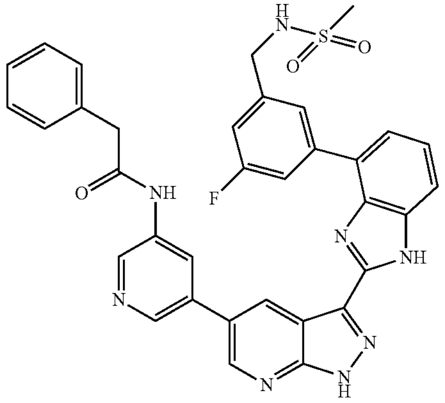 [SMILES: CS(=O)(=O)NCc1cc(F)cc(-c2cccc3[nH]c(-c4n[nH]c5ncc(-c6cncc(NC(=O)Cc7ccccc7)c6)cc45)nc23)c1]
872
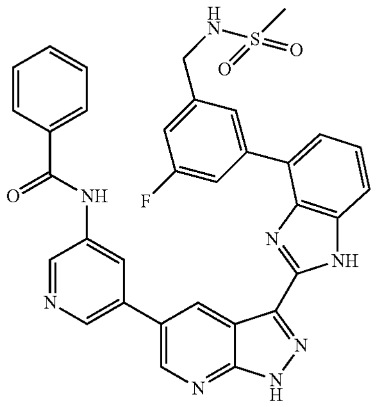 [SMILES: CS(=O)(=O)NCc1cc(F)cc(-c2cccc3[nH]c(-c4n[nH]c5ncc(-c6cncc(NC(=O)c7ccccc7)c6)cc45)nc23)c1]
873
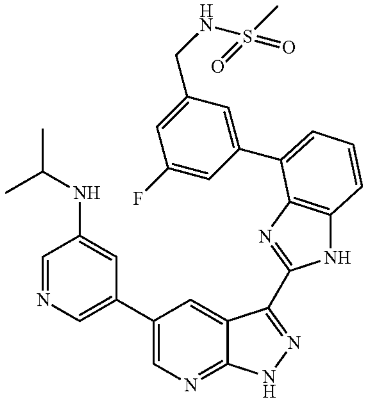 [SMILES: CC(C)Nc1cncc(-c2cnc3[nH]nc(-c4nc5c(-c6cc(F)cc(CNS(C)(=O)=O)c6)cccc5[nH]4)c3c2)c1]

TABLE 1-continued
874
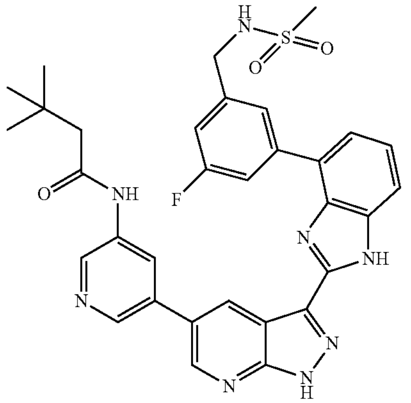 [SMILES: CC(C)(C)CC(=O)Nc1cncc(-c2cnc3[nH]nc(-c4nc5c(-c6cc(F)cc(CNS(C)(=O)=O)c6)cccc5[nH]4)c3c2)c1]
875
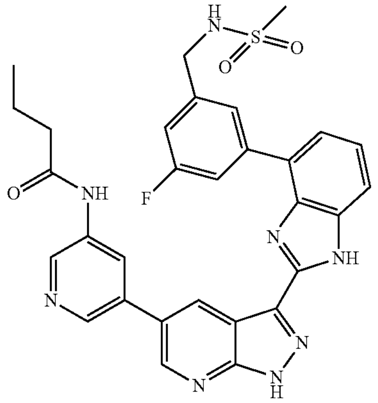 [SMILES: CCCC(=O)Nc1cncc(-c2cnc3[nH]nc(-c4nc5c(-c6cc(F)cc(CNS(C)(=O)=O)c6)cccc5[nH]4)c3c2)c1]
876
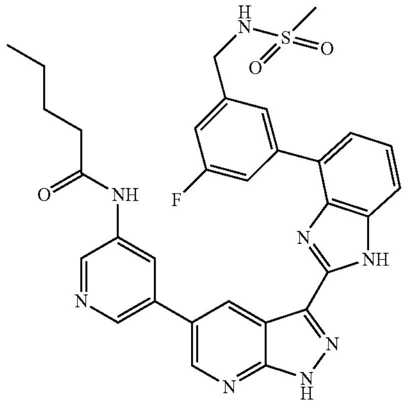 [SMILES: CCCCC(=O)Nc1cncc(-c2cnc3[nH]nc(-c4nc5c(-c6cc(F)cc(CNS(C)(=O)=O)c6)cccc5[nH]4)c3c2)c1]
877
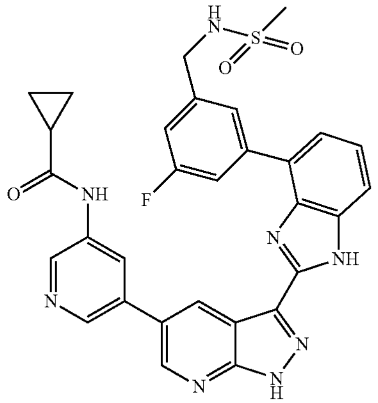 [SMILES: CS(=O)(=O)NCc1cc(F)cc(-c2cccc3[nH]c(-c4n[nH]c5ncc(-c6cncc(NC(=O)C7CC7)c6)cc45)nc23)c1]
TABLE 1-continued
878
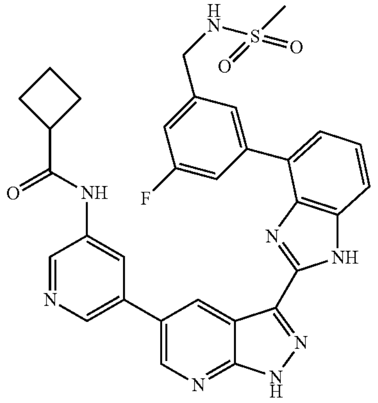 [SMILES: CS(=O)(=O)NCc1cc(F)cc(-c2cccc3[nH]c(-c4n[nH]c5ncc(-c6cncc(NC(=O)C7CCC7)c6)cc45)nc23)c1]
879
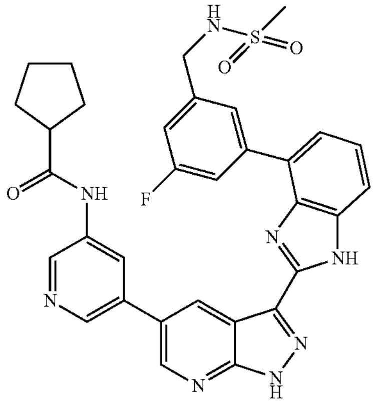 [SMILES: CS(=O)(=O)NCc1cc(F)cc(-c2cccc3[nH]c(-c4n[nH]c5ncc(-c6cncc(NC(=O)C7CCCC7)c6)cc45)nc23)c1]
880
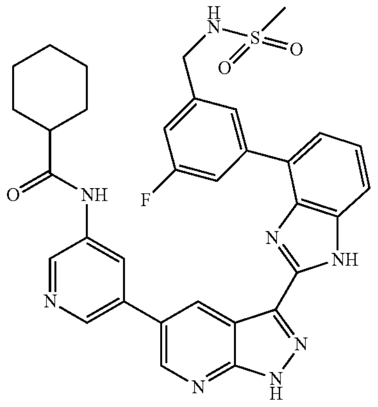 [SMILES: CS(=O)(=O)NCc1cc(F)cc(-c2cccc3[nH]c(-c4n[nH]c5ncc(-c6cncc(NC(=O)C7CCCCC7)c6)cc45)nc23)c1]
881
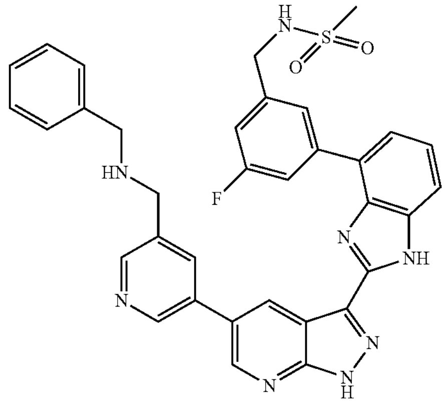 [SMILES: CS(=O)(=O)NCc1cc(F)cc(-c2cccc3[nH]c(-c4n[nH]c5ncc(-c6cncc(CNCc7ccccc7)c6)cc45)nc23)c1]

TABLE 1-continued
882
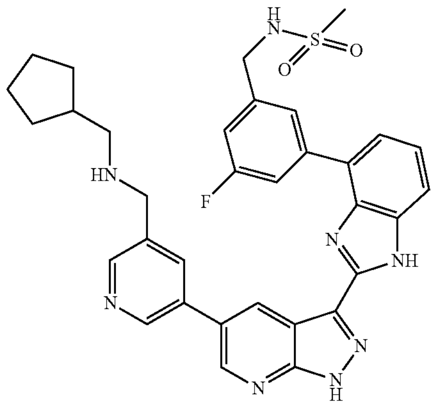 [SMILES: CS(=O)(=O)NCc1cc(F)cc(-c2cccc3[nH]c(-c4n[nH]c5ncc(-c6cncc(CNCC7CCCC7)c6)cc45)nc23)c1]
883
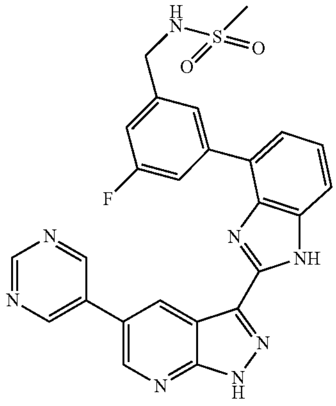 [SMILES: CS(=O)(=O)NCc1cc(F)cc(-c2cccc3[nH]c(-c4n[nH]c5ncc(-c6cncnc6)cc45)nc23)c1]
884
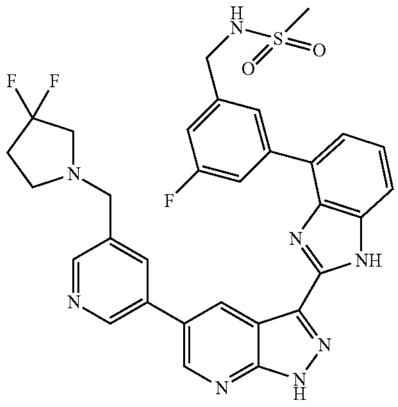 [SMILES: CS(=O)(=O)NCc1cc(F)cc(-c2cccc3[nH]c(-c4n[nH]c5ncc(-c6cncc(CN7CCC(F)(F)C7)c6)cc45)nc23)c1]
885
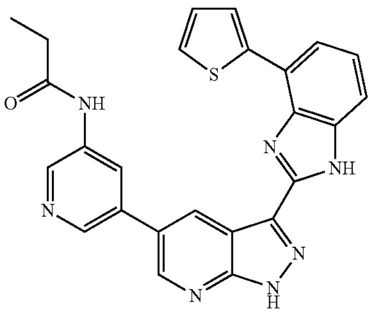 [SMILES: CCC(=O)Nc1cncc(-c2cnc3[nH]nc(-c4nc5c(-c6cccs6)cccc5[nH]4)c3c2)c1]
TABLE 1-continued
886
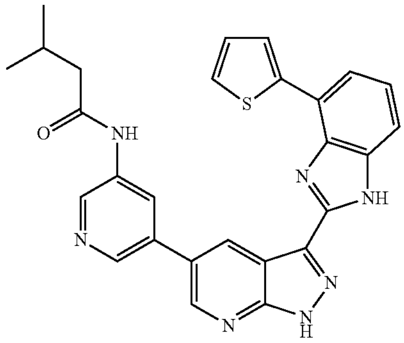 [SMILES: CC(C)CC(=O)Nc1cncc(-c2cnc3[nH]nc(-c4nc5c(-c6cccs6)cccc5[nH]4)c3c2)c1]
887
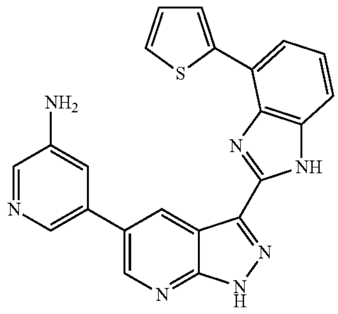 [SMILES: Nc1cncc(-c2cnc3[nH]nc(-c4nc5c(-c6cccs6)cccc5[nH]4)c3c2)c1]
888
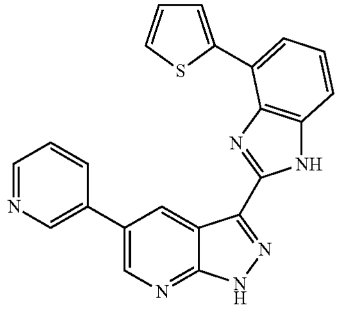
889
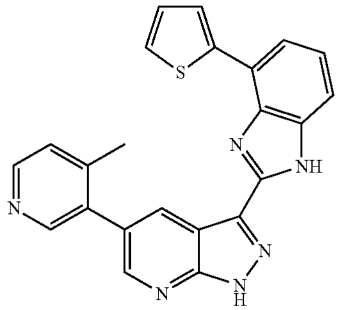
890
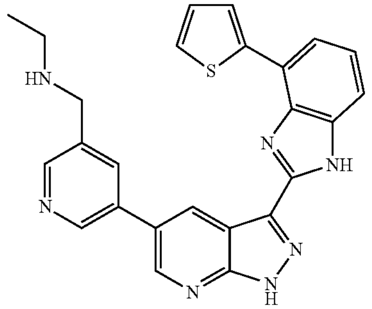 [SMILES: CCNCc1cncc(-c2cnc3[nH]nc(-c4nc5c(-c6cccs6)cccc5[nH]4)c3c2)c1]

TABLE 1-continued
891
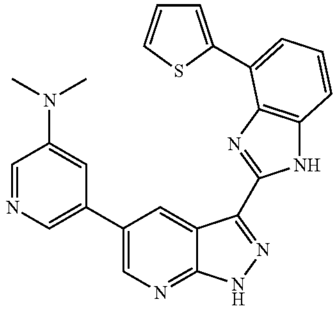 [SMILES: CN(C)c1cncc(-c2cnc3[nH]nc(-c4nc5c(-c6cccs6)cccc5[nH]4)c3c2)c1]
892
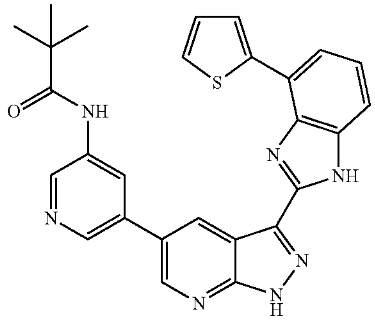 [SMILES: CC(C)(C)C(=O)Nc1cncc(-c2cnc3[nH]nc(-c4nc5c(-c6cccs6)cccc5[nH]4)c3c2)c1]
893
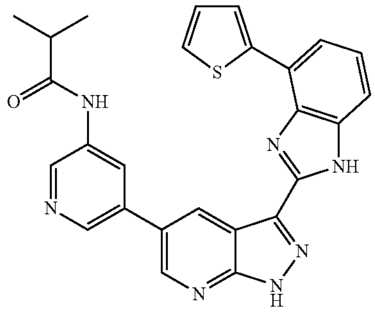 [SMILES: CC(C)C(=O)Nc1cncc(-c2cnc3[nH]nc(-c4nc5c(-c6cccs6)cccc5[nH]4)c3c2)c1]
894
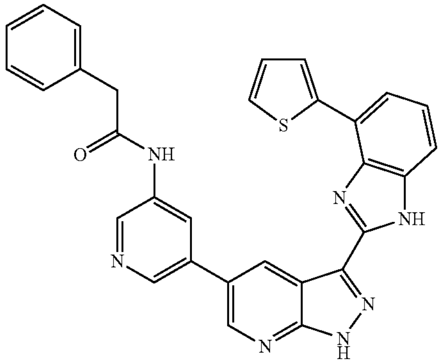 [SMILES: O=C(Cc1ccccc1)Nc1cncc(-c2cnc3[nH]nc(-c4nc5c(-c6cccs6)cccc5[nH]4)c3c2)c1]
895
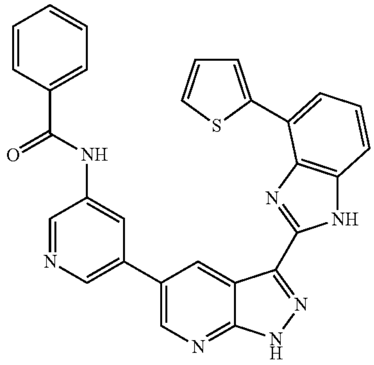 [SMILES: O=C(Nc1cncc(-c2cnc3[nH]nc(-c4nc5c(-c6cccs6)cccc5[nH]4)c3c2)c1)c1ccccc1]
896
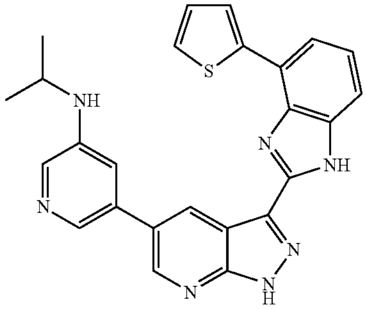 [SMILES: CC(C)Nc1cncc(-c2cnc3[nH]nc(-c4nc5c(-c6cccs6)cccc5[nH]4)c3c2)c1]
897
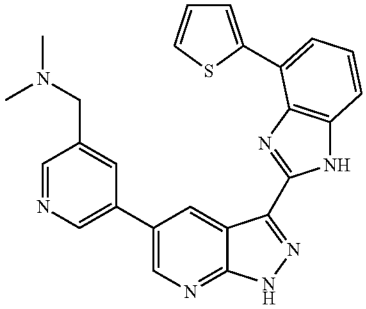 [SMILES: CN(C)Cc1cncc(-c2cnc3[nH]nc(-c4nc5c(-c6cccs6)cccc5[nH]4)c3c2)c1]
898
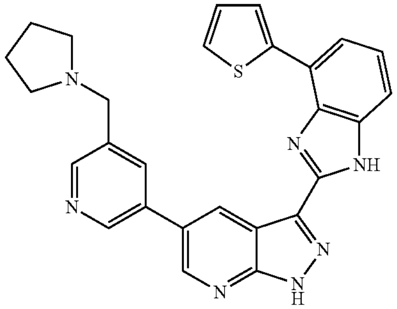 [SMILES: c1csc(-c2cccc3[nH]c(-c4n[nH]c5ncc(-c6cncc(CN7CCCC7)c6)cc45)nc23)c1]
899
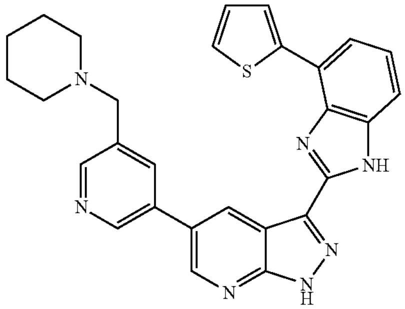 [SMILES: c1csc(-c2cccc3[nH]c(-c4n[nH]c5ncc(-c6cncc(CN7CCCCC7)c6)cc45)nc23)c1]

TABLE 1-continued
900
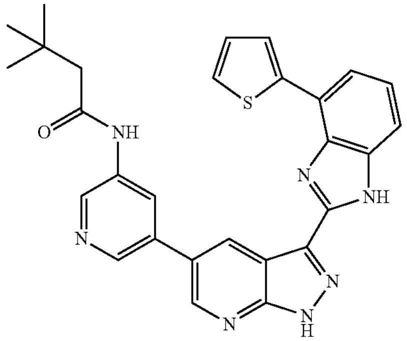 [SMILES: CC(C)(C)CC(=O)Nc1cncc(-c2cnc3[nH]nc(-c4nc5c(-c6cccs6)cccc5[nH]4)c3c2)c1]
901
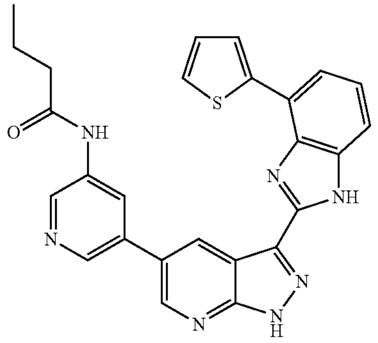 [SMILES: CCCC(=O)Nc1cncc(-c2cnc3[nH]nc(-c4nc5c(-c6cccs6)cccc5[nH]4)c3c2)c1]
902
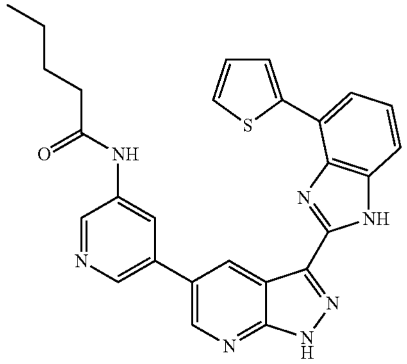
903
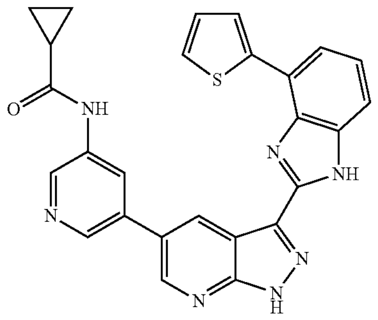 [SMILES: O=C(Nc1cncc(-c2cnc3[nH]nc(-c4nc5c(-c6cccs6)cccc5[nH]4)c3c2)c1)C1CC1]
TABLE 1-continued
904
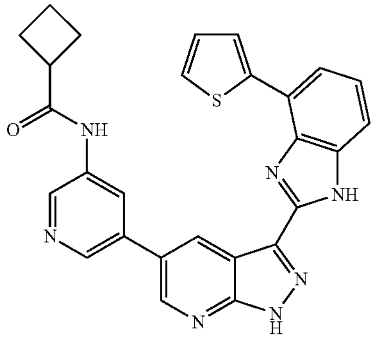 [SMILES: O=C(Nc1cncc(-c2cnc3[nH]nc(-c4nc5c(-c6cccs6)cccc5[nH]4)c3c2)c1)C1CCC1]
905
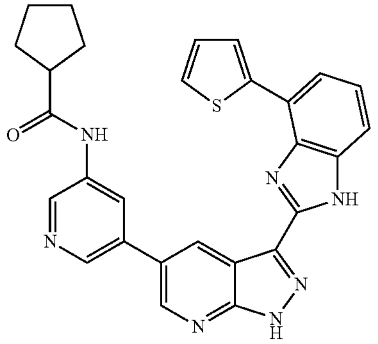 [SMILES: O=C(Nc1cncc(-c2cnc3[nH]nc(-c4nc5c(-c6cccs6)cccc5[nH]4)c3c2)c1)C1CCCC1]
906
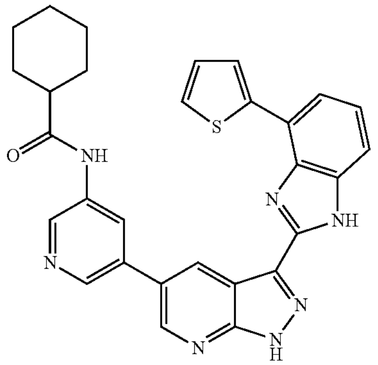 [SMILES: O=C(Nc1cncc(-c2cnc3[nH]nc(-c4nc5c(-c6cccs6)cccc5[nH]4)c3c2)c1)C1CCCCC1]
907
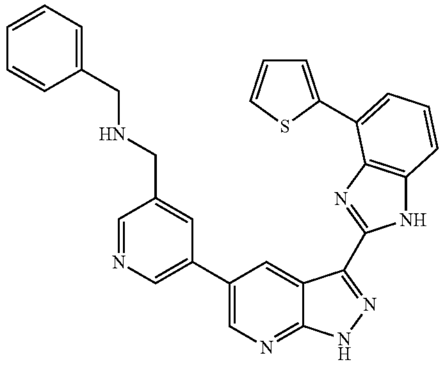 [SMILES: c1ccc(CNCc2cncc(-c3cnc4[nH]nc(-c5nc6c(-c7cccs7)cccc6[nH]5)c4c3)c2)cc1]

TABLE 1-continued
908
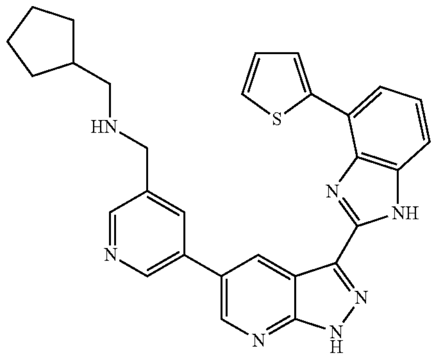 [SMILES: c1csc(-c2cccc3[nH]c(-c4n[nH]c5ncc(-c6cncc(CNCC7CCCC7)c6)cc45)nc23)c1]
909
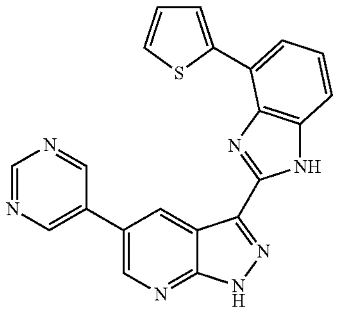 [SMILES: c1csc(-c2cccc3[nH]c(-c4n[nH]c5ncc(-c6cncnc6)cc45)nc23)c1]
910
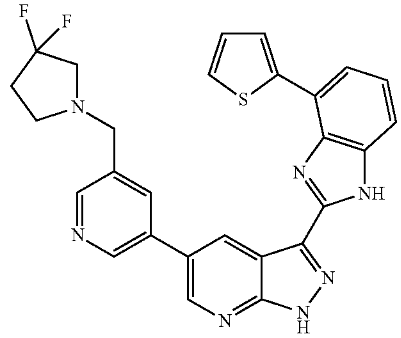 [SMILES: FC1(F)CCN(Cc2cncc(-c3cnc4[nH]nc(-c5nc6c(-c7cccs7)cccc6[nH]5)c4c3)c2)C1]
911
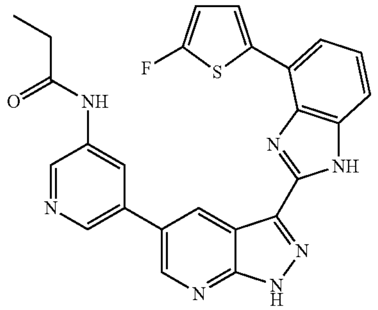
TABLE 1-continued
912
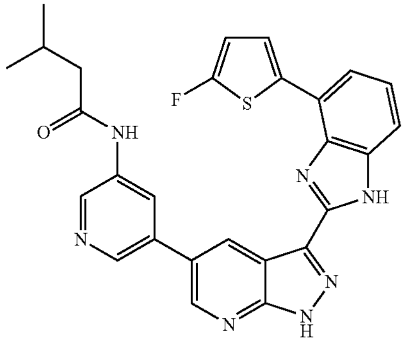 [SMILES: CC(C)CC(=O)Nc1cncc(-c2cnc3[nH]nc(-c4nc5c(-c6ccc(F)s6)cccc5[nH]4)c3c2)c1]
913
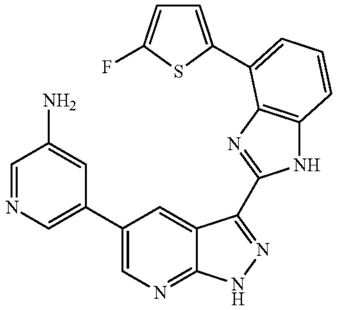
914
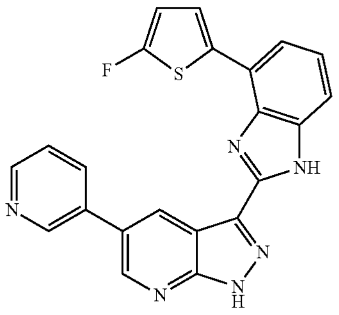 [SMILES: Fc1ccc(-c2cccc3[nH]c(-c4n[nH]c5ncc(-c6cccnc6)cc45)nc23)s1]
915
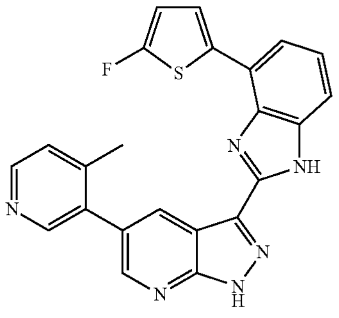
916
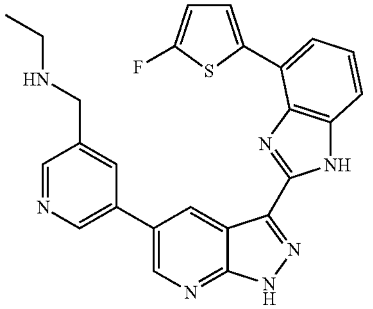

TABLE 1-continued
917
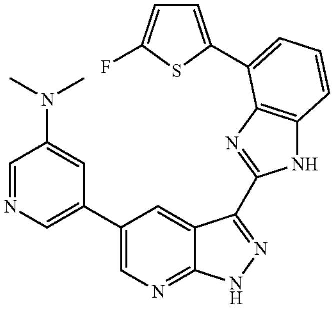 [SMILES: CN(C)c1cncc(-c2cnc3[nH]nc(-c4nc5c(-c6ccc(F)s6)cccc5[nH]4)c3c2)c1]
918
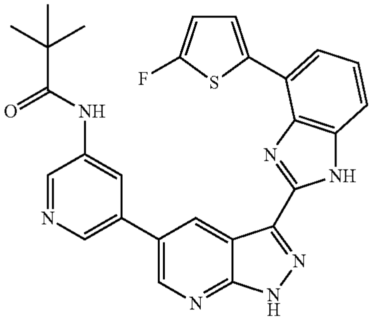 [SMILES: CC(C)(C)C(=O)Nc1cncc(-c2cnc3[nH]nc(-c4nc5c(-c6ccc(F)s6)cccc5[nH]4)c3c2)c1]
919
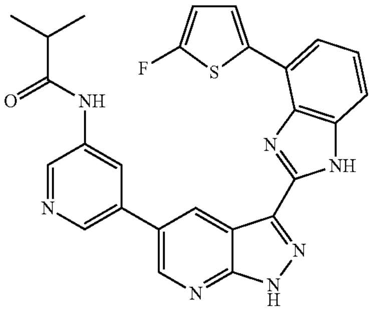 [SMILES: CC(C)C(=O)Nc1cncc(-c2cnc3[nH]nc(-c4nc5c(-c6ccc(F)s6)cccc5[nH]4)c3c2)c1]
920
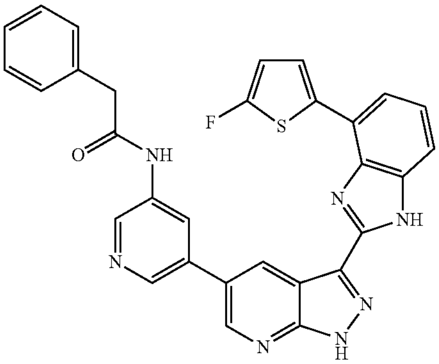 [SMILES: O=C(Cc1ccccc1)Nc1cncc(-c2cnc3[nH]nc(-c4nc5c(-c6ccc(F)s6)cccc5[nH]4)c3c2)c1]
TABLE 1-continued
921
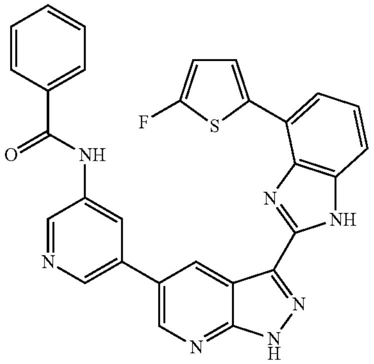
922
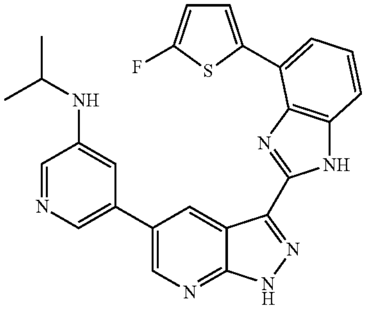
923
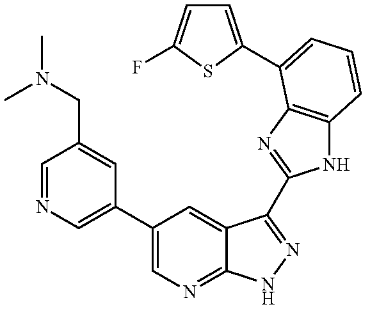 [SMILES: CN(C)Cc1cncc(-c2cnc3[nH]nc(-c4nc5c(-c6ccc(F)s6)cccc5[nH]4)c3c2)c1]
924
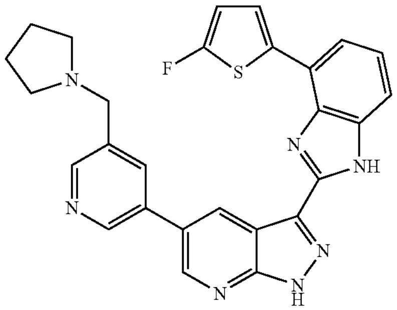 [SMILES: Fc1ccc(-c2cccc3[nH]c(-c4n[nH]c5ncc(-c6cncc(CN7CCCC7)c6)cc45)nc23)s1]
925
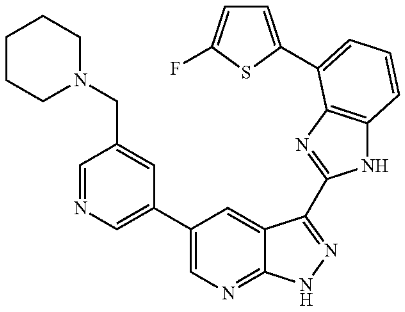 [SMILES: Fc1ccc(-c2cccc3[nH]c(-c4n[nH]c5ncc(-c6cncc(CN7CCCCC7)c6)cc45)nc23)s1]

TABLE 1-continued
926
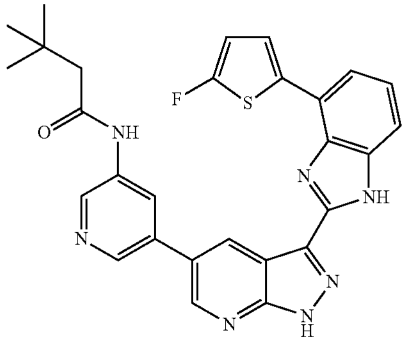 [SMILES: CC(C)(C)CC(=O)Nc1cncc(-c2cnc3[nH]nc(-c4nc5c(-c6ccc(F)s6)cccc5[nH]4)c3c2)c1]
927
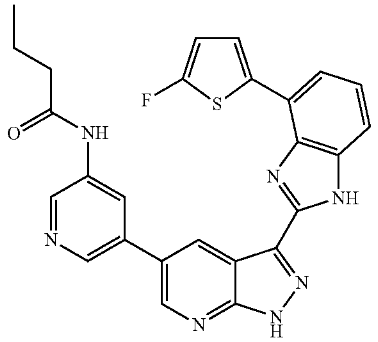 [SMILES: CCCC(=O)Nc1cncc(-c2cnc3[nH]nc(-c4nc5c(-c6ccc(F)s6)cccc5[nH]4)c3c2)c1]
928
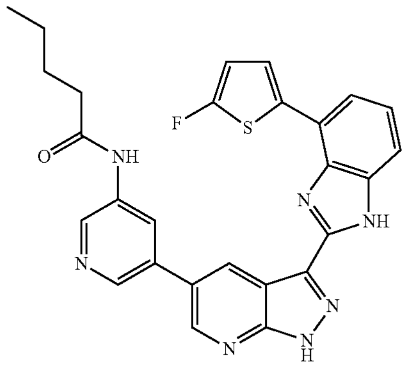 [SMILES: CCCCC(=O)Nc1cncc(-c2cnc3[nH]nc(-c4nc5c(-c6ccc(F)s6)cccc5[nH]4)c3c2)c1]
929
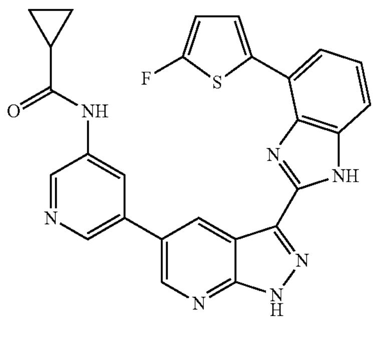 [SMILES: O=C(Nc1cncc(-c2cnc3[nH]nc(-c4nc5c(-c6ccc(F)s6)cccc5[nH]4)c3c2)c1)C1CC1]
TABLE 1-continued
930
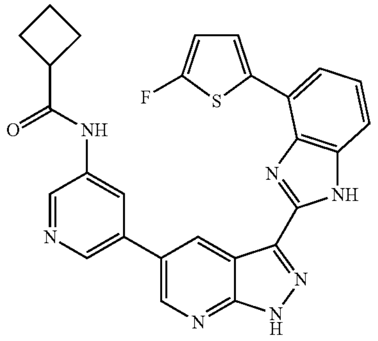 [SMILES: O=C(Nc1cncc(-c2cnc3[nH]nc(-c4nc5c(-c6ccc(F)s6)cccc5[nH]4)c3c2)c1)C1CCC1]
931
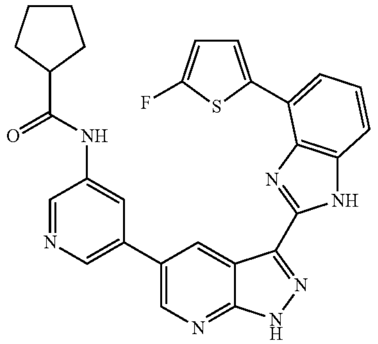
932
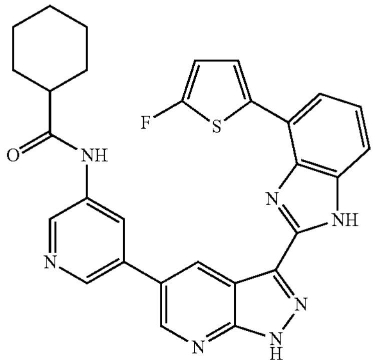
933
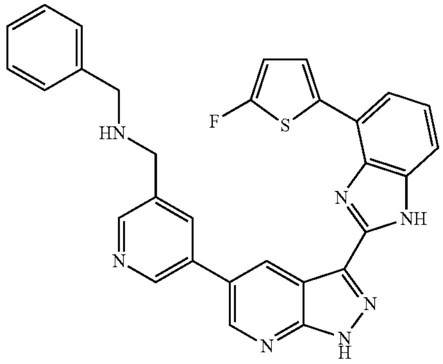 [SMILES: Fc1ccc(-c2cccc3[nH]c(-c4n[nH]c5ncc(-c6cncc(CNCc7ccccc7)c6)cc45)nc23)s1]

TABLE 1-continued
934
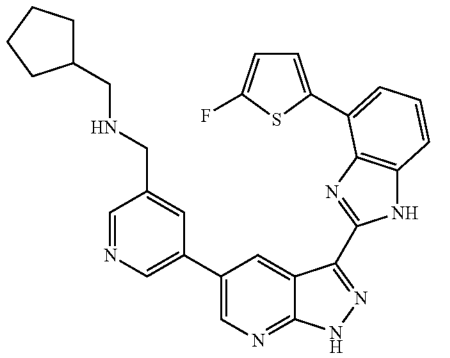 [SMILES: Fc1ccc(-c2cccc3[nH]c(-c4n[nH]c5ncc(-c6cncc(CNCC7CCCC7)c6)cc45)nc23)s1]
935
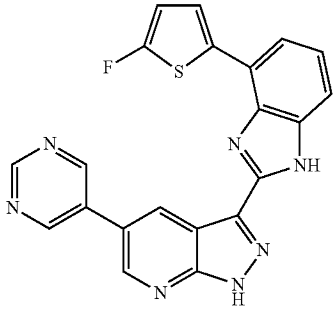
936
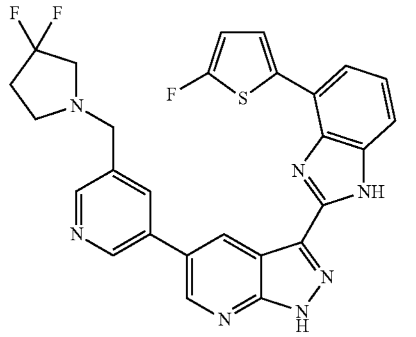 [SMILES: Fc1ccc(-c2cccc3[nH]c(-c4n[nH]c5ncc(-c6cncc(CN7CCC(F)(F)C7)c6)cc45)nc23)s1]
937
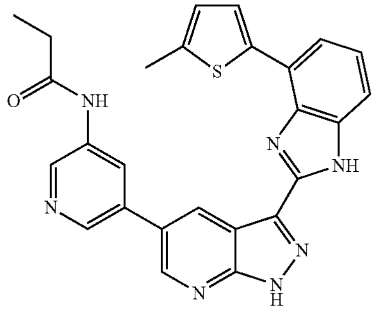 [SMILES: CCC(=O)Nc1cncc(-c2cnc3[nH]nc(-c4nc5c(-c6ccc(C)s6)cccc5[nH]4)c3c2)c1]
TABLE 1-continued
938
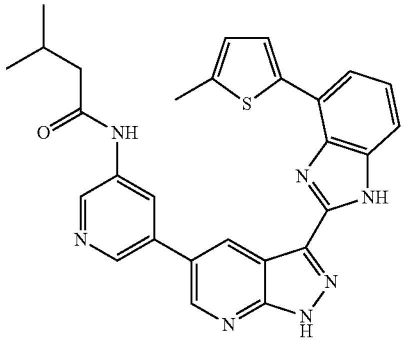 [SMILES: Cc1ccc(-c2cccc3[nH]c(-c4n[nH]c5ncc(-c6cncc(NC(=O)CC(C)C)c6)cc45)nc23)s1]
939
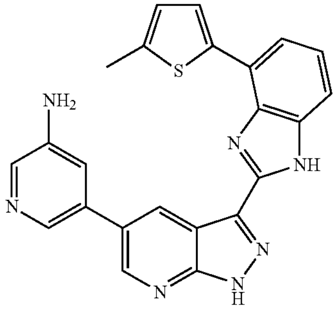
940
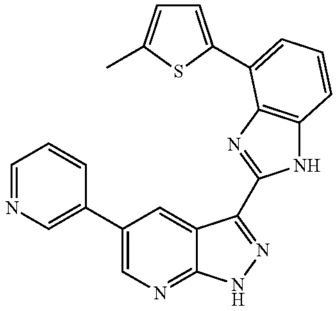 [SMILES: Cc1ccc(-c2cccc3[nH]c(-c4n[nH]c5ncc(-c6cccnc6)cc45)nc23)s1]
941
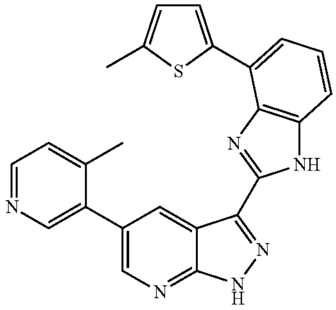 [SMILES: Cc1ccc(-c2cccc3[nH]c(-c4n[nH]c5ncc(-c6cnccc6C)cc45)nc23)s1]
942
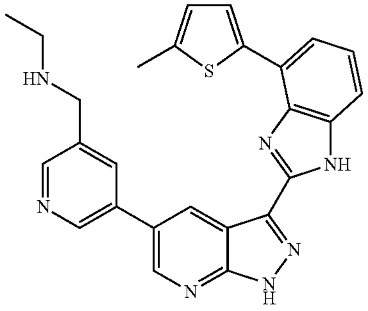

TABLE 1-continued
943 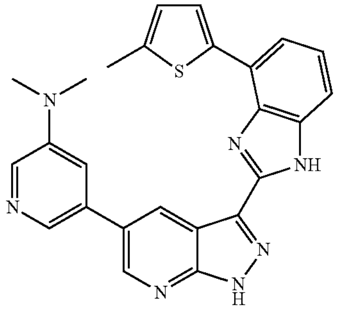 [SMILES: Cc1ccc(-c2cccc3[nH]c(-c4n[nH]c5ncc(-c6cncc(N(C)C)c6)cc45)nc23)s1]
944 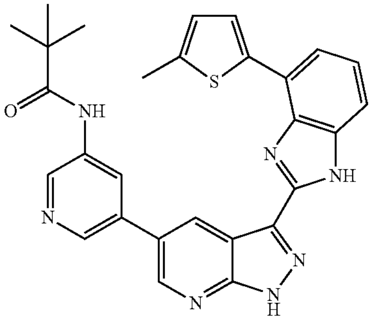 [SMILES: Cc1ccc(-c2cccc3[nH]c(-c4n[nH]c5ncc(-c6cncc(NC(=O)C(C)(C)C)c6)cc45)nc23)s1]
945 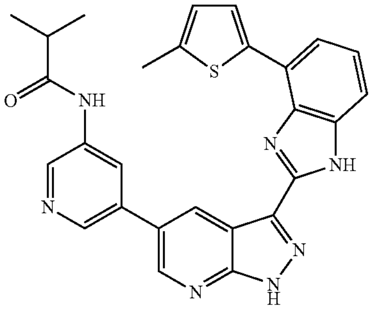 [SMILES: Cc1ccc(-c2cccc3[nH]c(-c4n[nH]c5ncc(-c6cncc(NC(=O)C(C)C)c6)cc45)nc23)s1]
946 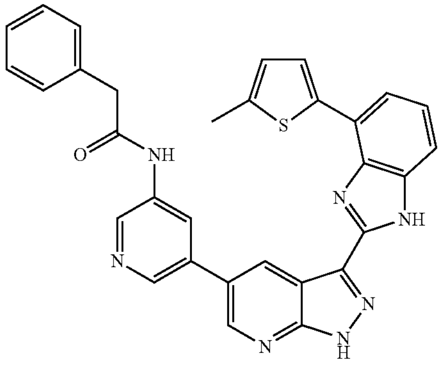
TABLE 1-continued
947 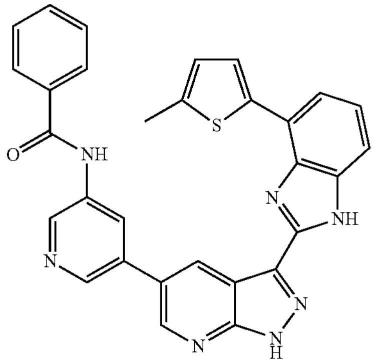 [SMILES: Cc1ccc(-c2cccc3[nH]c(-c4n[nH]c5ncc(-c6cncc(NC(=O)c7ccccc7)c6)cc45)nc23)s1]
948 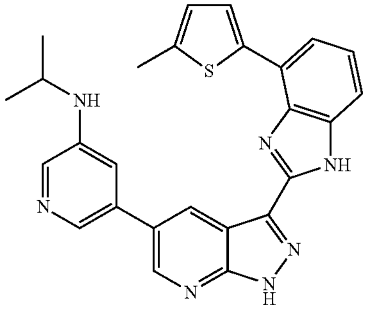 [SMILES: Cc1ccc(-c2cccc3[nH]c(-c4n[nH]c5ncc(-c6cncc(NC(C)C)c6)cc45)nc23)s1]
949 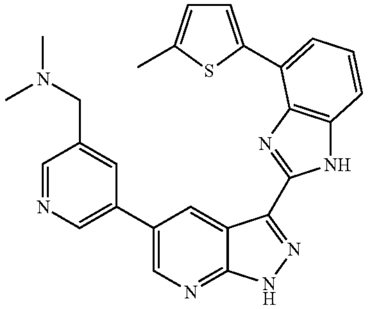
950 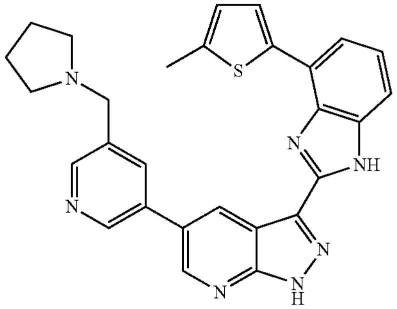 [SMILES: Cc1ccc(-c2cccc3[nH]c(-c4n[nH]c5ncc(-c6cncc(CN7CCCC7)c6)cc45)nc23)s1]
951 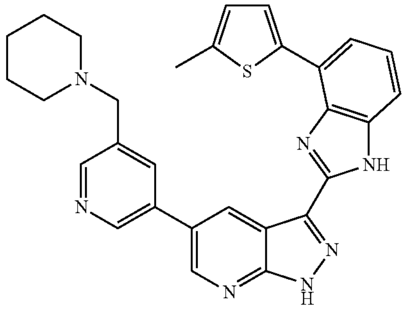 [SMILES: Cc1ccc(-c2cccc3[nH]c(-c4n[nH]c5ncc(-c6cncc(CN7CCCCC7)c6)cc45)nc23)s1]

TABLE 1-continued
952
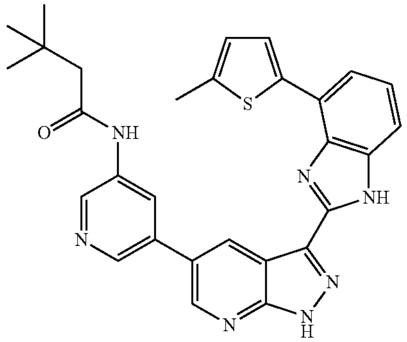
953
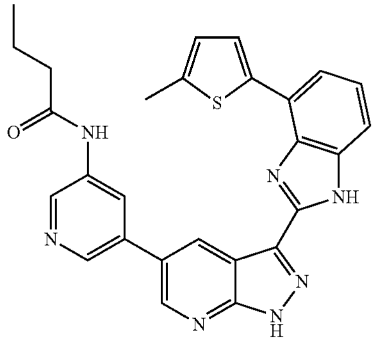
954
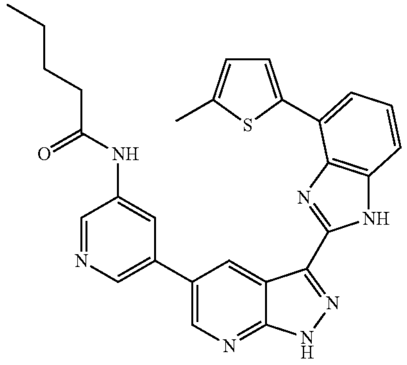
955
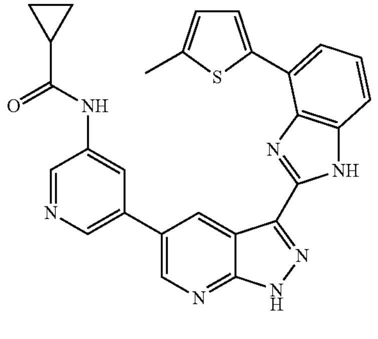
TABLE 1-continued
956
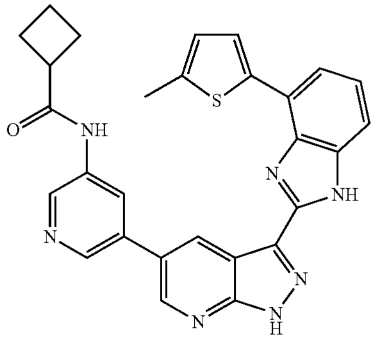 [SMILES: Cc1ccc(-c2cccc3[nH]c(-c4n[nH]c5ncc(-c6cncc(NC(=O)C7CCC7)c6)cc45)nc23)s1]
957
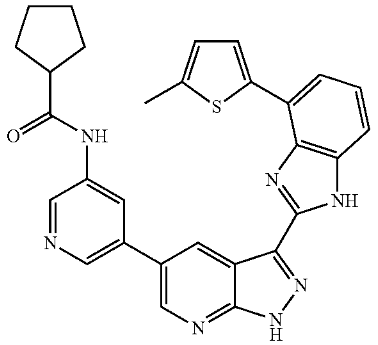 [SMILES: Cc1ccc(-c2cccc3[nH]c(-c4n[nH]c5ncc(-c6cncc(NC(=O)C7CCCC7)c6)cc45)nc23)s1]
958
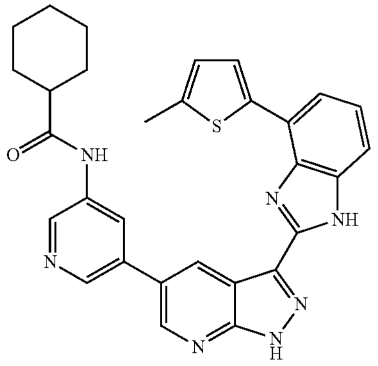 [SMILES: Cc1ccc(-c2cccc3[nH]c(-c4n[nH]c5ncc(-c6cncc(NC(=O)C7CCCCC7)c6)cc45)nc23)s1]
959
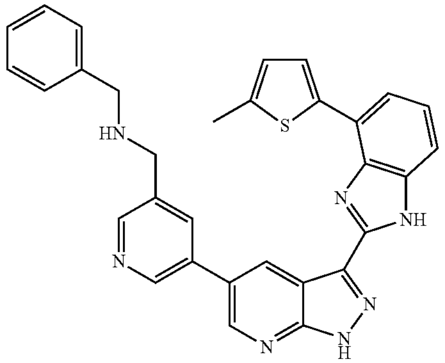 [SMILES: Cc1ccc(-c2cccc3[nH]c(-c4n[nH]c5ncc(-c6cncc(CNCc7ccccc7)c6)cc45)nc23)s1]

TABLE 1-continued
960
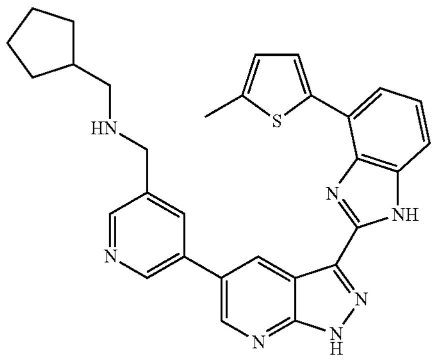
961
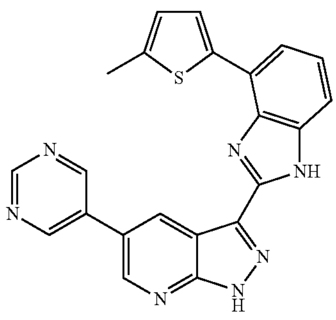 [SMILES: Cc1ccc(-c2cccc3[nH]c(-c4n[nH]c5ncc(-c6cncnc6)cc45)nc23)s1]
962
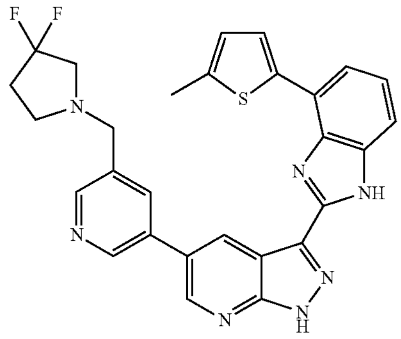 [SMILES: Cc1ccc(-c2cccc3[nH]c(-c4n[nH]c5ncc(-c6cncc(CN7CCC(F)(F)C7)c6)cc45)nc23)s1]
963
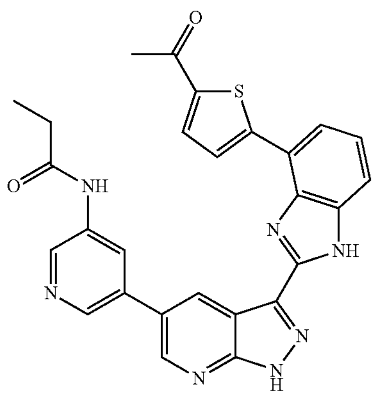 [SMILES: CCC(=O)Nc1cncc(-c2cnc3[nH]nc(-c4nc5c(-c6ccc(C(C)=O)s6)cccc5[nH]4)c3c2)c1]
TABLE 1-continued
964
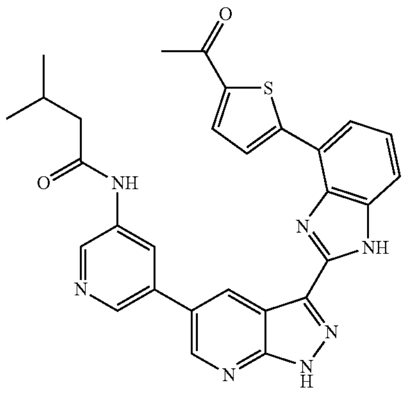 [SMILES: CC(=O)c1ccc(-c2cccc3[nH]c(-c4n[nH]c5ncc(-c6cncc(NC(=O)CC(C)C)c6)cc45)nc23)s1]
965
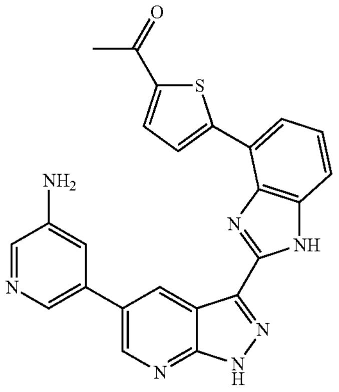 [SMILES: CC(=O)c1ccc(-c2cccc3[nH]c(-c4n[nH]c5ncc(-c6cncc(N)c6)cc45)nc23)s1]
966
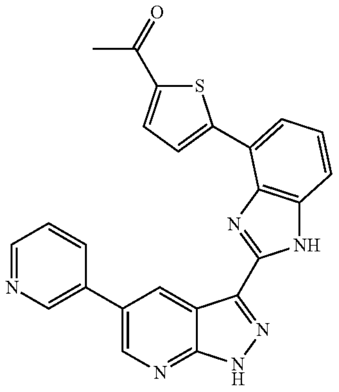 [SMILES: CC(=O)c1ccc(-c2cccc3[nH]c(-c4n[nH]c5ncc(-c6cccnc6)cc45)nc23)s1]
967
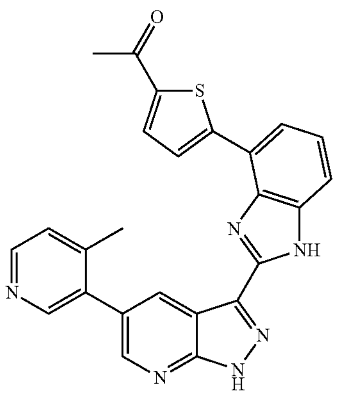 [SMILES: CC(=O)c1ccc(-c2cccc3[nH]c(-c4n[nH]c5ncc(-c6cnccc6C)cc45)nc23)s1]

TABLE 1-continued
968
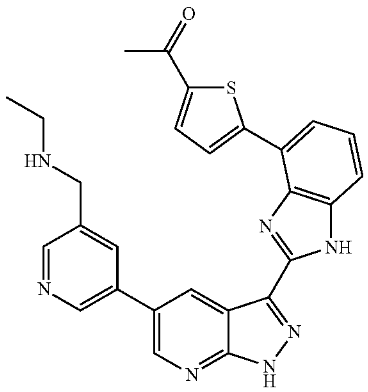
969
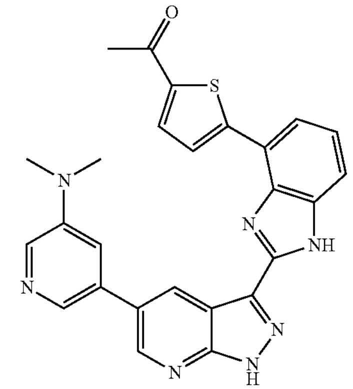 [SMILES: CC(=O)c1ccc(-c2cccc3[nH]c(-c4n[nH]c5ncc(-c6cncc(N(C)C)c6)cc45)nc23)s1]
970
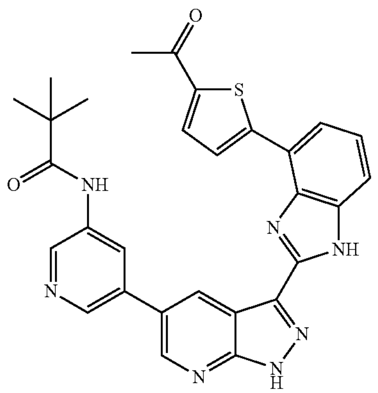 [SMILES: CC(=O)c1ccc(-c2cccc3[nH]c(-c4n[nH]c5ncc(-c6cncc(NC(=O)C(C)(C)C)c6)cc45)nc23)s1]
971
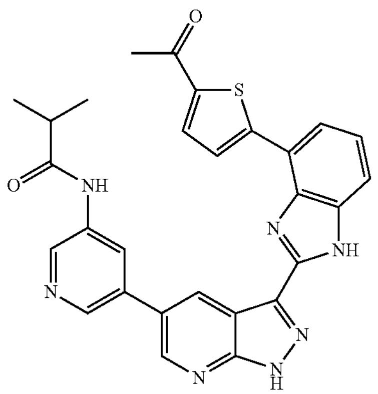 [SMILES: CC(=O)c1ccc(-c2cccc3[nH]c(-c4n[nH]c5ncc(-c6cncc(NC(=O)C(C)C)c6)cc45)nc23)s1]
TABLE 1-continued
972
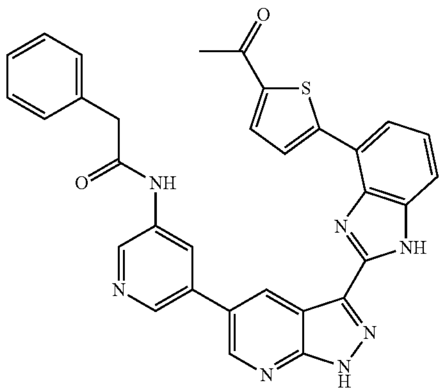 [SMILES: CC(=O)c1ccc(-c2cccc3[nH]c(-c4n[nH]c5ncc(-c6cncc(NC(=O)Cc7ccccc7)c6)cc45)nc23)s1]
973
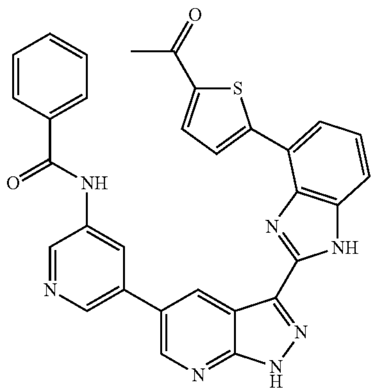 [SMILES: CC(=O)c1ccc(-c2cccc3[nH]c(-c4n[nH]c5ncc(-c6cncc(NC(=O)c7ccccc7)c6)cc45)nc23)s1]
974
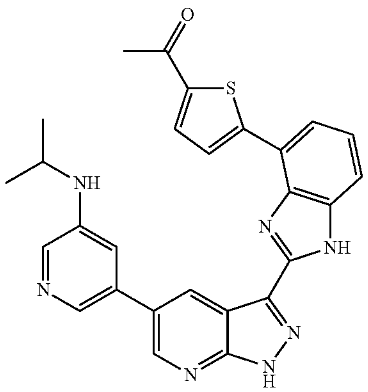 [SMILES: CC(=O)c1ccc(-c2cccc3[nH]c(-c4n[nH]c5ncc(-c6cncc(NC(C)C)c6)cc45)nc23)s1]
975
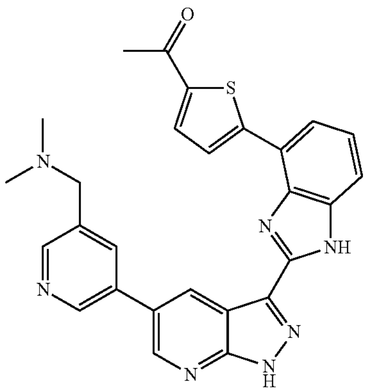 [SMILES: CC(=O)c1ccc(-c2cccc3[nH]c(-c4n[nH]c5ncc(-c6cncc(CN(C)C)c6)cc45)nc23)s1]

TABLE 1-continued
976
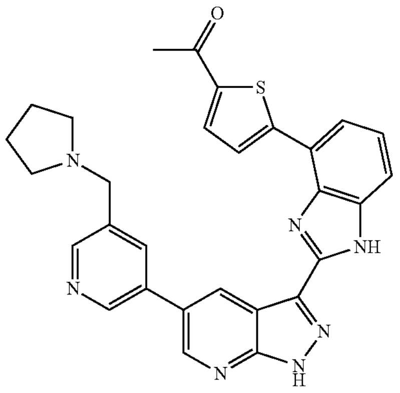
977
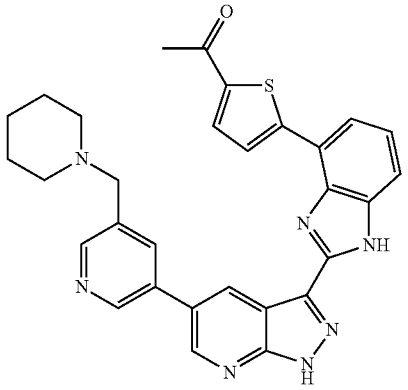 [SMILES: CC(=O)c1ccc(-c2cccc3[nH]c(-c4n[nH]c5ncc(-c6cncc(CN7CCCCC7)c6)cc45)nc23)s1]
978
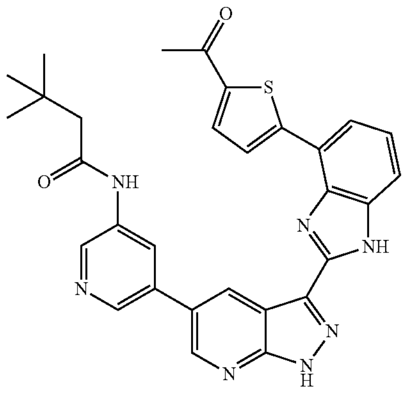 [SMILES: CC(=O)c1ccc(-c2cccc3[nH]c(-c4n[nH]c5ncc(-c6cncc(NC(=O)CC(C)(C)C)c6)cc45)nc23)s1]
979
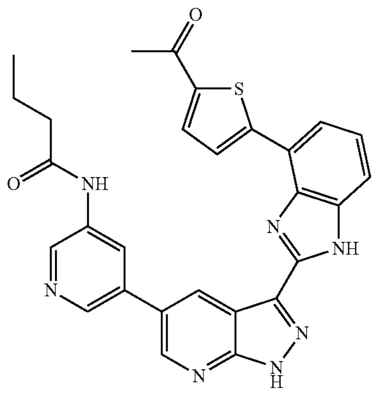 [SMILES: CCCC(=O)Nc1cncc(-c2cnc3[nH]nc(-c4nc5c(-c6ccc(C(C)=O)s6)cccc5[nH]4)c3c2)c1]
TABLE 1-continued
980
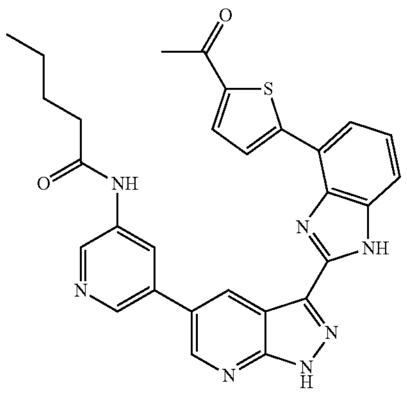 [SMILES: CCCCC(=O)Nc1cncc(-c2cnc3[nH]nc(-c4nc5c(-c6ccc(C(C)=O)s6)cccc5[nH]4)c3c2)c1]
981
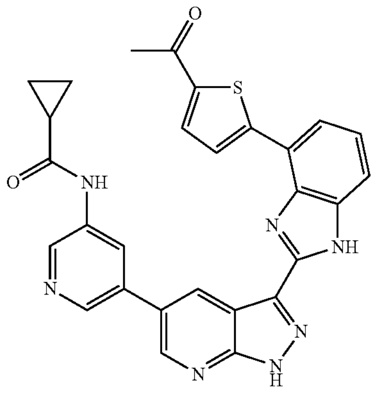
982
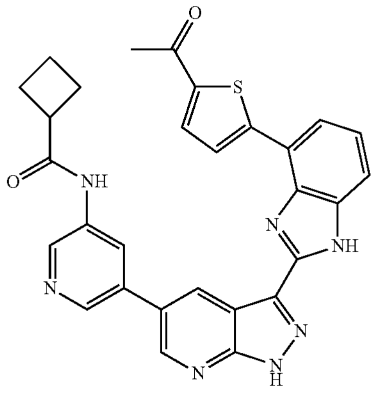 [SMILES: CC(=O)c1ccc(-c2cccc3[nH]c(-c4n[nH]c5ncc(-c6cncc(NC(=O)C7CCC7)c6)cc45)nc23)s1]
983
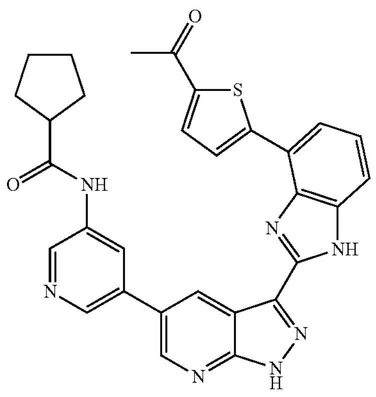 [SMILES: CC(=O)c1ccc(-c2cccc3[nH]c(-c4n[nH]c5ncc(-c6cncc(NC(=O)C7CCCC7)c6)cc45)nc23)s1]

TABLE 1-continued

984

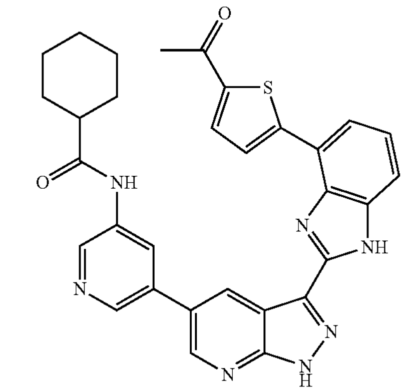 [SMILES: CC(=O)c1ccc(-c2cccc3[nH]c(-c4n[nH]c5ncc(-c6cncc(NC(=O)C7CCCCC7)c6)cc45)nc23)s1]

985

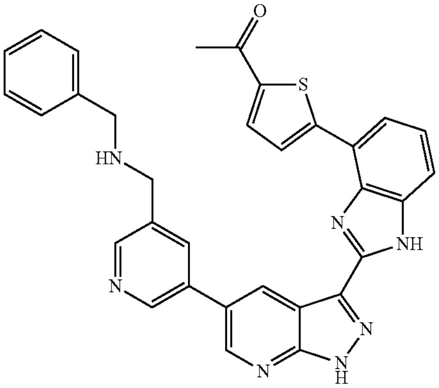 [SMILES: CC(=O)c1ccc(-c2cccc3[nH]c(-c4n[nH]c5ncc(-c6cncc(CNCc7ccccc7)c6)cc45)nc23)s1]

986

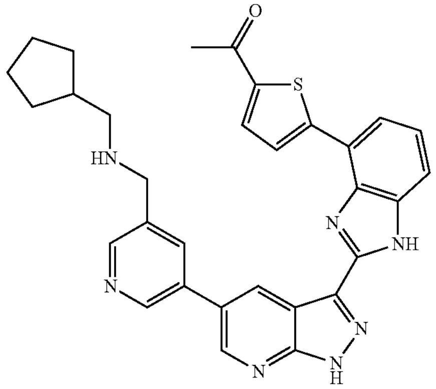 [SMILES: CC(=O)c1ccc(-c2cccc3[nH]c(-c4n[nH]c5ncc(-c6cncc(CNCC7CCCC7)c6)cc45)nc23)s1]

987

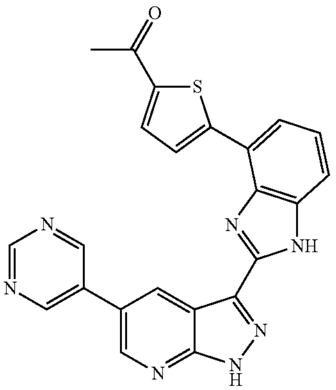

TABLE 1-continued

988

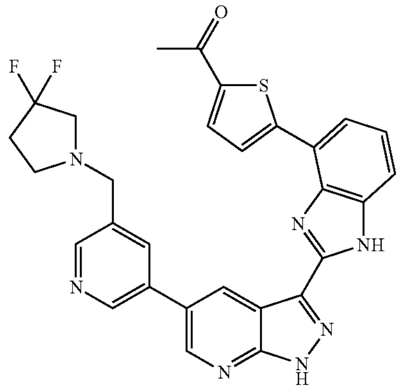 [SMILES: CC(=O)c1ccc(-c2cccc3[nH]c(-c4n[nH]c5ncc(-c6cncc(CN7CCC(F)(F)C7)c6)cc45)nc23)s1]

Administration and Pharmaceutical Compositions

Some embodiments include pharmaceutical compositions comprising: (a) a safe and therapeutically effective amount of the 1H-pyrazolo[3,4-b]pyridine compound, or its corresponding enantiomer, diastereoisomer or tautomer, or pharmaceutically acceptable salt; and (b) a pharmaceutically acceptable carrier.

The compounds of this invention may also be useful in combination (administered together or sequentially) with other known agents.

Non-limiting examples of diseases which can be treated with a combination of a compound of Formulas (I) or (II) and other known agents are colorectal cancer, ovarian cancer, retinitis pigmentosa, macular degeneration, idiopathic pulmonary fibrosis and osteoarthritis.

In some embodiments, colorectal cancer can be treated with a combination of a compound of either Formulas (I) or (II) and one or more of the following drugs: 5-Fluorouracil (5-FU), which is often given with the vitamin-like drug leucovorin (also called folinic acid); Capecitabine (Xeloda®), Irinotecan (Camptosar®), Oxaliplatin (Eloxatin®). Examples of combinations of these drugs which could be further combined with a compound of either Formulas (I) or (II) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of either Formulas (I) or (II) and one or more of the following drugs: Topotecan, Liposomal doxorubicin (Doxil®), Gemcitabine (Gemzar®), Cyclophosphamide (Cytoxan®), Vinorelbine (Navelbine®), Ifosfamide (Ifex®), Etoposide (VP-16), Altretamine (Hexylen®), Capecitabine (Xeloda®), Irinotecan (CPT-11, Camptosar®), Melphalan, Pemeterxed (Alimta®) and Albumin bound paclitaxel (nab-paclitaxel, Abraxane®). Examples of combinations of these drugs which could be further combined with a compound of either Formulas (I) or (II) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of either Formulas (I) or (II) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (Gleevec®, also known as STI-571), Gefitinib (Iressa, also known as ZD1839), Erlotinib (marketed as Tarceva®), Bortezomib (Velcade®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (eg. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MabThera® or Rituxan®), Trastuzumab (Herceptin also known as ErbB2), Cetuximab (marketed as Erbitux®) and Bevacizumab (marketed as Avastin®); and (k) radiation therapy.

In some embodiments, idiopathic pulmonary fibrosis can be treated with a combination of a compound of either Formulas (I) or (II) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of either Formulas (I) or (II) can be used to treat idiopathic pulmonary fibrosis in combination with any of the following methods: oxygen therapy, pulmonary rehabilitation and surgery.

In some embodiments, a compound of either Formulas (I) or (II) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of either Formulas (I) or (II) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of either Formulas (I) or (II) and one or more of the following drugs: UF-021 (Ocuseva™), vitamin A palmitate and pikachurin or with any of the following methods: (a) with the Argus® II retinal implant; and (b) with stem cell and/or gene therapy.

Compounds of the invention intended for pharmaceutical use may be administered as crystalline or amorphous products. Pharmaceutical compositions as provided herein may be formulated as solids, semi solids, liquids, solutions, colloidals, liposomes, emulsions, suspensions, complexes, coacervates, or aerosols. Dosage forms, such as, e.g., tablets, capsules, powders, liquids, suspensions, suppositories, aerosols, implants, controlled release or the like are also provided herein. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate. Preferably, the compositions are provided in unit dosage forms suitable for single administration of a precise dose.

Compounds of the invention intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like. The term "excipient" is used herein to describe any ingredient other than the compound(s) of the invention. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds described herein. Dosage forms or compositions containing a compound as described herein in the range of 0.005% to 100% with the balance made up from non-toxic carrier may be prepared. The contemplated compositions may contain 0.001%-100% active ingredient, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* $22^{nd}$ Edition (Pharmaceutical Press, London, UK. 2012).

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which the two active ingredients are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrine derivatives, sorbitan monolaurate, triethanolamine acetate, triethanolamine oleate, and the like).

In some embodiments, the unit dosage of compounds of Formulas (I) or (II) is 0.25 mg/Kg to 50 mg/Kg in humans In some embodiments, the unit dosage of compounds of Formulas (I) or (II) is 0.25 mg/Kg to 20 mg/Kg in humans.

In some embodiments, the unit dosage of compounds of Formulas (I) or (II) is 0.50 mg/Kg to 19 mg/Kg in humans.

In some embodiments, the unit dosage of compounds of Formulas (I) or (II) is 0.75 mg/Kg to 18 mg/Kg in humans.

In some embodiments, the unit dosage of compounds of Formulas (I) or (II) is 1.0 mg/Kg to 17 mg/Kg in humans In some embodiments, the unit dosage of compounds of Formulas (I) or (II) is 1.25 mg/Kg to 16 mg/Kg in humans.

In some embodiments, the unit dosage of compounds of Formulas (I) or (II) is 1.50 mg/Kg to 15 mg/Kg in humans.

In some embodiments, the unit dosage of compounds of Formulas (I) or (II) is 1.75 mg/Kg to 14 mg/Kg in humans.

In some embodiments, the unit dosage of compounds of Formulas (I) or (II) is 2.0 mg/Kg to 13 mg/Kg in humans.

In some embodiments, the unit dosage of compounds of Formulas (I) or (II) is 3.0 mg/Kg to 12 mg/Kg in humans In some embodiments, the unit dosage of compounds of Formulas (I) is 4.0 mg/Kg to 11 mg/Kg in humans.

In some embodiments, the unit dosage of compounds of Formulas (I) or (II) is 5.0 mg/Kg to 10 mg/Kg in humans.

In some embodiments, the compositions are provided in unit dosage forms suitable for single administration of a precise dose.

In some embodiments, the compositions are provided in unit dosage forms suitable for twice a day administration of a precise dose.

In some embodiments, the compositions are provided in unit dosage forms suitable for three times a day administration of a precise dose.

Injectables can be prepared in conventional forms, either as liquid solutions, colloid, liposomes, complexes, coacervate or suspensions, as emulsions, or in solid forms suitable for reconstitution in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and could be higher if the composition is a solid or suspension, which could be subsequently diluted to the above percentages.

In some embodiments, the composition will comprise 0.1-10% of the active agent in solution.

In some embodiments, the composition will comprise 0.1-5% of the active agent in solution.

In some embodiments, the composition will comprise 0.1-4% of the active agent in solution.

In some embodiments, the composition will comprise 0.15-3% of the active agent in solution.

In some embodiments, the composition will comprise 0.2-2% of the active agent in solution.

In some embodiments, the compositions are provided in dosage forms suitable for continuous dosage by intravenous infusion over a period of 1-96 hours.

In some embodiments, the compositions are provided in dosage forms suitable for continuous dosage by intravenous infusion over a period of 1-72 hours.

In some embodiments, the compositions are provided in dosage forms suitable for continuous dosage by intravenous infusion over a period of 1-48 hours.

In some embodiments, the compositions are provided in dosage forms suitable for continuous dosage by intravenous infusion over a period of 1-24 hours.

In some embodiments, the compositions are provided in dosage forms suitable for continuous dosage by intravenous infusion over a period of 1-12 hours.

In some embodiments, the compositions are provided in dosage forms suitable for continuous dosage by intravenous infusion over a period of 1-6 hours.

In some embodiments, these compositions can be administered by intravenous infusion to humans at doses of 5 $mg/m^2$ to 300 $mg/m^2$.

In some embodiments, these compositions can be administered by intravenous infusion to humans at doses of 5 $mg/m^2$ to 200 $mg/m^2$.

In some embodiments, these compositions can be administered by intravenous infusion to humans at doses of 5 $mg/m^2$ to 100 $mg/m^2$.

In some embodiments, these compositions can be administered by intravenous infusion to humans at doses of 10 $mg/m^2$ to 50 $mg/m^2$.

In some embodiments, these compositions can be administered by intravenous infusion to humans at doses of 50 $mg/m^2$ to 200 $mg/m^2$.

In some embodiments, these compositions can be administered by intravenous infusion to humans at doses of 75 $mg/m^2$ to 175 $mg/m^2$.

In some embodiments, these compositions can be administered by intravenous infusion to humans at doses of 100 $mg/m^2$ to 150 $mg/m^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one preferred embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size is desired to maximize impaction on the nasal mucosa and to minimize or prevent pulmonary deposition of the administered formulation. In some embodiments, aerosols intended for delivery to the lung are provided for inhalation through the nose or the mouth. For optimal delivery to the lung, inhaled aerodynamic particle sizes of about less than 10 μm are useful, with an aerodynamic particle size of about 1 to about 10 microns being preferred. Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formulas (I) or (II) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formulas (I) or (II) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the invention can be incorporated into a gel formulation (e.g., U.S. Pat. Nos. 4,474,752 and 6,911,211).

In some embodiments, compounds of Formulas (I) or (II) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments, compounds of Formulas (I) or (II) can be delivered from the reservoir of an external or internal implanted pumping system.

Formulations of the invention also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formulas (I) or (II) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing the drug with a suitable non-irritating excipient that is solid at ordinary temperatures but liquid at the rectal temperature and will therefore melt or erode/dissolve in the rectum and release the drug. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter is first melted.

Solid compositions can be provided in various different types of dosage fauns, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided above, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, idiopathic pulmonary fibrosis (IPF), pulmonary fibrosis, rheumatoid arthritis, scleroderma, mycotic and viral infections, bone and cartilage diseases, Alzheimer's disease, lung disease, osteoarthritis, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome The actual dose of the active compounds of the present invention depends on the specific compound, and on the condition to be treated; the selection of the appropriate dose is well within the knowledge of the skilled artisan.

Methods of Treatment

The compounds and compositions provided herein can be used as inhibitors and/or modulators of one or more members of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, idiopathic pulmonary fibrosis (IPF), pulmonary fibrosis, rheumatoid arthritis, scleroderma, sarcoidosis, mycotic and viral infections, bone and cartilage diseases, neurological conditions/diseases such as Alzheimer's disease, amyotrophic lateral sclerosis (ALS), motor neuron disease, Down's syndrome, frontotemporal dementia (FTDP-17), Pick's disease, surpanuclear palsy, corticobasal degeneration, multiple sclerosis or autism, lung disease, osteoarthritis, polyposis coli, bone density and vascular defects in the eye (Osteoporosis-pseudoglioma Syndrome, OPPG), familial exudative vitreoretinopathy, retinal angiogenesis, retinal tumors, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL, T-ALL, myelodysplastic syndromes and Mantle Cell Lympohomas. The constitutive activation is due to constitutively active β-catenin, perhaps due to its stabilization by interacting factors or inhibition of the degradation pathway. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compound, compositions and methods described herein include, but are not limited to, the following:

1) Breast cancers, including, for example $ER^+$ breast cancer, $ER^-$ breast cancer, her2$^-$ breast cancer, her2$^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma, basal cell carcinoma, squamous cell carcinoma, Kaposi's sarcoma, moles dysplastic nevi, lipoma, angioma, dermatofibroma, keloids, desmoid tumors, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; adhesions, such as those occurring in the abdomen, pelvis, spine or tendons; chronic obstructive pulmonary disease; fibrosis following myocardial infarction; pulmonary fibrosis; idiopathic pulmonary fibrosis (IPF); fibrosis and scarring associated with diffuse/interstitial lung disease; central nervous system fibrosis, such as fibrosis following stroke; fibrosis associated with neurodegenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, scleroderma, autoimmune mediated glomerulonephritis, inflammatory bowel disease and autoimmune diabetes mellitus), neurodegenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetraamelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome and Rett syndrome.

Furthermore, the compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Menieres disease, meningitis, Menkes disease, etachromatic leukodystrophy, microcephaly, micropsia, Miller Fisher syndrome, misophonia, mitochondrial myopathy, Mobius syndrome, monomelic amyotrophy, motor neurone disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease and Zellweger syndrome.

The compounds and compositions may also be useful in the inhibition of the development of invasive cancer, tumor angiogenesis and metastasis.

In some embodiment, the invention provides a method for treating a disease or disorder associated with aberrant cellular proliferation by administering to a patient in need of such treatment an effective amount of one or more of the compounds of Formulas (I) or (II), in combination (simultaneously or sequentially) with at least one other agent.

In some embodiments, the pharmaceutical composition comprises a therapeutically effective amount of a compound of Formulas (I) or (II), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formulas (I) or (II), or a pharmaceutically acceptable salt thereof.

In some embodiments, the disorder or disease is cancer.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is dementia.

In some embodiments, the disorder or disease is Parkinson's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the compound of Formulas (I) or (II) inhibits one or more proteins in the Wnt pathway.

In some embodiments, the compound of Formulas (I) or (II) inhibits signaling induced by one or more Wnt proteins.

In some embodiments, the Wnt proteins are chosen from: WNT1, WNT2, WNT2B, WNT3, WNT3A, WNT4. WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formulas (I) or (II) inhibits a kinase activity.

In some embodiments, the method of treats a disease or disorder mediated by the Wnt pathway in a patient, the method comprises administering to the patient a therapeutically effective amount of a compound (or compounds) of Formulas (I) or (II), or a pharmaceutically acceptable salt thereof.

In some embodiments, the compound of Formulas (I) or (II) inhibits one or more Wnt proteins.

In some embodiments, the method of treats a disease or disorder mediated by kinase activity in a patient, the method comprises administering to the patient a therapeutically effective amount of a compound (or compounds) of Formulas (I) or (II), or a pharmaceutically acceptable salt thereof.

In some embodiments, the disease or disorder comprises tumor growth, cell proliferation, or angiogenesis.

In some embodiments, the method of inhibits the activity of a protein kinase receptor, the method comprises contacting the receptor with an effective amount of a compound (or compounds) of Formulas (I) or (II), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formulas (I) or (II), or a pharmaceutically acceptable salt thereof.

In some embodiments, the method prevents or reduces angiogenesis in a patient; the method comprises administering to the patient a therapeutically effective amount of a compound (or compounds) of Formulas (I) or (II), or a pharmaceutically acceptable salt thereof.

In some embodiments, the method prevents or reduces abnormal cellular proliferation in a patient; the method comprises administering to the patient a therapeutically effective amount of a compound (or compounds) of Formulas (I) or (II), or a pharmaceutically acceptable salt thereof.

In some embodiments, the method of treats a disease or disorder associated with aberrant cellular proliferation in a patient, the method comprising administering to the patient a pharmaceutical composition comprising one or more of the compounds of Formulas (I) or (II) in combination with a pharmaceutically acceptable carrier and one or more other agents Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_{-0}$, $G_{-1}$ or mitotic stage of the cell cycle, e.g., CDK1, CDK2, CDK4, and/or CDK6 complexes.

Evaluation of Biological Activity

The biological activity of the compounds described herein can be tested using any suitable assay known to those of skill in the art, e.g., WO 2001/053268 or WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a Wnt composition in the presence of a candidate inhibitor with cells, e.g. mouse L cells. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin In a further example, the activity of a candidate compound can be measured in a Xenopus secondary axis bioassay (Leyns, L. et al. *Cell* (1997), 88(6), 747-756).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7th Ed., John Wiley & Sons (2013), Carey and Sundberg, *Advanced Organic Chemistry* 5th Ed., Springer (2007), *Comprehensive Organic Transformations: A Guide to Functional Group Transformations,* 2nd Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis,* 4th Ed., John Wiley & Sons (2007), incorporated herein by reference in its entirety.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1H$) nuclear magnetic resonance spectra (NMR) were measured in the indicated solvents on a Bruker NMR spectrometer (Avance TM DRX300, 300 MHz for $^1H$ or Avance TM DRX500, 500 MHz for $^1H$) or Varian NMR spectrometer (Mercury 400BB, 400 MHz for $^1H$). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; d/ABq, doublet of AB quartet; dt, doublet of triplets; td, triplet of doublets; m, multiplet.

The following abbreviations have the indicated meanings:

n-BuOH=n-butyl alcohol
brine=saturated aqueous sodium chloride
$CDCl_3$=deuterated chloroform
CDI=1,1'-carbonyldiimidazole
DCE=dichloroethane
DCM=dichloromethane
DIPEA=diisopropylethylamine
DMF=N,N-dimethylformamide
DMSO-$d_6$=deuterated dimethylsulfoxide
EDC=1-ethyl-3-(3-dimethylaminopropyl)carbodiimide
ESIMS=electron spray mass spectrometry
EtOAc=ethyl acetate
EtOH=ethanol
HCl=hydrochloric acid
HOAc=acetic acid
$H_2SO_4$=sulfuric acid
$K_3CO_4$=potassium carbonate
$KMnO_4$=potassium permanganate
KOAc=potassium acetate
KO$^t$Bu=potassium t-butoxide
$K_3PO_4$=potassium phosphate
LDA=lithium diisopropylamide
MeOH=methanol
$MgSO_4$=magnesium sulfate
$NaBH(OAc)_3$=sodium triacetoxyborohydride
$NaCNBH_3$=sodium cyanoborohydride
$NaHCO_3$=sodium bicarbonate $NaHSO_4$=sodium bisulfate
NaOAc=sodium acetate
NaOCl=sodium hypochlorite
NaOH=sodium hydroxide
$Na_2S_2O_3.7H_2O$=sodium thiosulfate pentahydrate
$NH_4OH$=ammonium hydroxide
NMR=nuclear magnetic resonance
Pd/C=palladium(0) on carbon
$Pd(dppf)_2Cl_2$=1,1'-bis(diphenylphosphino)ferrocene]palladium(II) chloride
$Pd(PPh_3)_4$=tetrakis(triphenylphosphine)palladium(0)
$Pd(PPh_3)_2Cl_2$=bis(triphenylphosphine)palladium(II) chloride
PPTS=pyridinium p-toluenesulfonate
r.t.=room temperature
S(0)=elemental sulfur
TEA=triethylamine
TEMPO=(2,2,6,6-Tetramethylpiperidin-1-yl)oxyl or (2,2,6,6-tetramethyl piperidin-1-yl)oxidanyl
TFA=trifluoroacetic acid
THF=tetrahydrofuran
TLC=thin layer chromatography
TrCl=triphenylmethyl chloride or trityl chloride The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formulas (I) or (II) of the present invention can be prepared as depicted in Scheme 1.

Scheme 1

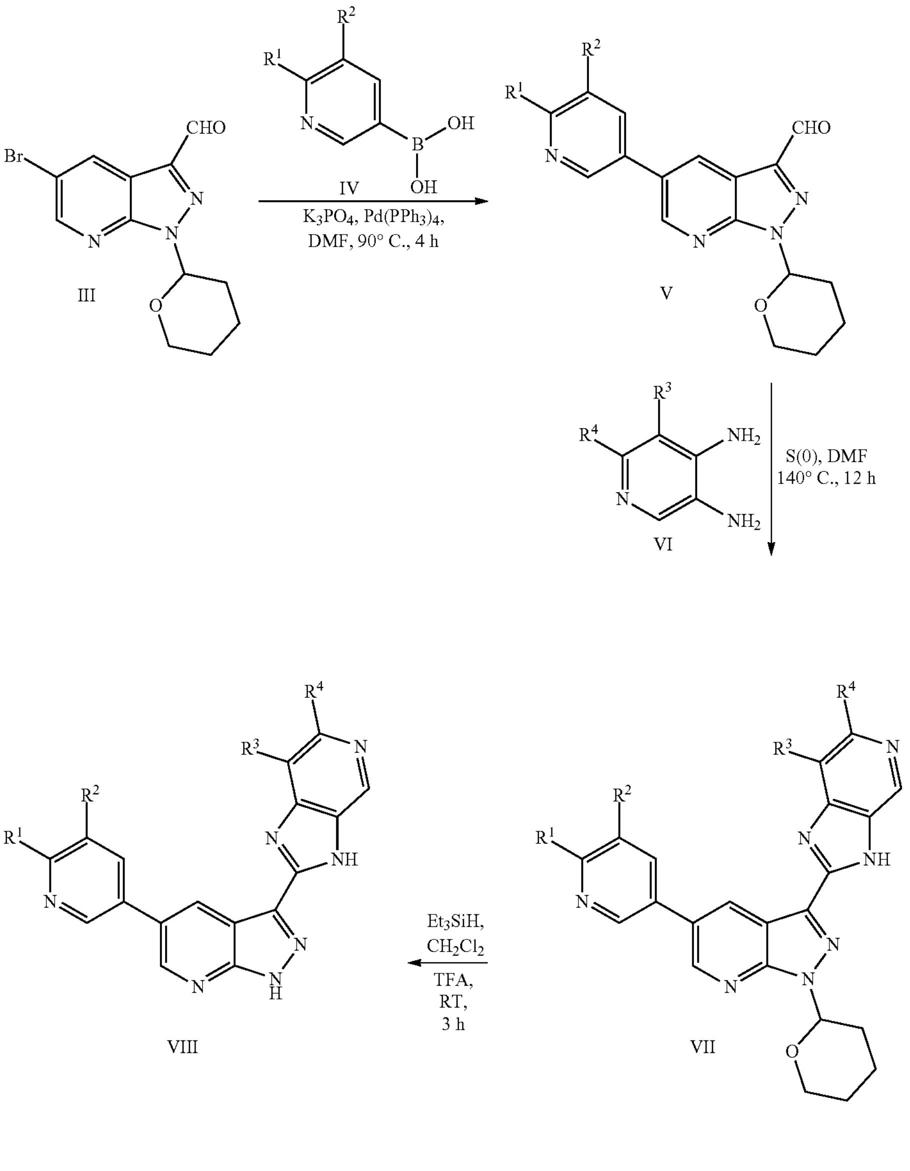

III
IV
V
VI
VII
VIII

Scheme 1 describes a method for preparation of 1H-pyrazolo[3,4-b]pyridine derivatives (VIII) by reacting aldehyde III with various boronic acid derivatives (XII) under Suzuki coupling conditions to give aldehyde V. Aldehyde V is reacted with various substituted and unsubstituted aryl/heteroaryl-3,4-diamines (VI) to form VII. Final deprotection of the pyrazolone nitrogen yields the desired 1H-pyrazolo[3,4-b]pyridine derivative (VIII).

Compounds of Formulas (I) or (II) of the present invention can also be prepared as depicted in Scheme 2.

Scheme 2 describes an alternative method for preparation of 1H-pyrazolo[3,4-b]pyridine derivatives (VIII) by reacting 5-bromo-1-(tetrahydro-2H-pyran-2-yl)-1H-pyrazolo[3,4-b]pyridine-3-carbaldehyde (III) with bis(pinacolato)diboron to form the borate ester (IX). Suzuki coupling with various bromides (X) or chlorides yields 1H-pyrazolo[3,4-b]pyridine derivatives (V). Aldehyde (V) is reacted with various 1,2-diamines (VI) to produce (VII). Final deprotection of the pyrazole nitrogen yields the desired 1H-pyrazolo[3,4-b]pyridine derivatives (VIII).

Scheme 2

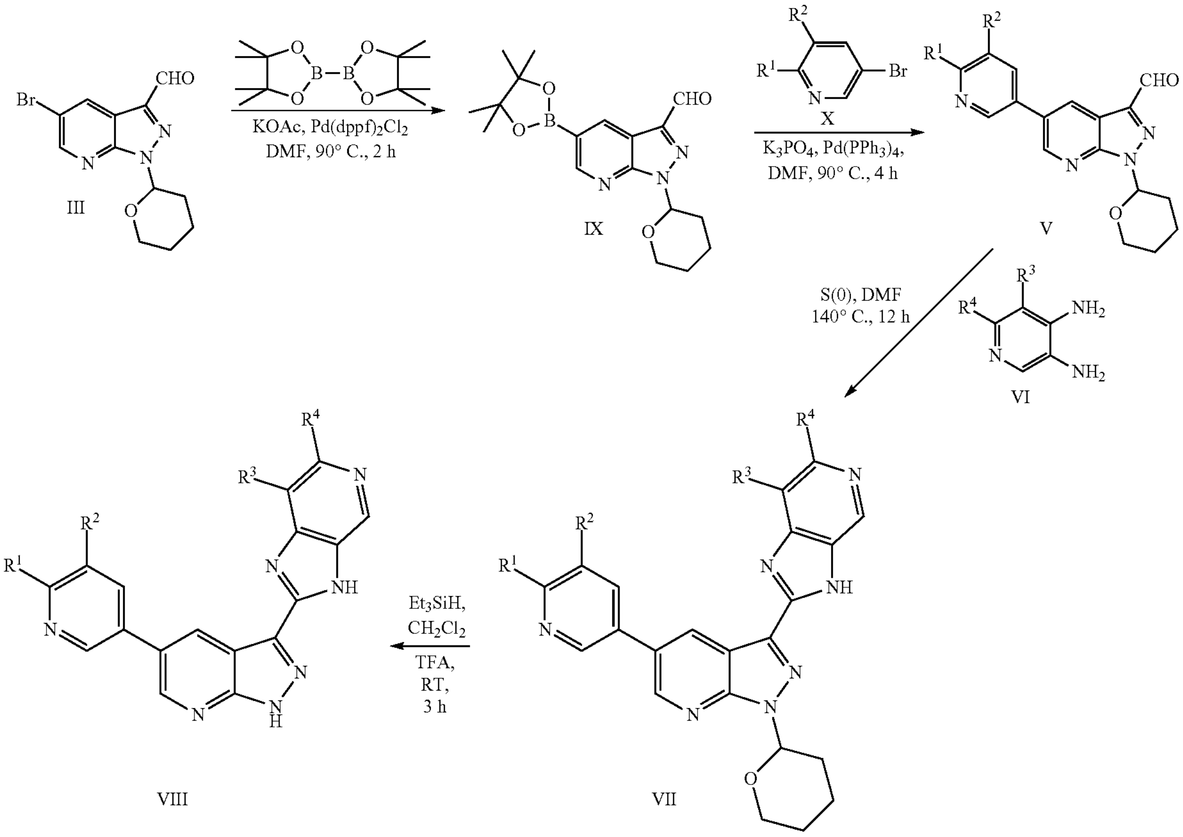

Illustrative Compound Examples

Synthesis of intermediate 5-bromo-1-(tetrahydro-2H-pyran-2-yl)-1H-pyrazolo[3,4-b]pyridine-3-carbaldehyde (III) is depicted below in Scheme 3.

Scheme 3

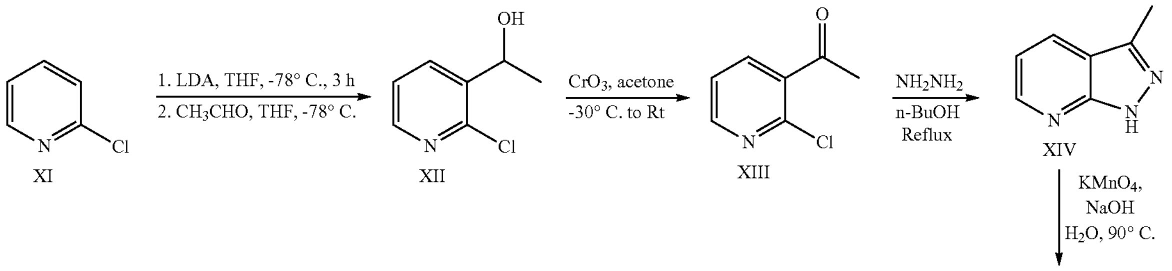

-continued

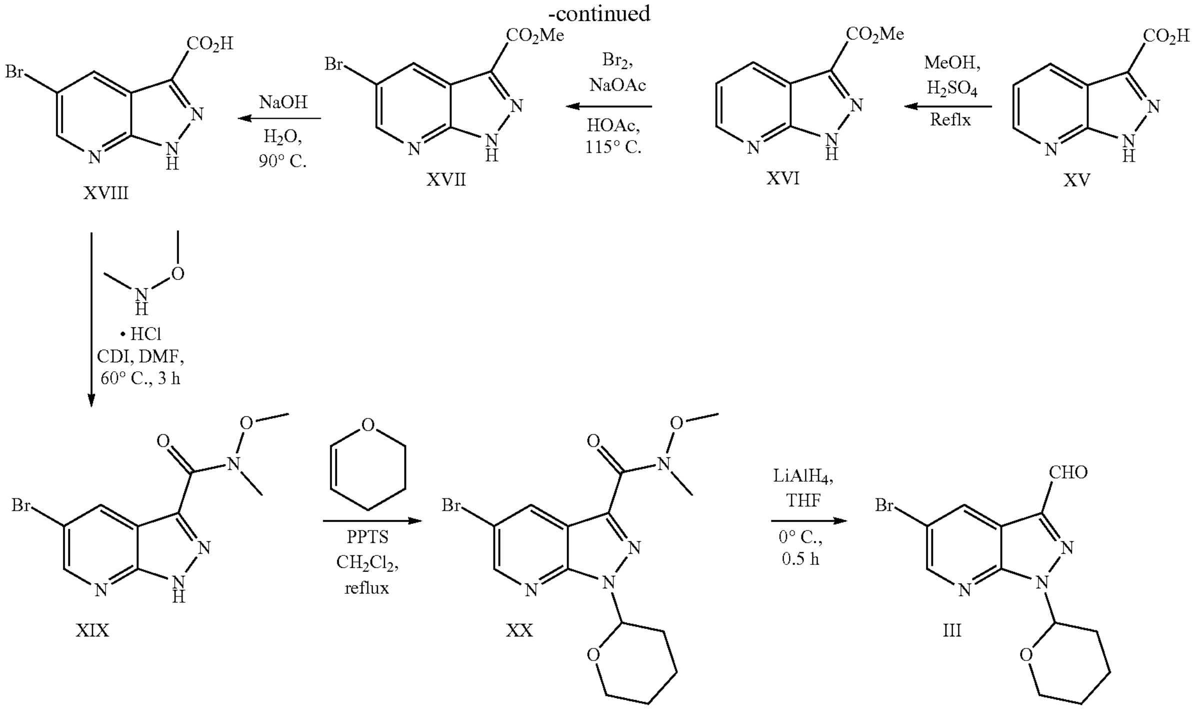

Step 1

A solution of 2-chloropyridine (XI) (9.39 mL, 0.1 mol) in anhydrous THF (50 mL) was added slowly to a solution of LDA (2.0 M solution in THF/hexane/ethylbenzene, 50 mL, 0.1 mol) in THF (200 mL) stirred at −78° C. under nitrogen. The stirring was continued at −78° C. for an additional 3 h before adding acetaldehyde (6.17 mL, 0.110 mol). The solution was stirred at −78° C. for another 2 h before allowing the temperature to rise to −40° C. A solution of water (4 mL) in THF (40 mL) was added slowly to the solution. When the temperature reached −10° C., additional water (200 mL) was added to the solution. The solution was extracted with ethyl ether (3×100 mL). The combined organic phase was dried over $MgSO_4$, filtered and evaporated under reduced pressure to get a brown viscous residue. The crude product was purified on a flash silica gel column (1:1 DCM:hexane→100% DCM) to produce 1-(2-chloropyridin-3-yl)ethanol (XII) as a brown viscous oil (6 g, 38.1 mmol, 38% yield). $^1H$ NMR ($CDCl_3$) δ ppm 1.52 (d, J=6.41 Hz, 3H), 2.51 (brs, 1H), 5.24 (m, 1H), 7.28 (m, 1H), 7.97 (dd, J=7.72 Hz, J=1.70 Hz, 1H), 8.27 (dd, J=7.72 Hz, J=1.79 Hz, 1H).

Step 2

To a solution of 1-(2-chloropyridin-3-yl)ethanol (XII) in dry acetone at −30° C. under nitrogen was added in portions chromium (VI) oxide (1.80 g, 18 mmol). The solution was further stirred 15 min at −30° C. and allowed to warm to room temperature. The solution was stirred for 3 h at room temperature before adding isopropanol (10 mL). The solution was made alkaline by slowly adding a saturated aqueous $NaHCO_3$ solution. The solution was filtered through a bed of Celite. The solids were washed by DCM. The organic phase of the filtrate was separated and the aqueous phase extracted with DCM (2×50 mL). The combined organic layers were dried over $MgSO_4$, filtered and concentrated under reduced pressure to yield 1-(2-chloropyridin-3-yl)ethanone (XIII) as a brown liquid (0.72 g, 4.63 mmol, 77% yield). $^1H$ NMR ($CDCl_3$) δ ppm 2.71 (s, 3H), 7.35 (dd, J=7.63 Hz, J=4.80 Hz, 1H), 7.91 (dd, J=7.54 Hz, J=1.88 Hz, 1H), 8.55 (dd, J=4.71 Hz, J=1.88 Hz, 1H).

Step 3

To a solution of 1-(2-Chloropyridin-3-yl)ethanone (XIII) (0.311 g, 2 mmol) in n-butanol (10 mL) was added hydrazine hydrate (1.45 mL, 30 mmol). The reaction was refluxed overnight. The solution was cooled and the solvent was evaporated under vacuum. The residue was dissolved in DCM and washed successively by water and brine. The organic layers were dried over $MgSO_4$, filtered and concentrated under reduced pressure to give 3-methyl-1H-pyrazolo[3,4-b]pyridine (XIV) as a white solid (192 mg, 1.44 mmol, 72% yield). $^1H$ NMR ($CDCl_3$) δ ppm 2.64 (s, 3H), 7.14 (dd, J=8.01 Hz, J=4.62 Hz, 1H), 8.14 (dd, J=7.54 Hz, J=1.88 Hz, 1H), 8.59 (dd, J=4.52 Hz, J=1.32 Hz, 1H), 11.68 (brs, 1H).

Step 4

To a solution of NaOH (0.88 g, 22 mmol) in water (20 mL) was added 3-methyl-1H-pyrazolo[3,4-b]pyridine (XIV) (0.4 g, 3 mmol). The suspension was heated at 80° C. until a clear solution was obtained. A solution of $KMnO_4$ (1.73 g, 11 mmol) in water (180 mL) was added slowly over 2 h while heating the solution at 80° C. The solution was heated at 90° C. for an additional 2 h until the complete disappearance of starting material was observed by TLC. The solution was cooled to 70° C. and filtered through a pad of Celite. The solids were washed by boiling water. The combined filtrate was cooled to 0° C., acidified with conc. $H_2SO_4$ to pH=2 and extracted with n-butanol (2×10 mL). The n-butanol layer was concentrated under reduced pressure to get a white residue which was dissolved in DCM by adding minimum amount of MeOH and then filtered. The filtrate was concentrated to give 1H-pyrazolo[3,4-b]pyridine-3-carboxylic acid (XV) as a white solid (390 mg, 2.39 mmol, 81% yield). $^1H$ NMR ($CDCl_3$) δ ppm 7.37 (dd, J=8.10 Hz, J=4.52 Hz, 1H), 8.47 (dd, J=7.54 Hz, J=1.88 Hz, 1H), 8.62 (dd, J=4.52 Hz, J=1.32 Hz, 1H), 14.37 (brs, 1H).

Step 5

To a solution of 1H-pyrazole[3,4-b]pyridine-3-carboxylic acid (XV) (0.39 g, 2.4 mmol) in dry MeOH (10 mL) was added concentrated $H_2SO_4$ (4 drops) and refluxed for 6 h under nitrogen. The solution was cooled and the solvent was evaporated under vacuum. The residue was partitioned between DCM and saturated aqueous $NaHCO_3$ solution. The organic layer was separated, dried over $MgSO_4$, filtered and concentrated under reduced pressure. The crude product was purified on a flash silica gel column (100% DCM→3:97 MeOH:DCM) to produce methyl 1H-pyrazolo[3,4-b]pyridine-3-carboxylate (XVI) as a white solid (382 mg, 2.16 mmol, 90% yield). $^1H$ NMR ($CDCl_3$) δ ppm 4.08 (s, 3H), 7.38 (m, 1H), 8.63 (dd, J=8.10 Hz, J=1.51 Hz, 1H), 8.72 (dd, J=4.62 Hz, J=1.41 Hz, 1H); ESIMS found for $C_8H_7N_3O_2$ m/z 178.2 (M+H).

Step 6

A mixture of methyl 1H-pyrazolo[3,4-b]pyridine-3-carboxylate (XVI) (0.177 g, 1 mmol), sodium acetate (0.492 g, 6 mmol) and bromine (0.308 mL, 6 mmol) in glacial acetic acid (5 mL) was heated overnight at 120° C. in a sealed tube. The solution was cooled and poured into water. The solids formed were filtered, washed with water and dried at room temperature under vacuum. The crude product was purified on a flash silica gel column (100% DCM→2:98 MeOH:DCM) to produce methyl 5-bromo-1H-pyrazolo[3,4-b]pyridine-3-carboxylate (XVII) as a white solid (78 mg, 0.31 mmol, 30% yield). $^1H$ NMR ($CDCl_3$) δ ppm 3.95 (s, 3H), 8.62 (d, J=3.01 Hz, 1H), 8.73 (d, J=3.01 Hz, 1H); ESIMS found for $C_8H_6BrN_3O_2$ m/Z 256.3 (M+H).

Step 7

A suspension of methyl 5-bromo-1H-pyrazolo[3,4-b]pyridine-3-carboxylate (XVII) (70 mg, 0.27 mmol) in aqueous 1N NaOH solution (20 mL) was heated at 90° C. for 3 h until the solution became clear. The solution was then cooled to 0° C. and acidified with a 10% HCl solution. The solids formed were filtered, washed with cold water and dried at room temperature under vacuum to give 5-bromo-1H-pyrazolo[3,4-b]pyridine-3-carboxylic acid (XVIII) as a white solid (60 mg, 0.25 mmol, 92% yield). $^1H$ NMR ($CDCl_3$) δ ppm 8.58 (d, J=3.01 Hz, 1H), 8.66 (d, J=3.01 Hz, 1H); ESIMS found for $C_7H_4BrN_3O_2$ m/z 242.1 (M+H).

Step 8

To a solution of 5-bromo-1H-pyrazole[3,4-b]pyridine-3-carboxylic acid (XVIII) (0.242 g, 1 mmol) in dry DMF (5 mL) was added CDI (0.178 g, 1.1 mmol) and heated for 3 h at 65° C. under nitrogen. The solution was cooled to room temperature and N,O-dimethyl hydroxylamine hydrochloride (0.107 g, 1.1 mmol) was added to the solution. The solution was again heated for 3 h at 65° C. under nitrogen. The solution was cooled and the solvent was evaporated under reduced pressure. The residue was dissolved in DCM, washed successively with a 10% HCl solution, a saturated aqueous $NaHCO_3$ solution and brine. The organic phase was dried over $MgSO_4$, filtered and concentrated under reduced pressure to produce 5-bromo-N-methoxy-N-methyl-1H-pyrazolo[3,4-b]pyridine-3-carboxamide (XIX) as a white solid (260 mg, 0.91 mmol, 92% yield). $^1H$ NMR ($CDCl_3$) δ ppm 3.55 (s, 3H), 3.78 (s, 3H), 8.59 (d, J=3.01 Hz, 1H), 8.67 (d, J=3.01 Hz, 1H); ESIMS found for $C_9H_9BrN_4O_2$ m/z 285.4 (M+H).

Step 9

To a solution of 5-bromo-N-methoxy-N-methyl-1H-pyrazolo[3,4-b]pyridine-3-carboxamide (XIX) (0.250 g, 0.88 mmol) in dry DCM (10 mL) was added 3,4-dihydro-2H-pyran (0.179 mL, 1.98 mmol) and PPTS (22 mg, 0.08 mmol) and refluxed 5 h under nitrogen. Another equivalent of 3,4-dihydro-2H-pyran (0.179 mL, 1.98 mmol) and PPTS (22 mg, 0.08 mmol) was added and the solution was further heated at refluxed overnight under nitrogen. The solution was cooled, diluted with DCM, washed subsequently with a saturated aqueous $NaHCO_3$ solution and brine. The organic layer was dried over $MgSO_4$, filtered and concentrated under reduced pressure to give 5-bromo-N-methoxy-N-methyl-1-(tetrahydro-2H-pyran-2-yl)-1H-pyrazolo[3,4-b]pyridine-3-carboxamide (XX) as a viscous liquid (302 mg, 0.82 mmol, 93% yield). $^1H$ NMR ($CDCl_3$) δ ppm 1.51-1.62 (m, 2H), 1.91-2.13 (m, 2H), 2.33-2.44 (m, 2H), 3.40 (s, 3H), 3.66 (m, 1H), 3.75 (s, 3H), 3.87-3.98 (m, 1H), 6.07 (dd, J=10.07 Hz, J=2.52 Hz, 1H), 8.57 (d, J=3.01 Hz, 1H), 8.73 (d, J=3.01 Hz, 1H); ESIMS found for $C_{14}H_{17}BrN_4O_3$ m/z 369.4 (M+H).

Step 10

To a solution of 5-bromo-N-methoxy-N-methyl-1-(tetrahydro-2H-pyran-2-yl)-1H-pyrazolo[3,4-b]pyridine-3-carboxamide (XX) (0.290 g, 0.78) in dry THF (5 mL) stirred at 0° C. under nitrogen was added lithium aluminum hydride (36 mg, 0.94 mmol). The solution was further stirred at 0° C. for 30 min. The reaction was quenched with a 0.4 N $NaHSO_4$ solution (10 mL). The solution was extracted with DCM (3×15 mL). The combined organic layer was washed subsequently with water and brine. The organic layer was dried over $MgSO_4$, filtered and concentrated under reduced pressure to produce 5-bromo-1-(tetrahydro-2H-pyran-2-yl)-1H-pyrazolo[3,4-b]pyridine-3-carbaldehyde (III) as a viscous liquid (218 mg, 0.70 mmol, 91% yield). $^1H$ NMR ($CDCl_3$) δ ppm 1.52-1.74 (m, 2H), 1.95-2.18 (m, 2H), 2.37-2.49 (m, 2H) 3.87-3.98 (m, 1H), 3.99 (m, 1H), 6.18 (dd, J=10.20 Hz, J=2.39 Hz, 1H), 8.73 (d, J=3.01 Hz, 1H), 8.85 (d, J=3.01 Hz, 1H), 10.16 (s, 1H); ESIMS found for $C_{12}H_{12}BrN_3O_2$ m/z 310.4 (M+H).

Synthesis of intermediate 5-bromo-1-trityl-1H-pyrazolo[3,4-b]pyridine-3-carbaldehyde (XI) is depicted below in Scheme 4.

Scheme 4

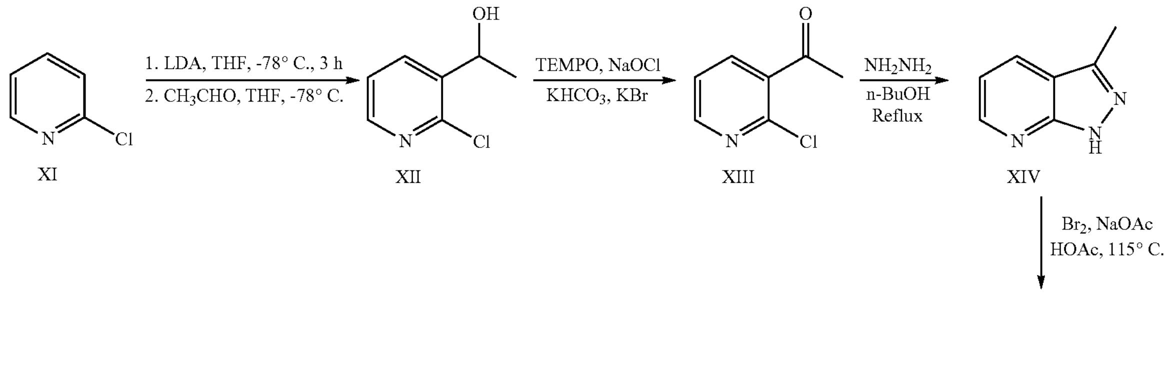

XI XII XIII XIV

-continued

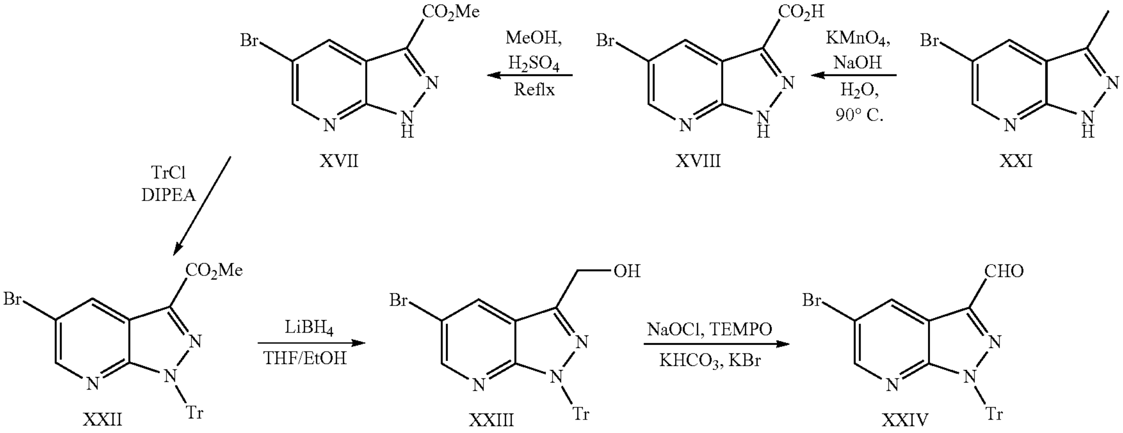

XVII XVIII XXI XXII XXIII XXIV

Step 1-2

To a solution of 2-chloropyridine (XI) (31.0 kg, 273 mol) in dry THF (275 L) cooled to −78° C. under nitrogen was added LDA (113 L, 1220 mol) dropwise while maintaining the temperature at −78° C. and stirred for 5 hours. Acetaldehyde (16 L, 463 mol) was then added and the reaction was stirred at −78° C. for another 5 hours before warming to 0° C. and adding water (310 L) to quench the reaction. The solution was stirred for 50 min and then warmed to room temperature. The solution was extracted 3×EtOAc (279 L) by adding EtOAc, stiffing for 50 min, allowing to stand for 50 min, separating the layers and then repeating twice. The combined EtOAc was concentrated under vacuum to a volume of 300-500 L. To the crude 1-(2-chloropyridin-3-yl)ethanol (XII) was added DCM (705 L) followed by an aqueous solution of KBr (3.3 Kg, 27.7 mol) dissolved in water (33 L). The solution was cooled to 0° C. before adding TEMPO (1.7 Kg, 10.9 mol) and then stirred for 50 min. In a second container, water (980 L) was added followed by $KHCO_3$ (268 Kg, 2677 mol) and 10% aqueous NaClO (233 L, 313 mol). This aqueous mixture was then added dropwise to the TEMPO mixture. This combined mixture was stirred at 0° C. for 5 hours. To this mixture was added dropwise $Na_2S_2O_3.7H_2O$ (22.5 Kg, 90 mol) in water (107 L) with stirring for 50 min at 0° C. The mixture was allowed to warm to room temperature and the organic phase was separated. The aqueous phase was extracted 2×DCM (353 L) by adding DCM, stirring for 50 min, allowing to stand for 50 min, separating the layers and then repeating. The combined organic layers were washed with aqueous 25% NaCl (274 L) and concentrated under vacuum to give crude 1-(2-chloropyridin-3-yl)ethanone (XIII) which was used for the next step without additional purification.

Step 3

To a solution of the above crude 1-(2-chloropyridin-3-yl) ethanone (XIII) in n-BuOH (512 L) was added 85% hydrazine hydrate (78 L, 1360 mol). The reaction was heated at refluxed (~120° C.) for 48 hours. The reaction was cooled and evaporated under vacuum. The crude material was taken up in DCM (834 L) and washed with 2× aqueous 25% NaCl (214 L) by adding aqueous 25% NaCl, stirring for 50 min, allowing to stand for 50 min, separating the layers and then repeating. The organic layer was evaporated to produce 3-methyl-1H-pyrazolo[3,4-b]pyridine (XIV) as a solid (13.2 Kg, 99 mol, 94.1% purity, 36.3% assay yield for 3 steps). $^1H$ NMR (DMSO-$d_6$, 400 MHz) δ ppm 2.50 (s, 3H), 7.13 (dd, J=4.4 Hz, J=8 Hz, 1H), 8.19 (dd, J=1.2 Hz, J=8 Hz, 1H), 8.47 (dd, J=1.6 Hz, J=4.8 Hz, 1H), 13.18 (brs, 1H); ESIMS found $C_7H_7N_3$ m/z 133.8 (M+H).

Step 4

To a solution of 3-methyl-1H-pyrazolo[3,4-b]pyridine (XIV) (12.7 Kg, 95.4 mol) in HOAc (57 L) was added NaOAc (20.4 Kg, 248 mol), water (13.3 L), and $Br_2$ (40 L, 780 mol). The reaction was stirred at room temperature for 5 hours and then at 115° C. for 6 hours. The reaction was cooled to room temperature and diluted with DCM (686 L). To this solution was added water (508 L) and cooled to 0° C. followed by dropwise addition of aqueous 30% NaOH while maintaining the temperature <20° C. under pH=9. The mixture was filtered through diatomaceous earth (14 Kg) followed by washing the diatomaceous earth with 3×DCM (50 L). The organic layer was separated, washed with aqueous 25% NaCl (200 L) and concentrated under vacuum to a volume of 70 L. The product was crystallized by charging the solution with 3×n-heptane (88 L) while concentrating the volume to 70 L after each addition of n-heptane. The solid was filtered and washed 3×n-heptane (22 L). The solid was dried under vacuum at 45° C. to yield 5-bromo-3-methyl-1H-pyrazolo[3,4-b]pyridine (X) (9.8 Kg, 46.2 mol, 92.6% purity, 48.4% assay yield). $^1H$ NMR (DMSO-$d_6$, 400 MHz) δ ppm 2.48 (s, 3H), 8.50-8.55 (m, 2H), 13.42 (brs, 1H); ESIMS found $C_7H_6BrN_3$ m/z 213.7 (M+H).

Step 5

To a solution of NaOH (27 Kg, 675 mol) in water (617 L) was added 5-bromo-3-methyl-1H-pyrazolo[3,4-b]pyridine (XXI) (9.8 Kg, 46.2 mol). The solution was heated at 90° C. for 3 hours under nitrogen before adding a solution of $KMnO_4$ (53.6 Kg, 339 mol) in water (870 L) slowly over 2 hours. The reaction was heated at 95° C. for 5 hours under nitrogen. The solution was cooled to 75° C. and filtered through diatomaceous earth (11 Kg) followed by washing the diatomaceous earth with water (150 L) heated at 75° C. The solution was cooled to 0° C. under nitrogen before the pH was adjusted to 1 with aqueous 35% HCl (~75 L). The solution was warmed to room temperature before adding n-BuOH (473 L) which was stirred for 25 min and then the organic layer was separated. n-BuOH (473 L) was again added to the aqueous layer, stirred for 25 min and separated. The combined organic phases were concentrated under vacuum to a volume of ~54 L. The n-BuOH was removed by adding to the solution 9×n-heptane (78 L) dropwise over 1 hour and then concentrating the volume to ~54 L after each addition of n-heptane. The solid was filtered and washed 3×n-heptane (17 L). The solid was dried under vacuum at 45° C. to give 5-bromo-1H-pyrazolo[3,4-b]pyridine-3-carboxylic acid (XVIII) (3.2 Kg, 13.2 mol, 64.4% purity, 29.0% assay yield). $^1H$ NMR (DMSO-$d_6$, 400 MHz) δ ppm 8.57 (d, J=2.4 Hz, 1H), 8.71 (d, J=2 Hz, 1H), 13.45 (brs, 1H), 14.65 (s, 1H); ESIMS found $C_7H_4BrN_3O_2$ m/z 243.8 (M+H).

Step 6

To a solution of 5-bromo-1H-pyrazolo[3,4-b]pyridine-3-carboxylic acid (XVIII) (1.6 Kg, 6.6 mol) in anhydrous MeOH (32 L) was added $H_2SO_4$ (160 mL). The reaction was slowly heated to 70° C. and stirred for 20 hours. The solution was concentrated under vacuum to a volume of 1.6 L. The residue was partitioned between DCM (120 L) and aqueous 10% $NaHCO_3$ (32 L). The organic phase was separated and washed with aqueous 25% NaCl (32 L), dried over $Na_2SO_4$ and concentrated to a volume of 4.8 L. The product was crystallized by charging the solution with 3×n-heptane (8 L) while concentrating the volume to 4.8 L after each addition of n-heptane. The solid was filtered and dried under vacuum at 50° C. to produce methyl 5-bromo-1H-pyrazolo[3,4-b]pyridine-3-carboxylate (XVII) (1.53 Kg, 6.0 mol, 80.6% purity, 90.4% assay yield). $^1$H NMR (DMSO-$d_6$, 400 MHz) δ ppm 3.95 (s, 3H), 8.62 (d, J=2 Hz, 1H), 8.73 (d, J=2.4 Hz, 1H), 14.78 (brs, 1H); ESIMS found $C_8H_6BrN_3O_2$ m/z 256.0 (M+H).

Step 7

To a solution of methyl 5-bromo-1H-pyrazolo[3,4-b]pyridine-3-carboxylate (XVII) (2.92 Kg, 11.4 mol) in anhydrous DCM (88 L) was added TEA (2.38 L, 17.1 mol). The solution was cooled to 0° C. before adding dropwise a solution of TrCl (4.0 Kg, 14.3 mol) in anhydrous DCM (51 L). The solution was warmed to room temperature and stirred for 20 hours. The reaction was then washed once with water (29 L), once with aqueous 25% NaCl (29 L), dried over $Na_2SO_4$ and concentrated to a volume of 3.0 L to give methyl 5-bromo-1-trityl-1H-pyrazolo[3,4-b]pyridine-3-carboxylate (XXII) (5.69 Kg, 11.4 mol, 77.3% purity, 99.5% assay yield). $^1$H NMR (DMSO-$d_6$, 400 MHz) δ ppm 3.91 (s, 3H), 7.19 (d, J=8.4 Hz, 5H), 7.21-7.32 (m, 10H), 8.45 (d, J=2.4 Hz, 1H), 8.61 (d, J=2 Hz, 1H); ESIMS found $C_{27}H_{20}BrN_3O_2$ m/z 520.0 (M+Na).

Step 8

To a solution of methyl 5-bromo-1-trityl-1H-pyrazolo[3,4-b]pyridine-3-carboxylate (XXII) (4.16 Kg, 8.3 mol) in anhydrous THF (62 L) cooled to 10° C. was added anhydrous EtOH (0.97 L, 16.6 mol) and $LiBH_4$ (271 g, 12.5 mol). The reaction was warmed to room temperature and stirred for 24 hours. The solution was concentrated under vacuum to a volume of 4 L then taken up in DCM (80 L). The pH was then adjusted to 8.0 by dropwise addition of aqueous 0.4N HCl (~280 L). The organic layer was separated and washed with aqueous 25% NaCl (28 L) and then concentrated under vacuum to a volume of 4 L to produce (5-bromo-1-trityl-1H-pyrazolo[3,4-b]pyridin-3-yl)methanol (XXIII) (3.9 Kg, 8.3 mol, 82.3% purity, 100% assay yield). $^1$H NMR (DMSO-$d_6$, 400 MHz) δ ppm 4.70 (d, J=6 Hz, 2H), 5.49 (t, J=6 Hz, 1H), 7.19 (d, J=7.2 Hz, 5H), 7.20-7.35 (m, 10H), 8.31 (d, J=2.4 Hz, 1H), 8.51 (d, J=2.4 Hz, 1H); ESIMS found $C_{26}H_{20}BrN_3O$ m/z 492.0 (M+Na).

Step 9

To a solution of (5-bromo-1-trityl-1H-pyrazolo[3,4-b]pyridin-3-yl)methanol (XXIII) (4.05 Kg, 8.6 mol) in DCM (97 L) was added a solution of KBr (205 g, 1.72 mol) in water (4 L). The solution was cooled to 0° C. before adding TEMPO (107.5 g, 688 mmol) and stirring for 30 min. To this solution was added a solution of $KHCO_3$ (10.8 Kg, 107.4 mol) and aqueous 7% NaClO (13.4 L) in water (40 L). The reaction was stirred at 0° C. for 18 hours. A solution of $Na_2S_2O_3$.5$H_2O$ (1.4 Kg, 5.7 mol) in water (9.1 L) was added dropwise to the reaction at 0° C. and stirred for 30 min. The aqueous layer was then separated and washed with DCM (48 L). The combined organic phases were washed with aqueous 25% NaCl (48 L), dried over $Na_2SO_4$, filtered and concentrated under vacuum. The residue was co-evaporated with 3×MeOH (20 L) and the solid was washed with 2×n-heptane (8 L). The solid was dried under vacuum at 45° C. to give 5-bromo-1-trityl-1H-pyrazolo[3,4-b]pyridine-3-carbaldehyde (XXIV) (3.25 Kg, 6.94 mol, 92.3% purity, 80.6% assay yield). $^1$H NMR ($CDCl_3$, 400 MHz) δ ppm 7.19 (d, J=6 Hz, 5H), 7.22-7.34 (m, 10H), 8.28 (d, J=2.4 Hz, 1H), 8.70 (d, J=2.4 Hz, 1H), 10.07 (s, 1H); ESIMS found $C_{26}H_{18}BrN_3O$ m/z 490.0 (M+Na).

Preparation of intermediate N-(5-bromopyridin-3-yl)-2,2,2-trifluoroacetamide (XXVI) is depicted below in Scheme 5.

Scheme 5

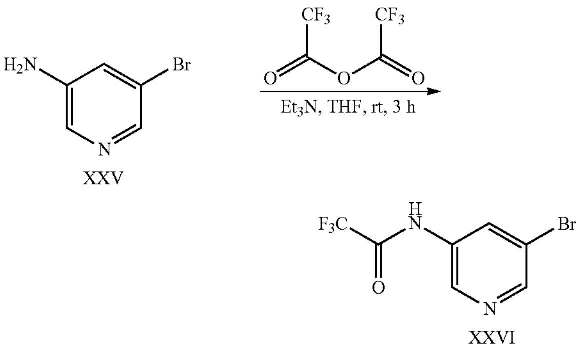

XXV

XXVI

Step 1

To a solution of 5-bromopyridin-3-amine (XXV) (1.0 g, 5.78 mmol) in dry THF (20 mL) under argon was added TEA (0.826 mL, 6.35 mmol) and dropwise trifluoroacetic anhydride (0.902 mL, 6.35 mmol). The solution was stirred at room temperature for 3 h. The reaction was poured into ice water, basified by saturated aqueous $NaHCO_3$, and then extracted with EtOAc. The combined organic phases were dried over $MgSO_4$, concentrated and concentrated under vacuum to yield N-(5-bromopyridin-3-yl)-2,2,2-trifluoroacetamide (XXVI) as an off-white solid (1.5 g, 5.60 mmol, 96% yield). $^1$H NMR (DMSO-$d_6$, 500 MHz) δ ppm 8.36 (t, J=2 Hz, 1H), 8.58 (d, J=2 Hz, 1H), 8.81 (d, J=2 Hz, 1H), 11.57, (brs, 1H); ESIMS found $C_7H_4BrF_3N_2O$ m/z 269.0 (M+H).

The following intermediate was prepared in accordance with the procedure described in the above Scheme 5.

XXVII

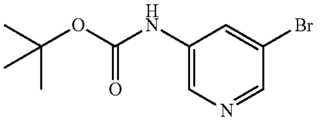

tent-Butyl 5-bromopyridin-3-ylcarbamate (XXVII): Brown viscous oil (421 mg, 1.54 mmol, 23% yield). $^1$H NMR (DMSO-$d_6$, 500 MHz) δ ppm 1.48 (s, 9H), 8.17-8.18 (m, 1H), 8.29 (d, J=2 Hz, 1H), 8.56 (d, J=2 Hz, 1H), 9.82 (s, 1H); ESIMS found $C_{10}H_{13}BrN_2O_2$ m/z 273 (M+H).

Preparation of intermediate N-(5-bromopyridin-3-yl)pivalamide (XXIX) is depicted below in Scheme 6.

Scheme 6

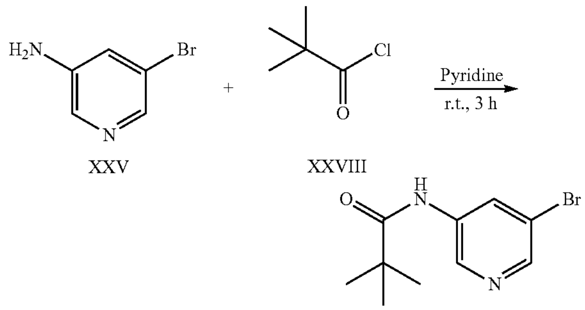

XXV XXVIII XXIX

Step 1

To a solution of 3-amino-5-bromo pyridine (XXV) (1.0 g, 5.78 mmol) in dry pyridine (10 mL) was added pivaloyl chloride (XXVIII) (769 mg, 6.38 mmol). The reaction mixture was stirred at room temperature for 3 h. The reaction was poured into an ice water/saturated aqueous $NaHCO_3$ mixture and stirred for 30 min. The precipitate was filtered, washed with cold water and dried at room temperature to yield N-(5-bromopyridin-3-yl)pivalamide (XXIX) as an off-white solid (1.082 g, 4.22 mmol, 73.1% yield). $^1$H NMR (DMSO-$d_6$, 500 MHz) δ ppm 1.23 (s, 9H), 8.37 (d, J=2 Hz, 1H), 8.39 (t, J=2 Hz, 1H), 8.80 (d, J=2 Hz, 1H), 9.58 (brs, 1H); ESIMS found $C_{10}H_{13}BrN_2O$ m/z 257.0 (M+H).

The following intermediates were prepared in accordance with the procedure described in the above Scheme 6.

XXX

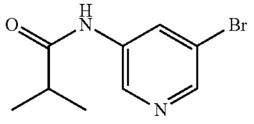

N-(5-Bromopyridin-3-yl)isobutyramide (XXX): Off-white solid, (71% yield). $^1$H NMR ($CDCl_3$) δ ppm 8.55-8.35 (m, 3H), 7.32 (s, 1H), 2.59-2.48 (m, 1H), 1.28-1.27 (d, 6H); ESIMS found $C_9H_{11}BrN_2O$ m/z 243.05 (M+H).

XXXI

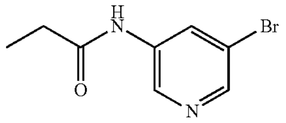

N-(5-Bromopyridin-3-yl)propionamide (XXXI): Off white solid (92% yield). $^1$H NMR (DMSO-$d_6$) δ ppm 1.09 (t, J=7.54 Hz, 3H), 2.36 (q, J=7.54 Hz, 2H), 8.36 (m, 2H), 8.65 (d, J=2.07 Hz, 1H), 10.26 (s, 1H); ESIMS found $C_8H_9BrN_2O$ m/z 231 (M+H).

XXXII

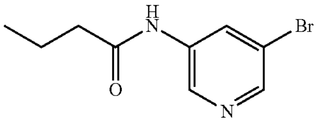

N-(5-Bromopyridin-3-yl)butyramide (XXXII): Yellow solid (2.1 g, 8.64 mmol, 88.8% yield). ESIMS found $C_9H_{11}BrN_2O$ m/z 243 (M+H).

XXXIII

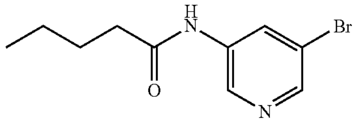

N-(5-Bromopyridin-3-yl)pentanamide (XXXIII): Yellow solid (2.0 g, 7.78 mmol, 85.3% yield). ESIMS found $C_{10}H_{13}BrN_2O$ m/z 257 (M+H).

XXXIV

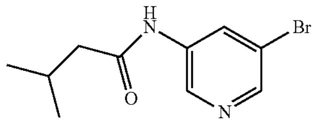

N-(5-Bromopyridin-3-yl)-3-methylbutanamide (XXXIV): Off white solid, (67% yield), $^1$H NMR ($CDCl_3$, 500 MHz) δ ppm 8.55-8.42 (m, 3H), 7.62 (s, 1H), 2.31-2.18 (m, 3H), 1.02-1.01 (d, J=6 Hz, 6H); ESIMS found $C_{10}H_{13}BrN_2O$ m/z 258.80 (M+H).

XXXV

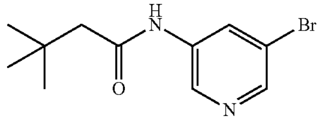

N-(5-Bromopyridin-3-yl)-3,3-dimethylbutanamide (VOW): Yellow solid (1.7 g, 6.27 mmol, 78.6% yield). ESIMS found $C_{11}H_{15}BrN_2O$ m/z 271 (M+H).

XXXVI

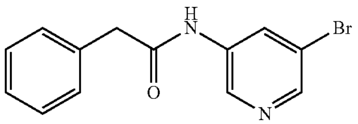

N-(5-Bromopyridin-3-yl)-2-phenylacetamide (XXXVI): White solid (2.5 g, 8.59 mmol, 77.9% yield). ESIMS found $C_{13}H_{11}BrN_2O$ m/z 291 (M+H).

XXXVII

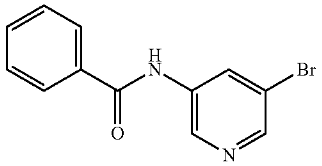

N-(5-Bromopyridin-3-yl)benzamide (XXXVII): White solid (2.7 g, 9.74 mmol, 60% yield). ESIMS found $C_{12}H_9BrN_2O$ m/z 277 (M+H).

XXXVIII

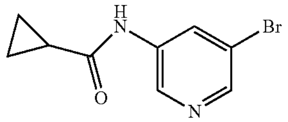

N-(5-Bromopyridin-3-yl)cyclopropanecarboxamide (XXXVIII): Off-white solid, (83% yield), $^1$H NMR ($CDCl_3$, 500 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for $C_9H_9BrN_2O$ m/z 240.9 (M+H).

XXXIX

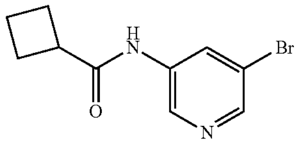

N-(5-Bromopyridin-3-yl)cyclobutanecarboxamide (XXXIX): Yellow solid (2.1 g, 6.27 mmol, 86.6% yield). ESIMS found $C_{10}H_{11}BrN_2O$ m/z 255 (M+H).

XL

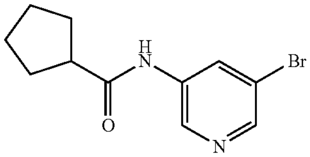

N-(5-Bromopyridin-3-yl)cyclopentanecarboxamide (XL): Yellow solid (1.9 g, 7.06 mmol, 80.2% yield). ESIMS found $C_{11}H_{13}BrN_2O$ m/z 269 (M+H).

XLI

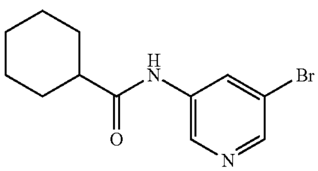

N-(5-bromopyridin-3-yl)cyclohexanecarboxamide (XLI): Yellow solid (2.0 g, 7.06 mmol, 84.3% yield). ESIMS found $C_{12}H_{15}BrN_2O$ m/z 283 (M+H).

Preparation of intermediate 5-bromo-N,N-dimethylpyridin-3-amine (XLIII) is depicted below in Scheme 7.

Scheme 7

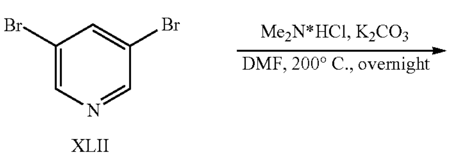

XLII

-continued

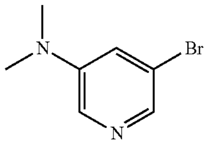

XLIII

Step 1

To a solution of 3,5-dibromopyridine (XLII) (2.37 g, 10.0 mmol) in dry DMF (20.0 mL) was added $K_2CO_3$ (4.5 g, 33 mmol) and dimethylamino hydrochloride (1.79 g, 22 mmol). The mixture was heated overnight at 200° C. in a sealed tube. The solution was cooled to room temperature and excess DMF was removed under vacuum. The residue was partitioned between EtOAc and water. The organic phase was separated. The aqueous phase was washed with EtOAc and the combined organic phases were dried over $MgSO_4$, and concentrated to afford 5-bromo-N,N-dimethylpyridin-3-amine (XLIII) as an off-white solid (1.78 g, 8.85 mmol, 88% yield). $^1$H NMR (DMSO-$d_6$, 500 MHz) δ ppm 2.94 (s, 6H), 7.25 (t, J=2 Hz, 1H), 7.91 (d, J=2 Hz, 1H), 8.07 (d, J=2 Hz, 1H); ESIMS found $C_7H_9BrN_2$ m/z 201.1 (M+H).

The following intermediates were prepared in accordance with the procedure described in the above Scheme 7.

XLIV

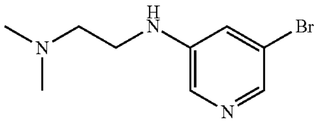

$N^1$-(5-bromopyridin-3-yl)-$N^2$,$N^2$-dimethylethane-1,2-diamine (XLIV): Brown viscous oil (326 mg, 1.33 mmol, 14% yield). $^1$H NMR (DMSO-$d_6$, 500 MHz) δ ppm 2.17 (s, 6H), 2.42 (t, J=6.4 Hz, 2H), 3.08-3.12 (m, 2H), 6.03 (t, J=5.2 Hz, 1H), 7.12-7.13 (m, 1H), 7.78 (d, J=2 Hz, 1H), 7.97 (d, J=2 Hz, 1H); ESIMS found $C_9H_{14}BrN_3$ m/z 244 (M+H).

XLV

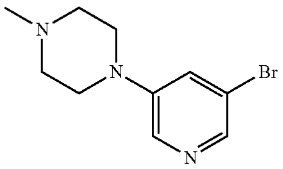

1-(5-bromopyridin-3-yl)-4-methylpiperazine (XLV): Brown viscous oil (815 mg, 3.18 mmol, 28% yield). $^1$H NMR (DMSO-$d_6$, 500 MHz) δ ppm 2.21 (s, 3H), 2.41-2.43 (m, 4H), 3.22-3.24 (m, 4H), 7.51-7.52 (m, 1H), 8.02 (d, J=2 Hz, 1H), 8.28 (d, J=2 Hz, 1H); ESIMS found $C_{10}H_{14}BrN_3$ m/z 256 (M+H).

Preparation of intermediate 5-bromo-N-isopropylpyridin-3-amine (XLVI) is depicted below in Scheme 8.

Scheme 8

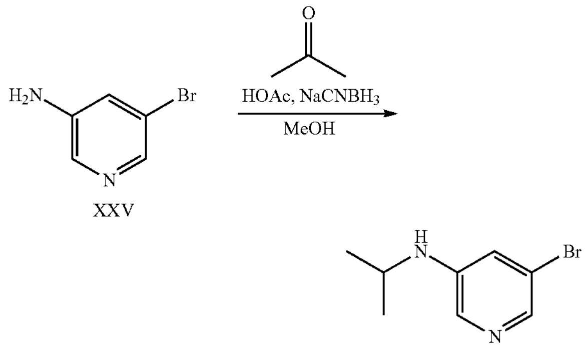

XXV

XLVI

Steps 1

To a solution of 5-bromopyridin-3-amine (XXV) (535 mg, 3.09 mmol) in MeOH (62 mL) was added acetone (296 μL, 4.02 mL). The pH was adjusted to 4 using HOAc and stirred for 30 min. $NaCNBH_3$ (272 mg, 4.33 mmol) was added and stirred at room temperature overnight. The MeOH was removed under vacuum and the residue was partitioned between EtOAc and saturated aqueous $NaHCO_3$. The organic layer was dried over $MgSO_4$ and evaporated under vacuum. The crude product was purified on a silica gel column (100% hexane→90:10 hexane:EtOAc) to produce 5-bromo-N-isopropylpyridin-3-amine (XLVI) as an oil which slowly solidified into an off-white solid (309 mg, 1.44 mmol, 47% yield). $^1$H NMR (DMSO-$d_6$, 500 MHz) δ ppm 1.12 (d, J=6.3 Hz, 6H), 3.55-3.59 (m, 1H), 6.03 (d, J=7.9 Hz, 1H), 7.05-7.06 (m, 1H), 7.75 (d, J=2 Hz, 1H), 7.90 (d, J=2 Hz, 1H); ESIMS found $C_8H_{11}BrN_2$ m/z 215 (M+H).

Preparation of intermediate 1-(5-bromopyridin-3-yl)-N,N-dimethylmethanamine (XLVIII) is depicted below in Scheme 9.

Scheme 9

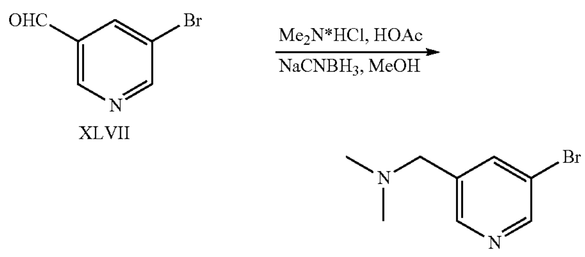

XLVII

XLVIII

Steps 1

Preparation of 1-(5-bromopyridin-3-yl)-N,N-dimethylmethanamine (XLVIII) was performed following the procedure listed in Scheme 6, Step 1. Brown oil (1.20 g, 5.59 mmol, 45% yield). $^1$H NMR (DMSO-$d_6$, 500 MHz) δ ppm 2.15 (s, 6H), 3.43 (s, 2H), 7.94 (s, 1H), 8.47 (d, J=1.1 Hz, 1H), 8.59 (d, J=2.2 Hz, 1H); ESIMS found $C_8H_{11}BrN_2$ m/z 215 ($M^{Br79}$+H) and 217 ($M^{Br81}$+H).

Preparation of intermediate N-(3-bromo-5-fluorobenzyl) methanesulfonamide (L) is depicted below in Scheme 10.

Scheme 10

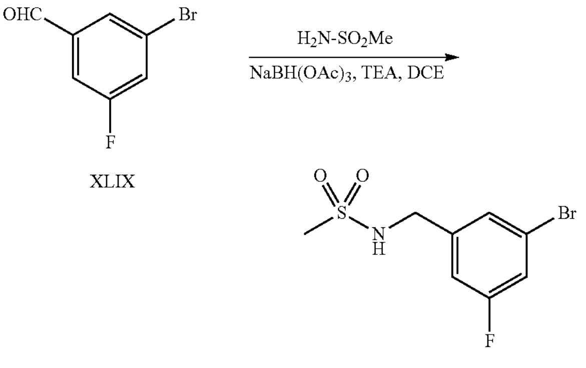

XLIX

L

Steps 1

Preparation of 3-bromo-5-fluorobenzaldehyde (XLIX) (2.03 g, 10.0 mmol) in DCE (50 mL) was added methanesulfonamide (1.43 g, 15.0 mmol) and TEA (2.79 mL, 20.0 mmol). The solution was stirred for a few minutes before $NaBH(OAc)_3$ (3.00 g, 14.1 mmol) was added. The reaction was stirred at room temperature overnight. The solvent was removed under vacuum and the residue was partitioned between EtOAc and water. The organic layer was separated, dried over $MgSO_4$ and evaporated under vacuum to give N-(3-bromo-5-fluorobenzyl)methanesulfonamide (L) as a clear oil (2.65 g, 9.39 mmol, 99% yield). ESIMS found $C_8H_9BrFNO_2S$ m/z 282 (M+H).

The following intermediates were prepared in accordance with the procedure described in the above Scheme 9 or Scheme 10.

LI

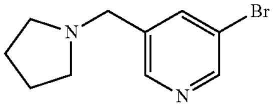

3-Bromo-5-(pyrrolidin-1-ylmethyl)pyridine (LI): Golden liquid (1.35 g, 97% yield). $^1$H NMR (DMSO-$d_6$) 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for $C_{10}H_{13}BrN_2$ m/z 242 (M+H).

LII

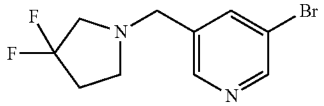

3-Bromo-5-((3,3-difluoropyrrolidin-1-yl)methyl)pyridine (LII): Brown oil (6.4 g, 81% yield). ESIMS found for $C_{10}H_{11}BrF_2N_2$ m/z 277.0 (M+H).

LIII

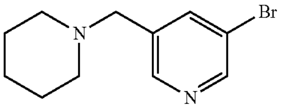

3-Bromo-5-(piperidin-1-ylmethyl)pyridine (LIII): Brown liquid (13.1 g, 94% yield). $^1$H NMR (DMSO-$d_6$) 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for $C_{11}H_{15}BrN_2$ m/z 257 (M+H).

LIV

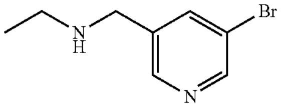

N-((5-Bromopyridin-3-yl)methyl)ethanamine (LIV): Golden liquid (1.29 g, 6.00 mmol, 60% yield). ESIMS found for $C_8H_{11}BrN_2$ m/z 215 (M+H).

LV

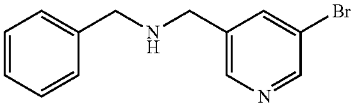

N-Benzyl-1-(5-bromopyridin-3-yl)methanamine (LV): Golden liquid (77 mg, 0.28 mmol, 25% yield). ESIMS found for $C_{13}H_{13}BrN_2$ m/z 277 (M+H).

Preparation of intermediate tert-butyl (5-bromopyridin-3-yl)methyl (cyclopentylmethyl)carbamate (LX) is depicted below in Scheme 11.

Step 2

To a stirred solution of (5-bromopyridin-3-yl)methanol (LVI) (1.60 g, 8.5 mmol, 1 eq), phthalimide (1.24 g, 8.5 mmol, 1 eq) and $PPh_3$ (3.33 g, 12.75 mmol, 1.5 eq) in anhydrous THF (15 mL) was added DEAD (2.21 g, 12.75 mmol, 1.5 eq) dropwise at 0° C. under $N_2$. Then the reaction mixture was stirred at room temperature for 6 h. The mixture was washed with saturated $NaHCO_3$ solution (15 mL), water (15 mL) and brine (15 mL) subsequently. The organic layers were dried over $MgSO_4$, concentrated under reduced pressure, the resultant residue was purified by flash chromatography on silica gel (PE:EtOAc=4:1) to give 2-((5-bromopyridin-3-yl)methyl)isoindoline-1,3-dione (LVII) (2.5 g, 7.88 mmol, 82.3% yield) as a white solid. ESIMS found for $C_{14}H_9BrN_2O_2$ m/z 317 (M+H).

Step 3

A solution of 2-((5-bromopyridin-3-yl)methyl)isoindoline-1,3-dione (LVII) (1.9 g, 6.0 mmol, 1 eq) and hydrazine hydrate (2.0 g, 40 mmol, 6 eq) in EtOH (20 mL) was heated at 70° C. for 3 h. The mixture was filtered through a Celite® pad and the filtrate was concentrated in vacuo, the crude product was dissolved in 1N HCl solution (15 mL) and concentrated to dryness, then it was washed with acetone (10 mL×3), the precipitate was collected by filtration, dried in Scheme 11

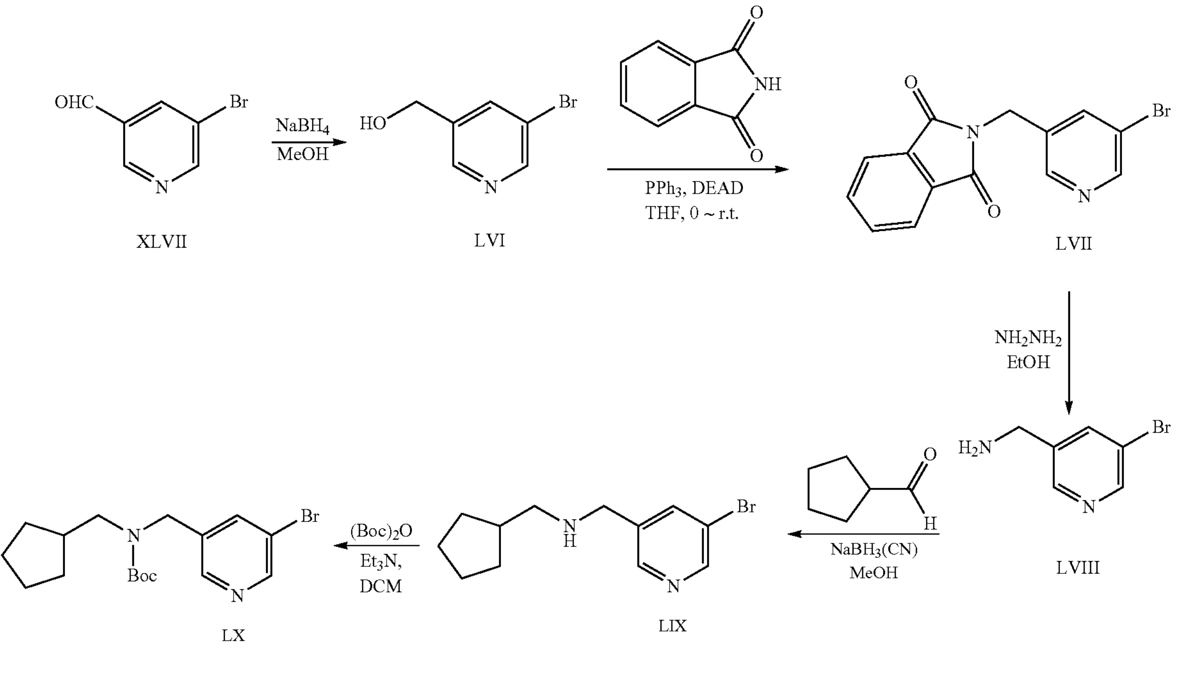

Step 1

To a solution of 5-bromonicotinaldehyde (XLVII) (2.0 g, 10.8 mmol, 1 eq) in MeOH (20 mL) was added $NaBH_4$ (2.4 g, 64.9 mmol, 6 eq) and the reaction mixture was stirred at room temperature for 3 h. The mixture was concentrated in vacuo and the residue was diluted in water (15 mL), the aqueous phase was extracted with DCM (10 mL×3). The combined organic layers were dried over $MgSO_4$, filtered and concentrated in vacuo to afford (5-bromopyridin-3-yl)methanol (LVI) (1.8 g, 9.57 mmol, 90.0% yield) as a colorless oil. $^1H$ NMR ($CDCl_3$, 500 MHz) δ ppm 4.73 (s, 2H), 7.90 (s, 1H), 8.47 (s, 1H), 8.57 (s, 1H). ESIMS found for $C_6H_6BrNO$ m/z 188 (M+H).

vacuo to give (5-bromopyridin-3-yl)methanamine (LVIII) (1.3 g, 6.95 mmol, 97.7% yield) as a white solid. $^1H$ NMR ($D_2O$, 500 MHz) δ ppm 4.34 (s, 2H), 8.56 (s, 1H), 8.75 (d, J=1.2 Hz, 1H), 8.91 (d, J=1.6 Hz, 1H). ESIMS found for $C_6H_7BrN_2$ m/z 187 (M+H).

Step 4

A solution of (5-bromopyridin-3-yl)methanamine (LVIII) (1.30 g, 5.8 mmol, 1.0 eq), cyclopentanecarbaldehyde (0.57 g, 5.8 mmol, 1.0 eq) and TEA (0.60 g, 5.8 mmol, 1.0 eq) in MeOH (15 mL) was stirred at room temperature for 2 h. Then $NaBH_3CN$ (1.98 g, 34.6 mmol, 6.0 eq) was added and the mixture was stirred at the same temperature for another 3 h. The solvent was removed under reduced pressure and the residue was diluted in water (20 mL) and extracted with DCM (10 mL×3), combined organic layers were dried over $MgSO_4$ and concentrated in vacuo to give 1-(5-bromopyridin-3-yl)-N-(cyclopentylmethyl)methanamine (LIX) (1.23 g, 4.57 mmol, 79.3% yield) as a brown oil. ESIMS found for $C_{12}H_{17}BrN_2$ m/z 269 (M+H).

Step 5

To a solution of 1-(5-bromopyridin-3-yl)-N-(cyclopentylmethyl)methanamine (LIX) (1.00 g, 3.7 mmol, 1 eq) and TEA (0.93 g, 9.2 mmol, 2.5 eq) in DCM (20 mL) was added portionwise $(Boc)_2O$ (0.85 g, 4.0 mmol, 1.1 eq) at 0° C., the reaction mixture was stirred at room temperature for 1 h. The mixture was washed with water (10 mL), brine (10 mL), the organic layer was separated, dried over $MgSO_4$ and concentrated in vacuo to give tert-butyl (5-bromopyridin-3-yl)methyl (cyclopentylmethyl)carbamate (LX) (1.25 g, 3.38 mmol, 91.9% yield) as a white solid. ESIMS found for $C_{17}H_{25}BrN_2O_2$ m/z 369 (M+H).

Preparation of intermediate 1-(3-bromo-5-fluorophenyl)-4-methylpiperazine (LXII) is depicted below in Scheme 12.

Scheme 12

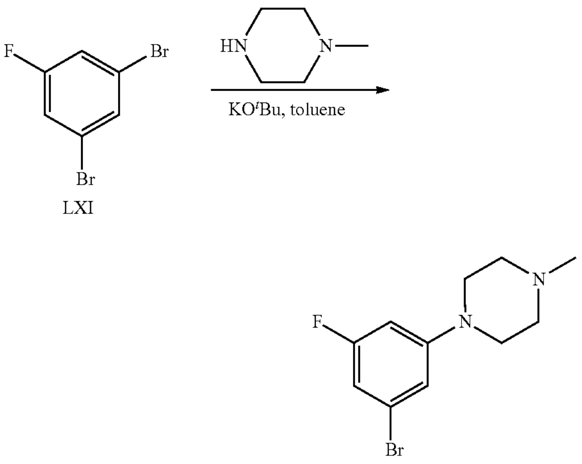

LXI

LXII

Step 1

To a solution of 1,3-dibromo-5-fluorobenzene (LXI) (2.0 g, 7.88 mmol) in toluene (20 ml) was added potassium t-butoxide (2.65 g, 23.6 mmol) and 1-methylpiperazine (1.75 mL, 15.8 mmol). The reaction was heated at 105° C. overnight. The toluene was removed under vacuum and the residue was dissolved in water and extracted with EtOAc. The organic phase was separated, washed with brine, dried over $MgSO_4$ and concentrated to dryness. The crude product was purified on a silica gel column (1:99 MeOH:$CHCl_3$→7:93 MeOH:$CHCl_3$) to produce 1-(3-bromo-5-fluorophenyl)-4-methylpiperazine (LXII) as an orange oil (800 mg, 2.93 mmol, 37.2% yield). $^1$H NMR (DMSO-$d_6$, 500 MHz) δ ppm 2.20 (s, 3H), 2.39 (t, J=5 Hz, 4H), 3.33 (t, J=5 Hz, 4H), 6.74-6.81 (m, 2H), 6.91 (s, 1H); ESIMS found for $C_{11}H_{14}BrFN_2$ m/z 273 (M+H).

The following intermediates were prepared in accordance with the procedure described in the above Scheme 12.

LXIII

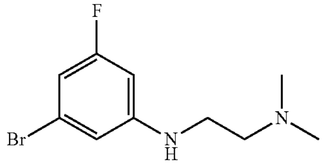

N1-(3-Bromo-5-fluorophenyl)-N2,N2-dimethylethane-1,2-diamine (LXIII) as an orange oil (800 mg, 3.06 mmol, 38.9% yield). $^1$H NMR (DMSO-$d_6$) δ ppm 1.28 (s, 6H), 2.39 (t, J=4 Hz, 2H), 3.07 (q, J=6 Hz, 2H), 6.10 (t, J=5 Hz, 1H), 6.38 (td, J=12 Hz, J=2 Hz, 1H), 6.51 (td, J=8.6 Hz, J=2 Hz, 1H), 6.61 (t, J=2 Hz, 1H); ESIMS found $C_{10}H_{14}BrFN_2$ m/z 262.9 (M+H$^{81Br}$).

LXIV

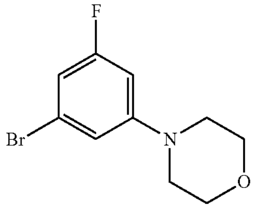

4-(3-Bromo-5-fluorophenyl)morpholine (LXIV) as a yellow oil (1.14 g, 4.38 mmol, 55.6% yield). $^1$H NMR (DMSO-$d_6$) δ ppm 3.16 (t, J=5 Hz, 4H), 3.70 (t, J=5 Hz, 4H), 6.79 (td, J=12.8 Hz, J=2 Hz, 1H), 6.83 (td, J=8 Hz, J=2 Hz, 1H), 6.93 (s, 1H); ESIMS found $C_{10}H_{11}BrFNO$ m/z 261.8 (M+H$^{81Br}$).

LXV

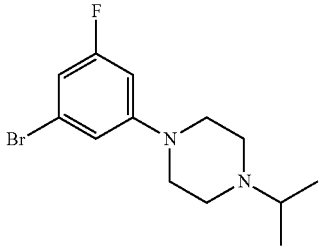

1-(3-Bromo-5-fluorophenyl)-4-isopropylpiperazine (LXV) as a light yellow oil (200 mg, 0.66 mmol, 34.1% yield). ESIMS found $C_{13}H_{18}BrFN_2$ m/z 301.1 (M+H$^{79Br}$).

LXVI

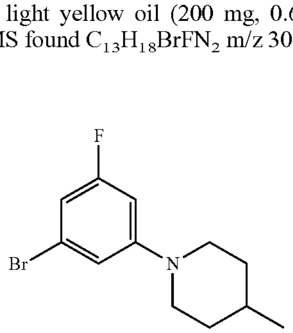

1-(3-Bromo-5-fluorophenyl)-4-methylpiperidine (LXVI) as a brown solid (870 mg, 3.20 mmol, 40.6% yield). $^1$H NMR (DMSO-$d_6$) δ ppm; ESIMS found $C_{12}H_{15}BrFN$ m/z 272.0 (M+H$^{79Br}$).

LXVII

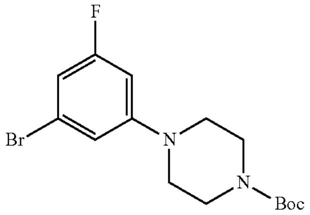

tert-Butyl 4-(3-bromo-5-fluorophenyl)piperazine-1-carboxylate (LXVII) as a yellow oil (232 mg, 0.65 mmol, 16.4% yield). ESIMS found $C_{15}H_{20}BrFN_2O_2$ m/Z 361.0 $(M+H^{81Br})$.

Preparation of intermediate 5'-fluoro-3,3'-bipyridine-4,5-diamine (LXXII) is depicted below in Scheme 13.

Scheme 13

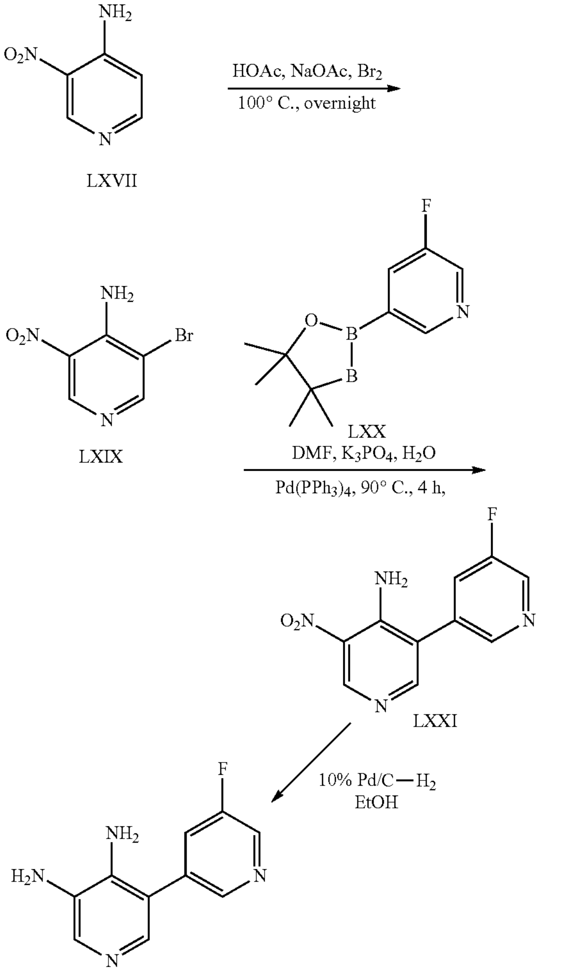

LXVII

LXIX

LXX

LXXI

LXXII

Step 1

A mixture of 3-nitropyridin-4-amine (LXVIII) (10 g, 71.88 mmol) and acetic acid (100 ml) was added to a sealed tube followed by addition of NaOAc (29.50 g, 359 mmol) and dropwise addition of bromine (4.43 ml 86.3 mmol) under stirring. The sealed tube was heated at 100° C. for overnight. The reaction mixture was concentrated under vacuum to obtain a solid which was dissolved in water, basified with saturated aqueous $NaHCO_3$ and extracted with DCM. The combined organic extracts were dried and concentrated to produce 3-bromo-5-nitropyridin-4-amine (LXIX) as a yellow solid (13.7 g, 62.8 mmol, 87% yield). $^1H$ NMR (DMSO-$d_6$, 500 MHz) δ ppm 8.58 (s, 1H), 9.19 (s, 1H); ESIMS found for $C_5H_4BrN_3O_2$ m/z 218.1 (M+H).

Step 2

A solution of 3-bromo-5-nitropyridin-4-amine (LXIX) (790 mg, 3.62 mmol), 3-fluoro-5-(4,4,5,5-tetramethyl-1,3,2-dioxaborolan-2-yl)pyridine (LXX) (1.01 g, 4.35 mmol), $K_3PO_4$ (1.15 g, 5.44 mmol), water (10 mL) and DMF (10 mL) was degassed with argon thrice. $Pd(PPh_3)_4$ (209 mg, 0.18 mmol) was added to the reaction and the solution was heated at 90° C. for 4 h. The reaction was passed through a pad of Celite and then concentrated under reduced pressure. The reaction mixture was concentrated and the residue was taken up in EtOAc. The organic extract was washed with water, dried and concentrated under vacuum. The crude product was purified on a silica gel column (100% $CHCl_3$→1.5:98.5 MeOH[7N $NH_3$]:$CHCl_3$) to give 5'-fluoro-5-nitro-3,3'-bipyridin-4-amine (LXXI) as a yellow solid (626 mg, 2.67 mmol, 74% yield). $^1H$ NMR (DMSO-$d_6$, 500 MHz) δ ppm 7.62 (brs, 2H), 7.86-7.89 (m, 1H), 8.15 (s, 1H), 8.47-8.48 (m, 1H), 8.67 (d, J=2.7 Hz, 1H), 9.07 (s, 1H); ESIMS found $C_{10}H_7FN_4O_2$ m/z 235 (M+H).

Step 3

To a solution of 5'-fluoro-5-nitro-3,3'-bipyridin-4-amine (LXXI) (621 mg, 2.65 mmol) in EtOH (18 mL) was added 10% Pd/C (93 mg, 15% by wt). The solution was purged with hydrogen and stirred for overnight at room temperature under hydrogen. The suspension was filtered through Celite and concentrated under vacuum. The crude product was purified through a silica gel column (100% $CHCl_3$→3:97MeOH[7N $NH_3$]:$CHCl_3$) to produce 5'-fluoro-3,3'-bipyridine-4,5-diamine (LXII) as an off-white solid (542 mg, 2.65 mmol, 100% yield). $^1H$ NMR (DMSO-$d_6$, 500 MHz) δ ppm 4.78 (brs, 2H), 5.28 (brs, 2H), 7.46 (s, 1H), 7.70 (s, 1H), 7.73-7.76 (m, 1H), 8.44-8.45 (m, 1H), 8.56 (d, J=2.8 Hz, 1H); ESIMS found $C_{10}H_9FN_4$ m/z 205 (M+H).

Preparation of intermediate 3,3'-bipyridine-4,5-diamine (LXXIV) is depicted below in Scheme 14.

Scheme 14

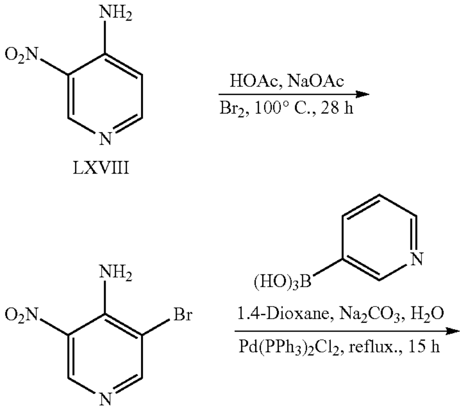

LXVIII

LXIX

-continued

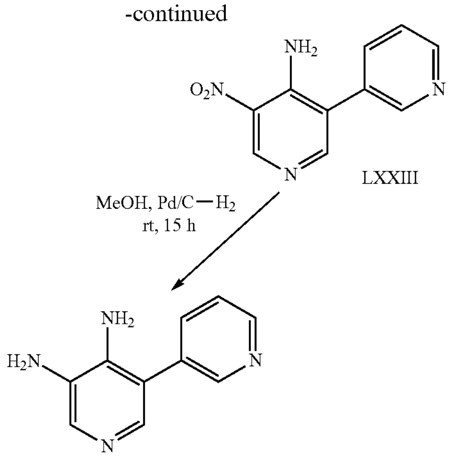

LXXIII

LXXIV

Step 1

A mixture of 3-nitropyridin-4-amine (LXVIII) (10 g, 71.94 mmol) and acetic acid (120 mL) was added to a sealed tube followed by addition of NaOAc (29.50 g, 93.52 mmol) and dropwise addition of bromine (4.7 ml 359.7 mmol) under stirring. The sealed tube was heated at 100° C. for 28 h until TLC showed consumption of starting material. The reaction mixture was concentrated to obtain a solid which was dissolved in water, basified with $NaHCO_3$ and extracted with EtOAc. The combined organic extracts were dried and concentrated to produce 3-bromo-5-nitropyridin-4-amine (LXIX) as a yellow solid (12 g, 55 mmol, 77% yield). $^1$H NMR (DMSO-$d_6$) δ ppm 9.19 (s, 1H), 8.58 (s, 1H); ESIMS found for $C_5H_4BrN_3O_2$ m/z 217, 219 (M+, M+2).

Step 2

A solution of 3-bromo-5-nitropyridin-4-amine (LXIX) (6 g, 26 mmol), pyridin-3-ylboronic acid (3.54 g, 29 mmol), 1N $Na_2CO_3$ solution (78 ml) and 1,4-dioxane (150 mL) was degassed with argon thrice. $Pd(PPh_3)_2Cl_2$ (927 mg, 5 mmol %) was added to the reaction and the solution was refluxed for 15 h until TLC showed the reaction was complete. The reaction was passed through a pad of Celite® and then concentrated under reduced pressure. The reaction mixture was concentrated and the residue was taken up in EtOAc. The organic extract was washed with water, dried and concentrated under vacuum. The crude product was purified on a silica gel column (100% EtOAc→2:98 MeOH:DCM) to give 5-nitro-3,3'-bipyridin-4-amine (LXXIII) as a yellow solid (5 g, 23.1 mmol, 87% yield). $^1$H NMR ($CDCl_3$, 500 MHz) δ ppm 9.31 (s, 1H), 8.80-8.79 (m, 1H), 8.70 (s, 1H), 8.23 (s, 1H), 7.80-7.73 (m, 1H), 7.52-7.48 (m, 1H). ESIMS found $C_{10}H_8N_4O_2$ m/z 216.95 (M+H).

Step 3

To a solution of 5-nitro-3,3'-bipyridin-4-amine (LXXIII) (5 g, 23 mmol) in MeOH (20 mL) was added 10% Pd/C. The solution was purged with hydrogen and stirred at room temperature under hydrogen for 15 h. The suspension was filtered through Celite® and the concentrated under vacuum to produce 3,3'-bipyridine-4,5-diamine (LXXIV) as off white solid (3.3 g, 17.7 mmol, 76% yield). $^1$H NMR (DMSO-d6, 500 MHz): δ ppm 8.63-8.53 (m, 1H), 7.90-7.83 (m, 1H), 7.75 (s, 1H), 7.58 (s, 1H), 7.48-7.43 (m, 2H), 6.13 (bs, 2H), 5.31 (bs, 2H). ESIMS found $C_{10}H_{10}N_4$ m/z 187.10 (M+H).

The following intermediates were prepared in accordance with the procedure described in the above Scheme 13 or Scheme 14.

LXXV

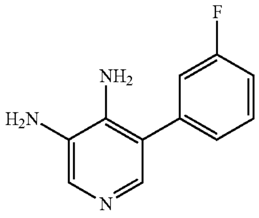

5-(3-Fluorophenyl)pyridine-3,4-diamine (LXXV) as a brown solid (2.03 g, 9.99 mmol, 50% yield). $^1$H NMR (DMSO-$d_6$) δ ppm 7.16-7.27 (m, 2H), 4.86 (brs, 2H), 5.34 (brs, 2H), 7.45-7.53 (m, 3H), 7.70 (s, 1H); ESIMS found $C_{11}H_{10}FN_3$ m/z 203.6 (M+H).

LXXVI

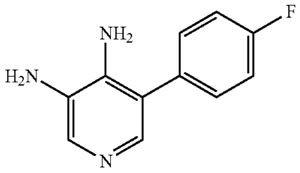

5-(4-Fluorophenyl)pyridine-3,4-diamine (LXXVI): Light yellow solid, (97% yield). ESIMS found $C_{11}H_{10}FN_3$ m/z 204.3 (M+H).

LXXVII

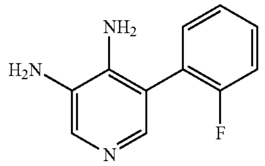

5-(2-Fluorophenyl)pyridine-3,4-diamine (LXXVII): Light red solid, (44% yield). ESIMS found $C_{11}H_{10}FN_3$ m/z 204.4 (M+H).

LXXVIII

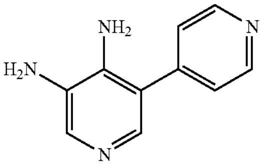

3,4'-Bipyridine-4,5-diamine (LXXVIII): Light tan solid, (84% yield). ESIMS found $C_{10}H_{10}N_4$ m/z 187.0 (M+H).

LXXIX

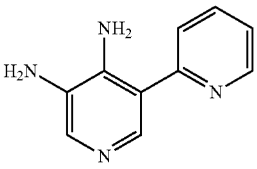

2,3'-Bipyridine-4',5'-diamine (LXXIX): Tan amorphous solid, (76% yield). ESIMS found $C_{10}H_{10}N_4$ m/z 187.0 (M+H).

LXXX

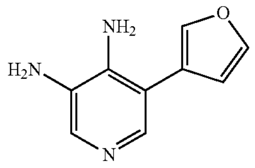

5-(Furan-3-yl)pyridine-3,4-diamine (LXXX): Light pink solid, (68% yield). ESIMS found $C_9H_9N_3O$ m/z 176.0 (M+H).

LXXXI

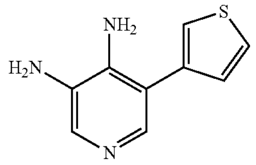

5-(Thiophen-3-yl)pyridine-3,4-diamine (LXXXI): Light brown amorphous solid (100% yield). ESIMS found $C_9H_9N_3S$ m/z 192.0 (M+H).

LXXXII

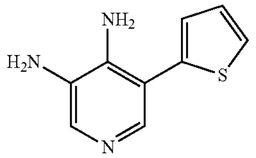

5-(Thiophen-2-yl)pyridine-3,4-diamine (LXXXII): White amorphous solid (1.257 g, 6.57 mmol, 100% yield). ESIMS found $C_9H_9N_3S$ m/z 192.2 (M+H).

LXXXIII

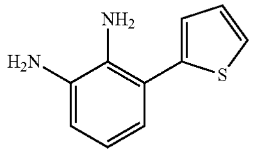

3-(Thiophen-2-yl)benzene-1,2-diamine (LXXXIII): Brown oil (925.5 mg, 4.86 mmol, 60.9% yield). ESIMS found $C_{10}H_{10}N_2S$ m/z 191.1 (M+H).

LXXXIV

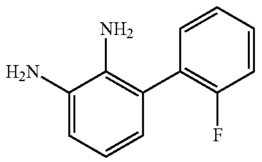

2'-Fluorobiphenyl-2,3-diamine (LXXXIV): Black solid (0.8 g, 3.96 mmol, 92% yield). $^1$H NMR (DMSO-$d_6$, 400 MHz) δ ppm 3.99 (s, 2H), 4.62 (s, 2H), 6.32 (d, J=7.6 Hz, 1H), 6.49 (t, J=7.6 Hz, 1H), 6.60 (d, J=7.6 Hz, 1H), 7.21-7.35 (m, 3H), 7.35-7.45 (m, 1H); ESIMS found for $C_{12}H_{11}FN_2$ m/z 203 (M+H).

LXXXV

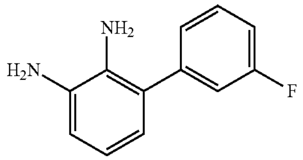

3'-Fluorobiphenyl-2,3-diamine (LXXXV): White solid (2.0 g, 9.89 mmol, 81% yield). $^1$H NMR (DMSO-$d_6$, 400 MHz) δ ppm 4.16 (s, 2H), 4.64 (s, 2H), 6.38 (dd, J=7.6 Hz, J=1.6 Hz, 1H), 6.51 (t, J=7.6 Hz, 1H), 6.60 (d, J=6 Hz, 1H), 7.11-7.26 (m, 3H), 7.48 (q, J=6.4 Hz, 1H); ESIMS found for $C_{12}H_{11}FN_2$ m/z 203 (M+H).

LXXXVI

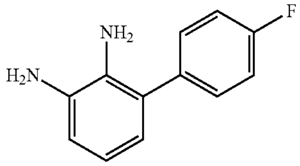

4'-Fluorobiphenyl-2,3-diamine (LXXXVI): White solid (2.4 g, 11.87 mmol, 98% yield). $^1$H NMR (DMSO-$d_6$, 400 MHz) δ ppm 4.07 (s, 2H), 4.60 (s, 2H), 6.34 (dd, J=7.6 Hz, J=1.6 Hz, 1H), 6.50 (t, J=7.6 Hz, 1H), 6.58 (dd, J=7.6 Hz, J=1.6 Hz, 1H), 7.26 (t, J=7.6 Hz, 2H), 7.40 (q, J=5.6 Hz, 2H); ESIMS found for $C_{12}H_{11}FN_2$ m/z 203 (M+H).

LXXXVII

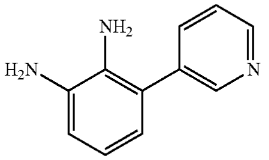

3-(Pyridin-3-yl)benzene-1,2-diamine (LXXXVII): White solid (1.36 g, 7.34 mmol, 92.5% yield). $^1$H NMR ($CDCl_3$, 400 MHz) δ ppm 1.57 (brs, 2H), 3.42 (brs, 2H), 6.66 (dd, J=6 Hz, J=3.2 Hz, 1H), 6.68-6.72 (m, 2H), 7.31 (dd, J=8 Hz, J=4.8 Hz, 1H), 7.71 (td, J=8 Hz, J=2 Hz, 1H), 8.54 (dd, J=4.8 Hz, J=1.6 Hz, 1H), 8.64 (d, J=1.6 Hz, 1H); ESIMS found for $C_{11}H_{11}N_3$ m/z 186 (M+H).

LXXXVIII

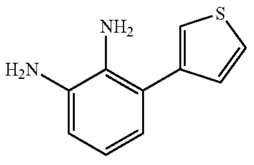

3-(Thiophen-3-yl)benzene-1,2-diamine (LXXXVIII): White solid (1.2 g, 6.31 mmol, mmol, 94% yield). $^1$H NMR (DMSO-$d_6$, 400 MHz) δ ppm 4.19 (s, 2H), 4.59 (s, 2H), 6.47 (dd, J=4.8 Hz, J=1 Hz, 2H), 6.55 (q, J=4.8 Hz, 1H), 7.24 (dd, J=4.8 Hz, J=1 Hz, 1H), 7.50 (t, J=1.6 Hz, 1H), 7.63 (dd, J=4.8 Hz, J=2.8 Hz, 1H); ESIMS found for $C_{10}H_{10}N_2S$ m/z 191 (M+H).

LXXXIX

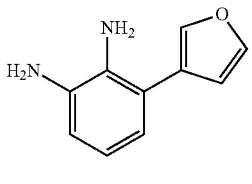

3-(Furan-3-yl)benzene-1,2-diamine (LXXXIX): White solid (1.3 g, 7.46 mmol, mmol, 85% yield). $^1$H NMR (DMSO-$d_6$, 400 MHz) δ ppm 4.24 (brs, 2H), 4.57 (brs, 2H), 6.46-6.50 (m, 1H), 6.50-6.56 (m, 2H), 6.72 (s, 1H), 7.74 (t, J=1.6 Hz, 1H), 7.87 (s, 1H); ESIMS found for $C_{10}H_{10}N_2O$ m/z 175 (M+H).

Preparation of intermediate 3-(pyridin-4-yl)benzene-1,2-diamine (XCV) is depicted below in Scheme 15.

Scheme 15

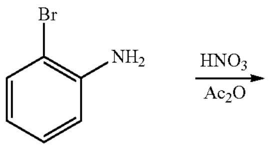

XC

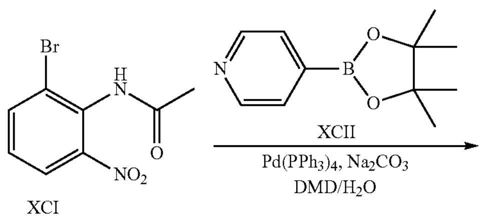

XCI

-continued

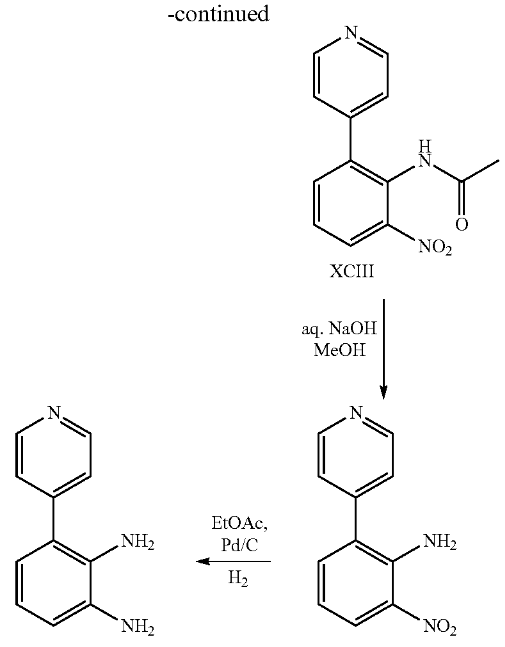

XCV XCIV

Step 1

To a solution of 2-bromoaniline (XC) (50 g, 0.29 mol, 1 eq) in acetic anhydride (265 mL) was added dropwise nitric acid (fuming) (36.75 mL, 0.93 mol, 3.2 eq) at 0° C. and then stirred at that temperature, when the starting material was consumed, the mixture was filtered, the filtrate was poured into ice water. The aqueous phase was basified with aqueous solution of sodium bicarbonate to pH=7, then the mixture was extracted with EtOAc (30 mL×3). The organic layers were combined, dried and concentrated in vacuo to give the N-(2-bromo-6-nitrophenyl)acetamide (XCI) (12.6 g, 48.6 mmol, 16.7% yield) as a white solid. $^1$H NMR (DMSO-$d_6$, 400 MHz) δ ppm 2.06 (s, 3H), 7.43 (t, J=8 Hz, 1H), 7.94 (d, J=8 Hz, 1H), 8.05 (d, J=8 Hz, 1H); ESIMS found for $C_8H_7BrN_2O_3$ m/z 259 (M+H).

Step 2

A degassed mixture of N-(2-bromo-6-nitrophenyl)acetamide (XCI) (2.59 g, 10 mmol, 1.0 eq), 4-(4,4,5,5-tetramethyl-1,3,2-dioxaborolan-2-yl)pyridine (XCII) (2.05 g, 10 mmol, 1.3 eq), $Na_2CO_3$ (2.12 g, 20 mmol, 2 eq) and $Pd(PPh_3)_4$ (1.16 g, 1 mmol, 0.1 eq) in a mixed solvent of DME (30 mL) and $H_2O$ (10 mL) was heated to reflux under nitrogen overnight, the mixture was poured onto water (40 ml) and extracted with ethyl acetate (30 mL×3). The combined organic layers were dried over $Na_2SO_4$, filtered and concentrated in vacuo, purification the resultant residue was purified by column chromatography (EtOAc:PE=1:4→100% EtOAc) to afford N-(2-nitro-6-(pyridin-4-yl)phenyl)acetamide (XCIII) (1.42 g, 5.52 mmol, 55% yield) as a yellow solid. $^1$H NMR (DMSO-$d_6$, 400 MHz) δ ppm 1.92 (s, 3H), 7.46 (d, J=5.6 Hz, 2H), 7.69 (t, J=8 Hz, 1H), 7.80 (dd, J=7.6 Hz, J=1.2 Hz, 1H), 8.06 (dd, J=8 Hz, J=1.6 Hz, 1H), 8.73 (d, J=6 Hz, 2H), 9.96 (s, 1H); ESIMS found for $C_{13}H_{11}N_3O_3$ m/z 258 (M+H).

Step 3

To a solution of N-(2-nitro-6-(pyridin-4-yl)phenyl)acetamide (XCIII) (3.94 g, 15 mmol, 1 eq) in methanol (20 mL) was added 2 N aqueous NaOH solution (50 mL) and the mixture was refluxed until the starting material was consumed completely, the precipitate was collected by filtration to afford the 2-nitro-6-(pyridin-4-yl)aniline (XCIV) (3.0 g, 13.9 mmol, 91% yield) as yellow solid. ESIMS found for $C_{11}H_9N_3O_2$ m/z 216 (M+H).

Step 4

To a solution of 2-nitro-6-(pyridin-4-yl)aniline (XCIV) (3 g, 14 mmol, 1 eq) in EtOAc (350 mL) was added Pd/C (0.3 g) and the mixture was stirred at room temperature under 1 atm of $H_2$ atmosphere overnight, the mixture was filtered and concentrated in vacuo to give the product 3-(pyridin-4-yl)benzene-1,2-diamine (XCV) (2.4 g, 13.0 mmol, 93% yield) as a white solid. $^1$H NMR (DMSO-$d_6$, 400 MHz) δ ppm 4.35 (s, 2H), 4.75 (s, 2H), 6.45 (dd, J=7.6 Hz, J=1 Hz, 1H), 6.58 (t, J=7.6 Hz, 1H), 6.67 (d, J=6.8 Hz, 1H), 7.47 (d, J=6 Hz, 2H), 8.65 (d, J=6 Hz, 2H); ESIMS found for $C_{11}H_{11}N_3$ m/z 186 (M+H).

Preparation of intermediate 3-(pyridin-2-yl)benzene-1,2-diamine 3HCl (LXII) is depicted below in Scheme 16.

Scheme 16

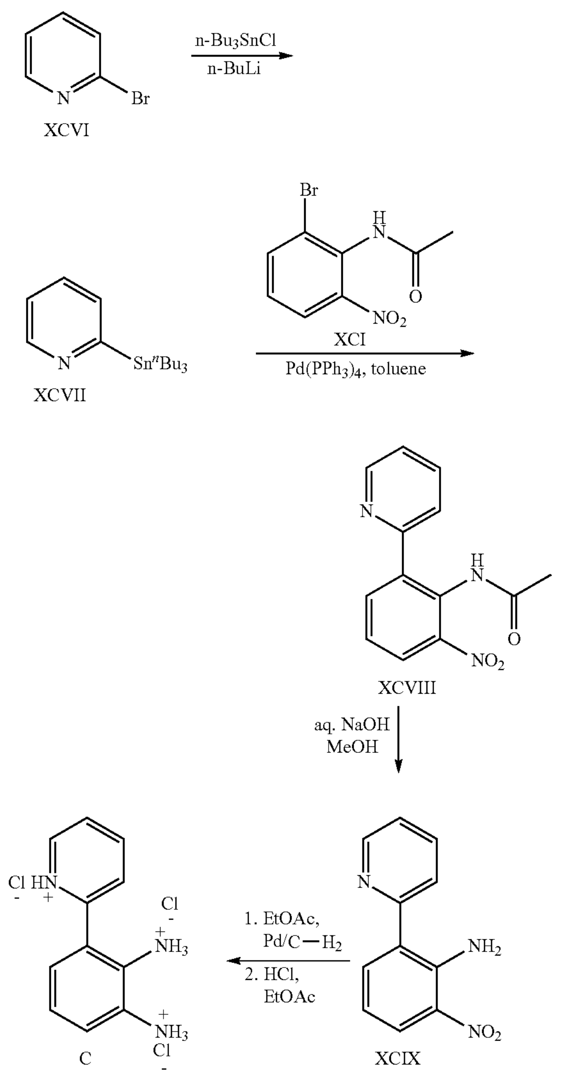

Step 1

To a solution of 2-bromopyridine (XCVI) (10 g, 63 mmol, 1.00 eq) in THF (150 mL) was added n-BuLi (25.3 mL, 63 mmol, 1.00 eq) and the mixture was stirred at −70° C. for 30 min under nitrogen atmosphere. Then n-$Bu_3SnCl$ (21.7 g, 67 mmol, 1.06 eq) was added and the mixture was stirred at the same temperature for another 2 h. Saturated ammonium chloride solution (150 mL) was added to the solution and extracted with ethyl acetate (150 mL×3). The combined organic layers were dried over $Na_2SO_4$, filtered and concentrated in vacuo to afford the crude 2-(tributylstannyl)pyridine (XCVII) (25.9 g, 63 mmol, 100% yield) as a yellow oil. The crude product was used without further purification.

Step 2

A degassed mixture of N-(2-bromo-6-nitrophenyl)acetamide (XCI) (4.8 g, 19 mmol, 1.00 eq), 2-(tributylstannyl)pyridine (XCVII) (7.5 g, 20 mmol, 1.05 eq) and $Pd(PPh_3)_4$ (2.1 g, 1.8 mmol, 0.01 eq) in toluene (60 mL) was heated to reflux under nitrogen overnight. Saturated sodium bicarbonate solution (50 mL) was then added to the mixture and it was extracted with ethyl acetate (50 mL×3). The combined organic layers were dried over $Na_2SO_4$, filtered and concentrated in vacuo, the residue was purified by column chromatography on silica gel (EtOAc:PE=1:2→100% EtOAc) to afford N-(2-nitro-6-(pyridin-2-yl)phenyl)acetamide (XCVIII) (4.4 g, 17.1 mmol, 92% yield) as a white-off solid. $^1$H NMR (DMSO-$d_6$, 400 MHz) δ ppm 1.93 (s, 3H), 7.43-7.51 (m, 1H), 7.51-7.65 (m, 1H), 7.67 (d, J=7.6 Hz, 1H), 7.97 (dd, J=7.6 Hz, J=2.4 Hz, 3H), 8.75 (d, J=4.4 Hz, 1H), 10.52 (s, 1H); ESIMS found for $C_{13}H_{11}N_3O_3$ m/z 258 (M+H).

Step 3

To a solution of N-(2-nitro-6-(pyridin-2-yl)phenyl)acetamide (XCVIII) (4.41 g, 17 mmol, 1 eq) in MeOH (20 mL) was added 2N NaOH aqueous (50 mL) and the mixture was refluxed until the stirring material was consumed completely. The mixture was concentrated in vacuo to remove the MeOH and the precipitate was collected by filtration to afford 2-nitro-6-(pyridin-2-yl)aniline (XCIX) (2.4 g, 11.2 mmol, 65% yield) as a yellow solid. ESIMS found for $C_{11}H_9N_3O_2$ m/z 216 (M+H).

Step 4

To a solution of 2-nitro-6-(pyridin-2-yl)aniline (XCIX) (2.4 g, 0.01 mmol, 1 eq) in EtOAc (350 mL) was added Pd/C (1 g) and the mixture was stirred at room temperature overnight, filtered and then concentrated in vacuo, to give 3-(pyridin-2-yl)benzene-1,2-diamine (1.9 g, 10.3 mmol, 89% yield) as a yellow oil. ESIMS found for $C_{11}H_{11}N_3$ m/z 186 (M+H).

Step 5

To a solution of 3-(pyridin-2-yl)benzene-1,2-diamine (1.86 g, 0.01 mmol) in EtOAc (200 mL) was added HCl in EtOAc (40 mL) and the mixture was stirred at 0° C. for 20 min. The precipitate was collected by filtration to give 3-(pyridin-2-yl)benzene-1,2-diamine-3HCl (C) as a yellow solid. $^1$H NMR (DMSO-$d_6$, 400 MHz) δ ppm 6.89 (t, J=7.6 Hz, 1H), 7.33 (brs, 1H), 7.51 (d, J=7.2 Hz, 1H), 7.54-7.66 (m, 2H), 7.97 (d, J=8 Hz, 1H), 8.16 (brs, 1H), 8.75 (brs, 1H).

Preparation of intermediate 5-(3-fluoro-5-((4-methylpiperazin-1-yl)methyl)phenyl)pyridine-3,4-diamine (XLV) is depicted below in Scheme 17.

Scheme 17

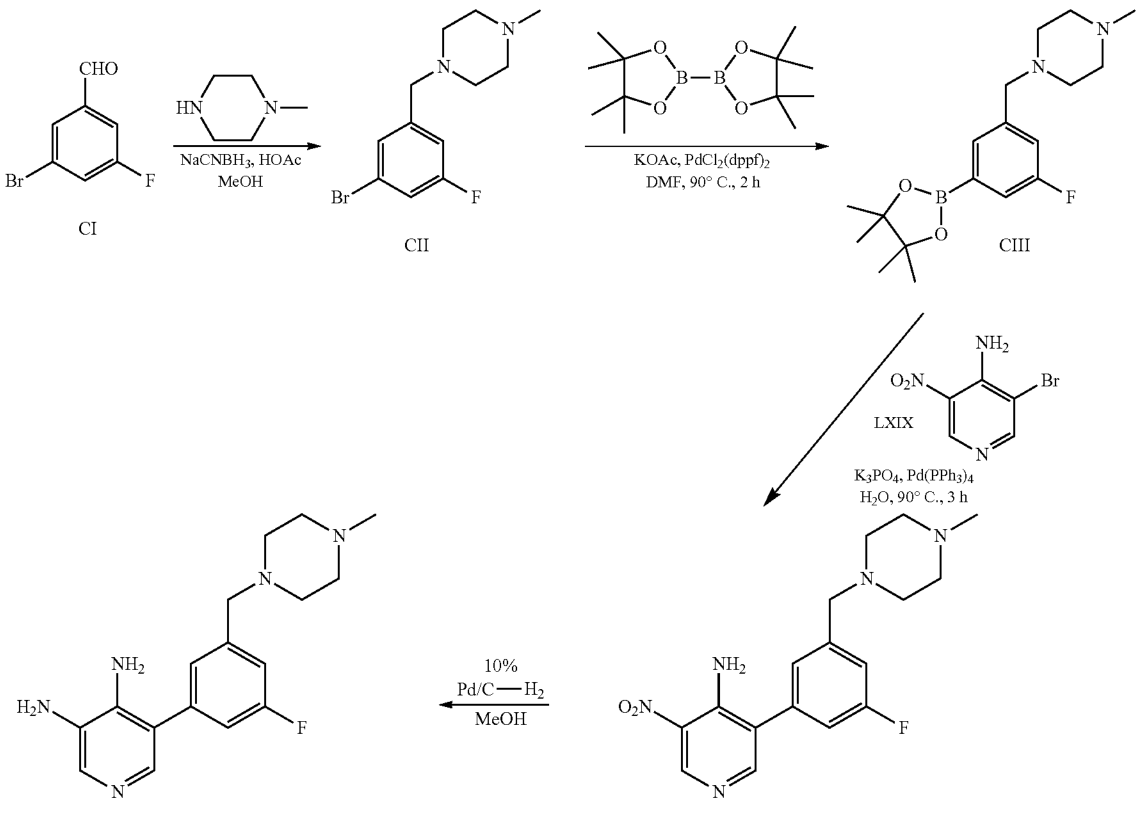

CI CII CIII CIV CV

Step 1

A solution of 3-bromo-5-fluorobenzaldehyde (CI) (2.12 g, 10.42 mmol) in MeOH (200 mL) was added 1-methylpiperazine (2.3 mL, 20.84 mL). The pH was adjusted to 6 using HOAc and stirred for 1 h. $NaCNBH_3$ (917 mg, 14.59 mmol) was added and stirred at room temperature overnight. The MeOH was removed under vacuum and the residue was partitioned between $CHCl_3$ and saturated aqueous $NaHCO_3$. The organic layer was dried over $MgSO_4$ and evaporated under vacuum. The crude product was purified on a silica gel column (100% $CHCl_3$→3:97 MeOH[7N $NH_3$]:$CHCl_3$) to produce 1-(3-bromo-5-fluorobenzyl)-4-methylpiperazine (CII) as a yellow oil (1.52 g, 5.29 mmol, 51% yield). $^1$H NMR (DMSO-$d_6$, 500 MHz) δ ppm 2.14 (s, 3H), 2.28-2.40 (m, 8H), 3.46 (s, 2H), 7.15-7.17 (m, 1H), 7.35 (s, 1H), 7.40-7.42 (m, 1H); ESIMS found $C_{12}H_{16}BrFN_2$ m/z 287 (M+H).

Step 2-3

A solution of 1-(3-bromo-5-fluorobenzyl)-4-methylpiperazine (CII) (528 mg, 1.84 mmol), bis(pinacolato)diboron (560 mg, 2.21 mmol), KOAc (541 mg, 5.51 mmol) and dry DMF (26 mL) was purged with argon. $PdCl_2(dppf)_2$ (90 mg, 0.11 mmol) was added to the reaction and purged again with argon. The solution was heated at 90° C. for 2 h. Once TLC showed the disappearance of (CII), the solution was cooled to room temperature. To this solution was added $K_3PO_4$ (588 mg, 2.76 mmol), 3-bromo-5-nitropyridin-4-amine (LXIX) (400 mg, 1.84 mmol), $Pd(PPh_3)_4$ (106 mg, 0.09 mmol) and water (5 mL). The solution was purged with argon and heated at 90° C. for 4 h. The solution was cooled to room temperature and then concentrated under reduced pressure. The residue was partitioned between $CHCl_3$ and water. The aqueous phase was separated and washed 2×$CHCl_3$. The combined organic phases were washed with brine, dried over $MgSO_4$, filtered and then evaporated under vacuum. The residue was purified on a silica gel column (100% $CHCl_3$→2:98 MeOH [7N $NH_3$]:$CHCl_3$) to give 3-(3-fluoro-5-((4-methylpiperazin-1-yl)methyl)phenyl)-5-nitropyridin-4-amine (CIV) as a yellow amorphous solid (419 mg, 1.21 mmol, 42% yield for 2 steps). $^1$H NMR (DMSO-$d_6$, 500 MHz) δ ppm 2.14 (s, 3H), 2.27-2.41 (m, 8H), 3.52 (s, 2H), 7.16-7.22 (m, 3H), 7.42 (brs, 2H), 8.11 (s, 1H), 9.04 (s, 1H); ESIMS found for $C_{17}H_{20}FN_5O_2$ m/z 346.0 (M+H).

Step 4

To a solution of 3-(3-fluoro-5-((4-methylpiperazin-1-yl)methyl)phenyl)-5-nitropyridin-4-amine (CIV) (265 mg, 0.77 mmol) in MeOH (5 mL) was added 10% Pd/C (40 mg, 15% by wt). The solution was purged with hydrogen and stirred for 4 h at room temperature under hydrogen. The suspension was filtered through Celite and concentrated under vacuum to produce 5-(3-fluoro-5-((4-methylpiperazin-1-yl)methyl)phenyl)pyridine-3,4-diamine (CV) as a tan solid (210 mg, 0.66 mmol, 86% yield). $^1$H NMR (DMSO-$d_6$, 500 MHz) δ ppm 2.14 (s, 3H), 2.32-2.40 (m, 8H), 3.51 (s, 2H), 4.71 (brs, 2H), 5.05 (brs, 2H), 7.06-7.10 (m, 2H), 7.14 (s, 1H), 7.43 (s, 1H), 7.67 (s, 1H); ESIMS found $C_{17}H_{22}FN_5$ m/z 316 (M+H).

The following intermediates were prepared in accordance with the procedure described in the above Scheme 17.

CVI

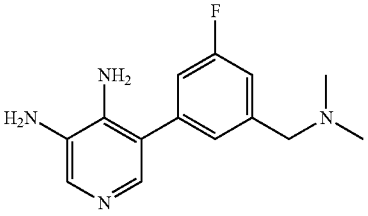

5-(3-((Dimethylamino)methyl)-5-fluorophenyl)pyridine-3,4-diamine (CVI): Light brown solid (551 mg, 2.11 mmol, 71% yield). $^1$H NMR (DMSO-$d_6$, 500 MHz) δ ppm 2.18 (s, 6H), 3.44 (s, 2H), 4.71 (brs, 2H), 5.04 (brs, 2H), 7.07-7.10 (m, 2H), 7.13 (s, 1H), 7.44 (s, 1H), 7.67 (s, 1H); ESIMS found $C_{14}H_{17}FN_4$ m/z 261 (M+H).

CVII

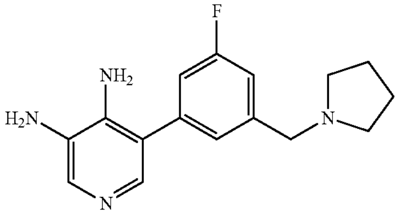

5-(3-fluoro-5-(pyrrolidin-1-ylmethyl)phenyl)pyridine-3,4-diamine (CVII): Light brown solid (551 mg, 2.11 mmol, 71% yield). $^1$H NMR (DMSO-$d_6$, 500 MHz) δ ppm 1.69-1.71 (m, 4H), 2.45-2.48 (m, 4H), 3.63 (s, 2H), 4.71 (brs, 2H), 5.04 (brs, 2H), 7.05-7.07 (m, 1H), 7.09-7.11 (m, 1H), 7.14 (s, 1H), 7.43 (s, 1H), 7.67 (s, 1H); ESIMS found $C_{16}H_{19}FN_4$ m/z 287 (M+H).

CVIII

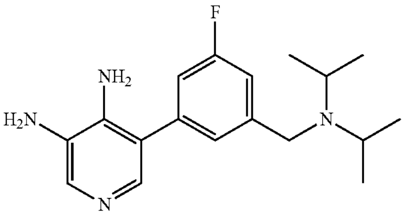

5-(3-((diisopropylamino)methyl)-5-fluorophenyl)pyridine-3,4-diamine (CVIII): Light brown solid (551 mg, 2.11 mmol, 71% yield). $^1$H NMR (DMSO-$d_6$, 500 MHz) δ ppm 1.00 (d, J=6.6 Hz, 12H), 2.99 (sep, J=6.6 Hz, 2H), 3.67 (s, 2H), 4.71 (brs, 2H), 5.03 (brs, 2H), 6.99-7.01 (m, 1H), 7.13-7.15 (m, 1H), 7.22 (s, 1H), 7.43 (s, 1H), 7.67 (s, 1H); ESIMS found $C_{18}H_{25}FN_4$ m/z 317 (M+H).

CIX

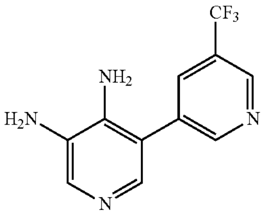

Preparation of 5'-(trifluoromethyl)-3,3'-bipyridine-4,5-diamine (CIX) was performed following the procedure listed in Scheme 11, Steps 2-4. Off-white solid (378 mg, 1.49 mmol, 98% yield). $^1$H NMR (DMSO-$d_6$, 500 MHz) δ ppm 4.78 (brs, 2H), 5.30 (brs, 2H), 7.46 (s, 1H), 7.72 (s, 1H), 8.13-8.14 (m, m, 1H), 8.86 (d, J=1.7 Hz, 1H), 8.95 (d, J=1.1 Hz, 1H); ESIMS found $C_{11}H_9F_3N_4$ m/z 255 (M+H).

CX

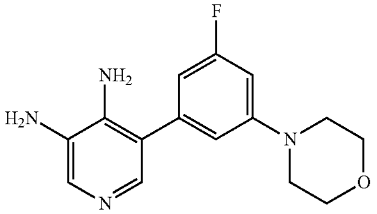

Preparation of 5-(3-fluoro-5-morpholinophenyl)pyridine-3,4-diamine (CX) was performed following the procedure listed in Scheme 11, Steps 2-4. Yellow solid (156 mg, 0.54 mmol, 86% yield). $^1$H NMR (DMSO-$d_6$, 500 MHz) δ ppm 3.18 (t, J=5 Hz, 4H), 3.72 (t, J=5 Hz, 4H), 4.69 (s, 2H), 5.02 (s, 2H), 6.57 (d, J=9 Hz, 1H), 6.70 (s, 1H), 6.76 (td, J=12 Hz, J=2 Hz, 1H), 7.45 (s, 1H), 7.73 (s, 1H); ESIMS found $C_{15}H_{17}FN_4O$ m/z 288.6 (M+H).

CXI

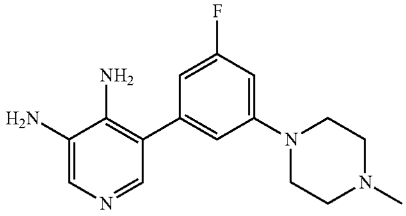

Preparation of 5-(3-fluoro-5-(4-methylpiperazin-1-yl)phenyl)pyridine-3,4-diamine (CXI) was performed following the procedure listed in Scheme 11, Steps 2-4. Amorphous solid (170 mg, 0.56 mmol, 98.4% yield). $^1$H NMR (DMSO-$d_6$, 500 MHz) δ ppm 2.22 (s, 3H), 2.44 (t, J=5 Hz, 4H), 3.21 (t, J=5 Hz, 1H), 4.90 (brs, 2H), 5.41 (brs, 2H), 6.55 (d, J=9 Hz, 1H), 6.69 (s, 1H), 6.77 (d, J=13 Hz, 1H), 7.12 (t, J=7 Hz, 1H), 7.60-7.71 (m, 1H); ESIMS found $C_{16}H_{20}FN_5$ m/z 302.0 (M+H).

CXII

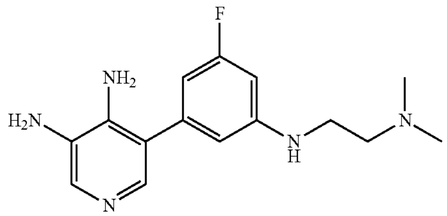

Preparation of 5-(3-(2-(dimethylamino)ethylamino)-5-fluorophenyl)pyridine-3,4-diamine (CXII) was performed following the procedure listed in Scheme 11, Steps 2-4. Brown solid (148 mg, 0.51 mmol, 94.9% yield). $^1$H NMR (DMSO-$d_6$, 500 MHz) δ ppm 2.20 (s, 6H), 2.46 (t, J=7 Hz, 2H), 3.12 (q, J=6 Hz, 2H), 4.79 (s, 2H), 5.21 (s, 2H), 5.91 (t, J=5 Hz, 1H), 6.28 (dd, J=9 Hz, J=1 Hz, 1H), 6.36 (t, J=2 Hz, 1H), 6.37-6.42 (m, 1H), 7.46 (s, 1H), 7.64 (s, 1H); ESIMS found $C_{15}H_{20}FN_5$ m/z 290.0 (M+H).

CXIII

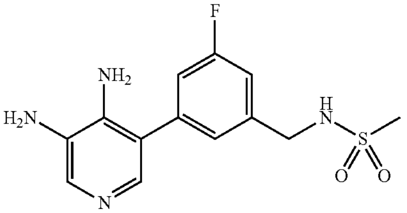

Preparation of N-(3-(4,5-Diaminopyridin-3-yl)-5-fluorobenzyl)methanesulfonamide (CXIII) was performed following the procedure listed in Scheme 11, Steps 2-4. Light tan solid (428.4 mg, 1.38 mmol, quantitative yield). $^1$H NMR (DMSO-$d_6$, 500 MHz) 8 ppm 2.92 (s, 3H), 4.24 (d, J=6.3 Hz, 2H), 4.80 (s, 2H), 5.23 (s, 2H), 7.11-7.13 (m, 1H), 7.16-7.18 (m, 1H), 7.22 (s, 1H), 7.47 (s, 1H), 7.64 (d, J=6.3 Hz, 1H), 7.68 (s, 1H); ESIMS found $C_{13}H_{15}FN_4O2S$ m/z 311 (M+H).

CXIV

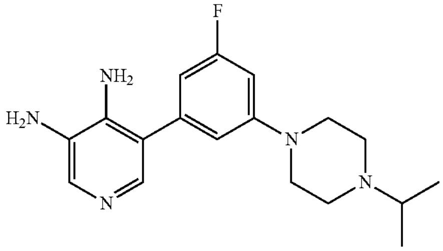

Preparation of 5-(3-fluoro-5-(4-isopropylpiperazin-1-yl)phenyl)pyridine-3,4-diamine (CXIV) was performed following the procedure listed in Scheme 11, Steps 2-4. Light yellow amorphous solid (100 mg, 0.30 mmol, 99% yield). $^1$H NMR (DMSO-$d_6$, 500 MHz) δ ppm 0.99 (d, J=6.5 Hz, 6H), 2.52-2.58 (m, 4H), 2.67 (sep, J=6.5 Hz, 1H), 3.14-3.23 (m, 4H), 4.74 (brs, 2H), 5.11 (s, 2H), 6.53 (d, J=9 Hz, 1H), 6.67 (s, 1H), 6.74 (d, J=13 Hz, 1H), 7.45 (brs, 1H), 7.66 (brs, 1H); ESIMS found $C_{18}H_{24}FN_5$ m/z 330.0 (M+H).

CXV

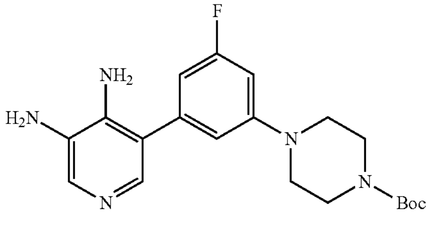

Preparation of tert-butyl 4-(3-(4,5-diaminopyridin-3-yl)-5-fluorophenyl)piperazine-1-carboxylate (CXV) was performed following the procedure listed in Scheme 11, Steps 2-4. Light brown amorphous solid (376 mg, 0.97 mmol, 87.4% yield). $^1$H NMR (DMSO-$d_6$, 500 MHz) δ ppm 1.42 (s, 9H), 3.20 (t, J=5 Hz, 4H), 3.44 (t, J=5 Hz, 4H), 4.69 (s, 2H), 5.02 (s, 2H), 6.56 (d, J=9 Hz, 1H), 6.71 (s, 1H), 6.77 (td, J=13 Hz, J=2 Hz, 1H), 7.44 (s, 1H), 7.66 (s, 1H); ESIMS found $C_{20}H_{26}FN_5O_2$ m/z 388.1 (M+H).

CXVI

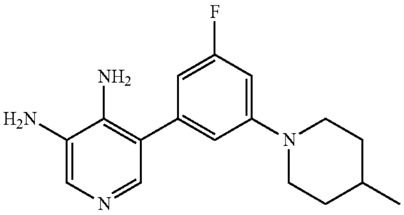

Preparation of 5-(3-fluoro-5-(4-methylpiperidin-1-yl)phenyl)pyridine-3,4-diamine (CXVI) was performed following the procedure listed in Scheme 11, Steps 2-4. Light brown amorphous solid (150 mg, 0.50 mmol, 99% yield). $^1$H NMR (DMSO-$d_6$, 500 MHz) δ ppm 0.93 (d, J=6.5 Hz, 3H), 1.20 (dq, J=12 Hz, J=4 Hz, 2H), 1.46-1.58 (m, 1H), 1.67 (d, J=11 Hz, 2H), 2.71 (dt, J=12 Hz, J=2 Hz, 2H), 3.74 (d, J=12.7 Hz, 2H), 4.68 (s, 2H), 5.00 (s, 2H), 6.48 (dd, J=8.7 Hz, J=1 Hz, 1H), 6.66 (s, 1H), 6.72 (td, J=13 Hz, J=2 Hz, 1H), 7.44 (s, 1H), 7.65 (s, 1H); ESIMS found $C_{17}H_{21}FN_4$ m/z 301.0 (M+H).

Preparation of intermediate 5-(4-methylpiperazin-1-yl)pyridine-3,4-diamine (CXVIII) is depicted below in Scheme 18.

Scheme 18

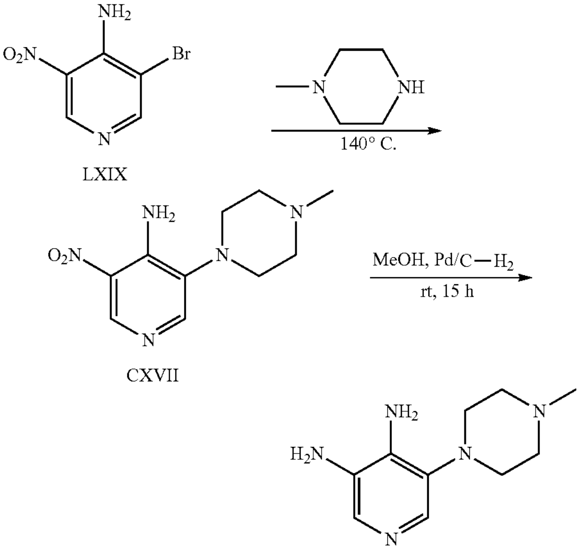

CXVIII

Step 1

A solution of 3-bromo-5-nitropyridin-4-amine (LXIX) (618 mg, 2.83 mmol) in 1-methylpiperazine (1 mL, 8.51 mmol) was heated at 140° C. overnight. The reaction was poured into an EtOAc/$H_2O$ mixture; the organic layer was separated, dried over $MgSO_4$ and concentrated under vacuum. The crude product was purified on a silica gel column (100% $CHCl_3$→3:97 MeOH(7N $NH_3$):$CHCl_3$) to give 3-(4-methylpiperazin-1-yl)-5-nitropyridin-4-amine (CXVII) as a yellow solid (382 mg, 1.61 mmol, 56.7% yield). $^1$H NMR ($CDCl_3$, 500 MHz) δ ppm 2.20 (s, 3H), 2.35-2.37 (m, 4H), 4.52-3.54 (m, 4H), 5.96 (s, 1H), 7.42 (s, 2H), 8.78 (s, 1H); ESIMS found $C_{10}H_{15}N_5O_2$ m/z 238 (M+H).

Step 2

To a solution of 3-(4-methylpiperazin-1-yl)-5-nitropyridin-4-amine (CXVII) (382 mg, 1.61 mmol) in MeOH (11 mL) was added 10% Pd/C. The solution was purged with hydrogen and stirred at room temperature under hydrogen for 4 h. The suspension was filtered through Celite® and the concentrated under vacuum to produce 5-(4-methylpiperazin-1-yl)pyridine-3,4-diamine (CXVIII) as purple solid (330 mg, 1.59 mmol, 99% yield). $^{1}H$ NMR (DMSO-d6, 500 MHz): δ 2.18 (s, 3H), 2.34-2.36 (m, 4H), 3.13-3.16 (m, 4H), 3.89 (s, 2H), 5.20 (s, 2H), 5.94 (s, 1H), 7.31 (s, 1H); ESIMS found $C_{10}H_{17}N_5$ m/z 208 (M+H).

The following intermediates were prepared in accordance with the procedure described in the above Scheme 18.

CXIX

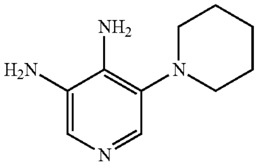

5-(Piperidin-1-yl)pyridine-3,4-diamine (CXIX): Purple solid, (83% yield). ESIMS found $C_{10}H_{16}N_4$ m/z 193.1 (M+H).

CXX

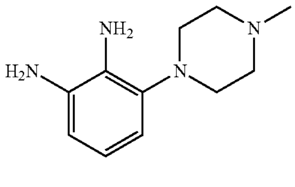

5-(Piperidin-1-yl)pyridine-3,4-diamine (CXX): Black solid (1.31 g, 6.35 mmol, 92% yield). $^{1}H$ NMR ($CDCl_3$, 400 MHz) δ ppm 2.30 (s, 3H), 3.30 (brs, 2H), 3.68 (brs, 2H), 6.46 (dd, J=7.2 Hz, J=2 Hz, 1H), 6.54-6.63 (m, 2H); ESIMS found for $C_{11}H_{18}N_4$ m/z 207 (M+H).

Preparation of intermediate 3-(piperidin-1-yl)benzene-1, 2-diamine (CXXIII) is depicted below in Scheme 19.

Scheme 19

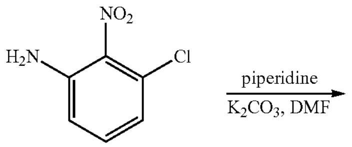

CXXI

-continued

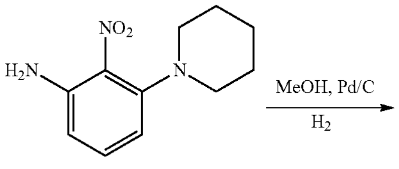

CXXI

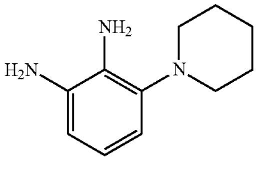

CXXIII

Step 1

To a solution of 3-chloro-2-nitroaniline (CXXI) (2.00 g, 11.6 mmol, 1 eq) and piperidine (2.95 g, 34.7 mmol, 3 eq) in DMF (60 ml) was added $K_2CO_3$ (4.78 g, 34.4 mmol, 3 eq) in one portion and the mixture was stirred at 120° C. under nitrogen overnight. The reaction mixture was diluted with ethyl acetate (60 ml) and washed with saturated $NaHCO_3$ solution (50 mL). The organic phases were dried over $Na_2SO_4$ and concentrated in vacuo, the resultant residue was purified by silica gel column chromatography (PE:EtOAc=5: 1→1:1) to give 2-nitro-3-(piperidin-1-yl)aniline (CXXII) (1.8 g, 8.14 mmol, 70.3% yield) as a black solid. ESIMS found for $C_{11}H_{15}N_3O_2$ m/z 222 (M+H).

Step 2

A mixture of 2-nitro-3-(piperidin-1-yl)aniline (CXXII) (1.64 g, 6.9 mmol, 1 eq) and Pd/C (0.50 g) in MeOH (20 mL) was stiffed at room temperature under 30 psi $H_2$ overnight. After the starting material was consumed completely, the mixture was filtered through a Celite pad and the filtrate was concentrated in vacuo to give the 3-(piperidin-1-yl)benzene-1,2-diamine (CXXIII) (1.1 g, 5.75 mmol, 76% yield) as a yellow solid. $^{1}H$ NMR ($CDCl_3$, 400 MHz) δ ppm 1.59 (brs, 2H), 1.73 (quin, J=5.6 Hz, 4H), 2.84 (brs, 4H), 3.50 (brs, 4H), 6.52 (dd, J=6.4 Hz, J=1.6 Hz, 1H), 6.59-6.75 (m, 2H); ESIMS found for $C_{11}H_{17}N_3$ m/z 192 (M+H).

Preparation of 4,5-diamino-N-ethylnicotinamide (LX) is depicted below in Scheme 20.

Scheme 20

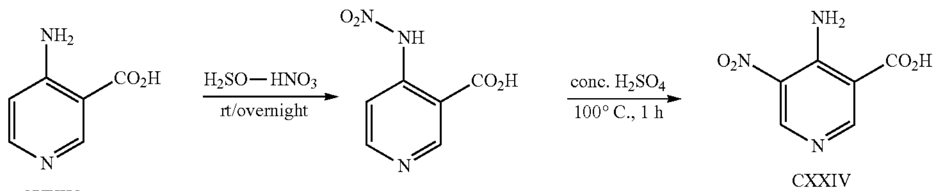

CXXIV CXXV CXXIV

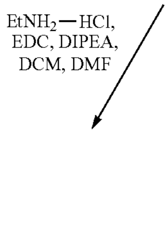

-continued

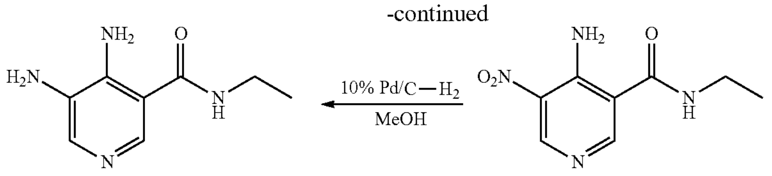

CXXVIII CXXVII

Step 1

To a solution of concentrated sulfuric acid (2 mL) was slowly added 2-aminobenzoic acid (CXXIV) (1.0 g, 7.24 mmol). A mixture of concentrated sulfuric acid (1.5 mL) and fuming nitric acid (1.5 mL) was then slowly added and the reaction was stirred at room temperature overnight. The reaction mixture was poured into crushed ice and treated with aqueous $NH_4OH$ until pH 3.0. The yellow-orange solid was washed with cold water and dried to produce 2-(nitroamino) benzoic acid (CXXV) as a yellow solid (1.0 g, 5.46 mmol, 75.4% yield). The crude product was used for the next step without further purification. ESIMS found for $C_7H_6N_2O_4$ m/z 183.9 (M+H).

Step 2

To a solution of concentrated sulfuric acid (2 mL) was slowly added 2-(nitroamino)benzoic acid (CXXV) (183 mg, 1.0 mmol). The mixture was stirred at 100° C. for 1 h. The solution was cooled, poured into crushed ice and treated with aqueous $NH_4OH$ until pH 3.0 while maintaining the temperature under 20° C. The solid was washed with cold water and dried to produce 2-amino-3-nitrobenzoic acid (CXXVI) as a yellow solid (55 mg, 0.30 mmol, 30.2% yield). Used for the next step without further purification. $^1H$ NMR (DMSO-$d_6$, 500 MHz) δ ppm 8.50 (brs, 1H), 8.89 (s, 1H), 8.99 (brs, 1H), 9.14 (s, 1H), 13.88 (brs, 1H); ESIMS found for $C_7H_6N_2O_4$ m/z 184.1 (M+H).

Step 3

To a solution of 2-amino-3-nitrobenzoic acid (CXXVI) (366 mg, 2.0 mmol) in DCM (5 mL) and DMF (1 mL) was added ethylamine hydrochloride and EDC. The mixture was cooled to 0° C. under argon before added DIPEA. The reaction was stirred at room temperature for 3 h. The solution was concentrated under vacuum, dissolved in water and extracted with EtOAc. The combined organic phases were washed with brine, dried over $MgSO_4$ and concentrated under vacuum. The residue was purified on a silica gel column (100% $CHCl_3$→5:95 MeOH[7N $NH_3$]:$CHCl_3$) to give 4-amino-N-ethyl-5-nitronicotinamide (CXXVII) as a yellow solid (200 mg, 0.95 mmol, 47.6% yield). $^1H$ NMR (DMSO-$d_6$, 500 MHz) δ ppm 1.14 (t, J=7 Hz, 3H), 3.28 (q, J=6 Hz, 2H), 8.97 (s, 1H), 9.06 (s, 1H).

Step 4

To a solution of 4-amino-N-ethyl-5-nitronicotinamide (CXXVII) (180 mg, 0.856 mmol) in MeOH (5 mL) was added 10% Pd/C (27 mg, 15% by wt). The solution was purged with hydrogen and stirred for 16 h at room temperature under hydrogen. The suspension was filtered through Celite and concentrated under vacuum. The residue was purified on a silica gel column (100% $CHCl_3$→10:90 MeOH[7N $NH_3$]:$CHCl_3$) to produce 4,5-diamino-N-ethylnicotinamide (CXXVIII) as a dark yellow solid (80 mg, 0.44 mmol, 51.9% yield). $^1H$ NMR (DMSO-$d_6$, 500 MHz) δ ppm 1.14 (t, J=7 Hz, 3H), 3.92 (q, J=7 Hz, 2H) 5.56 (brs, 2H), 6.60 (brs, 1H), 7.66 (s, 1H), 8.30 (s, 1H); ESIMS found $C_8H_{12}N_4O$ m/z 181 (M+H).

Preparation of intermediate 3-(4-methyl-imidazol-1-yl)-benzene-1,2-diamine (CXXX) is depicted below in Scheme 21.

Scheme 21

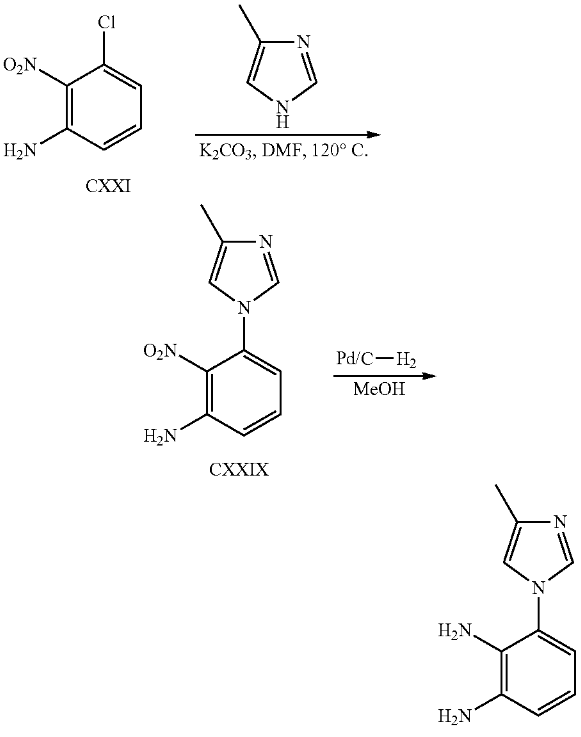

CXXI

CXXIX

CXXX

Step 1

A solution of 3-chloro-2-nitro-aniline (CXXI) (1.0 g, 5.8 mmol), potassium carbonate (2.4 g, 17.4 mmol), and 4-methylimidazole in dry DMF was heated overnight at 120° C. under nitrogen. The reaction was cooled and the solvent was evaporated in vacuo. The residue was suspended in a saturated $NaHCO_3$ solution and extracted with $CH_2Cl_2$. The combined organic phases were dried over $MgSO_4$ and concentrated in vacuo. The crude product was purified by flash chromatography to provide 3-(4-methyl-imidazol-1-yl)-2-nitro-phenylamine (CXXIX). $^1H$ NMR ($CDCl_3$, 400 MHz) δ ppm 2.19 (s, 3H), 6.53 (m, 1H), 6.79 (m, 1H), 6.93 (m, 1H), 7.32 (m, 1H), 7.60 (m, 1H).

Step 2

To a solution of 3-(4-methyl-imidazol-1-yl)-2-nitro-phenylamine (CXXIX) in methanol was added with 5% Pd/C. The combination was stirred under a hydrogen filled balloon at 40° C. for 6 hours. The solution was then filtered through a pad of Celite. The filtrate was concentrated in vacuo to get 3-(4-methyl-imidazol-1-yl)-benzene-1,2-diamine (CXXX). $^1H$ NMR ($CDCl_3$, 400 MHz) δ ppm 2.17 (s, 3H), 6.54 (m, 1H), 6.80 (m, 1H), 6.97 (m, 1H), 7.28 (m, 1H), 7.56 (m, 1H).

Example 1

Preparation of 3-(7-(3-fluorophenyl)-3H-imidazo[4,5-c]pyridin-2-yl)-5-(pyridin-3-yl)-1H-pyrazolo[3,4-b]pyridine (3) is depicted below in Scheme 22.

1H), 6.25 (dd, J=10 Hz, J=2 Hz, 1H), 7.58-7.64 (m, 1H), 8.25 (td, J=8 Hz, J=2 Hz, 1H), 8.66 (dd, J=5 Hz, J=2 Hz, 1H), 8.77 (d, J=2 Hz, 1H), 9.02 (d, J=2 Hz, 1H), 9.09 (d, J=2 Hz, 1H), 10.21 (s, 1H); ESIMS found for $C_{17}H_{16}N_4O_2$ m/z 309.4 (M+H).

Scheme 22

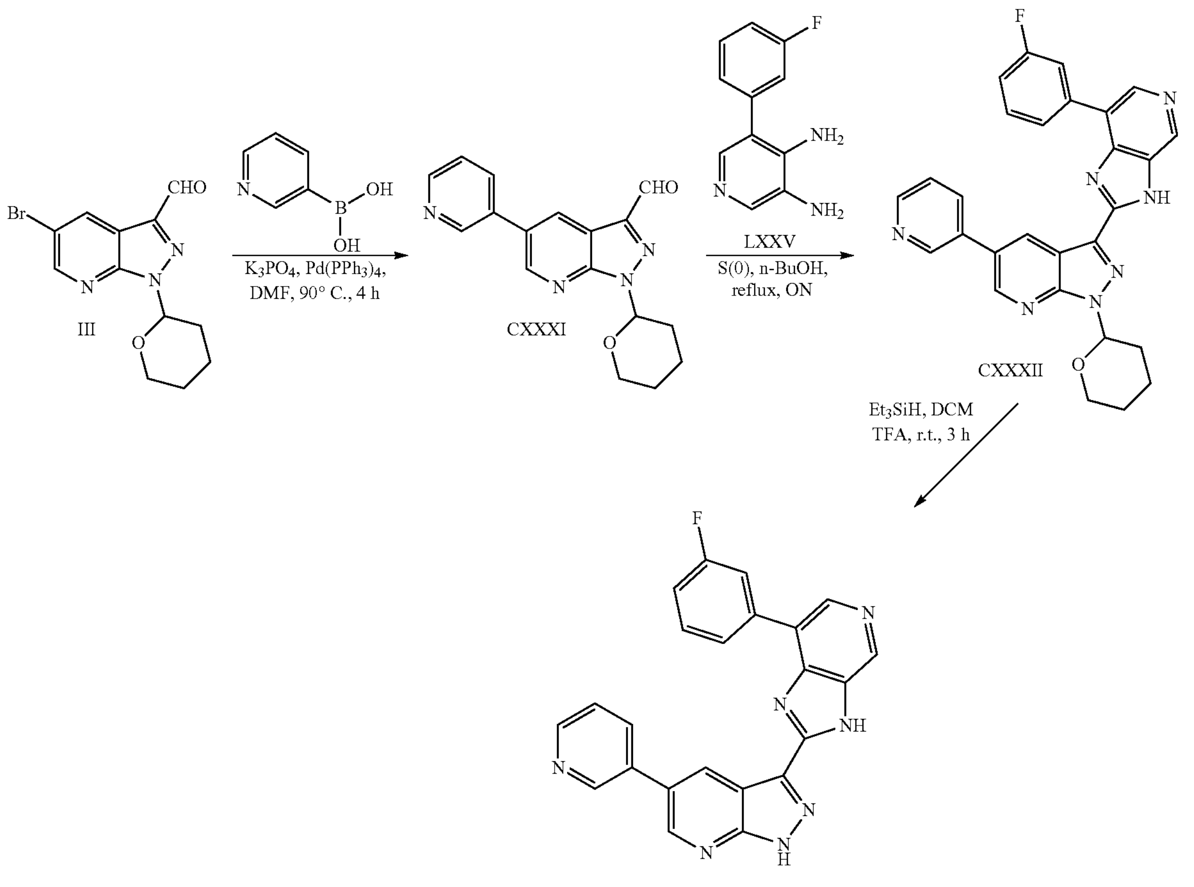

3

Step 1

To a heterogeneous solution of 5-bromo-1-(tetrahydro-2H-pyran-2-yl)-1H-pyrazolo[3,4-b]pyridine-3-carbaldehyde (III) (328 mg, 1.05 mmol) and $K_3PO_4$ (334 mg, 1.57 mmol) in DMF (10 mL) and water (2 mL) was added pyridin-3-ylboronic acid (143 mg, 1.16 mmol). The solution was purged with argon by using argon/vacuum cycle (3×). $Pd(PPh_3)_4$ (36 mg, 0.03 mmol) was added to the solution and again purged with argon. The solution was heated at 90° C. for 4 h under argon. The DMF was removed under vacuum. The residue was partitioned between EtOAc and water. The organic layer was separated and the aqueous layer was extracted with EtOAc. The combined EtOAc was dried over $MgSO_4$, filtered and concentrated under reduced pressure. The crude product was purified through a silica gel column (10:90 EtOAc:hexane→50:50 EtOAc:hexane) to produce 5-(pyridin-3-yl)-1-(tetrahydro-2H-pyran-2-yl)-1H-pyrazolo[3,4-b]pyridine-3-carbaldehyde (CXXXI) as an off-white waxy solid (283 mg, 0.92 mmol, 91% yield). $^1H$ NMR (DMSO-$d_6$) δ ppm 1.57-1.68 (m, 3H), 1.75-1.89 (m, 1H), 2.01-2.13 (m, 2H), 2.49-2.56 (m, 1H), 3.78 (dt, J=11 Hz, J=4 Hz, 1H), 3.94-4.03 (m, Step 2-3

A solution of 5-(pyridin-3-yl)-1-(tetrahydro-2H-pyran-2-yl)-1H-pyrazolo[3,4-b]pyridine-3-carbaldehyde (CXXXI) (65 mg, 0.21 mmol), 5-(3-fluorophenyl)pyridine-3,4-diamine (LXXV) (45 mg, 0.22 mmol) and sulfur (7 mg, 0.22 mmol) in n-butanol (10 mL) was heated at reflux overnight. The solution was cooled to room temperature, filtered and the solvent was evaporated under reduced pressure to give crude 3-(743-fluorophenyl)-3H-imidazo[4,5-c]pyridin-2-yl)-5-(pyridin-3-yl)-1-(tetrahydro-2H-pyran-2-yl)-1H-pyrazolo[3,4-b]pyridine (CXXXII). CXXXII was dissolved in dry DCM (5 mL) before adding triethylsilane (84 μL, 0.52 mmol) and TFA (2.5 mL). The reaction was stirred at room temperature for 2 h under argon. The solvent was evaporated under reduced pressure; the residue was taken up water (10 mL), and basified with 5N $NH_4OH$. The precipitates were filtered, washed by cold water and dried under vacuum at room temperature. The crude product was suspended in DCM (10 mL), sonicated briefly and then heated to boiling for 5 min. The solution was cooled to room temperature and the solids were filtered, washed with DCM and dried under vacuum at room temperature to produce 3-(7-(3-fluorophenyl)-3H-imidazo[4,5-c]pyridin-2-yl)-5-(pyridin-3-yl)-1H-pyrazolo[3,4-b]pyridine (3) as a yellow solid (53 mg, 0.13 mmol, 62% yield). $^1$H NMR (DMSO-$d_6$) δ ppm 7.25-7.34 (m, 1H), 7.54-7.65 (m, 2H), 8.11-8.21 (m, 1H), 8.23-8.30 (m, 1H), 8.37-8.50 (m, 1H), 8.63-8.70 (m, 1H), 8.70-8.80 (m, 1H), 9.02-9.09 (m, 2H), 9.09-9.15 (m, 1H), 13.94 (brs, 1H), 14.59 (s, 1H); ESIMS found for $C_{23}H_{14}FN_7$ m/z 408.1 (M+H).

The following compounds were prepared in accordance with the procedure described in the above Example 1.

8

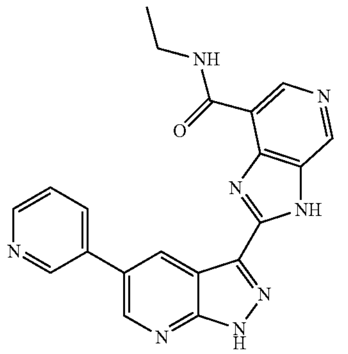

N-Ethyl-2-(5-(pyridin-3-yl)-1H-pyrazolo[3,4-b]pyridin-3-yl)-3H-imidazo[4,5-c]pyridine-7-carboxamide 8.

Brown solid (4.4 mg, 0.01 mmol, 35.8% yield). $^1$H NMR (DMSO-$d_6$, 500 MHz) δ ppm 1.23-1.34 (m, 3H), 3.48-3.59 (m, 2H), 5.76 (s, 1H), 7.58 (q, J=5 Hz, 1H), 8.27-8.33 (m, 1H), 8.67 (d, J=5 Hz, 1H), 9.01 (s, 1H), 9.03 (s, 1H), 9.07 (s, 1H), 9.33 (brs, 1H), 14.19 (brs, 1H), 14.75 (brs, 1H); ESIMS found $C_{20}H_{16}N_8O$ m/z 385.0 (M+H).

10

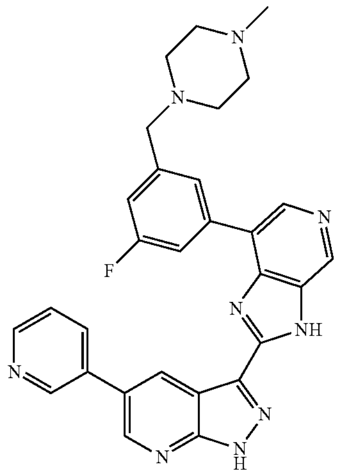

3-(743-Fluoro-5-((4-methylpiperazin-1-yl)methyl)phenyl)-3H-imidazo[4,5-c]pyridin-2-yl)-5-(pyridin-3-yl)-1H-pyrazolo[3,4-b]pyridine 10.

Off-white solid (62 mg, 0.12 mmol, 73% yield). $^1$H NMR (DMSO-$d_6$, 500 MHz) δ ppm 2.21 (brs, 3H), 2.30-2.47 (m, 8H), 3.59 (s, 2H), 7.21 (d, J=9 Hz, 1H), 7.59 (dd, J=8 Hz, J=5 Hz, 1H), 8.13-8.29 (m, 2H), 8.25 (d, J=8 Hz, 1H), 8.68 (dd, J=5 Hz, J=1.4 Hz, 1H), 8.75 (brs, 1H), 8.89 (brs, 1H), 9.04 (dd, J=9 Hz, J=2 Hz, 2H), 9.08 (s, 1H), 13.91 (brs, 1H), 14.61 (brs, 1H); ESIMS found $C_{29}H_{26}FN_9$ m/z 520.3 (M+H).

11

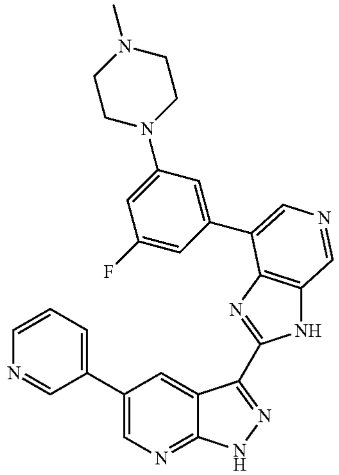

3-(7-(3-Fluoro-5-(4-methylpiperazin-1-yl)phenyl)-3H-imidazo[4,5-c]pyridin-2-yl)-5-(pyridin-3-yl)-1H-pyrazolo[3,4-b]pyridine 11.

Off-white solid (72 mg, 0.14 mmol, 75% yield). $^1$H NMR (DMSO-$d_6$, 500 MHz) δ ppm 2.16 (brs, 3H), 2.23-2.40 (m, 4H), 3.19-3.30 (m, 4H), 6.84 (d, J=12 Hz, 1H), 7.54-7.65 (m, 2H), 7.79 (s, 1H), 8.21 (d, J=8 Hz, 1H), 8.69 (d, J=2 Hz, 2H), 8.73 (s, 1H), 8.87 (s, 1H), 8.97-9.05 (m, 2H), 13.86 (brs, 1H), 14.61 (brs, 1H); ESIMS found $C_{28}H_{24}FN_9$ m/z 506.3 (M+H).

12

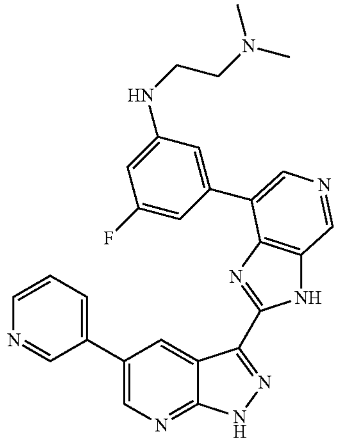

N1-(3-Fluoro-5-(2-(5-(pyridin-3-yl)-1H-pyrazolo[3,4-b]pyridin-3-yl)-3H-imidazo[4,5-c]pyridin-7-yl)phenyl)-N2,N2-dimethylethane-1,2-diamine 12.

Off-white solid (21 mg, 0.04 mmol, 50% yield). $^1$H NMR (DMSO-$d_6$, 500 MHz) δ ppm 2.14 (s, 6H), 2.40 (brs, 2H), 3.17 (t, J=6 Hz, 2H), 5.94 (brs, 1H), 6.48 (d, J=12 Hz, 1H), 7.32-7.47 (m, 2H), 7.58 (dd, J=8 Hz, J=5 Hz, 1H), 8.25 (d, J=8 Hz, 1H), 8.64 (s, 1H), 8.68 (dd, J=5 Hz, J=1.5 Hz, 1H), 8.85 (s, 1H), 9.06 (d, J=2 Hz, 2H), 9.11 (s, 1H), 13.83 (brs, 1H), 14.58 (brs, 1H); ESIMS found $C_{27}H_{24}FN_9$ m/z 494 (M+H).

13

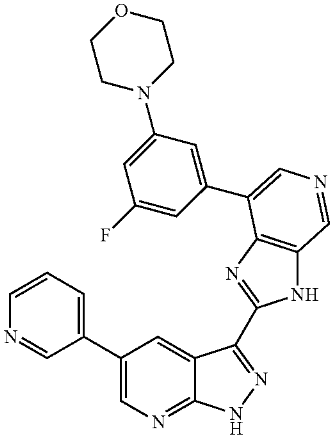

4-(3-Fluoro-5-(2-(5-(pyridin-3-yl)-1H-pyrazolo[3,4-b]pyridin-3-yl)-3H-imidazo[4,5-c]pyridin-7-yl)phenyl)morpholine 13.

Off-white solid (38 mg, 0.08 mmol, 77% yield). $^{1}$H NMR ($DMSO-d_6$, 500 MHz) δ ppm 3.14-3.21 (m, 4H), 3.51-3.59 (m, 4H), 6.86 (d, J=12 Hz, 1H), 7.58 (dd, J=8 Hz, J=5 Hz, 1H), 7.63 (d, J=10 Hz, 1H), 7.74 (s, 1H), 8.22 (d, J=8 Hz, 1H), 8.68 (d, J=5 Hz, 1H), 8.73 (s, 1H), 8.87 (s, 1H), 9.01 (d, J=2 Hz, 2H), 9.04 (s, 1H), 13.87 (s, 1H), 14.61 (s, 1H); ESIMS found $C_{27}H_{21}FN_8O$ m/z 493.1 (M+H).

14

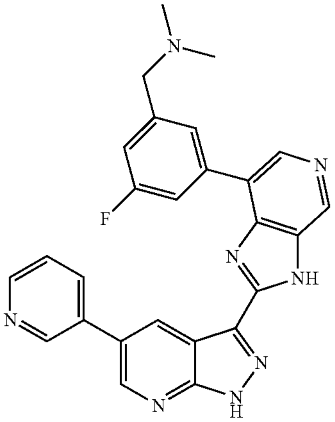

1-(3-Fluoro-5-(2-(5-(pyridin-3-yl)-1H-pyrazolo[3,4-b]pyridin-3-yl)-3H-imidazo[4,5-c]pyridin-7-yl)phenyl)-N,N-dimethylmethanamine 14.

Off-white solid (38 mg, 0.08 mmol, 62.9% yield). $^{1}$H NMR ($DMSO-d_6$, 500 MHz) δ ppm 2.10 (s, 6H), 3.51 (s, 2H), 7.20 (brd, 1H), 7.59 (dd, J=8 Hz, J=5 Hz, 1H), 8.13 (brd, 1H), 8.20-8.27 (m, 2H), 8.69 (d, J=3 Hz, 1H), 8.75 (s, 1H), 8.89 (s, 1H), 9.03 (d, J=2 Hz, 1H), 9.04 (d, J=2 Hz, 1H), 9.06 (s, 1H), 13.90 (s, 1H), 14.62 (s, 1H); ESIMS found $C_{26}H_{21}FN_8$ m/z 465.3 (M+H).

15

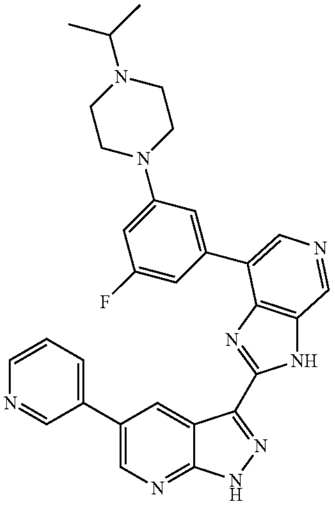

3-(743-Fluoro-5-(4-isopropylpiperazin-1-yl)phenyl)-3H-imidazo[4,5-c]pyridin-2-yl)-5-(pyridin-3-yl)-1H-pyrazolo[3,4-b]pyridine 15.

Off-white solid (41 mg, 0.08 mmol, 57.3% yield). $^{1}$H NMR ($DMSO-d_6$, 500 MHz) δ ppm 0.93 (brs, 6H), 2.32-2.41 (m, 4H), 2.51-2.60 (m, 1H), 3.13-3.23 (m, 4H), 6.84 (brd, 1H), 7.52-7.61 (m, 1H), 7.58 (dd, J=8 Hz, J=5 Hz, 1H), 7.77 (brs, 1H), 8.22 (brd, 1H), 8.68 (d, J=5 Hz, 1H), 8.72 (s, 1H), 9.02 (d, J=2 Hz, 1H), 9.02-9.06 (m, 2H), 13.87 (s, 1H), 14.61 (s, 1H); ESIMS found $C_{30}H_{28}FN_9$ m/z 534.5 (M+H).

16

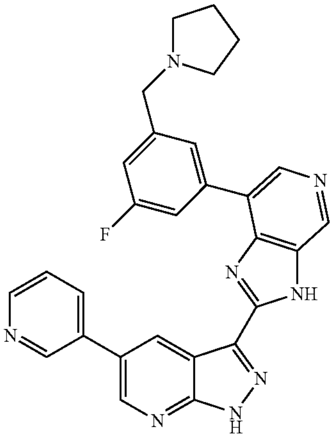

3-(7-(3-Fluoro-5-(pyrrolidin-1-ylmethyl)phenyl)-3H-imidazo[4,5-c]pyridin-2-yl)-5-(pyridin-3-yl)-1H-pyrazolo[3,4-b]pyridine 16.

Off-white solid (24 mg, 0.05 mmol, 33.5% yield). $^{1}$H NMR ($DMSO-d_6$, 500 MHz) δ ppm 1.54-1.67 (m, 4H), 2.33-2.47 (m, 4H), 3.69 (brs, 2H), 7.21 (brd, 1H), 7.59 (dd, J=8 Hz, J=5 Hz, 1H), 8.12 (brd, 1H), 8.22-8.30 (m, 2H), 8.69 (d, J=5 Hz, 1H), 8.75 (s, 1H), 8.89 (s, 1H), 9.01-9.05 (m, 2H), 9.08 (s, 1H), 13.90 (brs, 1H), 14.61 (brs, 1H); ESIMS found $C_{28}H_{23}FN_8$ m/z 491.1 (M+H).

17

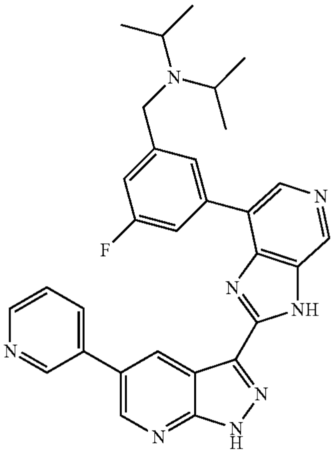

N-(3-Fluoro-5-(2-(5-(pyridin-3-yl)-1H-pyrazolo[3,4-b]pyridin-3-yl)-3H-imidazo[4,5-c]pyridin-7-yl)benzyl)-N-isopropylpropan-2-amine 17.

White solid (61 mg, 0.12 mmol, 65.1% yield). $^1H$ NMR (DMSO-$d_6$, 500 MHz) δ ppm 0.93 (d, J=6 Hz, 12H), 2.90-3.00 (m, 2H), 3.70 (s, 2H), 7.25 (d, J=9 Hz, 1H), 7.58 (dd, J=8 Hz, J=5 Hz, 1H), 8.09 (s, 1H), 8.14 (brd, 1H), 8.24 (d, J=8 Hz, 2H), 8.67 (dd, J=5 Hz, J=2 Hz, 1H), 8.70 (s, 1H), 8.88 (s, 1H), 9.03 (d, J=2 Hz, 1H), 9.05 (d, J=2 Hz, 1H), 9.07 (s, 1H), 13.88 (brs, 1H), 14.58 (brs, 1H); ESIMS found $C_{30}H_{29}FN_8$ m/z 521.3 (M+H).

19

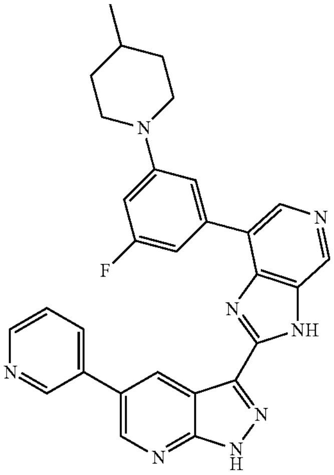

3-(7-(3-Fluoro-5-(4-methylpiperidin-1-yl)phenyl)-3H-imidazo[4,5-c]pyridin-2-yl)-5-(pyridin-3-yl)-1H-pyrazolo[3,4-b]pyridine 19.

Yellow solid (72 mg, 0.14 mmol, 100% yield). $^1H$ NMR (DMSO-$d_6$, 500 MHz) δ ppm 0.79 (brd, 3H), 0.96-1.09 (m, 2H), 1.12-1.23 (m, 1H), 1.34-1.44 (m, 2H), 2.55-2.66 (m, 2H), 3.77 (brd, 2H), 6.81 (brd, 1H), 7.38-7.47 (m, 1H), 7.59 (dd, J=8 Hz, J=5 Hz, 1H), 7.90 (s, 1H), 8.22 (brd, 1H), 8.68 (d, J=4 Hz, 1H), 8.72 (s, 1H), 8.88 (s, 1H), 9.00 (s, 1H), 9.02 (s, 2H), 13.92 (brs, 1H), 14.62 (s, 1H); ESIMS found $C_{29}H_{25}FN_8$ m/z 505.1 (M+H).

21

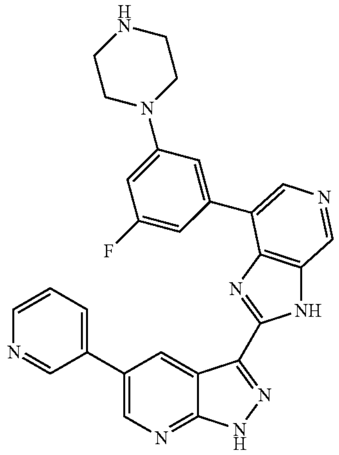

3-(7-(3-Fluoro-5-(piperazin-1-yl)phenyl)-3H-imidazo[4,5-c]pyridin-2-yl)-5-(pyridin-3-yl)-1H-pyrazolo[3,4-b]pyridine 21.

Yellow solid (68 mg, 0.14 mmol, 86.5% yield). $^1H$ NMR (DMSO-$d_6$, 500 MHz) δ ppm 2.69-2.77 (m, 4H), 3.13-3.21 (m, 4H), 6.82 (dd, J=10 Hz, J=2 Hz, 1H), 7.57 (dd, J=8 Hz, J=5 Hz, 1H), 7.56-7.67 (m, 2H), 8.20 (td, J=8 Hz, J=2 Hz, 1H), 8.66 (dd, J=5 Hz, J=2 Hz, 2H), 8.87 (s, 1H), 8.99 (d, J=2 Hz, 1H), 9.02 (s, 2H); ESIMS found $C_{27}H_{22}FN_9$ m/z 492.4 (M+H).

23

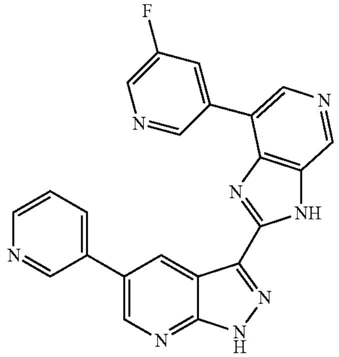

3-(7-(5-Fluoropyridin-3-yl)-3H-imidazo[4,5-c]pyridin-2-yl)-5-(pyridin-3-yl)-1H-pyrazolo[3,4-b]pyridine 23.

Off-white solid (69 mg, 0.17 mmol, 93.9% yield). $^1H$ NMR (DMSO-$d_6$, 500 MHz) δ ppm 7.60 (dd, J=8 Hz, J=5 Hz, 1H), 8.27 (d, J=8 Hz, 1H), 8.64-8.71 (m, 2H), 8.83-8.92 (m, 2H), 8.94 (s, 1H), 9.06 (d, J=2 Hz, 1H), 9.08 (s, 1H), 9.10 (s, 1H), 9.44 (s, 1H), 14.00 (brs, 1H), 14.63 (brs, 1H); ESIMS found $C_{22}H_{13}FN_8$ m/z 409.1 (M+H).

443

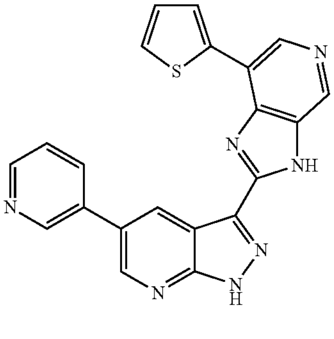

5-(Pyridin-3-yl)-3-(7-(thiophen-2-yl)-3H-imidazo[4,5-c]pyridin-2-yl)-1H-pyrazolo[3,4-b]pyridine 443.

Beige solid (3.4 mg, 0.009 mmol, 40.9% yield). $^1$H NMR (DMSO-$d_6$, 500 MHz) δ ppm 7.27 (t, J=4 Hz, 1H), 7.65 (dd, J=5 Hz, J=8 Hz, 1H), 7.74 (d, J=5.5 Hz, 1H), 8.22 (d, J=3.5 Hz, 1H), 8.29 (d, J=8 Hz, 1H), 8.70 (d, J=4.5 Hz, 1H), 8.79 (s, 1H), 8.82 (s, 1H), 9.09 (d, J=1.5 Hz, 2H), 9.26 (s, 1H), 13.87 (s, 1H), 14.60 (s, 1H); ESIMS found $C_{21}H_{13}N_7S$ m/z 396.1 (M+H).

590

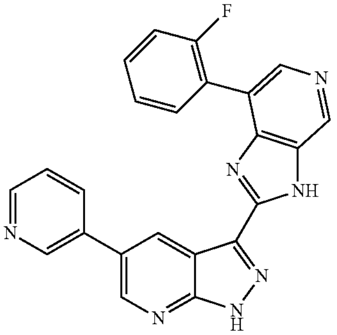

3-(4-(2-Fluorophenyl)-1H-benzo[d]imidazol-2-yl)-5-(pyridin-3-yl)-1H-pyrazolo[3,4-b]pyridine 590.

Brown solid (39.5 mg, 0.10 mmol, 30.0% yield). $^1$H NMR (DMSO-$d_6$, 500 MHz) δ ppm 7.31-7.40 (m, 4H), 7.45-7.52 (m, 1H), 7.54-7.63 (m, 2H), 8.09 (dt, J=1.5 Hz, J=7 Hz, 1H), 8.19 (d, J=8 Hz, 1H), 8.67 (d, J=4 Hz, 1H), 9.00 (d, J=2 Hz, 1H), 9.03 (s, 2H), 13.36 (brs, 1H), 14.35 (brs, 1H); ESIMS found $C_{24}H_{15}FN_6$ m/z 407.2 (M+H).

888

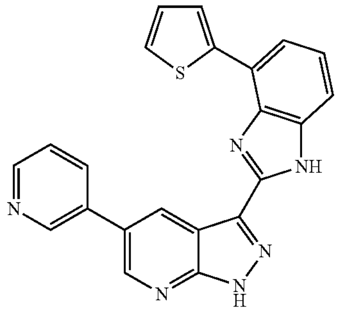

5-(Pyridin-3-yl)-3-(4-(thiophen-2-yl)-1H-benzo[d]imidazol-2-yl)-1H-pyrazolo[3,4-b]pyridine 888.

Off-white solid (32.3 mg, 0.08 mmol, 25.3% yield). $^1$H NMR (DMSO-$d_6$, 500 MHz) δ ppm 7.23 (dd, J=3.5 Hz, J=5 Hz, 1H), 7.31 (t, J=7.5 Hz, 1H), 7.48 (d, J=7.5 Hz, 1H), 7.62-7.68 (m, 3H), 8.16 (d, J=3 Hz, 1H), 8.29 (td, J=2 Hz, J=8 Hz, 1H), 8.70 (dd, J=1 Hz, J=4.5 Hz, 1H), 9.08 (d, J=2 Hz, 1H), 9.10 (d, J=2 Hz, 1H), 9.34 (d, J=2.5 Hz, 1H), 13.41 (s, 1H), 14.39 (s, 1H); ESIMS found $C_{22}H_{14}N_6S$ m/z 395.1 (M+H).

Example 2

Preparation of N-(5-(3-(743-fluorophenyl)-3H-imidazo[4,5-c]pyridin-2-yl)-1H-pyrazolo[3,4-b]pyridin-5-yl)pyridin-3-yl)pivalamide (2) is depicted below in Scheme 23.

Scheme 23

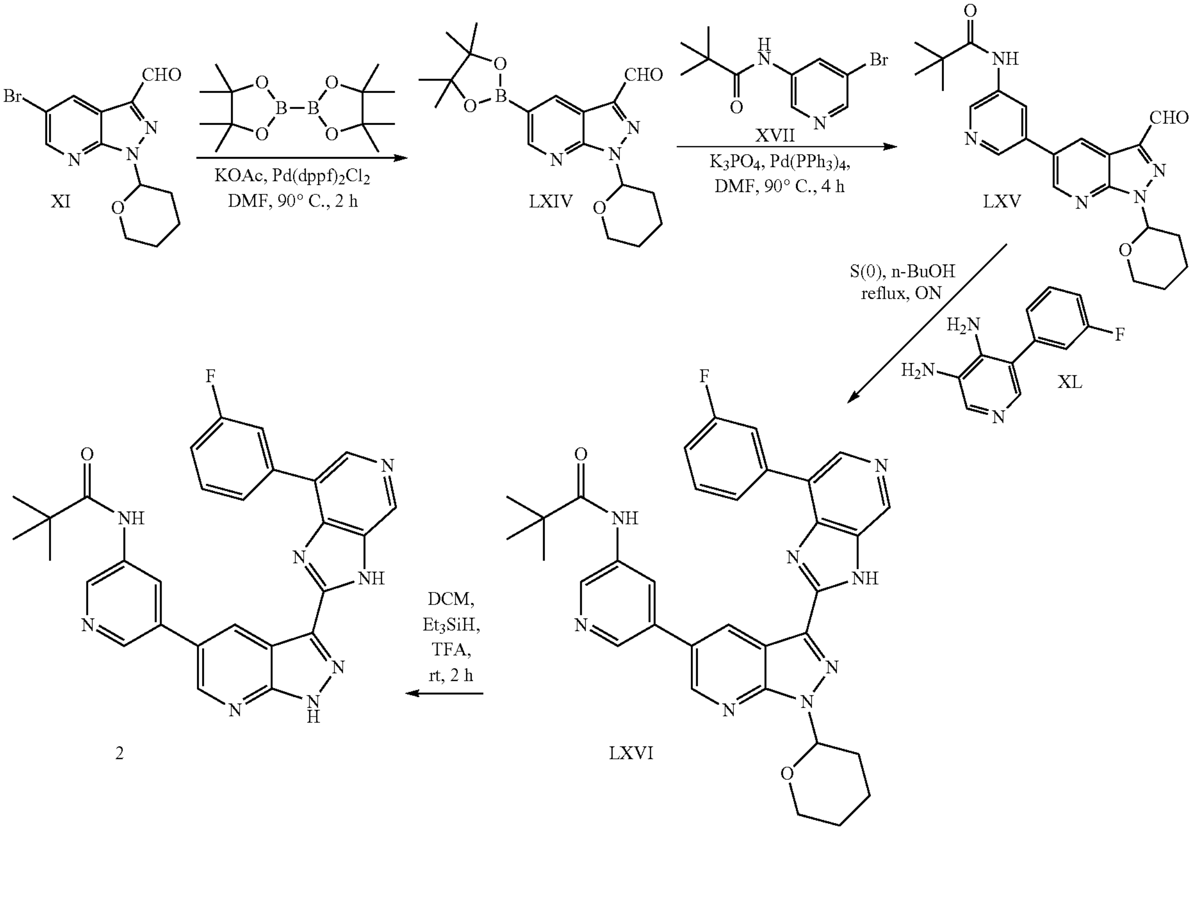

Steps 1-2

A solution of 5-bromo-1-(tetrahydro-pyran-2-yl)-1H-pyrazolo[3,4-b]pyridin-3-yl]-carbaldehyde (XI) (436 mg, 1.4 mmol), bis(pinacolato)diboron (426 mg, 1.6 mmol), and KOAc (412 mg, 4.2 mmol) in dry DMF (20 ml) was purged with argon. $PdCl_2(dppf)_2$ (68 mg, 0.08 mmol) was added to the solution and purged again with argon. The solution was heated at 90° C. for 2 h under argon and cooled to the room temperature. N-(5-bromopyridin-3-yl)pivalamide (XVII) (358 mg, 1.4 mmol), potassium phosphate (446 mg, 2.1 mmol) and water (2 mL) was added to the solution and purged with argon. $Pd(PPh_3)_4$ was then added and the solution was again purged with the argon. The solution was heated at 90° C. for 4 h under argon. The solution was filtered through a bed of Celite and the solvent was distilled under vacuum. The crude product was suspended in water, sonicated briefly. The solids were filtered, dried under vacuum and purified by flash chromatography (100% DCM→3:97 MeOH:DCM) to get N-(5-(3-formyl-1-(tetrahydro-2H-pyran-2-yl)-1H-pyrazolo[3,4-b]pyridin-5-yl)pyridin-3-yl)pivalamide (LXV) as a brown solid (390 mg, 0.96 mmol, 68% yield). $^1H$ NMR (DMSO-$d_6$, 500 MHz) δ ppm 1.27 (s, 9H), 1.58-1.69 (m, 2H), 1.78-1.90 (m, 1H), 2.02-2.14 (m, 2H), 2.49-2.57 (m, 1H), 3.78 (dt, J=11 Hz, J=4 Hz, 1H), 3.94-4.03 (d, J=11 Hz, 1H), 6.25 (dd, J=10 Hz, J=2 Hz, 1H), 8.44 (t, J=2 Hz, 1H), 8.72 (dd, J=4 Hz, J=2 Hz, 2H), 8.98 (d, J=2 Hz, 1H), 9.09 (d, J=2 Hz, 1H), 9.60 (s, 1H), 10.21 (s, 1H); ESIMS found $C_{22}H_{25}N_5O_3$ m/z 408 (M+H).

Steps 3-4

A solution of N-(5-(3-formyl-1-(tetrahydro-2H-pyran-2-yl)-1H-pyrazolo[3,4-b]pyridin-5-yl)pyridin-3-yl)pivalamide (LXV) (75 mg, 0.18 mmol), sulfur (64 mg, 0.20 mmol) and 5-(3-fluorophenyl)pyridine-3,4-diamine (XL) (41 mg, 0.20 mmol) in n-butanol (10 mL) was refluxed overnight under argon. The solution was cooled and filtered and dried under vacuum for 1 h. The residue was taken in dry DCM (5 mL). Triethylsilane (72 μL, 0.45 mmol) followed by TFA (2.5 mL) was added to the solution and stirred for 2 h at room temperature. The solvent was removed under vacuum. Water was added to the residue, sonicated briefly and basified with a 5N $NH_4OH$ solution. The solids formed were filtered, washed with cold water and dried at room temperature. The solids were boiled in DCM, cooled to room temperature and sonicated briefly. The solids were filtered, washed with DCM and dried under vacuum to give N-(5-(3-(7-(3-fluorophenyl)-3H-imidazo[4,5-c]pyridin-2-yl)-1H-pyrazolo[3,4-b]pyridin-5-yl)pyridin-3-yl)pivalamide (2) as a brown solid (66 mg, 0.13 mmol, 72% yield). $^1H$ NMR (DMSO-$d_6$, 500 MHz) δ ppm 1.30 (s, 9H), 7.22 (t, 1H), 7.57-7.66 (m, 1H), 8.25 (d, 1H), 8.36 (d, 1H), 8.55 (s, 1H), 8.74 (s, 1H), 8.78 (s, 1H), 8.89 (s, 1H), 8.97 (s, 1H), 9.04 (s, 1H), 9.07 (s, 1H), 9.61 (s, 1H), 13.92 (brs, 1H), 14.63 (brs, 1H); ESIMS found $C_{28}H_{23}FN_8O$ m/z 507.5 (M+H).

The following compounds were prepared in accordance with the procedure described in the above Example 2.

1

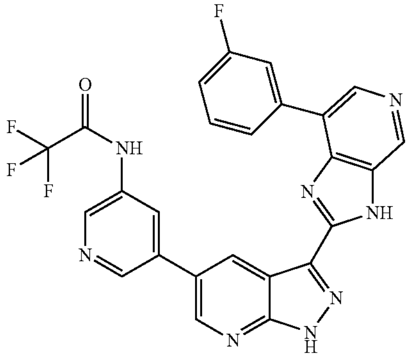

2,2,2-Trifluoro-N-(5-(3-(7-(3-fluorophenyl)-3H-imidazo[4,5-c]pyridin-2-yl)-1H-pyrazolo[3,4-b]pyridin-5-yl)pyridin-3-yl)acetamide 1.

Yellow solid (22 mg, 0.04 mmol, 92.3% yield). $^1H$ NMR (DMSO-$d_6$, 500 MHz) δ ppm 7.20 (t, 1H), 7.60 (q, J=7 Hz, 1H), 8.18 (d, 1H), 8.42 (d, 1H), 8.53 (s, 1H), 8.78 (s, 1H), 8.90 (s, 1H), 8.92 (s, 1H), 8.94 (s, 1H), 9.08 (s, 1H), 9.12 (s, 1H), 13.94 (brs, 1H), 14.64 (brs, 1H); ESIMS found $C_{25}H_{14}F_4N_8O$ m/z 519.3 (M+H).

4

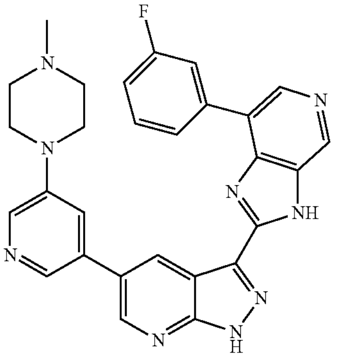

3-(743-Fluorophenyl)-3H-imidazo[4,5-c]pyridin-2-yl)-5-(5-(4-methylpiperazin-1-yl)pyridin-3-yl)-1H-pyrazolo[3,4-b]pyridine 4.

Brown solid (72 mg, 0.14 mmol, 53% yield). $^1H$ NMR (DMSO-$d_6$, 500 MHz) δ ppm 2.29 (s, 3H), 2.52-2.58 (m, 4H), 3.29-3.38 (m, 4H), 7.29 (t, 1H), 7.58 (q, J=7 Hz, 1H), 7.68 (s, 1H), 8.17 (d, J=8 Hz, 1H), 8.36 (d, J=11 Hz, 1H), 8.41 (d, J=6 Hz, 2H), 8.75 (s, 1H), 8.89 (s, 1H), 9.06 (s, 2H), 13.89 (brs, 1H), 14.59 (brs, 1H); ESIMS found $C_{28}H_{24}FN_9$ m/z 506.4 (M+H).

5

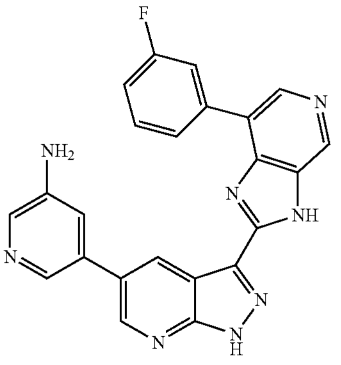

5-(3-(7-(3-Fluorophenyl)-3H-imidazo[4,5-c]pyridin-2-yl)-1H-pyrazolo[3,4-b]pyridin-5-yl)pyridin-3-amine 5.

Brown solid (68 mg, 0.16 mmol, 85% yield). $^1H$ NMR (DMSO-$d_6$, 500 MHz) δ ppm 5.51 (s, 2H), 7.26-7.34 (m, 2H), 7.61 (q, J=8 Hz, 1H), 8.03 (d, J=2 Hz, 1H), 8.17 (d, J=2 Hz, 1H), 8.21 (d, J=8 Hz, 1H), 8.35 (d, J=11 Hz, 1H), 8.68 (s, 1H), 8.89 (s, 1H), 8.93 (d, J=2 Hz, 1H), 9.01 (s, 1H), 13.89 (s, 1H), 14.57 (s, 1H); ESIMS found $C_{23}H_{15}FN_8$ m/z 423.1 (M+H).

6

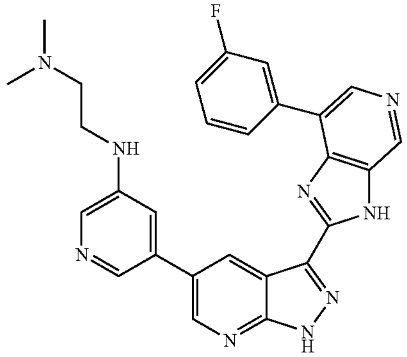

N1-(5-(3-(7-(3-Fluorophenyl)-3H-imidazo[4,5-c]pyridin-2-yl)-1H-pyrazolo[3,4-b]pyridin-5-yl)pyridin-3-yl)-N2,N2-dimethylethane-1,2-diamine 6.

Brown solid (68 mg, 0.14 mmol, 53% yield). $^1H$ NMR (DMSO-$d_6$, 500 MHz) δ ppm 2.26 (s, 6H), 2.53-2.61 (m, 2H), 3.22-3.31 (m, 2H), 5.91 (brs, 1H), 7.24-7.34 (m, 2H), 7.59 (q, J=8 Hz, 1H), 8.11 (d, J=2 Hz, 1H), 8.19 (d, J=2 Hz, 2H), 8.37 (brd, 1H), 8.75 (s, 1H), 8.90 (s, 1H), 9.00 (s, 1H), 9.03 (s, 1H), 13.87 (brs, 1H), 14.56 (brs, 1H); ESIMS found $C_{27}H_{24}FN_9$ m/z 494.4 (M+H).

7

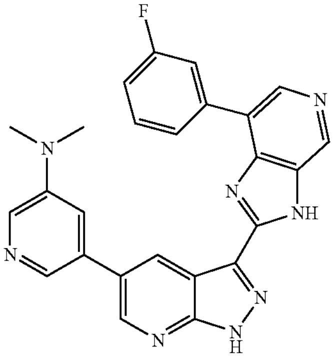

5-(3-(7-(3-Fluorophenyl)-3H-imidazo[4,5-c]pyridin-2-yl)-1H-pyrazolo[3,4-b]pyridin-5-yl)-N,N-dimethylpyridin-3-amine 7.

Brown solid (68 mg, 0.15 mmol, 63% yield). $^1H$ NMR (DMSO-$d_6$, 500 MHz) δ ppm 3.05 (s, 6H), 7.30 (t, J=7 Hz, 1H), 7.41 (s, 1H), 7.57 (q, J=7 Hz, 1H), 8.15 (d, J=8 Hz, 1H), 8.21 (d, J=2.5 Hz, 1H), 8.30 (s, 1H), 8.35 (d, J=11 Hz, 1H), 8.74 (s, 1H), 8.89 (s, 1H), 9.05 (s, 2H), 13.89 (s, 1H), 14.58 (s, 1H); ESIMS found $C_{25}H_{19}FN_8$ m/z 451.1 (M+H).

9

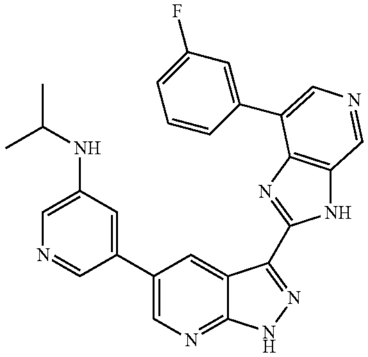

5-(3-(7-(3-Fluorophenyl)-3H-imidazo[4,5-c]pyridin-2-yl)-1H-pyrazolo[3,4-b]pyridin-5-yl)-N-isopropylpyridin-3-amine 9.

Brown solid (79 mg, 0.17 mmol, 68% yield). $^1H$ NMR (DMSO-$d_6$, 500 MHz) δ ppm 1.18 (d, J=6 Hz, 6H), 3.71 (sep, J=7 Hz, 1H), 5.91 (d, J=8 Hz, 1H), 7.21 (s, 1H), 7.28 (t, J=8 Hz, 1H), 7.58 (q, J=8 Hz, 1H), 8.04 (d, J=2.5 Hz, 1H), 8.14 (d, J=2 Hz, 1H), 8.17 (d, J=8 Hz, 1H), 8.32 (d, J=10 Hz, 1H), 8.74 (s, 1H), 8.89 (s, 1H), 8.97 (s, 1H), 9.00 (s, 1H), 13.89 (s, 1H), 14.57 (s, 1H); ESIMS found $C_{26}H_{21}FN_8$ m/z 465.3 (M+H).

18

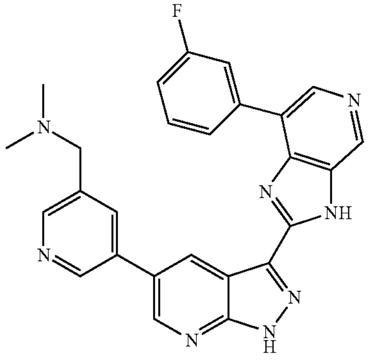

1-(5-(3-(7-(3-Fluorophenyl)-3H-imidazo[4,5-c]pyridin-2-yl)-1H-pyrazolo[3,4-b]pyridin-5-yl)pyridin-3-yl)-N,N-dimethylmethanamine 18.

Off-white solid (39 mg, 0.08 mmol, 76.4% yield). $^1H$ NMR (DMSO-$d_6$, 500 MHz) δ ppm 2.25 (s, 6H), 3.58 (s, 2H), 7.31 (t, J=8 Hz, 1H), 7.61 (q, J=7 Hz, 1H), 8.12 (s, 1H), 8.20 (d, J=8 Hz, 1H), 8.37 (d, J=10 Hz, 1H), 8.60 (s, 1H), 8.76 (s, 1H), 8.89 (s, 1H), 8.98 (s, 1H), 9.10 (s, 2H), 13.91 (s, 1H), 14.61 (s, 1H); ESIMS found $C_{26}H_{21}FN_8$ m/z 465.3 (M+H).

20

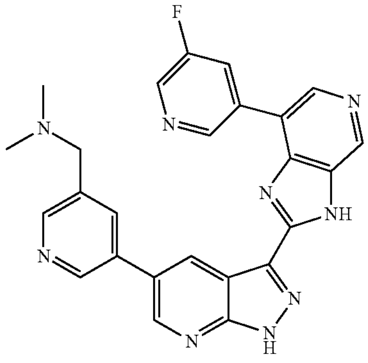

1-(5-(3-(7-(5-Fluoropyridin-3-yl)-3H-imidazo[4,5-c]pyridin-2-yl)-1H-pyrazolo[3,4-b]pyridin-5-yl)pyridin-3-yl)-N,N-dimethylmethanamine 20.

Off-white solid (14 mg, 0.03 mmol, 21.5% yield). $^{1}$H NMR ($DMSO-d_6$, 500 MHz) δ ppm 2.22 (s, 6H), 3.58 (s, 2H), 8.11 (s, 1H), 8.59 (s, 1H), 8.67 (s, 1H), 8.77-8.90 (m, 2H), 8.95 (s, 2H), 9.07 (s, 2H), 9.43 (brs, 1H), 13.99 (brs, 1H), 14.63 (brs, 1H); ESIMS found $C_{25}H_{20}FN_9$ m/z 466 (M+H).

22

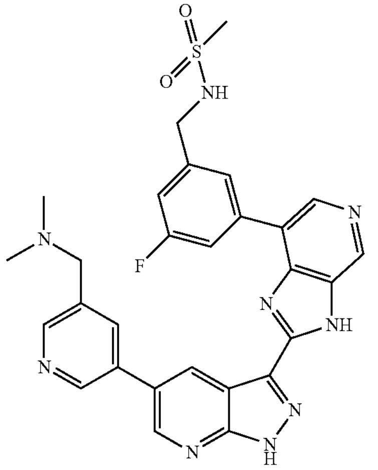

N-(3-(2-(5-(5-((Dimethylamino)methyl)pyridin-3-yl)-1H-pyrazolo[3,4-b]pyridin-3-yl)-3H-imidazo[4,5-c]pyridin-7-yl)-5-fluorobenzyl)methanesulfonamide 22.

Off-white solid (49 mg, 0.09 mmol, 62.6% yield). $^{1}$H NMR ($DMSO-d_6$, 500 MHz) δ ppm 2.23 (brs, 6H), 2.90 (s, 3H), 3.58 (brs, 2H), 4.32 (d, J=6 Hz, 2H), 7.28 (d, J=9 Hz, 1H), 7.73 (t, J=8 Hz, 1H), 8.08 (s, 1H), 8.35 (d, J=10 Hz, 1H), 8.60 (s, 1H), 8.75 (s, 1H), 8.90 (s, 1H), 8.97 (s, 1H), 9.07 (s, 1H), 9.09 (s, 1H), 13.92 (s, 1H), 14.61 (s, 1H); ESIMS found $C_{28}H_{26}FN_9O_2S$ m/z 572.0 (M+H).

24

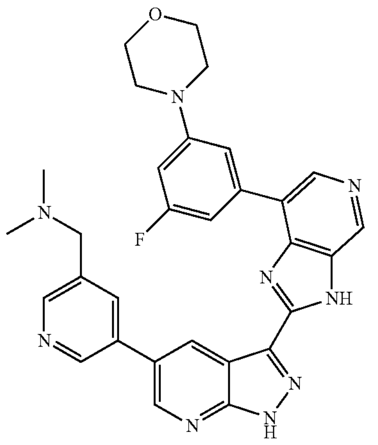

1-(5-(3-(7-(3-Fluoro-5-morpholinophenyl)-3H-imidazo[4,5-c]pyridin-2-yl)-1H-pyrazolo[3,4-b]pyridin-5-yl)pyridin-3-yl)-N,N-dimethylmethanamine 24.

Off-white solid (52 mg, 0.09 mmol, 72.8% yield). $^{1}$H NMR ($DMSO-d_6$, 500 MHz) δ ppm 2.22 (s, 6H), 3.14-3.21 (m, 4H), 3.47-3.56 (m, 4H), 3.57 (s, 2H), 6.85 (d, J=12 Hz, 1H), 7.62 (d, J=10 Hz, 1H), 7.74 (s, 1H), 8.07 (s, 1H), 8.59 (s, 1H), 8.72 (s, 1H), 8.87 (s, 1H), 8.90 (s, 1H), 9.02 (s, 1H), 9.03 (s, 1H), 13.86 (brs, 1H), 14.60 (brs, 1H); ESIMS found $C_{30}H_{28}FN_9O$ m/z 550.5 (M+H).

25

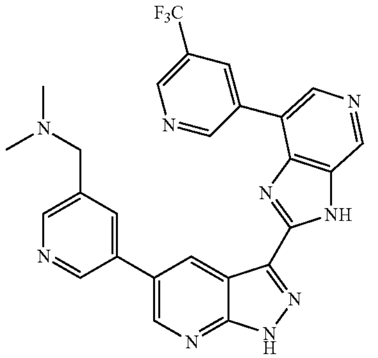

N,N-Dimethyl-1-(5-(3-(7-(5-(trifluoromethyl)pyridin-3-yl)-3H-imidazo[4,5-c]pyridin-2-yl)-1H-pyrazolo[3,4-b]pyridin-5-yl)pyridin-3-yl)methanamine 25.

Off-white solid (51 mg, 0.10 mmol, 91.6% yield). $^{1}$H NMR ($DMSO-d_6$, 500 MHz) δ ppm 2.20 (s, 6H), 3.56 (s, 2H), 8.03 (s, 1H), 8.60 (d, J=1.5 Hz, 1H), 8.87 (s, 1H), 8.91-9.00 (m, 3H), 9.02 (d, J=2 Hz, 1H), 9.03 (s, 1H), 9.36 (s, 1H), 9.73 (s, 1H), 14.01 (brs, 1H), 14.65 (brs, 1H); ESIMS found $C_{26}H_{20}F_3N_9$ m/z 516.3 (M+H).

27

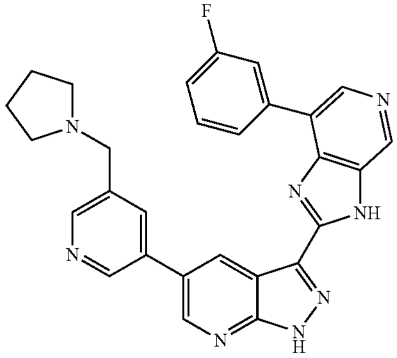

3-(7-(3-Fluorophenyl)-3H-imidazo[4,5-c]pyridin-2-yl)-5-(5-(pyrrolidin-1-ylmethyl)pyridin-3-yl)-1H-pyrazolo[3,4-b]pyridine 27.

Beige solid (13.5 mg, 0.028 mmol, 15.1% yield). $^{1}$H NMR ($DMSO-d_6$, 500 MHz) δ ppm 1.75 (brs, 4H), 2.62 (brs, 4H), 3.84 (brs, 2H), 7.39 (t, J=9 Hz, 2H), 8.17 (s, 1H), 8.41 (brs, 2H), 8.62 (d, J=1.5 Hz, 1N), 8.65 (brs, 1H), 8.86 (brs, 1H), 8.98 (s, 1H), 9.09 (s, 2H), 13.84 (brs, 1H), 14.57 (brs, 1H); ESIMS found $C_{28}H_{23}FN_8$ m/z 491.2 (M+H).

28

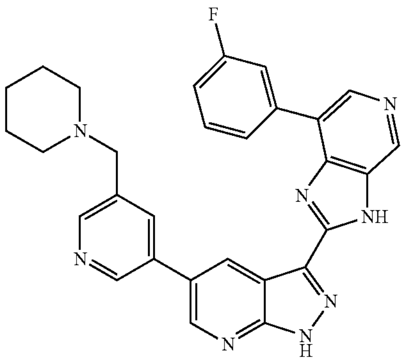

3-(7-(3-Fluorophenyl)-3H-imidazo[4,5-c]pyridin-2-yl)-5-(5-(piperidin-1-ylmethyl)pyridin-3-yl)-1H-pyrazolo[3,4-b]pyridine 28.

Yellow solid (23 mg, 0.046 mmol, 35.1% yield). $^1$H NMR (DMSO-$d_6$, 500 MHz) δ ppm 1.40 (brs, 2H), 1.50 (brs, 4H), 2.40 (brs, 4H), 3.60 (s, 2H), 7.28 (t, J=7 Hz, 1H), 7.60 (q, J=7 Hz, 1H), 8.09 (s, 1H), 8.17 (brs, 1H), 8.39 (brd, J=9 Hz, 1H), 8.58 (s, 1H), 8.75 (brs, 1H), 8.89 (s, 1H), 8.95 (s, 1H), 9.08 (s, 1H), 9.09 (s, 1H), 13.90 (brs, 1H), 14.58 (brs, 1H); ESIMS found $C_{29}H_{25}FN_8$ m/z 505.5 (M+H).

114

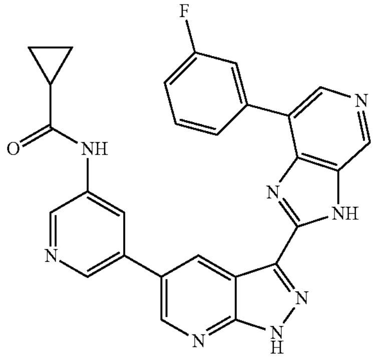

N-(5-(3-(7-(3-Fluorophenyl)-3H-imidazo[4,5-c]pyridin-2-yl)-1H-pyrazolo[3,4-b]pyridin-5-yl)pyridin-3-yl)cyclopropanecarboxamide 114.

Off-white solid (6.8 mg, 0.014 mmol, 12.7% yield). $^1$H NMR (DMSO-$d_6$, 500 MHz) δ ppm 0.81-0.92 (m, 4H), 1.82-1.91 (m, 1H), 7.27 (brs, 1H), 7.61 (ABq, J=8 Hz, 1H), 8.25 (brs, 1H), 8.30 (brs, 1H), 8.55 (brs, 1H), 8.72 (d, J=2 Hz, 1H), 8.77 (brs, 2H), 8.91 (brs, 1H), 9.01 (d, J=2 Hz, 1H), 9.06 (s, 1H), 10.62 (s, 1H), 13.96 (brs, 1H), 14.61 (s, 1H); ESIMS found $C_{27}H_{19}FN_8O$ m/z 491.2 (M+H).

128

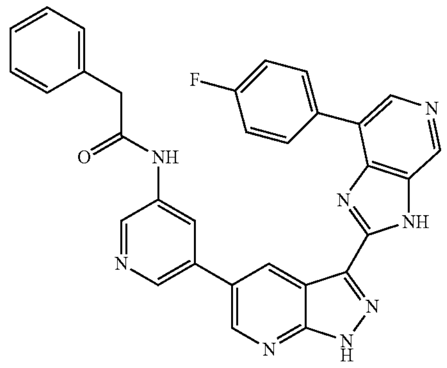

N-(5-(3-(7-(4-Fluorophenyl)-3H-imidazo[4,5-c]pyridin-2-yl)-1H-pyrazolo[3,4-b]pyridin-5-yl)pyridin-3-yl)-2-phenylacetamide 128.

Brown solid (42.6 mg, 0.08 mmol, 42.4% yield). $^1$H NMR (DMSO-$d_6$, 500 MHz) δ ppm 3.78 (s, 2H), 7.26 (t, J=7 Hz, 1H), 7.34 (t, J=8 Hz, 2H), 7.39 (d, J=7 Hz, 2H), 7.45 (t, J=8.5 Hz, 2H), 8.32 (brs, 2H), 8.60 (s, 1H), 8.74 (brs, 1H), 8.75 (d, J=1.5 Hz, 1H), 8.78 (s, 1H), 9.00 (d, J=2 Hz, 1H), 9.04 (d, J=2 Hz, 1H), 9.08 (brs, 1H), 10.67 (s, 1H), 14.76 (s, 1H); ESIMS found $C_{31}H_{21}FN_8O$ m/z 541.4 (M+H).

142

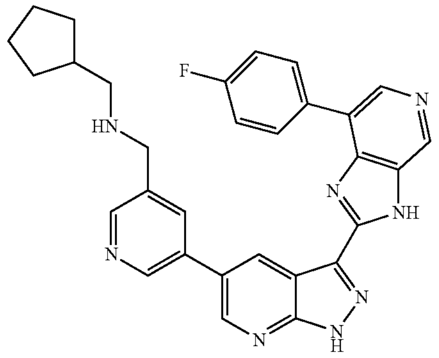

1-Cyclopentyl-N-((5-(3-(7-(4-fluorophenyl)-3H-imidazo[4,5-c]pyridin-2-yl)-1H-pyrazolo[3,4-b]pyridin-5-yl)pyridin-3-yl)methyl)methanamine 142.

Tan solid (6.4 mg, 0.012 mmol, 7.1% yield). $^1$H NMR (DMSO-$d_6$, 500 MHz) δ ppm 1.13-1.26 (m, 2H), 1.39-1.55 (m, 4H), 1.58-1.76 (m, 2H), 2.56 (d, J=5.5 Hz, 2H), 2.03 (quin, J=7.5 Hz, 1H), 3.93 (brs, 2H), 7.40 (t, J=9 Hz, 2H), 8.24 (s, 1H), 8.43 (brs, 2H), 8.64 (s, 2H), 8.88 (brs, 1H), 8.96 (s, 1H), 9.08 (s, 1H), 9.11 (s, 1H); ESIMS found $C_{30}H_{27}FN_8$ m/z 519.1 (M+H).

158

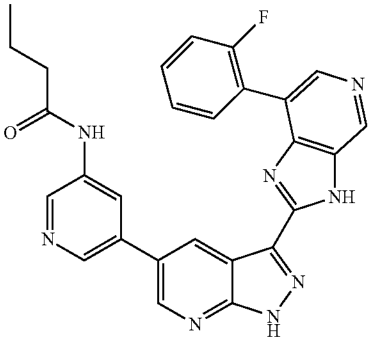

N-(5-(3-(7-(2-Fluorophenyl)-3H-imidazo[4,5-c]pyridin-2-yl)-1H-pyrazolo[3,4-b]pyridin-5-yl)pyridin-3-yl)butyramide 158.

Brown solid (36.4 mg, 0.074 mmol, 40.8% yield). $^{1}$H NMR (DMSO-$d_6$, 500 MHz) δ ppm 0.92-1.02 (m, 3H), 1.69 (brs, 2H), 2.35-2.44 (m, 2H), 7.33-7.45 (m, 2H), 7.45-7.59 (m, 1H), 8.52 (s, 1H), 8.73 (d, J=13 Hz, 1H), 8.91 (t, J=6.5 Hz, 2H), 8.99 (s, 2H), 10.31 (s, 1H), 13.84 (s, 1H), 14.48-14.63 (m, 1H); ESIMS found $C_{27}H_{21}FN_8O$ m/z 493.4 (M+H).

176

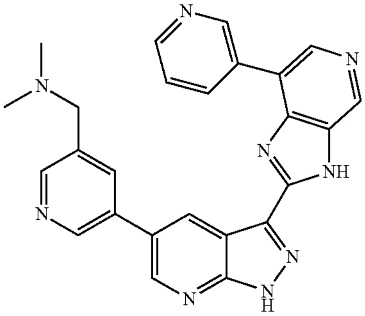

N,N-Dimethyl-1-(5-(3-(7-(pyridin-3-yl)-3H-imidazo[4,5-c]pyridin-2-yl)-1H-pyrazolo[3,4-b]pyridin-5-yl)pyridin-3-yl)methanamine 176.

Dark brown solid (24.5 mg, 0.055 mmol, 28.7% yield). $^{1}$H NMR (DMSO-$d_6$, 500 MHz) δ ppm 2.26 (s, 6H), 3.60 (s, 2H), 7.59 (dd, J=5.5 Hz, J=8 Hz, 1H), 8.11 (s, 1H), 8.58 (d, J=1.5 Hz, 1H), 8.66 (d, J=3.5 Hz, 1H), 8.73 (brs, 2H), 8.91 (brs, 1H), 8.96 (d, J=2 Hz, 1H), 9.06 (brs, 2H), 9.49 (brs, 1H), 13.91 (brs, 1H), 14.58 (brs, 1H); ESIMS found $C_{25}H_{21}N_9$ m/z 448.1 (M+H).

178

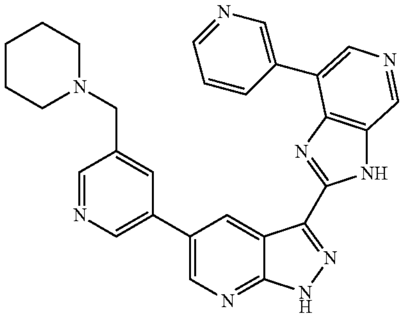

5-(5-(Piperidin-1-ylmethyl)pyridin-3-yl)-3-(7-(pyridin-3-yl)-3H-imidazo[4,5-c]pyridin-2-yl)-1H-pyrazolo[3,4-b]pyridine 178.

Brown solid (1.2 mg, 0.002 mmol, 0.9% yield). $^{1}$H NMR (DMSO-$d_6$, 500 MHz) δ ppm 1.36-1.79 (m, 6H), 2.42-251 (m, 4H), 3.62 (s, 2H), 7.60 (dd, J=7.5 Hz, J=4.5 Hz, 2H), 8.66 (d, J=4.5 Hz, 1H), 8.70 (s, 1H), 8.72 (s, 1H), 8.75 (s, 1H), 8.93 (s, 1H), 9.09 (brs, 3H), 9.58 (brs, 1H), 13.94 (s, 1H), 14.64 (brs, 1H); ESIMS found $C_{28}H_{25}N_9$ m/z 488.3 (M+H).

179

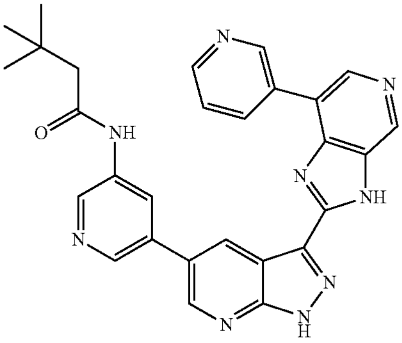

3,3-Dimethyl-N-(5-(3-(7-(pyridin-3-yl)-3H-imidazo[4,5-c]pyridin-2-yl)-1H-pyrazolo[3,4-b]pyridin-5-yl)pyridin-3-yl)butanamide 179.

Brown solid (4.1 mg, 0.008 mmol, 4.7% yield). $^{1}$H NMR (DMSO-$d_6$, 500 MHz) δ ppm 1.07 (s, 9H), 2.30 (s, 2H), 7.65 (dd, J=5 Hz, J=8 Hz, 1H), 8.52 (s, 1H), 8.66 (d, J=3.5 Hz, 1H), 8.70 (d, J=2 Hz, 1H), 8.77 (brs, 1H), 8.81 (s, 2H), 8.99 (d, J=2 Hz, 1H), 9.01 (d, J=2 Hz, 1H), 9.05 (brs, 1H), 9.39 (brs, 1H), 10.27 (s, 1H), 14.71 (s, 1H); ESIMS found $C_{28}H_{25}N_9O$ m/z 504.3 (M+H).

185

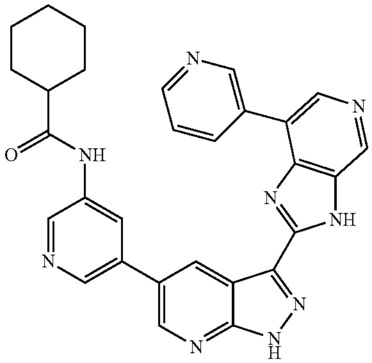

N-(5-(3-(7-(Pyridin-3-yl)-3H-imidazo[4,5-c]pyridin-2-yl)-1H-pyrazolo[3,4-b]pyridin-5-yl)pyridin-3-yl)cyclohexanecarboxamide 185.

Brown solid (16.2 mg, 0.03 mmol, 18.6% yield). $^{1}$H NMR (DMSO-$d_6$, 500 MHz) δ ppm 1.20-1.38 (m, 3H), 1.47 (dq, J=2.5 Hz, J=12 Hz, 2H), 1.69 (d, J=12.5 Hz, 1H), 1.81 (d, J=12.5 Hz, 2H), 1.90 (d, J=10.5 Hz, 2H), 2.43 (tt, J=3.5 Hz, J=11.5 Hz, 1H), 7.64 (dd, J=4.5 Hz, J=8 Hz, 1H), 8.56 (brs, 1H), 8.63 (brs, 1H), 8.70 (d, J=2 Hz, 1H), 8.80 (brs, 3H), 8.96 (brs, 1H), 9.00 (s, 2H), 9.41 (brs, 1H), 10.26 (s, 1H), 13.98 (brs, 1H), 14.63 (s, 1H); ESIMS found $C_{29}H_{25}N_9O$ m/z 516.3 (M+H).

192

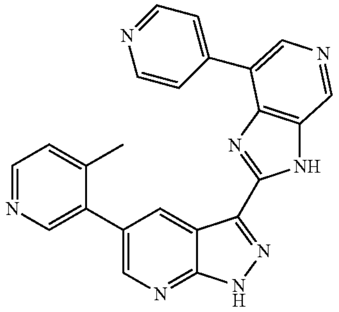

5-(4-Methylpyridin-3-yl)-3-(7-(pyridin-4-yl)-3H-imidazo[4,5-c]pyridin-2-yl)-1H-pyrazolo[3,4-b]pyridine 192.

Beige solid (25.6 mg, 0.06 mmol, 71.1% yield). $^1$H NMR (DMSO-$d_6$, 500 MHz) δ ppm 2.42 (s, 3H), 7.49 (d, J=5 Hz, 1H), 8.34 (brs, 2H), 8.55 (d, J=5 Hz, 1H), 8.60 (s, 1H), 8.69 (d, J=4.5 Hz, 2H), 8.78 (s, 2H), 8.87 (s, 1H), 8.97 (s, 1H), 13.99 (brs, 1H), 14.63 (s, 1H); ESIMS found $C_{23}H_{16}N_8$ m/z 405.2 (M+H).

198

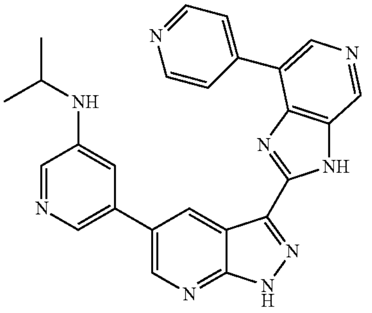

N-Isopropyl-5-(3-(7-(pyridin-4-yl)-3H-imidazo[4,5-c]pyridin-2-yl)-1H-pyrazolo[3,4-b]pyridin-5-yl)pyridin-3-amine 198.

Tan solid (1.3 mg, 0.003 mmol, 1.5% yield). $^1$H NMR (DMSO-$d_6$, 500 MHz) δ ppm 2.04 (d, J=6.5 Hz, 6H), 3.76 (sep, J=6.5 Hz, 1H), 6.06 (brs, 1H), 7.34 (s, 1H), 8.06 (d, J=2 Hz, 1H), 8.21 b(s, 1H), 8.40 (brs, 2H), 8.69 (d, J=6 Hz, 2H), 8.83 (brs, 1H), 8.97 (brs, 1H), 9.00 (s, 1H), 9.04 (s, 1H), 14.03 (brs, 1H), 14.60 (s, 1H); ESIMS found $C_{25}H_{21}N_9$ m/z 448.0 (M+H).

209

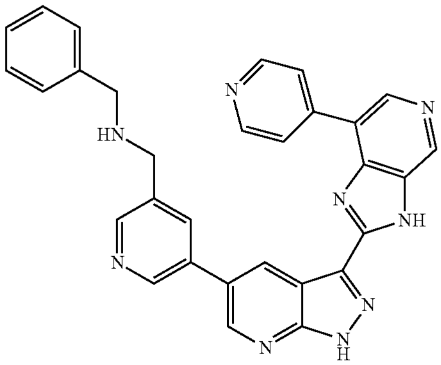

N-Benzyl-1-(5-(3-(7-(pyridin-4-yl)-3H-imidazo[4,5-c]pyridin-2-yl)-1H-pyrazolo[3,4-b]pyridin-5-yl)pyridin-3-yl)methanamine 209.

Beige solid (17.2 mg, 0.034 mmol, 33.8% yield). $^1$H NMR (DMSO-$d_6$, 500 MHz) δ ppm 4.01 (s, 2H), 4.09 (s, 2H), 7.30 (t, J=7 Hz, 1H), 7.37 (t, J=8 Hz, 2H), 7.45 (d, J=7.5 Hz, 2H), 8.31 (s, 1H), 8.33 (d, J=5 Hz, 2H), 8.67 (s, 1H), 8.68 (dd, J=1.5 Hz, J=5 Hz, 1H), 8.73 (dd, J=1.5 Hz, J=4.5 Hz, 2H), 8.76 (d, J=6 Hz, 2H), 9.15 (s, 2H), 14.65 (brs, 1H); ESIMS found $C_{30}H_{23}N_9$ m/z 510.2 (M+H).

229

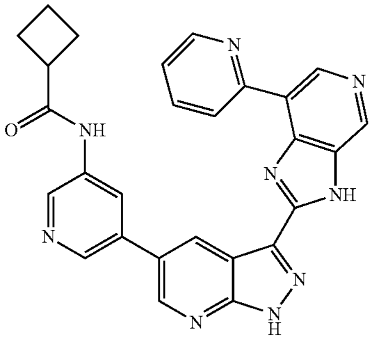

N-(5-(3-(7-(Pyridin-2-yl)-3H-imidazo[4,5-d]pyridin-2-yl)-1H-pyrazolo[3,4-b]pyridin-5-yl)pyridin-3-yl)cyclobutanecarboxamide 229.

Tan solid (8.5 mg, 0.017 mmol, 5.1% yield). $^1$H NMR (DMSO-$d_6$, 500 MHz) δ ppm 1.82-1.93 (m, 1H), 1.95-2.06 (m, 1H), 2.15-2.25 (m, 2H), 2.26-2.34 (m, 2H), 7.40-7.47 (m, 2H), 7.95 (dt, J=2 Hz, J=8 Hz, 1H), 8.15 (d, J=8 Hz, 1H), 8.42 (s, 1H), 8.75 (s, 1H), 8.77 (d, J=1 Hz, 1H), 8.78 (s, 1H), 8.89 (s, 1H), 9.06 (s, 2H), 10.20 (s, 1H), 13.05 (brs, 1H), 14.65 (s, 1H); ESIMS found $C_{27}H_{21}N_9O$ m/z 488.2 (M+H).

238

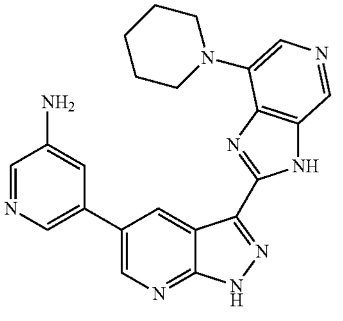

5-(3-(7-(Piperidin-1-yl)-3H-imidazo[4,5-c]pyridin-2-yl)-1H-pyrazolo[3,4-b]pyridin-5-yl)pyridin-3-amine 238.

Tan solid (7.5 mg, 0.018 mmol, 8.9% yield). $^1$H NMR (DMSO-$d_6$, 500 MHz) δ ppm 1.61 (brs, 6H), 3.49 (brs, 4H), 5.65 (brs, 2H), 6.69 (s, 1H), 7.36 (s, 1H), 8.02 (s, 1H), 8.19 (s, 1H), 8.65 (s, 1H), 8.89 (s, 1H), 8.92 (d, J=2 Hz, 1H), 13.04 (s, 1H), 14.36 (s, 1H); ESIMS found $C_{22}H_{21}N_9$ m/z 412.3 (M+H).

241

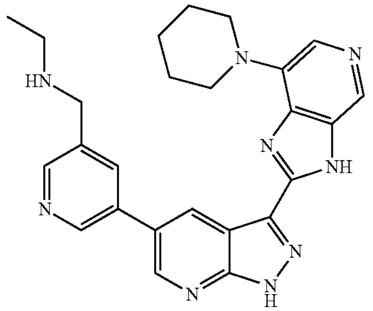

N-((5-(3-(7-(Piperidin-1-yl)-3H-imidazo[4,5-c]pyridin-2-yl)-1H-pyrazolo[3,4-b]pyridin-5-yl)pyridin-3-yl)methyl)ethanamine 241.

Brown solid (9.9 mg, 0.022 mmol, 11.4% yield). $^1$H NMR (DMSO-$d_6$, 500 MHz) δ ppm 1.08 (t, J=7 Hz, 3H), 1.60 (brs, 6H), 2.61 (q, J=7 Hz, 2H), 3.48 (brs, 4H), 3.85 (s, 2H), 6.67 (brs, 1H), 8.19 (s, 1H), 8.60 (d, J=1.5 Hz, 1H), 8.64 (brs, 1H), 8.89 (d, J=2.5 Hz, 1H), 8.97 (d, J=2 Hz, 1H), 9.00 (d, J=2.5 Hz, 1H), 12.95 (brs, 1H); ESIMS found $C_{25}H_{27}N_9$ m/z 454.2 (M+H).

246

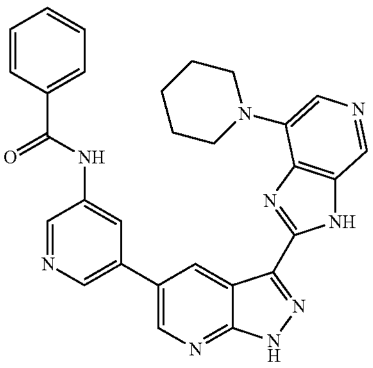

N-(5-(3-(7-(Piperidin-1-yl)-3H-imidazo[4,5-c]pyridin-2-yl)-1H-pyrazolo[3,4-b]pyridin-5-yl)pyridin-3-yl)benzamide 246.

Brown solid (33.1 mg, 0.064 mmol, 37.6% yield). $^1$H NMR (DMSO-$d_6$, 500 MHz) δ ppm 1.60 (brs, 6H), 3.49 (brs, 4H), 6.67 (s, 1H), 7.59 (t, J=7 Hz, 2H), 7.65 (t, J=7 Hz, 1H), 8.05 (d, J=8 Hz, 2H), 8.58 (t, J=2 Hz, 1H), 8.65 (s, 1H), 8.79 (d, J=2 Hz, 1H), 8.97 (d, J=2 Hz, 1H), 9.02 (d, J=2 Hz, 1H), 9.14 (d, J=2 Hz, 1H), 10.65 (s, 1H), 13.01 (s, 1H), 14.40 (s, 1H); ESIMS found $C_{29}H_{25}N_9O$ m/z 516.4 (M+H).

249

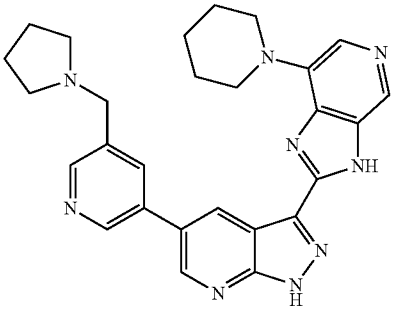

3-(7-(Piperidin-1-yl)-3H-imidazo[4,5-c]pyridin-2-yl)-5-(5-(pyrrolidin-1-ylmethyl)pyridin-3-yl)-1H-pyrazolo[3,4-b]pyridine 249.

Beige solid (26.5 mg, 0.055 mmol, 30.4% yield). $^1$H NMR (DMSO-$d_6$, 500 MHz) δ ppm 1.61 (brs, 6H), 1.74 (brs, 4H), 2.54 (brs, 4H), 3.49 (brs, 4H), 3.76 (brs, 2H), 6.67 (s, 1H), 8.13 (s, 1H), 8.59 (d, J=1.5 Hz, 1H), 8.65 (s, 1H), 8.91 (d, J=2 Hz, 1H), 8.95 (d, J=2 Hz, 1H), 9.00 (d, J=2.5 Hz, 1H), 12.99 (s, 1H), 14.37 (brs, 1H); ESIMS found $C_{27}H_{29}N_9$ 480.1 (M+H).

254

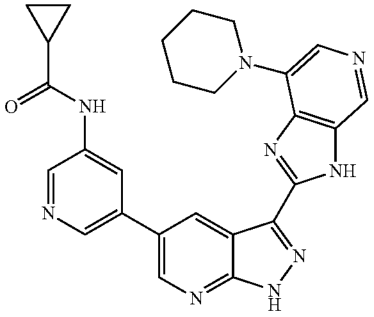

N-(5-(3-(7-(Piperidin-1-yl)-3H-imidazo[4,5-c]pyridin-2-yl)-1H-pyrazolo[3,4-b]pyridin-5-yl)pyridin-3-yl)cyclopropanecarboxamide 254.

Yellow-white solid (8.6 mg, 0.018 mmol, 8.2% yield). $^1$H NMR (DMSO-$d_6$, 500 MHz) δ ppm 0.82-0.92 (m, 4H), 1.61 (brs, 6H), 1.81-1.88 (m, 1H), 3.49 (brs, 4H), 6.67 (s, 1H), 8.40 (s, 1H), 8.65 (s, 1H), 8.71 (d, J=2 Hz, 1H), 8.88 (d, J=2 Hz, 1H), 8.91 (d, J=1.5 Hz, 1H), 8.97 (d, J=2 Hz, 1H), 10.63 (s, 1H), 13.00 (s, 1H), 14.38 (s, 1H); ESIMS found $C_{26}H_{25}N_9O$ m/z 480.1 (M+H).

305

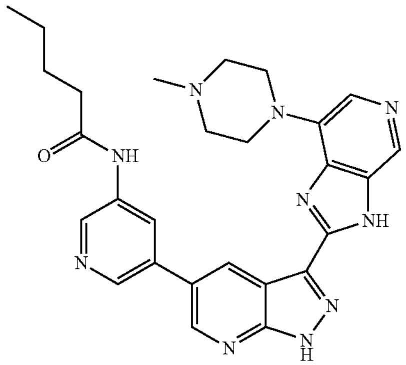

N-(5-(3-(7-(4-Methylpiperazin-1-yl)-3H-imidazo[4,5-c]pyridin-2-yl)-1H-pyrazolo[3,4-b]pyridin-5-yl)pyridin-3-yl)pentanamide 305.

Brown solid (30.4 mg, 0.06 mmol, 33.7% yield). $^1$H NMR ($CD_3OD$, 500 MHz) δ ppm 1.00 (t, J=7.5 Hz, 3H), 1.46 (sex, J=7.5 Hz, 2H), 1.74 (quin, J=7.5 Hz, 2H), 2.48 (t, J=7.5 Hz, 2H), 2.79 (s, 3H), 3.19 (brs, 4H), 3.72 (brs, 4H), 6.94 (brs, 1H), 8.54 (s, 1H), 8.65 (brs, 1H), 8.70 (d, J=2 Hz, 1H), 8.79 (d, J=2 Hz, 1H), 8.91 (d, J=2 Hz, 1H), 9.10 (d, J=1.5 Hz, 1H); ESIMS found $C_{27}H_{30}N_{10}O$ m/z 511.5 (M+H).

309

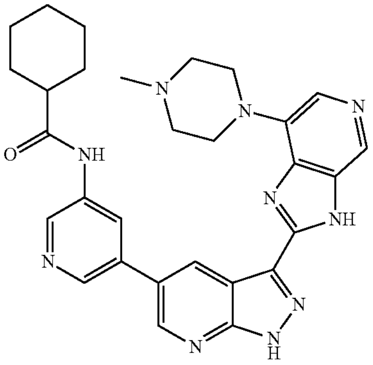

N-(5-(3-(7-(4-Methylpiperazin-1-yl)-3H-imidazo[4,5-c]pyridin-2-yl)-1H-pyrazolo[3,4-b]pyridin-5-yl)pyridin-3-yl)cyclohexanecarboxamide 309.

Brown solid (25.9 mg, 0.05 mmol, 28.6% yield). $^1$H NMR (DMSO-$d_6$, 500 MHz) δ ppm 1.15-1.36 (m, 3H), 1.45 (dq, J=3 Hz, J=12 Hz, 2H), 1.67 (d, J=12.5 Hz, 1H), 1.78 (d, J=12 Hz, 2H), 1.87 (d, J=12.5 Hz, 2H), 2.34-2.45 (m, 4H), 2.66 (brs, 4H), 3.52 (brs, 4H), 6.73 (s, 1H), 8.42 (t, J=2 Hz, 1H), 8.68 (s, 1H), 8.70 (d, J=2 Hz, 1H), 8.89 (d, J=2.5 Hz, 1H), 8.91 (d, J=2 Hz, 1H), 8.97 (d, J=2 Hz, 1H), 10.24 (s, 1H), 13.13 (s, 1H), 14.42 (s, 1H); ESIMS found $C_{29}H_{32}N_{10}O$ m/z 537.4 (M+H).

325

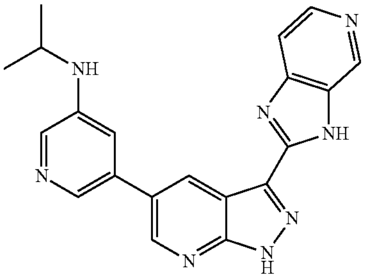

5-(3-(3H-Imidazo[4,5-c]pyridin-2-yl)-1H-pyrazolo[3,4-b]pyridin-5-yl)-N-isopropylpyridin-3-amine 325.

Tan solid (11.8 mg, 0.032 mmol, 16.7% yield). $^1$H NMR (DMSO-$d_6$, 500 MHz) δ ppm 1.20 (d, J=6 Hz, 6H), 3.75 (sep, J=6.5 Hz, 1H), 5.91 (d, J=8 Hz, 1H), 7.27 (t, J=2.5 Hz, 1H), 8.03 (d, J=2.5 Hz, 1H), 8.14 (d, J=1.5 Hz, 1H), 8.35 (d, J=5.5 Hz, 1H), 8.93 (d, J=2 Hz, 1H), 8.95 (d, J=2.5 Hz, 1H), 9.01 (brs, 1H), 13.63 (brs, 1H); ESIMS found $C_{20}H_{18}N_8$ m/z 370.9 (M+H).

336

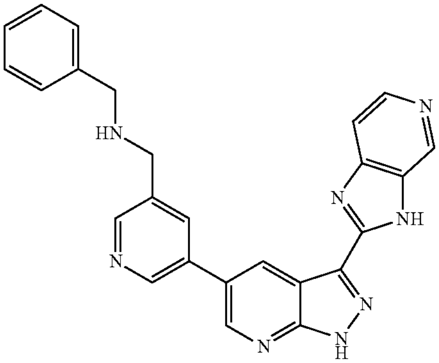

1-(5-(3-(3H-Imidazo[4,5-c]pyridin-2-yl)-1H-pyrazolo[3,4-b]pyridin-5-yl)pyridin-3-yl)-N-benzylmethanamine 336.

Beige solid (12.0 mg, 0.028 mmol, 27.7% yield). $^1$H NMR (DMSO-$d_6$, 500 MHz) δ ppm 3.77 (s, 2H), 3.85 (s, 2H), 7.23 (t, J=7.5 Hz, 1H), 7.33 (t, J=8 Hz, 2H), 7.40 (d, J=7 Hz, 2H), 7.61 (s, 1H), 8.21 (s, 1H), 8.35 (d, J=5.5 Hz, 1H), 8.61 (d, J=2 Hz, 1H), 8.90 (d, J=2.5 Hz, 1H), 9.02 (dd, J=2 Hz, J=6.5 Hz, 3H), 13.60 (brs, 1H); ESIMS found $C_{25}H_{20}N_8$ m/z 433.1 (M+H).

346

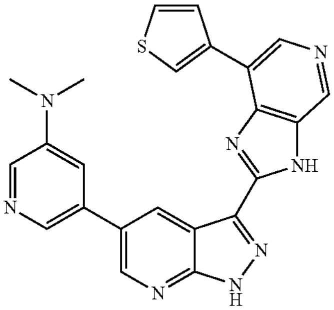

N,N-Dimethyl-5-(3-(7-(thiophen-3-yl)-3H-imidazo[4,5-c]pyridin-2-yl)-1H-pyrazolo[3,4-b]pyridin-5-yl)pyridin-3-amine 346.

Tan solid (5.8 mg, 0.013 mmol, 6.7% yield). $^1$H NMR (DMSO-$d_6$, 500 MHz) δ ppm 3.14 (s, 6H), 7.74 (s, 1H), 7.78 (dd, J=3 Hz, J=5 Hz, 1H), 8.15 (d, J=4.5 Hz, 1H), 8.25 (d, J=3 Hz, 1H), 8.46 (d, J=1.5 Hz, 1H), 8.92 (s, 2H), 9.02 (s, 1H), 9.13 (d, J=2 Hz, 1H), 9.14 (d, J=2.5 Hz, 1H), 14.83 (s, 1H); ESIMS found $C_{23}H_{18}N_8S$ m/z 439.1 (M+H).

352

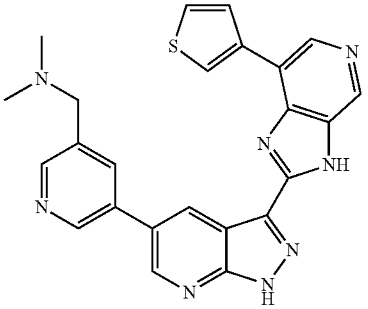

N,N-Dimethyl-1-(5-(3-(7-(thiophen-3-yl)-3H-imidazo[4,5-c]pyridin-2-yl)-1H-pyrazolo[3,4-b]pyridin-5-yl)pyridin-3-yl)methanamine 352.

Dark brown solid (24.4 mg, 0.054 mmol, 28.2% yield). $^1$H NMR (DMSO-$d_6$, 500 MHz) δ ppm 2.28 (s, 6H), 3.62 (brs, 2H), 7.74 (dd, J=3 Hz, J=5 Hz, 1H), 8.12-8.18 (m, 2H), 8.59 (s, 1H), 8.78 (brs, 1H), 8.81 (s, 2H), 9.00 (s, 1H), 9.09 (s, 1H), 9.13 (s, 1H), 13.80 (brs, 1H), 14.59 (brs, 1H); ESIMS found $C_{24}H_{20}N_8S$ m/z 453.0 (M+H).

354

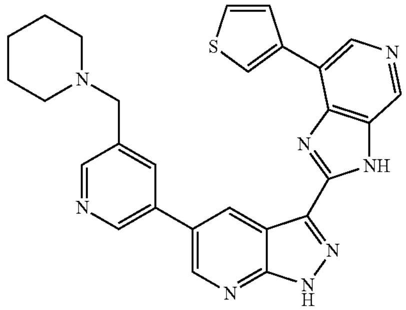

5-(5-(Piperidin-1-ylmethyl)pyridin-3-yl)-3-(7-(thiophen-3-yl)-3H-imidazo[4,5-c]pyridin-2-yl)-1H-pyrazolo[3,4-b]pyridine 354.

Brown solid (17.8 mg, 0.04 mmol, 52.4% yield). $^1$H NMR ($DMSO-d_6$, 500 MHz) δ ppm 1.40 (brs, 2H), 1.52 (brs, 4H), 2.43 (brs, 4H), 3.63 (s, 2H), 7.74 (dd, J=3 Hz, J=4.5 Hz, 1H), 8.11-8.18 (m, 2H), 8.60 (s, 1H), 8.78 (s, 1H), 8.81 (s, 2H), 8.98 (s, 1H), 9.08 (s, 1H), 9.14 (s, 1H), 13.81 (brs, 1H), 14.59 (brs, 1H); ESIMS found $C_{27}H_{24}N_8S$ m/z 493.3 (M+H).

373

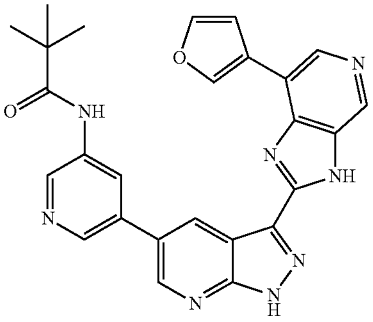

N-(5-(3-(7-(Furan-3-yl)-3H-imidazo[4,5-c]pyridin-2-yl)-1H-pyrazolo[3,4-b]pyridin-5-yl)pyridin-3-yl)pivalamide 373.

Tan solid (21.6 mg, 0.045 mmol, 25.5% yield). $^1$H NMR ($DMSO-d_6$, 500 MHz) δ ppm 1.30 (s, 9H), 7.43 (brs, 1H), 7.85 (s, 1H), 8.59 (brs, 1H), 8.71 (s, 1H), 8.78 (d, J=1.5 Hz, 1H), 8.83 (brs, 2H), 8.95 (d, J=2 Hz, 1H), 9.04 (d, J=2.5 Hz, 1H), 9.09 (s, 1H), 9.63 (s, 1H), 13.86 (brs, 1H), 14.61 (s, 1H); ESIMS found $C_{26}H_{22}N_8O_2$ m/z 479.0 (M+H).

376

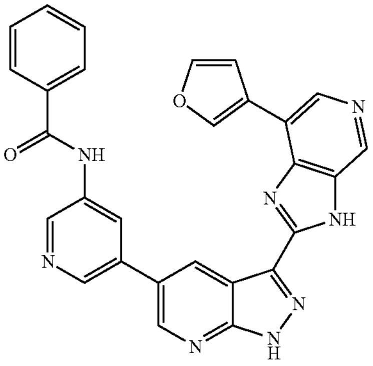

N-(5-(3-(7-(Furan-3-yl)-3H-imidazo[4,5-c]pyridin-2-yl)-1H-pyrazolo[3,4-b]pyridin-5-yl)pyridin-3-yl)benzamide 376.

Brown solid (49.9 mg, 0.10 mmol, 58.6% yield). $^1$H NMR ($DMSO-d_6$, 500 MHz) δ ppm 7.47 (brs, 1H), 7.60 (t, J=7.5 Hz, 2H), 7.66 (t, J=7 Hz, 1H), 7.86 (t, J=2 Hz, 1H), 8.06 (d, J=8 Hz, 2H), 8.76 (s, 1H), 8.78 (s, 1H), 8.85 (d, J=2 Hz, 1H), 8.90 (brs, 1H), 8.93 (brs, 1H), 9.05 (d, J=2 Hz, 1H), 9.08 (d, J=2 Hz, 1H), 9.13 (d, J=2 Hz, 1H), 10.68 (s, 1H), 14.74 (s, 1H); ESIMS found $C_{28}H_{18}N_8O_2$ m/z 499.3 (M+H).

382

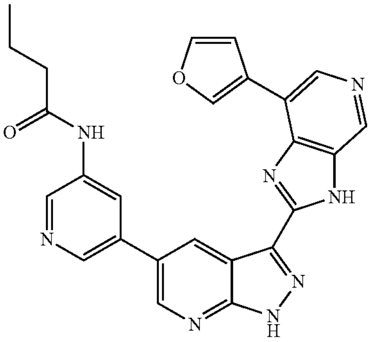

N-(5-(3-(7-(Furan-3-yl)-3H-imidazo[4,5-c]pyridin-2-yl)-1H-pyrazolo[3,4-b]pyridin-5-yl)pyridin-3-yl)butyramide 382.

Brown solid (32.2 mg, 0.069 mmol, 38.3% yield). $^1$H NMR ($DMSO-d_6$, 500 MHz) δ ppm 0.96 (t, J=7 Hz, 3H), 1.67 (sex, J=7 Hz, 2H), 2.39 (t, J=7.5 Hz, 2H), 7.44 (s, 1H), 7.86 (t, J=1.5 Hz, 1H), 8.58 (s, 1H), 8.72 (s, 1H), 8.75 (d, J=2 Hz, 1H), 8.80 (d, J=2 Hz, 1H), 8.81 (s, 1H), 8.83 (s, 1H), 9.01 (d, J=2.5 Hz, 1H), 9.07 (d, J=2 Hz, 1H), 10.32 (s, 1H), 13.92 (brs, 1H), 14.62 (s, 1H); ESIMS found $C_{25}H_{20}N_8O_2$ m/z 465.0 (M+H).

440

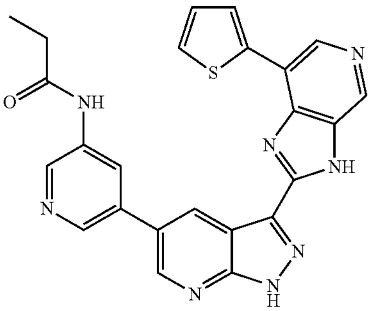

N-(5-(3-(7-(Thiophen-2-yl)-3H-imidazo[4,5-c]pyridin-2-yl)-1H-pyrazolo[3,4-b]pyridin-5-yl)pyridin-3-yl)propionamide 440.

Dark brown solid (33.7 mg, 0.07 mmol, 38.8% yield). $^1$H NMR ($DMSO-d_6$, 500 MHz) δ ppm 1.17 (t, J=7.5 Hz, 3H), 2.48 (q, J=7.5 Hz, 2H), 7.29 (dd, J=4 Hz, J=5 Hz, 1H), 7.69-7.76 (m, 2H), 8.21 (brs, 1H), 8.73 (s, 2H), 8.76 (s, 1H), 8.82 (s, 1H), 8.84 (s, 1H), 9.07 (d, J=2 Hz, 1H), 9.21 (s, 1H), 10.37 (s, 1H), 14.65 (s, 1H); ESIMS found $C_{24}H_{18}N_8OS$ m/z 466.9 (M+H).

452

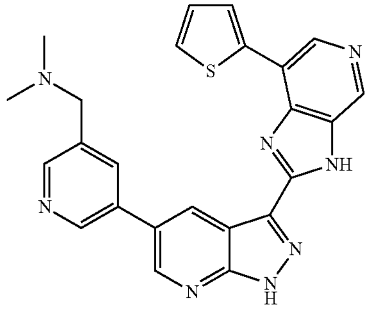

N,N-Dimethyl-1-(5-(3-(7-(thiophen-2-yl)-3H-imidazo[4,5-c]pyridin-2-yl)-1H-pyrazolo[3,4-b]pyridin-5-yl)pyridin-3-yl)methanamine 452.

Beige solid (100.3 mg, 0.22 mmol, 29.0% yield). $^1$H NMR (DMSO-$d_6$, 500 MHz) δ ppm 2.24 (s, 6H), 3.58 (s, 2H), 7.27 (dd, J=3.5 Hz, J=5 Hz, 1H), 7.69 (d, J=5 Hz, 1H), 8.15 (s, 1H), 8.22 (brs, 1H), 8.59 (s, 1H), 8.79 (s, 1H), 8.81 (s, 1H), 9.00 (d, J=2 Hz, 1H), 9.10 (d, J=2 Hz, 1H), 9.24 (s, 1H), 13.87 (brs, 1H), 14.59 (brs, 1H); ESIMS found $C_{24}H_{20}N_8S$ m/z 453.1 (M+H).

458

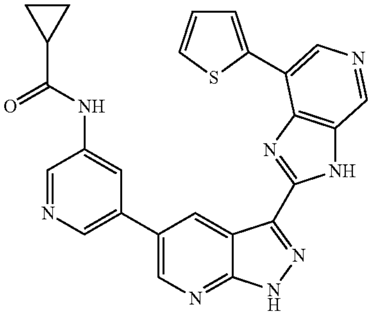

N-(5-(3-(7-(Thiophen-2-yl)-3H-imidazo[4,5-c]pyridin-2-yl)-1H-pyrazolo[3,4-b]pyridin-5-yl)pyridin-3-yl)cyclopropanecarboxamide 458.

Dark yellow solid (15 mg, 0.03 mmol, 36.0% yield). $^1$H NMR (DMSO-$d_6$, 500 MHz) δ ppm 0.90 (d, J=6 Hz, 4H), 1.90 (quin, J=6 Hz, 1H), 7.27 (t, J=5 Hz, 1H), 7.66 (d, J=5 Hz, 1H), 8.22 (d, J=3 Hz, 1H), 8.67 (s, 1H), 8.73 (s, 1H), 8.76 (s, 1H), 8.79 (s, 1H), 8.82 (s, 1H), 9.06 (s, 1H), 9.21 (s, 1H), 10.67 (s, 1H), 13.88 (brs, 1H), 14.61 (s, 1H); ESIMS found $C_{25}H_{18}N_8OS$ m/z 479.1 (M+H).

463

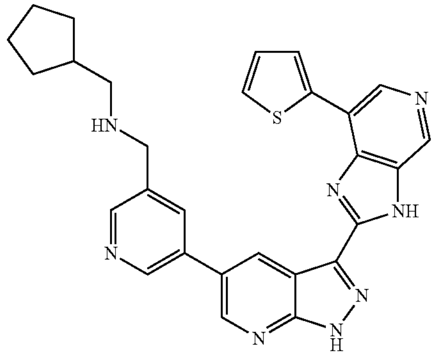

1-Cyclopentyl-N-((5-(3-(7-(thiophen-2-yl)-3H-imidazo[4,5-c]pyridin-2-yl)-1H-pyrazolo[3,4-b]pyridin-5-yl)pyridin-3-yl)methyl)methanamine 463.

Tan solid (15.0 mg, 0.03 mmol, 17.1% yield). $^1$H NMR (DMSO-$d_6$, 500 MHz) δ ppm 1.12-1.21 (m, 2H), 1.40-1.55 (m, 4H), 1.65-1.74 (m, 2H), 2.01 (quin, J=7.5 Hz, 1H), 2.52 (d, J=5.5 Hz, 2H), 3.90 (s, 2H), 2.27 (dd, J=3.5 Hz, J=5 Hz, 1H), 7.71 (d, J=5 Hz, 1H), 8.22 (brs, 1H), 8.25 (s, 1H), 8.64 (d, J=1.5 Hz, 1H), 8.79 (s, 1H), 8.80 (s, 1H), 8.97 (d, J=2 Hz, 1H), 9.10 (d, J=2 Hz, 1H), 9.27 (d, J=1.5 Hz, 1H); ESIMS found $C_{28}H_{26}N_8S$ m/z 507.1 (M+H).

547

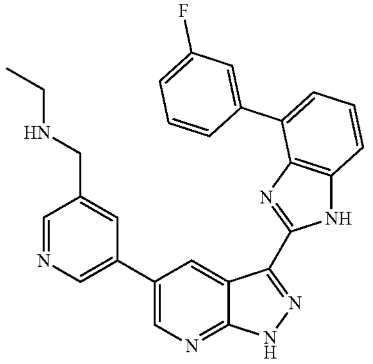

N-((5-(3-(4-(3-Fluorophenyl)-1H-benzo[d]imidazol-2-yl)-1H-pyrazolo[3,4-b]pyridin-5-yl)pyridin-3-yl)methyl)ethanamine 547.

Tan solid (9.4 mg, 0.02 mmol, 10.6% yield). $^1$H NMR (DMSO-$d_6$, 500 MHz) δ ppm 1.06 (t, J=7.5 Hz, 3H), 2.60 (q, J=7.5 Hz, 2H), 3.85 (s, 2H), 7.23 (dt, J=2.5 Hz, J=8.5 Hz, 1H), 7.38 (t, J=8 Hz, 1H), 7.53-7.65 (m, 3H), 8.14 (d, J=8 Hz, 1H), 8.17 (s, 1H), 8.39 (d, J=11 Hz, 1H), 8.62 (d, J=1.5 Hz, 1H), 8.92 (d, J=2 Hz, 1H), 9.06 (d, J=2 Hz, 1H), 9.13 (s, 1H), 13.43 (brs, 1H); ESIMS found $C_{27}H_{22}FN_7$ m/z 464.0 (M+H).

551

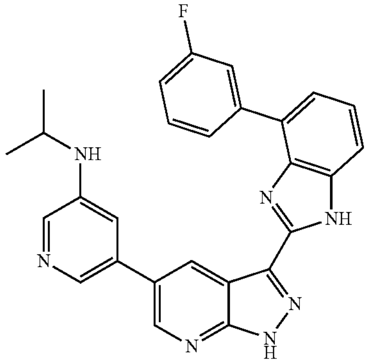

5-(3-(4-(3-Fluorophenyl)-1H-benzo[d]imidazol-2-yl)-1H-pyrazolo[3,4-b]pyridin-5-yl)-N-isopropylpyridin-3-amine 551.

Dark yellow solid (15.6 mg, 0.03 mmol, 17.6% yield). $^1$H NMR (DMSO-$d_6$, 500 MHz) δ ppm 1.19 (d, J=6.5 Hz, 6H), 3.72 (sep, J=6.5 Hz, 1H), 5.87 (d, J=8 Hz, 1H), 7.21 (dd, J=5 Hz, J=2.5 Hz, 2H), 7.37 (t, J=7.5 Hz, 1H), 7.54 (q, J=8 Hz, 1H), 7.55-7.61 (m, 2H), 8.04 (d, J=2.5 Hz, 1H), 8.12 (d, J=8 Hz, 1H), 8.14 (d, J=2 Hz, 1H), 8.32 (dd, J=2 Hz, J=8 Hz, 1H), 8.95 (d, J=2.5 Hz, 1H), 9.02 (d, J=2.5 Hz, 1H), 13.41 (s, 1H), 14.35 (s, 1H); ESIMS found $C_{27}H_{22}FN_7$ m/z 464.2 (M+H).

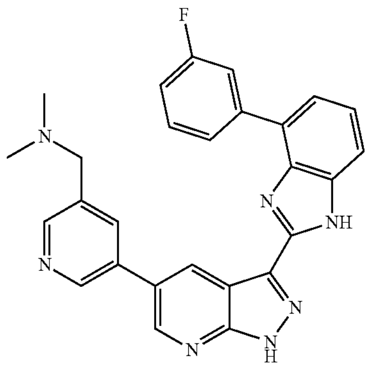

552

1-(5-(3-(4-(3-Fluorophenyl)-1H-benzo[d]imidazol-2-yl)-1H-pyrazolo[3,4-b]pyridin-5-yl)pyridin-3-yl)-N,N-dimethylmethanamine 552.

Brown solid (23.6 mg, 0.051 mmol, 26.7% yield). $^1$H NMR (DMSO-$d_6$, 500 MHz) δ ppm 2.22 (s, 6H), 3.56 (s, 2H), 7.24 (dt, J=2.5 Hz, J=8.5 Hz, 1H), 7.37 (t, J=8 Hz, 1H), 7.53-7.61 (m, 3H), 8.09 (s, 1H), 8.13 (d, J=8 Hz, 1H), 8.36 (dd, J=2 Hz, J=11.5 Hz, 1H), 8.58 (d, J=1.5 Hz, 1H), 8.96 (d, J=2.5 Hz, 1H), 9.06 (d, J=2 Hz, 1H), 9.11 (d, J=2.5 Hz, 1H), 13.43 (brs, 1H), 14.39 (brs, 1H); ESIMS found $C_{27}H_{22}FN_7$ m/z 464.3 (M+H).

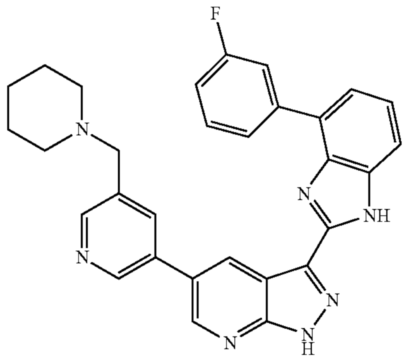

554

3-(4-(3-Fluorophenyl)-1H-benzo[d]imidazol-2-yl)-5-(5-(piperidin-1-ylmethyl)pyridin-3-yl)-1H-pyrazolo[3,4-b]pyridine 554.

Light brown solid (57.4 mg, 0.11 mmol, 43.7% yield). $^1$H NMR (DMSO-$d_6$, 500 MHz) δ ppm 1.39 (brs, 2H), 1.50 (brs, 4H), 2.40 (brs, 4H), 3.60 (s, 2H), 7.22 (dt, J=3 Hz, J=8.5 Hz, 1H), 3.78 (t, J=8 Hz, 1H), 7.51-7.62 (m, 3H), 8.09 (s, 1H), 8.11 (d, J=7.5 Hz, 1H), 8.40 (d, J=11 Hz, 1H), 8.59 (s, 1H), 8.95 (s, 1H), 9.06 (d, J=2.5 Hz, 1H), 9.11 (d, J=2 Hz, 1H), 13.44 (s, 1H), 14.40 (s, 1H); ESIMS found $C_{30}H_{26}FN_7$ m/z 504.1 (M+H).

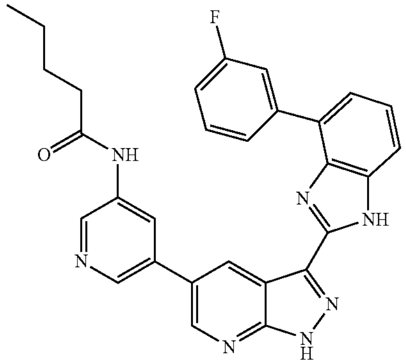

557

N-(5-(3-(443-Fluorophenyl)-1H-benzo[d]imidazol-2-yl)-1H-pyrazolo[3,4-b]pyridin-5-yl)pyridin-3-yl)pentanamide 557.

Brown solid (36.9 mg, 0.073 mmol, 41.3% yield). $^1$H NMR (DMSO-$d_6$, 500 MHz) δ ppm 0.93 (t, J=7.5 Hz, 3H), 1.38 (sex, J=7.5 Hz, 2H), 1.64 (quin, J=7.5 Hz, 2H), 2.42 (t, J=7.5 Hz, 2H), 7.17 (dt, J=2 Hz, J=8 Hz, 1H), 7.38 (t, J=7.5 Hz, 1H), 7.51-7.63 (m, 3H), 8.16 (brs, 1H), 8.31 (brs, 1H), 8.52 (s, 1H), 8.72 (d, J=2 Hz, 1H), 8.81 (d, J=1.5 Hz, 1H), 8.98 (d, J=2 Hz, 1H), 9.08 (d, J=2 Hz, 1H), 10.30 (s, 1H), 13.44 (brs, 1H), 14.41 (s, 1H); ESIMS found $C_{29}H_{24}FN_7O$ m/z 506.3 (M+H).

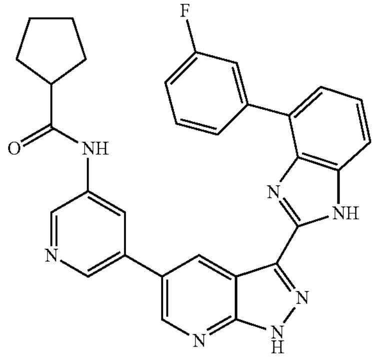

560

N-(5-(3-(4-(3-Fluorophenyl)-1H-benzo[d]imidazol-2-yl)-1H-pyrazolo[3,4-b]pyridin-5-yl)pyridin-3-yl)cyclopentanecarboxamide 560.

Brown solid (14.8 mg, 0.029 mmol, 16.5% yield). $^1$H NMR (DMSO-$d_6$, 500 MHz) δ ppm 1.55-1.64 (m, 2H), 1.64-1.73 (m, 2H), 1.73-1.83 (m, 2H), 1.86-1.96 (m, 2H), 2.88 (quin, J=8 Hz, 1H), 7.16 (dt, J=2.5 Hz, J=8.5 Hz, 1H), 7.38 (t, J=8 Hz, 1H), 7.51-7.61 (m, 3H), 8.19 (d, J=8 Hz, 1H), 8.32 (dd, J=2 Hz, J=10 Hz, 1H), 8.55 (t, J=2 Hz, 1H), 8.71 (d, J=2 Hz, 1H), 8.80 (d, J=2 Hz, 1H), 8.98 (d, J=2 Hz, 1H), 9.08 (d, J=2 Hz, 1H), 10.27 (s, 1H), 13.44 (s, 1H), 14.41 (s, 1H); ESIMS found $C_{30}H_{24}FN_7O$ m/z 518.0 (M+H).

561

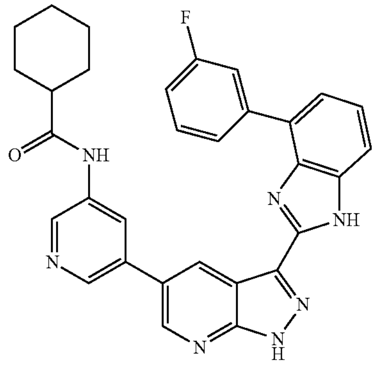

N-(5-(3-(4-(3-Fluorophenyl)-1H-benzo[d]imidazol-2-yl)-1H-pyrazolo[3,4-b]pyridin-5-yl)pyridin-3-yl)cyclohexanecarboxamide 561.

Brown solid (14.0 mg, 0.026 mmol, 15.6% yield). $^1$H NMR (DMSO-$d_6$, 500 MHz) δ ppm 1.15-1.36 (m, 3H), 1.46 (dq, J=3 Hz, J=12.5 Hz, 2H), 1.68 (d, J=12.5 Hz, 1H), 1.80 (dd, J=2.5 Hz, J=11.5 Hz, 2H), 1.90 (d, J=12.5 Hz, 2H), 2.42 (tt, J=3.5 Hz, J=11.5 Hz, 1H), 7.15 (t, J=7.5 Hz, 1H), 7.38 (t, J=7.5 Hz, 1H), 7.53-7.65 (m, 3H), 8.19 (d, J=7 Hz, 1H), 8.32 (d, J=10.5 Hz, 1H), 8.54 (s, 1H), 8.70 (d, J=2 Hz, 1H), 8.82 (d, J=1.5 Hz, 1H), 8.98 (d, J=2 Hz, 1H), 9.07 (s, 1H), 10.22 (s, 1H), 13.44 (s, 1H), 14.41 (s, 1H); ESIMS found $C_{31}H_{26}FN_7O$ m/z 532.2 (M+H).

573

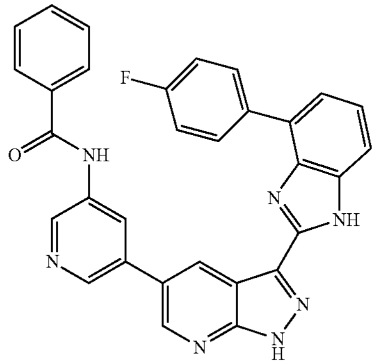

N-(5-(3-(4-(4-Fluorophenyl)-1H-benzo[d]imidazol-2-yl)-1H-pyrazolo[3,4-b]pyridin-5-yl)pyridin-3-yl)benzamide 573.

Tan solid (37.9 mg, 0.072 mmol, 42.2% yield). $^1$H NMR (DMSO-$d_6$, 500 MHz) δ ppm 7.32-7.41 (m, 3H), 7.50 (brd, J=6.5 Hz, 1H), 7.55 (brd, J=7.5 Hz, 1H), 7.60 (t, J=7.5 Hz, 2H), 7.66 (t, J=7.5 Hz, 1H), 8.07 (d, J=7.5 Hz, 2H), 8.40 (brs, 2H), 8.79 (brs, 1H), 8.82 (d, J=2 Hz, 1H), 9.01 (s, 1H), 9.05 (d, J=2 Hz, 1H), 9.11 (s, 1H), 10.71 (s, 1H), 13.39 (brs, 1H), 14.41 (s, 1H); ESIMS found $C_{31}H_{20}FN_7O$ m/z 526.1 (M+H).

581

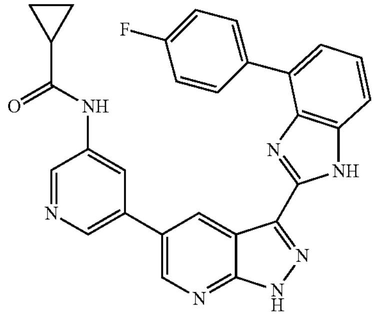

N-(5-(3-(4-(4-Fluorophenyl)-1H-benzo[d]imidazol-2-yl)-1H-pyrazolo[3,4-b]pyridin-5-yl)pyridin-3-yl)cyclopropanecarboxamide 581.

Brown solid (34.5 mg, 0.07 mmol, 40.0% yield). $^1$H NMR (DMSO-$d_6$, 500 MHz) δ ppm 0.85-0.96 (m, 4H), 1.85-1.93 (m, 1H), 7.26-7.29 (m, 3H), 7.50 (d, J=7 Hz, 1H), 7.55 (d, J=7 Hz, 1H), 8.39 (brs, 2H), 8.66 (s, 1H), 8.73 (d, J=2 Hz, 1H), 9.01 (d, J=2 Hz, 1H), 9.05 (d, J=1.5 Hz, 1H), 10.69 (s, 1H), 13.38 (brs, 1H), 14.40 (s, 1H); ESIMS found $C_{28}H_{20}FN_7O$ m/z 490.2 (M+H).

586

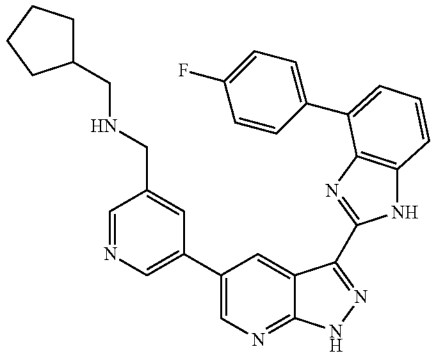

1-Cyclopentyl-N-((5-(3-(4-(4-fluorophenyl)-1H-benzo[d]imidazol-2-yl)-1H-pyrazolo[3,4-b]pyridin-5-yl)pyridin-3-yl)methyl)methanamine 586.

Tan solid (13.8 mg, 0.027 mmol, 15.4% yield). $^1$H NMR (DMSO-$d_6$, 500 MHz) δ ppm 1.11-1.23 (m, 2H), 1.40-1.58 (m, 4H), 1.65-1.74 (m, 2H), 2.04 (quin, J=7.5 Hz, 1H), 2.58 (d, J=6.5 Hz, 2H), 3.94 (s, 2H), 7.36 (t, J=8.5 Hz, 2H), 7.50 (d, J=7 Hz, 1H), 7.54 (d, J=7.5 Hz, 1H), 8.24 (s, 1H), 8.34-8.42 (m, 3H), 8.65 (s, 1H), 8.97 (d, J=1.5 Hz, 1H), 9.13 (d, J=2 Hz, 1H), 9.14 (d, J=2 Hz, 1H), 13.38 (brs, 1H), 14.36 (brs, 1H); ESIMS found $C_{31}H_{28}FN_7$ m/z 518.0 (M+H).

594

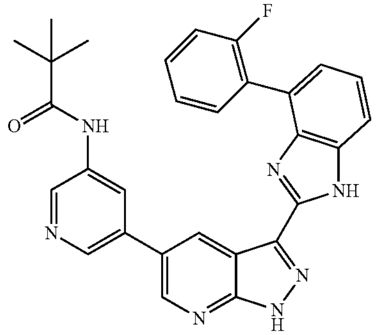

N-(5-(3-(4-(2-Fluorophenyl)-1H-benzo[d]imidazol-2-yl)-1H-pyrazolo[3,4-b]pyridin-5-yl)pyridin-3-yl)pivalamide 594.

Tan solid (54.7 mg, 0.108 mmol, 61.2% yield). $^1$H NMR (DMSO-$d_6$, 500 MHz) δ ppm 1.32 (s, 9H), 7.32-7.40 (m, 3H), 7.51 (d, J=7.5 Hz, 1H), 7.54 (d, J=8 Hz, 1H), 8.41 (dd, 6 Hz, J=9 Hz, 2H), 8.67 (t, J=2 Hz, 1H), 8.74 (d, J=2 Hz, 1H), 8.92 (d, J=2 Hz, 1H), 9.02 (d, J=2.5 Hz, 1H), 9.05 (d, J=2 Hz, 1H), 9.66 (s, 1H), 13.38 (s, 1H), 14.41 (s, 1H); ESIMS found $C_{29}H_{24}FN_7O$ m/z 506.0 (M+H).

595

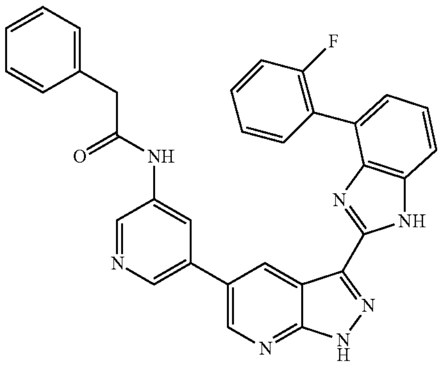

N-(5-(3-(4-(2-Fluorophenyl)-1H-benzo[d]imidazol-2-yl)-1H-pyrazolo[3,4-b]pyridin-5-yl)pyridin-3-yl)-2-phenylacetamide 595.

Beige solid (15.5 mg, 0.029 mmol, 15.4% yield). $^1$H NMR (DMSO-$d_6$, 500 MHz) δ ppm 3.78 (s, 2H), 7.23-7.29 (m, 4H), 7.29-7.42 (m, 6H), 7.52-7.61 (m, 1H), 8.00-8.07 (m, 1H), 8.51 (t, J=2 Hz, 1H), 8.66 (d, J=2 Hz, 1H), 8.77 (d, J=2.5 Hz, 1H), ABq, J=2 Hz, J=11 Hz, 2H), 10.61 (s, 1H), 13.34 (s, 1H), 14.36 (s, 1H); ESIMS found $C_{32}H_{22}FN_7O$ m/z 540.3 (M+H).

599

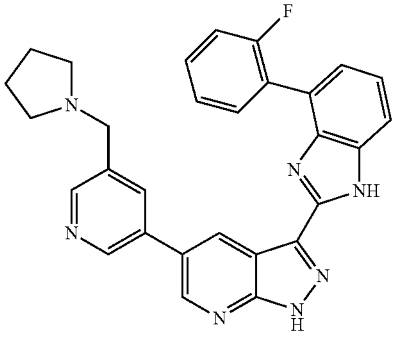

3-(4-(2-Fluorophenyl)-1H-benzo[d]imidazol-2-yl)-5-(5-(pyrrolidin-1-ylmethyl)pyridin-3-yl)-1H-pyrazolo[3,4-b]pyridine 599.

Beige solid (6.2 mg, 0.013 mmol, 7.0% yield). $^1$H NMR (DMSO-$d_6$, 500 MHz) δ ppm 1.73 (brs, 4H), 2.54 (brs, 4H), 3.75 (s, 2H), 7.30-7.41 (m, 4H), 7.43-7.52 (m, 1H), 7.60 (dd, J=2.5 Hz, J=7 Hz, 1H), 8.05 (s, 1H), 8.08 (t, J=7.5 Hz, 1H), 8.58 (s, 1H), 8.89 (d, J=1.5 Hz, 1H), 9.00 (d, J=2 Hz, 1H), 9.03 (d, J=2 Hz, 1H), 13.35 (s, 1H), 14.59 (brs, 1H); ESIMS found $C_{29}H_{24}FN_7$ m/z 490.0 (M+H).

602

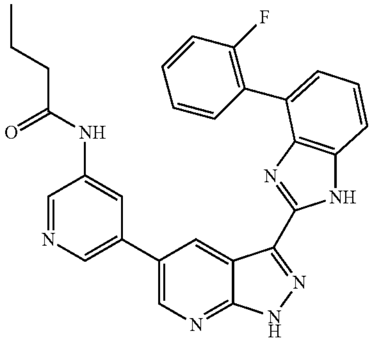

N-(5-(3-(4-(2-Fluorophenyl)-1H-benzo[d]imidazol-2-yl)-1H-pyrazolo[3,4-b]pyridin-5-yl)pyridin-3-yl)butyramide 602.

Tan solid (31.9 mg, 0.065 mmol, 35.8% yield). $^1$H NMR (DMSO-$d_6$, 500 MHz) δ ppm 0.98 (t, J=7 Hz, 3H), 1.69 (sex, J=7 Hz, 2H), 2.42 (t, J=7.5 Hz, 2H), 7.30-7.46 (m, 5H), 7.59 (d, J=7 Hz, 1H), 8.09 (t, J=7 Hz, 1H), 8.43 (s, 1H), 8.64 (s, 1H), 8.76 (s, 1H), 8.95 (s, 2H), 10.30 (s, 1H), 13.35 (s, 1H), 14.37 (s, 1H); ESIMS found $C_{28}H_{22}FN_7O$ m/z 492.1 (M+H).

605

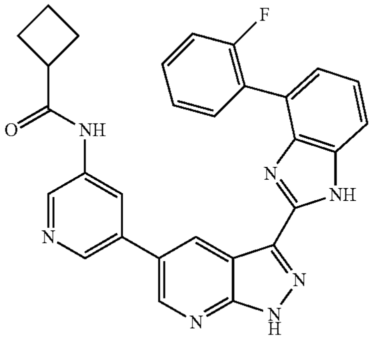

N-(5-(3-(4-(2-Fluorophenyl)-1H-benzo[d]imidazol-2-yl)-1H-pyrazolo[3,4-b]pyridin-5-yl)pyridin-3-yl)cyclobutanecarboxamide 605.

Beige solid (60.3 mg, 0.12 mmol, 35.1% yield). $^1$H NMR (DMSO-$d_6$, 500 MHz) δ ppm 1.81-1.91 (m, 1H), 1.93-2.07 (m, 1H), 2.13-2.25 (m, 2H), 2.25-2.37 (m, 2H), 7.31-7.45 (m, 5H), 7.59 (dd, J=1.5 Hz, J=7 Hz, 1H), 8.10 (dt, J=2 Hz, J=7.5 Hz, 1H), 8.53 (t, J=2 Hz, 1H), 8.64 (d, J=2 Hz, 1H), 8.76 (d, J=2 Hz, 1H), 8.92-8.97 (m, 2H), 10.16 (s, 1H), 13.35 (s, 1H), 14.37 (s, 1H); ESIMS found $C_{29}H_{22}FN_7O$ m/z 504.2 (M+H).

616

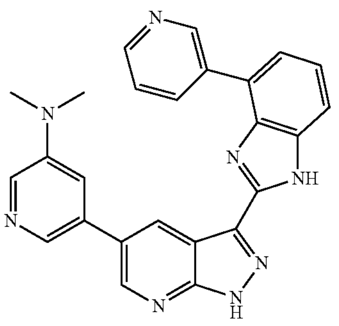

N,N-Dimethyl-5-(3-(4-(pyridin-3-yl)-1H-benzo[d]imidazol-2-yl)-1H-pyrazolo[3,4-b]pyridin-5-yl)pyridin-3-amine 616.

Tan solid (11.4 mg, 0.026 mmol, 13.4% yield). $^1$H NMR (DMSO-$d_6$, 500 MHz) δ ppm 3.09 (s, 6H), 7.59 (d, J=4.58 Hz, 2H), 7.72 (dd, J=3 Hz, J=5 Hz, 2H), 8.03 (brs, 2H), 8.32 (s, 2H), 8.48 (s, 2H), 8.81 (brs, 2H), 13.79 (brs, 1H), 14.56 (brs, 1H); ESIMS found $C_{25}H_{20}N_8$ m/z 433.0 (M+H).

621

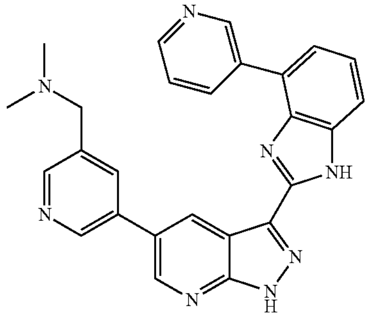

N,N-Dimethyl-1-(5-(3-(4-(pyridin-3-yl)-1H-benzo[d]imidazol-2-yl)-1H-pyrazolo[3,4-b]pyridin-5-yl)pyridin-3-yl)methanamine 621.

Dark brown solid (19.6 mg, 0.044 mmol, 23.0% yield). $^1$H NMR (DMSO-$d_6$, 500 MHz) δ ppm 2.24 (s, 6H), 3.57 (s, 2H), 7.36 (t, J=8 Hz, 1H), 7.41 (t, J=7.5 Hz, 1H), 7.51 (d, J=7 Hz, 1H), 7.55 (t, J=7.5 Hz, 2H), 8.11 (d, J=2 Hz, 1H), 8.32 (d, J=7.5 Hz, 2H), 8.58 (d, 1.5 Hz, 1H), 8.98 (d, J=2.5 Hz, 1H), 9.07 (d, J=2.5 Hz, 1H), 9.14 (d, J=2 Hz, 1H), 13.36 (brs, 1H), 14.33 (brs, 1H); ESIMS found $C_{26}H_{22}N_8$ m/z 447.2 (M+H).

635

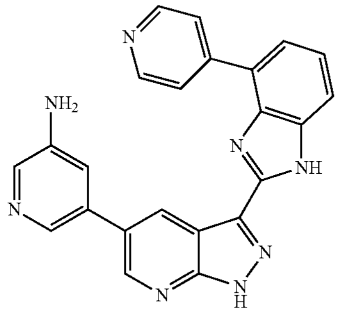

5-(3-(4-(Pyridin-4-yl)-1H-benzo[d]imidazol-2-yl)-1H-pyrazolo[3,4-b]pyridin-5-yl)pyridin-3-amine 635.

Brown solid (3.3 mg, 0.008 mmol, 4.0% yield). $^1$H NMR (DMSO-$d_6$, 500 MHz) δ ppm 5.65 (brs, 2H), 7.38 (s, 1H), 7.42 (t, J=7.5 Hz, 1H), 7.66 (d, J=8 Hz, 1H), 7.71 (d, J=7.5 Hz, 1H), 8.05 (s, 1H), 8.22 (s, 1H), 8.41 (d, J=5.5 Hz, 2H), 8.73 (d, J=5 Hz, 2H), 8.93 (d, J=1.5 Hz, 1H), 9.07 (s, 1H), 13.51 (s, 1H), 14.39 (s, 1H); ESIMS found $C_{23}H_{16}N_8$ m/z 405.1 (M+H).

637

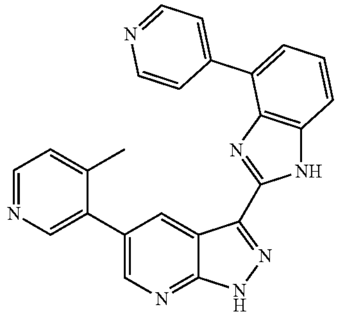

5-(4-Methylpyridin-3-yl)-3-(4-(pyridin-4-yl)-1H-benzo[d]imidazol-2-yl)-1H-pyrazolo[3,4-b]pyridine 637.

Tan solid (6.8 mg, 0.017 mmol, 18.9% yield). $^1$H NMR (DMSO-$d_6$, 500 MHz) δ ppm 2.43 (s, 3H), 7.42 (t, J=4.5 Hz, 1H), 7.49 (d, J=5 Hz, 1H), 7.65 (t, J=7.5 Hz, 3H), 8.30 (d, J=6 Hz, 2H), 8.55 (d, J=4.5 Hz, 1H), 8.62 (d, J=6.5 Hz, 2H), 8.76 (d, J=2 Hz, 1H), 8.89 (d, J=2 Hz, 1H), 13.49 (s, 1H), 14.42 (s, 1H); ESIMS found $C_{24}H_{17}N_7$ m/z 404.2 (M+H).

643

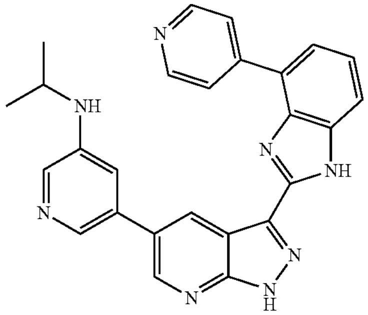

N-Isopropyl-5-(3-(4-(pyridin-4-yl)-1H-benzo[d]imidazol-2-yl)-1H-pyrazolo[3,4-b]pyridin-5-yl)pyridin-3-amine 643.

Brown solid (2.9 mg, 0.06 mmol, 3.4% yield). $^1$H NMR (DMSO-$d_6$, 500 MHz) δ ppm 1.20 (d, J=6 Hz, 6H), 3.74 (sep, J=6.5 Hz, 1H), 5.93 (d, J=8 Hz, 1H), 7.26 (s, 1H), 7.41 (t, J=8 Hz, 1H), 7.63.74 (sep, J=6.5 Hz, 1H), 5.93 (d, J=8 Hz, 1H), 7.26 (s, 1H), 7.41 (t, J=8 Hz, 1H), 7.6 (dd, J=15 Hz, J=7.5 Hz, 2H), 8.05 (d, J=2 Hz, 1H), 8.17 (d, J=1.5 Hz, 1H), 8.36 (d, J=6 Hz, 2H), 8.68 (d, J=6 Hz, 2H), 8.97 (d, J=2.5 Hz, 1H), 9.06 (d, J=2 Hz, 1H), 13.49 (s, 1H), 14.38 (s, 1H); ESIMS found $C_{26}H_{22}N_8$ m/z 447.0 (M+H).

647

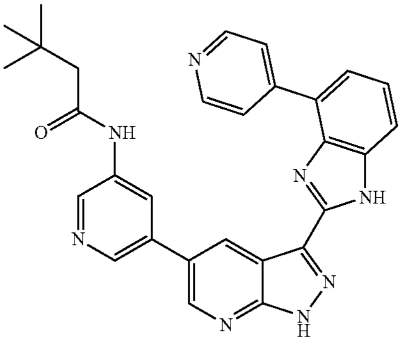

3,3-Dimethyl-N-(5-(3-(4-(pyridin-4-yl)-1H-benzo[d]imidazol-2-yl)-1H-pyrazolo[3,4-b]pyridin-5-yl)pyridin-3-yl)butanamide 647.

Beige solid (1.2 mg, 0.002 mmol, 1.4% yield). $^{1}$H NMR (DMSO-$d_6$, 500 MHz) δ ppm 1.08 (s, 9H), 2.32 (s, 2H), 7.42 (t, J=8.5 Hz, 1H), 7.66 (d, J=8 Hz, 1H), 7.71 (d, J=7.5 Hz, 1H), 8.40 (d, J=5.5 Hz, 2H), 8.62 (s, 1H), 8.72 (d, J=6 Hz, 2H), 8.74 (d, J=2 Hz, 1H), 8.77 (d, J=2.5 Hz, 1H), 9.00 (d, J=2.5 Hz, 1H), 9.09 (d, J=2 Hz, 1H), 10.28 (s, 1H), 13.52 (s, 1H), 14.45 (s, 1H); ESIMS found $C_{29}H_{26}N_8O$ m/z 503.3 (M+H).

654

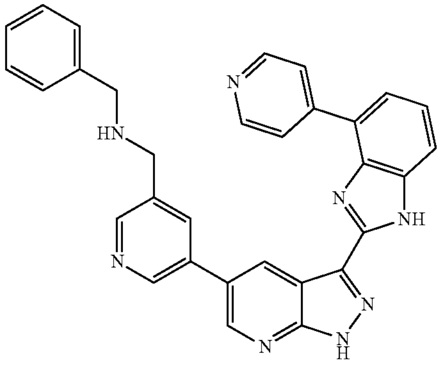

N-Benzyl-1-(5-(3-(4-(pyridin-4-yl)-1H-benzo[d]imidazol-2-yl)-1H-pyrazolo[3,4-b]pyridin-5-yl)pyridin-3-yl)methanamine 654.

Beige solid (26.1 mg, 0.051 mmol, 51.3% yield). $^{1}$H NMR (DMSO-$d_6$, 500 MHz) δ ppm 3.77 (s, 2H), 3.85 (s, 2H), 7.23 (t, J=7 Hz, 1H), 7.32 (t, J=8 Hz, 2H), 7.37-7.46 (m, 3H), 7.65 (d, J=8 Hz, 1H), 7.69 (d, J=7.5 Hz, 1H), 8.28 (s, 1H), 8.39 (dd, J=1.5 Hz, J=4.5 Hz, 2H), 8.64 (s, 1H), 8.73 (dd, J=1.5 Hz, J=4.5 Hz, 2H), 8.99 (s, 1H), 9.08 (d, J=2 Hz, 1H), 9.18 (d, J=2 Hz, 1H), 13.51 (s, 1H), 14.42 (brs, 1H); ESIMS found $C_{31}H_{24}N_8$ m/z 509.6 (M+H).

680

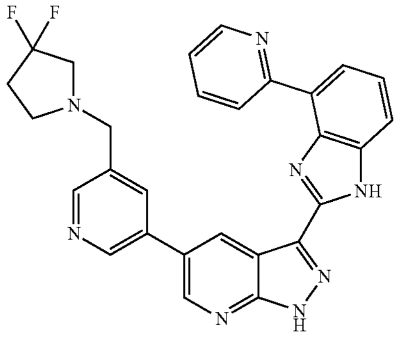

5-(5-((3,3-Difluoropyrrolidin-1-yl)methyl)pyridin-3-yl)-3-(4-(pyridin-2-yl)-1H-benzo[d]imidazol-2-yl)-1H-pyrazolo[3,4-b]pyridine 680.

Beige solid (26.4 mg, 0.052 mmol, 30.4% yield). $^{1}$H NMR (DMSO-$d_6$, 500 MHz) δ ppm 2.30 (quin, J=7 Hz, J=8 Hz, 2H), 2.84 (brs, 2H), 3.03 (brs, 2H), 3.87 (s, 2H), 7.35 (s, 1H), 7.41 (t, J=7.5 Hz, 2H), 7.72 (brs, 1H), 7.97 (t, J=7.5 Hz, 1H), 8.13 (d, J=6 Hz, 1H), 8.22 (s, 1H), 8.63 (s, 1H), 8.79 (brs, 1H), 9.01 (s, 1H), 9.06 (d, J=2 Hz, 1H), 9.14 (brs, 1H), 14.47 (s, 1H); ESIMS found $C_{28}H_{22}F_2N_8$ m/z 509.4 (M+H).

691

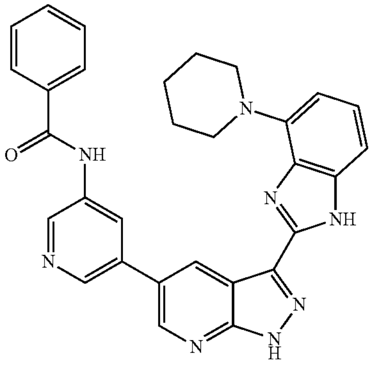

N-(5-(3-(4-(Piperidin-1-yl)-1H-benzo[d]imidazol-2-yl)-1H-pyrazolo[3,4-b]pyridin-5-yl)pyridin-3-yl)benzamide 691.

Brown solid (14.8 mg, 0.029 mmol, 16.8% yield). $^{1}$H NMR (DMSO-$d_6$, 500 MHz) δ ppm 1.74 (brs, 6H), 3.56 (brs, 4H), 6.53 (brd, J=7 Hz, 1H), 7.02 (brd, J=8 Hz, 1H), 7.09 (t, J=8 Hz, 1H), 7.59 (t, J=7.5 Hz, 2H), 7.66 (t, J=7.5 Hz, 1H), 8.05 (d, J=8 Hz, 2H), 8.72 (s, 1H), 8.81 (d, J=2 Hz, 1H), 8.98 (s, 1H), 9.06 (d, J=2 Hz, 1H), 9.14 (s, 1H), 10.64 (s, 1H), 13.06 (s, 1H), 14.26 (s, 1H); ESIMS found $C_{30}H_{26}N_8O$ m/z 515.2 (M+H).

698

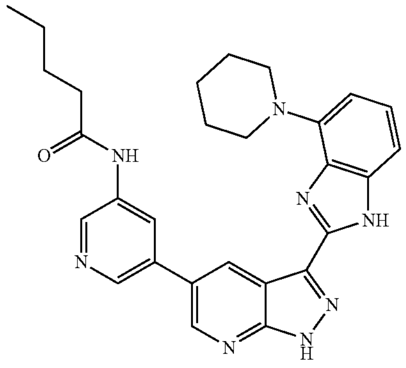

N-(5-(3-(4-(Piperidin-1-yl)-1H-benzo[d]imidazol-2-yl)-1H-pyrazolo[3,4-b]pyridin-5-yl)pyridin-3-yl)pentanamide 698.

Brown solid (47.0 mg, 0.095 mmol, 53.7% yield). $^{1}$H NMR (DMSO-$d_6$, 500 MHz) δ ppm 0.93 (t, J=7.5 Hz, 3H), 1.36 (sex, J=7.5 Hz, 2H), 1.55-167 (m, 4H), 1.68-1.81 (m, 4H), 2.40 (t, J=7.5 Hz, 2H), 3.59 (brs, 4H), 6.56 (brs, 1H), 7.04 (brs, 1H), 7.10 (t, J=7.5 Hz, 1H), 8.59 (s, 1H), 8.70 (d, J=2 Hz, 1H), 8.72 (s, 1H), 8.99 (d, J=2 Hz, 1H), 9.06 (s, 1H), 10.29 (s, 1H), 13.06 (brs, 1H), 14.27 (s, 1H); ESIMS found $C_{28}H_{30}N_8O$ m/z 495.4 (M+H).

701

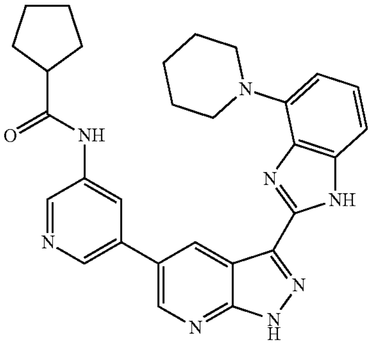

N-(5-(3-(4-(Piperidin-1-yl)-1H-benzo[d]imidazol-2-yl)-1H-pyrazolo[3,4-b]pyridin-5-yl)pyridin-3-yl)cyclopentanecarboxamide 701.

Brown solid (3.9 mg, 0.008 mmol, 4.4% yield). $^1$H NMR (DMSO-$d_6$, 500 MHz) δ ppm 1.54-1.63 (m, 4H), 1.63-1.73 (m, 2H), 1.72-1.83 (m, 6H), 1.85-1.95 (m, 2H), 2.87 (quin, J=6.5 Hz, 1H), 3.58 (t, J=5 Hz, 4H), 6.53 (d, J=8 Hz, 1H), 7.01 (d, J=8 Hz, 1H), 7.09 (t, J=8 Hz, 1H), 8.64 (t, J=2 Hz, 1H), 8.71 (dd, J=3.5 Hz, J=2 Hz, 2H), 9.00 (d, J=2.5 Hz, 1H), 9.06 (d, J=2 Hz, 1H), 10.28 (s, 1H), 13.03 (s, 1H), 14.25 (s, 1H); ESIMS found $C_{29}H_{30}N_8O$ m/z 507.1 (M+H).

719

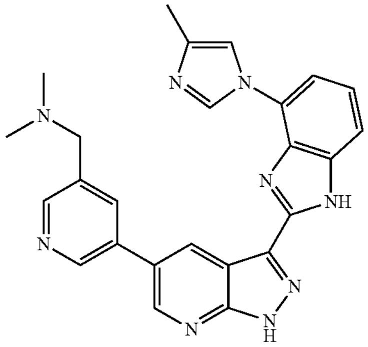

N,N-Dimethyl-1-(5-(3-(4-(4-methyl-1H-imidazol-1-yl)-1H-benzo[d]imidazol-2-yl)-1H-pyrazolo[3,4-b]pyridin-5-yl)pyridin-3-yl)methanamine 719.

Light brown solid (12.3 mg, 0.027 mmol, 14.3% yield). $^1$H NMR (DMSO-$d_6$, 500 MHz) δ ppm 2.24 (s, 6H), 2.25 (s, 3H), 3.58 (s, 2H), 7.35 (t, J=8 Hz, 1H), 7.48 (t, J=8.5 Hz, 2H), 7.96 (s, 1H), 8.13 (s, 1H), 8.59 (d, J=1.5 Hz, 1H), 8.74 (s, 1H), 8.96 (d, J=2 Hz, 1H), 9.04 (d, J=2 Hz, 1H), 9.07 (d, J=2.5 Hz, 1H), 13.58 (brs, 1H), 14.44 (brs, 1H); ESIMS found $C_{25}H_{23}N_9$ m/z 450.2 (M+H).

704

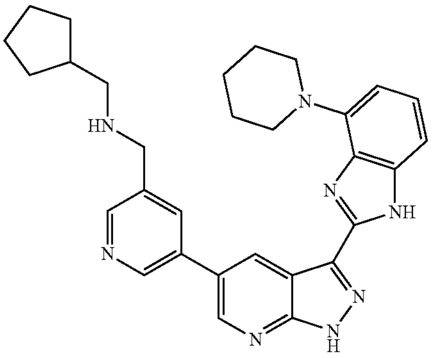

1-Cyclopentyl-N-((5-(3-(4-(piperidin-1-yl)-1H-benzo[d]imidazol-2-yl)-1H-pyrazolo[3,4-b]pyridin-5-yl)pyridin-3-yl)methyl)methanamine 704.

Brown solid (10.1 mg, 0.02 mmol, 11.5% yield). $^1$H NMR (DMSO-$d_6$, 500 MHz) δ ppm 1.15-1.25 (m, 2H), 1.43-1.83 (m, 12H), 2.04 (quin, J=7.5 Hz, 1H), 2.63 (d, J=6 Hz, 2H), 3.55-3.62 (m, 4H), 3.97 (brs, 2H), 6.54 (d, J=8 Hz, 1H), 7.02 (d, J=8 Hz, 1H), 7.09 (t, J=8 Hz, 1H), 8.24 (brs, 1H), 8.65 (s, 1H), 8.96 (s, 1H), 9.05 (d, J=2 Hz, 1H), 9.13 (d, J=2 Hz, 1H), 13.05 (s, 1H), 14.27 (brs, 1H); ESIMS found $C_{30}H_{34}N_8$ m/z 507.0 (M+H).

728

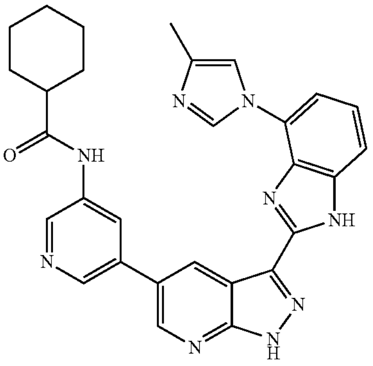

N-(5-(3-(4-(4-Methyl-1H-imidazol-1-yl)-1H-benzo[d]imidazol-2-yl)-1H-pyrazolo[3,4-b]pyridin-5-yl)pyridin-3-yl)cyclohexanecarboxamide 728.

Brown solid (30.7 mg, 0.06 mmol, 35.1% yield). $^1$H NMR (DMSO-$d_6$, 500 MHz) δ ppm 1.15-1.36 (m, 3H), 1.45 (dq, J=2.5 Hz, J=12 Hz, 2H), 1.67 (d, J=12.5 Hz, 1H), 1.78 (d, J=12.5 Hz, 2H), 1.88 (d, J=11.5 Hz, 2H), 2.22 (s, 3H), 2.41 (tt, J=3 Hz, J=11.5 Hz, 1H), 7.35 (t, J=7.5 Hz, 1H), 7.48 (d, J=2 Hz, 1H), 7.49 (d, J=2.5 Hz, 1H), 8.01 (s, 1H), 8.47 (t, J=2 Hz, 1H), 8.70 (d, J=1.5 Hz, 2H), 8.87 (d, J=2.5 Hz, 1H), 8.96 (d, J=2.5 Hz, 1H), 9.02 (d, J=2.5 Hz, 1H), 10.23 (s, 1H), 13.59 (s, 1H), 14.46 (s, 1H); ESIMS found $C_{29}H_{27}N_9O$ m/z 518.4 (M+H).

738

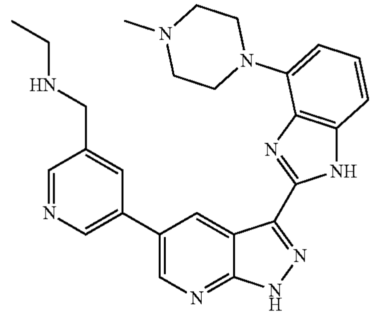

N-((5-(3-(4-(4-Methylpiperazin-1-yl)-1H-benzo[d]imidazol-2-yl)-1H-pyrazolo[3,4-b]pyridin-5-yl)pyridin-3-yl)methyl)ethanamine 738.

Brown solid (15.2 mg, 0.033 mmol, 17.0% yield). $^1$H NMR (DMSO-$d_6$, 500 MHz) δ ppm 1.07 (t, J=7.5 Hz, 3H), 2.28 (s, 3H), 2.54-2.66 (m, 6H), 3.63 (brs, 4H), 3.86 (s, 2H), 6.54 (d, J=8 Hz, 1H), 7.05 (d, J=8 Hz, 1H), 7.10 (t, J=8 Hz, 1H), 8.16 (s, 1H), 8.62 (d, J=1.5 Hz, 1H), 8.92 (d, J=2.5 Hz, 1H), 9.05 (d, J=2.5 Hz, 1H), 9.06 (d, J=2 Hz, 1H), 13.08 (brs, 1H); ESIMS found $C_{26}H_{29}N_9$ m/z 468.2 (M+H).

752

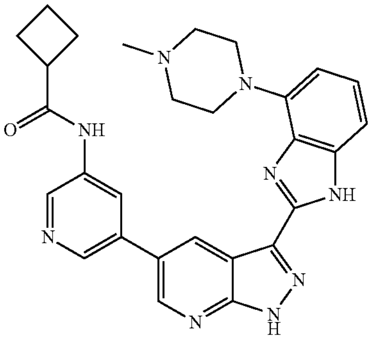

N-(5-(3-(4-(4-Methylpiperazin-1-yl)-1H-benzo[d]imidazol-2-yl)-1H-pyrazolo[3,4-b]pyridin-5-yl)pyridin-3-yl)cyclobutanecarboxamide 752.

Dark yellow solid (4.1 mg, 0.008 mmol, 2.4% yield). $^1$H NMR (DMSO-$d_6$, 500 MHz) δ ppm 1.78-1.89 (m, 1H), 1.92-2.05 (m, 1H), 2.11-2.21 (m, 2H), 2.23 (s, 3H), 2.23-2.34 (m, 2H), 2.58 (brs, 4H), 3.63 (brs, 4H), 6.54 (d, J=8 Hz, 1H), 7.04 (d, J=8 Hz, 1H), 7.10 (t, J=8 Hz, 1H), 8.58 (s, 1H), 8.69 (d, J=2 Hz, 1H), 8.76 (d, J=2.5 Hz, 1H), 8.98 (d, J=2 Hz, 1H), 9.01 (d, J=2 Hz, 1H), 10.15 (s, 1H), 13.08 (s, 1H), 14.27 (s, 1H); ESIMS found $C_{28}H_{29}N_9O$ m/z 507.9 (M+H).

758

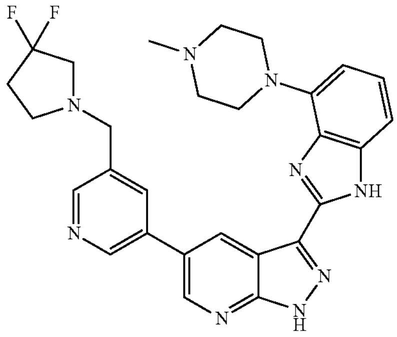

5-(5-((3,3-Difluoropyrrolidin-1-yl)methyl)pyridin-3-yl)-3-(4-(4-methylpiperazin-1-yl)-1H-benzo[d]imidazol-2-yl)-1H-pyrazolo[3,4-b]pyridine 758.

Beige solid (39.6 mg, 0.075 mmol, 43.8% yield). $^1$H NMR (DMSO-$d_6$, 500 MHz) δ ppm 2.27 (quirt, J=8.5 Hz, 2H), 2.28 (s, 3H), 2.61 (brs, 4H), 2.78 (t, J=7 Hz, 2H), 2.96 (t, J=13 Hz, 2H), 3.63 (brs, 4H), 3.81 (s, 2H), 6.54 (d, J=8 Hz, 1H), 7.05 (d, J=8 Hz, 1H), 7.11 (t, J=8 Hz, 1H), 8.11 (s, 1H), 8.61 (d, J=1.5 Hz, 1H), 8.95 (d, J=2 Hz, 1H), 9.05 (s, 2H), 13.08 (s, 1H), 14.27 (brs, 1H); ESIMS found $C_{28}H_{29}F_2N_9$ m/z 530.4 (M+H).

761

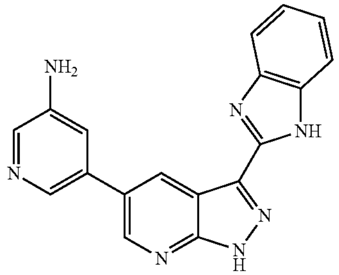

5-(3-(1H-Benzo[d]imidazol-2-yl)-1H-pyrazolo[3,4-b]pyridin-5-yl)pyridin-3-amine 761.

Brown solid (7.9 mg, 0.024 mmol, 11.8% yield). $^1$H NMR (DMSO-$d_6$, 500 MHz) δ ppm 6.01 (brs, 1H), 7.20-7.31 (m, 2H), 7.56 (s, 1H), 7.66 (brs, 2H), 8.05 (d, J=1.5 Hz, 1H), 8.30 (s, 1H), 8.94 (d, J=1.5 Hz, 1H), 8.98 (s, 1H), 13.24 (brs, 1H), 14.41 (s, 1H); ESIMS found $C_{18}H_{13}N_7$ m/z 327.6 (M+H).

765

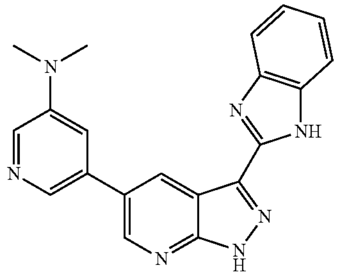

5-(3-(1H-Benzo[d]imidazol-2-yl)-1H-pyrazolo[3,4-b]pyridin-5-yl)-N,N-dimethylpyridin-3-amine 765.

Tan solid (19.6 mg, 0.055 mmol, 28.1% yield). $^1$H NMR (DMSO-$d_6$, 500 MHz) δ ppm 3.09 (s, 6H), 7.25 (dd, J=3 Hz, J=6 Hz, 2H), 7.65 (s, 1H), 7.67 (d, J=3.5 Hz, 2H), 8.22 (d, J=3 Hz, 1H), 8.38 (d, J=1.5 Hz, 1H), 9.01 (d, J=2 Hz, 1H), 9.03 (d, J=2 Hz, 1H), 14.40 (s, 1H); ESIMS found $C_{20}H_{17}N_7$ m/z 356.0 (M+H).

774

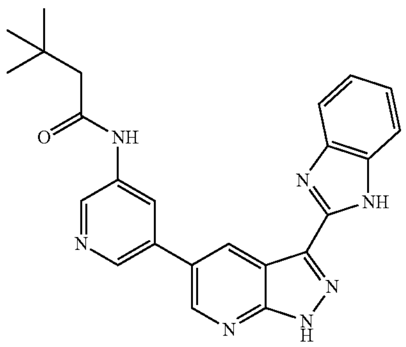

N-(5-(3-(1H-Benzo[d]imidazol-2-yl)-1H-pyrazolo[3,4-b]pyridin-5-yl)pyridin-3-yl)-3,3-dimethylbutanamide 774.

Brown solid (22.3 mg, 0.05 mmol, 30.3% yield). $^1$H NMR (DMSO-$d_6$, 500 MHz) δ ppm 1.07 (s, 9H), 2.29 (s, 2H), 7.24-7.31 (m, 2H), 7.68 (brs, 2H), 8.46 (t, J=2 Hz, 1H), 8.75 (d, J=2 Hz, 1H), 8.91 (d, J=2.5 Hz, 1H), 8.99 (d, J=2 Hz, 1H), 9.01 (d, J=2.5 Hz, 1H), 10.29 (s, 1H), 14.47 (s, 1H); ESIMS found $C_{24}H_{23}N_7O$ m/z 426.2 (M+H).

781

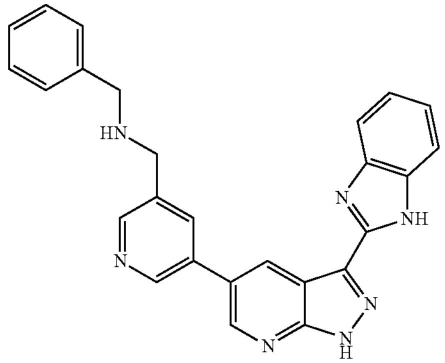

1-(5-(3-(1H-Benzo[d]imidazol-2-yl)-1H-pyrazolo[3,4-b]pyridin-5-yl)pyridin-3-yl)-N-benzylmethanamine 781.

Beige solid (21.0 mg, 0.049 mmol, 48.7% yield). $^1$H NMR (DMSO-$d_6$, 500 MHz) δ ppm 3.77 (s, 2H), 3.85 (s, 2H), 7.18-7.29 (m, 3H), 7.33 (t, J=8 Hz, 2H), 7.39 (d, J=7.5 Hz, 2H), 7.55 (d, J=8 Hz, 1H), 7.77 (d, J=7.5 Hz, 1H), 8.20 (s, 1H), 8.60 (d, J=1.5 Hz, 1H), 8.89 (d, J=2 Hz, 1H), 9.00 (d, J=2 Hz, 1H), 9.03 (d, J=2 Hz, 1H), 13.17 (s, 1H), 14.27 (brs, 1H); ESIMS found $C_{26}H_{21}N_7$ m/z 432.1 (M+H).

785

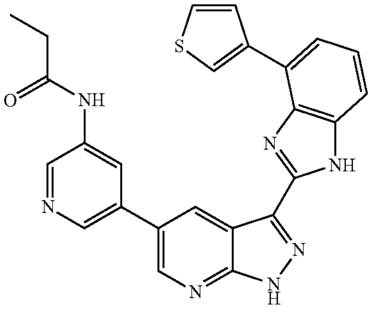

N-(5-(3-(4-(Thiophen-3-yl)-1H-benzo[d]imidazol-2-yl)-1H-pyrazolo[3,4-b]pyridin-5-yl)pyridin-3-yl)propionamide 785.

Brown solid (33.5 mg, 0.072 mmol, 38.7% yield). $^1$H NMR (DMSO-$d_6$, 500 MHz) δ ppm 1.17 (t, J=7.5 Hz, 3H), 2.46 (q, J=7.5 Hz, 2H), 7.32 (t, J=7.5 Hz, 1H), 7.48 (d, J=8 Hz, 1H), 7.64 (d, J=7.5 Hz, 1H), 7.68 (dd, J=3.5 Hz, J=5 Hz, 1H), 8.12 (dd, J=1 Hz, J=5 Hz, 1H), 8.65 (t, J=2 Hz, 1H), 8.68 (dd, J=1 Hz, J=3 Hz, 1H), 8.75 (d, J=2 Hz, 2H), 9.02 (d, J=2 Hz, 1H), 9.12 (d, J=2.5 Hz, 1H), 10.32 (s, 1H), 13.35 (s, 1H), 14.40 (s, 1H); ESIMS found $C_{25}H_{19}N_7OS$ m/z 466.1 (M+H).

793

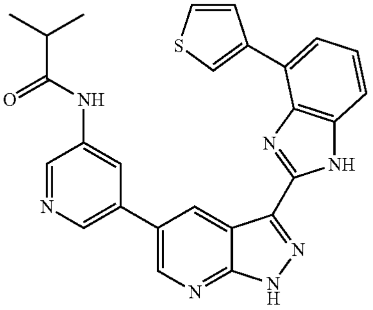

N-(5-(3-(4-(Thiophen-3-yl)-1H-benzo[d]imidazol-2-yl)-1H-pyrazolo[3,4-b]pyridin-5-yl)pyridin-3-yl)isobutyramide 793.

Tan solid (17.0 mg, 0.035 mmol, 19.6% yield). $^1$H NMR (DMSO-$d_6$, 500 MHz) δ ppm 1.20 (d, J=6.5 Hz, 6H), 2.71 (sep, J=6.5 Hz, 1H), 7.32 (t, J=8 Hz, 1H), 7.49 (d, J=8 Hz, 1H), 7.64 (d, J=7.5 Hz, 1H), 7.68 (dd, J=3.5 Hz, J=5 Hz, 1H), 8.14 (d, J=4.5 Hz, 1H), 8.66 (d, J=2 Hz, 1H), 8.68 (d, J=2 Hz, 1H), 8.75 (d, J=2 Hz, 1H), 8.79 (d, J=2 Hz, 1H), 9.02 (d, J=2.5 Hz, 1H), 9.12 (d, J=2 Hz, 1H), 10.28 (s, 1H), 13.35 (s, 1H), 14.40 (s, 1H); ESIMS found $C_{26}H_{21}H_7OS$ m/z 479.8 (M+H).

797

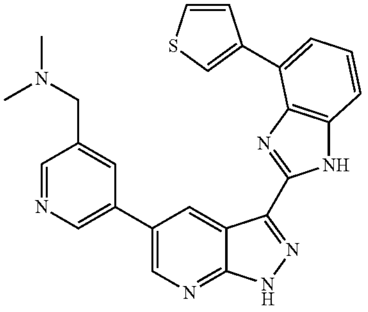

N,N-Dimethyl-1-(5-(3-(4-(thiophen-3-yl)-1H-benzo[d]imidazol-2-yl)-1H-pyrazolo[3,4-b]pyridin-5-yl)pyridin-3-yl)methanamine 797.

Brown solid (26.7 mg, 0.059 mmol, 31.0% yield). $^1$H NMR (DMSO-$d_6$, 500 MHz) δ ppm 2.25 (s, 6H), 3.59 (s, 2H), 7.32 (t, J=8 Hz, 1H), 7.49 (d, J=8 Hz, 1H), 7.63 (d, J=7.5 Hz, 1H), 7.68 (dd, J=3 Hz, J=5 Hz, 1H), 8.11 (dd, J=1 Hz, J=5 Hz, 1H), 8.15 (s, 1H), 8.59 (d, J=1.5 Hz, 1H), 8.74 (dd, J=1.5 Hz, J=3 Hz, 1H), 9.00 (d, J=2 Hz, 1H), 9.08 (d, J=2 Hz, 1H), 9.16 (d, J=2.5 Hz, 1H), 13.35 (brs, 1H), 14.38 (brs, 1H); ESIMS found $C_{25}H_{21}N_7S$ m/z 452.1 (M+H).

799

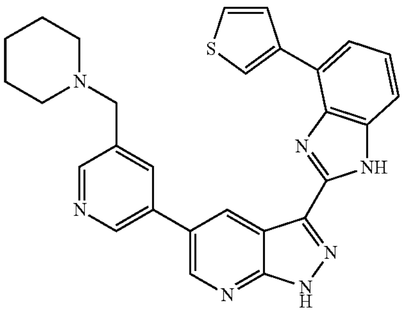

5-(5-(Piperidin-1-ylmethyl)pyridin-3-yl)-3-(4-(thiophen-3-yl)-1H-benzo[d]imidazol-2-yl)-1H-pyrazolo[3,4-b]pyridine 799.

Beige solid (55.8 mg, 0.11 mmol, 43.5% yield). $^1$H NMR (DMSO-d$_6$, 500 MHz) δ ppm 1.40 (brs, 2H), 1.47-1.56 (m, 4H), 2.42 (brs, 1H), 3.63 (s, 2H), 7.32 (t, J=7.5 Hz, 1H), 7.49 (d; J=8 Hz, 1H), 7.63 (d, J=7 Hz, 1H), 7.68 (dd, J=5 Hz, J=3 Hz, 1H), 8.11 (dd, J=1 Hz, J=5.5 Hz, 1H), 8.13 (s, 1H), 8.59 (d, J=1 Hz, 1H), 8.74 (dd, J=1 Hz, J=3 Hz, 1H), 8.98 (d, J=2 Hz, 1H), 9.07 (d, J=2 Hz, 1H), 9.16 (d, J=2 Hz, 1H), 13.35 (s, 1H), 14.38 (s, 1H) ESIMS found $C_{28}H_{25}N_7S$ m/z 492.2 (M+H).

803

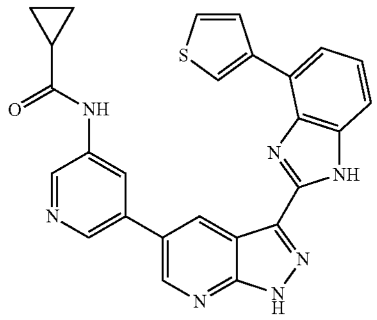

N-(5-(3-(4-(Thiophen-3-yl)-1H-benzo[d]imidazol-2-yl)-1H-pyrazolo[3,4-b]pyridin-5-yl)pyridin-3-yl)cyclopropanecarboxamide 803.

Yellow-white solid (20.2 mg, 0.04 mmol, 56.4% yield). $^1$H NMR (DMSO-d$_6$, 500 MHz) δ ppm 0.85-0.95 (m, 4H), 1.85-1.92 (m, 1H), 7.32 (t, J=8 Hz, 1H), 7.49 (d, J=8 Hz, 1H), 7.60-7.69 (m, 2H), 8.11 (brs, 1H), 8.64 (s, 1H), 8.67 (s, 1H), 8.75 (s, 1H), 9.01 (d, J=2 Hz, 1H), 9.11 (s, 1H), 10.65 (s, 1H), 13.35 (brs, 1H), 14.40 (s, 1H); ESIMS found $C_{26}H_{19}N_7OS$ m/z 478.1 (M+H).

818

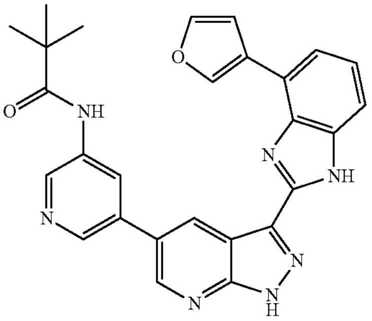

N-(5-(3-(4-(Furan-3-yl)-1H-benzo[d]imidazol-2-yl)-1H-pyrazolo[3,4-b]pyridin-5-yl)pyridin-3-yl)pivalamide 818.

Brown solid (36.0 mg, 0.075 mmol, 42.6% yield). $^1$H NMR (DMSO-d$_6$, 500 MHz) δ ppm 1.30 (s, 9H), 7.30 (t, J=7.5 Hz, 1H), 7.35 (d, J=1 Hz, 1H), 7.45 (d, J=7.5 Hz, 1H), 7.53 (d, J=7.5 Hz, 1H), 7.78 (t, J=1.5 Hz, 1H), 8.59 (t, J=2 Hz, 1H), 8.78 (d, J=2 Hz, 1H), 8.83 (s, 1H), 8.96 (d, J=2 Hz, 1H), 9.02 (d, J=2.5 Hz, 1H), 9.11 (d, J=2 Hz, 1H), 9.62 (s, 1H), 13.32 (s, 1H), 14.40 (s, 1H); ESIMS found $C_{27}H_{23}N_7O_2$ m/z 478.1 (M+H).

827

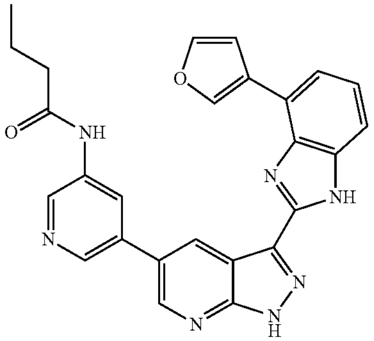

N-(5-(3-(4-(Furan-3-yl)-1H-benzo[d]imidazol-2-yl)-1H-pyrazolo[3,4-b]pyridin-5-yl)pyridin-3-yl)butyramide 827.

Brown solid (29.6 mg, 0.064 mmol, 36.9% yield). $^1$H NMR (DMSO-d$_6$, 500 MHz) δ ppm 0.96 (t, J=7.5 Hz, 3H), 1.68 (sex, J=7.5 Hz, 2H), 2.39 (t, J=7 Hz, 1H), 7.29 (t, J=8 Hz, 1H), 7.36 (d, J=1.5 Hz, 1H), 7.45 (d, J=7.5 Hz, 1H), 7.53 (d, J=7.5 Hz, 1H), 7.79 (t, J=1.5 Hz, 1H), 8.57 (d, J=2 Hz, 1H), 8.75 (d, J=1.5 Hz, 1H), 8.80 (d, J=2 Hz, 1H), 8.81 (s, 1H), 8.98 (d, J=2.5 Hz, 1H), 9.08 (d, J=2 Hz, 1H), 10.31 (s, 1H), 13.32 (s, 1H), 14.40 (s, 1H); ESIMS found $C_{26}H_{21}N_7O_2$ m/z 464.2 (M+H).

898

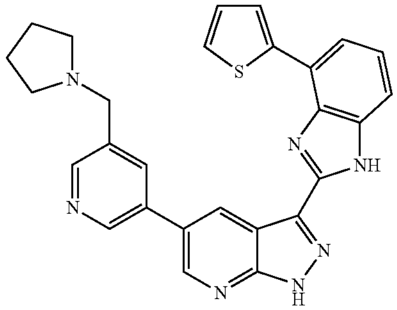

5-(5-(Pyrrolidin-1-ylmethyl)pyridin-3-yl)-3-(4-(thiophen-2-yl)-1H-benzo[d]imidazol-2-yl)-1H-pyrazolo[3,4-b]pyridine 898.

Beige solid (15.4 mg, 0.032 mmol, 17.7% yield). $^1$H NMR (DMSO-d$_6$, 500 MHz) δ ppm 1.74 (brs, 4H), 2.52 (brs, 4H), 3.80 (brs, 2H), 7.23 (dd, J=3.5 Hz, J=5 Hz, 1H), 7.31 (t, J=8 Hz, 1H), 7.48 (d, J=7.5 Hz, 1H), 7.61 (dd, J=1 Hz, J=5 Hz, 1H), 7.66 (d, J=7.5 Hz, 1H), 8.18 (dd, J=1 Hz, J=3.5 Hz, 1H), 8.19 (brs, 1H), 8.63 (brs, 1H), 9.01 (brs, 1H), 9.09 (d, J=2 Hz, 1H), 9.32 (d, J=2 Hz, 1H), 13.42 (s, 1H), 14.40 (s, 1H); ESIMS found $C_{27}H_{23}N_7S$ m/z 478.0 (M+H).

Example 3

The above synthesized compounds were screened using the assay procedure for Wnt activity described below.

Reporter cell lines can be generated by stably transducing cells of cancer cell lines (e.g., colon cancer) with a lentiviral construct that include a wnt-responsive promoter driving expression of the firefly luciferase gene.

Lentiviral constructs can be made in which the SP5 promoter, a promoter having eight TCF/LEF binding sites derived from the SP5 promoter, is linked upstream of the firefly luciferase gene. The lentiviral constructs can also include a hygromycin resistance gene as a selectable marker. The SP5 promoter construct can be used to transduce SW480 cells, a colon cancer cell line having a mutated APC gene that generates a truncated APC protein, leading to de-regulated accumulation of β-catenin A control cell line can be generated using another lentiviral construct containing the luciferase gene under the control of the SV40 promoter which does not require fβ-catenin for activation.

Cultured SW480 cells bearing a reporter construct can be distributed at approximately 10,000 cells per well into 96 well or 384 well plates. Compounds from a small molecule compound library can then be added to the wells in half-log dilutions using a ten micromolar top concentration. A series of control wells for each cell type receive only buffer and compound solvent. Twenty-four to forty hours after the addition of compound, reporter activity for luciferase can be assayed, for example, by addition of the BrightGlo luminescence reagent (Promega) and the Victor3 plate reader (Perkin Elmer). Readings can be normalized to DMSO only treated cells, and normalized activities can then be used in the $IC_{50}$ calculations. Table 2 shows the activity of selected compounds of the invention.

TABLE 2

| Compound | Wnt inhibition (μM) | Compound | Wnt inhibition (μM) | Compound | Wnt inhibition (μM) |
|---|---|---|---|---|---|
| 1 | 0.006 | 192 | 1.05 | 594 | 0.12 |
| 2 | 0.038 | 198 | 1.13 | 595 | 0.354 |
| 2 | 0.006 | 209 | 9.8 | 599 | 0.22 |
| 4 | 0.333 | 229 | 0.012 | 602 | 0.018 |
| 5 | 0.0039 | 238 | 0.35 | 605 | 0.018 |
| 6 | 0.55 | 241 | 0.19 | 616 | 1.41 |
| 7 | 0.006 | 246 | 1.27 | 621 | 0.036 |
| 8 | 8.25 | 249 | 10 | 635 | 0.034 |
| 9 | 0.0012 | 254 | 0.235 | 637 | 0.11 |
| 10 | 0.263 | 305 | 7.35 | 643 | 0.03 |
| 11 | 0.099 | 309 | 1.02 | 647 | 1.52 |
| 12 | 0.021 | 325 | 0.058 | 654 | 1.5 |
| 13 | 0.172 | 336 | 0.79 | 680 | 0.17 |
| 14 | 0.138 | 346 | 0.056 | 691 | 0.187 |
| 15 | 0.326 | 352 | 0.057 | 698 | 0.3 |
| 16 | 0.384 | 354 | 0.293 | 701 | 0.625 |
| 17 | 0.55 | 373 | 0.07 | 704 | 0.81 |
| 18 | 0.013 | 376 | 0.051 | 719 | 0.2 |
| 19 | 0.499 | 382 | 0.003 | 728 | 0.039 |
| 20 | 10 | 440 | 0.004 | 738 | 0.55 |
| 21 | 0.167 | 443 | 0.001 | 752 | 0.226 |
| 22 | 0.032 | 452 | 0.048 | 758 | 0.048 |
| 23 | 10 | 458 | 0.022 | 761 | 0.32 |
| 24 | 0.021 | 463 | 0.098 | 765 | 0.027 |
| 25 | 10 | 547 | 0.097 | 774 | 0.2 |
| 27 | 1.78 | 551 | 0.033 | 781 | 1.44 |
| 28 | 0.72 | 552 | 0.022 | 785 | 0.01 |
| 114 | 0.011 | 554 | 0.2 | 793 | 0.016 |
| 128 | 0.09 | 557 | 0.053 | 797 | 0.032 |
| 142 | 0.645 | 560 | 0.09 | 799 | 0.082 |
| 158 | 0.008 | 561 | 0.143 | 803 | 0.017 |
| 176 | 1.55 | 573 | 0.082 | 818 | 0.05 |
| 178 | 0.392 | 581 | 0.048 | 827 | 0.063 |
| 179 | 1.45 | 586 | 0.42 | 888 | 0.012 |
| 185 | 1.32 | 590 | 0.02 | 898 | 0.12 |

TABLE 3

| Approximate solubility of a compound of Formulas (I) or (II) | | |
|---|---|---|
| Sample | mg/mL | pH |
| water | 0.12 | |
| 1 mM HCl | 0.72 | 5.8 |
| 2 mM HCl | 1.38 | 5.5 |
| 3 mM HCl | 1.84 | 5.4 |
| EtOH | 0.56 | |
| Propylene Glycol | 2.17 | |

Preparation of a 220 μg/mL suspension in 0.5% CMC/0.05% tween 80 begins by dispensing 597 g±1 g of Gibco 1×PBS into the 1 L glass bottle. Using a 1 mL sterile syringe, measure 0.3 mL of Tween 80. In a weigh boat, weigh out 3 g±0.1 g of Carboxymethyl Cellulose 7LXF PH (CMC). Mix with the Tween80/PBS solution and slowly sprinkle the CMC into the 1 L bottle containing the PBS/Tween mixture (increase mixing speed as necessary). Once visually dispersed and the polymer is hydrated, start heating the container on a heating plate to promote phase inversion (turbidity). Once the solution is cool to the touch, filter NLT 120 mL into the 250 mL glass bottle. Weigh 27 mg of a compound of Formulas (I) or (II) and suspend by mixing with the aid of 120 g of the sterile filtered CMC/tween solution. Fill 2 mL schott glass vials and 13 mm Fluorotec coated stoppers (West Pharma) and autoclave the vials at 260° F. for NLT 25 minutes.

Example 3

Preparation of a parenteral suspension with a compound of Formulas (I) or (II) for the treatment of bone/cartilage diseases.

Example 4

Preparation of a parenteral preparation with a compound of Formulas (I) or (II).

10 mg of a compound of Formulas (I) or (II) (or its salt) is dissolved with the aid of 10 mL of propylene glycol (USP grade), using aseptic techniques, sterile filter the solution using a millex GP syringe filter into a sterile glass (type II) container. Before parenteral administration, add 10 mL of the above solution in propylene glycol to a vial containing 90 mL of sterile water, mix well.

Example 5

Preparation of a suspension for intravitreal injection with a compound of Formulas (I) or (II).

Weigh 10 mg of a micronized compound of Formulas (I) or (II) (median particle size of 5 μm) and add slowly while mixing to 100 mL of solution of 0.5% carboxymethyl cellulose (Aqualon 7LXF) and 0.05% tween 80 HP-LQ-MH (Croda) dissolved in PBS (Gibco, pH 7.4). The final suspension is loaded into 2 mL glass vials and terminally sterilized by autoclaving.

It is also contemplated to heat sterilize a micronized compound of Formulas (I) or (II) and aseptic mixing with the sterile filtered solution of 0.5% carboxymethyl cellulose (Aqualon 7LXF) and 0.05% tween 80 HP-LQ-MH (Croda) dissolved in PBS (Gibco, pH 7.4).

Administration is performed using a 30 G needle and a volume of approximately 50 μL for intravitreal injection in rabbits.

Example 6

Composition for intratympanic injection with a compound of Formulas (I) or (II).

10 mg of a compound of Formulas (I) or (II) is dissolved with the aid of 100 mL of propylene glycol (USP grade), using aseptic techniques, sterile filter the solution using a millex GP syringe filter into a sterile glass (type II) container. Before parenteral administration, add 10 mL of the above solution in propylene glycol to a vial containing 90 mL of sterile water, mix well.

Administration is performed using a 25 G needle and a volume of approximately 200 μL for intratympanic injection targeting the round window membrane.

Example 7

Primary Screening Assay for Idiopathic Pulmonary Fibrosis (IPF).

Compounds of Formulas (I) or (II) were screened in a β-catenin-based reporter assay in a transformed human bronchial epithelial cell line (NL-20). The results shown in Table 4 demonstrated that compounds of Formulas (I) or (II) are able to inhibit β-catenin activity in these cells, supporting the drug's mechanism of action for the treatment of idiopathic pulmonary fibrosis (IPF). Compounds of Formulas (I) or (II) are significantly more potent than ICG-001, a small molecule β-catenin inhibitor [*Proc. Natl. Acad. Sci. U.S.A* (2010), 107 (32), 14309-14314].

TABLE 4

| Compound | NL-20 β-catenin reporter assay ($IC_{50}$, μM) | Compound | NL-20 β-catenin reporter assay ($IC_{50}$, μM) |
|---|---|---|---|
| ICG-001 (β-catenin inhibitor) | 7 | 11 | 0.21 |
| 5 | 0.175 | 12 | 0.31 |
| 7 | 1.9 | 14 | 2.03 |
| 9 | 0.067 | 18 | 0.44 |
| 10 | 0.247 | 452 | 1.09 |

Example 8

Preparation of a composition for pulmonary delivery with a compound of Formulas (I) or (II) for the treatment of pulmonary fibrosis.

Weigh 100 mg of a compound of Formulas (I) or (II) (or its salt) an added slowly while mixing to 100 mL of solution of 1.5% dextrose (or lactose)+0.05% tyloxapol. The final solution is sterile filter the solution using a millex GP syringe filter.

Administration is performed using a jet nebulizer (Pan LC plus) or an aerodose nebulizer.

C57B1/6 mice were dosed for 30 minutes via a nose only chamber (CH Technology) at a flow rate of 15 LPM, particle size distribution and dose was measured by a 7 stage impactor (1 LPM) placed in one of the ports. A median aerosol particle size of 1.2 μm with a GSD of 1.8 μm was obtained and a dosing rate of 1.5 μM/min/mouse.

TABLE 5

Concentrations of a compound of Formulas (I) or (II) in Mice (C57B1/6)

| Inhalation | Conc. (ng/mL) | | |
|---|---|---|---|
| Time Point (h) | Plasma | Lung | Ratio |
| 0.25 | 21.9 | 467.2 | 21.3 |
| 2 | 0.8 | 400.1 | 500.1 |
| 6 | 8.8 | 392.5 | 44.6 |
| 23 | 0.03 | 260.7 | 8690 |

A diluted formulation of 0.5 mg/mL of compound of Formulas (I) or (II) was nebulized for 10 and 30 minutes to bleomycin-induced pulmonary fibrotic C57B1/6 mice. Bleomycin is a chemotherapeutic agent which use has been shown to cause pulmonary fibrosis in humans. As a result, it became widely used as a research tool to induce and study pulmonary fibrosis in animals [Walters, D. M. and Kleeberger, S. R., "*Mouse models of bleomycin-induced pulmonary fibrosis*" *Current Protocols in Pharmacology* (2008) Chapter 5: Unit 5.46, 1-17]. Male C57B1/6 mice were anesthetized and 2 U/kg Bleomycin (Henry Schien) was orophrayngeally administered. After 7 days, the compound of Formulas (I) or (II) was delivered via a nose only chamber (CH Technology) at a flow rate of 20 LPM daily for 30 minutes for 13 days. After the last dose, 13 days, the animals were sacrificed, and their lungs were perfused and with 10% buffered formalin and processed for tissue histology. The plasma was obtained and published biomarkers of disease, MMP-7, TIMP-1 and TGF-β, 1 were evaluated by ELISA [*British Journal of Pharmacology* (2010), 160(7), 1699-1713; *American journal of respiratory and critical care medicine* (2012), 185(1), 67-76]. H&E sections of the lungs and scored in a blinded fashion according to the Ashcroft system to evaluate pulmonary fibrosis [*Biotechniques* (2008), 44(4), 507-517]. A reduction in pulmonary fibrosis and plasma biomarkers were demonstrated in Compound-treated animals (Table 6).

TABLE 6

| Treatment | Grade of Fibrosis-Ashcroft Score | MMP-7 levels (ng/mL) | TIMP-1 levels (ng/mL) | TGF-β levels (ng/mL) |
|---|---|---|---|---|
| PBS/no dose | 0.25 | 10.0 | 1203 | 10.0 |
| Bleomycin/vehicle | 3.04 | 13.6 | 2763 | 14.5 |
| Bleomycin/10 min aerosol of a compound of Formulas (I) or (II) | 3.52 | 10.7 | 2023 | 14.2 |
| Bleomycin/30 min aerosol of a compound of Formulas (I) or (II) | 2.08* | 9.4** | 1958 | 9.7 |

*$p < 0.05$ vs Bleo/Vehicle,
**$p = 0.035$ vs Bleo/Vehicle

Example 9

Preparation of a suspension of drug-eluting material with a compound of Formulas (I) or (II).

Solution 1 (PLGA containing active): Weigh 425 mg of PLGA 50:50 (PLGA 0.55-0.75, Lactel B6010-2P)+4.5 mg of a compound of Formulas (I) or (II)+4 mL of dichloromethane, mix well to dissolve.

Solution 2 (1% PVA solution): Add 40 mL of DI water, then add 413 mg of polyvinyl alcohol (Sigma 87-89% hydrolyzed, PN 363170-25), mix to dissolve then sterile filter through a 0.22μ PES syringe filter (Millipore Millex GP).

PLGA microparticle formation: Add 20 mL of solution 2 into a clean sterile container, while mixing (high speed mixing) slowly add the entire 4 mL of solution 1 to solution 2.

The term "comprising" as used herein is synonymous with "including," "containing," or "characterized by," and is inclusive or open-ended and does not exclude additional, unrecited elements or method steps.

What is claimed is:

1. A compound, or pharmaceutically acceptable salt thereof, having the structure of Formula I:

I

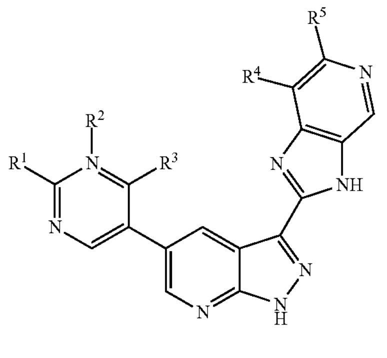

wherein:

$R^1$ is H;

$R^2$ is independently selected from the group consisting of H and —$(C_{1-9}$ alkyl$)_n N(R^9)_2$;

$R^3$ is H;

$R^4$ is independently selected from the group consisting of -aryl$(R^{13})_q$, -furyl$(R^{15})_q$, and -thiophenyl$(R^{15})_q$;

$R^5$ is H;

each $R^8$ is a substituent attached to the heterocyclyl ring and independently selected from the group consisting of H, halide, and —$C_{1-4}$ alkyl;

each $R^9$ is independently selected from the group consisting of H, —$C_{1-9}$ alkyl, —$(C_{1-3}$ alkyl$)_n$carbocyclyl and —$(C_{1-9}$ alkyl$)N(R^{16})_2$;

each $R^{13}$ is 1-2 substituents each attached to the aryl ring and independently selected from the group consisting of H, halide, —$(C_{1-3}$ alkyl$)_n$heterocyclyl$(R^8)_q$, —$(C_{1-9}$ alkyl$)_n N(R^9)_2$ and —$(C_{1-9}$ alkyl$)_n NHSO_2R^{18}$;

each $R^{15}$ is a substituent attached to the heteroaryl ring and independently selected from the group consisting of H, lower alkyl, halide, —$CF_3$, CN, and —C(═O)$(C_{1-3}$ alkyl);

each $R^{16}$ is independently selected from the group consisting of H and lower alkyl;

each $R^{18}$ is a lower alkyl;

A is C;

each q is independently an integer of 1 or 2; and each n is independently an integer of 0 or 1.

2. The compound of claim 1, wherein the $R^4$ aryl is phenyl.

3. The compound of claim 1, wherein the $R^{13}$ heterocyclyl is selected from the group consisting of azetidinyl$(R^8)_q$, pyrrolidinyl$(R^8)_q$, piperidinyl$(R^8)_q$, piperazinyl$(R^8)_q$, and morpholinyl$(R^8)_q$.

4. The compound of claim 1, wherein $R^2$ is H.

5. The compound of claim 1, wherein $R^2$ is —$(C_{1-9}$ alkyl$)_n N(R^9)_2$.

6. The compound of claim 5, wherein $R^2$ is —$CH_2N(R^9)_2$ or —$N(R^9)_2$.

7. The compound of claim 6, wherein $R^9$ is independently selected from the group consisting of H, Me, Et, n-propyl, isopropyl, and —$CH_2$carbocyclyl.

8. The compound of claim 7, wherein $R^4$ is phenyl$(R^{13})_q$.

9. The compound of claim 7, wherein $R^4$ is -furyl$(R^{15})_q$.

10. The compound of claim 7, wherein $R^4$ is -thiophenyl $(R^{15})_q$.

11. The compound of claim 8, wherein $R^{13}$ is one substituent attached to the phenyl ring and the substituent is a fluorine atom.

12. The compound of claim 8, wherein $R^{13}$ is two substituents each attached to the phenyl ring and the substituents are a fluorine atom and —$N(R^9)_2$, wherein $R^9$ is independently selected from the group consisting of H and —$CH_2CH_2N(R^{16})_2$, and wherein $R^{16}$ is independently selected from the group consisting of H, Me, and Et.

13. The compound of claim 8, wherein $R^{13}$ is two substituents each attached to the phenyl ring and the substituents are a fluorine atom and —$(CH_2)_n NHSO_2R^{18}$, wherein $R^9$ is independently selected from the group consisting of Me and Et.

14. The compound of claim 10, wherein $R^{15}$ is one substituent attached to the thiophenyl ring and the substituents are selected from the group consisting of H, F, Me, and —C(═O)Me.

15. The compound of claim 1, wherein the compound of Formula (I) has a structure selected from the group consisting of:

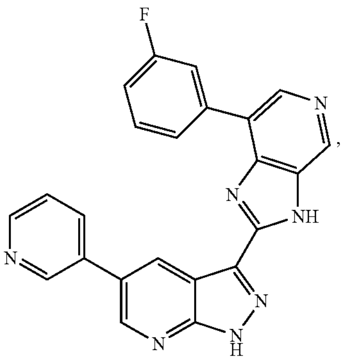
,
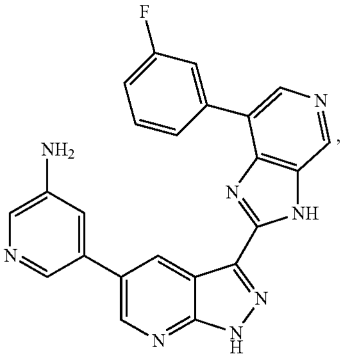
,
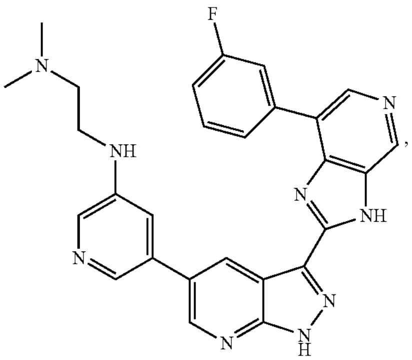
,
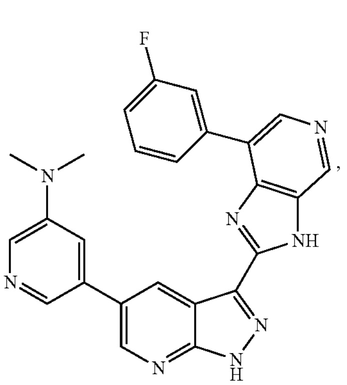
,
-continued
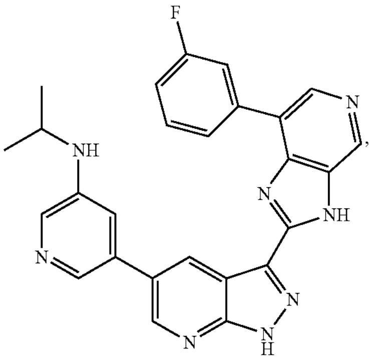
,
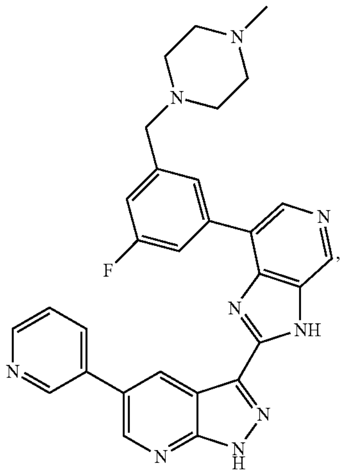
,
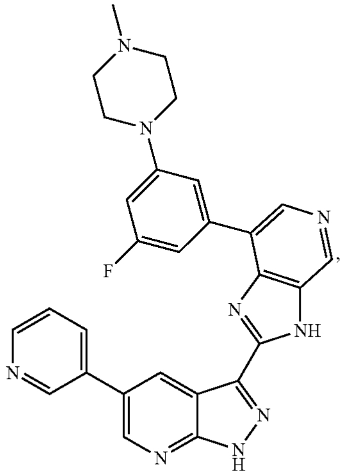
, -continued
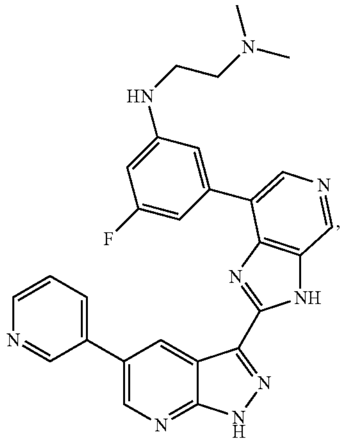
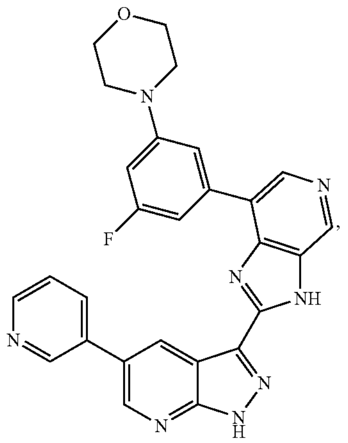
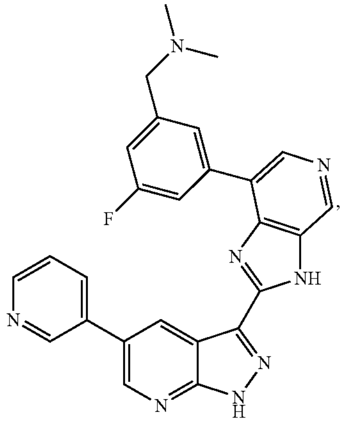
-continued
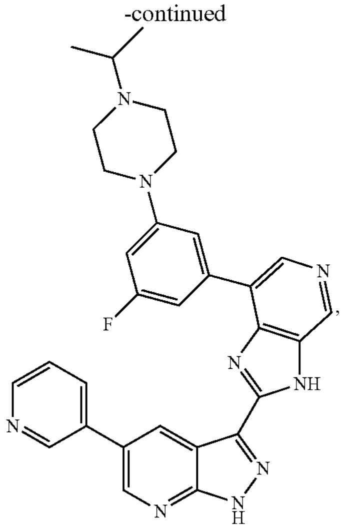
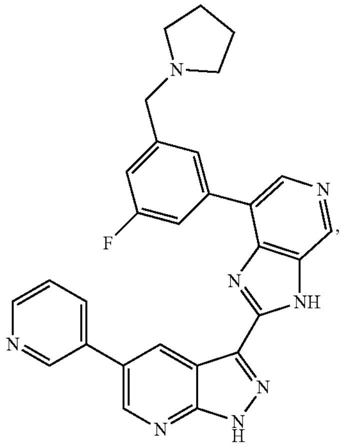
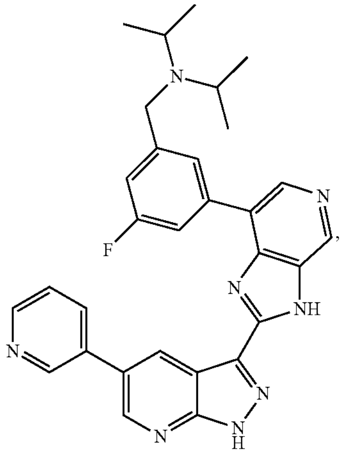

-continued
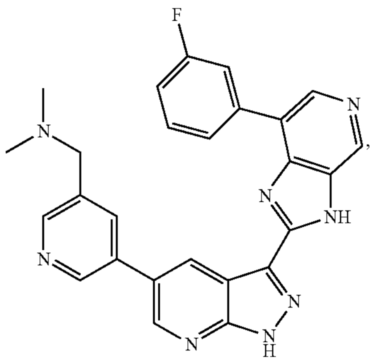
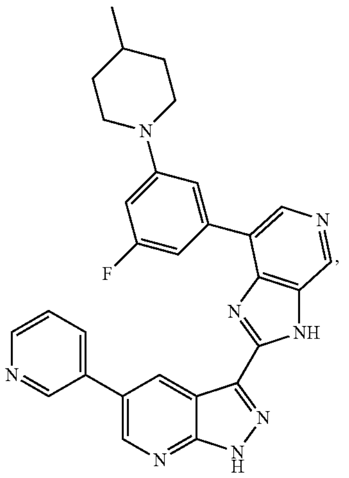
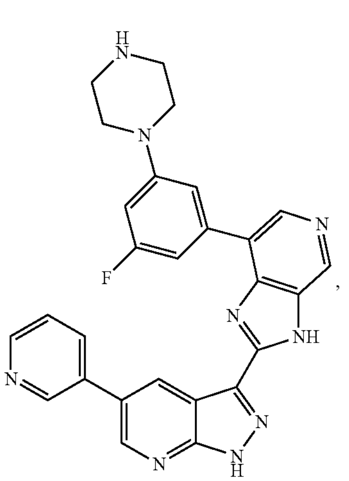
-continued
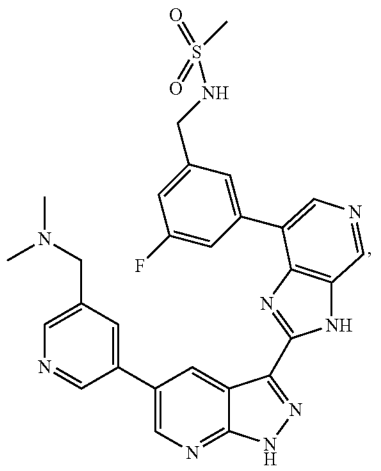
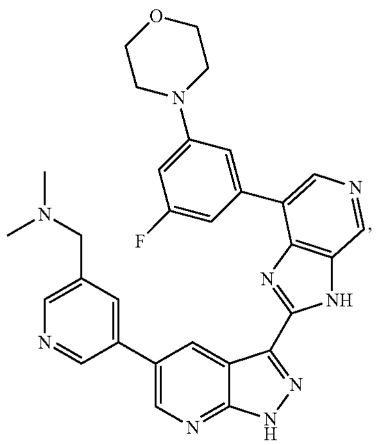
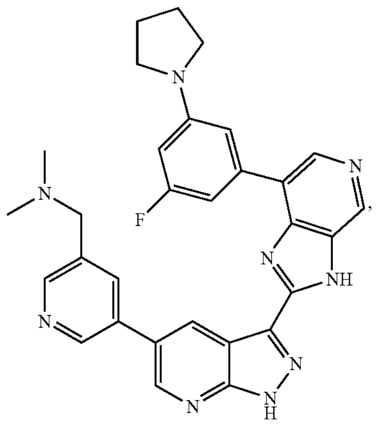

-continued
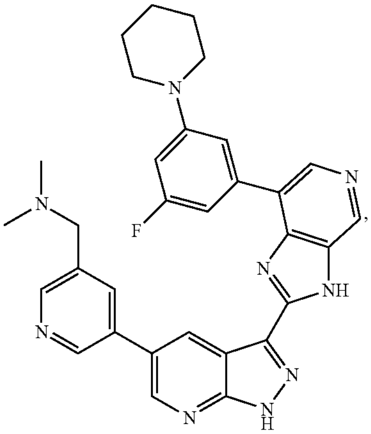
,
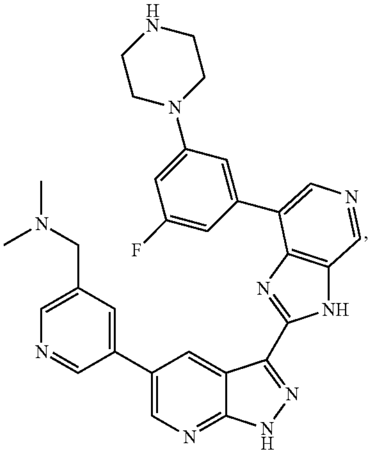
,
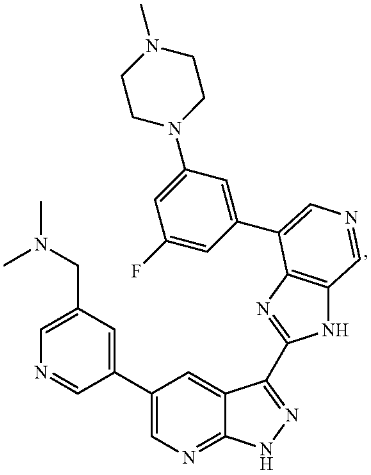
,
-continued
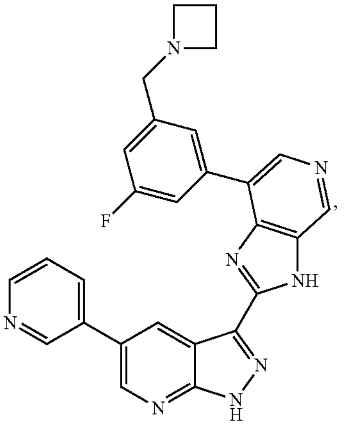
,
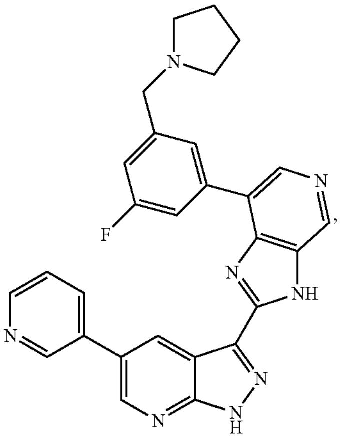
,
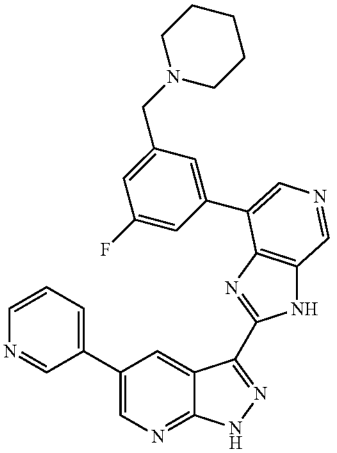

-continued
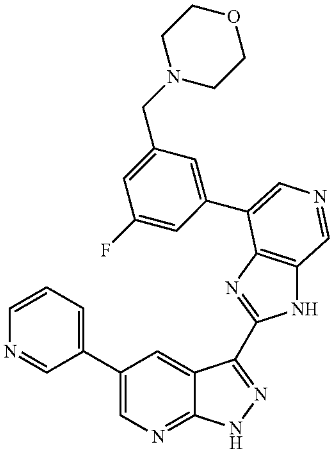
,
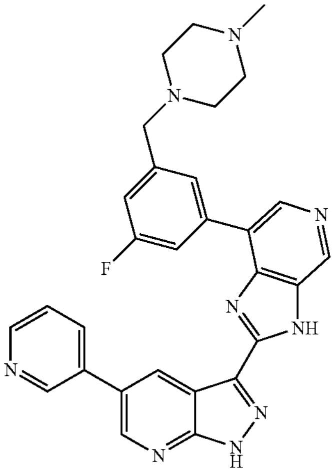
,
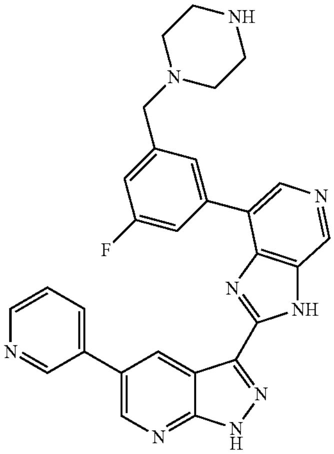
,
-continued
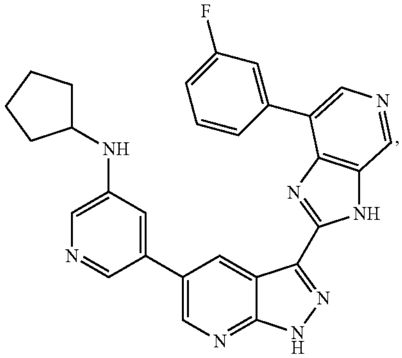
,
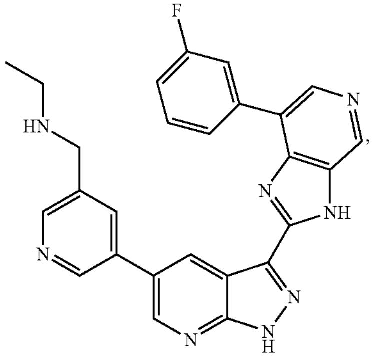
,
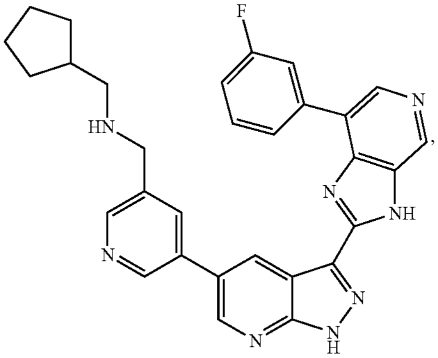
,
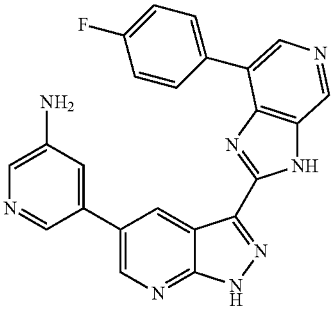
,
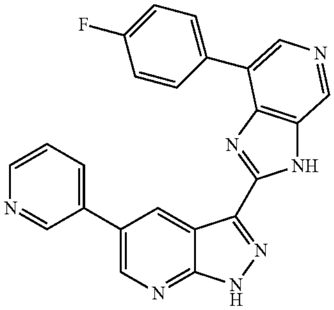
, -continued
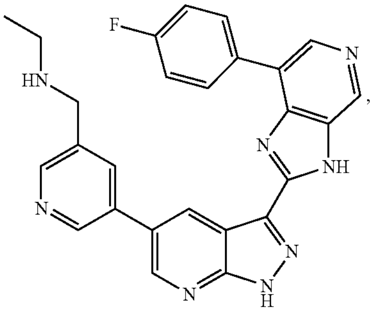
,
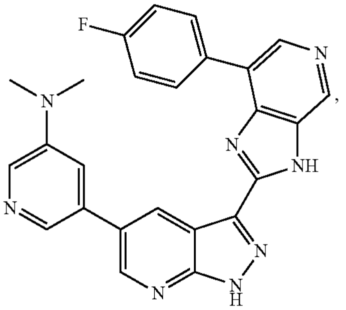
,
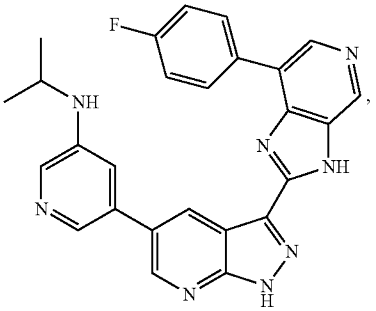
,
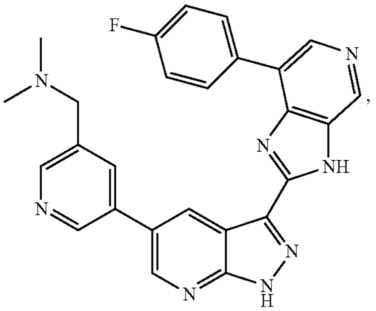
,
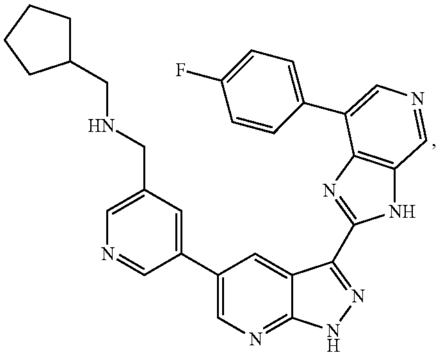
,
-continued
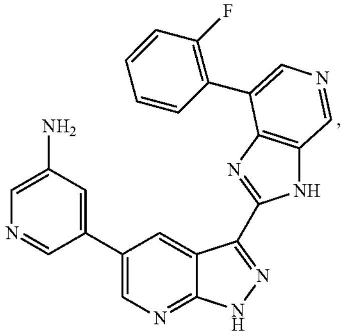
,
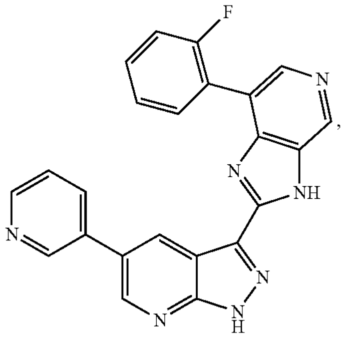
,
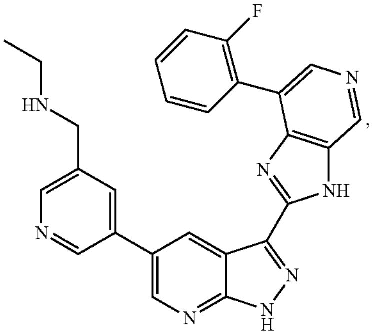
,
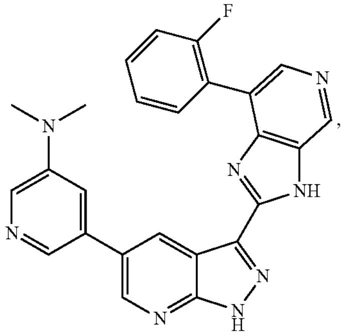
,
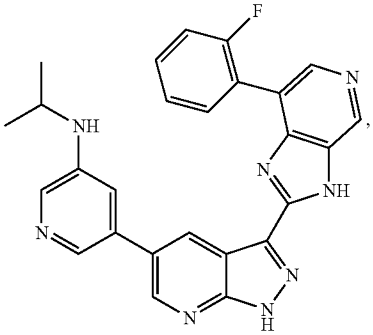
, -continued
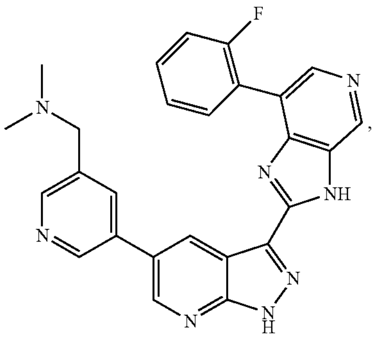
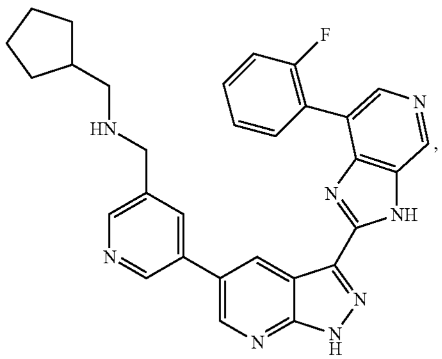
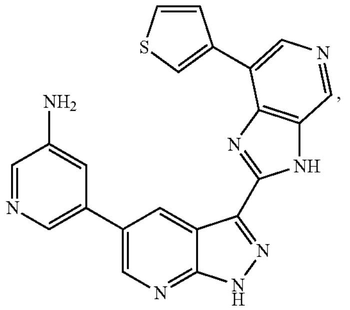
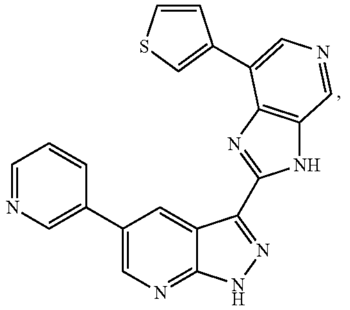
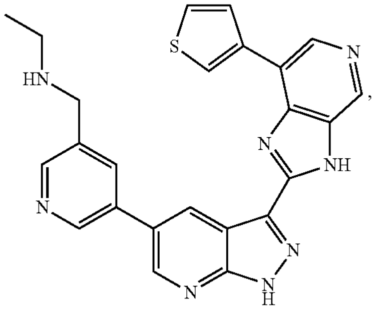
-continued
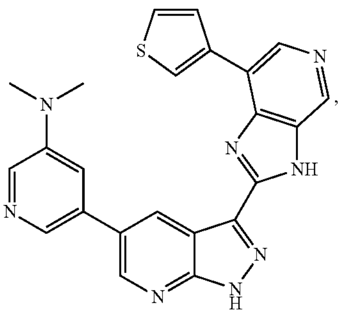
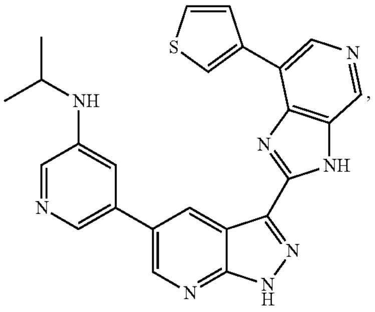
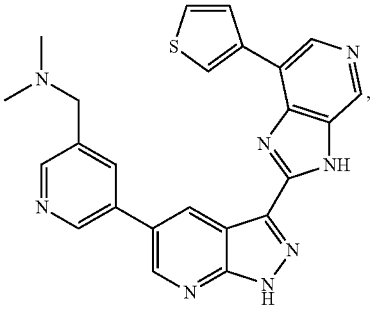
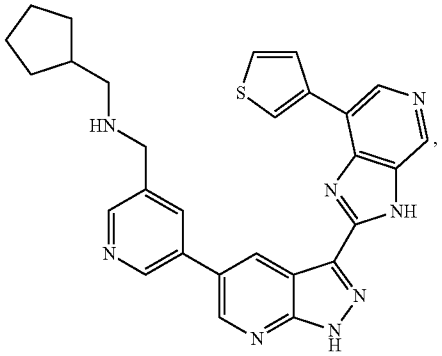
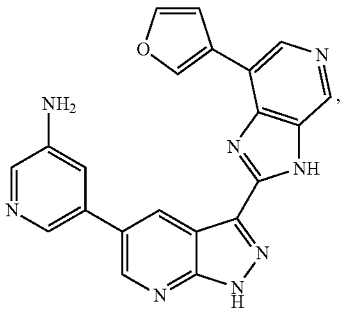

-continued
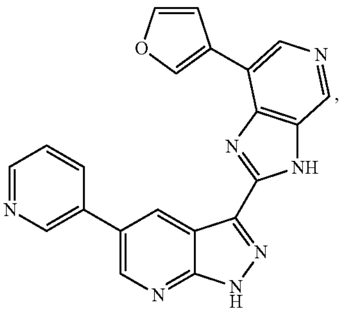
,
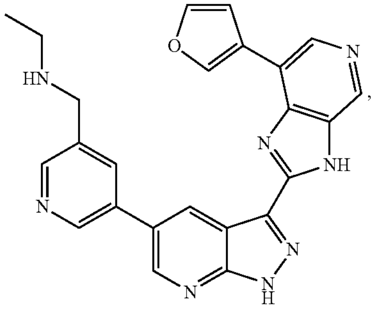
,
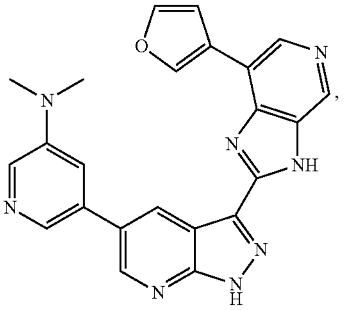
,
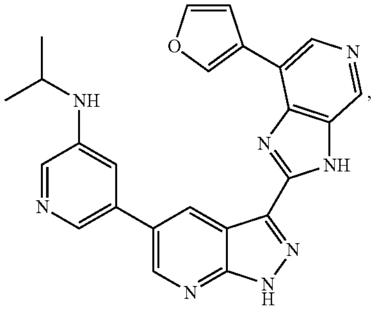
,
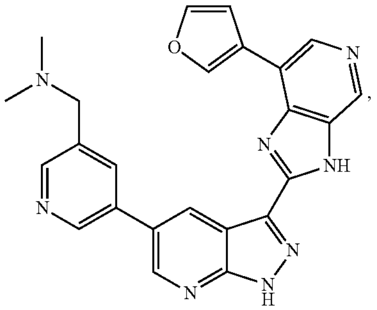
,
-continued
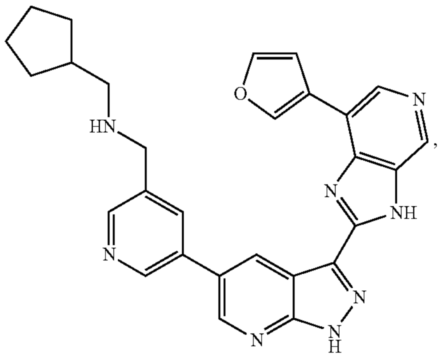
,
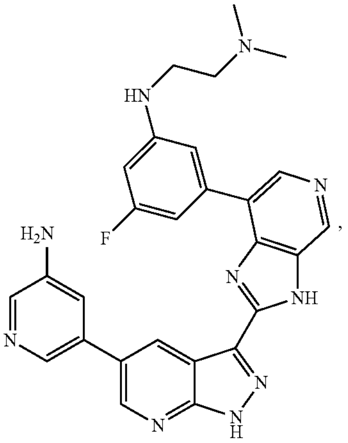
,
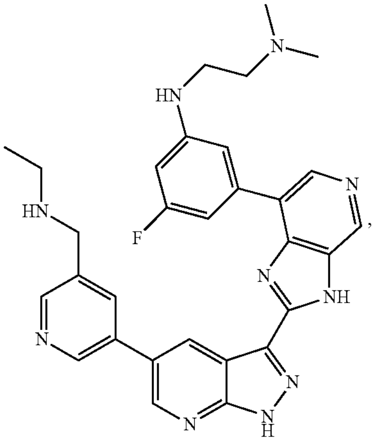
,
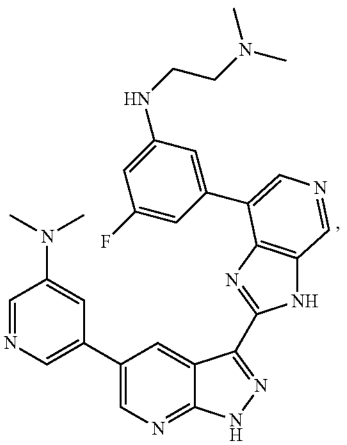
, -continued
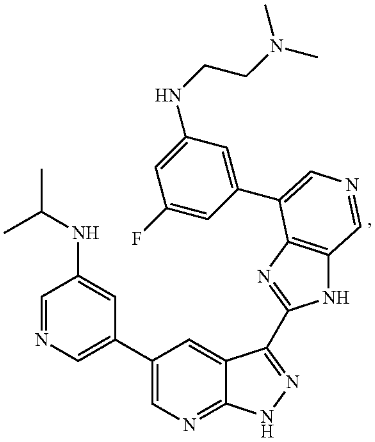
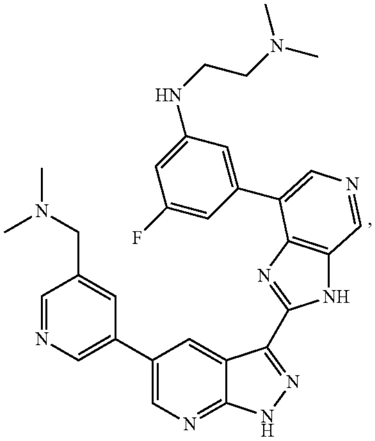
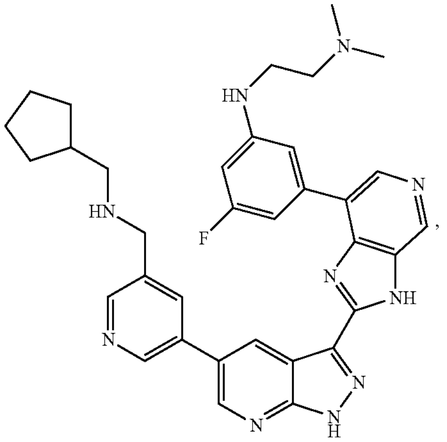
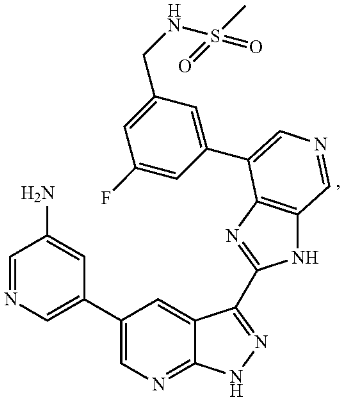
-continued
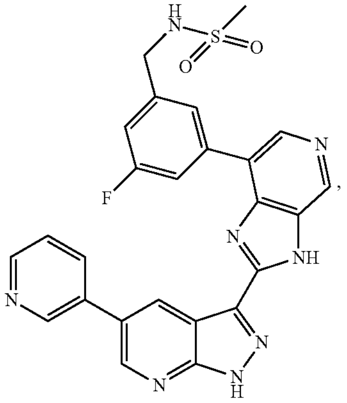
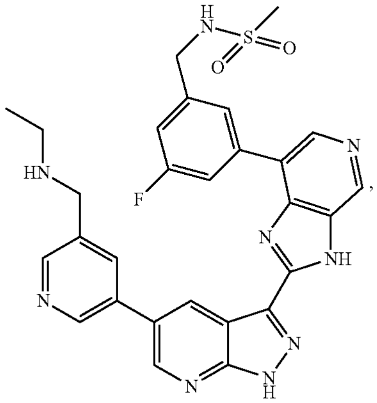
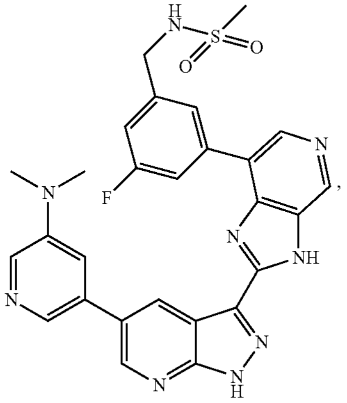
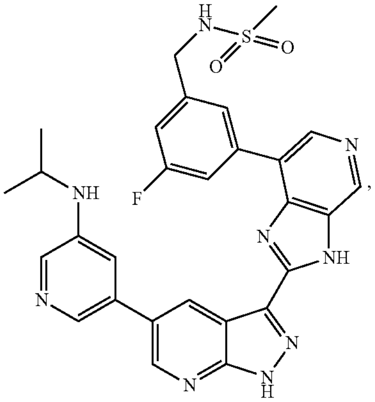

-continued
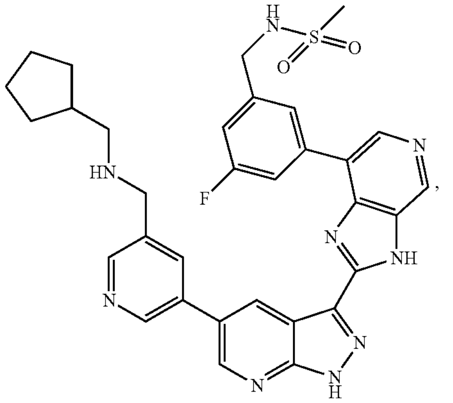
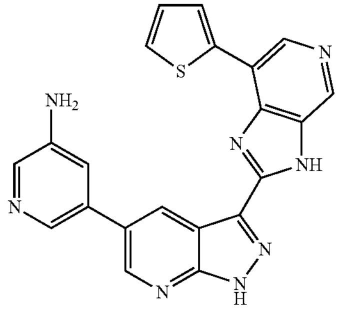
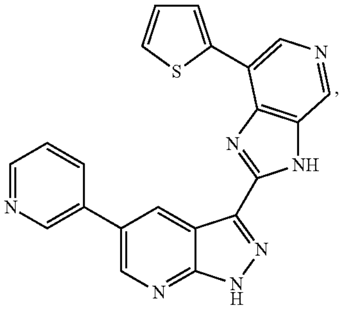
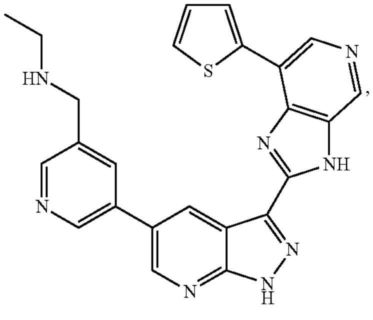
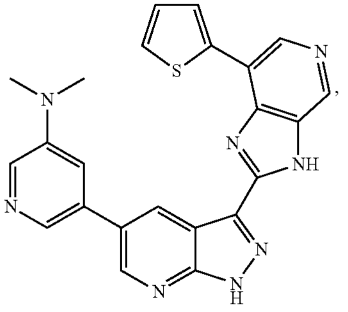
-continued
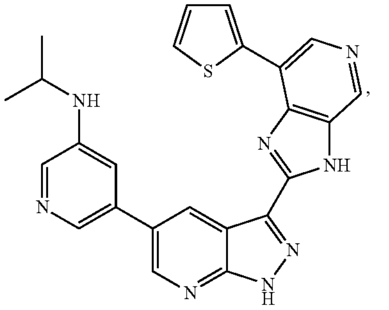
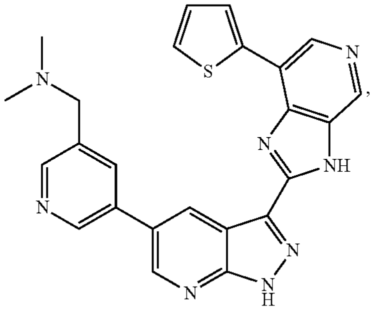
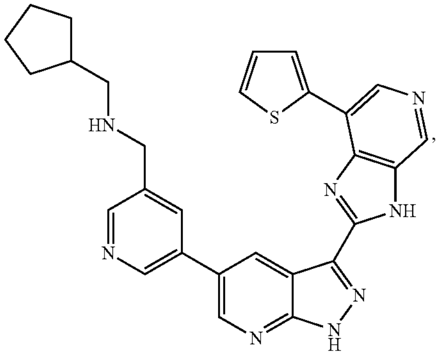
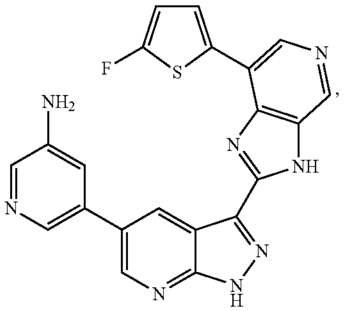
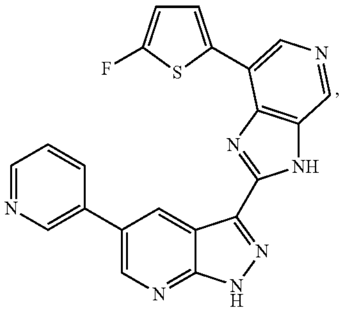

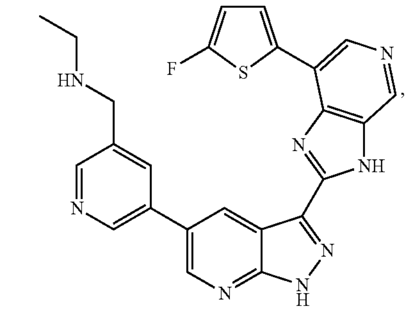
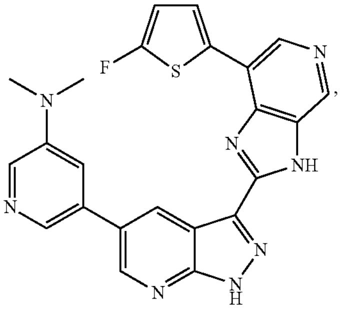
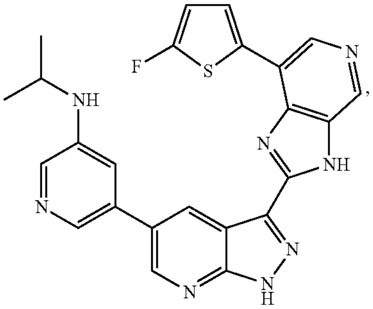
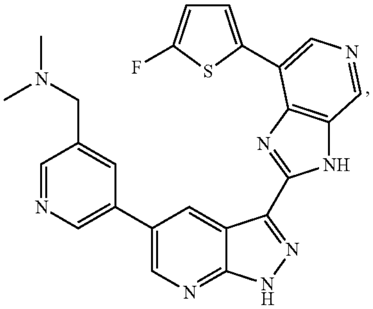
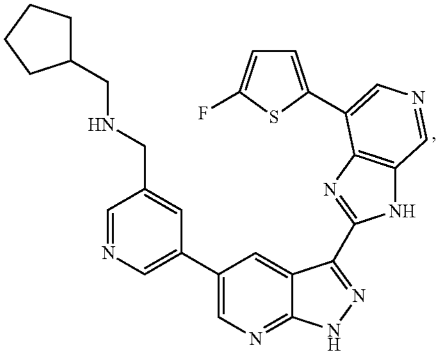
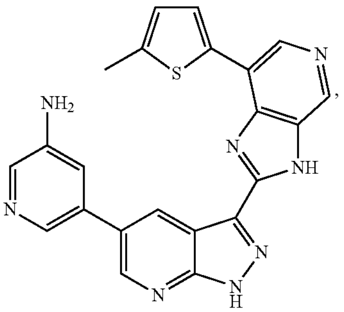
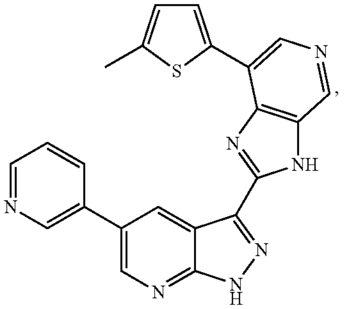
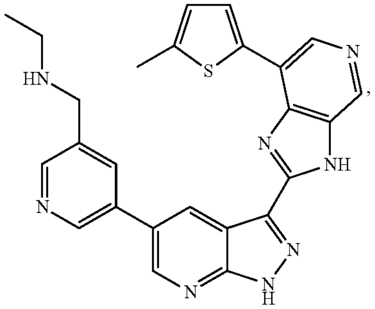
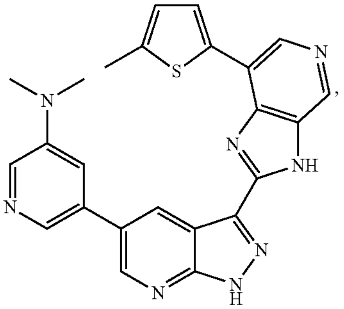
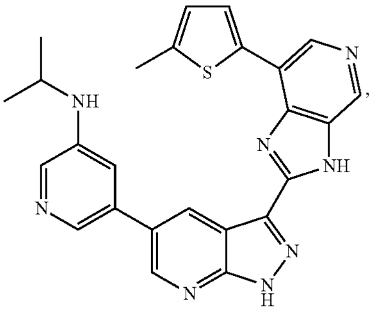

-continued
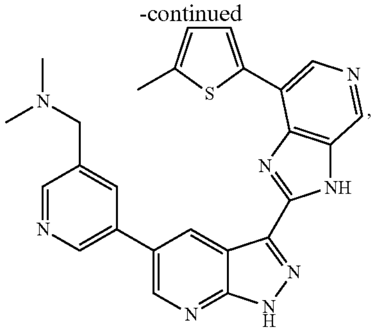
,
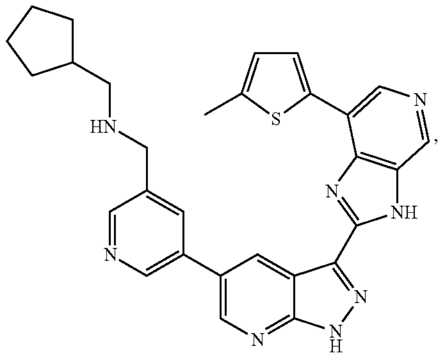
,
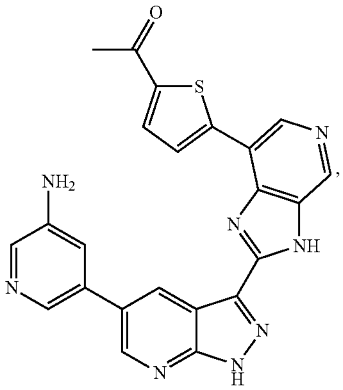
,
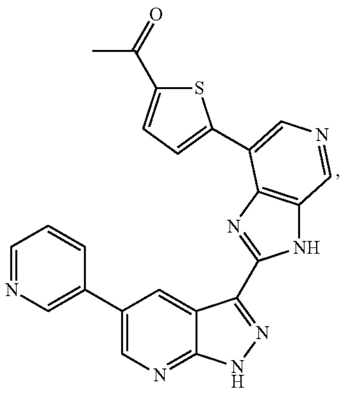
,
-continued
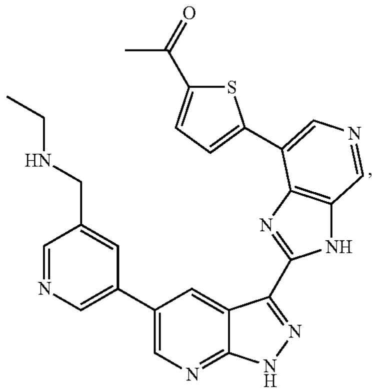
,
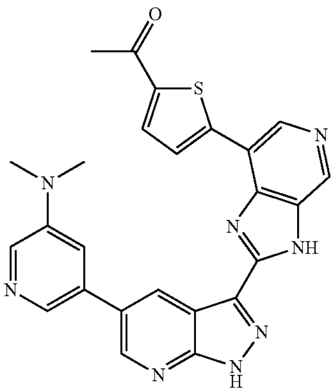
,
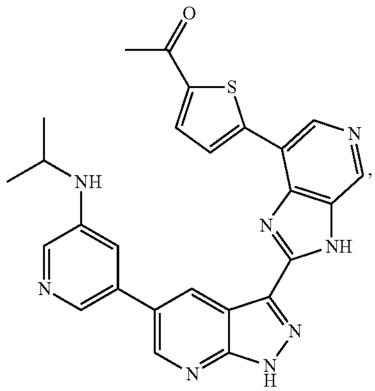
,
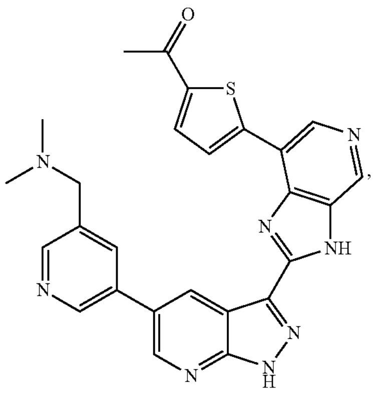
, and -continued
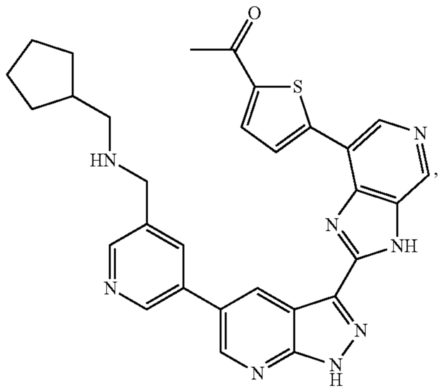
or a pharmaceutically acceptable salt thereof.
16. A compound having a structure selected from the group consisting of:
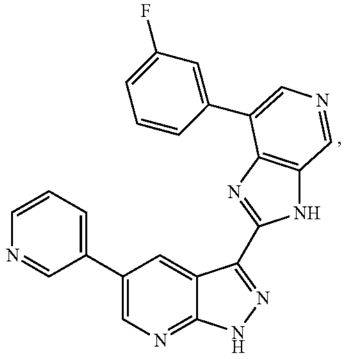
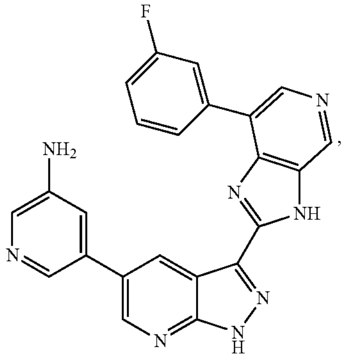
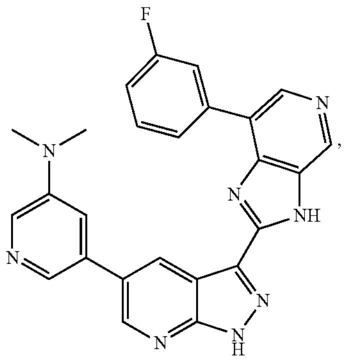
-continued
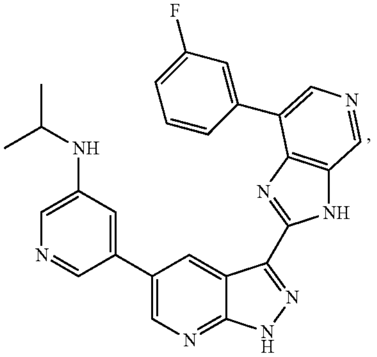
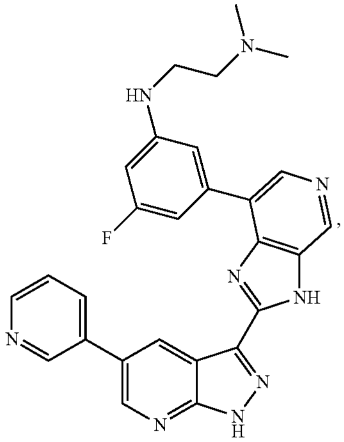
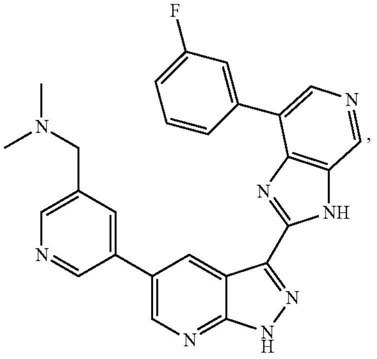
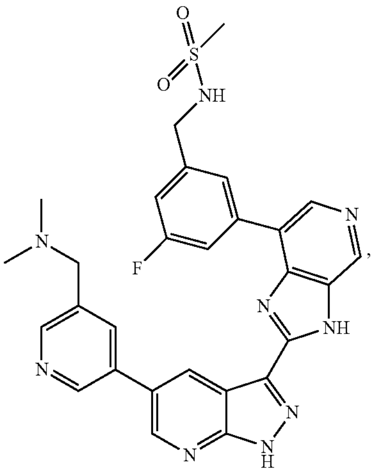

-continued

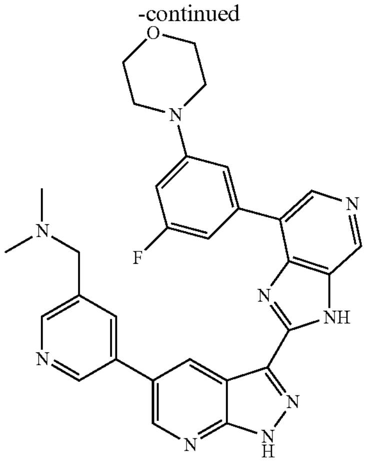,

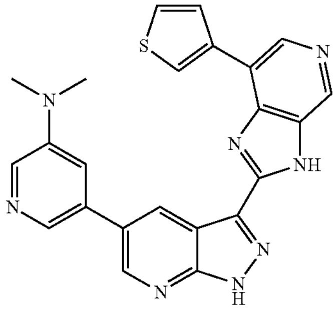,

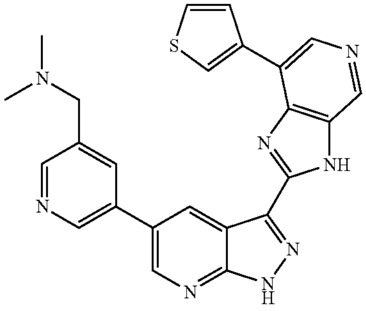,

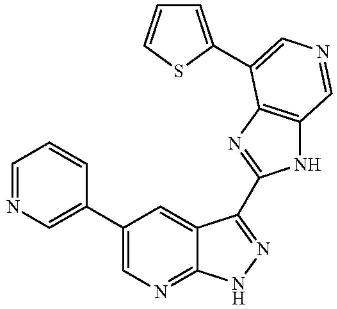, and

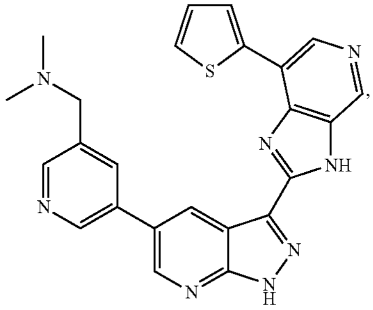, or a pharmaceutically acceptable salt thereof.

17. A pharmaceutical composition comprising a therapeutically effective amount of a compound, or pharmaceutically acceptable salt thereof, having the structure of Formula I:

I

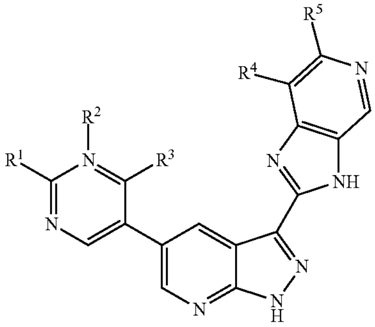

wherein:

$R^1$ is H;

$R^2$ is independently selected from the group consisting of H and —$(C_{1-9}$ alkyl$)_n N(R^9)_2$;

$R^3$ is H;

$R^4$ is independently selected from the group consisting of -aryl$(R^{13})_q$, -furyl$(R^{15})_q$, and -thiophenyl$(R^{15})_q$;

$R^5$ is H;

each $R^8$ is a substituent attached to the heterocyclyl ring and independently selected from the group consisting of H, halide, and —$C_{1-4}$ alkyl;

each $R^9$ is independently selected from the group consisting of H, —$C_{1-9}$ alkyl, —$(C_{1-3}$ alkyl$)_n$carbocyclyl, and —$(C_{1-9}$ alkyl$)N(R^{16})_2$;

each $R^{13}$ is 1-2 substituents each attached to the aryl ring and independently selected from the group consisting of H, halide, —$(C_{1-3}$ alkyl$)_n$heterocyclyl$(R^8)_q$, —$(C_{1-9}$ alkyl$)_n N(R^9)_2$, and —$(C_{1-9}$ alkyl$)_n NHSO_2R^{18}$;

each $R^{15}$ is a substituent attached to the heteroaryl ring and independently selected from the group consisting of H, lower alkyl, halide, —$CF_3$, CN, and —C(═O)$(C_{1-3}$ alkyl);

each $R^{16}$ is independently selected from the group consisting of H and lower alkyl;

each $R^{18}$ is a lower alkyl;

A is C;

each q is independently an integer of 1 or 2;

each n is independently an integer of 0 or 1; and a pharmaceutically acceptable excipient.

18. The pharmaceutical composition of claim 1, wherein the $R^4$ aryl is phenyl.

19. The pharmaceutical composition of claim 1, wherein the $R^{13}$ heterocyclyl is selected from the group consisting of azetidinyl$(R^8)_q$, pyrrolidinyl$(R^8)_q$, piperidinyl$(R^8)_q$, piperazinyl$(R^8)_q$, and morpholinyl$(R^8)_q$.

20. The pharmaceutical composition of claim 17, wherein $R^2$ is H.

21. The pharmaceutical composition of claim 17, wherein $R^2$ is —$(C_{1-9}$ alkyl$)_n N(R^9)_2$.

22. The pharmaceutical composition of claim 21, wherein $R^2$ is —$CH_2N(R^9)_2$ or —$N(R^9)_2$.

23. The pharmaceutical composition of claim 22, wherein $R^9$ is independently selected from the group consisting of H, Me, Et, n-propyl, isopropyl, and —$CH_2$carbocyclyl.

24. The pharmaceutical composition of claim 23, wherein $R^4$ is phenyl$(R^{13})_q$.

25. The pharmaceutical composition of claim 23, wherein $R^4$ is -thiophenyl$(R^{15})_q$.

26. The pharmaceutical composition of claim 24, wherein $R^{13}$ is one substituent attached to the phenyl ring and the substituent is a fluorine atom.

27. The pharmaceutical composition of claim 24, wherein $R^{13}$ is two substituents each attached to the phenyl ring and the substituents are a fluorine atom and —$N(R^9)_2$, wherein $R^9$ is independently selected from the group consisting of H and —$CH_2CH_2N(R^{16})_2$, and wherein $R^{16}$ is independently selected from the group consisting of H, Me, and Et.

28. The pharmaceutical composition of claim 24, wherein $R^{13}$ is two substituents each attached to the phenyl ring and the substituents are a fluorine atom and —$(CH_2)_nNHSO_2R^{18}$, wherein $R^9$ is independently selected from the group consisting of Me and Et.

29. The pharmaceutical composition of claim 25, wherein $R^{15}$ is one substituent attached to the phenyl and the substituents are selected from the group consisting of H, F, Me, and —C(=O)Me.

30. A pharmaceutical composition comprising a therapeutically effective amount of a compound having the structure of:

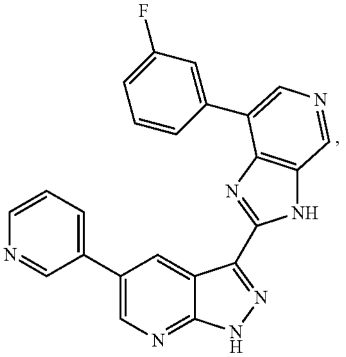

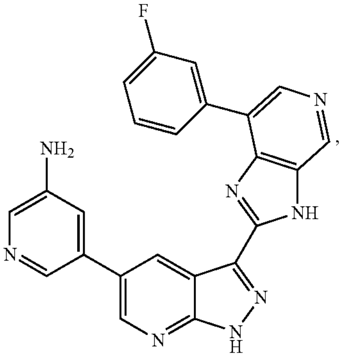

-continued

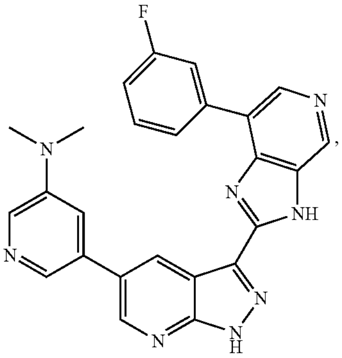

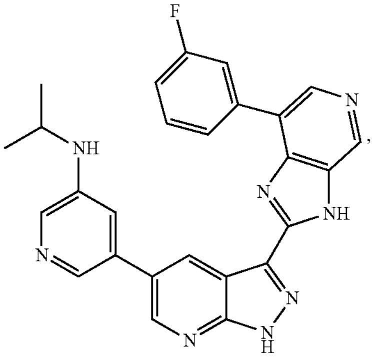

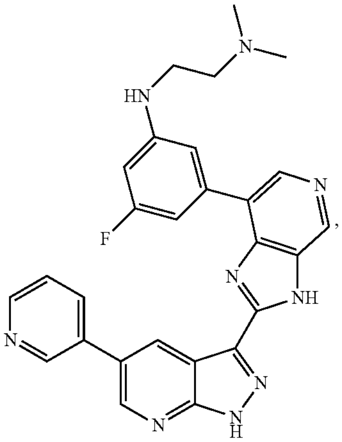

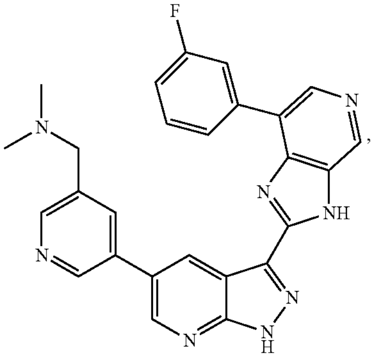

-continued
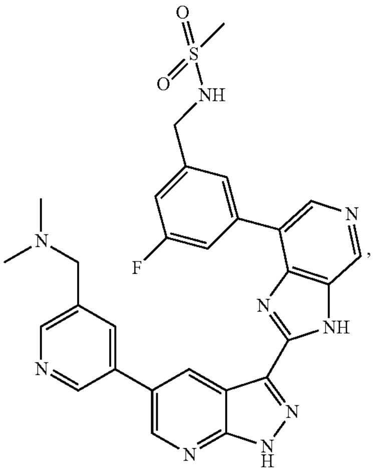
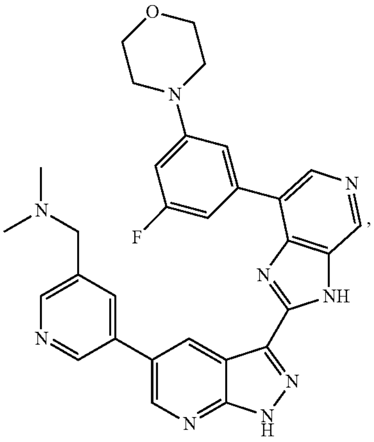
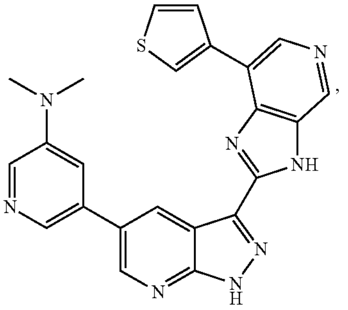
-continued
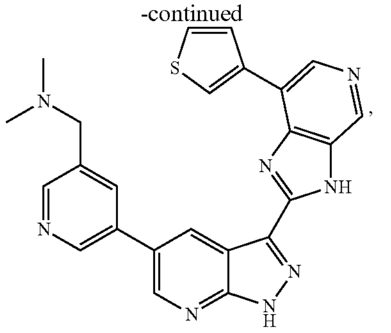
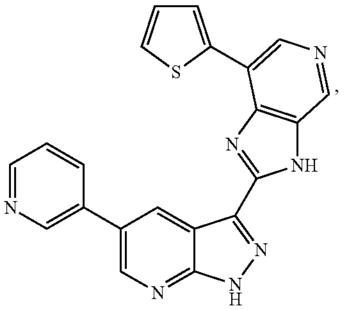
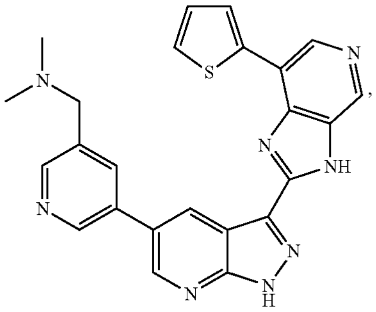
or a pharmaceutically acceptable salt thereof; and a pharmaceutically acceptable excipient.
* * * * *

UNITED STATES PATENT AND TRADEMARK OFFICE

CERTIFICATE OF CORRECTION

PATENT NO. : 8,618,128 B1
APPLICATION NO. : 14/019147
DATED : December 31, 2013
INVENTOR(S) : John Hood, Sunil Kumar KC and David Mark Wallace It is certified that error appears in the above-identified patent and that said Letters Patent is hereby corrected as shown below:

On the Title Page, Item (56)

Column 1, Page 3, Line 1 (Other Publications), please delete “1205 signaling” and insert -- signaling --, therefor.

Column 1, Page 4, Line 59 (Other Publications), please delete “Wnt Wnt” and insert -- Wnt --, therefor.

Column 2, Page 4, Line 2, please delete “fatcors” and insert -- factors --, therefor.

In the Claims

Column 421, Lines 45-58 (Approx.), in Claim 1, please delete

“ 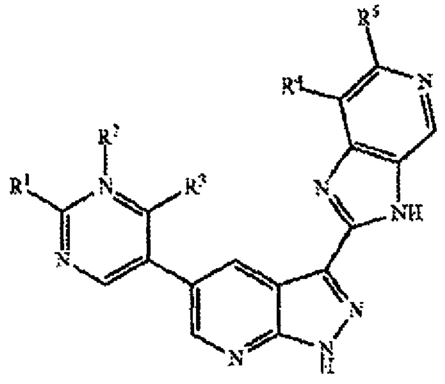 ” and insert -- 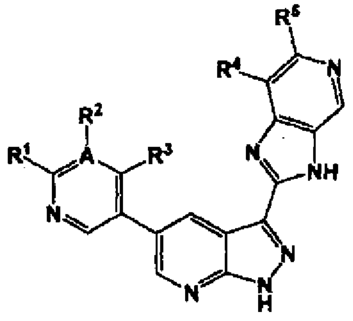 --, therefor.

Signed and Sealed this
Eleventh Day of November, 2014

Michelle K. Lee
*Deputy Director of the United States Patent and Trademark Office*

Column 450, Lines 8-20 (Approx.), in Claim 17, please delete
"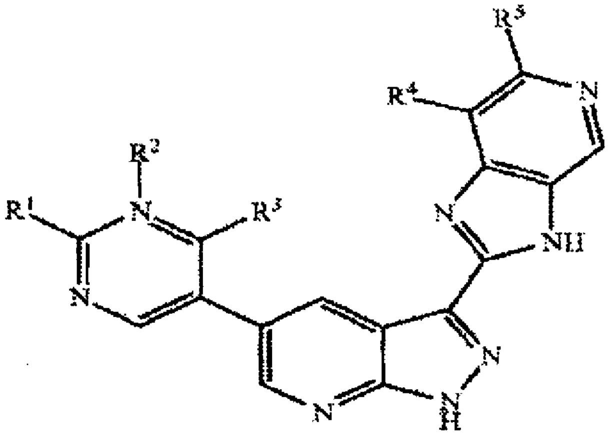" and insert
--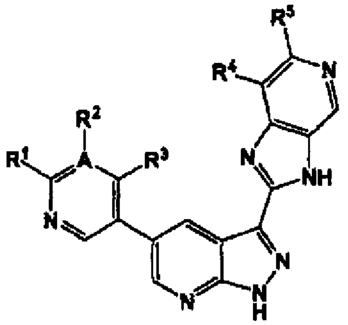--, therefor.